United States Patent
Regev et al.

(10) Patent No.: US 11,913,075 B2
(45) Date of Patent: Feb. 27, 2024

(54) METHODS AND COMPOSITIONS FOR DETECTING AND MODULATING AN IMMUNOTHERAPY RESISTANCE GENE SIGNATURE IN CANCER

(71) Applicants: The Broad Institute, Inc., Cambridge, MA (US); Massachusetts Institute of Technology, Cambridge, MA (US); Dana-Farber Cancer Institute, Inc., Boston, MA (US)

(72) Inventors: Aviv Regev, Cambridge, MA (US); Orit Rozenblatt-Rosen, Cambridge, MA (US); Benjamin Izar, Boston, MA (US); Livnat Jerby, Cambridge, MA (US); Asaf Rotem, Boston, MA (US)

(73) Assignees: The Broad Institute, Inc., Cambridge, MA (US); Massachusetts Institute of Technology, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/499,908

(22) PCT Filed: Mar. 30, 2018

(86) PCT No.: PCT/US2018/025507
§ 371 (c)(1),
(2) Date: Oct. 1, 2019

(87) PCT Pub. No.: WO2018/183921
PCT Pub. Date: Oct. 4, 2018

(65) Prior Publication Data
US 2020/0157633 A1    May 21, 2020

Related U.S. Application Data

(60) Provisional application No. 62/630,158, filed on Feb. 13, 2018, provisional application No. 62/595,327, filed on Dec. 6, 2017, provisional application No. 62/588,025, filed on Nov. 17, 2017, provisional application No. 62/573,117, filed on Oct. 16, 2017, provisional application No. 62/567,153, filed on Oct. 2, 2017, provisional application No. 62/519,784, filed on Jun. 14, 2017, provisional application No. 62/480,407, filed on Apr. 1, 2017.

(51) Int. Cl.
C12Q 1/68          (2018.01)
C12Q 1/6886      (2018.01)

(52) U.S. Cl.
CPC ..... C12Q 1/6886 (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,737,323 A | 4/1988 | Martin et al. |
| 4,837,028 A | 6/1989 | Allen |
| 5,641,870 A | 6/1997 | Rinderknecht et al. |
| 5,686,281 A | 11/1997 | Roberts |
| 5,811,097 A | 9/1998 | Allison et al. |
| 5,843,728 A | 12/1998 | Seed et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,040,177 A | 3/2000 | Riddell et al. |
| 6,284,240 B1 | 9/2001 | Seed et al. |
| 6,352,694 B1 | 3/2002 | June et al. |
| 6,392,013 B1 | 5/2002 | Seed et al. |
| 6,410,014 B1 | 6/2002 | Seed et al. |
| 6,489,458 B2 | 12/2002 | Hackett et al. |
| 6,534,055 B1 | 3/2003 | June et al. |
| 6,753,162 B1 | 6/2004 | Seed et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,232,566 B2 | 6/2007 | June et al. |
| 7,446,190 B2 | 11/2008 | Sadelain et al. |
| 7,572,631 B2 | 8/2009 | Berenson et al. |

(Continued)

FOREIGN PATENT DOCUMENTS

| | | |
|---|---|---|
| EP | 0 404 097 A2 | 12/1990 |
| EP | 2 784 162 A1 | 10/2014 |
| EP | 2 771 468 B1 | 2/2015 |
| EP | 2 784 162 B1 | 4/2015 |
| EP | 2 764 103 B1 | 8/2015 |

(Continued)

OTHER PUBLICATIONS

Cristescu et al. Pan-tumor genomic biomarkers for PD-1 checkpoint blockade-based immunotherapy. Science; 2018; 362; 197 (Year: 2018).*

(Continued)

*Primary Examiner* — Jehanne S Sitton
(74) *Attorney, Agent, or Firm* — F. Brent Nix, Esq.; Johnson, Marcou, Isaacs & Nix, LLC; Michael B. Scher, Esq.

(57) ABSTRACT

The subject matter disclosed herein is generally directed to detecting and modulating novel gene signatures for the treatment and prognosis of cancer. The novel gene signatures predict overall survival in cancer and can be targeted therapeutically.

10 Claims, 108 Drawing Sheets

Specification includes a Sequence Listing.

(56) References Cited

U.S. PATENT DOCUMENTS

| | | |
|---|---|---|
| 7,741,465 B1 | 6/2010 | Eshhar et al. |
| 7,985,739 B2 | 7/2011 | Kay et al. |
| 8,034,334 B2 | 10/2011 | Dudley et al. |
| 8,088,379 B2 | 1/2012 | Robbins et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,697,359 B1 | 4/2014 | Zhang |
| 8,697,854 B2 | 4/2014 | Schendel et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,181,527 B2 | 11/2015 | Sentman |
| 9,215,322 B1 | 12/2015 | Wu et al. |
| 9,233,125 B2 | 1/2016 | Wu et al. |
| 9,259,399 B2 | 2/2016 | Chen-Kiang et al. |
| 2003/0229026 A1 | 12/2003 | Al-Awar et al. |
| 2004/0006074 A1 | 1/2004 | Kelley et al. |
| 2004/0048915 A1 | 3/2004 | Engler et al. |
| 2004/0224402 A1 | 11/2004 | Bonyhadi et al. |
| 2007/0027147 A1 | 2/2007 | Hayama et al. |
| 2007/0179118 A1 | 8/2007 | Barvian et al. |
| 2010/0104509 A1 | 4/2010 | King et al. |
| 2011/0265198 A1 | 10/2011 | Gregory et al. |
| 2012/0017290 A1 | 1/2012 | Cui et al. |
| 2012/0244133 A1 | 9/2012 | Rosenberg et al. |
| 2013/0071414 A1 | 3/2013 | Dotti et al. |
| 2013/0236946 A1 | 9/2013 | Gouble |
| 2013/0303543 A1 | 11/2013 | Dirocco et al. |
| 2014/0031325 A1 | 1/2014 | Bartlett et al. |
| 2014/0080838 A1 | 3/2014 | Wendel et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0368342 A1 | 12/2015 | Wu et al. |
| 2015/0368360 A1 | 12/2015 | Liang et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2017/0107577 A1* | 4/2017 | Al-Ejeh ............... C12Q 1/6886 |
| 2018/0051347 A1* | 2/2018 | Ribas ................ C07K 16/2818 |
| 2018/0163265 A1 | 6/2018 | Zhang et al. |
| 2018/0312824 A1 | 11/2018 | Zhang et al. |
| 2020/0347456 A1* | 11/2020 | Regev ................. A61K 31/506 |

FOREIGN PATENT DOCUMENTS

| | | |
|---|---|---|
| WO | 92/15322 A1 | 9/1992 |
| WO | 93/11161 A1 | 6/1993 |
| WO | 96/40281 A2 | 12/1996 |
| WO | 98/17299 A1 | 4/1998 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/146862 A1 | 11/2011 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/065964 A1 | 5/2015 |
| WO | 2015/089419 A2 | 6/2015 |
| WO | 2015/089486 A2 | 6/2015 |
| WO | 2015/120096 A2 | 8/2015 |
| WO | 2015/142675 A2 | 9/2015 |
| WO | 2015/164743 A2 | 10/2015 |
| WO | 2015/187528 A1 | 12/2015 |
| WO | 2016/000304 A1 | 1/2016 |
| WO | 2016/011210 A2 | 1/2016 |
| WO | 2016/025650 A1 | 2/2016 |
| WO | 2016/040476 A1 | 3/2016 |
| WO | 2016/049024 A2 | 3/2016 |
| WO | 2016/049251 A1 | 3/2016 |
| WO | 2016/049258 A2 | 3/2016 |
| WO | 2016/057705 A1 | 4/2016 |
| WO | 2016054555 A2 | 4/2016 |
| WO | WO-2016057705 A1 * | 4/2016 ........ G01N 33/57426 |
| WO | 2016/070061 A1 | 5/2016 |
| WO | 2016/094867 A1 | 6/2016 |
| WO | 2016/094872 A1 | 6/2016 |

(56) References Cited

FOREIGN PATENT DOCUMENTS

| | | |
|---|---|---|
| WO | 2016/094874 A1 | 6/2016 |
| WO | 2016/094880 A1 | 6/2016 |
| WO | 2016/106244 A1 | 6/2016 |
| WO | 2016/108926 A1 | 7/2016 |
| WO | 2016/168584 A1 | 10/2016 |
| WO | 2016/191756 A1 | 12/2016 |
| WO | 2016/196388 A1 | 12/2016 |
| WO | 2017/004916 A1 | 1/2017 |
| WO | 2017/011804 A1 | 1/2017 |
| WO | 2017/070395 A1 | 4/2017 |
| WO | 2017/075294 A1 | 5/2017 |
| WO | 2019/046636 A1 | 3/2019 |

OTHER PUBLICATIONS

Buchbinder and Desai. CTLA-4 and PD-1 Pathways Similarities, Differences, and Implications of Their Inhibition. American Journal of Clinical Oncology; 2016; 39; 1: p. 98-106. (Year: 2016).*
Cristescu et al., Science; 2018; 362; 197: p. 1-10. (Year: 2018).*
Buchbinder and Desai. American Journal of Clinical Oncology; 2016; 39; 1: p. 98-106. (Year: 2016).*
Robert et al. Chemotherapy and CDK4/6 Inhibitors: Unexpected Bedfellows. Mol Cancer Ther; 2020; 19: 1575-1588. (Year: 2020).*
Mohr et al. Immune Signature of Malignant Pleural Mesothelioma as Assessed by Transcriptome Analysis; Cancer Genomics & Proteomics 2; 2005: 125-136. (Year: 2005).*
Scully, Role of Complement Component 1, Q Subcomponent Binding Protein (C1QBP) in Breast Carcinogenesis (Thesis), National University of Singapore 2015; p. 1-242. (Year: 2015).*
Sun et al. Synergistic activity of BET protein antagonist-based combinations in mantle cell lymphoma cells sensitive or resistant to ibrutinib. Blood; 2015; 126(13):1565-1574. (Year: 2015).*
Sherr et al., Targeting CDK4 and CDK6: From Discovery to Therapy. Cancer Discovery; 2016; 353-367, published online on Dec. 11, 2015. (Year: 2016).*
Sun et al. Synergistic activity of BET protein antagonist-based combinations in mantle cell lymphoma cells sensitive or resistant to ibrutinib. Blood; 2015; 126(13):1565-1574. (supplemental method) (Year: 2015).*
Leonard et al. Selective CDK4/6 inhibition with tumor responses by PD0332991 in patients with mantle cell lymphoma. Blood; 2012; 119: 4597-4607. (Year: 2012).*
Robert et al. Mol Cancer Ther; 2020;19:1575-1588. (Year: 2020).*
Mohr et al. Cancer Genomics & Proteomics 2; 2005: 125-136. (Year: 2005).*
Peguero et al. Journal of Clinical Oncology; 2016; vol. 34, Issue 15_suppl; Meeting Abstract 2016 ASCO Annual Meeting I: abstract# 2528. (Year: 2016).*
Ceresoli et al. Expert Review of Anticancer Therapy; 2016; vol. 16, No. 7: 673-675. (Year: 2016).*
Bronte et al. Critical Reviews in Oncology/Hematology; 2016; 107: 20-32. (Year: 2016).*
Patnaik et al. Cancer Discov; 2016;6(7); 740-753. (Year: 2016).*
Scully, National University of Singapore; Thesis; 2015; p. 1-242. (Year: 2015).*
Mesias, et al., "Use of CD200 Blockade Inhibitor to Enhance Glioma Immunotherapy", Journal of ImmunoTherapy of Cancer, 3(supp. 2), 2015, p. 38.
Sheng, "Different Strategies of Covalent Attachment of Oligonucleotide Probe onto Glass Beads and the Hybridization Properties", Applied Biochemistry and Biotechnology, 2008, 54-65.
Sweis, et al., "Molecular Drivers of the Non-T Cell-Inflamed Tumor Microenvironment in Urothelial Bladder Cancer", Cancer Immune Res., 4(7), 2016, pp. 563-568.
The Broad Institute, Inc., "Notification of Transmittal of the International Search Report and the Written Opinion of the International Searching Authority, or the Declarationcation for PCT/US2018/025507", dated Aug. 28, 2018, 13 pages.

The Broad Institute, Inc., "Notification of Transmittal of the International Search Report and the Written Opinion of the International Searching Authority, or the Declarationcation for PCT/US2018/054020", dated Jan. 24, 2019, 13 pages.
Xu, "Microengineering Methods for Cell-based Microarrays and High-Throughput Drug-Screening Applications", Biofabrication, 2011, 1-14.
Yamamoto, "In situ Modification of Cell-Culture Scaffolds by Photocatalytic Decomposition of Organosilane Monolayers", Biofabrication, 2014, 1-9.
Akbani, et al., "Genomic Classification of Cutaneous Melanoma", Cell, vol. 161, No. 7, Jun. 2015, 1681-1696.
Algazi, et al., "Clinical Outcomes in Metastatic Uveal Melanoma Treated with PD-1 and PD-L1 Antibodies", Cancer, vol. 122, No. 21, Nov. 15, 2016, 3344-3353.
Ayers, et al., "IFN- γ-Related mRNA Profile Predicts Clinical Response to PD-1 Blockade", Journal of Clinical Investigation, vol. 127, No. 8, Aug. 1, 2017, 2930-2940.
Azimi, et al., "Tumor-Infiltrating Lymphocyte Grade Is an Independent Predictor of Sentinel Lymph Node Status and Survival in Patients With Cutaneous Melanoma", Journal of Clinical Oncology, vol. 30, No. 21, Jul. 20, 2012, 2678-2683.
Barretina, et al., "The Cancer Cell Line Encyclopedia Enables Predictive Modelling of Anticancer Drug Sensitivity", Nature, vol. 483, No. 7391, Mar. 28, 2012, 603-607.
Bogunovic, et al., "Immune Profile and Mitotic Index of Metastatic Melanoma Lesions Enhance Clinical Staging in Predicting Patient Survival", Proceedings of the National Academy of Sciences, vol. 106, No. 48, Dec. 1, 2009, 20429-20434.
Challa-Malladi, et al., "Combined Genetic Inactivation of Beta2-Microglobulin and CD58 Reveals Frequent Escape from Immune Recognition in Diffuse Large B-cell Lymphoma", Cancer Cell, vol. 20, No. 6, Dec. 13, 2011, 728-740.
Dickson, et al., "Development of Cell-Cycle Inhibitors for Cancer Therapy", Current Oncology, vol. 16, No. 2, 2009, 36-43.
Fridman, et al., "The Immune Contexture in Human Tumours: Impact on Clinical Outcome", Nature Reviews Cancer, vol. 12, No. 4, Mar. 2012, 298-306.
Gao, et al., "Loss of IFN-γ Pathway Genes in Tumor Cells as a Mechanism of Resistance to Anti-CTLA-4 Therapy", Cell, vol. 167, Oct. 6, 2016, 397-404.
Gibney, et al., "Predictive Biomarkers for Checkpoint Inhibitor-Based Immunotherapy", The Lancet Oncology, vol. 17, No. 12, Dec. 2016, e542-e551.
Gilmore, et al., "Inhibitors of NF-Kb Signaling: 785 and Counting", Oncogene, vol. 25, 2006, 6887-6899.
Goel, et al., "CDK4/6 Inhibition Triggers Anti-Tumor Immunity", Nature, vol. 548, No. 7668, Aug. 24, 2017, 471-475.
Gong, et al., "Genomic Aberrations that Activate D-type Cyclins Are Associated with Enhanced Sensitivity to the CDK4 and CDK6 Inhibitor Abemaciclib", Cancer Cell, vol. 32, No. 6, Dec. 2017, 761-776.
Gordy, et al., "Fusion of the Dendritic Cell-Targeting Chemokine MIP3α to Melanoma Antigen Gp100 in a Therapeutic DNA Vaccine Significantly Enhances Immunogenicity and Survival in a Mouse Melanoma Model", Journal for Immuno Therapy of Cancer, vol. 4, No. 96, 2016, 11 pages.
Hamilton, et al., "Targeting CDK4/6 in Patients with Cancer", Cancer Treatment Reviews, vol. 45, Apr. 2016, 129-138.
Hangauer, "Drug-Tolerant Persister Cancer Cells are Vulnerable to GPX4 Inhibition", Nature, vol. 551, No. 7679, Nov. 9, 2017, 247-250.
Herbst, et al., "Predictive Correlates of Response to the Anti-PD-L1 Antibody MPDL3280A in Cancer Patients", Nature, vol. 515, No. 7528, Nov. 27, 2014, 563-567.
Hodi, et al., "Durable, Long-Term Survival in Previously Treated Patients With Advanced Melanoma (MEL) Who Received Nivolumab (NIVO) Monotherapy in a Phase I Trial", AACR 107th Annual Meeting, Apr. 17, 2016, 5 pages.
Hodi, et al., "Improved Survival with Ipilimumab in Patients with Metastatic Melanoma", The New England Journal of Medicine, vol. 363, No. 8, Aug. 19, 2010, 711-723.

(56) References Cited

OTHER PUBLICATIONS

Hugo, et al., "Genomic and Transcriptomic Features of Response to Anti-PD-1 Therapy in Metastatic Melanoma", Cell, vol. 165, No. 1, Mar. 24, 2016, 35-44.
King, et al., "Can we Unlock the Potential of IGF-1R Inhibition in Cancer Therapy?", Cancer Treatment Reviews, vol. 40, No. 9, Oct. 2014, 1096-1105.
Lamb, "The Connectivity Map: A New Tool for Biomedical Research", Nature Reviews Cancer, vol. 7, No. 1, Jan. 2007, 54-60.
Lamb, et al., "The Connectivity Map: Using Gene-Expression Signatures to Connect Small Molecules, Genes, and Disease", Science, vol. 313, Issue 5795, Sep. 29, 2006, 1929-1935.
Landsberg, et al., "Melanomas Resist T-Cell Therapy Through Inflammation-Induced Reversible Dedifferentiation", Nature, vol. 490, No. 7420, Oct. 2012, 412-416.
Larkin, et al., "Combined Nivolumab and Ipilimumab or Monotherapy in Previously Untreated Melanoma", The New England Journal of Medicine, vol. 373, No. 1, Jul. 2, 2015, 23-34.
Lesterhuis, et al., "Network Analysis of Immunotherapy-Induced Regressing Tumours Identifies Novel Synergistic Drug Combinations", Scientific Reports, vol. 5, Jul. 21, 2015, 11 pages.
Li, et al., "Reference Component Analysis of Single-Cell Transcriptomes Elucidates Cellular Heterogeneity in Human Colorectal Tumors", Nature Genetics, vol. 49, No. 5, May 2017, 708-718.
Manguso, et al., "In Vivo CRISPR Screening Identifies Ptpn2 as a Cancer Immunotherapy Target", Nature, vol. 547, No. 7664, Jul. 27, 2017, 413-418.
Mariathasan, et al., "TGFβ Attenuates Tumour Response to PD-L1 Blockade by Contributing to Exclusion of T Cells", Nature, vol. 544, 2018, 544-548.
Miao, et al., "Genomic Correlates of Response to Immune Checkpoint Therapies in Clear Cell Renal Cell Carcinoma", Science, vol. 359, No. 6337, Feb. 16, 2018, 801-806.
Mochly-Rosen, et al., "Protein Kinase C, an Elusive Therapeutic Target?", Nature Reviews Drug Discovery, vol. 11, No. 12, Dec. 2012, 937-957.
Muthuswamy, et al., "NF-kB Hyperactivation in Tumor Tissues Allows Tumor-Selective Reprogramming of the Chemokine Microenvironment to Enhance the Recruitment of Cytolytic T Effector Cells", Cancer Research, vol. 72, No. 15, Aug. 2012, 3735-3743.
Nelson, et al., "Membrane-Anchored Chemokine Fusion Proteins", OncoImmunology, vol. 1, No. 11, Nov. 2013, 3 pages.
Oki, et al., "Integrative Analysis of Transcription Factor Occupancy at Enhancers and Disease Risk Loci in Noncoding Genomic Regions", bioRxiv, Feb. 2018, 27 pages.
Pan, et al., "A Major Chromatin Regulator Determines Resistance of Tumor Cells To T Cell-Mediated Killing", Science, vol. 359, No. 6377, Feb. 16, 2018, 770-775.
Patel, et al., "Identification of Essential Genes for Cancer Immunotherapy", Nature, vol. 548, No. 7669, Aug. 31, 2017, 537-542.
Peng, et al., "Loss of PTEN Promotes Resistance to T Cell-Mediated Immunotherapy", Cancer Discovery, vol. 6, No. 2, Feb. 2016, 202-216.
Pikarsky, et al., "NF-Kb Functions as a Tumour Promoter in Inflammation-Associated Cancer", Nature, vol. 431, 2004, 461-466.
Postow, et al., "Nivolumab and Ipilimumab versus Ipilimumab in Untreated Melanoma", The New England Journal of Medicine, vol. 372, No. 21, May 21, 2015, 2006-2017.
Puram, et al., "Single-Cell Transcriptomic Analysis of Primary and Metastatic Tumor Ecosystems in Head and Neck Cancer", Cell, vol. 171, No. 7, Dec. 14, 2017, 1611-1624.
Riaz, et al., "Recurrent SERPINB3 and SERPINB4 Mutations in Patients that Respond to Anti-CTLA4 Immunotherapy", Nature Genetics, vol. 48, No. 11, Nov. 2016, 1327-1329.
Riaz, et al., "Tumor and Microenvironment Evolution during Immunotherapy with Nivolumab", Cell, vol. 171, Nov. 2, 2017, 934-949.
Ribas, et al., "Pembrolizumab Versus Investigator-Choice Chemotherapy for Ipilimumab-Refractory Melanoma (KEYNOTE-002): A Randomised, Controlled, Phase 2 Trial", The Lancet Oncology, vol. 16, Issue 8, Aug. 2015, 908-918.
Rooney, et al., "Molecular and Genetic Properties of Tumors Associated with Local Immune Cytolytic Activity", Cell, vol. 160, No. (1-2), Jan. 15, 2015, 48-61.
Shaffer, et al., "Rare Cell Variability and Drug-Induced Reprogramming as a Mode of Cancer Drug Resistance", Nature, vol. 546, No. 7658, Jun. 15, 2017, 431-435.
Sharma, et al., "Primary, Adaptive and Acquired Resistance to Cancer Immunotherapy", Cell, vol. 168, No. 4, Feb. 9, 2017, 707-723.
Sharma, et al., "The Future of Immune Checkpoint Therapy", Science, vol. 348, Issue 6230, 2015, 56-61.
Singer, et al., "A Distinct Gene Module for Dysfunction Uncoupled from Activation in Tumor-Infiltrating T Cells", Cell, vol. 166, No. 6, Sep. 8, 2016, 1500-1511.
Spranger, et al., "Melanoma-Intrinsic B-Catenin Signalling Prevents Anti-Tumour Immunity", Nature, vol. 523, Jul. 9, 2015, 231-235.
The Broad Institute, Inc., "extended European Search Report for EP 18776069.9", dated Mar. 9, 2021, 18 pages.
Zimmer, et al., "Phase II DeCOG-Study of Ipilimumab in Pretreated and Treatment-Naïve Patients with Metastatic Uveal Melanoma", PLoS One, vol. 10, No. 3, Mar. 11, 2015, 13 pages.
Taube, et al., "Colocalization of Inflammatory Response with B7-H1 Expression in Human Melanocytic Lesions Supports an Adaptive Resistance Mechanism of Immune Escape", Science Translational Medicine, vol. 04, Issue 127, Mar. 28, 2012, 22 pages.
Tirosh, et al., "Dissecting The Multicellular Ecosystem of Metastatic Melanoma By Single-Cell RNA-Seq", Science, vol. 352, No. 6282, Apr. 8, 2016, 189-196.
Tumeh, et al., "PD-1 Blockade Induces Responses by Inhibiting Adaptive Immune Resistance", Nature, vol. 515, No. 7528, Nov. 27, 2014, 568-571.
Van Allen, et al., "Genomic Correlates of Response to CTLA-4 Blockade in Metastatic Melanoma", Science , vol. 350, Issue 6257, Sep. 2015, 207-211.
Vasan, et al., "CDK4/6 Inhibitors in ER+ Metastatic Breast Cancer | Oncology CME", American Journal of Hematology/Oncology, vol. 13, No. 4, 2017, 16-22.
Viswanathan, et al., "Dependency of a Therapy-Resistant State of Cancer Cells on a Lipid Peroxidase Pathway", Nature, vol. 547, No. 7664, Jul. 27, 2017, 453-457.
Zaretsky, et al., "Mutations Associated with Acquired Resistance to PD-1 Blockade in Melanoma", The New England Journal of Medicine, vol. 375, No. 9, 2016, 819-829.
Zheng, et al., "Landscape of Infiltrating T Cells in Liver Cancer Revealed by Single-Cell Sequencing", Cell, vol. 169, Issue 7, Jun. 15, 2017, 1342-1356.
Zhou, et al., "In Vivo Discovery of Immunotherapy Targets in the Tumor Microenvironment", Nature, vol. 506, No. 7486, Feb. 6, 2014, 52-57.
The Broad Institute, Inc., "Communication Pursuant to Rule 164(1) EPC for EP 18776069.9", dated Dec. 3, 2020, 23 pages.
The Broad Institute, Inc., "Communication pursuant to Rule 164(1) EPC for EP 18864615.2", dated Aug. 10, 2021, 19 pages.
Schaer, et al., "The CDK4/6 Inhibitor Abemaciclib Induces a T cell Inflamed Tumor Microenvironment and Enhances the Efficacy of PD-L1 Checkpoint Blockade", Cell Reports, 22, Mar. 13, 2018, pp. 2978-2994.

* cited by examiner

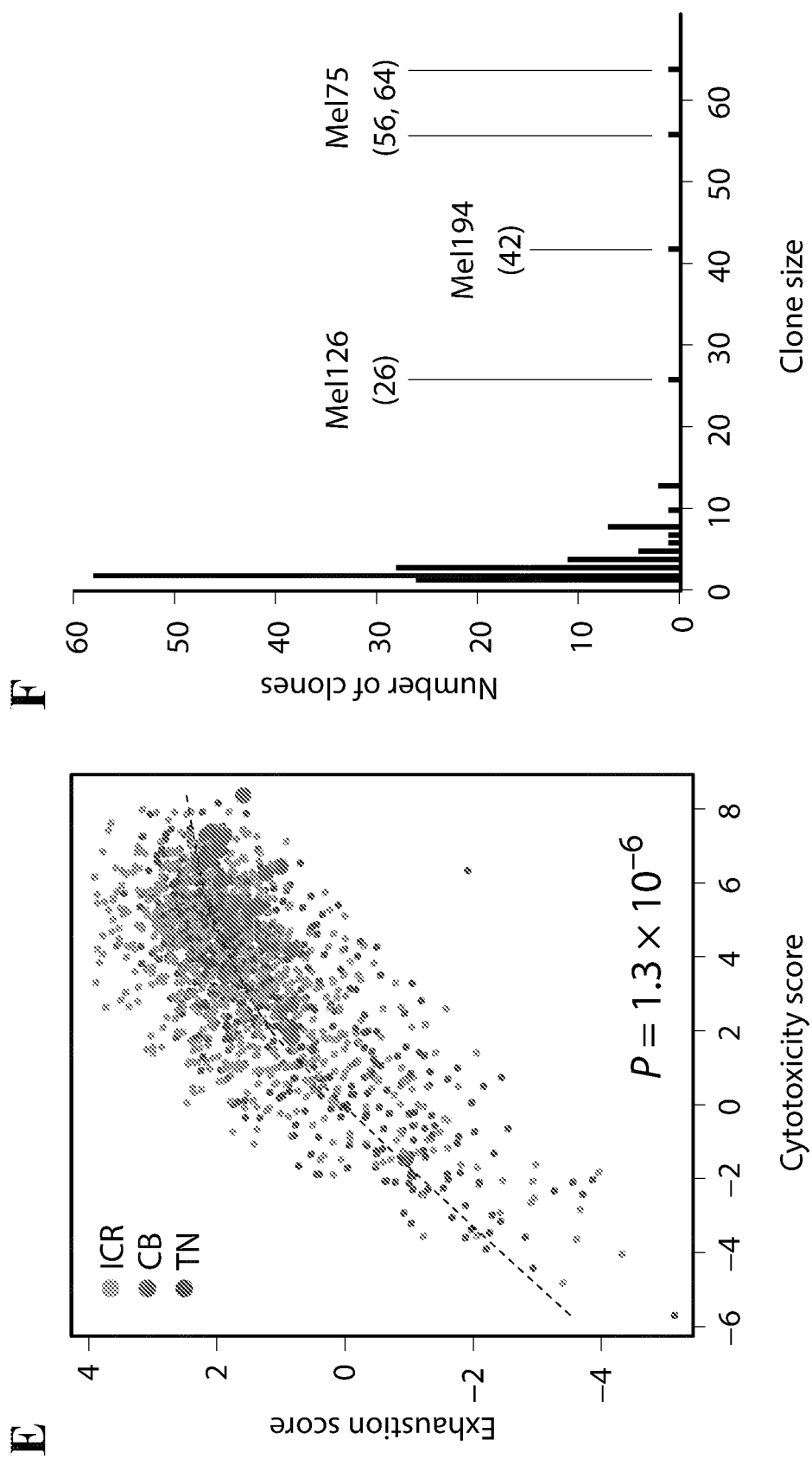
FIG. 1E-F

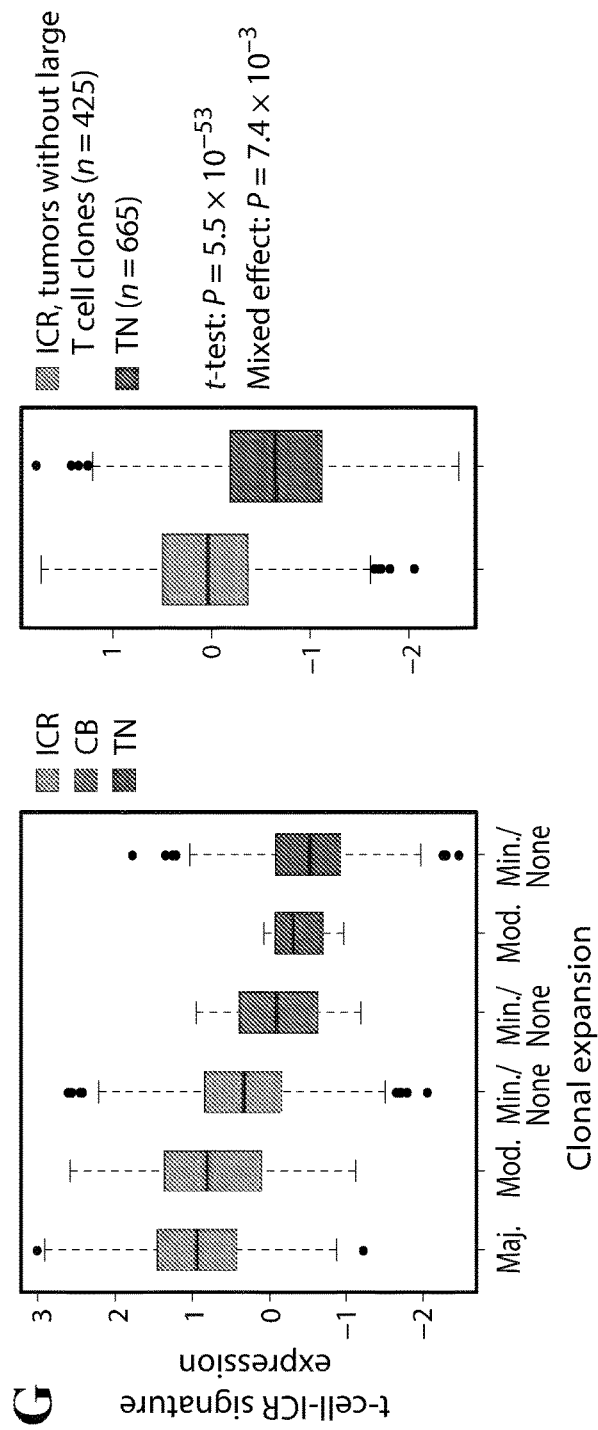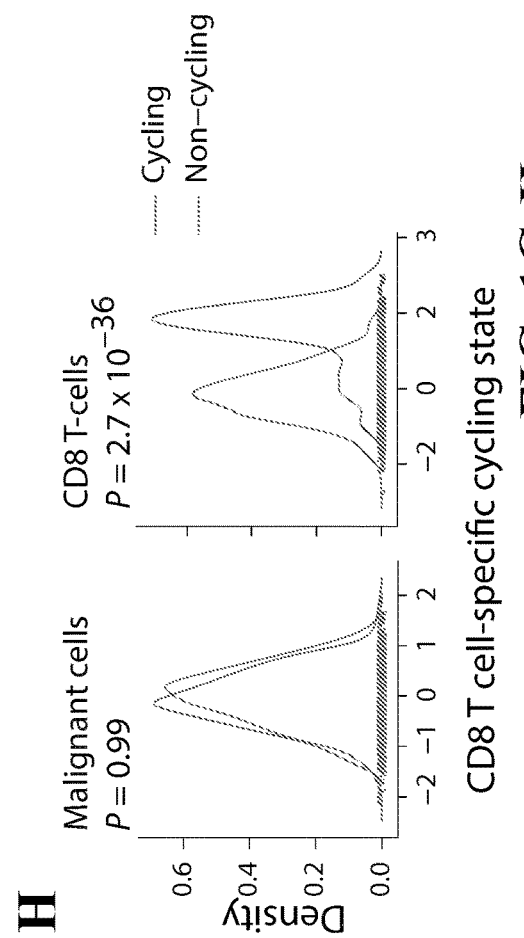
FIG. 1G-H

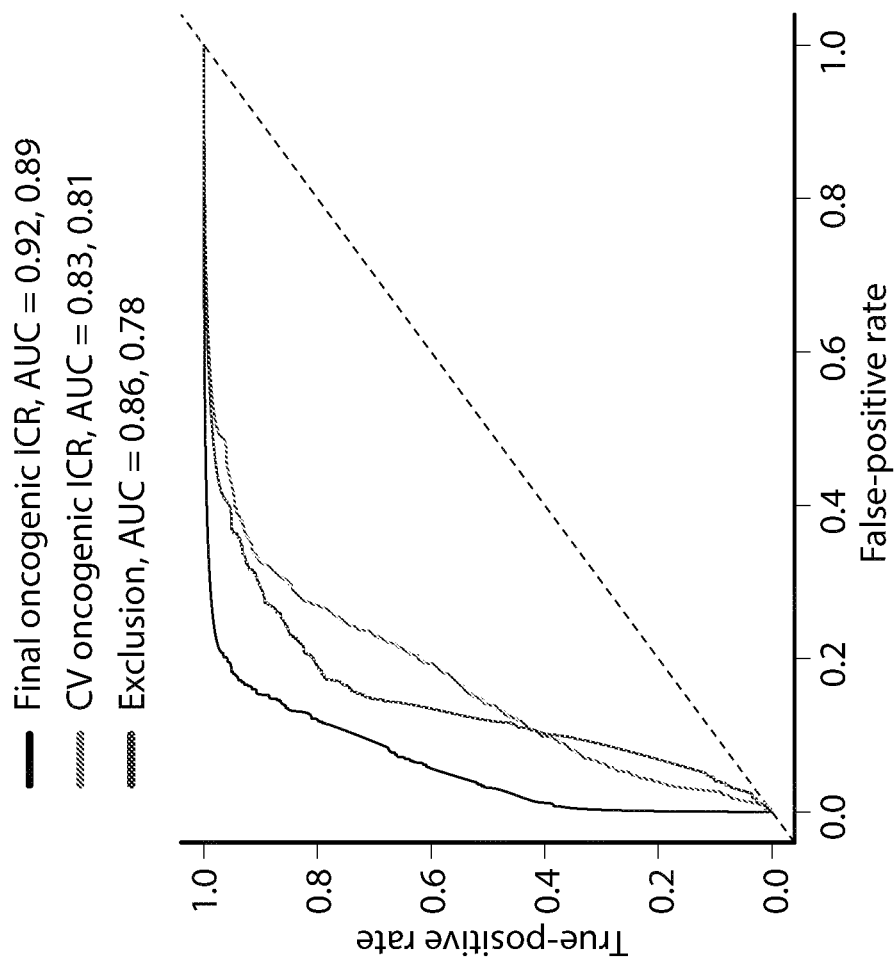
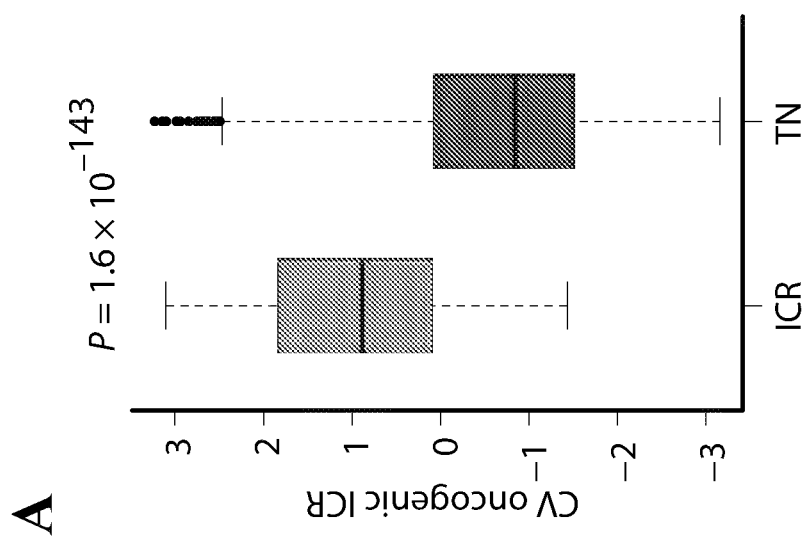
FIG. 2A

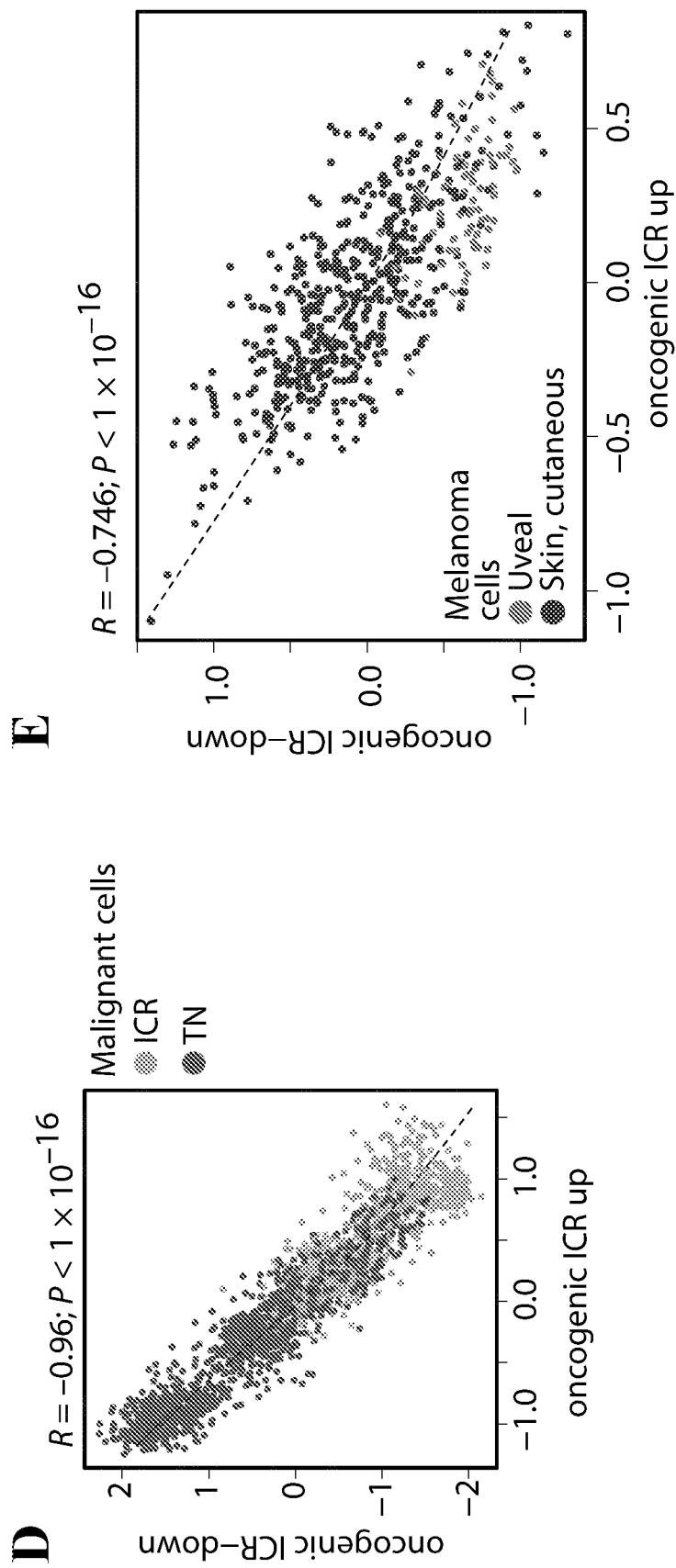
FIG. 2D-E

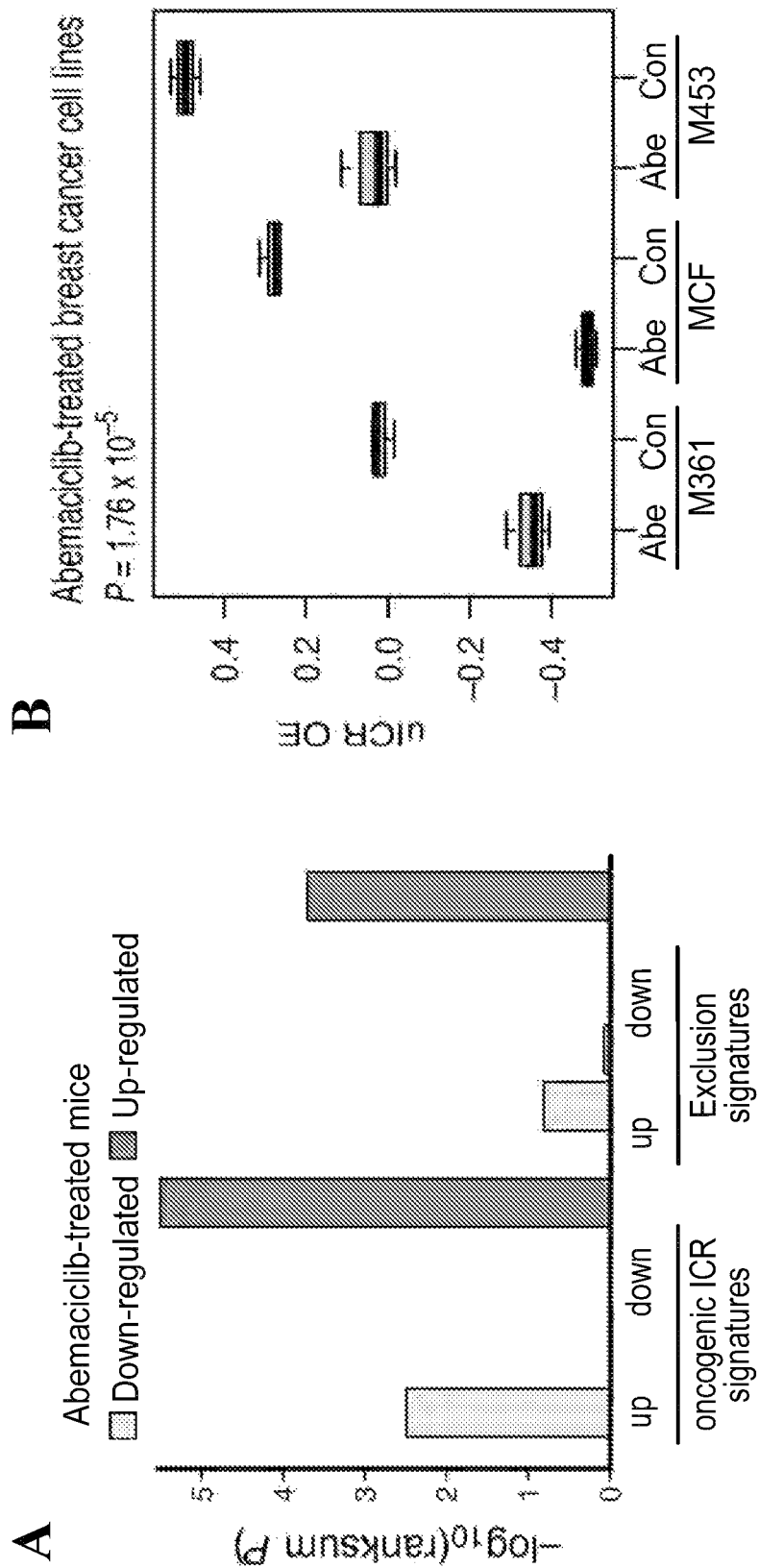
FIG. 3A-B

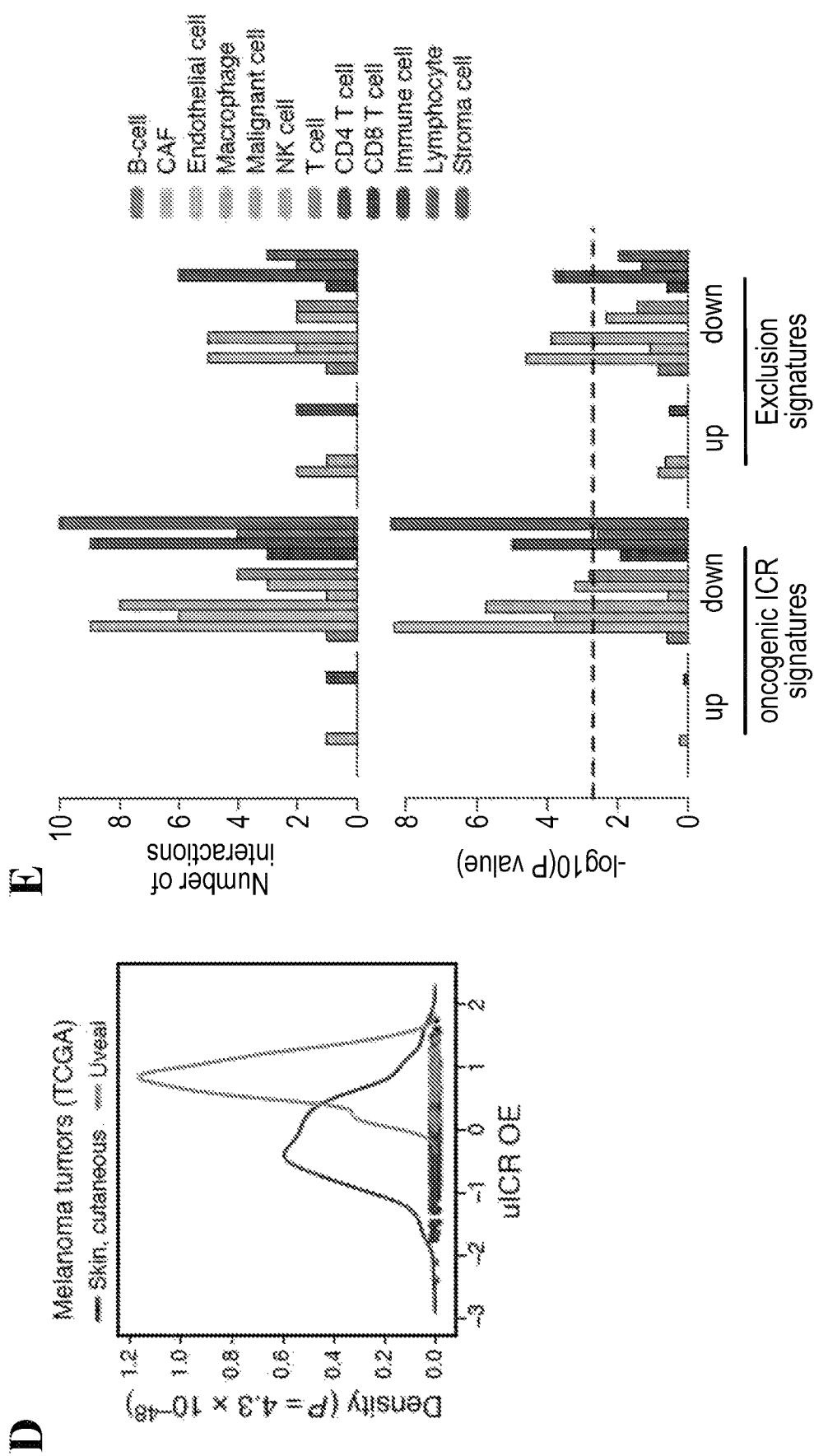
FIG. 3D-E

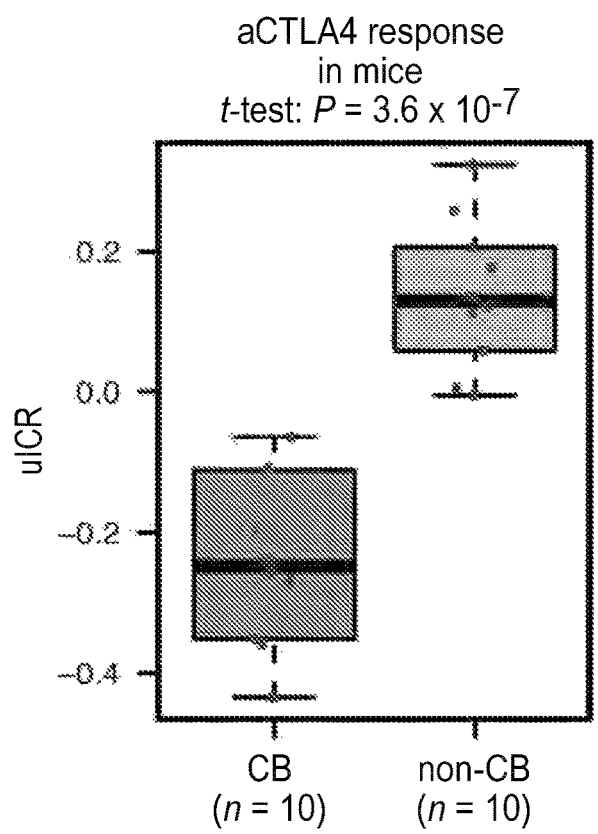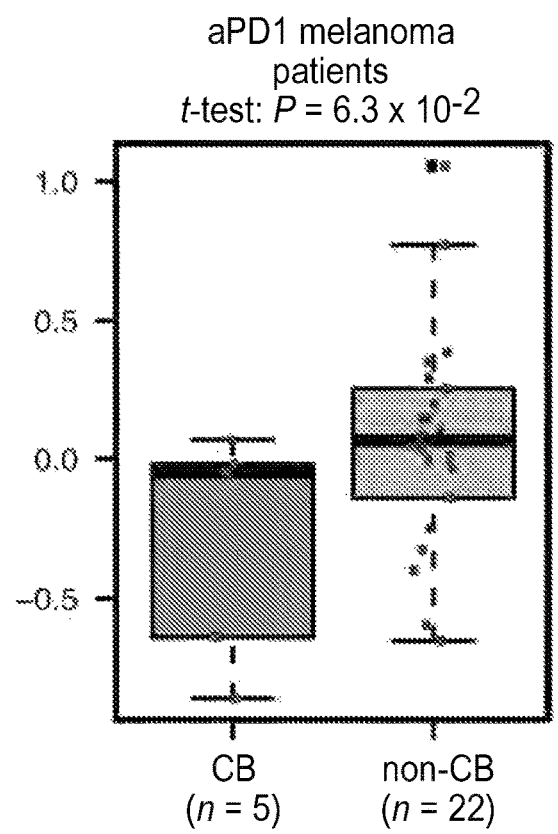
FIG. 4B-C

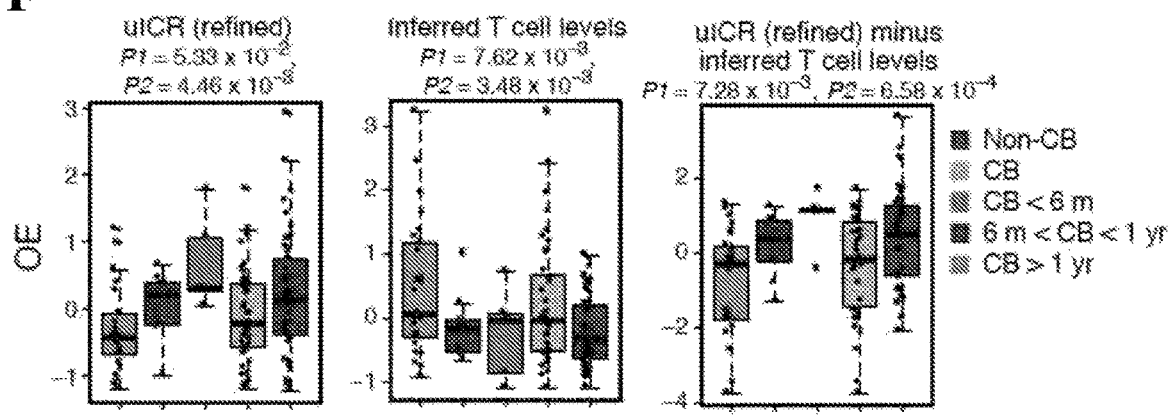
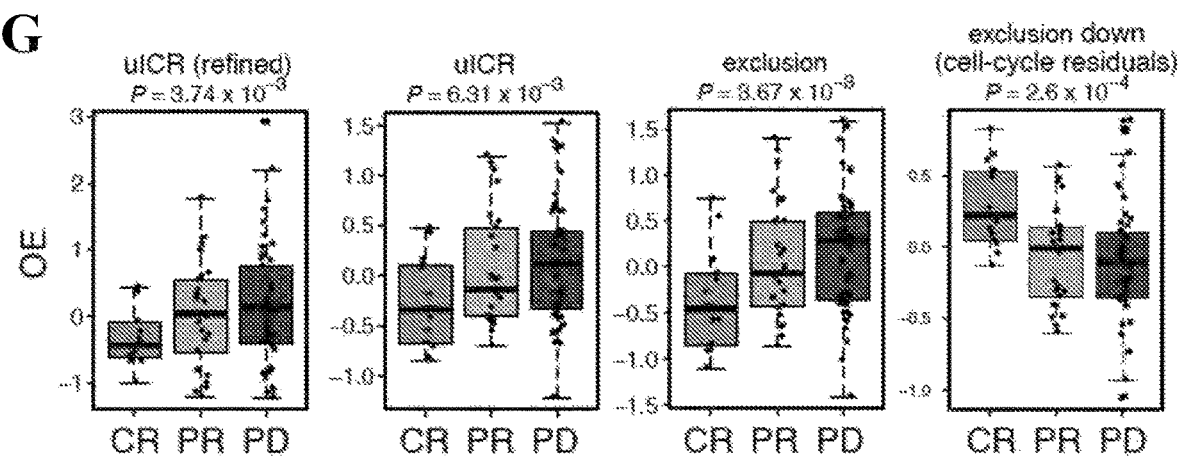
FIG. 4F-G

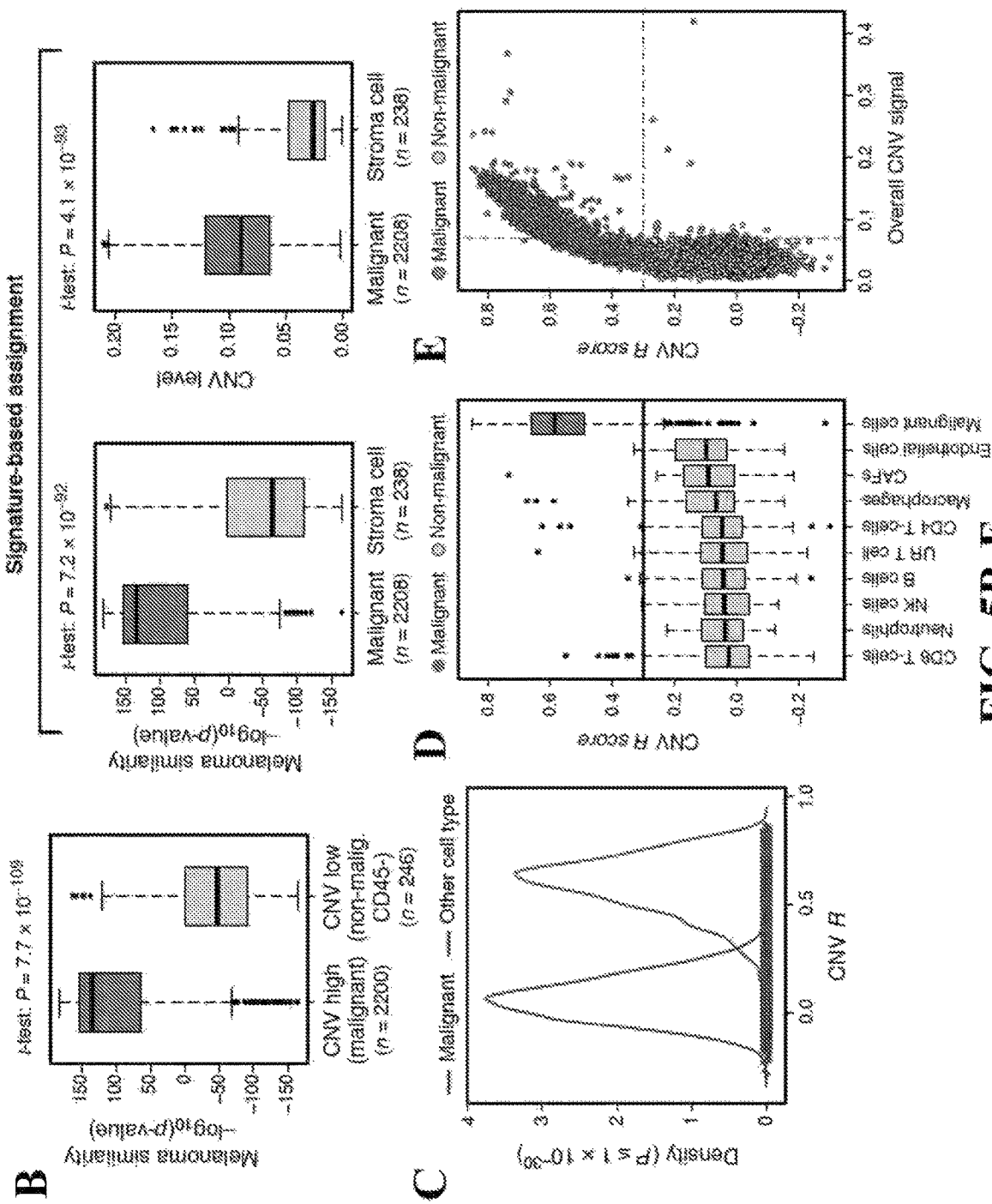
FIG. 5B-E

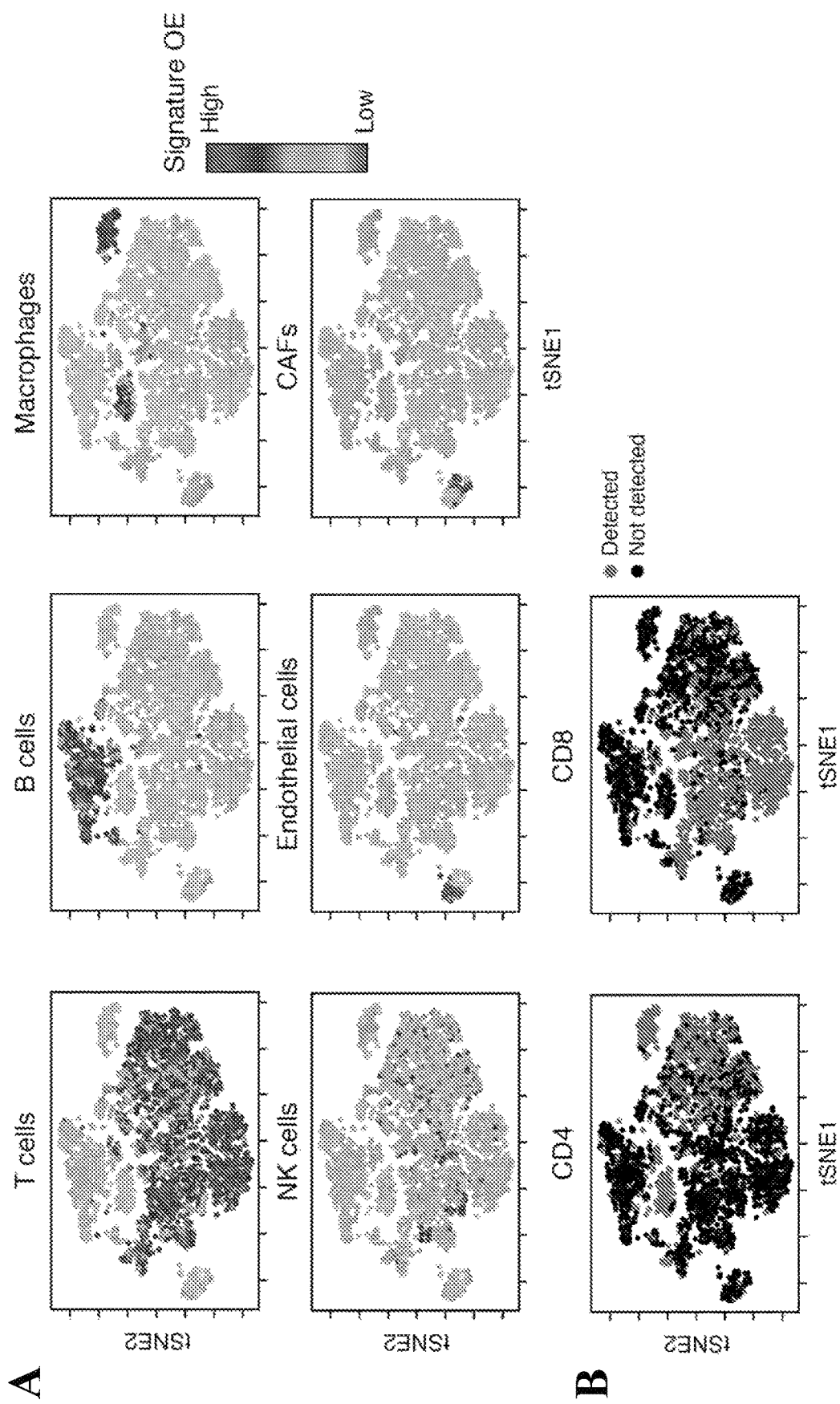
FIG. 6A-B

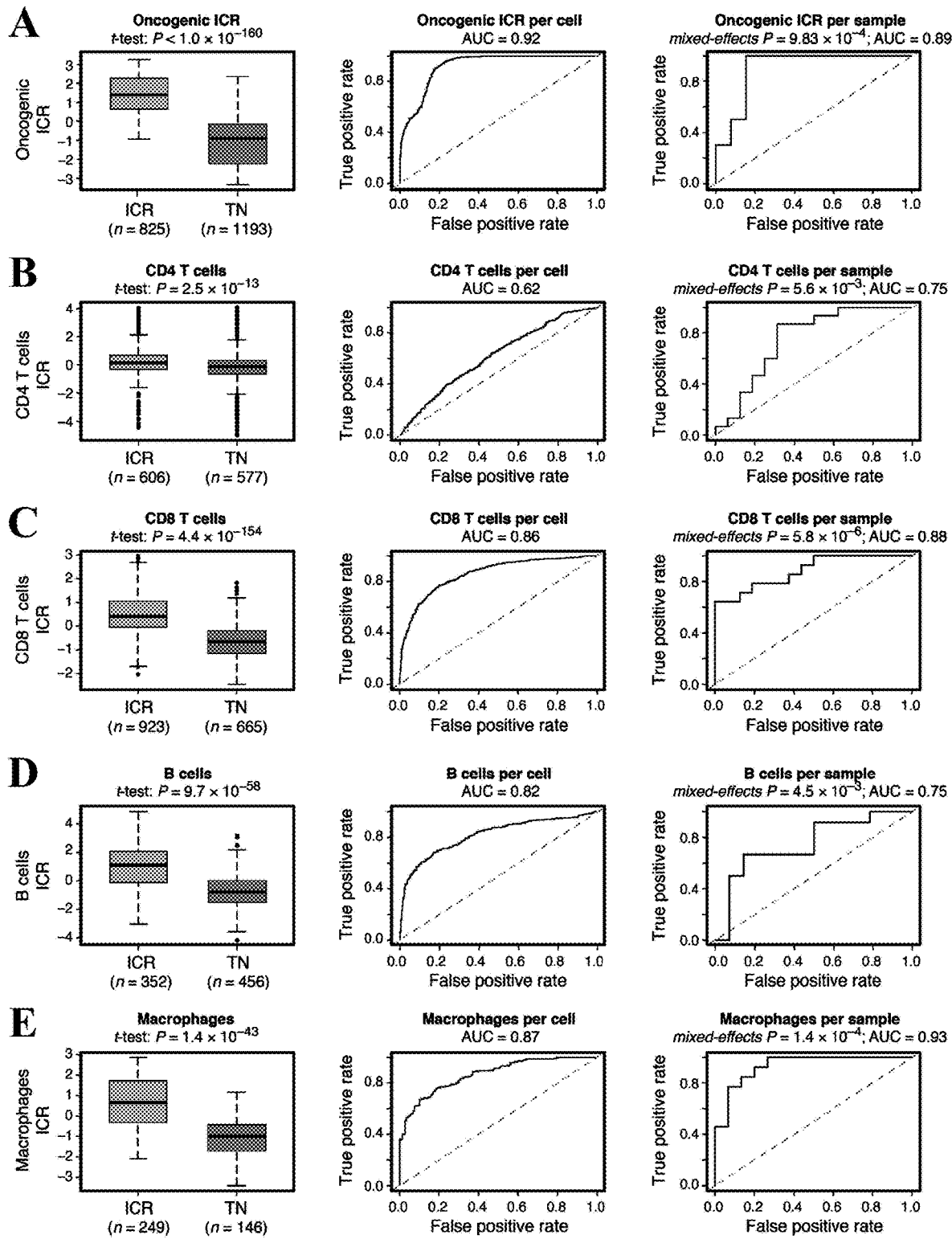
FIG. 7A-E

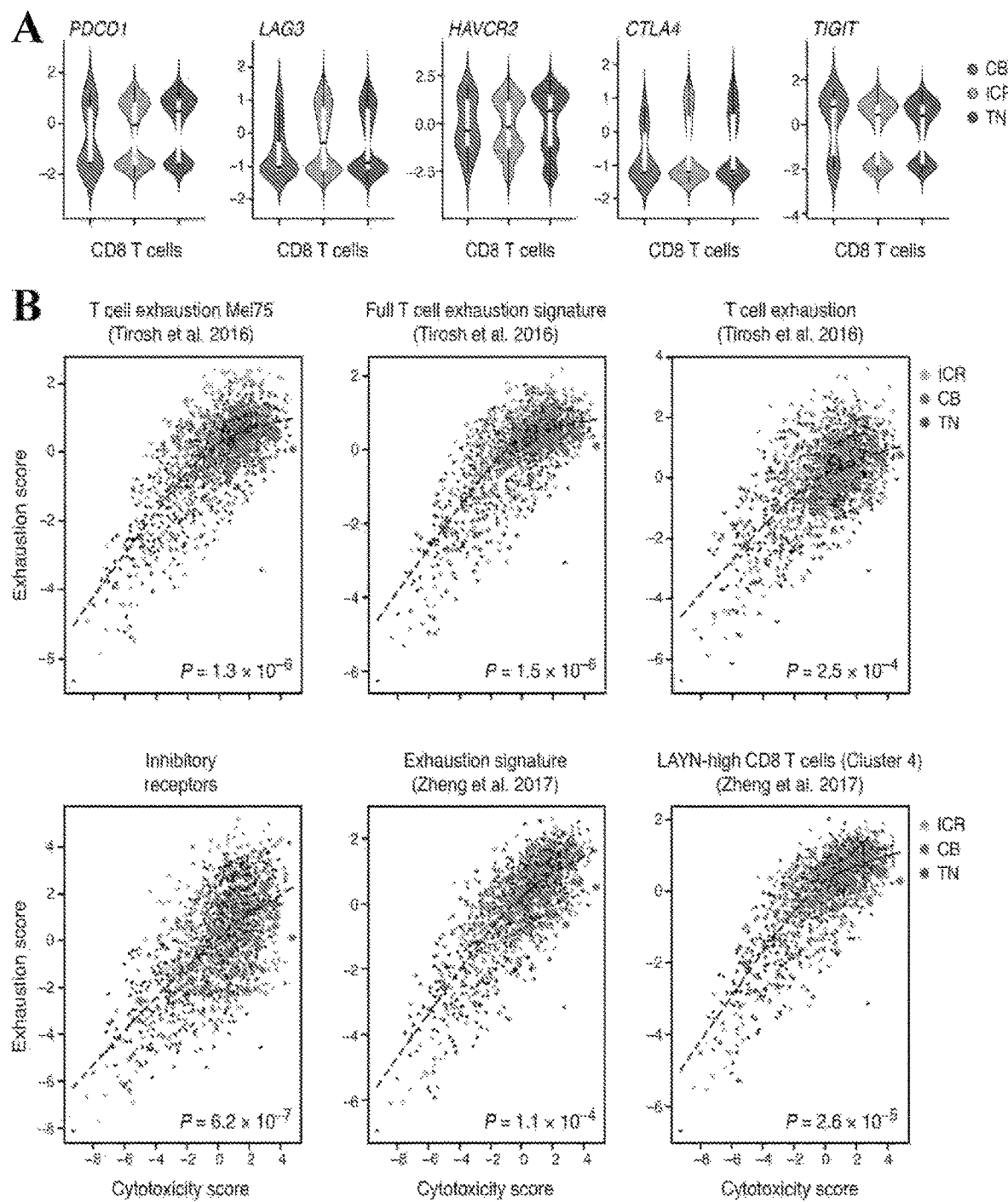
FIG. 8A-B

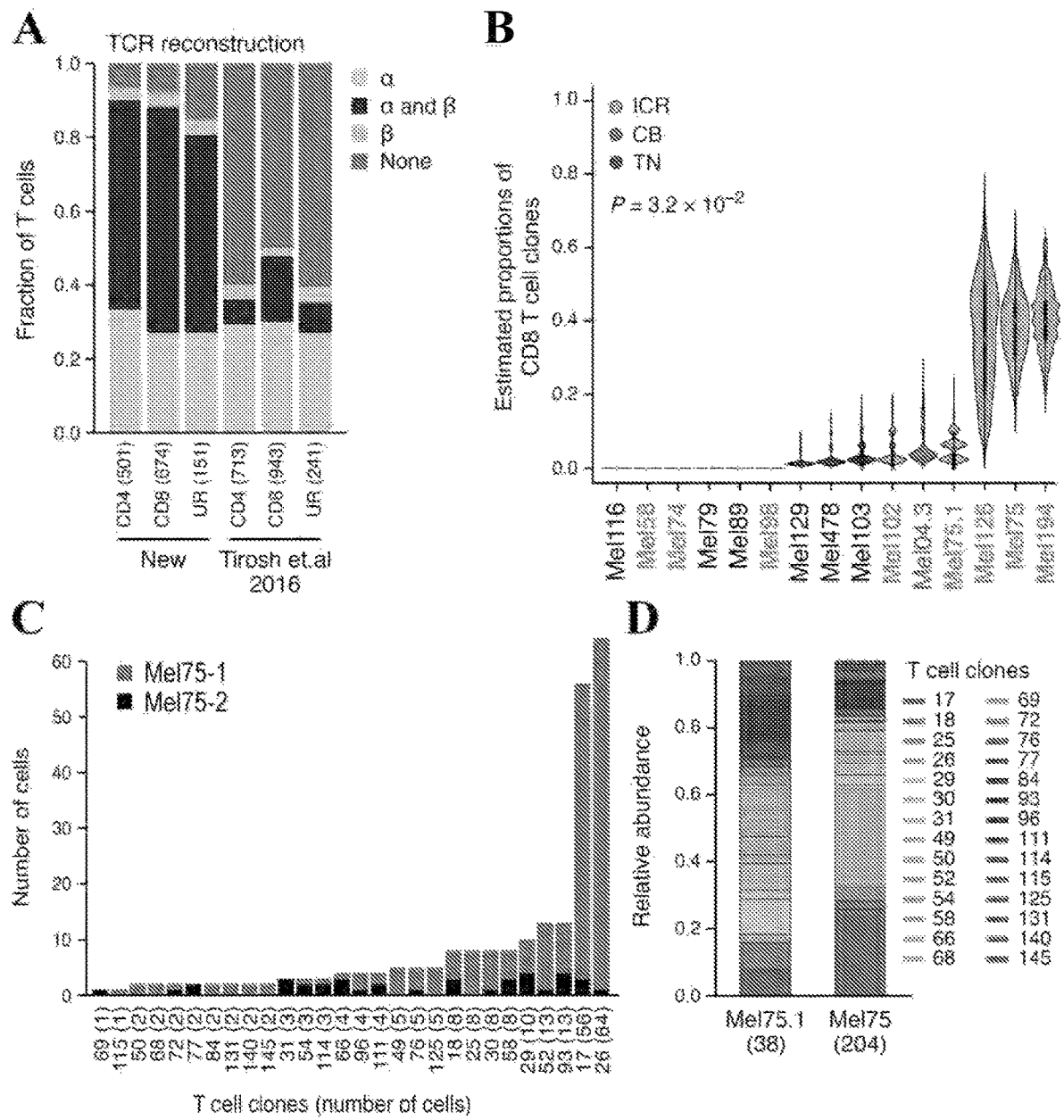
FIG. 9A-D

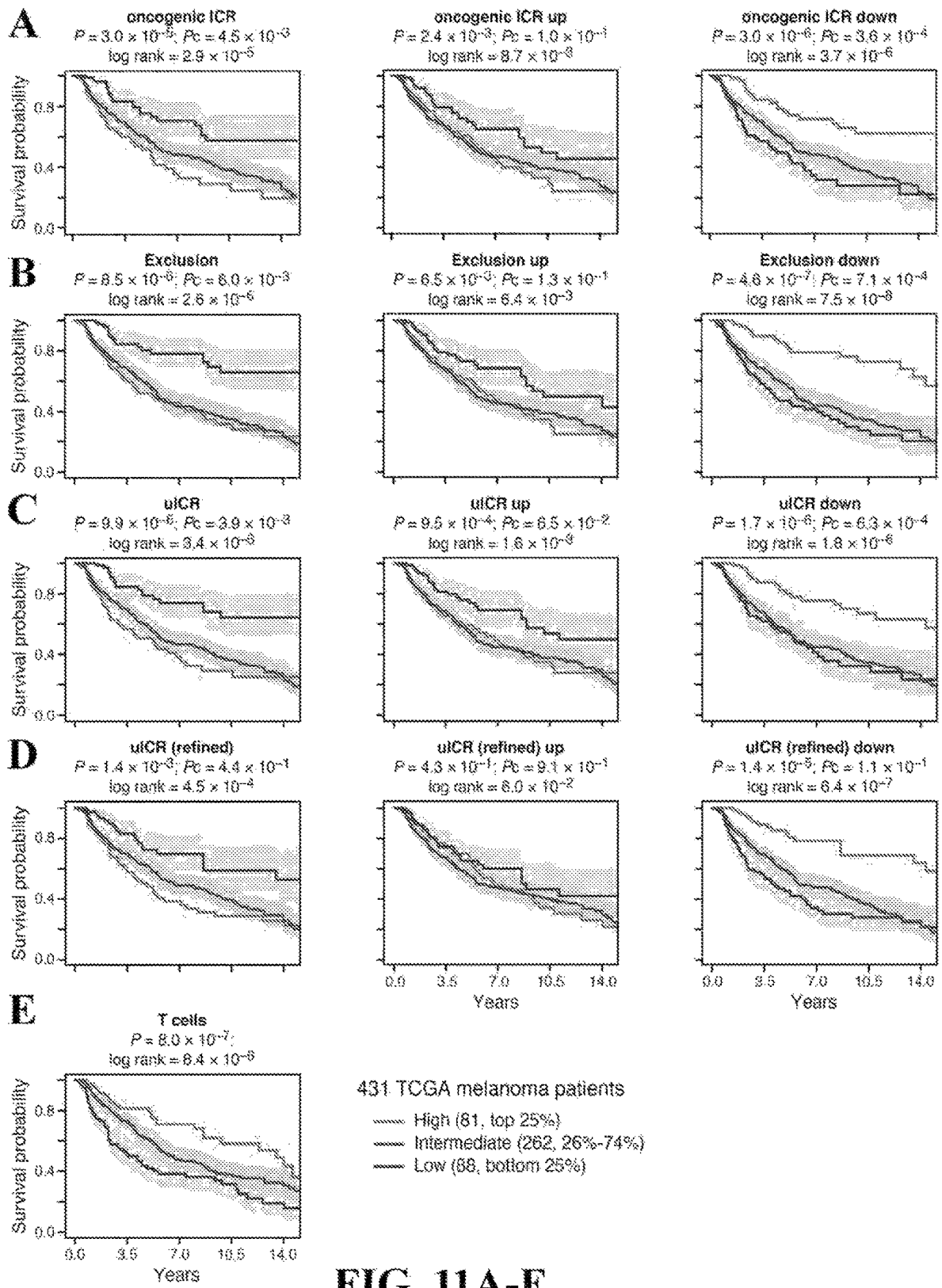
FIG. 11A-E

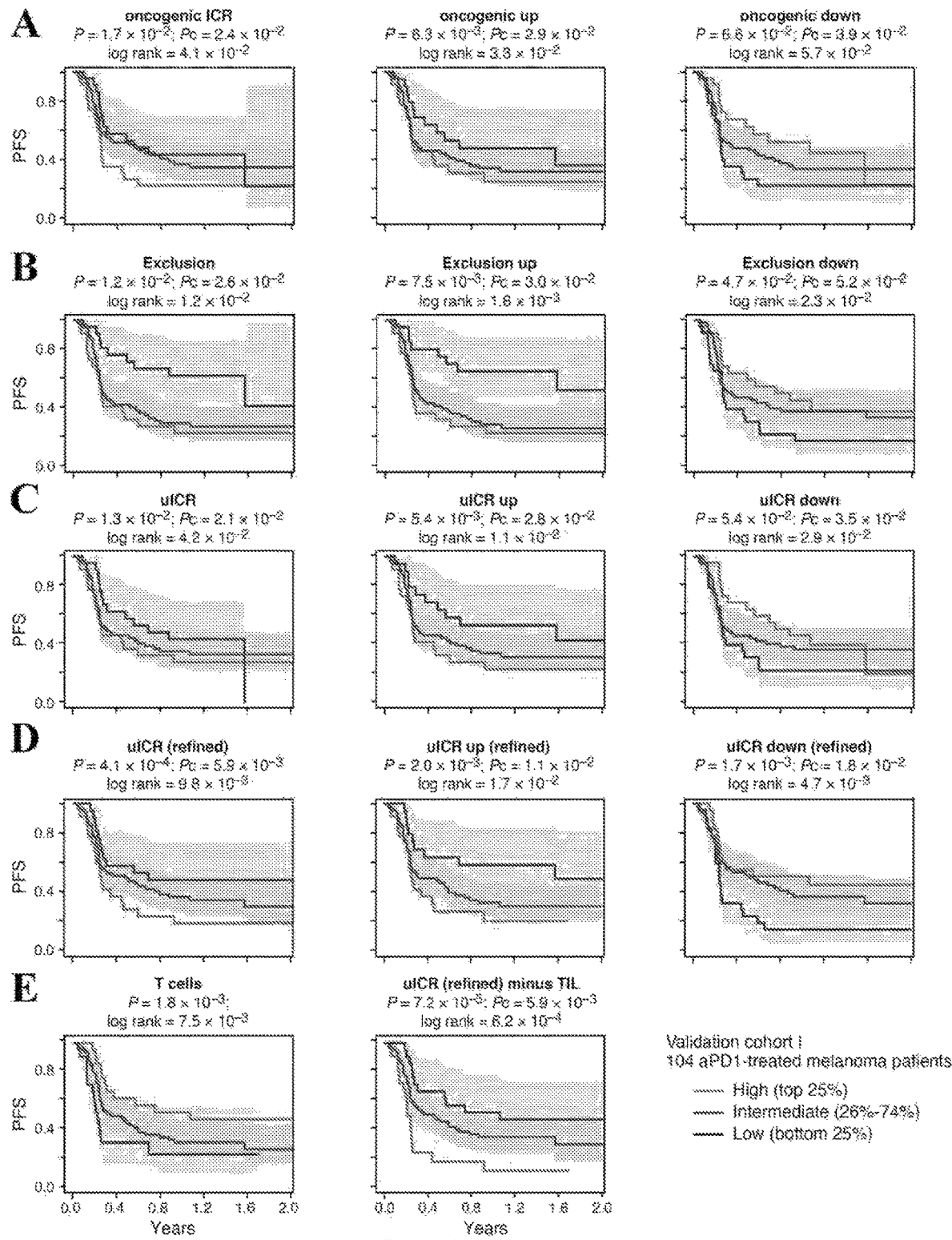
FIG. 12A-E

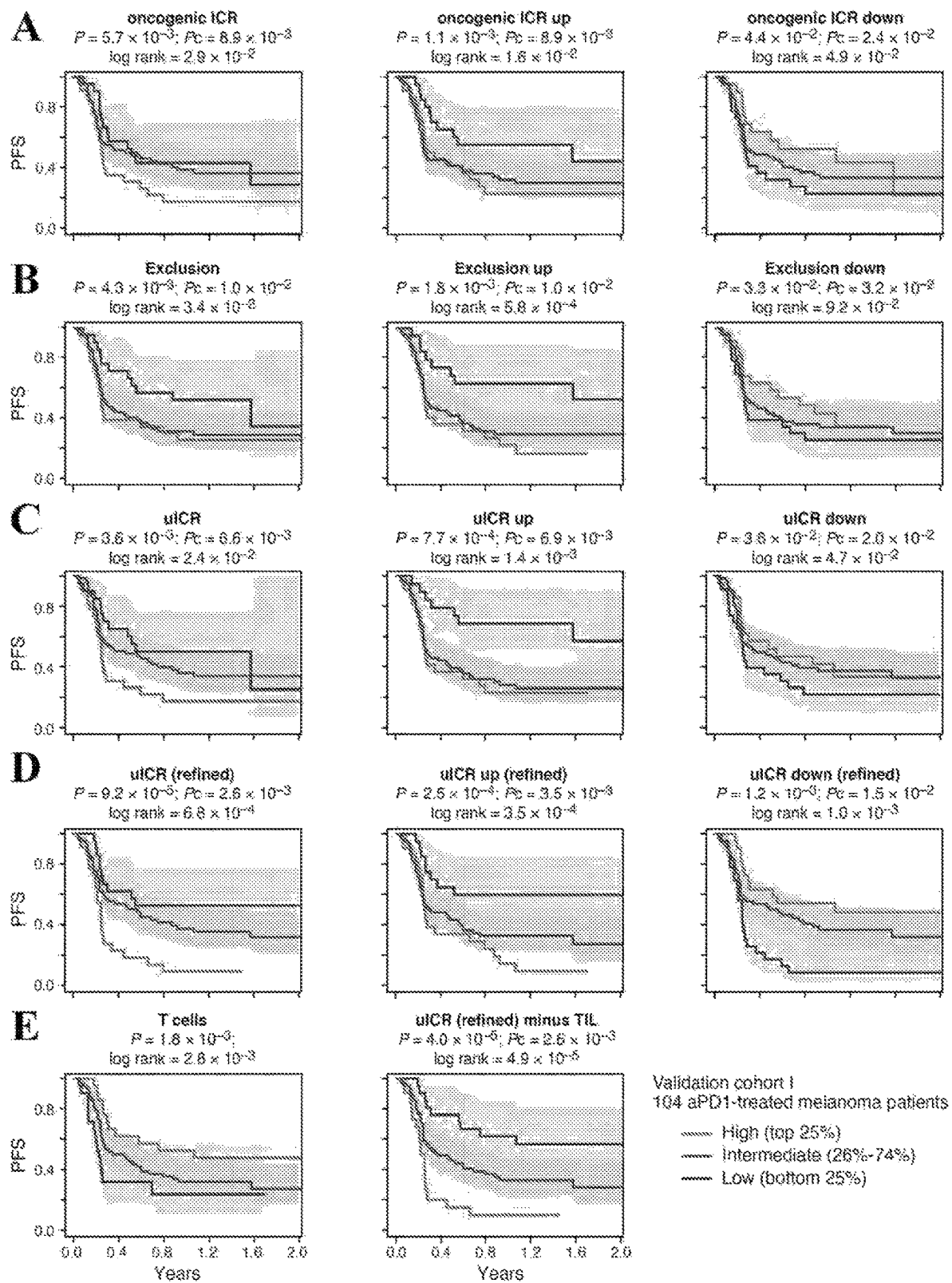
FIG. 13A-E

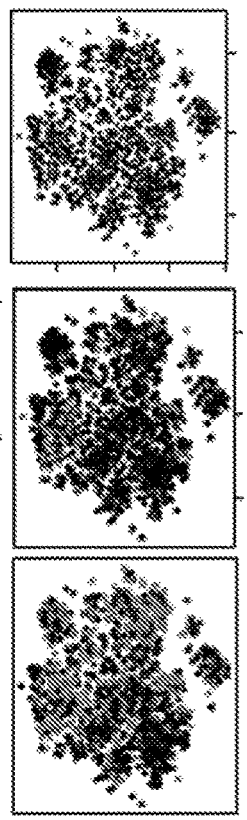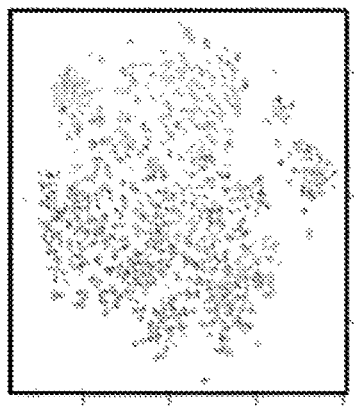
FIG. 32

- CDK4/6 inhibitors sensitize melanoma cells
- Short term melanoma culture (P = 4.4e-23) ✔
- Melanoma cell lines
  1. IGR37 (P = 1.7e-36) ✔
  2. UACC257 (P = 4.9e-240) ✔
  3. A2058 (RB1-deficient) (P = 1) ✗

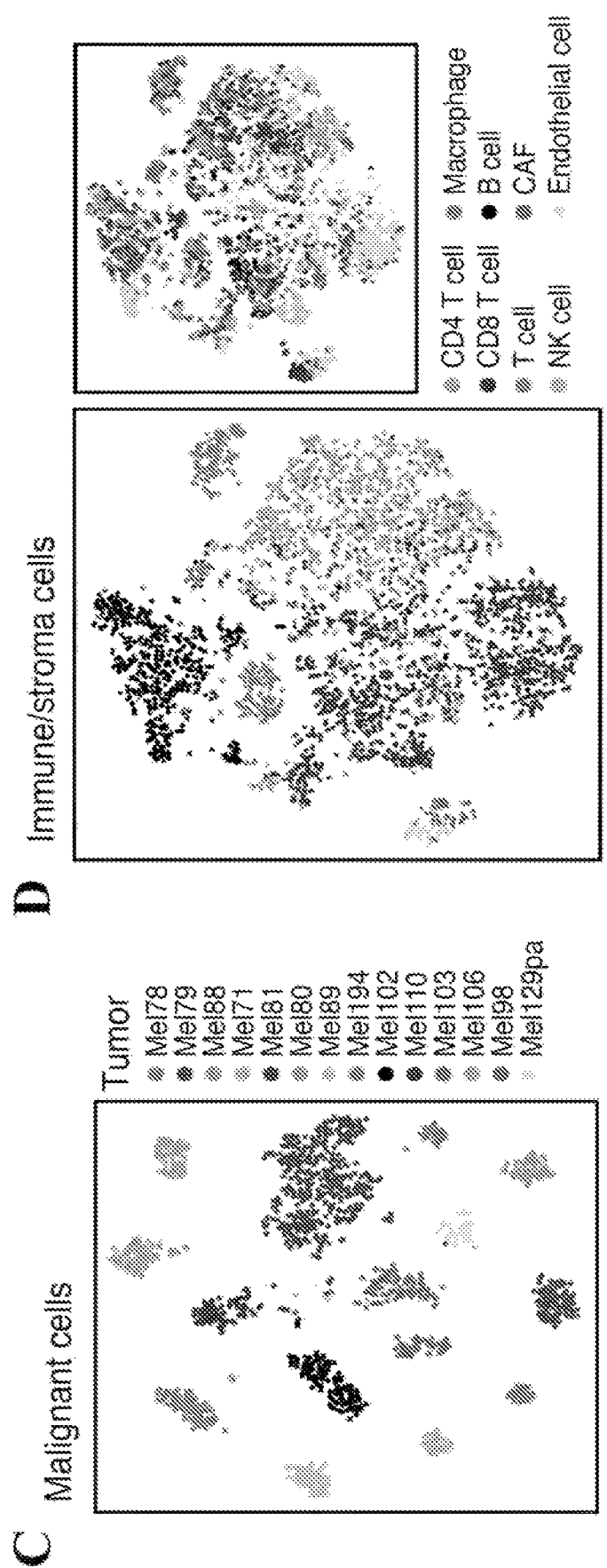
FIG. 44C-D

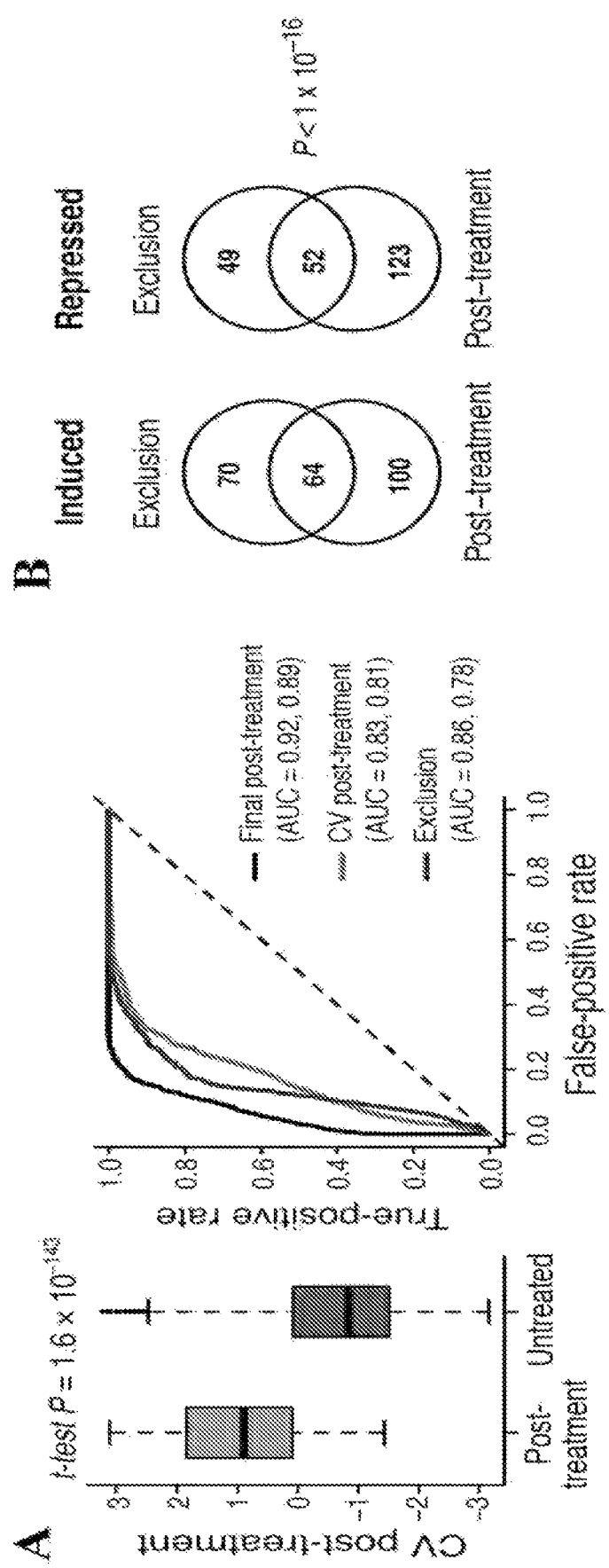
FIG. 45A-B

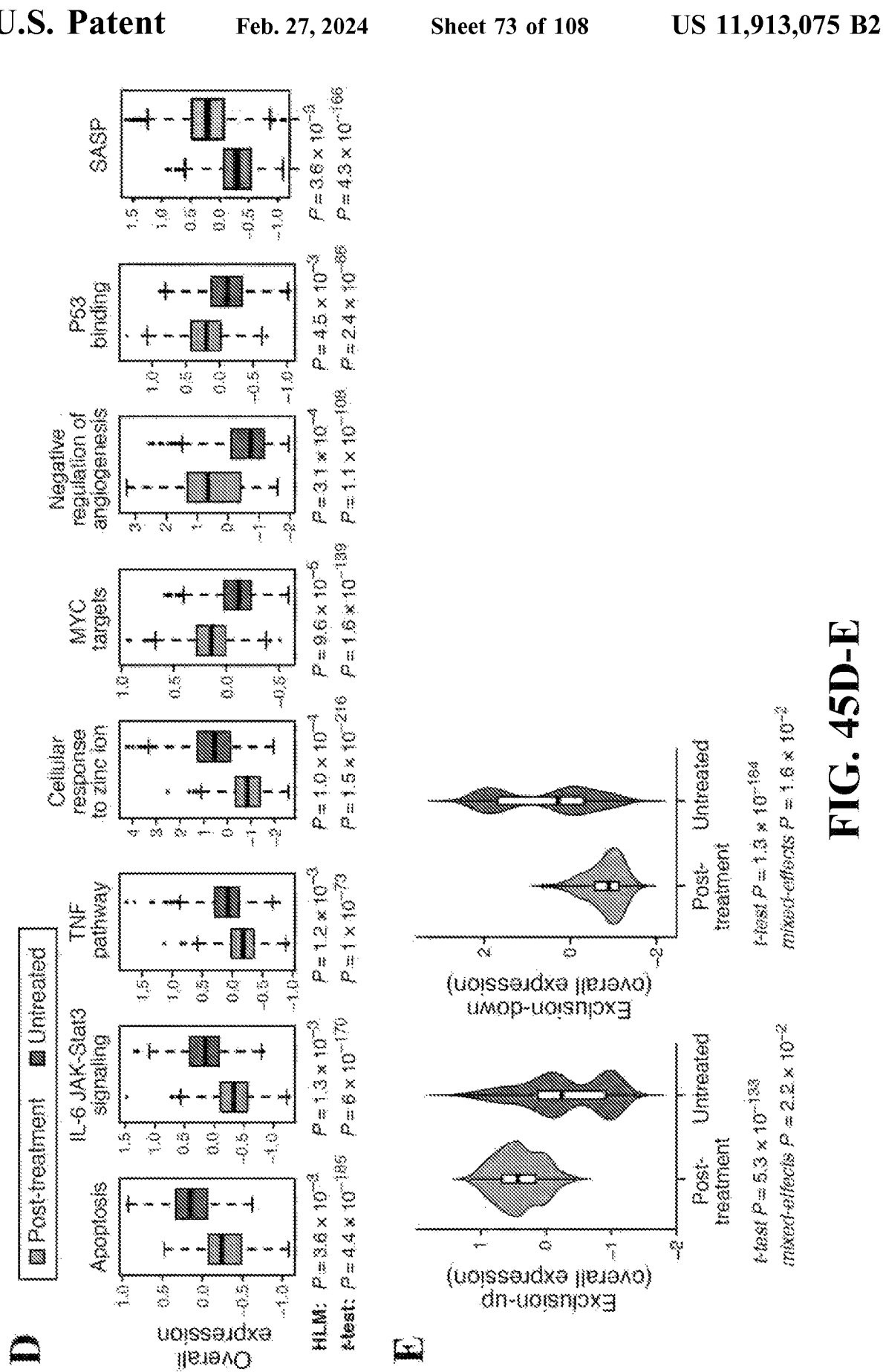
FIG. 45D-E

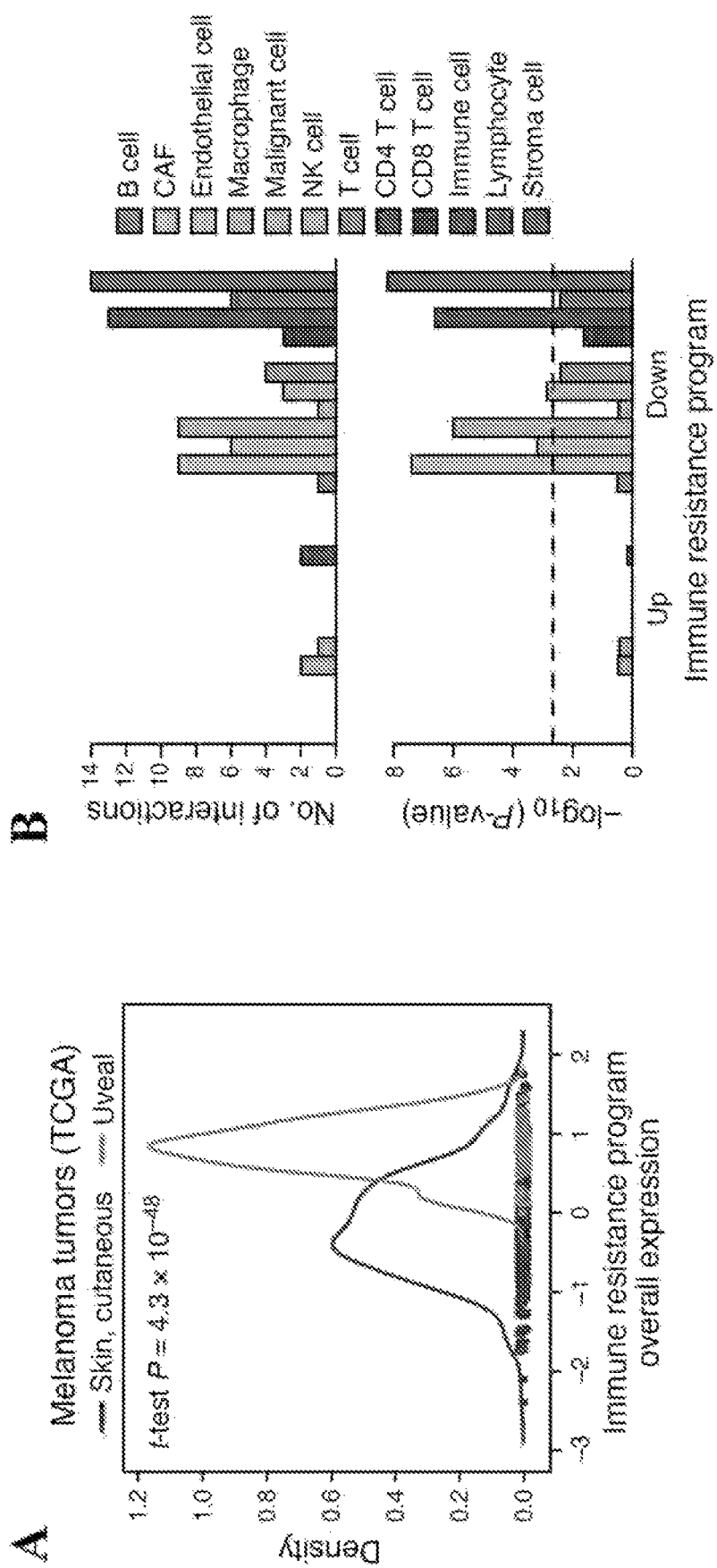
FIG. 46A-B

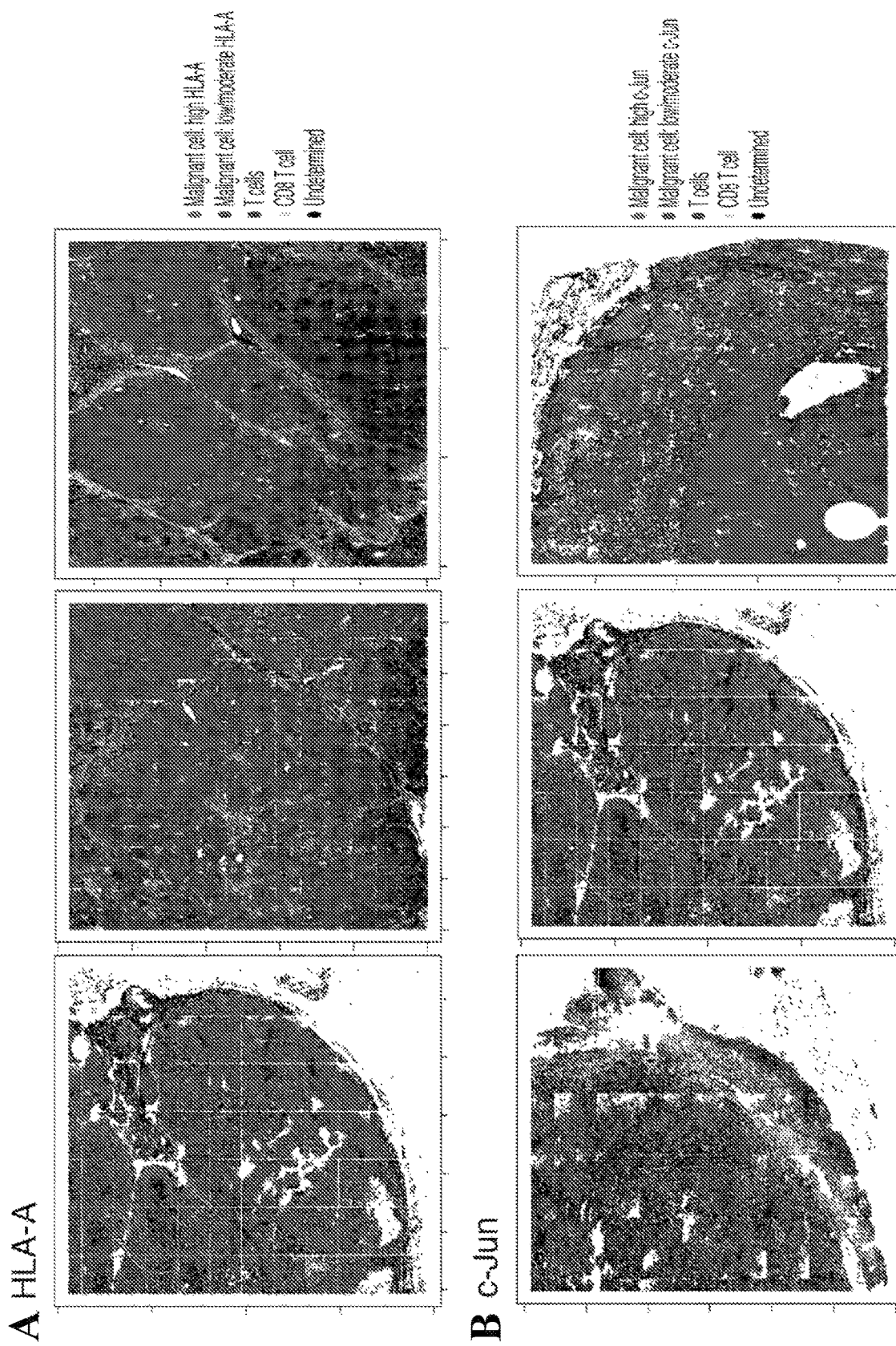
FIG. 47A-B

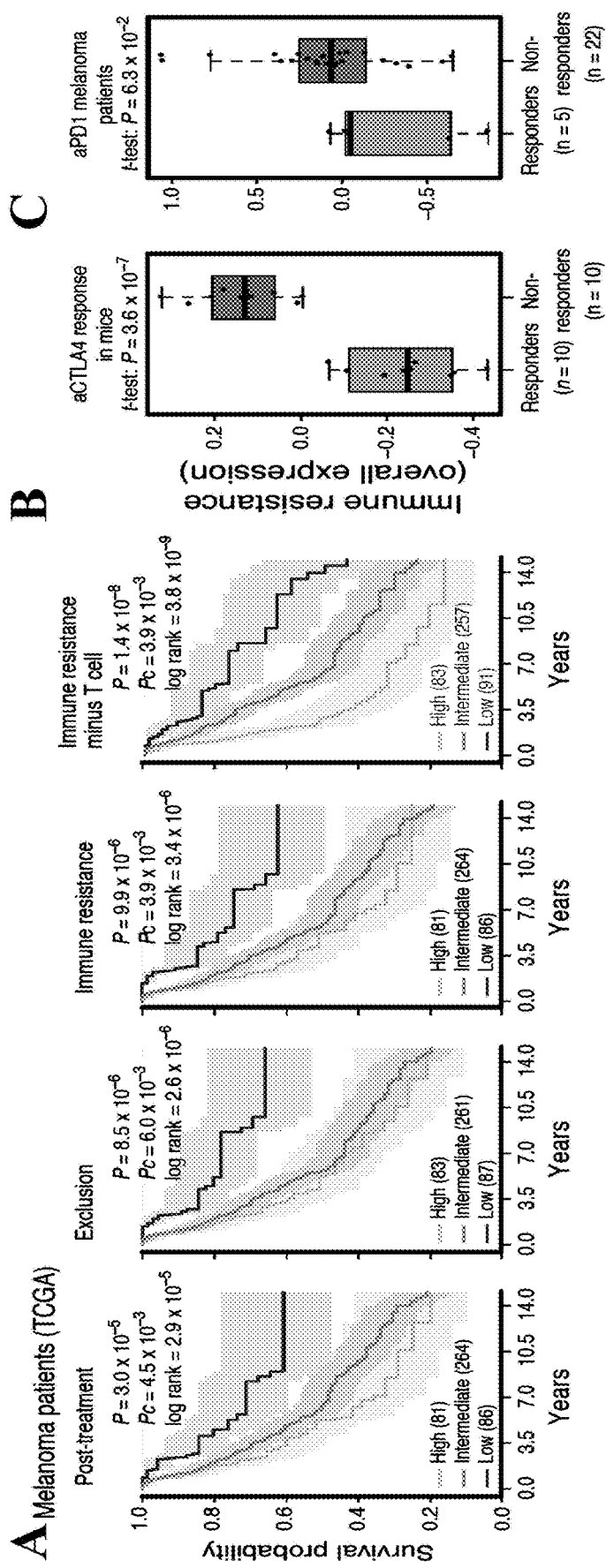
FIG. 48A-C

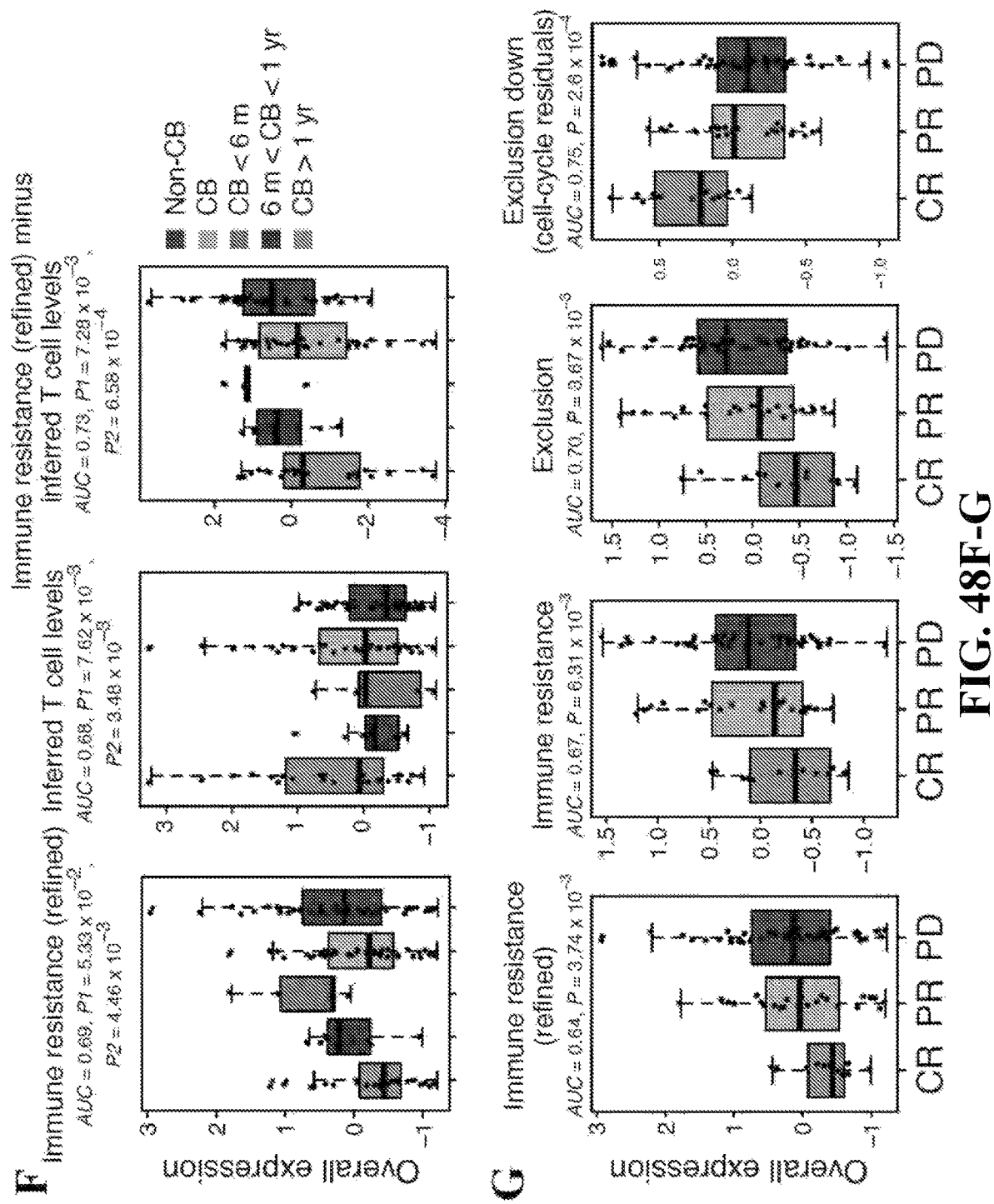
FIG. 48F-G

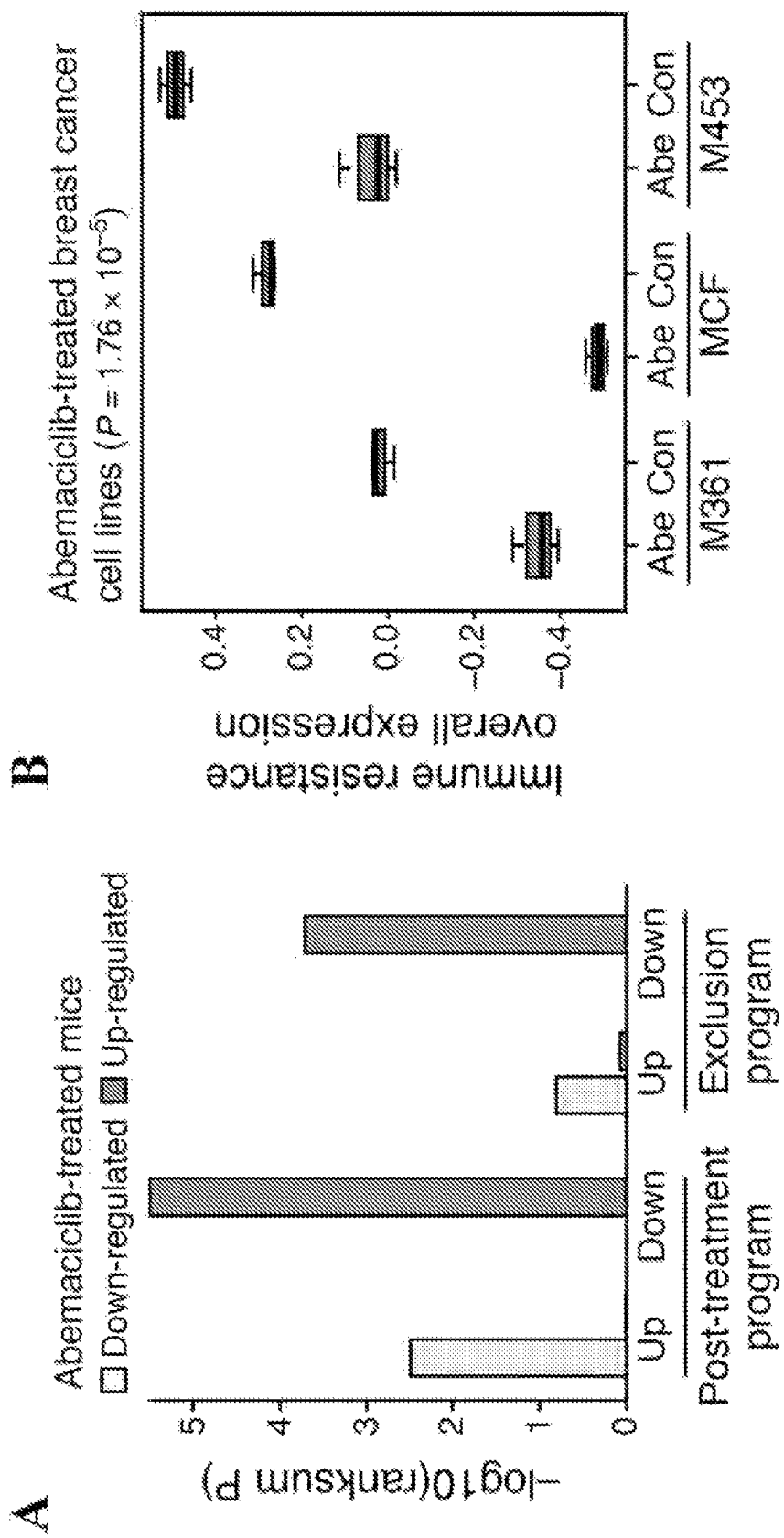
FIG. 49A-B

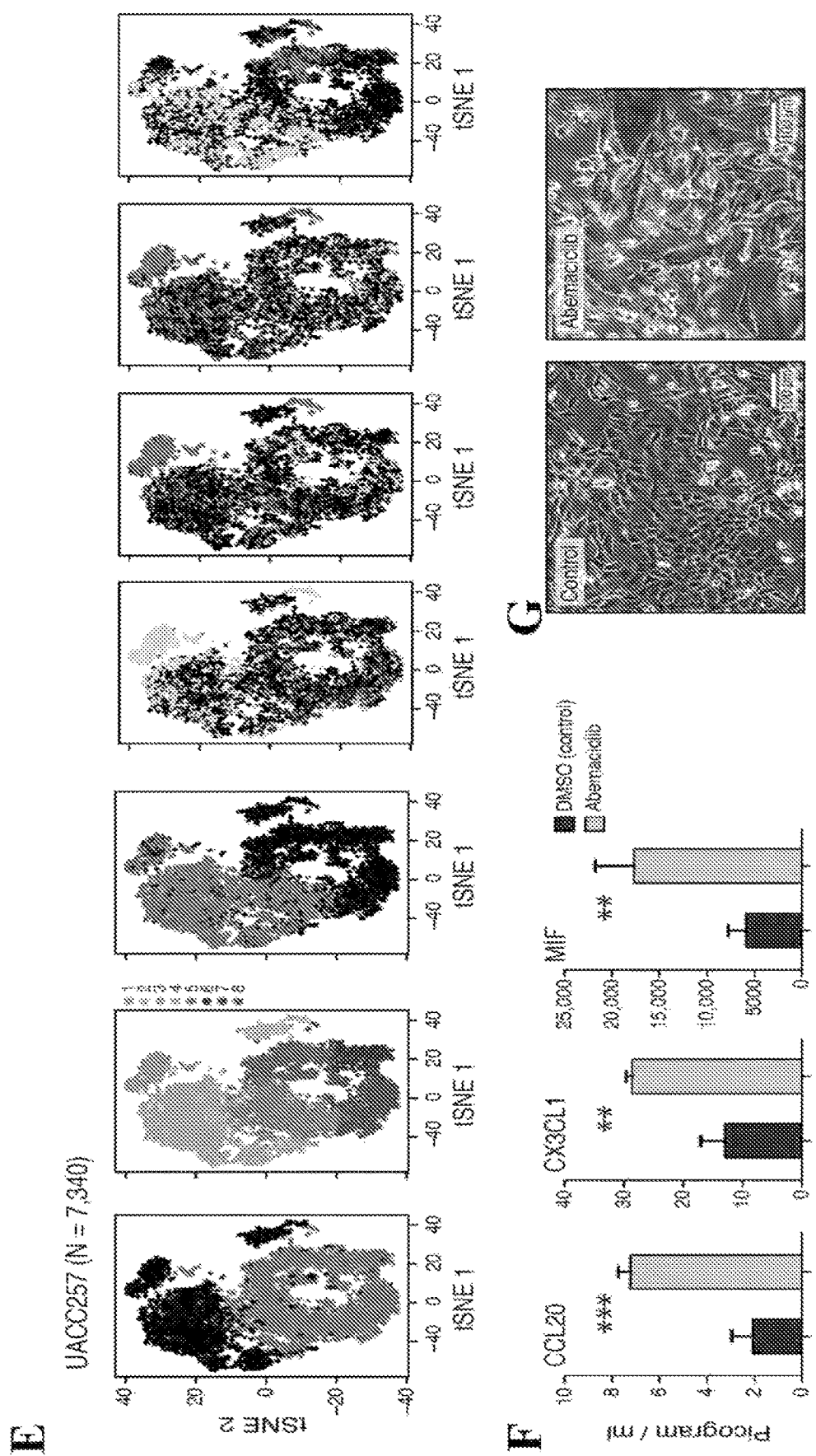
FIG. 49E-G

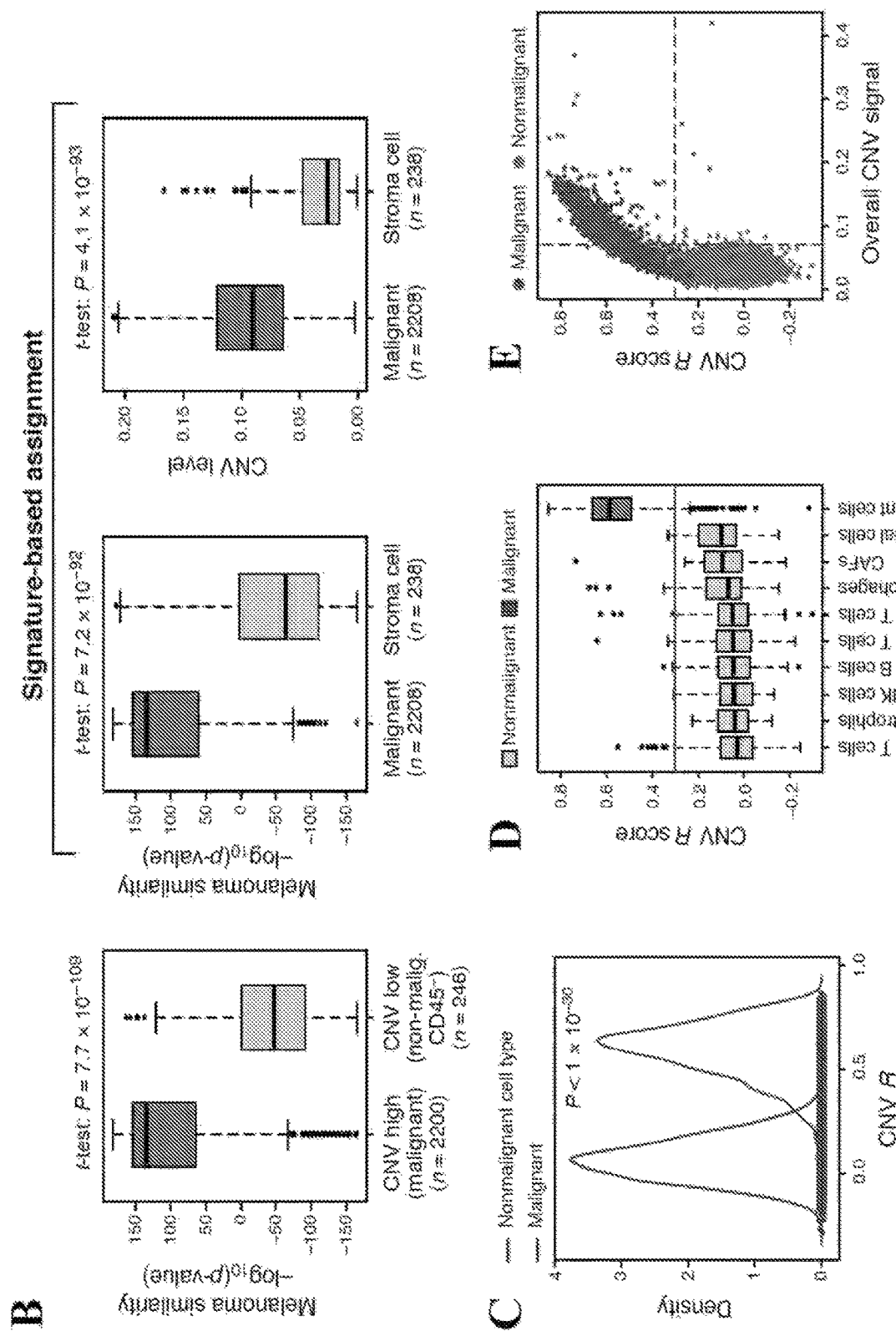
FIG. 51B-E

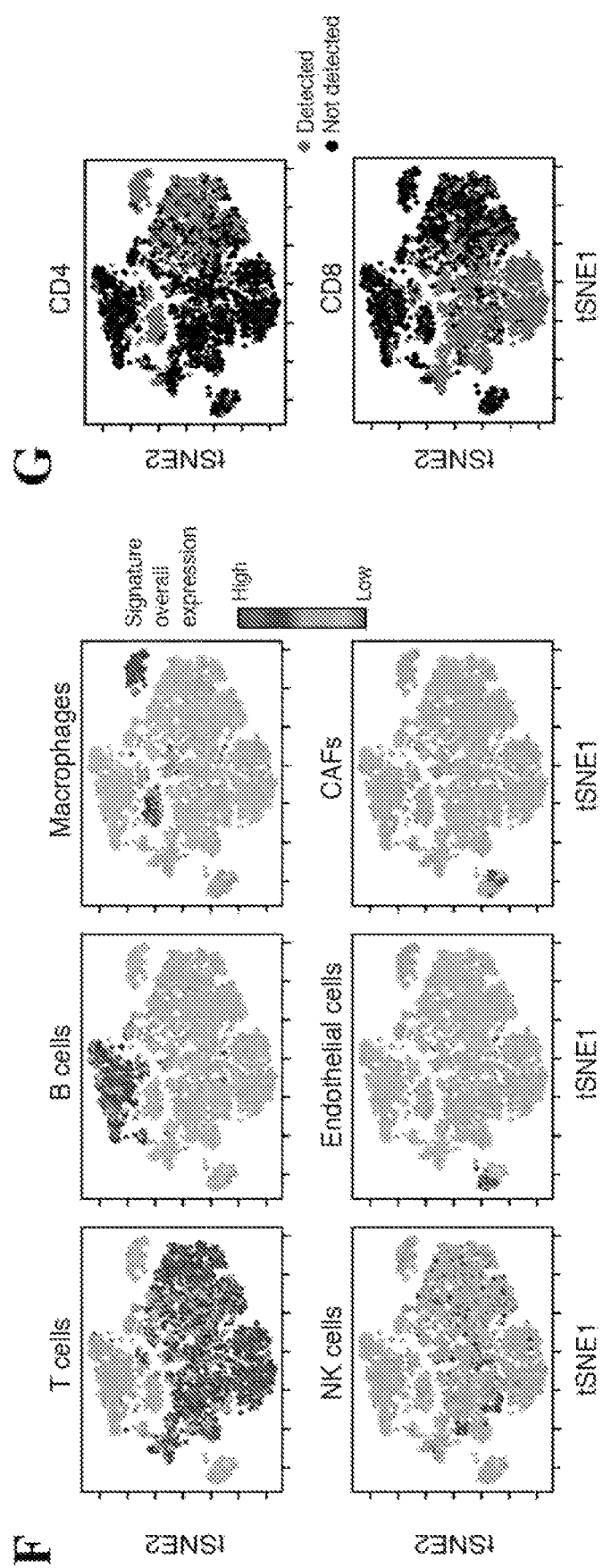
FIG. 51F-G

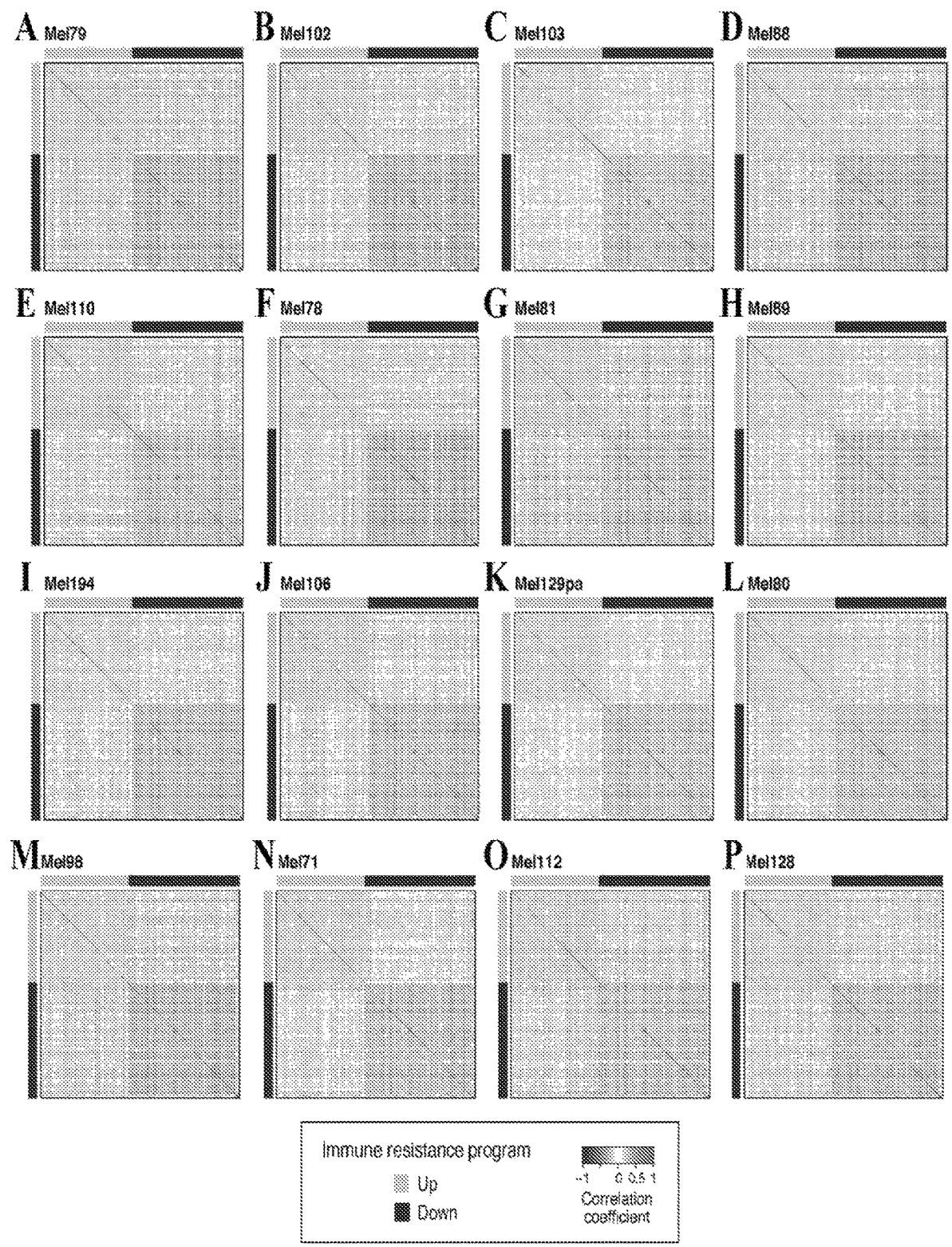
FIG. 52A-P

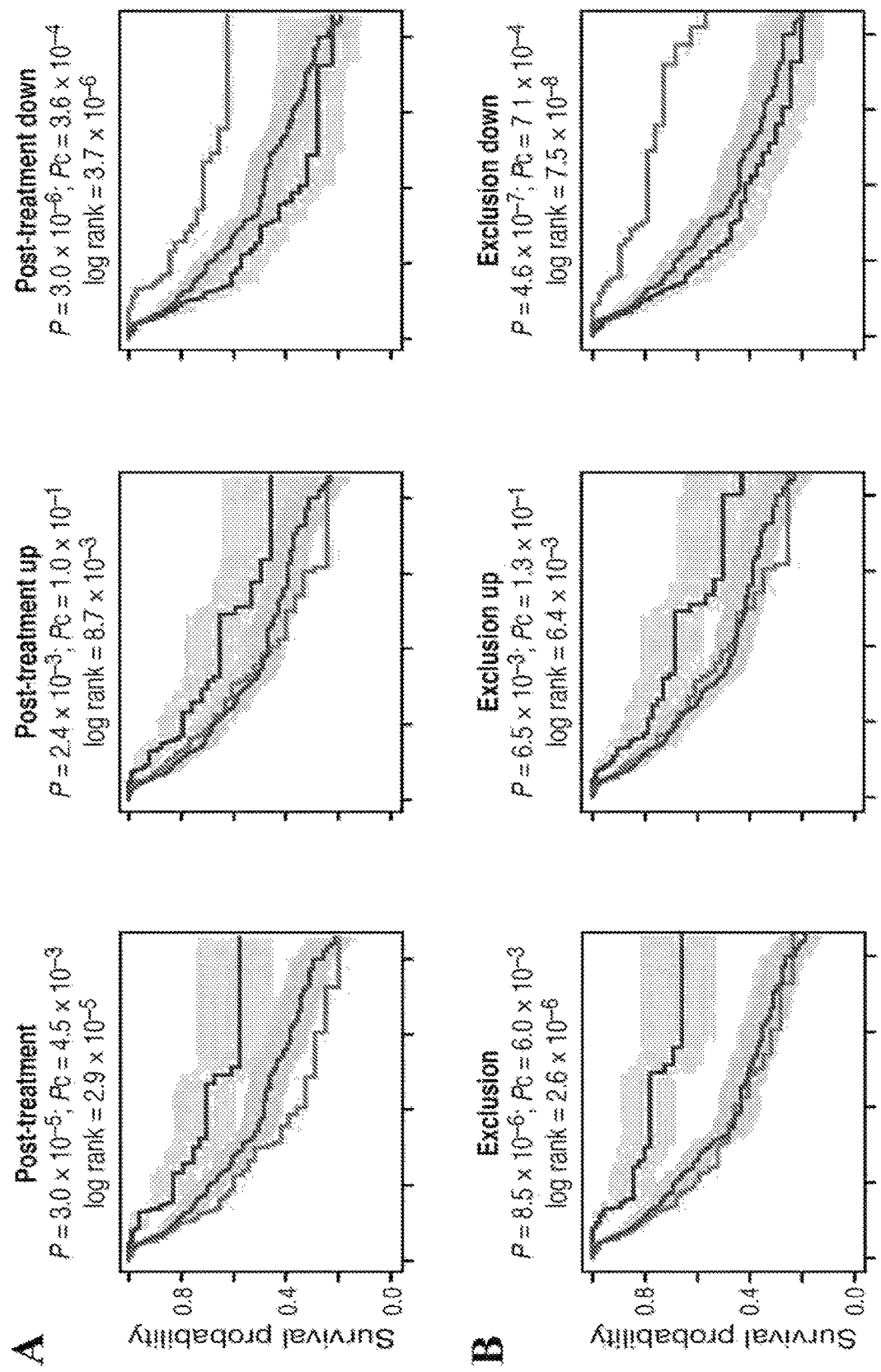
FIG. 54A-B

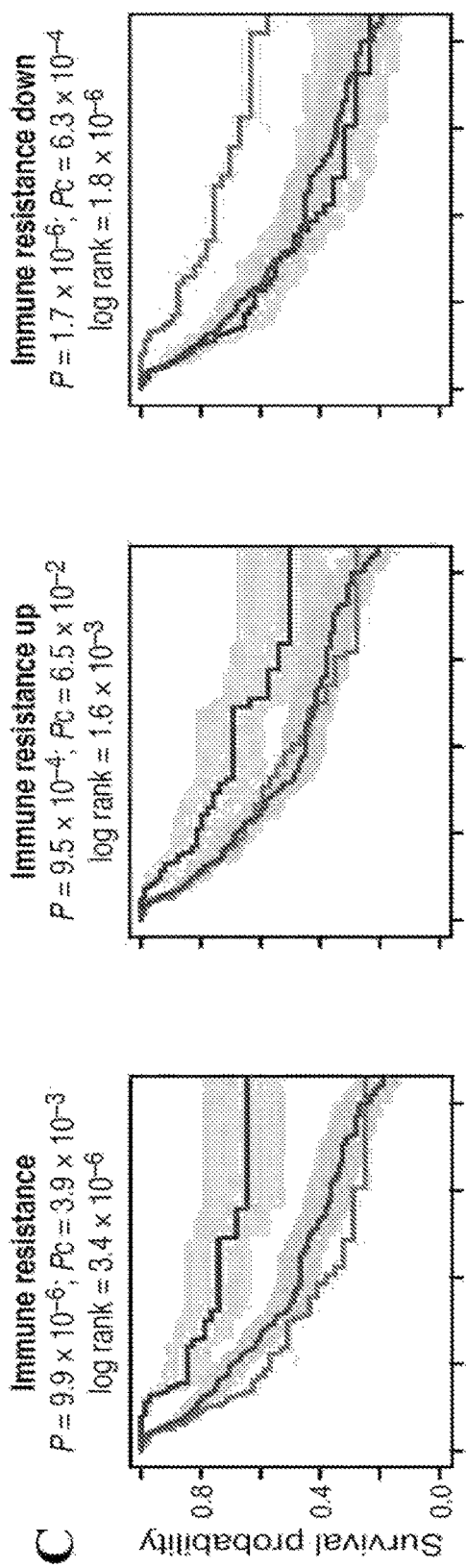
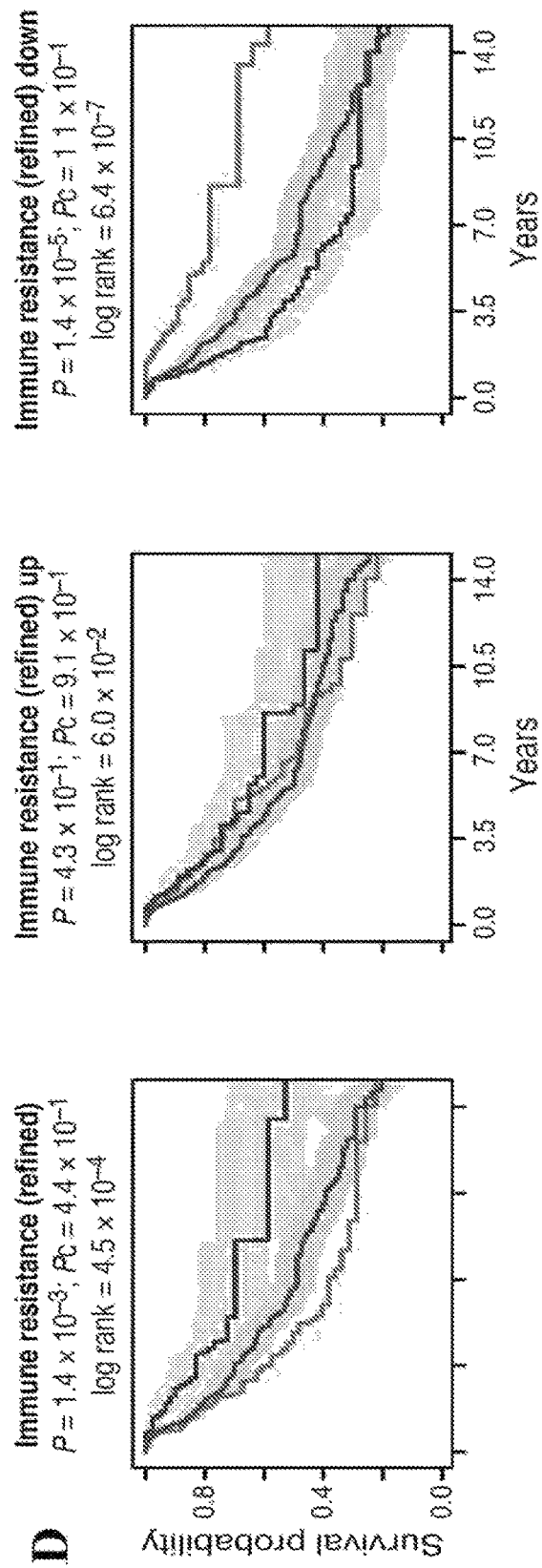
FIG. 54C-D

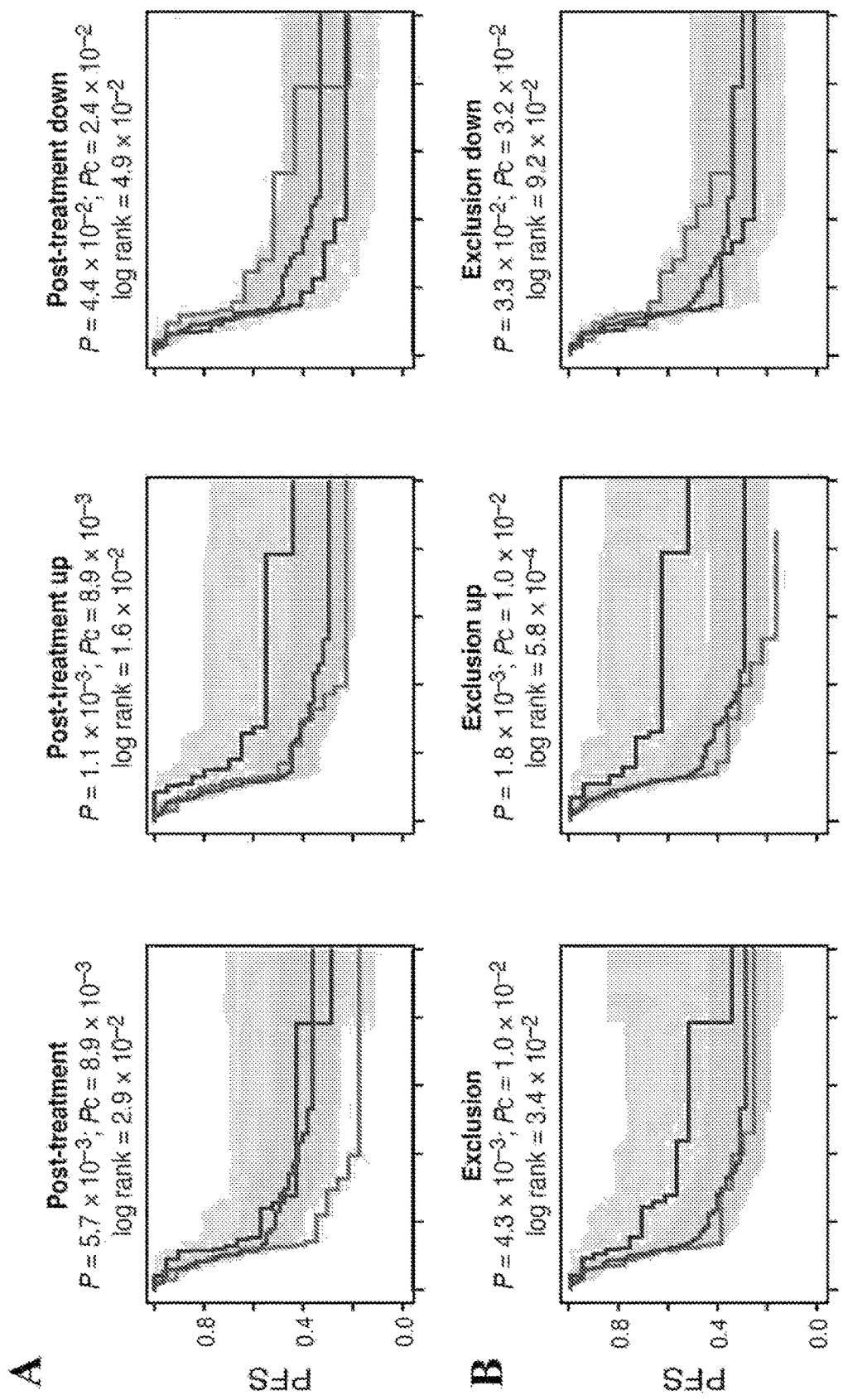
FIG. 55A-B

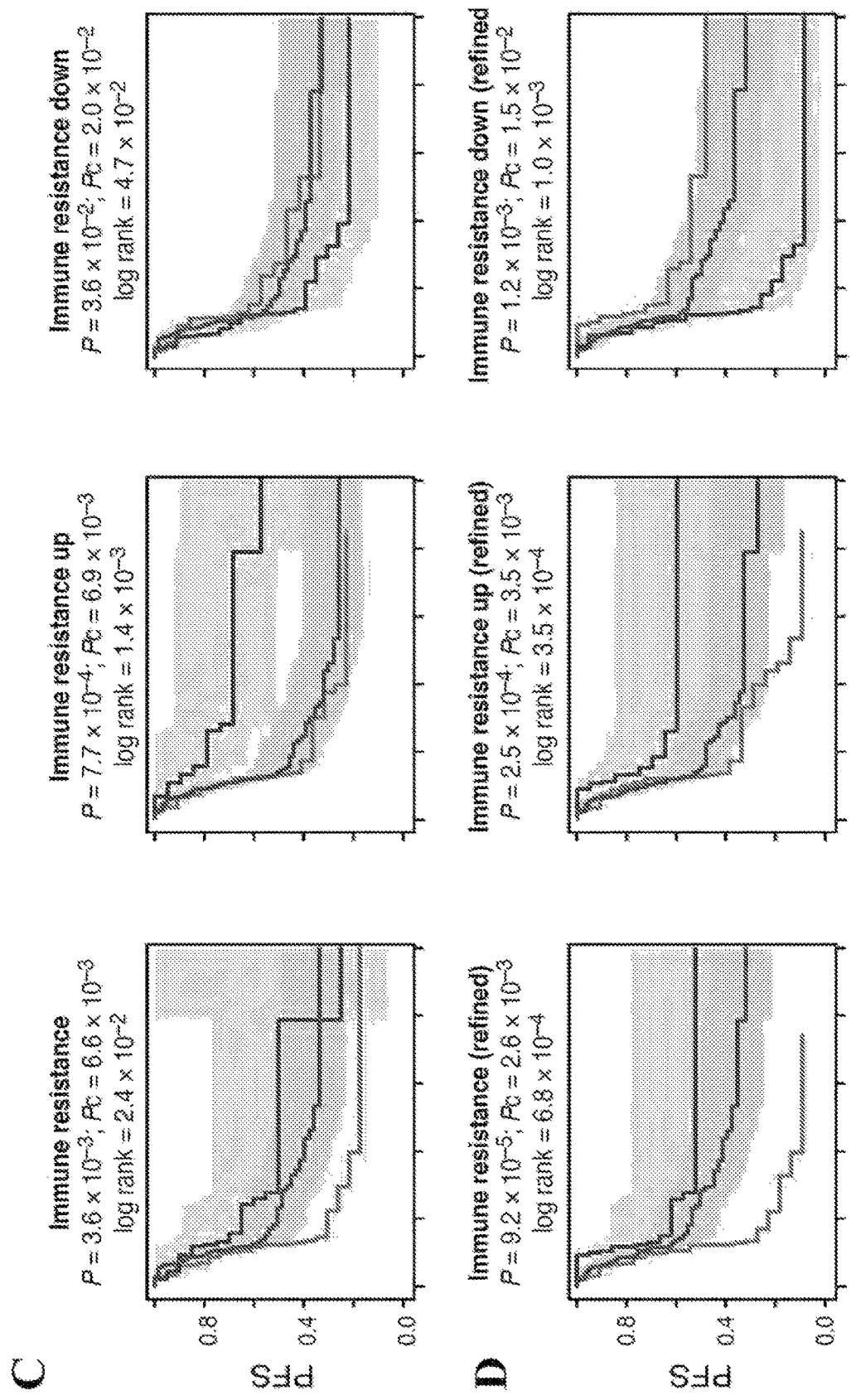
FIG. 55C-D

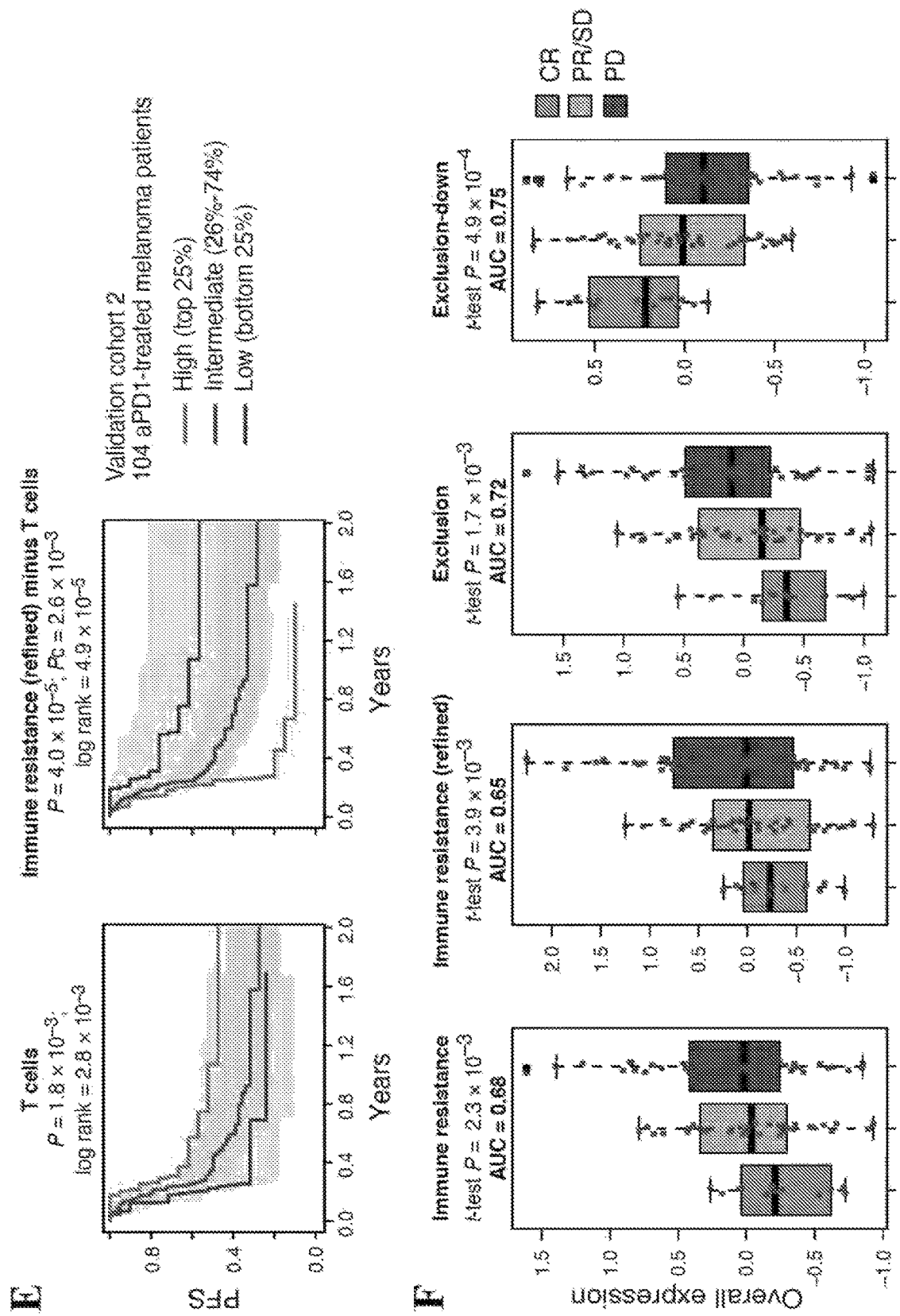
FIG. 55E-F

METHODS AND COMPOSITIONS FOR DETECTING AND MODULATING AN IMMUNOTHERAPY RESISTANCE GENE SIGNATURE IN CANCER

CROSS-REFERENCE TO RELATED APPLICATIONS

This application claims the benefit of U.S. Provisional Application Nos. 62/480,407, filed Apr. 1, 2017, 62/519,784, filed Jun. 14, 2017, 62/567,153, filed Oct. 2, 2017, 62/573,117, filed Oct. 16, 2017, 62/588,025, filed Nov. 17, 2017, 62/595,327, filed Dec. 6, 2017 and 62/630,158, filed Feb. 13, 2018. The entire contents of the above-identified applications are hereby fully incorporated herein by reference.

STATEMENT REGARDING FEDERALLY SPONSORED RESEARCH

This invention was made with government support under grant Nos. CA222663, CA180922, CA202820 and CA14051 awarded by the National Institutes of Health. The government has certain rights in the invention.

TECHNICAL FIELD

The subject matter disclosed herein is generally directed to detecting and modulating novel gene signatures for the treatment and prognosis of cancer.

BACKGROUND

One reason that cancer cells thrive is because they are able to hide from the immune system. Certain cancer cells avoid the immune system better than others and could be a factor in determining survival. Immunotherapies have been developed to enhance immune responses against cancer and lead to prolonged survival. Immunotherapies have transformed the therapeutic landscape of several cancer types. In particular, immune checkpoint inhibitors (ICI) lead to durable responses in ~35% of patients with metastatic melanoma by unleashing T cells from oncogenic suppression (1, 2). Nonetheless, the tumors of most melanoma patients manifest either intrinsic or acquired ICI resistance (ICR). ICR is often unpredictable and poorly understood (3), hampering appropriate selection of patients for therapies, rational enrollment to clinical trials and the development of new therapeutic strategies that could overcome ICR (1).

Recent clinical studies attempted to characterize and predict ICR based on analyses of Whole Exome Sequencing (WES) and transcriptional profiles of tumors at the bulk level (4, 5). These studies demonstrated that tumors with a high mutational load (4) or high immune cell infiltration (6, 7) are more likely to respond, and linked ICR in patients to functional immune evasion phenotypes, including defects in the JAK/STAT pathway (8) and interferon gamma (IFN-γ) response (8, 9), impaired antigen presentation (5, 8), PTEN loss (10), and increased WNT-B-catenin signaling (11). However, thus far, the predictive power of these and other (12) approaches has been limited, either because they report on only some facets of the causes of resistance (WES) and/or because they are highly confounded by tumor composition (RNA and copy-number variations). Indeed, because ICI targets the interactions between different cells in the tumor, its impact depends on multicellular circuits of malignant and non malignant cells (13), which are challenging to study in bulk tumor specimens. Single-cell genomics, especially single-cell RNA-Seq (scRNA-Seq), provides a unique tool to comprehensively map the tumor ecosystem (13-17), but has thus far not been used to study ICR. Thus, there is a need to better understand tumor immunity and resistance to immunotherapy.

Citation or identification of any document in this application is not an admission that such document is available as prior art to the present invention.

SUMMARY

Immune checkpoint inhibitors (ICI) produce durable responses in some patients with melanoma. Yet most patients derive no clinical benefit, and molecular underpinnings of ICI resistance (ICR) are elusive.

It is an objective of the present invention to identify molecular signatures for diagnosis, prognosis and treatment of subjects suffering from cancer. It is a further objective to understand tumor immunity and to leverage this knowledge for treating subjects suffering from cancer. It is another objective for identifying gene signatures for predicting response to checkpoint blockade therapy. It is another objective, for modulating the molecular signatures in order to increase efficacy of immunotherapy (e.g., checkpoint blockade therapy).

Here, Applicants leveraged single-cell RNA-seq (scRNA-seq) from 31 melanoma tumors and novel computational methods to systematically interrogate malignant cell states that promote immune evasion. Applicants identified a resistance program expressed by malignant cells that is strongly associated with T cell exclusion and direct evasion from immunity. The program is present prior to immunotherapy, is apparent in situ, and predicts clinical responses to anti-PD-1 therapy in an independent cohort of 112 melanoma patients. CDK4/6-inhibition represses this program in individual malignant cells and induces a Senescence Associated Secretory Phenotype (SASP). This study provides a high-resolution landscape of ICI resistant cell states, identifies clinically predictive signatures, and forms a basis to develop novel therapeutic strategies that could overcome immunotherapy resistance. Applicants additionally applied single-nuclei RNA-seq (sNuc-seq) to characterize thousands of cells from estrogen-receptor-positive metastatic breast cancer (MBC). ER+ MBC is currently treated with CDK4/6-inhibitors (see, e.g., Vasan et al., State-of-the-Art Update: CDK4/6 Inhibitors in ER+ Metastatic Breast Cancer, AJHO. 2017; 13(4):16-22). Finally, Applicants applied single-cell RNA-seq (scRNA-seq) to characterize thousands of cells from colon cancer.

In one aspect, the present invention provides for a method of detecting an immune checkpoint inhibitor resistance (ICR) gene signature in a tumor comprising, detecting in tumor cells obtained from a subject in need thereof the expression or activity of a malignant cell gene signature comprising: one or more genes or polypeptides selected from the group consisting of C1QBP, CCT2, CCT6A, DCAF13, EIF4A1, ILF2, MAGEA4, NONO, PA2G4, PGAM1, PPA1, PPIA, RPL18A, RPL26, RPL31, RPS11, RPS15, RPS21, RPS5, RUVBL2, SAE1, SNRPE, UBA52, UQCRH, VDAC2, AEBP1, AHNAK, APOC2, APOD, APOE, B2M, C10orf54, CD63, CTSD, EEA1, EMP1, FBXO32, FYB, GATSL3, HCP5, HLA-A, HLA-B, HLA-C, HLA-E, HLA-F, HLA-H, ITGA3, LAMP2, LYRM9, MFGE8, MIA, NPC2, NSG1, PROS1, RDH5, SERPINA1, TAPBP, TIMP2, TNFSF4 and TRIML2 (refined uICR, see table S6); or one or more genes or polypeptides selected from the group consisting of ACAT1, ACP5, ACTB, ACTG1, ADSL, AEN, AK2, ANP32E, APP, ASAP1, ATP5A1, ATP5D, ATP5G2, BANCR, BCAN, BZW2, C17orf76-AS1, C1QBP, C20orf112, C6orf48, CA14, CBX5, CCT2, CCT3, CCT6A, CDK4, CEP170, CFL1, CHP1, CNRIP1, CRABP2, CS, CTPS1, CYC1, DAP3, DCAF13, DCT, DDX21, DDX39B, DLL3, EDNRB, EEF1D, EEF1 G, EEF2, EIF1AX, EIF2S3, EIF3E, EIF3K, EIF3L, EIF4A1, EIF4EBP2, ESRP1, FAM174B, FAM178B, FAM92A1, FBL, FBLN1, FOXRED2, FTL, FUS, GABARAP, GAS5, GNB2L1, GPATCH4, GPI, GRWD1, GSTO1, H3F3A, H3F3AP4, HMGA1, HNRNPA1, HNRNPA1P10, HNRNPC, HSPA8, IDH2, IFI16, ILF2, IMPDH2, ISYNA1, ITM2C, KIAA0101, LHFPL3-A51, LOC100190986, LYPLA1, MAGEA4, MARCK5, MDH2, METAP2, MID1, MIR4461, MLLT11, MPZL1, MRPL37, MRPS12, MRPS21, MYC, NACA, NCL, NDUFS2, NF2, NID1, NOLC1, NONO, NPM1, NUCKS1, OAT, PA2G4, PABPC1, PAFAH1B3, PAICS, PFDN2, PFN1, PGAM1, PIH1D1, PLTP, PPA1, PPIA, PPP2R1A, PSAT1, PSMD4, PTMA, PYCARD, RAN, RASA3, RBM34, RNF2, RPAIN, RPL10, RPL10A, RPL11, RPL12, RPL13, RPL13A, RPL13 AP5, RPL14, RPL17, RPL18, RPL18A, RPL21, RPL26, RPL28, RPL29, RPL3, RPL30, RPL31, RPL35, RPL36A, RPL37, RPL37A, RPL39, RPL4, RPL41, RPL5, RPL6, RPL7, RPL7A, RPL8, RPLP0, RPLP1, RPS10, RPS11, RPS12, RPS15, RPS15A, RPS16, RPS17, RPS17L, RPS18, RPS19, RPS2, RPS21, RPS23, RPS24, RPS26, RPS27, RPS27A, RPS3, RPS3A, RPS4X, RPS5, RPS6, RPS7, RPS8, RPS9, RPSA, RSL1D1, RUVBL2, SAE1, SCD, SCNM1, SERBP1, SERPINF1, SET, SF3B4, SHMT2, SKP2, SLC19A1, SLC25A3, SLC25A5, SLC25A6, SMS, SNAI2, SNHG16, SNHG6, SNRPE, SORD, SOX4, SRP14, SSR2, TIMM13, TIMM50, TMC6, TOP1MT, TP53, TRAP1, TRPM1, TSR1, TUBA1B, TUBB, TUBB4A, TULP4, TXLNA, TYRP1, UBA52, UCK2, UQCRFS1, UQCRH, USP22, VCY1B, VDAC2, VPS72, YWHAE, ZFAS1, ZNF286A, A2M, ACSL3, ACSL4, ADM, AEBP1, AGA, AHNAK, ANGPTL4, ANXA1, ANXA2, APLP2, APOC2, APOD, APOE, ARF5, ARL6IP5, ATF3, ATP1A1, ATP1B1, ATP1B3, ATRAID, B2M, BACE2, BBX, BCL6, C10orf54, C4A, CALU, CASP1, CAST, CAV1, CBLB, CCND3, CD151, CD44, CD47, CD58, CD59, CD63, CD9, CDH19, CHI3L1, CHN1, CLIC4, CLU, CPVL, CRELD1, CRYAB, CSGALNACT1, CSPG4, CST3, CTSA, CTSB, CTSD, CTSL1, DAG1, DCBLD2, DDR1, DDX5, DPYSL2, DSCR8, DUSP4, DUSP6, DYNLRB1, ECM1, EEA1, EGR1, EMP1, EPHX2, ERBB3, EVA1A, EZH1, EZR, FAM3C, FBXO32, FCGR2C, FCRLA, FGFR1, FLJ43663, FOS, FYB, GAA, GADD45B, GATSL3, GEM, GOLGB1, GPNMB, GRN, GSN, HCP5, HLA-A, HLA-B, HLA-C, HLA-E, HLA-F, HLA-H, HPCAL1, HSPA1A, HSPA1B, HTATIP2, ID2, IFI27L2, IFI35, IGF1R, IL1RAP, IL6ST, ISCU, ITGA3, ITGA6, ITGA7, ITGB1, ITGB3, ITM2B, JUN, KCNN4, KLF4, KLF6, KRT10, LAMP2, LEPROT, LGALS1, LGALS3, LGALS3BP, LOC100506190, LPL, LRPAP1, LTBP3, LYRM9, MAEL, MAGEC2, MAP1B, MATN2, MFGE8, MFI2, MIA, MRPS6, MT1E, MT1M, MT1X, MT2A, NDRG1, NEAT1, NFKBIA, NFKBIZ, NNMT, NPC1, NPC2, NR4A1, NSG1, OCIAD2, PAGES, PDK4, PERP, PKM, PLP2, PRKCDBP, PRNP, PROS1, PRSS23, PSAP, PSMB9, PTRF, RDH5, RNF145, RPS4Y1, S100A13, S100A6, S100B, SAT1, SCARB2, SCCPDH, SDC3, SEL1L, SEMA3B, SERPINA1, SERPINA3, SERPINE2, SGCE, SGK1, SLC20A1, SLC26A2, SLC39A14, SLC5A3, SNX9, SOD1, SPON2, SPRY2, SQSTM1, SRPX, STOM, SYNGR2, SYPL1, TAPBP, TAPBPL, TF, TGOLN2, THBD, TIMP1, TIMP2, TIMP3, TIPARP, TM4SF1, TMBIM6, TMED10, TMED9, TMEM66, TMX4, TNC, TNFSF4, TPP1, TRIML2, TSC22D3, TSPYL2, TXNIP, TYR, UBC, UPP1, XAGE1A, XAGE1B, XAGE1C, XAGE1D, XAGE1E, ZBTB20 and ZBTB38 (uICR, see table S6); or one or more genes or polypeptides selected from the group consisting of ANP32E, CTPS1, DDX39B, EIF4A1, ESRP1, FBL, FUS, HNRNPA1, ILF2, KIAA0101, NUCKS1, PTMA, RPL21, RUVBL2, SET, SLC25A5, TP53, TUBA1B, UCK2, YWHAE, APLP2, ARL6IP5, CD63, CLU, CRELD1, CTSD, CTSL1, FOS, GAA, GRN, HLA-F, ITM2B, LAMP2, MAP1B, NPC2, PSAP, SCARB2, SDC3, SEL1L, TMED10 and TSC22D3 (uICR, see FIG. 3C); or one or more genes or polypeptides selected from the group consisting of MT1E, MT1M, MT1X and MT2A.

In certain embodiments, the ICR signature may comprises a ICR-down signature, said signature comprising one or more genes selected from the group consisting of: AEBP1, AHNAK, APOC2, APOD, APOE, B2M, C10orf54, CD63, CTSD, EEA1, EMP1, FBXO32, FYB, GATSL3, HCP5, HLA-A, HLA-B, HLA-C, HLA-E, HLA-F, HLA-H, ITGA3, LAMP2, LYRM9, MFGE8, MIA, NPC2, NSG1, PROS1, RDH5, SERPINA1, TAPBP, TIMP2, TNFSF4 and TRIML2 (refined uICR-down, see table S6); or A2M, ACSL3, ACSL4, ADM, AEBP1, AGA, AHNAK, ANGPTL4, ANXA1, ANXA2, APLP2, APOC2, APOD, APOE, ARF5, ARL6IP5, ATF3, ATP1A1, ATP1B1, ATP1B3, ATRAID, B2M, BACE2, BBX, BCL6, C10orf54, C4A, CALU, CASP1, CAST, CAV1, CBLB, CCND3, CD151, CD44, CD47, CD58, CD59, CD63, CD9, CDH19, CHI3L1, CHN1, CLIC4, CLU, CPVL, CRELD1, CRYAB, CSGALNACT1, CSPG4, CST3, CTSA, CTSB, CTSD, CTSL1, DAG1, DCBLD2, DDR1, DDX5, DPYSL2, DSCR8, DUSP4, DUSP6, DYNLRB1, ECM1, EEA1, EGR1, EMP1, EPHX2, ERBB3, EVA1A, EZH1, EZR, FAM3C, FBXO32, FCGR2C, FCRLA, FGFR1, FLJ43663, FOS, FYB, GAA, GADD45B, GATSL3, GEM, GOLGB1, GPNMB, GRN, GSN, HCP5, HLA-A, HLA-B, HLA-C, HLA-E, HLA-F, HLA-H, HPCAL1, HSPA1A, HSPA1B, HTATIP2, ID2, IFI27L2, IFI35, IGF1R, IL1RAP, IL6ST, ISCU, ITGA3, ITGA6, ITGA7, ITGB1, ITGB3, ITM2B, JUN, KCNN4, KLF4, KLF6, KRT10, LAMP2, LEPROT, LGALS1, LGALS3, LGALS3BP, LOC100506190, LPL, LRPAP1, LTBP3, LYRM9, MAEL, MAGEC2, MAP1B, MATN2, MFGE8, MFI2, MIA, MRPS6, MT1E, MT1M, MT1X, MT2A, NDRG1, NEAT1, NFKBIA, NFKBIZ, NNMT, NPC1, NPC2, NR4A1, NSG1, OCIAD2, PAGES, PDK4, PERP, PKM, PLP2, PRKCDBP, PRNP, PROS1, PRSS23, PSAP, PSMB9, PTRF, RDH5, RNF145, RPS4Y1, S100A13, S100A6, S100B, SAT1, SCARB2, SCCPDH, SDC3, SEL1L, SEMA3B, SERPINA1, SERPINA3, SERPINE2, SGCE, SGK1, SLC20A1, SLC26A2, SLC39A14, SLC5A3, SNX9, SOD1, SPON2, SPRY2, SQSTM1, SRPX, STOM, SYNGR2, SYPL1, TAPBP, TAPBPL, TF, TGOLN2, THBD, TIMP1, TIMP2, TIMP3, TIPARP, TM4SF1, TMBIM6, TMED10, TMED9, TMEM66, TMX4, TNC, TNFSF4, TPP1, TRIML2, TSC22D3, TSPYL2, TXNIP, TYR, UBC, UPP1, XAGE1A, XAGE1B, XAGE1C, XAGE1D, XAGE1E, ZBTB20 and ZBTB38 (uICR-down, see table S6); or APLP2, ARL6IP5, CD63, CLU, CRELD1, CTSD, CTSL1, FOS, GAA, GRN, HLA-F, ITM2B, LAMP2, MAP1B, NPC2, PSAP, SCARB2, SDC3, SEL1L, TMED10 and TSC22D3 (uICR-down, see FIG.

3C), wherein said ICR-down signature is downregulated in a tumor with a high ICR score and upregulated in a tumor with a low ICR score.

In certain embodiments, the ICR signature comprises a ICR-up signature, said signature comprising one or more genes selected from the group consisting of: C1QBP, CCT2, CCT6A, DCAF13, EIF4A1, ILF2, MAGEA4, NONO, PA2G4, PGAM1, PPA1, PPIA, RPL18A, RPL26, RPL31, RPS11, RPS15, RPS21, RPS5, RUVBL2, SAE1, SNRPE, UBA52, UQCRH and VDAC2 (refined uICR-up, see table S6); or ACAT1, ACP5, ACTB, ACTG1, ADSL, AEN, AK2, ANP32E, APP, ASAP1, ATP5A1, ATP5D, ATP5G2, BANCR, BCAN, BZW2, C17orf76-AS1, C1QBP, C20orf112, C6orf48, CA14, CBX5, CCT2, CCT3, CCT6A, CDK4, CEP170, CFL1, CHP1, CNRIP1, CRABP2, CS, CTPS1, CYC1, DAP3, DCAF13, DCT, DDX21, DDX39B, DLL3, EDNRB, EEF1D, EEF1G, EEF2, EIF1AX, EIF2S3, EIF3E, EIF3K, EIF3L, EIF4A1, EIF4EBP2, ESRP1, FAM174B, FAM178B, FAM92A1, FBL, FBLN1, FOXRED2, FTL, FUS, GABARAP, GAS5, GNB2L1, GPATCH4, GPI, GRWD1, GSTO1, H3F3A, H3F3AP4, HMGA1, HNRNPA1, HNRNPA1P10, HNRNPC, HSPA8, IDH2, IFI16, ILF2, IMPDH2, ISYNA1, ITM2C, KIAA0101, LHFPL3-A51, LOC100190986, LYPLA1, MAGEA4, MARCK5, MDH2, METAP2, MID1, MIR4461, MLLT11, MPZL1, MRPL37, MRPS12, MRPS21, MYC, NACA, NCL, NDUFS2, NF2, NID1, NOLC1, NONO, NPM1, NUCKS1, OAT, PA2G4, PABPC1, PAFAH1B3, PAICS, PFDN2, PFN1, PGAM1, PIH1D1, PLTP, PPA1, PPIA, PPP2R1A, PSAT1, PSMD4, PTMA, PYCARD, RAN, RASA3, RBM34, RNF2, RPAIN, RPL10, RPL10A, RPL11, RPL12, RPL13, RPL13A, RPL13AP5, RPL14, RPL17, RPL18, RPL18A, RPL21, RPL26, RPL28, RPL29, RPL3, RPL30, RPL31, RPL35, RPL36A, RPL37, RPL37A, RPL39, RPL4, RPL41, RPL5, RPL6, RPL7, RPL7A, RPL8, RPLP0, RPLP1, RPS10, RPS11, RPS12, RPS15, RPS15A, RPS16, RPS17, RPS17L, RPS18, RPS19, RPS2, RPS21, RPS23, RPS24, RPS26, RPS27, RPS27A, RPS3, RPS3A, RPS4X, RPS5, RPS6, RPS7, RPS8, RPS9, RPSA, RSL1D1, RUVBL2, SAE1, SCD, SCNM1, SERBP1, SERPINF1, SET, SF3B4, SHMT2, SKP2, SLC19A1, SLC25A3, SLC25A5, SLC25A6, SMS, SNAI2, SNHG16, SNHG6, SNRPE, SORD, SOX4, SRP14, SSR2, TIMM13, TIMM50, TMC6, TOP1MT, TP53, TRAP1, TRPM1, TSR1, TUBA1B, TUBB, TUBB4A, TULP4, TXLNA, TYRP1, UBA52, UCK2, UQCRFS1, UQCRH, USP22, VCY1B, VDAC2, VPS72, YWHAE, ZFAS1 and ZNF286A (uICR-up, see table S6); or ANP32E, CTPS1, DDX39B, EIF4A1, ESRP1, FBL, FUS, HNRNPA1, ILF2, KIAA0101, NUCKS1, PTMA, RPL21, RUVBL2, SET, SLC25A5, TP53, TUBA1B, UCK2 and YWHAE (uICR-up, see FIG. 3C), wherein said ICR-up signature is upregulated in a tumor with a high ICR score and downregulated in a tumor with a low ICR score.

In another aspect, the present invention provides for a method of detecting an immune checkpoint inhibitor resistance (ICR) gene signature in a tumor comprising, detecting in tumor cells obtained from a subject in need thereof the expression or activity of a malignant cell gene signature comprising: one or more genes or polypeptides selected from the group consisting of ACTB, AEN, ANP32E, ATP5A1, ATP5G2, BZW2, C17orf76-AS1, C1QBP, C20orf112, CA14, CBX5, CCT2, CCT3, CDK4, CFL1, CNRIP1, CRABP2, CS, CTPS1, DCAF13, DDX39B, DLL3, EEF1G, EIF2S3, EIF3K, EIF4A1, EIF4EBP2, FAM174B, FBL, FBLN1, FOXRED2, FTL, FUS, GABARAP, GAS5, GNB2L1, GPATCH4, GPI, GRWD1, H3F3A, H3F3AP4, HMGA1, HNRNPA1, HNRNPA1P10, HNRNPC, HSPA8, IDH2, ILF2, ISYNA1, ITM2C, KIAA0101, MAGEA4, MDH2, METAP2, MID1, MIR4461, MLLT11, MPZL1, MRPS21, NACA, NCL, NDUFS2, NOLC1, NONO, PA2G4, PABPC1, PAFAH1B3, PFDN2, PFN1, PGAM1, PIH1D1, PPA1, PPIA, PPP2R1A, PSMD4, PTMA, RAN, RBM34, RNF2, RPAIN, RPL10A, RPL11, RPL12, RPL13, RPL13A, RPL13AP5, RPL17, RPL18, RPL18A, RPL21, RPL26, RPL28, RPL29, RPL3, RPL31, RPL36A, RPL37, RPL37A, RPL39, RPL4, RPL41, RPL5, RPL6, RPL8, RPLP0, RPLP1, RPS10, RPS11, RPS12, RPS15A, RPS16, RPS17, RPS17L, RPS18, RPS19, RPS21, RPS23, RPS24, RPS26, RPS27, RPS27A, RPS3, RPS4X, RPS5, RPS6, RPS7, RPS8, RPS9, RPSA, RUVBL2, SAE1, SCD, SCNM1, SERPINF1, SET, SF3B4, SHMT2, SKP2, SLC25A3, SMS, SNAI2, SNHG6, SNRPE, SOX4, SRP14, SSR2, TIMM50, TMC6, TP53, TRPM1, TSR1, TUBA1B, TUBB, TULP4, UBA52, UQCRFS1, UQCRH, USP22, VCY1B, VDAC2, VPS72, YWHAE, ZNF286A, A2M, ACSL3, ACSL4, ADM, AEBP1, AGA, AHNAK, ANGPTL4, ANXA1, ANXA2, APLP2, APOD, APOE, ARL6IP5, ATF3, ATP1A1, ATP1B1, ATP1B3, B2M, BACE2, BBX, BCL6, CALU, CASP1, CAST, CAV1, CCND3, CD151, CD44, CD47, CD58, CD59, CD63, CD9, CDH19, CHI3L1, CLIC4, CRELD1, CRYAB, CSGAL-NACT1, CSPG4, CST3, CTSA, CTSB, CTSD, CTSL1, DAG1, DCBLD2, DDR1, DDX5, DPYSL2, DUSP4, DUSP6, ECM1, EEA1, EGR1, EMP1, EPHX2, ERBB3, EVA1A, EZH1, FAM3C, FBXO32, FCGR2C, FCRLA, FGFR1, FLJ43663, FOS, GAA, GADD45B, GEM, GOLGB1, GPNMB, GRN, GSN, HLA-A, HLA-B, HLA-C, HLA-E, HLA-F, HLA-H, HPCAL1, HSPA1A, HTATIP2, 1E135, IGF1R, IL1RAP, IL6ST, ITGA3, ITGA6, ITGB1, ITGB3, ITM2B, JUN, KCNN4, KLF4, KLF6, LAMP2, LEPROT, LGALS1, LGALS3, LGALS3BP, LPL, LRPAP1, MAGEC2, MFGE8, MFI2, MIA, MT1E, MT1M, MT1X, MT2A, NEAT1, NFKBIA, NFKBIZ, NNMT, NPC1, NPC2, NR4A1, NSG1, PDK4, PLP2, PRKCDBP, PRNP, PROS1, PRSS23, PSAP, PSMB9, PTRF, RNF145, RPS4Y1, S100A6, S100B, SAT1, SCARB2, SCCPDH, SDC3, SEL1L, SEMA3B, SERPINA3, SERPINE2, SGCE, SGK1, SLC20A1, SLC26A2, SLC39A14, SLC5A3, SOD1, SPRY2, SQSTM1, SRPX, STOM, SYNGR2, SYPL1, TAPBP, TAPBPL, TF, TGOLN2, TIMP1, TIMP2, TIMP3, TIPARP, TM4SF1, TMED10, TMED9, TMEM66, TMX4, TNC, TPP1, TSC22D3, TYR, UBC, UPP1, ZBTB20 and ZBTB38 (oncogenic ICR, see table S6); or one or more genes or polypeptides selected from the group consisting of AEN, ATP5A1, C20orf112, CCT2, DCAF13, DDX39B, ISYNA1, NDUFS2, NOLC1, PA2G4, PPP2R1A, RBM34, RNF2, RPL6, RPL21, SERPINF1, SF3B4, SMS, TMC6, VPS72, ANXA1, ATF3, BCL6, CD58, CD9, CTSB, DCBLD2, EMP1, HLA-F, HTATIP2, IL1RAP, ITGA6, KCNN4, KLF4, MT1E, MT1M, MT1X, MT2A, NNMT, PRKCDBP, S100A6 and TSC22D3 (oncogenic ICR, see FIG. 2B); or one or more genes or polypeptides selected from the group consisting of ACTB, ANP32E, CBX5, FUS, HNRNPA1, IDH2, KIAA0101, NCL, PFN1, PPIA, PTMA, RAN, RPLP0, TUBA1B, TUBB, VCY1B, A2M, APOD, BCL6, CD44, CD59, CD63, CDH19, CHI3L1, CTSA, CTSB, CTSD, FOS, GPNMB, GRN, HLA-A, HLA-B, HLA-H, ITM2B, LGALS3BP, NEAT1, PDK4, PSAP, SCARB2, SERPINA3, SLC26A2, TAPBPL, TMEM66 and TYR (oncogenic ICR, see FIG. 10B); or one or more genes or polypeptides selected from the group consisting of MT1E, MT1M, MT1X and MT2A.

In certain embodiments, the ICR signature comprises an ICR-down signature, said signature comprising one or more genes selected from the group consisting of: A2M, ACSL3, ACSL4, ADM, AEBP1, AGA, AHNAK, ANGPTL4, ANXA1, ANXA2, APLP2, APOD, APOE, ARL6IP5, ATF3, ATP1A1, ATP1B1, ATP1B3, B2M, BACE2, BBX, BCL6, CALU, CASP1, CAST, CAV1, CCND3, CD151, CD44, CD47, CD58, CD59, CD63, CD9, CDH19, CHI3L1, CLIC4, CRELD1, CRYAB, CSGALNACT1, CSPG4, CST3, CTSA, CTSB, CTSD, CTSL1, DAG1, DCBLD2, DDR1, DDX5, DPYSL2, DUSP4, DUSP6, ECM1, EEA1, EGR1, EMP1, EPHX2, ERBB3, EVA1A, EZH1, FAM3C, FBXO32, FCGR2C, FCRLA, FGFR1, FLJ43663, FOS, GAA, GADD45B, GEM, GOLGB1, GPNMB, GRN, GSN, HLA-A, HLA-B, HLA-C, HLA-E, HLA-F, HLA-H, HPCAL1, HSPA1A, HTATIP2, IFI35, IGF1R, IL1RAP, IL6ST, ITGA3, ITGA6, ITGB1, ITGB3, ITM2B, JUN, KCNN4, KLF4, KLF6, LAMP2, LEPROT, LGALS1, LGALS3, LGALS3BP, LPL, LRPAP1, MAGEC2, MFGE8, MFI2, MIA, MT1E, MT1M, MT1X, MT2A, NEAT1, NFKBIA, NFKBIZ, NNMT, NPC1, NPC2, NR4A1, NSG1, PDK4, PLP2, PRKCDBP, PRNP, PROS1, PRSS23, PSAP, PSMB9, PTRF, RNF145, RPS4Y1, S100A6, S100B, SAT1, SCARB2, SCCPDH, SDC3, SEL1L, SEMA3B, SERPINA3, SERPINE2, SGCE, SGK1, SLC20A1, SLC26A2, SLC39A14, SLC5A3, SOD1, SPRY2, SQSTM1, SRPX, STOM, SYNGR2, SYPL1, TAPBP, TAPBPL, TF, TGOLN2, TIMP1, TIMP2, TIMP3, TIPARP, TM4SF1, TMED10, TMED9, TMEM66, TMX4, TNC, TPP1, TSC22D3, TYR, UBC, UPP1, ZBTB20 and ZBTB38 (oncogenic ICR down, see table S6); or ANXA1, ATF3, BCL6, CD58, CD9, CTSB, DCBLD2, EMP1, HLA-F, HTATIP2, IL1RAP, ITGA6, KCNN4, KLF4, MT1E, MT1M, MT1X, MT2A, NNMT, PRKCDBP, S100A6 and TSC22D3 (oncogenic ICR down, see FIG. 2B); or A2M, APOD, BCL6, CD44, CD59, CD63, CDH19, CHI3L1, CTSA, CTSB, CTSD, FOS, GPNMB, GRN, HLA-A, HLA-B, HLA-H, ITM2B, LGALS3BP, NEAT1, PDK4, PSAP, SCARB2, SERPINA3, SLC26A2, TAPBPL, TMEM66 and TYR (oncogenic ICR down, see FIG. 10B), wherein said ICR-down signature is downregulated in a tumor with a high ICR score and upregulated in a tumor with a low ICR score.

In certain embodiments, the ICR signature comprises an ICR-up signature, said signature comprising one or more genes selected from the group consisting of: ACTB, AEN, ANP32E, ATP5A1, ATP5G2, BZW2, C17orf76-AS1, C1QBP, C20orf112, CA14, CBX5, CCT2, CCT3, CDK4, CFL1, CNRIP1, CRABP2, CS, CTPS1, DCAF13, DCT, DDX39B, DLL3, EEF1G, EIF2S3, EIF3K, EIF4A1, EIF4EBP2, FAM174B, FBL, FBLN1, FOXRED2, FTL, FUS, GABARAP, GAS5, GNB2L1, GPATCH4, GPI, GRWD1, H3F3A, H3F3AP4, HMGA1, HNRNPA1, HNRNPA1P10, HNRNPC, HSPA8, IDH2, ILF2, ISYNA1, ITM2C, KIAA0101, MAGEA4, MDH2, METAP2, MID1, MIR4461, MLLT11, MPZL1, MRPS21, NACA, NCL, NDUFS2, NOLC1, NONO, PA2G4, PABPC1, PAFAH1B3, PFDN2, PFN1, PGAM1, PIH1D1, PPA1, PPIA, PPP2R1A, PSMD4, PTMA, RAN, RBM34, RNF2, RPAIN, RPL10A, RPL11, RPL12, RPL13, RPL13A, RPL13 AP5, RPL17, RPL18, RPL18A, RPL21, RPL26, RPL28, RPL29, RPL3, RPL31, RPL36A, RPL37, RPL37A, RPL39, RPL4, RPL41, RPL5, RPL6, RPL8, RPLP0, RPLP1, RPS10, RPS11, RPS12, RPS15A, RPS16, RPS17, RPS17L, RPS18, RPS19, RPS21, RPS23, RPS24, RPS26, RPS27, RPS27A, RPS3, RPS4X, RPS5, RPS6, RPS7, RPS8, RPS9, RPSA, RUVBL2, SAE1, SCD, SCNM1, SERPINF1, SET, SF3B4, SHMT2, SKP2, SLC25A3, SMS, SNAI2, SNHG6, SNRPE, SOX4, SRP14, SSR2, TIMM50, TMC6, TP53, TRPM1, TSR1, TUBA1B, TUBB, TULP4, UBA52, UQCRFS1, UQCRH, USP22, VCY1B, VDAC2, VPS72, YWHAE and ZNF286A (oncogenic ICR up, see table S6); or AEN, ATP5A1, C20orf112, CCT2, DCAF13, DDX39B, ISYNA1, NDUFS2, NOLC1, PA2G4, PPP2R1A, RBM34, RNF2, RPL6, RPL21, SERPINF1, SF3B4, SMS, TMC6, VPS72 (oncogenic ICR up, see FIG. 2B); or ACTB, ANP32E, CBX5, FUS, HNRNPA1, IDH2, KIAA0101, NCL, PFN1, PPIA, PTMA, RAN, RPLP0, TUBA1B, TUBB and VCY1B (oncogenic ICR up, see FIG. 10B), wherein said ICR-up signature is upregulated in a tumor with a high ICR score and downregulated in a tumor with a low ICR score. In certain embodiments, the ICR signature is detected in cycling cells.

In another aspect, the present invention provides for a method of detecting an immune cell exclusion gene signature in a tumor comprising, detecting in tumor cells obtained from a subject in need thereof the expression or activity of a malignant cell gene signature comprising: one or more genes or polypeptides selected from the group consisting of ACAT1, ACP5, ACTG1, ADSL, AK2, APP, ASAP1, ATP5D, BANCR, BCAN, BZW2, C17orf76-AS1, C1QBP, C6orf48, CA14, CCT3, CCT6A, CEP170, CHP1, CTPS1, CYC1, DAP3, DCT, DDX21, EDNRB, EEF1D, EEF1G, EEF2, EIF1AX, EIF2S3, EIF3E, EIF3K, EIF3L, EIF4A1, ESRP1, FAM178B, FAM92A1, FTL, GAS5, GNB2L1, GPI, GSTO1, IFI16, ILF2, IMPDH2, LHFPL3-AS1, LOC100190986, LYPLA1, MARCK5, MDH2, MRPL37, MRPS12, MYC, NCL, NF2, NID1, NOLC1, NPM1, NUCKS1, OAT, PABPC1, PAICS, PLTP, PSAT1, PYCARD, RASA3, RPL10, RPL10A, RPL11, RPL12, RPL13, RPL13A, RPL13AP5, RPL14, RPL17, RPL18, RPL18A, RPL28, RPL29, RPL3, RPL30, RPL35, RPL37A, RPL39, RPL4, RPL5, RPL6, RPL7, RPL7A, RPL8, RPLP0, RPLP1, RPS10, RPS11, RPS15, RPS15A, RPS16, RPS17, RPS17L, RPS18, RPS19, RPS2, RPS24, RPS27, RPS3, RPS3A, RPS4X, RPS5, RPS7, RPS8, RPS9, RPSA, RSL1D1, SCD, SERBP1, SERPINF1, SLC19A1, SLC25A5, SLC25A6, SNAI2, SNHG16, SNHG6, SORD, SOX4, TIMM13, TIMM50, TOP1MT, TRAP1, TUBB4A, TXLNA, TYRP1, UCK2, UQCRFS1, ZFAS1, A2M, AGA, AHNAK, ANXA1, APLP2, APOC2, ARF5, ATP1A1, ATP1B1, ATRAID, B2M, C10orf54, C4A, CBLB, CCND3, CD151, CD47, CD58, CD59, CDH19, CHN1, CLU, CPVL, CST3, CTSB, CTSD, CTSL1, DDR1, DPYSL2, DSCR8, DUSP6, DYNLRB1, EMP1, EZR, FAM3C, FGFR1, FYB, GAA, GATSL3, GRN, GSN, HCP5, HLA-B, HLA-C, HLA-F, HLA-H, HSPA1A, HSPA1B, ID2, IFI27L2, ISCU, ITGA3, ITGA7, ITGB3, KCNN4, KRT10, LOC100506190, LTBP3, LYRM9, MAEL, MAP1B, MATN2, MFGE8, MFI2, MIA, MRPS6, MT2A, NDRG1, NFKBIA, NPC1, OCIAD2, PAGES, PERP, PKM, RDH5, S100A13, S100A6, SERPINA1, SERPINA3, SERPINE2, SGCE, SLC26A2, SLC5A3, SNX9, SPON2, THBD, TIMP1, TM4SF1, TMBIM6, TNFSF4, TPP1, TRIML2, TSC22D3, TSPYL2, TXNIP, UBC, XAGE1A, XAGE1B, XAGE1C, XAGE1D and XAGE1E (exclusion, see table S6); or one or more genes or polypeptides selected from the group consisting of ACTG1, ADSL, C17orf76-AS1, C1QBP, CTPS1, EIF2S3, EIF3E, ILF2, NCL, NF2, NOLC1, PABPC1, PAICS, RPL10A, RPL18, RPL6, RPS24, RSL1D1, SERPINF1, SOX4, AHNAK, ANXA1, CCND3, CD151, CD47, CD58, CST3, CTSB, CTSD, EMP1, FGFR1, HLA-C, HLA-F, ITGB3, KCNN4, MIA, MT2A, S100A6, SLC5A3, TIMP1 and TSC22D3 (exclusion, see FIG. 2H); or one or more genes or polypeptides selected from the group consisting of C17orf76-AS1, C1QBP, CTPS1, EIF2 S3, ILF2, NCL, NOLC1, PABPC1, RPL10A, RPL18, RPL6, RPS24, SERPINF1, SOX4, AHNAK, ANXA1, CCND3, CD151, CD47, CD58, CST3, CTSB, CTSD, EMP1, FGFR1, HLA-C, HLA-F, ITGB3, KCNN4, MIA, MT2A, S100A6, SLC5A3, TIMP1 and TSC22D3 (exclusion, see FIG. 2H).

In certain embodiments, the exclusion signature comprises an exclusion-down signature, said signature comprising one or more genes selected from the group consisting of: A2M, AGA, AHNAK, ANXA1, APLP2, APOC2, ARF5, ATP1A1, ATP1B1, ATRAID, B2M, C10orf54, C4A, CBLB, CCND3, CD151, CD47, CD58, CD59, CDH19, CHN1, CLU, CPVL, CST3, CTSB, CTSD, CTSL1, DDR1, DPYSL2, DSCR8, DUSP6, DYNLRB1, EMP1, EZR, FAM3C, FGFR1, FYB, GAA, GATSL3, GRN, GSN, HCP5, HLA-B, HLA-C, HLA-F, HLA-H, HSPA1A, HSPA1B, ID2, IFI27L2, ISCU, ITGA3, ITGA7, ITGB3, KCNN4, KRT10, LOC100506190, LTBP3, LYRM9, MAEL, MAP1B, MATN2, MFGE8, MFI2, MIA, MRPS6, MT2A, NDRG1, NFKBIA, NPC1, OCIAD2, PAGES, PERP, PKM, RDH5, S100A13, S100A6, SERPINA1, SERPINA3, SERPINE2, SGCE, SLC26A2, SLC5A3, SNX9, SPON2, THBD, TIMP1, TM4SF1, TMBIM6, TNFSF4, TPP1, TRIML2, TSC22D3, TSPYL2, TXNIP, UBC, XAGE1A, XAGE1B, XAGE1C, XAGE1D and XAGE1E (exclusion-down, see table S6); or AHNAK, ANXA1, CCND3, CD151, CD47, CD58, CST3, CTSB, CTSD, EMP1, FGFR1, HLA-C, HLA-F, ITGB3, KCNN4, MIA, MT2A, S100A6, SLC5A3, TIMP1 and TSC22D3 (exclusion-down, see FIG. 2H), wherein said exclusion-down signature is downregulated in a tumor with T cell exclusion and is upregulated in a tumor with T cell infiltration.

In certain embodiments, the exclusion signature comprises an exclusion-up signature, said signature comprising one or more genes selected from the group consisting of: ACAT1, ACP5, ACTG1, ADSL, AK2, APP, ASAP1, ATP5D, BANCR, BCAN, BZW2, C17orf76-AS1, C1QBP, C6orf48, CA14, CCT3, CCT6A, CEP170, CHP1, CTPS1, CYC1, DAP3, DCT, DDX21, EDNRB, EEF1D, EEF1G, EEF2, EIF1AX, EIF2S3, EIF3E, EIF3K, EIF3L, EIF4A1, ESRP1, FAM178B, FAM92A1, FTL, GAS5, GNB2L1, GPI, GSTO1, IFI16, ILF2, IMPDH2, LHFPL3-AS1, LOC100190986, LYPLA1, MARCK5, MDH2, MRPL37, MRPS12, MYC, NCL, NF2, NID1, NOLC1, NPM1, NUCKS1, OAT, PABPC1, PAICS, PLTP, PSAT1, PYCARD, RASA3, RPL10, RPL10A, RPL11, RPL12, RPL13, RPL13A, RPL13 AP5, RPL14, RPL17, RPL18, RPL18A, RPL28, RPL29, RPL3, RPL30, RPL35, RPL37A, RPL39, RPL4, RPL5, RPL6, RPL7, RPL7A, RPL8, RPLP0, RPLP1, RPS10, RPS11, RPS15, RPS15A, RPS16, RPS17, RPS17L, RPS18, RPS19, RPS2, RPS24, RPS27, RPS3, RPS3A, RPS4X, RPS5, RPS7, RPS8, RPS9, RPSA, RSL1D1, SCD, SERBP1, SERPINF1, SLC19A1, SLC25A5, SLC25A6, SNAI2, SNHG16, SNHG6, SORD, SOX4, TIMM13, TIMM50, TOP1MT, TRAP1, TUBB4A, TXLNA, TYRP1, UCK2, UQCRFS1 and ZFAS1 (exclusion-up, see table S6); or ACTG1, ADSL, C17orf76-AS1, C1QBP, CTPS1, EIF2S3, EIF3E, ILF2, NCL, NF2, NOLC1, PABPC1, PAICS, RPL10A, RPL18, RPL6, RPS24, RSL1D1, SERPINF1 and SOX4 (exclusion-up, see FIG. 2H); or C17orf76-AS1, C1QBP, CTPS1, EIF2S3, ILF2, NCL, NOLC1, PABPC1, RPL10A, RPL18, RPL6, RP 524, SERPINF1 and SOX4 (exclusion-up, see FIG. 2H), wherein said exclusion-up signature is upregulated in a tumor with T cell exclusion and is downregulated in a tumor with T cell infiltration.

In certain embodiments, the method according to any embodiment herein further comprises detecting tumor infiltrating lymphocytes (TIL). Not being bound by a theory, detecting tumor infiltration of immune cells is an independent indicator of immunotherapy resistance and progression free survival and combining detection of TILs with any of the above signatures may increase the prognostic value.

In certain embodiments, the gene signature according to any embodiment herein is detected in a bulk tumor sample, whereby the gene signature is detected by deconvolution of bulk expression data such that gene expression is assigned to malignant cells and non malignant cells in said tumor sample.

In certain embodiments, detecting the gene signature comprises detecting downregulation of the down signature and/or upregulation of the up signature. In certain embodiments, not detecting the gene signature comprises detecting upregulation of the down signature and/or downregulation of the up signature. In certain embodiments, detecting the signature and/or TILs indicates lower progression free survival and/or resistance to checkpoint blockade therapy. In certain embodiments, not detecting the signature and/or TILs indicates higher progression free survival and/or sensitivity to checkpoint blockade therapy. In certain embodiments, detecting the gene signature indicates a 10-year survival rate less than 40% and wherein not detecting the signature indicates a 10-year survival rate greater than 60%.

In certain embodiments, detecting an ICR signature in a tumor further comprises detecting in tumor infiltrating lymphocytes (TIL) obtained from the subject in need thereof the expression or activity of a CD8 T cell gene signature, said signature comprising one or more genes or polypeptides selected from the group consisting of CEP19, EXO5, FAM153C, FCRL6, GBP2, GBP5, HSPA1B, IER2, IRF1, KLRK1, LDHA, LOC100506083, MBOAT1, SEMA4D, SIRT3, SPDYE2, SPDYE2L, STAT1, STOM, UBE2Q2P3, ACP5, AKNA, BTN3A2, CCDC141, CD27, CDC42SE1, DDIT4, FAU, FKBP5, GPR56, HAVCR2, HLA-B, HLA-C, HLA-F, IL6ST, ITGA4, KIAA1551, KLF12, MIR155HG, MTA2, MTRNR2L1, MTRNR2L3, PIK3IP1, RPL26, RPL27, RPL27A, RPL35A, RPS11, RPS16, RPS20, RPS26, SPOCK2, SYTL3, TOB1, TPT1, TTN, TXNIP, WNK1 and ZFP36L2. In certain embodiments, detecting an ICR signature in a tumor further comprises detecting in macrophages obtained from the subject in need thereof the expression or activity of a macrophage gene signature, said signature comprising one or more genes or polypeptides selected from the group consisting of APOL1, CD274, CSTB, DCN, HLA-DPB2, HLA-DQA1, HLA-G, HSPA8, HSPB1, IL18BP, TMEM176A, UBD, A2M, ADAP2, ADORA3, ARL4C, ASPH, BCAT1, C11orf31, C3, C3AR1, C6orf62, CAPN2, CD200R1, CD28, CD9, CD99, COMT, CREM, CRTAP, CYFIP1, DDOST, DHRS3, EGFL7, EIFIAY, ETS2, FCGR2A, FOLR2, GATM, GBP3, GNG2, GSTT1, GYPC, HIST1H1E, HPGDS, IFI44L, IGFBP4, ITGA4, KCTD12, LGMN, LOC441081, LTC4S, LYVE1, MERTK, METTL7B, MS4A4A, MS4A7, MTSS1, NLRP3, OLFML3, PLA2G15, PLXDC2, PMP22, POR, PRDX2, PTGS1, RNASE1, ROCK1, RPS4Y1, S100A9, SCAMP2, SEPP1, SESN1, SLC18B1, SLC39A1, SLC40A1, SLC7A8, SORL1, SPP1, STAB1, TMEM106C, TMEM86A, TMEM9, TNFRSF1B, TNFRSF21, TPD52L2, ULK3 and ZFP36L2.

In another aspect, the present invention provides for a method of stratifying cancer patients into a high survival group and a low survival group comprising detecting the expression or activity of an ICR and/or exclusion signature in a tumor according to any embodiment herein, wherein if the signature is detected the patient is in the low survival group and if the signature is not detected the patient is in the high survival group. The patients in the high survival group may be immunotherapy responders and patients in the low survival group may be immunotherapy non-responders.

In another aspect, the present invention provides for a method of treating a cancer in a subject in need thereof comprising detecting the expression or activity of an ICR and/or exclusion signature according to any embodiment herein in a tumor obtained from the subject and administering a treatment, wherein if an ICR and/or exclusion signature is detected the treatment comprises administering an agent capable of reducing expression or activity of said signature, and wherein if an ICR and/or exclusion signature is not detected the treatment comprises administering an immunotherapy. The agent capable of reducing expression or activity of said signature may comprise a CDK4/6 inhibitor, a drug selected from Table 3, a cell cycle inhibitor, a PKC activator, an inhibitor of the NFKB pathway, an IGF1R inhibitor, or Reserpine. The agent capable of reducing expression or activity of said signature may comprise an agent capable of modulating expression or activity of a gene selected from the group consisting of MAZ, NFKBIZ, MYC, ANXA1, SOX4, MT2A, PTP4A3, CD59, DLL3, SERPINE2, SERPINF1, PERP, EGR1, SERPINA3, SEMA3B, SMARCA4, IFNGR2, B2M, and PDL1. The agent capable of reducing expression or activity of said signature may comprise an agent capable of targeting or binding to one or more up-regulated secreted or cell surface exposed ICR and/or exclusion signature genes or polypeptides. The method may further comprise detecting the expression or activity of an ICR and/or exclusion signature according to any embodiment herein in a tumor obtained from the subject after the treatment and administering an immunotherapy if said signature is reduced or below a reference level. The agent capable of reducing expression or activity of said signature may be a CDK4/6 inhibitor. The method may further comprise detecting the expression or activity of an ICR and/or exclusion signature according to any embodiment herein in a tumor obtained from the subject before the treatment and administering an immunotherapy if said signature is not detected or below a reference level.

In certain embodiments, the method further comprises administering an immunotherapy to the subject administered an agent capable of reducing the expression or activity of said signature. The immunotherapy may comprise a check point inhibitor or adoptive cell transfer (ACT). The adoptive cell transfer may comprise a CAR T cell or activated autologous T cells. The checkpoint inhibitor may comprise anti-CTLA4, anti-PD-L1 and/or anti-PD1 therapy.

In another aspect, the present invention provides for a method of treating a cancer in a subject in need thereof comprising detecting the expression or activity of an ICR and/or exclusion signature according to any embodiment herein in a tumor obtained from the subject, wherein if an ICR and/or exclusion signature is detected the treatment comprises administering an agent capable of modulating expression or activity of one or more genes or polypeptides in a network of genes disrupted by perturbation of a gene selected from the group consisting of MAZ, NFKBIZ, MYC, ANXA1, SOX4, MT2A, PTP4A3, CD59, DLL3, SERPINE2, SERPINF1, PERP, EGR1, SERPINA3, SEMA3B, SMARCA4, IFNGR2, B2M, and PDL1.

In another aspect, the present invention provides for a method of treating a cancer in a subject in need thereof comprising administering to the subject a therapeutically effective amount of an agent: capable of modulating the expression or activity of one or more ICR and/or exclusion signature genes or polypeptides according to any embodiment herein; or capable of targeting or binding to one or more cell surface exposed ICR and/or exclusion signature genes or polypeptides, wherein the gene or polypeptide is up-regulated in the ICR and/or exclusion signature; or capable of targeting or binding to one or more receptors or ligands specific for a cell surface exposed ICR and/or exclusion signature gene or polypeptide, wherein the gene or polypeptide is up-regulated in the ICR and/or exclusion signature; or comprising a secreted ICR and/or exclusion signature gene or polypeptide, wherein the gene or polypeptide is down-regulated in the ICR and/or exclusion signature; or capable of targeting or binding to one or more secreted ICR and/or exclusion signature genes or polypeptides, wherein the genes or polypeptides are up-regulated in the ICR and/or exclusion signature; or capable of targeting or binding to one or more receptors specific for a secreted ICR and/or exclusion signature gene or polypeptide, wherein the secreted gene or polypeptide is up-regulated in the ICR and/or exclusion signature; or comprising a CDK4/6 inhibitor, a drug selected from Table 3, a cell cycle inhibitor, a PKC activator, an inhibitor of the NFKB pathway, an IGF1R inhibitor, or Reserpine.

In certain embodiments, the agent comprises a therapeutic antibody, antibody fragment, antibody-like protein scaffold, aptamer, protein, CRISPR system or small molecule.

In certain embodiments, the agent capable of targeting or binding to one or more cell surface exposed ICR and/or exclusion signature polypeptides or one or more receptors specific for a secreted ICR and/or exclusion signature gene or polypeptide comprises a CAR T cell capable of targeting or binding to one or more cell surface exposed ICR and/or exclusion signature genes or polypeptides or one or more receptors specific for a secreted ICR and/or exclusion signature gene or polypeptide.

In certain embodiments, the agent capable of modulating the expression or activity of one or more ICR and/or exclusion signature genes or polypeptides comprises a CDK4/6 inhibitor. The CDK4/6 inhibitor may comprise Abemaciclib.

In certain embodiments, the method further comprises administering an immunotherapy to the subject. The immunotherapy may comprise a check point inhibitor. The checkpoint inhibitor may comprise anti-CTLA4, anti-PD-L1 and/or anti-PD1 therapy.

In another aspect, the present invention provides for a method of monitoring a cancer in a subject in need thereof comprising detecting the expression or activity of an ICR and/or exclusion gene signature according to any embodiment herein in tumor samples obtained from the subject for at least two time points. The at least one sample may be obtained before treatment. The at least one sample may be obtained after treatment.

In certain embodiments, the cancer according to any embodiment herein is melanoma.

In certain embodiments, the ICR and/or exclusion signature is expressed in response to administration of an immunotherapy.

In another aspect, the present invention provides for a method of detecting an ICR signature in a tumor comprising, detecting in tumor cells obtained from a subject in need thereof who has been treated with an immunotherapy the expression or activity of a malignant cell gene signature comprising: a) one or more down regulated genes selected from the group consisting of genes associated with coagulation, apoptosis, TNF-α signaling via NFKb, Antigen processing and presentation, metallothionein and IFNGR2; and/or b) one or more up regulated genes selected from the group consisting of genes associated with negative regulation of angiogenesis and MYC targets.

In another aspect, the present invention provides for a kit comprising reagents to detect at least one ICR and/or exclusion signature gene or polypeptide according to any embodiment herein. The kit may comprise at least one antibody, antibody fragment, or aptamer. The kit may comprise primers and/or probes for quantitative RT-PCR or fluorescently bar-coded oligonucleotide probes for hybridization to RNA.

In another aspect, the present invention provides for a CD8 T cell specific cycling signature (see Table S8). In certain embodiments, modulating target genes in this signature can allow boosting T cell proliferation without activating tumor growth. Not being bound by a theory proliferating CD8 T cells express features that are not present in proliferating malignant cells. In certain embodiments, induction of oxidative phosphorylation and/or repression of hematopoietic lineage genes (e.g., CD37, IL11RA, and IL7R) may increase CD8 T cell proliferation without affecting tumor proliferation.

In another aspect, the present invention provides for a method of detecting an immunotherapy resistance (ITR) gene signature in a tumor comprising, detecting in tumor cells obtained from a subject in need thereof the expression or activity of a malignant cell gene signature comprising:

a) one or more genes or polypeptides selected from the group consisting of ACOT7, ACSL3, ACTN1, ADAM15, ADI1, AEBP1, AGPAT1, AGRN, AHCY, AIF1L, AKAP12, AKT3, ANXA5, APOA1BP, APOD, APOE, ARL2, ARNT2, ARPC1A, ASPH, ATP1A1, ATP1B1, ATP6V0A1, B3GNT1, BACE2, BAIAP2, BCAN, BIRC7, BTBD3, C11orf24, C17orf89, C1orf198, C1orf21, C1orf85, CALD1, CALU, CAPN3, CAV1, CBR1, CCND1, CCT3, CD151, CD276, CD59, CD63, CD9, CDC42BPA, CDC42EP4, CDH19, CDK2, CDK2AP1, CECR7, CELSR2, CERCAM, CERS2, CHCHD6, CHL1, CHPF, CLDN12, CLIC4, CNIH4, CNN3, CNP, CNPY2, COA3, COL16A1, COMT, CRIP2, CRNDE, CRTAP, CRYAB, CSAG1, CSAG3, CSPG4, CSRP1, CTDSPL, CTHRC1, CTNNAL1, CTNNB1, CTSF, CTSK, CTTN, CYB5R1, CYP27A1, CYSTM1, CYTH3, DAAM2, DCBLD2, DCT, DDR1, DDR2, DIP2C, DLC1, DNAH14, DOCK7, DST, DSTN, DUSP6, ECM1, EDNRB, EFNA5, EIF4EBP1, EMP1, ENTPD6, EPS8, ERBB3, ETV4, ETV5, EVA1A, EXOSC4, FAM127A, FAM127B, FAM167B, FARP1, FARP2, FASN, FKBP10, FKBP4, FKBP9, FN1, FNBP1L, FRMD6, FSTL1, FXYD3, G6PC3, GALE, GCSH, GDF15, GJB1, GLI3, GNG12, GOLM1, GPM6B, GPR143, GPRC5B, GSTA4, GSTP1, GULP1, GYG2, H1F0, HIBADH, HMCN1, HMG20B, HOXB7, HOXC10, HSBP1, HSP90AB 1, HSPB1, HSPD1, HSPG2, IFI27, IGF1R, IGFBP7, IGSF11, IGSF3, IGSF8, IMPDH2, ISYNA1, ITFG3, ITGA3, ITGB3, KIRREL, LAMB1, LAMB2, LAMC1, LAPTM4A, LAPTM4B, LDLRAD3, LGALS1, LGALS3BP, LINC00473, LINC00673, LMNA, LOC100126784, LOC100130370, LOC645166, LOXL4, LRP6, MAGEA12, MAGEA2B, MAGEA3, MAGEA6, MAGED1, MAGED2, MAP1B, MARCKSL 1, MDK, MFAP2, MFGE8, MFI2, MGST3, MIA, MIF, MITF, MLANA, MLPH, MMP14, MORF4L2, MORN2, MPZL1, MRPL24, MT2A, MTUS1, MXI1, MYH10, MYO10, MYO1D, NAV2, NCKAP1, ND ST1, NENF, NES, NGFRAP1, NGRN, NHSL1, NID1, NME1, NME2, NME4, NRP2, NRSN2, NSG1, OSBPL1A, P4HA2, PACSIN2, PAX3, PCDHGC3, PEG10, PFDN2, PFKM, PFN2, PGRMC1, PHB, PHLDB1, PIR, PKNOX2, PLEKHB1, PLK2, PLOD1, PLOD3, PLP1, PLS3, PLXNA1, PLXNB3, PMEL, PMP22, POLR2F, POLR2L, PON2, PPT2, PRAME, PRDX4, PRDX6, PRKCDBP, PROS1, PRSS23, PSMB5, PTGFRN, PTGR1, PTK2, PTPLAD1, PTPRM, PTPRS, PTRH2, PTTG1IP, PYCR1, PYGB, PYGL, QDPR, QPCT, RAB13, RAB17, RAB34, RAB38, RAI14, RBFOX2, RCAN1, RCN1, RCN2, RDX, RGS20, RND3, ROBO1, ROPN1, ROPN1B, RTKN, S100A1, S100A13, S100A16, S100B, SCARB1, SCCPDH, SCD, SDC3, SDC4, SDCBP, SELENBP1, SEMA3B, SEMA3C, SEMA6A, SEPT10, SERPINA3, SERPINE2, SERPINH1, SGCD, SGCE, SHC1, SHC4, SLC19A2, SLC24A5, SLC25A13, SLC25A4, SLC35B2, SLC39A1, SLC39A6, SLC45A2, SLC6A15, SLC7A8, SMARCA1, SNAI2, SNCA, SNHG16, SNRPE, SORT1, SOX10, SOX13, SOX4, SPARC, SPR, SPRY4, SPTBN1, SRPX, SSFA2, ST3GAL4, ST5, ST6GALNAC2, STK32A, STMN1, STXBP1, SYNGR1, TANC1, TBC1D16, TBC1D7, TCEAL4, TEAD1, TENC1, TEX2, TFAP2A, TIMP2, TIMP3, TJP1, TMEM147, TMEM14C, TMEM9, TMEM98, TNFRSF19, TOM1L1, TRIM2, TRIM63, TSC22D1, TSPAN3, TSPAN4, TSPAN6, TTLL4, TUBB2A, TUBB2B, TUBB3, TYR, UBL3, VAT1, VIM, VKORC1, WASL, WBP5, WIPI1, WLS, XAGE1A, XAGE1B, XAGE1C, XAGE1D, XAGE1E, XYLB, YWHAE and ZNF462; or b) one or more genes or polypeptides selected from FIG. 3C; or c) one or more genes or polypeptides selected from the group consisting of ABHD2, ACSL4, AHNAK, AHR, AIM2, ANGPTL4, ANXA1, ANXA2, APOD, ATF3, ATP1A1, ATP1B3, BBX, BCL6, BIRC3, BSG, C16orf45, C8orf40, CALU, CARD16, CAV1, CBFB, CCDC109B, CCND3, CD151, CD200, CD44, CD46, CD47, CD58, CD59, CD9, CD97, CDH19, CERS5, CFB, CHI3L2, CLEC2B, CLIC4, COL16A1, COL5A2, CREG1, CRELD1, CRYAB, CSPG4, CST3, CTNNAL1, CTSA, CTSB, CTSD, DCBLD2, DCTN6, EGR1, EMP1, EPDR1, FAM114A1, FAM46A, FCRLA, FN1, FNDC3B, FXYD3, G6PD, GAA, GADD45B, GALNS, GBP2, GEM, GRAMD3, GSTM2, HLA-A, HLA-C, HLA-E, HLA-F, HPCAL1, HSP90B1, HTATIP2, IFI27L2, IFI44, IFI6, IFITM3, IGF1R, IGFBP3, IGFBP7, IL1RAP, ITGA6, ITGB3, ITM2B, JUNB, KCNN4, KIAA1551, KLF4, KLF6, LAMB1, LAMP2, LGALS1, LGALS3BP, LINC00116, LOC100127888, LOXL2, LOXL3, LPL, LXN, MAGEC2, MFI2, MIA, MT1E, MT1F, MT1G, MT1M, MT1X, MT2A, NFE2L1, NFKBIZ, NNMT, NOTCH2, NR4A1, 0S9, P4HA2, PDE4B, PELI1, PIGT, PMAIP1, PNPLA8, PPAPDC1B, PRKCDBP, PRNP, PROS1, PRSS23, PSMB9, PSME1, PTPMT1, PTRF, RAMP1, RND3, RNH1, RPN2, S100A10, S100A6, SCCPDH, SERINC1, SERPINA3, SERPINE1, SERPINE2, SLC20A1, SLC35A5, SLC39A1, SLC5A3, SMIM3, SPARC, SPRY2, SQRDL, STAT1, SUMF1, TAP1, TAPBP, TEKT4P2, TF, TFAP2C, TMEM43, TMX4, TNC, TNFRSF10B, TNFRSF12A, TSC22D3, TSPAN31, UBA7, UBC, UBE2L6, XPO7, ZBTB20, ZDHHC5, ZMYM6NB, ACAA2, ADSL, AEN, AHCY, ALDH1B1, ARHGEF1, ARPC5, ATXN10, ATXN2L, B4GALT3, BCCIP, BGN, C10orf32, C16orf88, C17orf76-AS1, C20orf112, CDCA7, CECR5, CPSF1, CS, CTCFL, CTPS1, DLL3, DTD2, ECHDC1, ECHS1, EIF4A1, EIF4EBP2, EIF6, EML4, ENY2, ESRG, FAM174B, FAM213A, FBL, FBLN1, FDXR, FOXRED2, FXN, GALT, GEMIN8, GLOD4, GPATCH4, HDAC2, HMGN3, HSD17B14, IDH2, ILF2, ISYNA1, KIAA0020, KLHDC8B, LMCD1, LOC100505876, LYPLA1, LZTS2, MAZ, METAP2, MID1, MIR4461, MPDU1, MPZL1, MRPS16, MSTO1, MTG1, MYADM, MYBBP1A, MYL6B, NARS2, NCBP1, NDUFAF6, NDUFS2, NF2, NHEJ1, NME6, NNT, NOLC1, NTHL1, OAZ2, OXA1L, PABPC1, PAICS, PAKIIP1, PFN1, POLR2A, PPA1, PRAME, PRDX3, PSTPIP2, PTGDS, PTP4A3, RBM34, RBM4, RPL10A, RPL17, RPP30, RPS3, RPS7, RPSA, RUVBL2, SAMM50, SBNO1, SERPINF1, SKP2, SLC45A2, SMC3, SMG7, SMS, SNAI2, SORD, SOX4, SRCAP, SRSF7, STARD10, TBXA2R, TH005, TIMM22, TIMM23, TMC6, TOMM22, TPM1, TSNAX, TSR1, TSTA3, TULP4, UBAP2L, UCHL5, UROS, VPS72, WDR6, XPNPEP1, XRCC5, YDJC, ZFP36L1, and ZNF286A; or d) one or more genes or polypeptides selected from the group consisting of AHNAK, AHR, ANXA1, ATP1B3, BBX, BCL6, BIN3, C16orf45, CARD16, CAST, CAV1, CAV2, CD59, CD9, CDH19, CLEC2B, CRYAB, CYSTM1, FAM114A1, FAM46A, FCRLA, FXYD3, G6PD, GBP2, HLA-A, HLA-E, HLA-F, IGF1R, IL1RAP, IL6ST, ITGB1, ITM2B, KCNN4, KLF4, KLF6, LAMP2, LEPROT, LGALS1, LOC100127888, MT1X, MT2A, MVP, NFAT5, NFE2L1, NFKBIZ, PLP2, PROS1, PRSS23, RNF145, S100A10, SEL1L, SERINC1, SERPINA3, SERPINE2, SPRY2, SQRDL, SQSTM1, TAPBP, TF, TMBIM1, TNFRSF10B, TNFRSF12A, UBE2B, and ZBTB20; or e) one or more genes or polypeptides selected from the group consisting of TM4SF1, ANXA1, MT2A, SERPINA3, EMP1, MIA, ITGA3, CDH19, CTSB, SERPINE2, MFI2, APOC2, ITGB8, S100A6, NNMT, SLC5A3, SEMA3B, TSC22D3, ITGB3, MATN2, CRYAB, PERP, CSPG4, SGCE, CD9, A2M, FGFR1, CST3, DDR1, CD59, DPYSL2, KCNN4, SLC26A2, CD151, SLC39A14, AHNAK, ATP1A1, PROS1, TIMP1, TRIML2, EGR1, TNC, DCBLD2, DUSP4, DUSP6, CD58, FAM3C, ATP1B1, MT1E, TNFRSF12A, FXYD3, SCCPDH, GAA, TIMP3, LEF1-AS1, CAV1, MFGE8, NR4A1, LGALS3, CCND3, CALU, RDH5, APOD, LINC00116, IL1RAP, SERPINA1, NFKBIZ, HSPA1A, PRSS23, MAP1B, ITGA7, PLP2, IGFBP7, GSN, LOXL3, PTRF, LGALS1, IGF1R, SERPINE1, MT1X, ATP1B3, SDC3, ZBTB38, NSG1, FCGR2A, KLF4, EGR3, DAG1, CTSD, CPVL, EEA1, SLC20A1, CLU, GBP2, SPON2, TNFSF4, NPC1, PRKCDBP, HTATIP2, C16orf45, SERPINF1, DCT, SNAI2, PTP4A3, RPS19, BCAN, FOXRED2, FAM174B, TRPM1, ESRP1, PABPC1, CA14, TMC6, C17orf76-AS1, RPL13AP5, TP53, BANCR, RPL28, IDH2, LOC100133445, TYRP1, DLL3, LHFPL3-AS1, SCIN, EIF4EBP2, TIMM50, CD68, GPI, MIR4461, RPS27, C1QBP, EGFL8, RPL21, FAM178B, RPS24, SAE1, KLHDC8B, KCNAB2, RPLP0, SCD, TULP4, IL6R, LINC00439, TSTD1, NF2, TUBB4A, SOX4, RPS3, NAPRT1, RPS6, LIMD2, CDKN2A, PTGDS, ISYNA1, ARHGDIB, CNRIP1, H3F3A, TBXA2R, PSTPIP2, SERPINB9, TMEM204, SORD, RPS5, CDH3, RPL18A, RPL8, VPS53, RBM34, FES, ESRG, RPS7, HSD17B14, TTC39A, FBLN1, SLC45A2, AEN, ACP5, BCL11A, CHP1, XIST, MAZ, FAM92A1, CTPS1, ASAP1, RPL6, MARCKS, MAGEA4, NPL, RPS16, NENF, SLC19A1, FTL, RNF2, MYBBP1A, PPAP2C, GRWD1, SKP2, WDR81, DCUN1D2, LAMP2 and MPZL1; or f) one or more genes or polypeptides selected from the group consisting of TM4SF1, MT2A, SERPINA3, CDH19, SERPINE2, CRYAB, SGCE, A2M, DDR1, CD59, DPYSL2, DUSP6, MFGE8, NFKBIZ, and PRSS23; or g) one or more genes or polypeptides selected from the group consisting of SERPINA3, MT2A, SERPINF1, SERPINE2, SOX4, DDR1, CD59, DUSP6, PERP, SEMA3B, PTP4A3, BANCR, DLL3, and LAMP2; or h) one or more genes or polypeptides selected from the group consisting of MT2A, MT1E, MT1X, MT1M, MT1F, MT1G, MTX1 and MTG1.

In one embodiment, the ITR signature further comprises one or more genes or polypeptides selected from the group consisting of IFNGR2, B2M, and PDL1.

In one embodiment, said ITR signature comprises a post-immunotherapy signature-down (PIT-down) module, said module comprising one or more genes selected from the group consisting of: ABHD2, ACSL4, AHNAK, AHR, AIM2, ANGPTL4, ANXA1, ANXA2, APOD, ATF3, ATP1A1, ATP1B3, BBX, BCL6, BIRC3, BSG, C16orf45, C8orf40, CALU, CARD16, CAV1, CBFB, CCDC109B, CCND3, CD151, CD200, CD44, CD46, CD47, CD58, CD59, CD9, CD97, CDH19, CERS5, CFB, CHI3L2, CLEC2B, CLIC4, COL16A1, COL5A2, CREG1, CRELD1, CRYAB, CSPG4, CST3, CTNNAL1, CTSA, CTSB, CTSD, DCBLD2, DCTN6, EGR1, EMP1, EPDR1, FAM114A1, FAM46A, FCRLA, FN1, FNDC3B, FXYD3, G6PD, GAA, GADD45B, GALNS, GBP2, GEM, GRAMD3, GSTM2, HLA-A, HLA-C, HLA-E, HLA-F, HPCAL1, HSP90B1, HTATIP2, IFI27L2, IFI44, IFI6, IFITM3, IGF1R, IGFBP3, IGFBP7, IL1RAP, ITGA6, ITGB3, ITM2B, JUNG, KCNN4, KIAA1551, KLF4, KLF6, LAMB1, LAMP2, LGALS1, LGALS3BP, LINC00116, LOC100127888, LOXL2, LOXL3, LPL, LXN, MAGEC2, MFI2, MIA, MT1E, MT1F, MT1G, MT1M, MT1X, MT2A, NFE2L1, NFKBIZ, NNMT, NOTCH2, NR4A1, OS9, P4HA2, PDE4B, *PELI*1, PIGT, PMAIP1, PNPLA8, PPAPDC1B, PRKCDBP, PRNP, PROS1, PRSS23, PSMB9, PSME1, PTPMT1, PTRF, RAMP1, RND3, RNH1, RPN2, S100A10, S100A6, SCCPDH, SERINC1, SERPINA3, SERPINE1, SERPINE2, SLC20A1, SLC35A5, SLC39A14, SLC5A3, SMIM3, SPARC, SPRY2, SQRDL, STAT1, SUMF1, TAP1, TAPBP, TEKT4P2, TF, TFAP2C, TMEM43, TMX4, TNC, TNFRSF10B, TNFRSF12A, TSC22D3, TSPAN31, UBA7, UBC, UBE2L6, XPO7, ZBTB20, ZDHHC5 and ZMYM6NB; or TM4SF1, ANXA1, MT2A, SERPINA3, EMP1, MIA, ITGA3, CDH19, CTSB, SERPINE2, MFI2, APOC2, ITGB8, 5100A6, NNMT, SLC5A3, SEMA3B, TSC22D3, ITGB3, MATN2, CRYAB, PERP, CSPG4, SGCE, CD9, A2M, FGFR1, CST3, DDR1, CD59, DPYSL2, KCNN4, SLC26A2, CD151, SLC39A14, AHNAK, ATP1A1, PROS1, TIMP1, TRIML2, EGR1, TNC, DCBLD2, DUSP4, DUSP6, CD58, FAM3C, ATP1B1, MT1E, TNFRSF12A, FXYD3, SCCPDH, GAA, TIMP3, LEF1-AS1, CAV1, MFGE8, NR4A1, LGALS3, CCND3, CALU, RDH5, APOD, LINC00116, IL1RAP, SERPINA1, NFKBIZ, HSPA1A, PRSS23, MAP1B, ITGA7, PLP2, IGFBP7, GSN, LOXL3, PTRF, LGALS1, IGF1R, SERPINE1, MT1X, ATP1B3, SDC3, ZBTB38, NSG1, FCGR2A, KLF4, EGR3, DAG1, CTSD, CPVL, EEA1, SLC20A1, CLU, GBP2, SPON2, TNFSF4, NPC1, PRKCDBP, HTATIP2, and C16orf45; or an mICR down gene in FIG. 3C, wherein said PIT-down module is downregulated in a tumor resistant to immunotherapy and upregulated in a tumor sensitive to immunotherapy as compared to a reference level.

In one embodiment, said ITR signature comprises a post-immunotherapy signature-up (PIT-up) module, said module comprising one or more genes selected from the group consisting of: ACAA2, ADSL, AEN, AHCY, ALDH1B1, ARHGEF1, ARPC5, ATXN10, ATXN2L, B4GALT3, BCCIP, BGN, C10orf32, C16orf88, C17orf76-AS1, C20orf112, CDCA7, CECR5, CPSF1, CS, CTCFL, CTPS1, DLL3, DTD2, ECHDC1, ECHS1, EIF4A1, EIF4EBP2, EIF6, EML4, ENY2, ESRG, FAM174B, FAM213A, FBL, FBLN1, FDXR, FOXRED2, FXN, GALT, GEMIN8, GLOD4, GPATCH4, HDAC2, HMGN3, HSD17B14, IDH2, ILF2, ISYNA1, KIAA0020, KLHDC8B, LMCD1, LOC100505876, LYPLA1, LZTS2, MAZ, METAP2, MID1, MIR4461, MPDU1, MPZL1, MRPS16, MSTO1, MTG1, MYADM, MYBBP1A, MYL6B, NARS2, NCBP1, NDUFAF6, NDUFS2, NF2, NHEJ1, NME6, NNT, NOLC1, NTHL1, OAZ2, OXA1L, PABPC1, PAICS, PAK1IP1, PFN1, POLR2A, PPA1, PRAME, PRDX3, PSTPIP2, PTGDS, PTP4A3, RBM34, RBM4, RPL10A, RPL17, RPP30, RPS3, RPS7, RPSA, RUVBL2, SAMM50, SBNO1, SERPINF1, SKP2, SLC45A2, SMC3, SMG7, SMS, SNAI2, SORD, SOX4, SRCAP, SRSF7, STARD10, TBXA2R, TH005, TIMM22, TIMM23, TMC6, TOMM22, TPM1, TSNAX, TSR1, TSTA3, TULP4, UBAP2L, UCHL5, UROS, VPS72, WDR6, XPNPEP1, XRCC5, YDJC, ZFP36L1 and ZNF286A; or SERPINF1, DCT, SNAI2, PTP4A3, RPS19, BCAN, FOXRED2, FAM174B, TRPM1, ESRP1, PABPC1, CA14, TMC6, C17orf76-AS1, RPL13AP5, TP53, BANCR, RPL28, IDH2, LOC100133445, TYRP1, DLL3, LHFPL3-AS1, SCIN, EIF4EBP2, TIMM50, CD68, GPI, MIR4461, RPS27, C1QBP, EGFL8, RPL21, FAM178B, RPS24, SAE1, KLHDC8B, KCNAB2, RPLP0, SCD, TULP4, IL6R, LINC00439, TSTD1, NF2, TUBB4A, SOX4, RPS3, NAPRT1, RPS6, LIMD2, CDKN2A, PTGDS, ISYNA1, ARHGDIB, CNRIP1, H3F3A, TBXA2R, PSTPIP2, SERPINB9, TMEM204, SORD, RPS5, CDH3, RPL18A, RPL8, VPS53, RBM34, FES, ESRG, RPS7, HSD17B14, TTC39A, FBLN1, SLC45A2, AEN, ACP5, BCL11A, CHP1, XIST, MAZ, FAM92A1, CTPS1, ASAP1, RPL6, MARCKS, MAGEA4, NPL, RPS16, NENF, SLC19A1, FTL, RNF2, MYBBP1A, PPAP2C, GRWD1, SKP2, WDR81, DCUN1D2, and MPZL1; or an mICR up gene in FIG. 3C, wherein said PIT-up module is upregulated in a tumor resistant to immunotherapy and downregulated in a tumor sensitive to immunotherapy as compared to a reference level.

Detecting an immunotherapy resistance gene signature in a tumor may further comprise detecting in tumor infiltrating lymphocytes (TIL) obtained from the subject in need thereof the expression or activity of a CD8 T cell gene signature, said signature comprising one or more genes or polypeptides selected from the group consisting of APOBEC3G, CBLB, CCL4, CCL4L1, CCL4L2, CCL5, CD27, CD8A, CD8B, CST7, CTSW, CXCL13, CXCR6, DTHD1, DUSP2, EOMES, FASLG, FCRL3, GBP5, GZMA, GZMB, GZMH, GZMK, HCST, HLA-A, HLA-B, HLA-H, ID2, IFNG, IL2RB, KLRC3, KLRC4, KLRC4-KLRK1, KLRD1, KLRK1, LAG3, LSP1, LYST, NKG7, PDCD1, PRF1, PSTPIP1, PYHIN1, RARRES3, SH2D1A, SH2D2A, TARP, TIGIT, TNFRSF9 and TOX.

Detecting an immunotherapy resistance gene signature in a tumor may further comprise detecting in tumor infiltrating lymphocytes (TIL) obtained from the subject in need thereof the expression or activity of a CD4 T cell gene signature, said signature comprising one or more genes or polypeptides selected from the group consisting of AIM1, ANK3, AQP3, CAMK4, CCR4, CCR8, CD28, CD40LG, DGKA, EML4, FAAH2, FBLN7, FKBP5, FLT3LG, FOXP3, FXYD5, IL6R, IL7R, ITGB2-AS1, JUNB, KLRB1, LEPROTL1, LOC100128420, MAL, OXNAD1, PBXIP1, PIK3IP1, PIM2, PRKCQ-AS1, RORA, RPL35A, RPL4, RPL6, RPS15A, RPS27, RPS28, 6-Sep, SLAMF1, SORL1, SPOCK2, SUSD3, TCF7, TMEM66, TNFRSF18, TNFRSF25, TNFRSF4, TNFSF8, TRABD2A, TSC22D3 and TXK.

Detecting an immunotherapy resistance gene signature in a tumor may further comprise detecting in macrophages obtained from the subject in need thereof the expression or activity of a macrophage gene signature, said signature comprising one or more genes or polypeptides selected from the group consisting of AIF1, ALDH2, ANPEP, C15orf48, C1orf162, C1QA, C1QB, C1QC, C3AR1, CCR1, CD14, CD163, CD300A, CD300C, CD300LF, CD33, CD86, CFP, CLEC10A, CLEC12A, CLEC4A, CLEC5A, CMKLR1, CSF1R, CSF2RB, CSF3R, CSTA, CXCL9, CXCR2P1, DSC2, FAM26F, FBP1, FCER1G, FCGR1A, FCGR1B, FCGR1C, FCGR3A, FCGR3B, FCN1, FOLR2, FPR1, FPR2, FPR3, GGTA1P, GNA15, GPR84, HCK, HK3, IGSF6, IL1B, IL1RN, IL4I1, ITGAM, KYNU, LGALS2, LILRA1, LILRA2, LILRA3, LILRA4, LILRB2, LILRB4, LILRB5, LST1, MAFB, MARCO, MNDA, MRC1, MS4A4A, MS4A6A, MSR1, NCF2, OLR1, P2RY13, PILRA, PLAU, PLBD1, PLXDC2, PRAM1, RAB20, RAB31, RASSF4, RBM47, RGS18, S100A8, S100A9, SECTM1, SIGLEC1, SIGLEC7, SIGLEC9, SLAMF8, SLC31A2, SLC43A2, SLC7A7, SLC8A1, SLCO2B1, SPI1, STAB1, TBXAS1, TFEC, TGFBI, TLR2, TLR4, TLR8, TMEM176A, TMEM176B, TNFSF13, TNFSF13B, TREM2, TYROBP, VSIG4 and ZNF385A.

Detecting an immunotherapy resistance gene signature in a tumor may further comprise detecting in B cells obtained from the subject in need thereof the expression or activity of a B cell gene signature, said signature comprising one or more genes or polypeptides selected from the group consisting of ADAM19, AKAP2, BACH2, BANK1, BCL11A, BLK, CD19, CD1C, CD22, CD79A, CD79B, CLEC17A, CNR2, COL19A1, COL4A3, CPNE5, CR2, CXCR5, EBF1, ELK2AP, FAM129C, FAM177B, FCER2, FCRL1, FCRL2, FCRL5, FCRLA, HLA-DOB, IGJ, IGLL1, IGLL3P, IGLL5, KIAA0125, KIAA0226L, LOC283663, MS4A1, P2RX5, PAX5, PNOC, POU2AF1, POU2F2, RASGRP3, SEL1L3, SNX29P1, ST6GAL1, STAP1, SWAP70, TCL1A, TMEM154 and VPREB3.

The gene signature may be detected in a bulk tumor sample, whereby the gene signature is detected by deconvolution of bulk expression data such that gene expression is assigned to malignant cells and non-malignant cells in said tumor sample.

Detecting the ITR gene signature may comprise detecting downregulation of the PIT-down module and/or upregulation of the PIT-up module. Not detecting the ITR gene signature may comprise detecting upregulation of the PIT-down module and/or downregulation of the PIT-up module.

The detecting an ITR gene signature may indicates a 10-year survival rate less than 40% and wherein not detecting said signature may indicate a 10-year survival rate greater than 60%. The detecting an ITR gene signature may indicate exclusion of T cells from a tumor and wherein not detecting said signature may indicate infiltration of T cells in a tumor.

In another aspect, the present invention provides for a method of stratifying cancer patients into a high survival group and a low survival group comprising detecting the expression or activity of an immunotherapy resistance gene signature in a tumor, wherein if an immunotherapy resistance gene signature is detected the patient is in the low survival group and if an immunotherapy resistance gene signature is not detected the patient is in the high survival group. The patients in the high survival group may be immunotherapy responders and patients in the low survival group may be immunotherapy non-responders.

In another aspect, the present invention provides for a method of treating a cancer in a subject in need thereof comprising detecting the expression or activity of an immunotherapy resistance gene signature according to any of claims 1 to 10 in a tumor obtained from the subject and administering a treatment, wherein if an immunotherapy resistance signature is detected the treatment comprises administering an agent capable of reducing expression or activity of said signature, and wherein if an immunotherapy resistance signature is not detected the treatment comprises administering an immunotherapy. The agent capable of reducing expression or activity of said signature may comprise a drug selected from Table 3, a PKC activator, an inhibitor of the NFKB pathway, an IGF1R inhibitor, or Reserpine. The agent capable of reducing expression or activity of said signature may comprise an agent capable of modulating expression or activity of a gene selected from the group consisting of MAZ, NFKBIZ, MYC, ANXA1, SOX4, MT2A, PTP4A3, CD59, DLL3, SERPINE2, SERPINF1, PERP, EGR1, SERPINA3, SEMA3B, SMARCA4, IFNGR2, B2M, and PDL1. The agent capable of reducing expression or activity of said signature may comprise an agent capable of targeting or binding to one or more up-regulated secreted or cell surface exposed immunotherapy resistance signature genes or polypeptides. The method may further comprise detecting the expression or activity of an immunotherapy resistance gene signature in a tumor obtained from the subject after the treatment and administering an immunotherapy if said signature is not detected. The method may further comprise administering an immunotherapy to the subject administered an agent capable of reducing the expression or activity of said signature. The immunotherapy may comprise a check point inhibitor or adoptive cell transfer (ACT). The adoptive cell transfer may comprise a CAR T cell or activated autologous T cells. The checkpoint inhibitor may comprise anti-CTLA4, anti-PD-L1 and/or anti-PD1 therapy.

In another aspect, the present invention provides for a method of treating a cancer in a subject in need thereof comprising detecting the expression or activity of an immunotherapy resistance gene signature according to any embodiment herein in a tumor obtained from the subject, wherein if an immunotherapy resistance signature is detected the treatment comprises administering an agent capable of modulating expression or activity of one or more genes or polypeptides in a network of genes disrupted by perturbation of a gene selected from the group consisting of MAZ, NFKBIZ, MYC, ANXA1, SOX4, MT2A, PTP4A3, CD59, DLL3, SERPINE2, SERPINF1, PERP, EGR1, SERPINA3, SEMA3B, SMARCA4, IFNGR2, B2M, and PDL1.

In another aspect, the present invention provides for a method of treating a cancer in a subject in need thereof comprising administering to the subject a therapeutically effective amount of an agent: capable of modulating the expression or activity of one or more immunotherapy resistance signature genes or polypeptides; or capable of targeting or binding to one or more cell surface exposed immunotherapy resistance signature genes or polypeptides, wherein the gene or polypeptide is up-regulated in the ITR signature; or capable of targeting or binding to one or more receptors or ligands specific for a cell surface exposed immunotherapy resistance signature gene or polypeptide, wherein the gene or polypeptide is up-regulated in the ITR signature; or comprising a secreted immunotherapy resistance signature gene or polypeptide, wherein the gene or polypeptide is down-regulated in the ITR signature; or capable of targeting or binding to one or more secreted immunotherapy resistance signature genes or polypeptides, wherein the genes or polypeptides are up-regulated in the ITR signature; or capable of targeting or binding to one or more receptors specific for a secreted immunotherapy resistance signature gene or polypeptide, wherein the secreted gene or polypeptide is up-regulated in the ITR signature; or comprising a drug selected from Table 3, a PKC activator, an inhibitor of the NFKB pathway, an IGF1R inhibitor, or Reserpine. The agent capable of modulating the expression or activity of one or more immunotherapy resistance signature genes or polypeptides may comprise a CDK4/6 inhibitor. The CDK4/6 inhibitor may comprise Abemaciclib. The method may further comprise administering an immunotherapy to the subject. The immunotherapy may comprise a check point inhibitor. The checkpoint inhibitor may comprise anti-CTLA4, anti-PD-L1 and/or anti-PD1 therapy. Not being bound by a theory, the CDK4/6 inhibitor may sensitize a subject to checkpoint blockade therapy. The agent may comprise a therapeutic antibody, antibody fragment, antibody-like protein scaffold, aptamer, protein, CRISPR system or small molecule. The agent capable of targeting or binding to one or more cell surface exposed immunotherapy resistance signature polypeptides or one or more receptors specific for a secreted immunotherapy resistance signature gene or polypeptide may comprise a CAR T cell capable of targeting or binding to one or more cell surface exposed immunotherapy resistance signature genes or polypeptides or one or more receptors specific for a secreted immunotherapy resistance signature gene or polypeptide.

In another aspect, the present invention provides for a method of monitoring a cancer in a subject in need thereof comprising detecting the expression or activity of an immunotherapy resistance gene signature according to any embodiment herein in tumor samples obtained from the subject for at least two time points. The at least one sample may be obtained before treatment. The at least one sample may be obtained after treatment.

The cancer according to any embodiment may be melanoma. The ITR gene signature may be expressed in response to administration of an immunotherapy.

In another aspect, the present invention provides for a method of detecting T cell infiltration of a tumor comprising detection in malignant cells expression or activity of one or more genes selected from the group consisting of: HLA-C, FGFR1, ITGB3, CD47, AHNAK, CTSD, TIMP1, SLC5A3, CST3, CD151, CCND3, MIA, CD58, CTSB, S100A6, EMP1, HLA-F, TSC22D3, ANXA1, KCNN4 and MT2A; or A2M, AEBP1, AHNAK, ANXA1, APOC2, APOD, APOE, ATP1A1, ATP1B1, C4A, CAPN3, CAV1, CD151, CD59, CD63, CDH19, CRYAB, CSPG4, CSRP1, CST3, CTSB, CTSD, DAG1, DDR1, DUSP6, ETV5, EVA1A, FBXO32, FCGR2A, FGFR1, GAA, GATSL3, GJB1, GRN, GSN, HLA-B, HLA-C, HLA-F, HLA-H, IFI35, IGFBP7, IGSF8, ITGA3, ITGA7, ITGB3, LAMP2, LGALS3, LOXL4, LRPAP1, LY6E, LYRM9, MATN2, MFGE8, MIA, MPZ, MT2A, MTRNR2L3, MTRNR2L6, NPC1, NPC2, NSG1, PERP, PKM, PLEKHB1, PROS1, PRSS23, PYGB, RDH5, ROPN1, S100A1, S100A13, S100A6, S100B, SCARB2, SCCPDH, SDC3, SEMA3B, SERPINA1, SERPINA3, SERPINE2, SGCE, SGK1, SLC26A2, SLC5A3, SPON2, SPP1, TIMP1, TIMP2, TIMP3, TM4SF1, TMEM255A, TMX4, TNFSF4, TPP1, TRIML2, TSC22D3, TXNIP, TYR, UBC and WBP2; or HLA-A, HLA-B, HLA-C, B2M, TAPBP, IFI27, IFI35, IRF4, IRF9 and STAT2; or B2M, CTSB, CTSL1, HLA-B/C/F, HSPA1A, HSPA1B, NFKBIA and CD58, wherein detection indicates sensitivity to immunotherapy.

In another aspect, the present invention provides for a method of detecting T cell exclusion of a tumor comprising detection in malignant cells expression or activity of one or more genes selected from the group consisting of: SERPINF1, RPL6, NOLC1, RSL1D1, ILF2, SOX4, ACTG1, C7orf76-AS1, PABPC1, RPS24, ADSL, C1QBP, PAICS, CTPS1, NF2, EIF2S3, RPL18 and RPL10A; or AHCY, BZW2, CCNB1IP1, CCT6A, EEF2, EIF3B, GGCT, ILF3, IMPDH2, MDH2, MYBBP1A, NT5DC2, PAICS, PFKM, POLD2, PTK7, SLC19A1, SMARCA4, STRAP, TIMM13, TOP1MT, TRAP1 and USP22; or MYC, STRAP and SMARCA4; or MYC, SNAI2 and SOX4, wherein detection indicates resistance to immunotherapy.

In another aspect, the present invention provides for a method of detecting an immunotherapy resistance gene signature in a tumor comprising, detecting in tumor cells obtained from a subject in need thereof who has been treated with an immunotherapy the expression or activity of a malignant cell gene signature comprising: one or more down regulated genes selected from the group consisting of genes associated with coagulation, apoptosis, TNF-α signaling via Nhcb, Antigen processing and presentation, metallothionein and IFNGR2, and/or one or more up regulated genes selected from the group consisting of genes associated with negative regulation of angiogenesis and MYC targets.

In another aspect, the present invention provides for a kit comprising reagents to detect at least one immunotherapy resistance signature gene or polypeptide according to the present invention. The kit may comprise at least one antibody, antibody fragment, or aptamer. The kit may comprise primers and/or probes for quantitative RT-PCR or fluorescently bar-coded oligonucleotide probes for hybridization to RNA.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

The following detailed description, given by way of example, but not intended to limit the invention solely to the specific embodiments described, may best be understood in conjunction with the accompanying drawings.

FIG. 6 illustrates non-malignant cells. Shown are tSNE plots of all non malignant cells (dots), shaded by (A) OE scores (bar) of well-established cell type markers (table S3), or (B) detection of CD4 or CD8 (CD8A or CD8B).

FIG. 7 illustrates cell type specific ICR signatures. Left panels: Box-plots show the distribution of OE scores for the ICR signature in each cell type in ICR (blue) and TN (grey) patients. Middle line: median; box edges: 25th and 75th percentiles; whiskers: most extreme points that do not exceed ±IQR*1.5; points beyond the distance: single points. Middle and right panels: Receiver Operating Characteristic (ROC) curves of the performances of different signatures in classifying cells (middle) or samples (left) as ICR or TN. (A) Malignant cells, (B) CD4 T cells, (C) CD8 T cells, (D) B cells, (E) macrophages.

FIG. 8 illustrates the shift in the balance of cytotoxicity and exhaustion states in CD8 T-cells in the patient with CB. (A) The distribution of expression levels of each of five key checkpoint genes in CD8 T cells from ICR, TN, and CB tumors. (B) Distinct relationship between exhaustion and cytotoxicity signatures in CD8 T cells from a CB patient. For each cell (dot) shown are the cytotoxicity (x-axis) and exhaustion (y-axis) scores (materials and methods), using different exhaustion signatures from (1) and (17). TN; ICR; CB. Cells from the CB patient have lower than expected exhaustion scores (p-values, hypergeometric test materials and methods).

FIG. 9 illustrates clonal expansion of CD8 T cells. (A) TCR reconstruction. Shown is the fraction (y-axis) of T-cells with one (α or β), both or no TCR chain reconstructed at full length (materials and methods). (B) Variation in CD8 T cell expansion across tumors. Violin plots show the distribution of estimated proportions of CD8 T cell clones in each tumor. Tumors are shaded by treatment group. The tumors of ICR patients have higher T-cell clonal expansion (P=3.2*10⁻², one-sided Wilcoxon ranksum test). (C,D) Persistence of clones over time in one patient (Mel75). Shown are the number (C) and relative proportions (D) of cells in each clone for two post-ICI lesions collected, a year apart, from patient Mel75.

FIG. 11 illustrates that the resistance signatures score in TCGA tumors predict survival of melanoma patients. Kaplan-Meier (KM) plots stratified by high, intermediate or low OE of the respective signature in bulk RNA-Seq of TCGA tumors. Pc p-values test if the signature further enhances the predictive power of models with inferred T-cell infiltration levels as a covariate.

FIG. 12 illustrates that the resistance signature scores in pre-treatment biopsies predict response to anti-PD-1 therapy in an independent cohort. KM plots of progression-free survival (PFS) for the 104 of 112 patients in validation cohort 1 with PFS data, with patients stratified by high, intermediate and low OE score of the respective signature. Pc p-values test if the signature further enhances the predictive power of models with inferred T cell infiltration levels as a covariate.

FIG. 13 illustrates that the predictive performance of resistance signatures is enhanced when controlling for the cell cycle. KM plots of progression-free survival (PFS) for the 104 of 112 patients in validation cohort 1 with PFS data, with patients stratified by high, intermediate and low OE score of the respective, after controlling for cell cycle as a confounding factor (materials and methods).

FIG. 32 illustrates analysis of CD8 T cells.

FIG. 52. Co-variation of the resistance signature genes across single-cells within each tumor; related to FIG. 46. Gene-gene Pearson correlation coefficients (bar) between the genes in the resistance program, across individual malignant cells from each specific tumor (as labeled). Genes are sorted in the same order in all heatmaps (and in FIG. 46D). The consistent intra-tumor correlation suggests shared regulation.

FIG. 55. The immune resistance program predicts response to anti-PD-1 therapy in an independent cohort; related to FIG. 48. (A-E) KM plots of progression-free survival (PFS) for the 104 of 112 patients in validation cohort 2 with PFS data, with patients stratified by high, intermediate and low over expression values of the respective signature, after controlling for cell cycle as a confounding factor (Methods). Pc p-values test if the signature further enhances the predictive power of models with inferred T cell infiltration levels as a covariate. (F) Distribution of overall expression values (y axis) of each signature in the pre-treatment bulk RNA-Seq profiles, showing overall 101 patients with either complete response (CR, n=14), partial response/stable disease (PR/SD, n=38), or progressive disease (PD, n=49). P is the one-sided t-test p-value obtained when comparing CR patients vs. PR, SD and PD patients. AUC is also marked on top. Middle line: median; box edges: 25th and 75th percentiles, whiskers: most extreme points that do not exceed ±IQR*1.5; further outliers are marked individually.

DETAILED DESCRIPTION OF THE EXAMPLE EMBODIMENTS

General Definitions

Figure 1A:
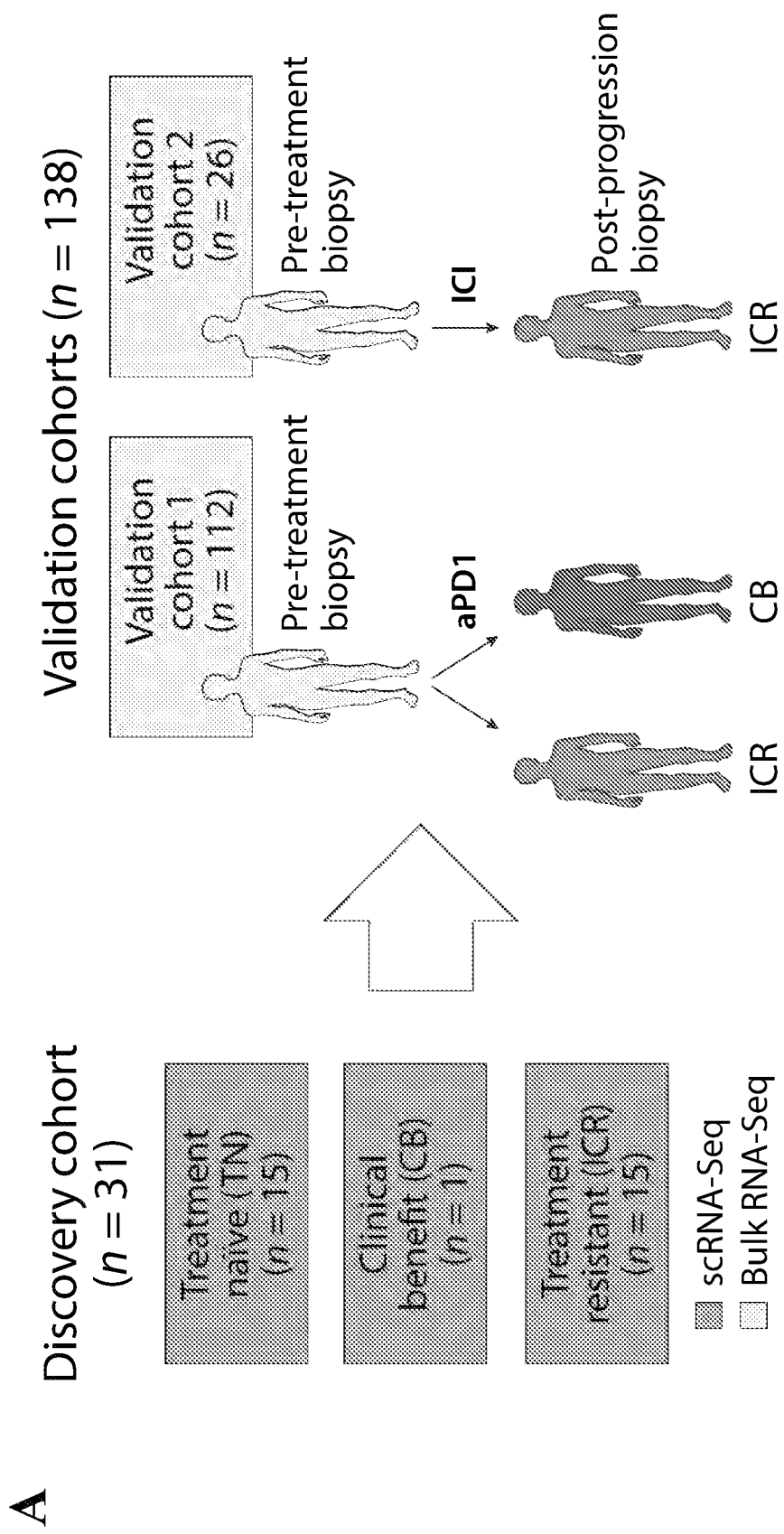
FIG. 1 illustrates the study design and T cell analysis of ICR. (A) Overview. 31 samples from patients with metastatic melanoma (discovery cohort) were profiled by scRNA-sequencing (left), of which 15 were TN, 15 had ICI resistance (ICR) and one had clinical benefit (CB). Signatures were tested in two validation cohorts collected independently (right), with bulk RNA-seq of melanoma tumors from 112 patients who underwent biopsies prior to receiving pembrolizumab (anti-PD-1; cohort 1) and from 26 patients, 12 with matched pre treatment and post-progression (ICR) biopsies (cohort 2). (B-C) Distinct profiles of malignant and non-malignant cells. Shown are tSNE plots of single-cell profiles (dots) from malignant (B) or non-malignant (C) cells, shaded by post-hoc annotation (materials and methods) or by patient. (D) Variation in T cells ICR. Shown is a tSNE plot of CD8 T cells that Applicants generated based on the genes of the tICR signatures, with cells shaded by treatment category (right), overall expression (OE) of the tICR signature (middle), and clonality (right). Larger dots: cells from large (>20 cells) clones. (E) Similar relationship between exhaustion and cytotoxicity signatures in TN and ICR CD8 T cells. For each cell (dot), the exhaustion (y axis) and cytotoxicity (x axis) scores are shown (materials and methods).: TN;: ICR;: CB. Cells from the CB patient have lower than expected exhaustion scores. (F) CD8 T cell clones. Shown is the distribution of clone sizes. Tumors with large (>20 cells) clones are marked. (G) Expanded clones have higher tICR expression. Box plots show the distribution of tICR OE scores (y axis) in CD8 T-cells from patients stratified by clinical context and by overall clonality level. Left: only CD8 T-cells with reconstructed TCRs are shown; Right: only CD8 T-cells that were not from the three ICR patients with major clonal expansion are shown (right). Box-plots: the middle line represents the median; box edges are the $25^{th}$ and $75^{th}$ percentiles, and whiskers represent the most extreme points that do not exceed ±IQR*1.5; points beyond the distance are plotted as single points. (H) CD8 T cell specific cell-cycle program. Shown are the distribution of OE scores for the CD8 specific cell cycle program in malignant cells (left) and CD8 T cells (right). The p-values were computed by comparing the cycling and non-cycling cells in each cell type with a one-sided t-test.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.); PCR 2: A Practical Approach (1995) (M. J. MacPherson, B. D. Hames, and G. R. Taylor eds.); Antibodies, A Laboratory Manual (1988) (Harlow and Lane, eds.); Antibodies A Laboraotry Manual, 2nd edition 2013 (E. A. Greenfield ed.); Animal Cell Culture (1987) (R.I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011)

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods and compositions for detecting and modulating an immunotherapy resistance gene signature in cancer. Embodiments disclosed herein also provide for diagnosing, prognosing, monitoring and treating tumors based on detection of an immunotherapy resistance gene signature.

As used herein, the immunotherapy resistance signature is referred to as "ITR", "immunotherapy resistance signature", "ICR", "immune checkpoint inhibitor resistance", "mICR", "malignant immune checkpoint inhibitor resistance", "PIT", "post-immunotherapy", "oncogenic-ICR", "unified-ICR", "uICR", "uICR-up", "uICR-down", "refined uICR", "immune resistant", "refined immune resistant", "post treatment", "exclusion-up", or "exclusion-down". All of these terms may be used in reference to a gene signature in malignant cells from a subject that is resistant to immune checkpoint inhibitors (ICI). In regards to the exclusion signatures, these signatures refer to signatures in malignant cells that correlate to immune cell exclusion. In other words, exclusion-up refers to genes that are upregulated in malignant cells and that are correlated with exclusion, while exclusion-down refer to genes downregulated in malignant cells that are correlated with exclusion. In certain embodiments, exclusion-down refers to genes upregulated when there is immune cell infiltration and thus can be referred to as the infiltration signature. In regards to "oncogenic ICR", "mICR", "malignant immune checkpoint inhibitor resistance", "Post-treatment", "PIT", or "post-immunotherapy", these terms all refer to genes differentially expressed in malignant cells after immunotherapy. "Immune resistance", "unified-ICR" or "uICR" refers to all genes in the exclusion signature and post treatment signature. The "refined uICR" and "refined immune resistant" are shortened lists from the immune resistance signature that include the best performing genes from the exclusion and post treatment signatures for predicting immunotherapy sensitivity. In regards to CD8 T cells "tICR" refers to T cell immune checkpoint inhibitor resistance signature.

As used herein the term "cancer-specific survival" refers to the percentage of patients with a specific type and stage of cancer who have not died from their cancer during a certain period of time after diagnosis. The period of time may be 1 year, 2 years, 5 years, etc., with 5 years being the time period most often used. Cancer-specific survival is also called disease-specific survival. In most cases, cancer-specific survival is based on causes of death listed in medical records.

As used herein the term "relative survival" refers to a method used to estimate cancer-specific survival that does not use information about the cause of death. It is the percentage of cancer patients who have survived for a certain period of time after diagnosis compared to people who do not have cancer.

As used herein the term "overall survival" refers to the percentage of people with a specific type and stage of cancer who have not died from any cause during a certain period of time after diagnosis.

As used herein the term "disease-free survival" refers to the percentage of patients who have no signs of cancer during a certain period of time after treatment. Other names for this statistic are recurrence-free or progression-free survival.

As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., immune evading tumor cells, immunotherapy resistant tumor cells, tumor infiltrating lymphocytes, macrophages). In certain embodiments, the expression of the immunotherapy resistant, T cell signature and/or macrophage signature is dependent on epigenetic modification of the genes or regulatory elements associated with the genes. Thus, in certain embodiments, use of signature genes includes epigenetic modifications that may be detected or modulated. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity may be compared between different cells in order to characterize or identify for instance signatures specific for cell (sub)populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and/or down-regulated genes that are representative of a cell type or subtype. A gene signature as used herein, may also refer to any set of up- and/or down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular pathological condition, or linked to a particular outcome or progression of the disease, or linked to a particular response to treatment of the disease (e.g. resistance to immunotherapy).

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different immune cells or immune cell (sub)populations (e.g., T cells), as well as comparing immune cells or immune cell (sub)populations with other immune cells or immune cell (sub)populations. It is to be understood that "differentially expressed" genes/proteins include genes/proteins which are up- or down-regulated as well as genes/proteins which are turned on or off. When referring to up-or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single-cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type (e.g., resistant) which can be distinguished or are uniquely identifiable and set apart from other cells of this cell type. The cell subpopulation may be phenotypically characterized, and is preferably characterized by the signature as discussed herein. A cell (sub) population as referred to herein may constitute of a (sub) population of cells of a particular cell type characterized by a specific cell state.

When referring to induction, or alternatively reducing or suppression of a particular signature, preferable is meant induction or alternatively reduction or suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signature, and/or other genetic or epigenetic signature based on single-cell analyses (e.g. single-cell RNA sequencing) or alternatively based on cell population analyses, as is defined herein elsewhere.

The invention further relates to various uses of the gene signatures, protein signature, and/or other genetic or epigenetic signature as defined herein, as well as various uses of the immune cells or immune cell (sub)populations as defined herein. Particular advantageous uses include methods for identifying agents capable of inducing or suppressing particular immune cell (sub)populations based on the gene signatures, protein signature, and/or other genetic or epigenetic signature as defined herein. The invention further relates to agents capable of inducing or suppressing particular immune cell (sub)populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular gene signature, protein signature, and/or other genetic or epigenetic signature may modify overall immune composition, such as immune cell composition, such as immune cell subpopulation composition or distribution, or functionality.

The signature genes of the present invention were discovered by analysis of expression profiles of single-cells within a population of tumor cells, thus allowing the discovery of novel cell subtypes that were previously invisible in a population of cells within a tumor. The presence of subtypes may be determined by subtype specific signature genes. The presence of these specific cell types may be determined by applying the signature genes to bulk sequencing data in a patient. Not being bound by a theory, many cells that make up a microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression in a tumor. The signature genes may indicate the presence of one particular cell type. In one embodiment, the expression may indicate the presence of immunotherapy resistant cell types. Not being bound by a theory, a combination of cell subtypes in a subject may indicate an outcome (e.g., resistant cells, cytotoxic T cells, Tregs).

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signature of the present may be used to screen for drugs that reduce the signature in cancer cells or cell lines having a resistant signature as described herein. The signature may be used for GE-HTS. In certain embodiments, pharmacological screens may be used to identify drugs that are selectively toxic to cancer cells having an immunotherapy resistant signature. In certain embodiments, drugs selectively toxic to cancer cells having an immunotherapy resistant signature are used for treatment of a cancer patient. In certain embodiments, cells having an immunotherapy resistant signature as described herein are treated with a plurality of drug candidates not toxic to non-tumor cells and toxicity is assayed.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). Cmap can be used to screen for a signature in silico.

In one embodiment, the signature genes may be detected by immunofluorescence, immunohistochemistry, fluorescence activated cell sorting (FACS), mass cytometry (CyTOF), Drop-seq, RNA-seq, scRNA-seq, InDrop, single-cell qPCR, MERFISH (multiplex (in situ) RNA FISH) and/or by in situ hybridization. Other methods including absorbance assays and colorimetric assays are known in the art and may be used herein.

All gene name symbols refer to the gene as commonly known in the art. The examples described herein refer to the human gene names and it is to be understood that the present invention also encompasses genes from other organisms (e.g., mouse genes). Gene symbols may be those referred to by the HUGO Gene Nomenclature Committee (HGNC) or National Center for Biotechnology Information (NCBI). Any reference to the gene symbol is a reference made to the entire gene or variants of the gene. The signature as described herein may encompass any of the genes described herein. In certain embodiments, the gene signature includes surface expressed and secreted proteins. Not being bound by a theory, surface proteins may be targeted for detection and isolation of cell types, or may be targeted therapeutically to modulate an immune response.

As used herein, "modulating" or "to modulate" generally means either reducing or inhibiting the expression or activity of, or alternatively increasing the expression or activity of a target gene. In particular, "modulating" or "to modulate" can mean either reducing or inhibiting the activity of, or alternatively increasing a (relevant or intended) biological activity of, a target or antigen as measured using a suitable in vitro, cellular or in vivo assay (which will usually depend on the target involved), by at least 5%, at least 10%, at least 25%, at least 50%, at least 60%, at least 70%, at least 80%, at least 90%, or more, compared to activity of the target in the same assay under the same conditions but without the presence of an agent. An "increase" or "decrease" refers to a statistically significant increase or decrease respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more. "Modulating" can also involve effecting a change (which can either be an increase or a decrease) in affinity, avidity, specificity and/or selectivity of a target or antigen, such as a receptor and ligand. "Modulating" can also mean effecting a change with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable assay known or described herein (e.g., in vitro or cellular assay), depending on the target or antigen involved.

Modulating can, for example, also involve allosteric modulation of the target and/or reducing or inhibiting the binding of the target to one of its substrates or ligands and/or competing with a natural ligand, substrate for binding to the target. Modulating can also involve activating the target or the mechanism or pathway in which it is involved. Modulating can for example also involve effecting a change in respect of the folding or confirmation of the target, or in respect of the ability of the target to fold, to change its conformation (for example, upon binding of a ligand), to associate with other (sub)units, or to disassociate. Modulating can for example also involve effecting a change in the ability of the target to signal, phosphorylate, dephosphorylate, and the like.

Modulating Agents

As used herein, an "agent" can refer to a protein-binding agent that permits modulation of activity of proteins or disrupts interactions of proteins and other biomolecules, such as but not limited to disrupting protein-protein interaction, ligand-receptor interaction, or protein-nucleic acid interaction. Agents can also refer to DNA targeting or RNA targeting agents. Agents may include a fragment, derivative and analog of an active agent. The terms "fragment," "derivative" and "analog" when referring to polypeptides as used herein refers to polypeptides which either retain substantially the same biological function or activity as such polypeptides. An analog includes a proprotein which can be activated by cleavage of the proprotein portion to produce an active mature polypeptide. Such agents include, but are not limited to, antibodies ("antibodies" includes antigen-binding portions of antibodies such as epitope- or antigen-binding peptides, paratopes, functional CDRs; recombinant antibodies; chimeric antibodies; humanized antibodies; nanobodies; tribodies; midibodies; or antigen-binding derivatives, analogs, variants, portions, or fragments thereof), protein-binding agents, nucleic acid molecules, small molecules, recombinant protein, peptides, aptamers, avimers and protein-binding derivatives, portions or fragments thereof. An "agent" as used herein, may also refer to an agent that inhibits expression of a gene, such as but not limited to a DNA targeting agent (e.g., CRISPR system, TALE, Zinc finger protein) or RNA targeting agent (e.g., inhibitory nucleic acid molecules such as RNAi, miRNA, ribozyme).

The agents of the present invention may be modified, such that they acquire advantageous properties for therapeutic use (e.g., stability and specificity), but maintain their biological activity.

It is well known that the properties of certain proteins can be modulated by attachment of polyethylene glycol (PEG) polymers, which increases the hydrodynamic volume of the protein and thereby slows its clearance by kidney filtration. (See, e.g., Clark et al., J. Biol. Chem. 271: 21969-21977 (1996)). Therefore, it is envisioned that certain agents can be PEGylated (e.g., on peptide residues) to provide enhanced therapeutic benefits such as, for example, increased efficacy by extending half-life in vivo. In certain embodiments, PEGylation of the agents may be used to extend the serum half-life of the agents and allow for particular agents to be capable of crossing the blood-brain barrier.

In regards to peptide PEGylation methods, reference is made to Lu et al., Int. J. Pept. Protein Res. 43: 127-38 (1994); Lu et al., Pept. Res. 6: 140-6 (1993); Felix et al., Int. J. Pept. Protein Res. 46: 253-64 (1995); Gaertner et al., Bioconjug. Chem. 7: 38-44 (1996); Tsutsumi et al., Thromb. Haemost. 77: 168-73 (1997); Francis et al., hit. J. Hematol. 68: 1-18 (1998); Roberts et al., J. Pharm. Sci. 87: 1440-45 (1998); and Tan et al., Protein Expr. Purif. 12: 45-52 (1998). Polyethylene glycol or PEG is meant to encompass any of the forms of PEG that have been used to derivatize other proteins, including, but not limited to, mono-(C1-10) alkoxy or aryloxy-polyethylene glycol. Suitable PEG moieties include, for example, 40 kDa methoxy poly(ethylene glycol) propionaldehyde (Dow, Midland, Mich.); 60 kDa methoxy poly(ethylene glycol) propionaldehyde (Dow, Midland, Mich.); 40 kDa methoxy poly(ethylene glycol) maleimido-propionamide (Dow, Midland, Mich.); 31 kDa alpha-methyl-w-(3-oxopropoxy), polyoxyethylene (NOF Corporation, Tokyo); mPEG2-NHS-40k (Nektar); mPEG2-MAL-40k (Nektar), SUNBRIGHT GL2-400MA ((PEG)240 kDa) (NOF Corporation, Tokyo), SUNBRIGHT ME-200MA (PEG20 kDa) (NOF Corporation, Tokyo). The PEG groups are generally attached to the peptide (e.g., neuromedin U receptor agonists or antagonists) via acylation or alkylation through a reactive group on the PEG moiety (for example, a maleimide, an aldehyde, amino, thiol, or ester group) to a reactive group on the peptide (for example, an aldehyde, amino, thiol, a maleimide, or ester group).

The PEG molecule(s) may be covalently attached to any Lys, Cys, or K(CO(CH2)2SH) residues at any position in a peptide. In certain embodiments, the neuromedin U receptor agonists described herein can be PEGylated directly to any amino acid at the N-terminus by way of the N-terminal amino group. A "linker arm" may be added to a peptide to facilitate PEGylation. PEGylation at the thiol side-chain of cysteine has been widely reported (see, e.g., Caliceti & Veronese, Adv. Drug Deliv. Rev. 55: 1261-77 (2003)). If there is no cysteine residue in the peptide, a cysteine residue can be introduced through substitution or by adding a cysteine to the N-terminal amino acid.

Substitutions of amino acids may be used to modify an agent of the present invention. The phrase "substitution of amino acids" as used herein encompasses substitution of amino acids that are the result of both conservative and non-conservative substitutions. Conservative substitutions are the replacement of an amino acid residue by another similar residue in a polypeptide. Typical but not limiting conservative substitutions are the replacements, for one another, among the aliphatic amino acids Ala, Val, Leu and Ile; interchange of Ser and Thr containing hydroxy residues, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met, and Gly. Non-conservative substitutions are the replacement, in a polypeptide, of an amino acid residue by another residue which is not biologically similar. For example, the replacement of an amino acid residue with another residue that has a substantially different charge, a substantially different hydrophobicity, or a substantially different spatial configuration.

The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, VHH and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, IgM antibodies exist in pentameric form, and IgA antibodies exist in monomeric, dimeric or multimeric form.

The term "IgG subclass" refers to the four subclasses of immunoglobulin class IgG—IgG1, IgG2, IgG3, and IgG4 that have been identified in humans and higher mammals by the heavy chains of the immunoglobulins, γ1-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by 0 pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins-harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 µM. Antibodies with affinities greater than $1\times10^7$ $M^{-1}$ (or a dissociation coefficient of 1 µM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the $C_H1$ domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')2 fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_h1$-$V_H$-$C_h1$) which, together with complementary light chain polypeptides, form a pair of antigen binding regions (Zapata et al., Protein Eng. 8(10): 1057-62 (1995); and U.S. Pat. No. 5,641,870).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

The disclosure also encompasses nucleic acid molecules, in particular those that inhibit a signature gene. Exemplary nucleic acid molecules include aptamers, siRNA, artificial microRNA, interfering RNA or RNAi, dsRNA, ribozymes, antisense oligonucleotides, and DNA expression cassettes encoding said nucleic acid molecules. Preferably, the nucleic acid molecule is an antisense oligonucleotide. Antisense oligonucleotides (ASO) generally inhibit their target by binding target mRNA and sterically blocking expression by obstructing the ribosome. ASOs can also inhibit their target by binding target mRNA thus forming a DNA-RNA hybrid that can be a substance for RNase H. Preferred ASOs include Locked Nucleic Acid (LNA), Peptide Nucleic Acid (PNA), and morpholinos Preferably, the nucleic acid molecule is an RNAi molecule, i.e., RNA interference molecule. Preferred RNAi molecules include siRNA, shRNA, and artificial miRNA. The design and production of siRNA molecules is well known to one of skill in the art (e.g., Hajeri P B, Singh S K. Drug Discov Today. 2009 14(17-18):851-8). The nucleic acid molecule inhibitors may be chemically synthesized and provided directly to cells of interest. The nucleic acid compound may be provided to a cell as part of a gene delivery vehicle. Such a vehicle is preferably a liposome or a viral gene delivery vehicle.

Adoptive Cell Therapy

In certain embodiments, tumor cells are targeted by using Adoptive cell therapy. As used herein, "ACT", "adoptive cell therapy" and "adoptive cell transfer" may be used interchangeably. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).

Aspects of the invention involve the adoptive transfer of immune system cells, such as T cells, specific for selected antigens, such as tumor associated antigens or tumor specific neoantigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127 144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostate; Prostatic acid phosphatase (PAP); elongation factor 2 mutant (ELF2M); Insulin-like growth factor 1 receptor (IGF-1R); gplOO; BCR-ABL (breakpoint cluster region-Abelson); tyrosinase; New York esophageal squamous cell carcinoma 1 (NY-ESO-1); K-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; protein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDG1cp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDG1cp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyltransferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (0Y-TES 1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyl-transferase); L1CAM (L1 cell adhesion molecule); MC1R (melanocortin 1 receptor); Myosin/m (myosin mutated);

MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML 1(translocation Ets-family leukemia/acute myeloid leukemia 1); TPI/m (triose-phosphate isomerase mutated); and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B1 (CYP1B1), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia. For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer.

Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088, 379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004, 811; 6,284,240; 6,392,013; 6,410,014; 6,753,162; 8,211, 422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD16, CD22, CD33, CD37, CD64, CD80, CD86, CD134, CD137, CD154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3; see U.S. Pat. Nos. 8,911,993; 8,916,381; 8,975,071; 9,101,584; 9,102,760; 9,102,761). Third-generation CARs include a combination of costimulatory endodomains, such a CD3-chain, CD97, GDI la-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-iBB-CD3t or scFv-CD28-OX40-CD3; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3t or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11 a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3 chain (such as amino acid residues 52 163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM 006139 (sequence version 1, 2 or 3): IEVMYPPPYLD-NEKSNGTIIHVKGKHLCPSPLFPGPSKPFWVLVVV GGVLACYSLLVTVAFIIFWVRSKRSRLLHSDYMNMT-PRRPGPTRKHYQPYAPPRDFA AYRS) SEQ ID No: 1). Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM 006139; the sequence included all amino acids starting with the amino acid sequence IEVMYPPPY and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637 1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3t chain, and a costimulatory signaling region comprising a signaling domain of CD28. Preferably, the CD28 amino acid sequence is as set forth in Genbank identifier NM 006139 (sequence version 1, 2 or 3) starting with the amino acid sequence IEVMYPPPY (SEQ ID No: 2) and continuing all the way to the carboxy-terminus of the protein. The sequence is reproduced herein: IEVMYPPPYLDNEKSNGTIIHVKGKHLCPSPLF-PGPSKPFWVLVVVGGVLACYSLLVTVAFIIFWVR-SKRSRLLHSDYMNMTPRRPGPTRKHYQPYAPPRD-FAAYRS (SEQ. ID. No: 3). Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signalling domains (CD28-CD3ζ; 4-1BB-CD3; CD27-CD3ζ; CD28-CD27-CD3ζ, 4-1BB-CD27-CD3ζ; CD27-4-1BB-CD3; CD28-CD27-FcεR1 gamma chain; or CD28-FcεRT gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signalling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its WIC-peptide ligand requires the engagement of several TCRs on the same T cell, which all must signal properly. Thus, if a TCR complex isdestabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3t and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+ Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787 98). Those studies involved an adoptive T cell transfer (ACT) therapy approach, which takes advantage of CD4$^+$ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1 13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CART cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2016, Multiplex genome editing to generate universal CAR T cells resistant to PD1 inhibition, Clin Cancer Res. 2016 Nov. 4; and Qasim et al., 2017, Molecular remission of infant B-ALL after infusion of universal TALEN gene-edited CAR T cells, Sci Transl Med. 2017 Jan. 25; 9(374)). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell; to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1.

Homology-directed repair (HDR) strategies are known and described elsewhere in this specification allowing to insert transgenes into desired loci.

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CART cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B1), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment T cells that have infiltrated a tumor are isolated. T cells may be removed during surgery. T cells may be isolated after removal of tumor tissue by biopsy. T cells may be isolated by any means known in the art. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal"

refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $5 \times 10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of 125I labeled 02-microglobulin (02m) into MHC class I/02m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting the T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™ BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

Diseases

It will be understood by the skilled person that treating as referred to herein encompasses enhancing treatment, or improving treatment efficacy. Treatment may include inhibition of tumor regression as well as inhibition of tumor growth, metastasis or tumor cell proliferation, or inhibition or reduction of otherwise deleterious effects associated with the tumor.

Efficaciousness of treatment is determined in association with any known method for diagnosing or treating the particular disease. The invention comprehends a treatment method comprising any one of the methods or uses herein discussed.

The phrase "therapeutically effective amount" as used herein refers to a sufficient amount of a drug, agent, or compound to provide a desired therapeutic effect.

As used herein "patient" refers to any human being receiving or who may receive medical treatment and is used interchangeably herein with the term "subject".

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the cancer, and how the patient responds to the treatment.

The disclosure also provides methods for reducing resistance to immunotherapy and treating disease. Not being bound by a theory, cancer cells have many strategies of avoiding the immune system and by reducing the signature of the present invention cancer cells may be unmasked to the immune system. Not being bound by a theory, reducing a gene signature of the present invention may be used to treat a subject who has not been administered an immunotherapy, such that the subject's tumor becomes unmasked to their natural or unamplified immune system. In other embodiments, the cancer is resistant to therapies targeting the adaptive immune system (see e.g., Rooney et al., Molecular and genetic properties of tumors associated with local immune cytolytic activity, Cell. 2015 Jan. 15; 160(1-2): 48-61). In one embodiment, modulation of one or more of the signature genes are used for reducing an immunotherapy resistant signature for the treatment of a subpopulation of tumor cells that are linked to resistance to targeted therapies and progressive tumor growth.

In general, the immune system is involved with controlling all cancers and the present application is applicable to treatment of all cancers. Not being bound by a theory, the signature of the present invention is applicable to all cancers and may be used for treatment, as well as for determining a prognosis and stratifying patients. The cancer may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or multiple myeloma.

The cancer may include, without limitation, solid tumors such as sarcomas and carcinomas. Examples of solid tumors include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, epithelial carcinoma, bronchogenic carcinoma, hepatoma, colorectal cancer (e.g., colon cancer, rectal cancer), anal cancer, pancreatic cancer (e.g., pancreatic adenocarcinoma, islet cell carcinoma, neuroendocrine tumors), breast cancer (e.g., ductal carcinoma, lobular carcinoma, inflammatory breast cancer, clear cell carcinoma, mucinous carcinoma), ovarian carcinoma (e.g., ovarian epithelial carcinoma or surface epithelial-stromal tumour including serous tumour, endometrioid tumor and mucinous cystadenocarcinoma, sex-cord-stromal tumor), prostate cancer, liver and bile duct carcinoma (e.g., hepatocellular carcinoma, cholangiocarcinoma, hemangioma), choriocarcinoma, seminoma, embryonal carcinoma, kidney cancer (e.g., renal cell carcinoma, clear cell carcinoma, Wilms' tumor or, nephroblastoma), cervical cancer, uterine cancer (e.g., endometrial adenocarcinoma, uterine papillary serous carcinoma, uterine clear-cell carcinoma, uterine sarcomas and leiomyosarcomas, mixed mullerian tumors), testicular cancer, germ cell tumor, lung cancer (e.g., lung adenocarcinoma, squamous cell carcinoma, large cell carcinoma, bronchioloalveolar carcinoma, non-small-cell carcinoma, small cell carcinoma, mesothelioma), bladder carcinoma, signet ring cell carcinoma, cancer of the head and neck (e.g., squamous cell carcinomas), esophageal carcinoma (e.g., esophageal adenocarcinoma), tumors of the brain (e.g., glioma, glioblastoma, medulloblastoma, astrocytoma, medulloblastoma, craniopharyngioma, ependymoma, pinealoma, hemangioblastoma, acoustic neuroma, oligodendroglioma, schwannoma, meningioma), neuroblastoma, retinoblastoma, neuroendocrine tumor, melanoma, cancer of the stomach (e.g., stomach adenocarcinoma, gastrointestinal stromal tumor), or carcinoids. Lymphoproliferative disorders are also considered to be proliferative diseases.

Administration It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The agents disclosed herein (e.g., antibodies) may be used in a pharmaceutical composition when combined with a pharmaceutically acceptable carrier. Such compositions comprise a therapeutically-effective amount of the agent and a pharmaceutically acceptable carrier. Such a composition may also further comprise (in addition to an agent and a carrier) diluents, fillers, salts, buffers, stabilizers, solubilizers, and other materials well known in the art. Compositions comprising the agent can be administered in the form of salts provided the salts are pharmaceutically acceptable. Salts may be prepared using standard procedures known to those skilled in the art of synthetic organic chemistry.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycolylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, pamoate, valerate, and the like which can be used as a dosage form for modifying the solubility or hydrolysis characteristics or can be used in sustained release or pro-drug formulations. It will be understood that, as used herein, references to specific agents (e.g., neuromedin U receptor agonists or antagonists), also include the pharmaceutically acceptable salts thereof.

Methods of administrating the pharmacological compositions, including agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

The amount of the agents which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range of a drug lie within the range known in the art for a particular drug or biologic. Effective doses may be extrapolated from dose-response curves derived from in vitro or animal model test systems. Ultimately the attending physician will decide on the appropriate duration of therapy using compositions of the present invention. Dosage will also vary according to the age, weight and response of the individual patient.

Methods for administering antibodies for therapeutic use is well known to one skilled in the art. In certain embodiments, small particle aerosols of antibodies or fragments thereof may be administered (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies are administered in metered-dose propellant driven aerosols. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In certain embodiments, antibodies may be topically administered to mucosa, such as the oropharynx, nasal cavity, respiratory tract, gastrointestinal tract, eye such as the conjunctival mucosa, vagina, urogenital mucosa, or for dermal application. In certain embodiments, antibodies are administered to the nasal, bronchial or pulmonary mucosa. In order to obtain optimal delivery of the antibodies to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

Other excipients suitable for pharmaceutical compositions intended for delivery of antibodies to the respiratory tract mucosa may be a) carbohydrates, e.g., monosaccharides such as fructose, galactose, glucose. D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like: d) peptides and proteins, such as aspartame, human serum albumin, gelatin, and the like; e) alditols, such mannitol, xylitol, and the like, and f) polycationic polymers, such as chitosan or a chitosan salt or derivative.

For dermal application, the antibodies of the present invention may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc. Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalkonium chloride, and benzylalcohol, or mixtures of preservatives.

Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives: wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carrageenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carrageenans, hyaluronates (e.g. hyaluronate gel optionally containing sodium chloride), and alginates including propylene glycol alginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and polysorbates.

Examples of other excipients are polymers such as carmellose, sodium carmellose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetearyl glucoside, collagen, carrageenan, hyaluronates and alginates and chitosans.

The dose of antibody required in humans to be effective in the treatment of cancer differs with the type and severity of the cancer to be treated, the age and condition of the patient, etc. Typical doses of antibody to be administered are in the range of 1 μg to 1 g, preferably 1 1000 μg, more preferably 2-500, even more preferably 5-50, most preferably 10-20 μg per unit dosage form. In certain embodiments, infusion of antibodies of the present invention may range from 10-500 mg/m$^2$.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transduction with viral (typically lentivirus, adeno associated virus (AAV) and adenovirus) vectors.

In certain embodiments, an agent that reduces a gene signature as described herein is used to treat a subject in need thereof having a cancer.

In one embodiment, the agent is a protein kinase C (PKC) activator. By "protein kinase C activator" is meant any compound that increases the catalytic activity of any protein kinase C (PKC) isoform (see, e.g., WO1998017299A1). The preferred catalytic activity that is enhanced is the kinase activity. Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, α, βt, βM and γPKC, contain four homologous domains (C1, C2, C3 and C4) and require calcium, phosphatidylserine, and diacylglycerol or phorbol esters for activation. In members of the "novel" or "nPKC" subfamily, δ, ε, η and θ PKC, a C2-like domain preceeds the C1 domain. However, that C2 domain does not bind calcium and therefore the nPKC subfamily does not require calcium for activation. Finally, members of the "atypical" or "αPKC" subfamily, ζ and λ/iPKC, lack both the C2 and one-half of the C1 homologous domains and are insensitive to diacylglycerol, phorbol esters and calcium. Studies on the subcellular distribution of PKC isozymes demonstrate that activation of PKC results in its redistribution in the cells (also termed trans location), such that activated PKC isozymes associate with the plasma membrane, cytoskeletal elements, nuclei, and other subcellular compartments (Saito, N. et al, Proc. Natl. Acad. Sci. USA 86:3409-3413 (1989); Papadopoulos, V. and Hall, P. F. J. Cell Biol. 108:553-567 (1989); Mochly-Rosen, D., et al., Molec. Biol. Cell (formerly Cell Reg.) 1:693-706, (1990)).

Mochly-Rosen, D., et al. discusses activation of PKC (Nat Rev Drug Discov. 2012 December; 11(12): 937-957). PKC isozymes are activated by a variety of hormones, such as adrenalin and angiotensin, by growth factors, including epidermal growth factor and insulin, and by neurotransmitters such as dopamine and endorphin; these stimulators, when bound to their respective receptors, activate members of the phospholipase C family, which generates diacylglycerol, a lipid-derived second messenger. The novel isozymes (PKC δ, ε, θ and η) are activated by diacylglycerol alone, whereas the four conventional PKC isozymes (PKCα, βI βII and γ) also require calcium for their activation. Cellular calcium levels are elevated along with diacylglycerol, because the latter is often co-produced with inositol trisphosphate (IP3), which triggers calcium release into the cytosol from internal stores. Activation of PKC can also occur in the absence of the above second messengers. High levels of cytosolic calcium can directly activate phospholipase C, thus leading to PKC activation in the absence of receptor activation. A number of post-translational modifications of PKC were also found to lead to activation of select PKC isozymes both in normal and disease states. These include activation by proteolysis between the regulatory and the catalytic domain that was noted to occur for PKCδ, for example. Phosphorylation of a number of sites may be required for maturation of the newly synthesized enzyme, but also for activation of mature isozymes, e.g. H2O2-induced tyrosine phosphorylation of PKCδ. Other modifications including oxidation, acetylation and nitration have also been found to activate PKC.

In one embodiment, the agent is an inhibitor of the NFκB pathway. Inhibitors of the NFκB pathway have been described (see, e.g., Gilmore and Herscovitch, Inhibitors of NF-kappaB signaling: 785 and counting. Oncogene (2006) 25, 6887-6899). These compounds include chemicals, metals, metabolites, synthetic compounds, antioxidants, peptides, small RNA/DNA, microbial and viral proteins, small molecules, and engineered dominant-negative or constitutively active polypeptides.

In one embodiment, the agent is an IGF1R inhibitor. IGF1R inhibitors are well known in the art (see, e.g., King et al., Can we unlock the potential of IGF-1R inhibition in cancer therapy? Cancer Treat Rev. 2014 October; 40(9): 1096-1105). IGF1R inhibitors may include, but are not limited to monoclonal anti-IGF1R antibodies, small molecule tyrosine kinase inhibitors (TKIs), and IGF ligand antibodies.

In one embodiment, the agent is Reserpine (methyl 18β-hydroxy-11,17 α-dimethoxy-3β, 20α-yohimban-16β-carboxylate, 3,4,5-trimethoxybenzoate) or derivative thereof. Reserpine is an alkaloid first isolated from *Rauwolfia serpentina*. Reserpine (also known by trade names Raudixin, Serpalan, Serpasil) is an indole alkaloid, antipsychotic, and antihypertensive drug that has been used for the control of high blood pressure and for the relief of psychotic symptoms, although because of the development of better drugs for these purposes and because of its numerous side-effects, it is rarely used today. The antihypertensive actions of reserpine are a result of its ability to deplete catecholamines (among other monoamine neurotransmitters) from peripheral sympathetic nerve endings. These substances are normally involved in controlling heart rate, force of cardiac contraction and peripheral vascular resistance. The daily dose of reserpine in antihypertensive treatment is as low as 0.1 to 0.25 mg. In certain embodiments, the dose is significantly higher for the treatment of cancer. A skilled practitioner would know to adjust the dose based on response to the drug. For example, reduction of an immunotherapy resistance signature or decrease in tumor size and/or proliferation. In certain embodiments, Reserpine is administered directly to a tumor. In certain embodiments, reserpine is administered over the course of a single day or week or month.

Typical of the known rauwolfia alkaloids are deserpidine, alseroxylon, reserpine, and rauwolfia serpentina. Oral dosage of the rauwolfia alkaloid should be carefully adjusted according to individual tolerance and response, using the lowest possible effective dosage. Typically, the amount of rauwolfia alkaloid administered daily is from about 0.001 to about 0.01 mg per kg of body weight.

In certain embodiments, the agent capable of modulating a signature as described herein is a cell cycle inhibitor (see e.g., Dickson and Schwartz, Development of cell-cycle inhibitors for cancer therapy, Curr Oncol. 2009 March; 16(2): 36-43). In one embodiment, the agent capable of modulating a signature as described herein is a CDK4/6 inhibitor, such as LEE011, palbociclib (PD-0332991), and Abemaciclib (LY2835219) (see, e.g., U.S. Pat. No. 9,259, 399B2; WO2016025650A1; US Patent Publication No. 20140031325; US Patent Publication No. 20140080838; US Patent Publication No. 20130303543; US Patent Publication No. 2007/0027147; US Patent Publication No. 2003/0229026; US Patent Publication No 2004/0048915; US Patent Publication No. 2004/0006074; US Patent Publication No. 2007/0179118; each of which is incorporated by reference herein in its entirety). Currently there are three CDK4/6 inhibitors that are either approved or in late-stage development: palbociclib (PD-0332991; Pfizer), ribociclib (LEE011; Novartis), and abemaciclib (LY2835219; Lilly) (see e.g., Hamilton and Infante, Targeting CDK4/6 in patients with cancer, Cancer Treatment Reviews, Volume 45, April 2016, Pages 129-138).

In certain embodiments, an agent that reduces an immunotherapy resistance signature is co-administered with an immunotherapy or is administered before administration of an immunotherapy. The immunotherapy may be adoptive cell transfer therapy, as described herein or may be an inhibitor of any check point protein described herein. Specific check point inhibitors include, but are not limited to anti-CTLA4 antibodies (e.g., Ipilimumab), anti-PD-1 antibodies (e.g., Nivolumab, Pembrolizumab), and anti-PD-L1 antibodies (e.g., Atezolizumab).

In another aspect, provided is a pharmaceutical pack or kit, comprising one or more containers filled with one or more of the ingredients of the pharmaceutical compositions.

In another aspect, provided is a kit for detecting the gene signature as described herein.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213, 991), US 2014 0273234 A1 (U.S. application Ser. No. 14/293,674), US 2014-0273232 A1 (U.S. App. Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014 0242700 A1 (U.S. application Ser. No. 14/222,930), US 2014-0242699 A1 (U.S. App. Ser. No. 14/183,512), US 2014-0242664 A1 (U.S. application Ser. No. 14/104,990), US 2014-0234972 A1 (U.S.

application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. App. Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104, 837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15,2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055, 484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US 14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US 14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WIDE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L.A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.103 8/Nature 12466. Epub 2013 Aug. 23 (2013);

Double Nicking by RNA-Guided CRISPR Cas9 for Enhanced Genome Editing Specificity. Ran, FA., Hsu, PD., Lin, CY., Gootenberg, J S., Konermann, S., Trevino, AE., Scott, DA., Inoue, A., Matoba, S., Zhang, Y., & Zhang, F. Cell August 28. pii: 50092-8674(13)01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, T J., Marraffini, LA., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, DA., Zhang, F. Nature Protocols November; 8(11):2281-308 (2013-B);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science Dec. 12. (2013). [Epub ahead of print];

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using Staphylococcus aureus Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., "CRISPR/Cas9 cleavage of viral DNA efficiently suppresses hepatitis B virus," Scientific Reports 5:10833. doi: 10.1038/srep10833 (Jun. 2, 2015).

Nishimasu et al., "Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.2015.10.008 Epub Oct. 22, 2015.

*Rationally engineered Cas9 nucleases with improved specificity*, Slaymaker et al., Science 2016 Jan. 1 351(6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA: Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated>700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED 12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bibbed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements.

The authors developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385 397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In advantageous embodiments of the invention, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-$(X_{12}X_{13})$-$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$-$(X_{12}X_{13})$-$X_{14-33}$ or 34 or 35$)_z$, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments, the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

In certain embodiments, the invention involves targeted nucleic acid profiling (e.g., sequencing, quantitative reverse transcription polymerase chain reaction, and the like) (see e.g., Geiss G K, et al., Direct multiplexed measurement of gene expression with color-coded probe pairs. Nat Biotechnol. 2008 March; 26(3):317-25). In certain embodiments, a target nucleic acid molecule (e.g., RNA molecule), may be sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. Methods for constructing sequencing libraries are known in the art (see, e.g., Head et al., Library construction for next-generation sequencing: Overviews and challenges. Biotechniques. 2014; 56(2): 61-77).

In certain embodiments, the invention involves plate based single-cell RNA sequencing (see, e.g., Picelli, S. et al., 2014, "Full-length RNA-seq from single cells using Smart-seg2" Nature protocols 9, 171-181, doi:10.1038/nprot.2014.006).

In certain embodiments, the invention involves high-throughput single-cell RNA-seq and/or targeted nucleic acid profiling where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014210353 A2; Zilionis, et al., 2017, "Single-cell barcoding and sequencing using droplet microfluidics" Nat Protoc. January;12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing (sn-RNA-seq). In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; and Habib et al., 2017, "Massively parallel single-nucleus RNA-seq with DroNc-seq" Nat Methods. 2017 October;14(10):955-958, which are herein incorporated by reference in their entirety.

In certain embodiments, the immunotherapy resistance signature comprises EGR1 and/or MAZ. In other embodiments, EGR1 and/or MAZ are targeted for therapeutic intervention. In one embodiment, EGR1 and/or MAZ are targeted to reduce a resistance signature. EGR1 and MAZ are zinc finger transcription factors (TF). EGR1 is down regulated in malignant cells of the post-treatment tumors, and MAZ (Myc-associated *zinc* finger protein) is up-regulated. These TFs may be connected to the decrease in metallothioneins post treatment and availability to metal ions. Applicants saw an enrichment in EGR1 targets in the genes which are down-regulated post-treatment. Applicants also saw an overlap with a signature identified in synovial sarcoma. In synovial sarcoma EGR1 is repressed. Mutations in the BAF complex are strongly associated with the response to immunotherapy/resistance to T-cells, and is related to the present invention.

In certain embodiments, the gene signatures described herein are screened by perturbation of target genes within said signatures. In certain embodiments, perturbation of any signature gene or gene described herein may reduce or induce the immunotherapy resistance signature. In preferred embodiments, the perturbed genes include MAZ, NFKBIZ, MYC, ANXA1, SOX4, MT2A, PTP4A3, CD59, DLL3, SERPINE2, SERPINF1, PERP, EGR1, SERPINA3, IFNGR2, B2M, and PDL1. In certain embodiments, after perturbation, gene expression may be evaluated to determine whether the gene signature is reduced.

Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; and International publication serial number WO/2017/075294). The present invention is compatible with perturb-seq, such that signature genes may be perturbed and the perturbation may be identified and assigned to the proteomic and gene expression readouts of single cells. In certain embodiments, signature genes may be perturbed in single cells and gene expression analyzed. Not being bound by a theory, networks of genes that are disrupted due to perturbation of a signature gene may be determined. Understanding the network of genes effected by a perturbation may allow for a gene to be linked to a specific pathway that may be targeted to modulate the signature and treat a cancer. Thus, in certain embodiments, perturb-seq is used to discover novel drug targets to allow treatment of specific cancer patients having the gene signature of the present invention.

The perturbation methods and tools allow reconstructing of a cellular network or circuit. In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single-cell RNA sequencing (RNA-seq). In preferred embodiments, the single-cell RNA-seq is performed by any method as described herein (e.g., Drop-seq, InDrop, 10x genomics). In certain embodiments, unique barcodes are used to perform Perturb-seq. In certain embodiments, a guide RNA is detected by RNA-seq using a transcript expressed from a vector encoding the guide RNA. The transcript may include a unique barcode specific to the guide RNA. Not being bound by a theory, a guide RNA and guide RNA barcode is expressed from the same vector and the barcode may be detected by RNA-seq. Not being bound by a theory, detection of a guide RNA barcode is more reliable than detecting a guide RNA sequence, reduces the chance of false guide RNA assignment and reduces the sequencing cost associated with executing these screens. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for single-cell sequencing methods. In certain embodiments, a Unique Molecular Identifier (UMI) is added to each individual transcript and protein capture oligonucleotide. Not being bound by a theory, the UMI allows for determining the capture rate of measured signals, or preferably the binding events or the number of transcripts captured. Not being bound by a theory, the data is more significant if the signal observed is derived from more than one protein binding event or transcript. In preferred embodiments, Perturb-seq is performed using a guide RNA barcode expressed as a polyadenylated transcript, a cell barcode, and a UMI.

Perturb-seq combines emerging technologies in the field of genome engineering, single-cell analysis and immunology, in particular the CRISPR-Cas9 system and droplet single-cell sequencing analysis. In certain embodiments, a CRISPR system is used to create an INDEL at a target gene. In other embodiments, epigenetic screening is performed by applying CRISPRa/i/x technology (see, e.g., Konermann et al. "Genome-scale transcriptional activation by an engineered CRISPR-Cas9 complex" Nature. 2014 Dec. 10. doi: 10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Kornor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353(6305); Yang et al., 2016, Engineering and optimising deaminase fusions for genome editing, Nat Commun. 7:13330; Hess et al., 2016, Directed evolution using dCas9-targeted somatic hyperm Cation in mammalian cells, Nature Methods 13, 1036-1042; and Ma et al., 2016, Targeted AID-mediated muta.genesis (TAM) enables efficient genomic diversification in mammalian cells, Nature Methods 13, 1029-1035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, other CRISPR-based perturbations are readily compatible with Perturb-seq, including alternative editors such as CRISPR/Cpf1. In certain embodiments, Perturb-seq uses Cpf1 as the CRISPR enzyme for introducing perturbations. Not being bound by a theory, Cpf1 does not require Tracr RNA and is a smaller enzyme, thus allowing higher combinatorial perturbations to be tested.

The cell(s) may comprise a cell in a model non-human organism, a model non human mammal that expresses a Cas protein, a mouse that expresses a Cas protein, a mouse that expresses Cpf1, a cell in vivo or a cell ex vivo or a cell in vitro (see e.g., WO 2014/093622 (PCT/US13/074667); US Patent Publication Nos. 20120017290 and 20110265198 assigned to Sangamo BioSciences, Inc.; US Patent Publication No. 20130236946 assigned to Cellectis; Platt et al., "CRISPR-Cas9 Knockin Mice for Genome Editing and Cancer Modeling" Cell (2014), 159(2): 440-455; "Oncogenic models based on delivery and use of the CRISPR-Cas systems, vectors and compositions" WO2014204723A1 "Delivery and use of the CRISPR-Cas systems, vectors and compositions for hepatic targeting and therapy" WO2014204726A1; "Delivery, use and therapeutic applications of the CRISPR-Cas systems and compositions for modeling mutations in leukocytes" WO2016049251; and Chen et al., "Genome-wide CRISPR Screen in a Mouse Model of Tumor Growth and Metastasis" 2015, Cell 160, 1246-1260). The cell(s) may also comprise a human cell. Mouse cell lines may include, but are not limited to neuro-2a cells and EL4 cell lines (ATCC TIB-39). Primary mouse T cells may be isolated from C57BL/6 mice. Primary mouse T cells may be isolated from Cas9-expressing mice.

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)). A genome-wide sgRNA mouse library (-10 sgRNAs/gene) may also be used in a mouse that expresses a Cas9 protein (see, e.g., WO2014204727A1).

In one embodiment, perturbation is by deletion of regulatory elements. Non-coding elements may be targeted by using pairs of guide RNAs to delete regions of a defined size, and by tiling deletions covering sets of regions in pools.

In one embodiment, perturbation of genes is by RNAi. The RNAi may be shRNA's targeting genes. The shRNA's may be delivered by any methods known in the art. In one embodiment, the shRNA's may be delivered by a viral vector. The viral vector may be a lentivirus, adenovirus, or adeno associated virus (AAV).

A CRISPR system may be delivered to primary mouse T-cells. Over 80% transduction efficiency may be achieved with Lenti-CRISPR constructs in CD4 and CD8 T-cells. Despite success with lentiviral delivery, recent work by Hendel et al, (Nature Biotechnology 33, 985-989 (2015) doi:10.1038/nbt.3290) showed the efficiency of editing human T-cells with chemically modified RNA, and direct RNA delivery to T-cells via electroporation. In certain embodiments, perturbation in mouse primary T-cells may use these methods.

In certain embodiments, whole genome screens can be used for understanding the phenotypic readout of perturbing potential target genes. In preferred embodiments, perturbations target expressed genes as defined by a gene signature using a focused sgRNA library. Libraries may be focused on expressed genes in specific networks or pathways. In other preferred embodiments, regulatory drivers are perturbed. In certain embodiments, Applicants perform systematic perturbation of key genes that regulate T-cell function in a high-throughput fashion. In certain embodiments, Applicants perform systematic perturbation of key genes that regulate cancer cell function in a high-throughput fashion (e.g., immune resistance or immunotherapy resistance). Applicants can use gene expression profiling data to define the target of interest and perform follow-up single-cell and population RNA-seq analysis. Not being bound by a theory, this approach will accelerate the development of therapeutics for human disorders, in particular cancer. Not being bound by a theory, this approach will enhance the understanding of the biology of T-cells and tumor immunity, and accelerate the development of therapeutics for human disorders, in particular cancer, as described herein.

Not being bound by a theory, perturbation studies targeting the genes and gene signatures described herein could (1) generate new insights regarding regulation and interaction of molecules within the system that contribute to suppression of an immune response, such as in the case within the tumor microenvironment, and (2) establish potential therapeutic targets or pathways that could be translated into clinical application.

In certain embodiments, after determining Perturb-seq effects in cancer cells and/or primary T-cells, the cells are infused back to the tumor xenograft models (melanoma, such as B16F10 and colon cancer, such as CT26) to observe the phenotypic effects of genome editing. Not being bound by a theory, detailed characterization can be performed based on (1) the phenotypes related to tumor progression, tumor growth, immune response, etc. (2) the TILs that have been genetically perturbed by CRISPR-Cas9 can be isolated from tumor samples, subject to cytokine profiling, qPCR/RNA-seq, and single-cell analysis to understand the biological effects of perturbing the key driver genes within the tumor-immune cell contexts. Not being bound by a theory, this will lead to validation of TILs biology as well as lead to therapeutic targets.

The invention is further described in the following examples, which do not limit the scope of the invention described in the claims.

EXAMPLES

Example 1—Identifying Signatures of Resistance

Applicants leveraged single-cell RNA-sequencing (scRNA-Seq) of thousands of cells from melanoma tumors and a novel data-driven method to systematically map cancer programs that promote ICR and T cell exclusion. Applicants collected 10,123 scRNA-seq profiles from the tumors of 31 patients, consisting of 15 treatment naïve (TN) patients, and 16 post-ICI tumors. Of these 16 post-ICI specimens, 15 had clinical resistance and were therefore termed ICI-resistant (ICR), and one had a partial response (PR) according to the RECIST criteria (18) (FIG. 1A, table 51), and was termed as having clinical benefit (CB). Applicants filtered lower-quality cells to retain 7,186 high-quality transcriptomes, including 4,199 cells from 16 patients that Applicants previously reported (13), and 2,987 cells from 16 newly collected patient tumors (table 51).

Applicants first aimed to determine the effects ICI has on different cell types in the tumor at the time of post-ICI progression, by comparing between the ICR and TN tumors. Although the specimens in the different treatment groups were not from the same patients, Applicants reasoned that the high resolution and large number of cells profiled will provide sufficient power to detect some of these effects.

It revealed that, despite the lack of clinical response, CD8 T-cells in the ICR tumors manifested heterogeneous phenotypes of T-cell activation. Conversely, the malignant cells of ICR tumors had a distinct transcriptional state that was substantially less frequent in the TN tumors.

Next, for any such transcriptional program that may reflect ICI effects, Applicants examined its potential causal connection to immune evasion or resistance. Applicants acknowledged the possibility that malignant cells derived from TN tumors could contain both treatment-sensitive and intrinsically resistant cells. Thus, Applicants tested the malignant signatures in two independent validation cohorts (FIG. 1A), where pre-ICI patient biopsies were profiled with bulk RNA-Seq, and the response to ICI therapy was monitored. Applicants demonstrated that this oncogenic state is tightly linked to immune evasion and exclusion, and that it can be used to predict ICR based on the bulk RNA-seq of the pre-ICI biopsy.

Figure 5A:
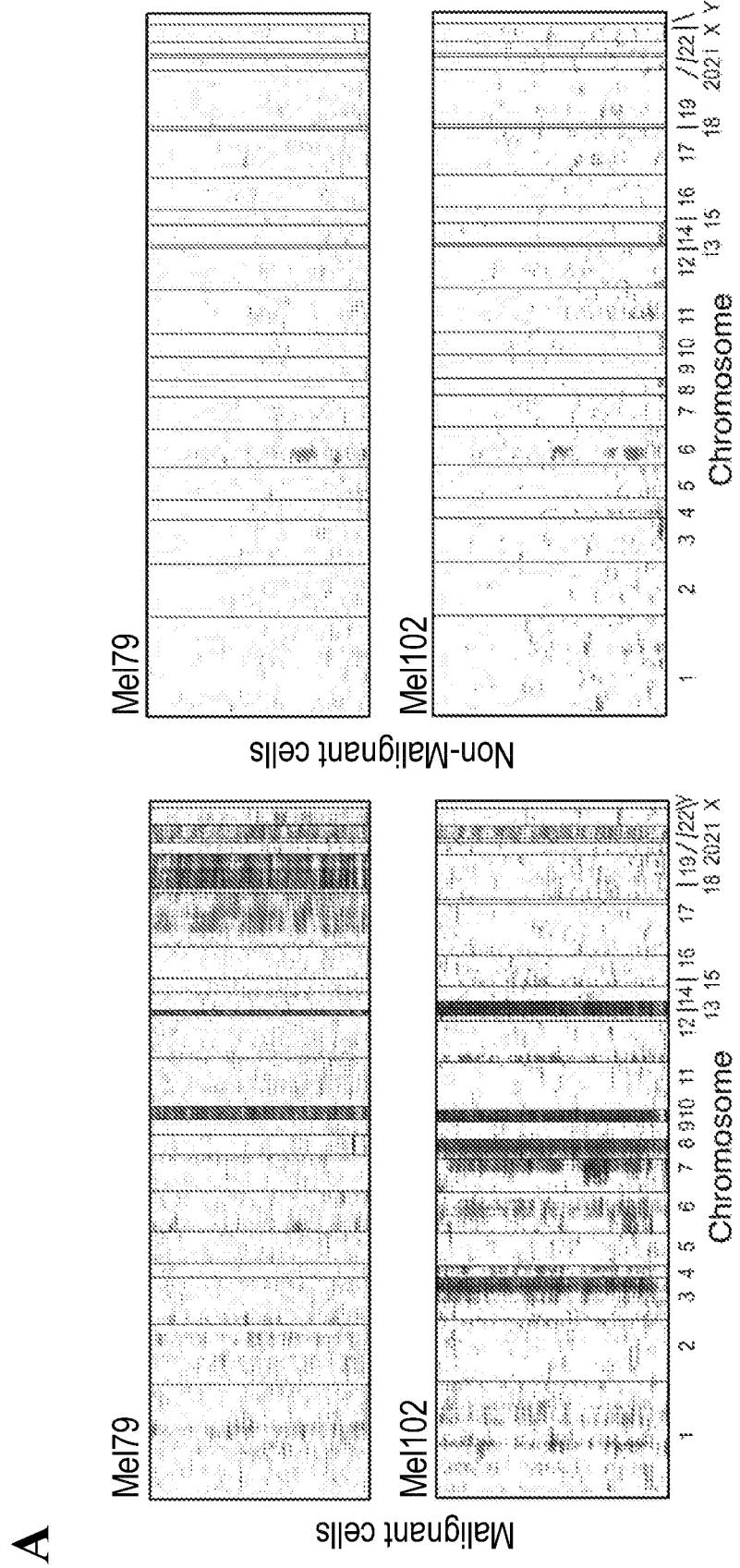
FIG. 5 illustrates the classification of malignant and non-malignant cells. (A) Inferred large-scale CNVs distinguish malignant (right) from nonmalignant (left) cells. Shown are the inferred CNVs (amplification, blue, deletion) along the chromosomes (x axis) for cells (y axis) in two representative tumors. (B-E) Congruence between different assignment methods. (B) Each plot shows the relation between two different scorings, by showing for CD45$^-$cells the distribution of scores (y axis) by one scheme, stratified to two categories by another scheme. CNV: inference of malignant and non-malignant CD45$^-$ cells as in (A, materials and methods); signature based: assignment of CD45$^-$ cells as malignant or stroma by scoring the corresponding expression signatures (materials and methods); differential similarity to melanoma: assignment of CD45⁻cells as malignant or non-malignant by similarity to bulk melanoma tumors compared to normal tissue. Middle line: median; box edges: 25th and 75th percentiles; whiskers: most extreme points that do not exceed ±IQR*1.5; points beyond the distance: single points. (C) Distribution of CNV-R-score for cells identified as malignant and non-malignant. The CNV-R-score of a cell is defined as the Spearman correlation coefficient (r) between the cell's CNV profile and its tumor's inferred CNV profile (materials and methods). (D) The distribution of CNV-R-scores across each identified cell type. (E) The CNV-R-score (y axis) at each overall CNV signal (materials and methods) for malignant and non-malignant cells; Non-malignant cells with values that exceed the dashed lines were considered unresolved and were omitted from further analyses.

Applicants collected scRNA-Seq of dissociated individual cells from fresh tumor resections, sorted into immune and non-immune cells based on the CD45 expression, and profiled them with a modified full-length SMART-Seg2 protocol (materials and methods, table S2). Applicants distinguished different cell subsets and clones both by their expression profiles and by their inferred genetic features. In the non-immune compartment (FIG. 1B), Applicants distinguished malignant from non-malignant cells (materials and methods) according to (1) their inferred CNV profiles (13) (FIG. 5); (2) under-expression of different non malignant cell-type signatures (FIG. 5B); and (3) high similarity to bulk RNA-Seq profiles of melanoma tumors compared to adjacent normal tissue. The cell assignments by the different criteria were highly consistent (hypergeometric p-value<$10^{17}$, FIG. 5, materials and methods). Within non-malignant cells, Applicants used unsupervised clustering to identify (materials and methods) CD8 and CD4 T cells, B cells, NK cells, macrophages, Cancer Associated Fibroblasts (CAFs) and endothelial cells (FIG. 1C, FIG. 6, table S4). Overall, malignant cells clustered first by their tumor of origin (FIG. 1B), while the non-malignant cells clustered primarily by their cell type, and only then by their tumor of origin (FIG. 1C).

Applicants identified transcriptional features that distinguish between the cells of TN and ICR tumors, analyzing separately each cell type with a sufficient number (>100) of cells: malignant cells, macrophages, B cells, CD8 T cells, and CD4 T cells. Applicants applied a subsampling procedure to prevent tumors with a particularly large number of cells of a given type from dominating the results and to mitigate the effects of outliers. For each cell type Applicants defined an ICR-up and ICR-down signature, consisting of genes that were significantly up or down regulated in the cells from the ICR tumors, respectively (19). Applicants used a mixed-effect model to test the ability of a given gene signature to distinguish between cells from ICR and TN tumors, while accounting for potential confounders, including other clinical characteristics and cell quality (materials and methods).

The CD8 T cells and malignant cells subset derived from ICR patients were markedly different from their TN counterparts (FIG. 7, tables S5 and S6), and are the focus of this analysis. Macrophages also showed ICR associated expression programs (table S5), but due to their relatively small number in the dataset, Applicants did not pursue them further. Conversely, very few genes where differentially expressed between the ICR vs. TN groups when analyzing B cells or CD4 T cells (table S5). Deeper sampling of these and other cell types might identify significant distinctions.

The CD8 T-cell-ICR signatures (FIG. 1D) revealed the induction of cytotoxicity genes and the repression of some exhaustion features. Compared to TN CD8 T cells, ICR CD8 T cells up regulated the T cell activation markers STAT1, GBP2, GBP5 and IRF1, and down regulated WNK1. Inhibition of WNK1 has been shown to increase T cell infiltration and accumulation in tumors in an in vivo shRNA screen (20). Lactate dehydrogenase A (LDHA) was also up regulated in the ICR CD8 T cells, suggesting that the cells may have infiltrated the hypoxic tumor microenvironment. Among the immune checkpoints, HAVCR2 (TIM3) and CD27 are significantly, though modestly, down-regulated. Although the inhibitory checkpoints CTLA-4, TIGIT, LAG-3, PD-1, and TIM3 co-vary across cells (along with the transcription factor PRDM1), as Applicants previously reported (13, 21), Applicants did not detect a significant difference in their expression between TN and ICR cells (FIG. 8A). Rather, CD8 T cells from both TN and ICR tumor specimens spanned a spectrum of states in the exhaustion-cytotoxicity space, even within the CD8 T cells of the same tumor (13), with a strong association between dysfunction ("exhaustion") and cytotoxicity scores at the single-cell level (FIG. 1E, FIG. 8B), as Applicants previously reported (13). Notably, the CD8 T cells of the one ICI responder patient are both highly cytotoxic and significantly less dysfunctional than cells of other patients (FIG. 1E, $P=1.31*10^{-6}$, hypergeometric test). However, since a similar trend was observed in one of the ICR patients (Mel126, $P=4.08*10^{-13}$, hypergeometric test), such an enhanced cytotoxic state may not necessarily mark clinical response. These findings were robust when using different T cell dysfunction signatures (materials and methods), including single-cell signatures that were recently identified in T cells from hepatocellular carcinoma tumors (22) (FIG. 8B, $P<2.46*10^{-4}$, hypergeometric test). A list of differentially expressed genes obtained when comparing the CD8 T cells of the CB patients to those from the ICR patients is provided in table S7.

To examine the association between CD8 T cell profiles and clonal expansion Applicants reconstructed full-length T cell receptors (TCR) and identified 137 CD8 T cell clones of varying sizes (23) (FIG. 1F, FIG. 9). Three patients, all of them ICR, had exceptionally large clonal expansions, with 39-51% of the CD8 T cells in these tumors as members of large (>20 cells) clonotypes (FIG. 1F). These three ICR patients had extremely expanded CD8 T cells, even after controlling for the number of CD8 T cells profiled and the success rate of TCR reconstruction (materials and methods, $P=4.54*10^{-3}$, one-sided Wilcoxon ranksum, FIG. 9B). For one ICR patient with extreme clonal expansions, Applicants obtained two lesions a year apart: 15 of the 28 clones identified in these specimens included cells from both lesions, such that 71% and 52% of the CD8 T cells in the early and late samples, respectively, were in the shared clones, demonstrating their stability and persistence (FIG. 9C,D). T cell clonality pre treatment has previously been identified as a potential predictive marker of response to anti-PD-1 therapy (6); the results herein suggest that the extent of clonal expansion post ICI may not be coupled to clinical response.

Figure 1B:
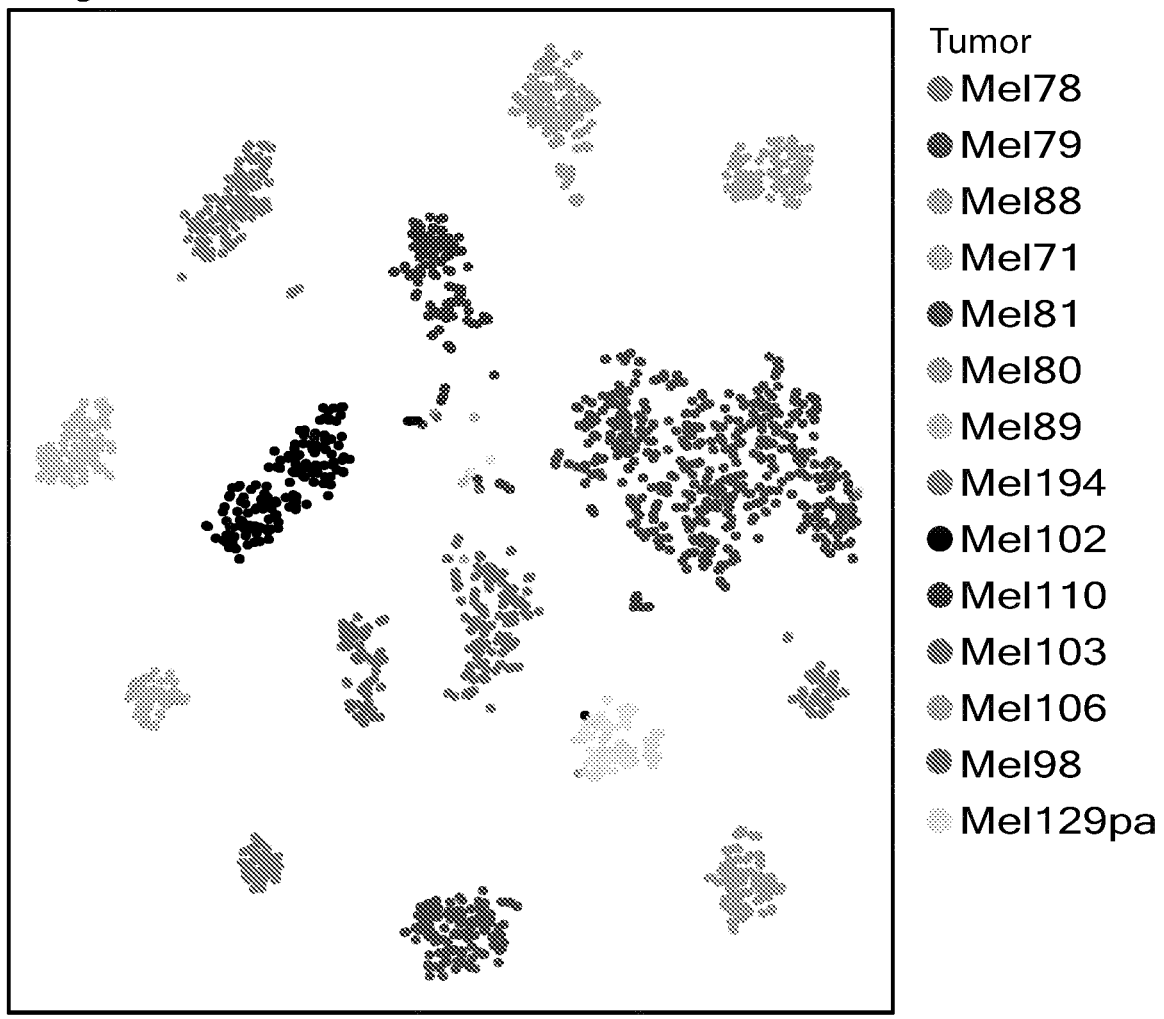
Figure 1C:
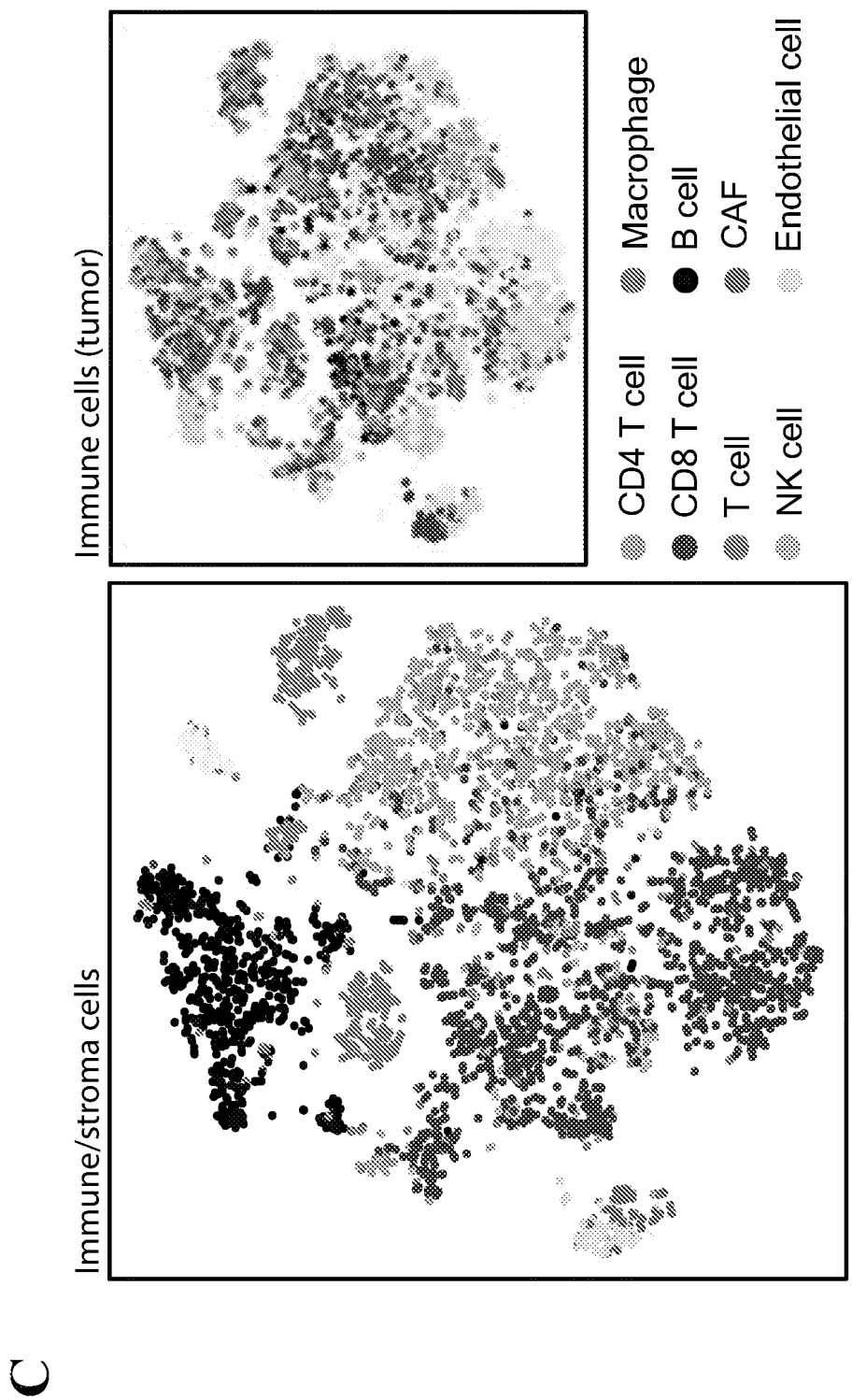
Figure 1D:
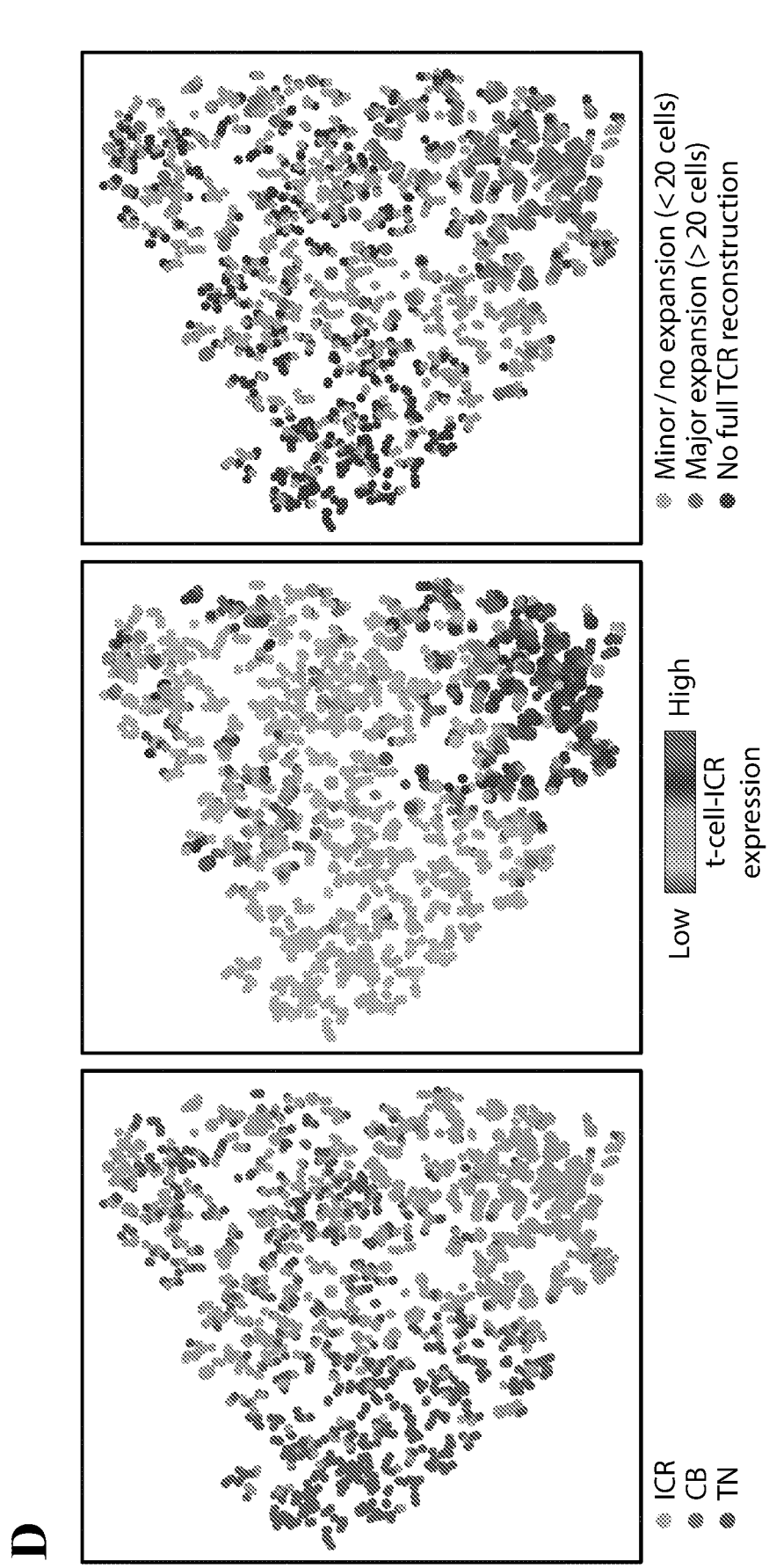

The expression of the ICR signature is higher in expanded CD8 T cells within each subset of patients, with the clonally expanded ICR CD8 T cells scoring highest (FIG. 1D,G, left, $P=3.23*10^{-5}$, mixed-effects test). Nonetheless, even when completely removing the T cells of the three ICR patients with the large T cell clonal expansion, the T-cell-ICR signature still significantly distinguished between the TN and ICR CD8 T cells (FIG. 1G, right, $P=5.56*10^{-53}$ and $7.41*10^{-3}$, t-test and mixed effects test, respectively). The expanded T cells had a gene signature that included significant down-regulation of KLRG1 (table S11).

According to the expression of cell cycle signatures in each cell (materials and methods), five patients had a significantly larger fraction of cycling CD8 T cells (hypergeometric p-value<0.01), four of them were ICR patients. Proliferating CD8 T cells expressed some unique genes compared to proliferating malignant cells (FIG. 1H, table S8), including induction of oxidative phosphorylation ($P=7.89*10^{-6}$, hypergeometric test) and repression of the hematopoietic lineage genes CD37, IL11RA, and IL7R ($P=1.28*10^{-4}$, hypergeometric test). Thus, it may be possible to perturb T cell proliferation specifically, without affecting tumor cells (i.e. tumor growth).

Taken together, these findings demonstrate that even in ICR patients CD8 T cells following ICI can show some indicators of enhanced functionality, such as expansion and transcriptional changes. In other words, these findings demonstrate that ICI can promote the expansion and functionality of the CD8 T cells without leading to a clinical response. Additional data from ICI responders is needed to examine if insufficient T cell functionality nonetheless limited the clinical response in such ICR patients. Nevertheless, Applicants hypothesized that the malignant cell compartment may contribute to ICR in these patients, at least in part.

Figure 2B:
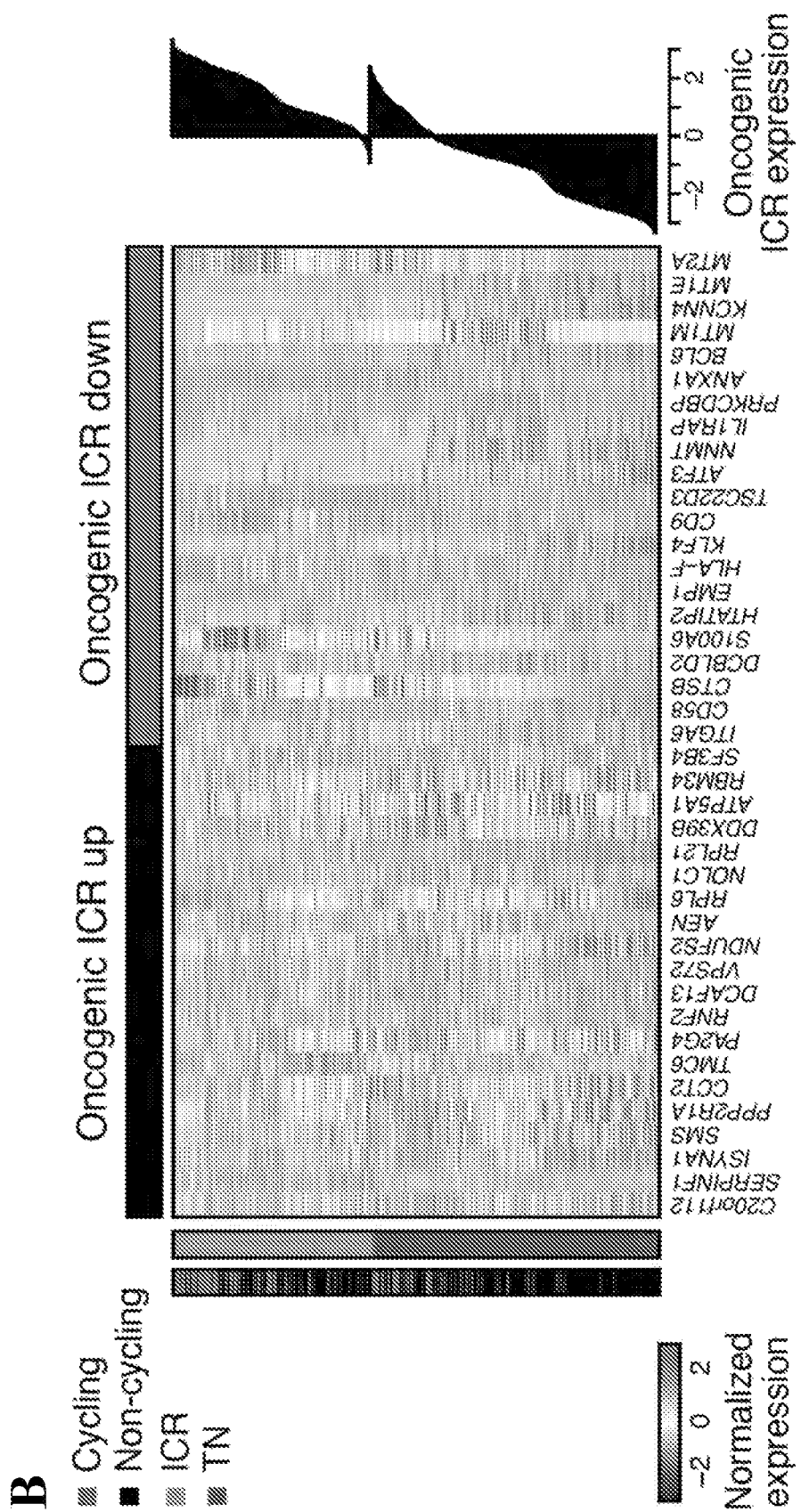
FIG. 2 illustrates the Malignant cell ICR programs. (A) Robust classification by the oncogenic-ICR signature. Left: Box-plot shows the distribution of OE scores for the oncogenic-ICR signature in malignant cells from ICR (blue) and TN (grey) patients, when obtained in a cross-validation (CV) procedure and tested on withheld data. Middle line: median; box edges: $25^{th}$ and $75^{th}$ percentiles, whiskers: most extreme points that do not exceed ±IQR*1.5; further outliers are marked individually. Right: Receiver Operating Characteristic (ROC) curve of the performances of different signatures in classifying cells as ICR or TN; the CV oncogenic-ICR signature was obtained by leave-one (patient) out CV; the first and second Area under the curve (AUC) values are for classification of cells and samples, respectively. (B) Genes in the oncogenic-ICR program. Heatmap shows the (centered and scaled) expression of the top 40 oncogenic-ICR-up and oncogenic-ICR-down genes (columns) across the malignant cells (rows), sorted by TN or ICR tumors (shaded bar, left) and clustered within each class. Leftmost bar: cycling and non-cycling cells within each group. Right: The OE of the oncogenic-ICR signature for each cell. (C) Differentially expressed gene sets in ICR vs. TN malignant cells. Box-plots (formatted as in (A)) show the distribution of OE scores for each signature in malignant cells from ICR vs. TN tumors. (D-E) Inverse relationship of the oncogenic-ICR-down and -up programs. Shown are the OE scores of the oncogenic-ICR-down (y-axis) and oncogenic-ICR-up (x-axis) programs in (D) the single-cell profiles from TN (grey) and ICR (blue) tumors, and in (E) lesions of cutaneous (grey) and uveal melanoma. The Pearson correlation coefficient (r) and p-value are marked. (F) Workflow for identification of the exclusion signatures. (G-H) Congruence between the oncogenic-ICR and exclusion programs. (G) Violin plots of the distribution of OE scores of exclusion signatures across malignant cells from ICR (blue) and TN (grey) patients. (H) Left: Heat map of the (centered and scaled) expression of the 40 most differentially expressed exclusion-up and exclusion-down (black) genes (columns) in the malignant cells (rows), sorted by ICR and TN tumors (left shaded bar) and clustered within class. Leftmost shaded bar labels cycling and non-cycling (black) cells within each group. Gene names in the oncogenic-ICR-up or oncogenic-ICR-down signatures (table S6) are marked by shading, respectively. Right: OE scores of the exclusion signature in each cell.

Applicants thus turned to examine the effect of ICI on the malignant cell profiles, and identified signatures that distinguish malignant cells from ICR vs. TN tumors: oncogenic-ICR-up and oncogenic-ICR-down (FIG. 2A,B, table S6). The signatures were robust and generalizable in cross-validation (withholding data from each patient in turn and classifying the withheld test set; materials and methods, FIG. 2A, AUC=0.86). The variation in the expression of the oncogenic-ICR signatures in either this data or across TCGA melanoma bulk tumors was not significantly associated with potential confounders (materials and methods, mixed-effect model and ANOVA, respectively). Finally, a proportion of malignant cells in TN tumors manifested the oncogenic-ICR state (FIG. 2B, right), suggesting that it may precede ICI at least in some patients. This is discussed further below.

Figure 2C:
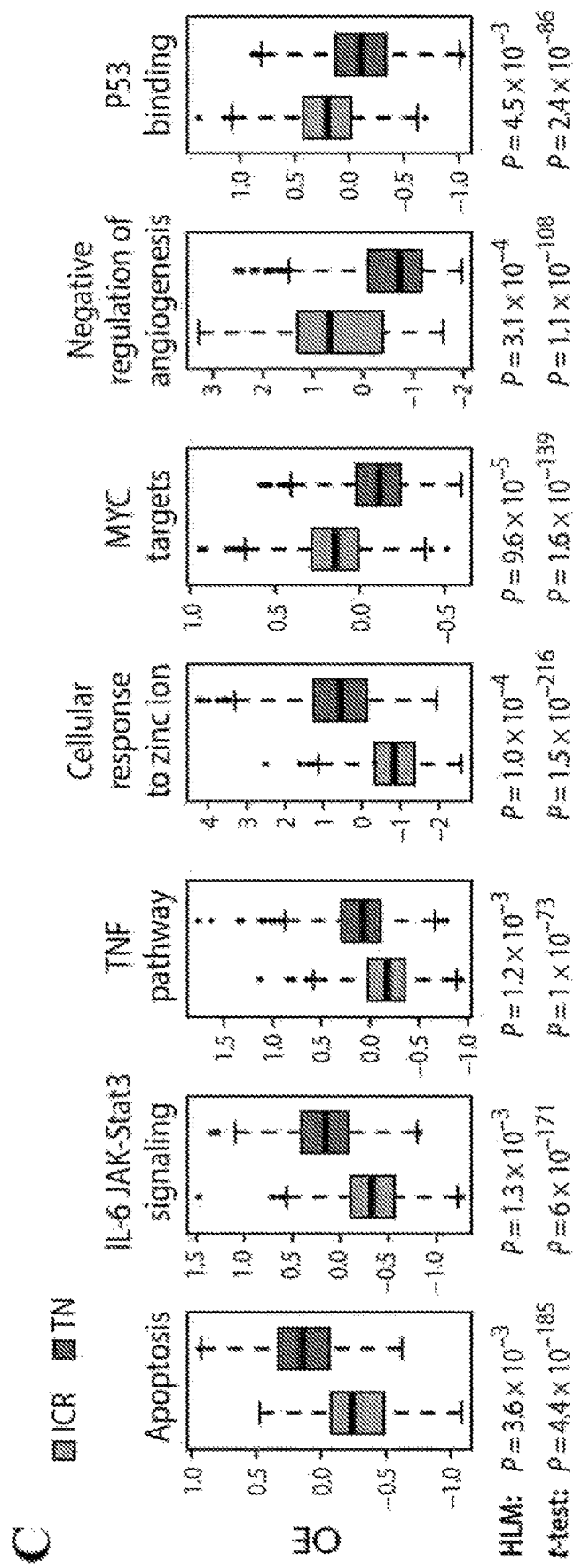

The oncogenic-ICR-down signature genes were enriched both in pathways that reflect established mechanisms of resistance, including downregulation of IFN-signaling and MHC class I presentation (8), and in additional processes, not previously implicated in ICR (FIG. 2B, tables S6 and S9, materials and methods). These include suppression of other innate immune responses, such as TNF-amediated NF B signaling, apoptosis, response to the complement system, IL2/STAT5 signaling, and the reduced expression of metallothioneins. NFKB pathway activation can induce expression of cytokines with either negative or positive immune-modulatory effects (24, 25). Our results suggest that underexpression of TNF-amediated NFKB signaling genes may be detrimental for response. The oncogenic-ICR-up genes include several transcriptional and chromatin regulators (e.g., SNAI2, HMGA1), and are enriched for Myc and CDK7/8 targets ($P<10^{-11}$, hypergeometric p-value). Myc-activation has been previously linked to increased expression of immunosuppressive signals, including the upregulation of PD-L1 and β-catenin, which in turn inhibits dendritic cell recruitment to the tumor microenvironment via CCL4 (11). Similar results were obtained when comparing pre defined gene modules directly between malignant cells of ICR and TN patients (FIG. 2C, materials and methods), including repression of the IL6/JAK/STAT3 pathway; mutations in this pathway were recently reported as an escape mechanism to anti-PD-1 therapy (8).

Gene modules are more robust to noise and provide more coherent signals than the expression of single genes. Applicants thus applied the mixed-effect models to test which biological pathways are differentially expressed between the two groups. The analysis revealed similar pathways to those outlined above, as well as the repression of the JAK/STAT pathway. Mutations in this pathway were previously reported as an escape mechanism to anti-PD-1 therapy.

Several lines of evidence suggest that the oncogenic-ICR-up and oncogenic-ICR-down signatures are under shared control by one or few master regulators with opposing effects on these two programs. First, the expression of the oncogenic-ICR-up and oncogenic-ICR-down signatures is anti-correlated within the malignant cells of the same tumor and across hundreds of (TCGA) melanoma tumors (FIG. 2D,E). Second, in the Connectivity Map (26), there is a significant overlap between the genetic perturbations that induce the oncogenic-ICR-down signature and those that repress the oncogenic-ICR-up signature (hypergeometric p-value=$1.9*10^{-6}$), including overexpression of IFN-γ and IFN-β and the knockdown of MYC. Indeed, MYC knockdown is the top perturbation to repress oncogenic-ICR-up, which is enriched for Myc targets. Moreover, there are 1,583 protein-protein interactions within and between the genes in the two oncogenic-ICR signatures ($P<10^{-3}$, empirical test), consistent with participation in convergent biological processes. Applicants therefore defined the oncogenic-ICR state as a concurrent induction of the oncogenic-ICR-up signature and repression of the oncogenic-ICR-down signature, which Applicants quantify by the overall expression (materials and methods) of the oncogenic-ICR-up signature minus the overall expression of the oncogenic-ICR-down signature.

Figure 2F:
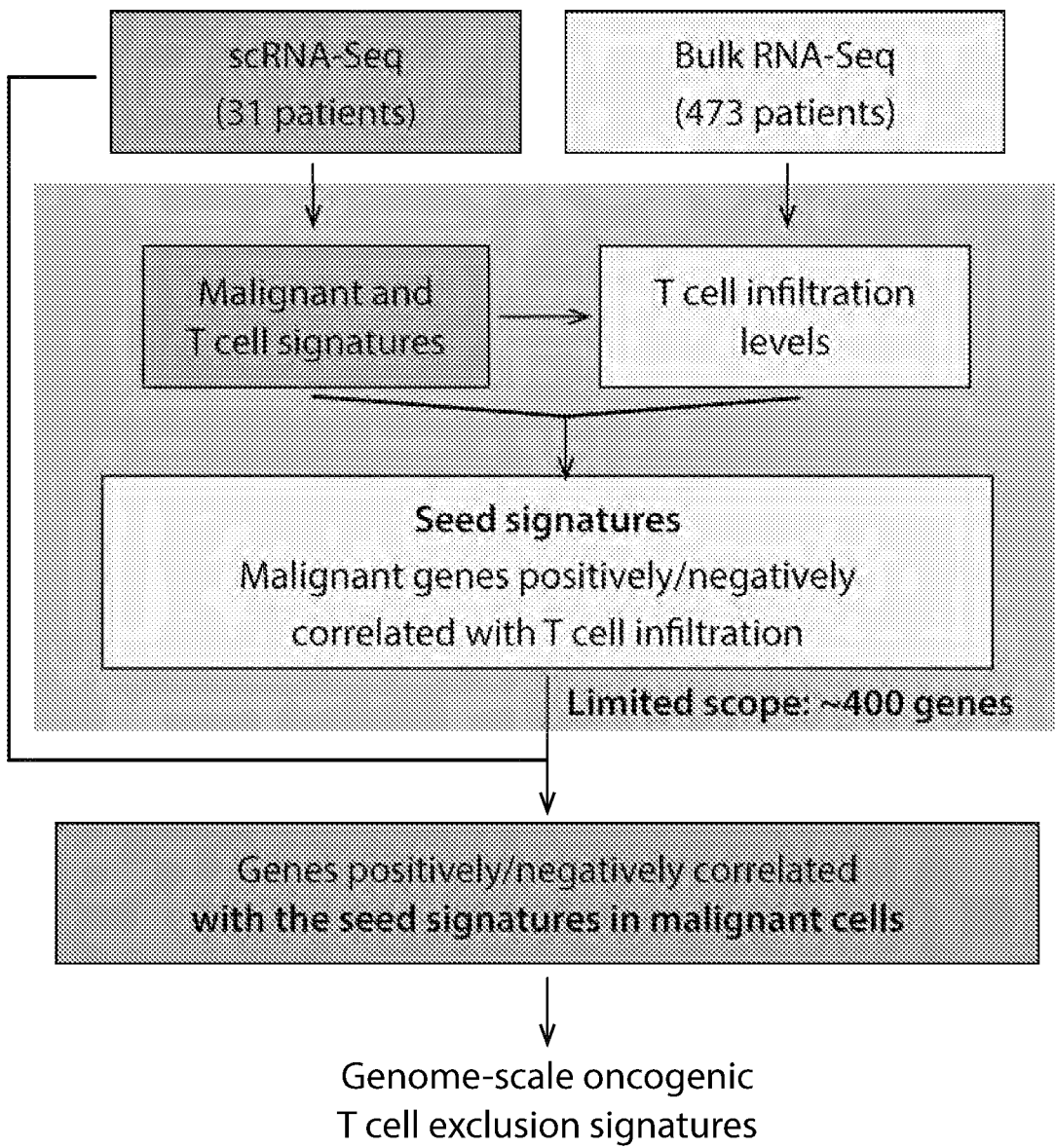

Next, Applicants hypothesized that the oncogenic-ICR signatures reflect an active resistance program, rather than only a post-ICI malignant cell state. This would be consistent with the presence of cells expressing the program in TN patients. In particular, to resist ICI, malignant cells may not only evade the immune cells (e.g., through the repression of MHC I and IFN-γ in oncogenic-ICR-down) but may also actively exclude the immune cells. The latter will impact the extent of CD8 T cell infiltration, which is a known pretreatment predictor of ICI response (6, 27). To explore this possibility, Applicants developed a data-driven approach that characterizes malignant cells in non-infiltrated niches or tumors (FIG. 2F). In this approach, Applicants combined single-cell profiles (irrespective of treatment status) with 473 melanoma bulk expression profiles from TCGA. First, Applicants used the single-cell profiles to define a T cell specific signature of 143 genes, and a signature of 332 genes that were primarily expressed by malignant cells (table S4). Then Applicants estimated the T cell infiltration level of the TCGA tumors based on their expression of the T cell signature (materials and methods), and identified malignant genes whose expression was correlated to the estimated T cell infiltration levels. Six and 20 of the 332 malignant cell genes were significantly correlated or anti-correlated to the T cell infiltration level, respectively, which Applicants termed the seed T cell exclusion (Exclusion)-down and -up modules, respectively. However, the seed modules would neglect genes that are expressed also by other, non malignant cells in the tumor (as MHC I, IFN-γ). To recover these, Applicants correlated the expression of each gene to the expression of the seed Exclusion modules across the entire malignant single-cell profiles. This yielded the final Exclusion-up and down modules, with 101 and 134 genes, respectively (table S6).

The Exclusion-down module was enriched for antigen processing and presentation genes (B2M, CTSB, CTSL1, HLA-B/C/F, HSPA1A, HSPA1B, $P=4.19*10^{-7}$, hypergeometric test), immune modulation genes ($P=3.84*10^{-9}$, as CD58 and the NFKB inhibitor, NFKBIA), and genes involved in the response to the Complement system ($P=2.26*10^{-7}$, e.g., CD59 and C4A). CD58 KO in malignant cells was recently shown to enhance the survival of melanoma cells in a genome-scale CRISPR screen of melanoma/T cell co-cultures (28), and its genetic loss or epigenetic inactivation are frequent immune evasion drivers in diffuse large B cell lymphoma (29). The Exclusion-up module included MYC itself and Myc targets ($P=6.8*10^{-12}$), as well as the transcription factors SNAI2 and SOX4.

Figure 2G:
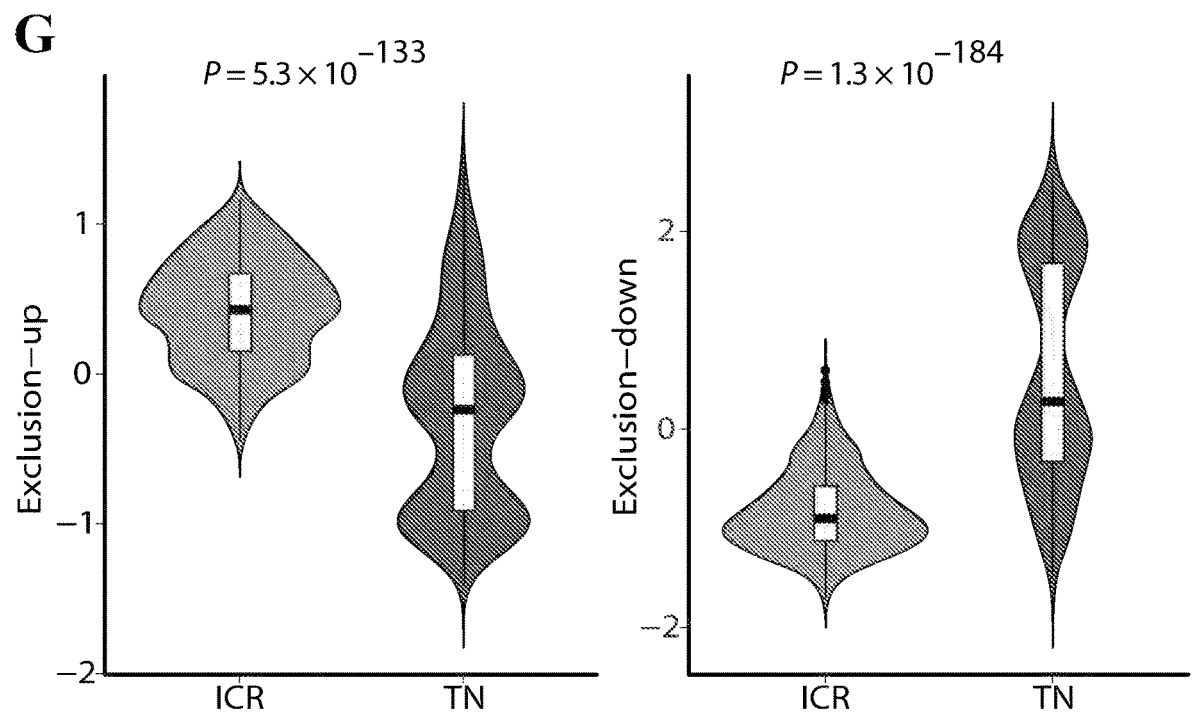
Figure 2H:
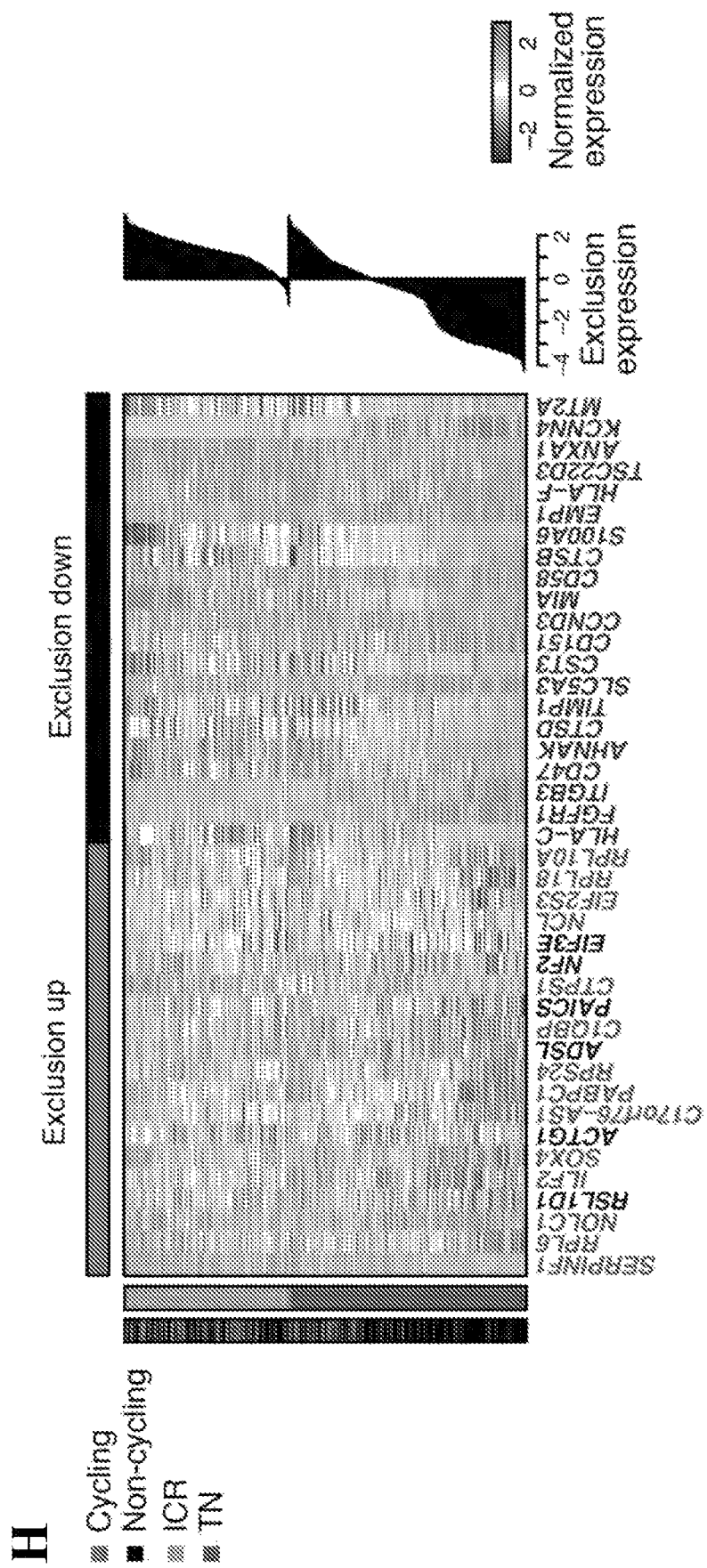

Even though the Exclusion modules were identified without considering the treatment status of the tumors (TN or ICR), they significantly overlapped the corresponding oncogenic-ICR signatures (64 and 52 overlapping genes in oncogenic-ICR-up and -down, respectively, $P<10^{-16}$, hypergeometric test, FIG. 2G,H). Both oncogenic-ICR (AUC=0.83, in cross-validation) and the Exclusion signatures (AUC=0.86 robustly classified individual cells as TN or ICR (FIG. 2A,G). In light of this congruence, Applicants defined a unified resistance program (uICR-up and uICR-down) as the union of the corresponding oncogenic-ICR and Exclusion signatures.

Figure 10A:
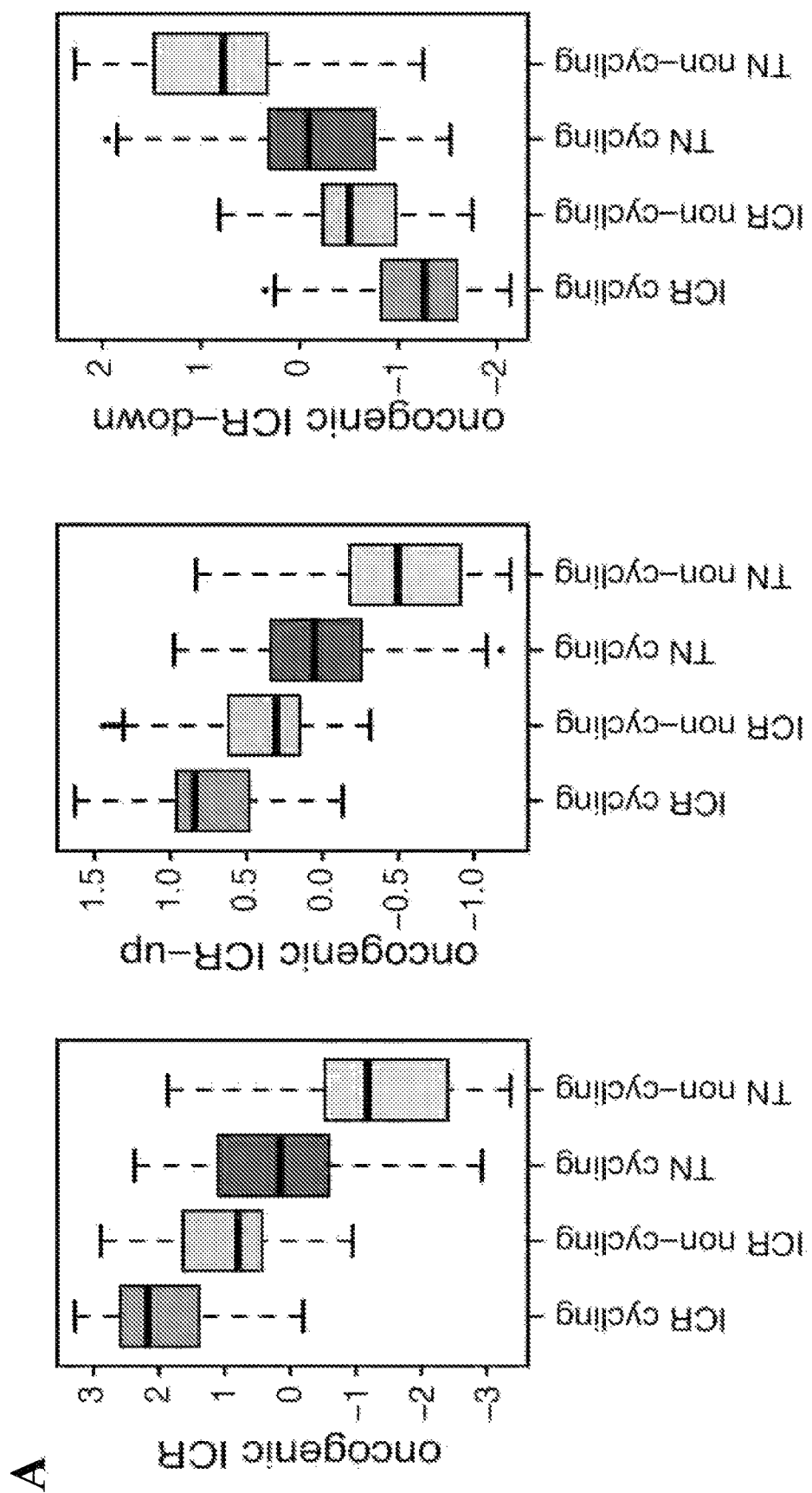
FIG. 10 illustrates the relationship between the malignant ICR program and cell cycle. (A, B) Higher ICR in cycling cells. (A) Box plots of the distribution of OE scores of the oncogenic-ICR signatures (y-axis) in cycling and non-cycling cells from ICR and TN tumors (x-axis). The middle line represents the median; box edges are the 25th and 75th percentiles, and whiskers represent the most extreme points that do not exceed ±IQR*1.5; points beyond the distance are plotted as single points. (B) Heatmap of the expression of ICR-up (bar) and down (black bar) genes (rows) that are also induced (repressed) in cycling vs. non-cycling malignant cells. Cells (columns) are sorted by TN and ICR tumors and clustered within each set (bar on top); the cells' cycling status in each category is marked by the bar on top. Bottom: Oncogenic ICR signature score (y axis) in each cell (x axis). (C) Abemaciclib represses the uICR program in breast cancer cell lines. Heatmap of the relative expression of all the uICR genes (rows) in Abemaciclib-treated and control breast cancer cells lines (columns), based on the data in (24). Gene expression is relative to the basal expression level in each cell line. Bottom: OE scores (y axis) of the uICR signature for each cell line (x axis).
Figure 10B:
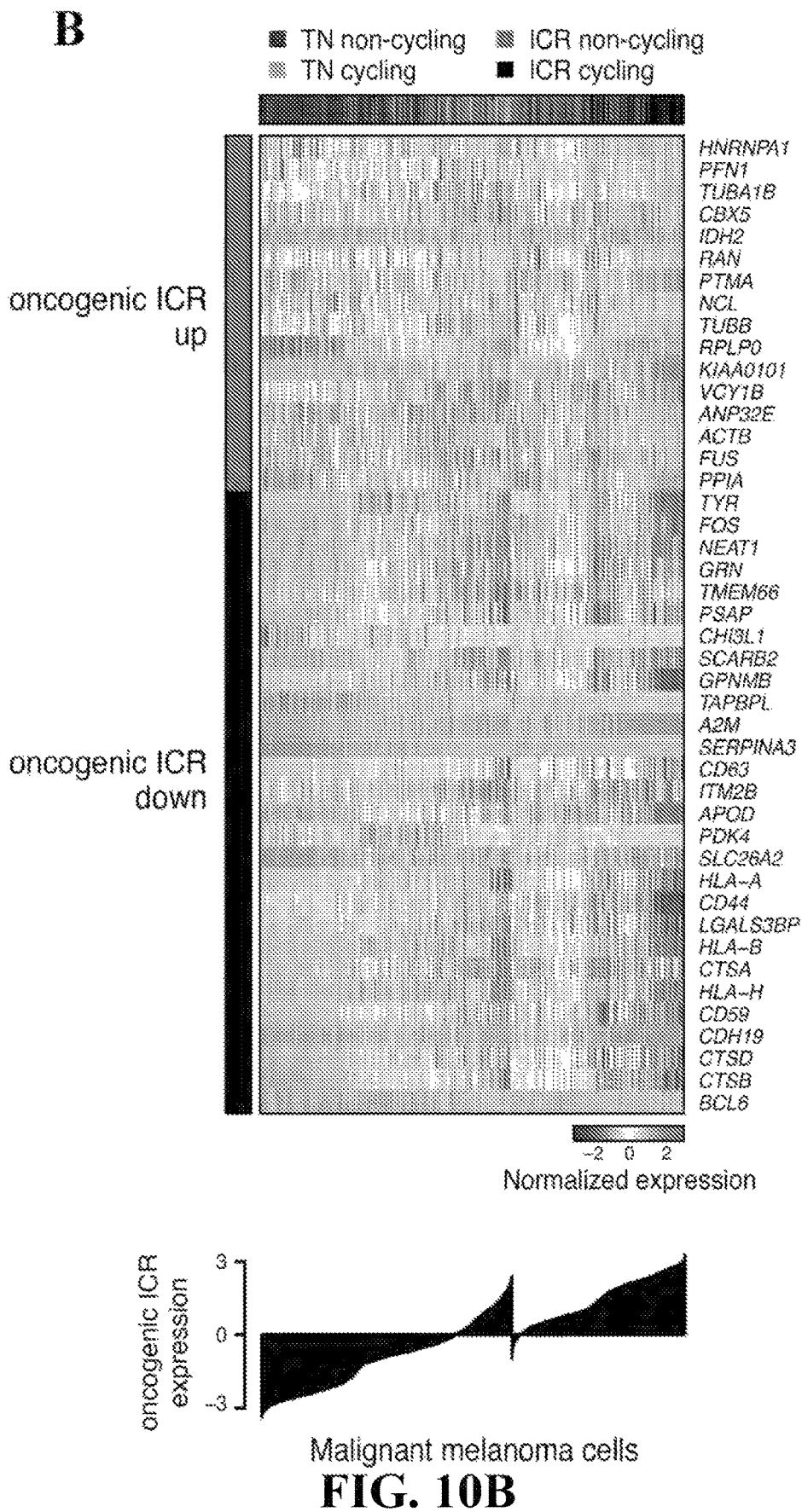

Importantly, there was no significant difference between the fraction of cycling cells in ICR vs. TN tumors (P=0.696, t-test), and the oncogenic-ICR signatures were identical when identified only based on non-cycling cells. Interestingly however, the oncogenic-ICR state was more pronounced in cycling cells, both within the same patient group and among cells of the same tumor (FIG. 2B,H, FIG. 10A,B, $P<10^{-16}$, mixed effects model). Thus, cycling malignant cells may have induced stronger immune evasion capacities compared to their non-cycling counterparts. Moreover, CDK4 was a member of the induced resistance program (uICR-up). Applicants thus hypothesized that its targeted inhibition could shift the malignant cells to a less resistant state.

Unlike other biomarkers, such as PDL1 expression, mutational load, or T cell infiltration levels, the immune resistance signature could potentially provide a basis to develop novel treatment strategies. Next, Applicants explored therapeutic strategies to overcome resistance by reversing the uICR cell state in cancer cells. As CDK4 and multiple CDK target were members of the induced resistance program (uICR-up) and as the ICR state was more pronounced in cycling cells, Applicants hypothesized that cell cycle arrest through CDK4/6 inhibition could shift the malignant cells to a less resistant state. Additionally, CDK4/6 inhibitors could potentially increase tumor cell immunogenicity by inducing SASP, which was significantly repressed in the cancer cells from the ICR tumors compared to those from the untreated ones.

Figure 3C:
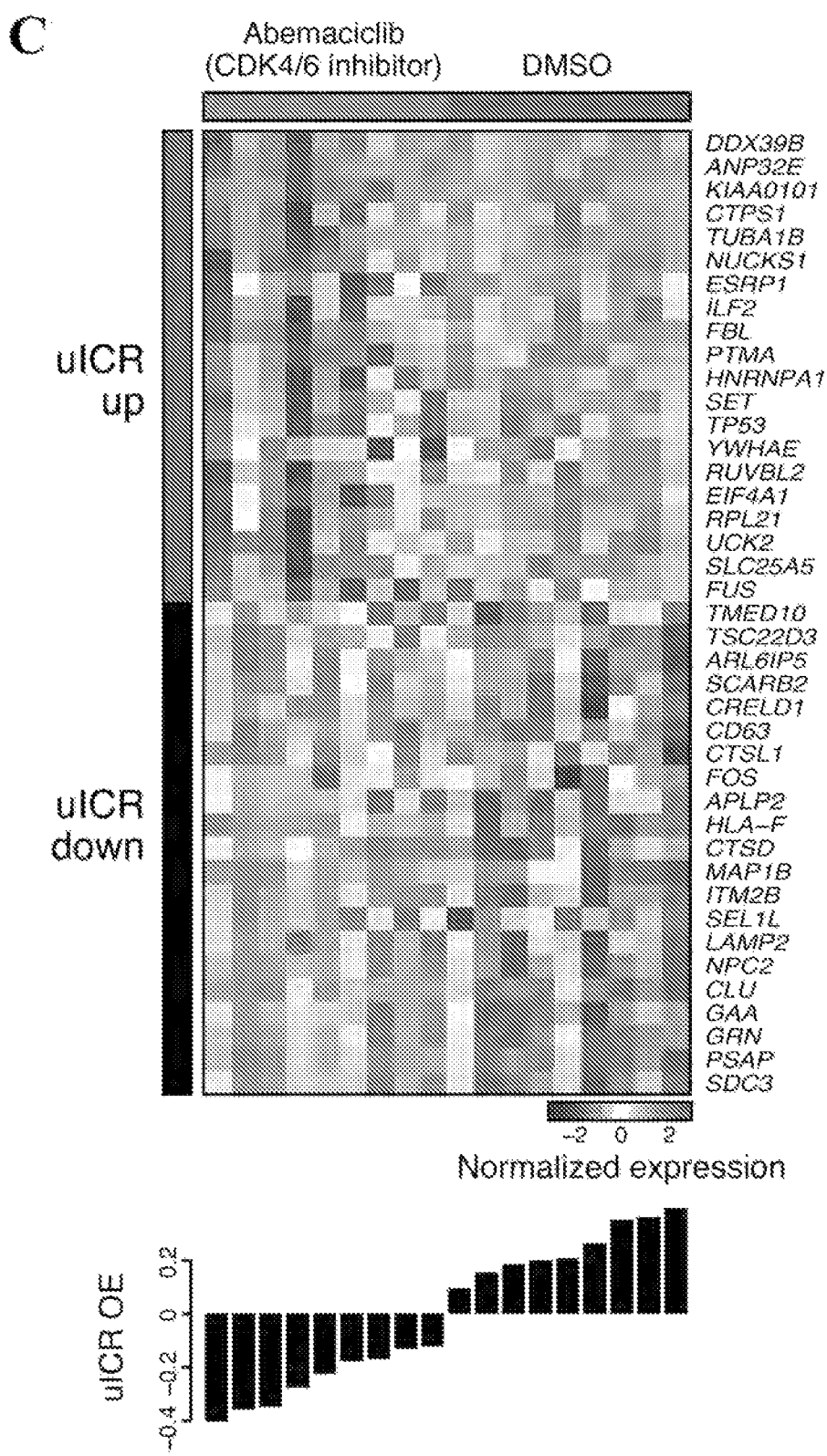
FIG. 3 illustrates that the uICR program has immune evasion properties, and can be reversed by CDK4/6 inhibition. (A-C) Reversal of resistance programs by a CDK4/6 inhibitor, abemaciclib. (A) Significance (y axis, $-\log_{10}$(p-value), Wilcoxon rank sum test) of induction (dark green) or repression (light green) of each signatures in tumors from abemaciclib treated mice compared to vehicle (31). (B) Distribution of uICR OE scores in breast cancer cell lines (M361, MCF and M453) treated with abemaciclib ("abe") or with DMSO vehicle ("con"). Box-plots: the middle line represents the median; box edges are the $25^{th}$ and $75^{th}$ percentiles, and whiskers represent the most extreme points that do not exceed $\pm IQR*1.5$; points beyond the distance are plotted as single points. (C) The relative expression of the 40 most differentially expressed uICR genes (rows) in abemaciclib-treated (green) and control (purple) breast cancer cells lines (columns). Expression values are normalized according to the cell-line specific expression in the control state or denote over- or under-expression, respectively. Bottom: OE scores of the uICR signature for each cell line. (D) Higher uICR scores in uveal melanoma. Shown are the distributions of OE scores of the uICR program in cutaneous (black) vs. uveal melanoma tumors from TCGA, scored after filtering TME contributions (materials and methods). P-value: t-test. (E) Suppression of cell-cell interactions in ICR. Bar plots show for each malignant signature (x-axis) the number of genes (y-axis, top) in the signature that can engage in a physical interaction with other cell types and the corresponding statistical enrichment (y-axis, $-\log_{10}$(P-value), hypergeometric test, bottom). Values above the dashed line are statistically significant.
Figure 10C:
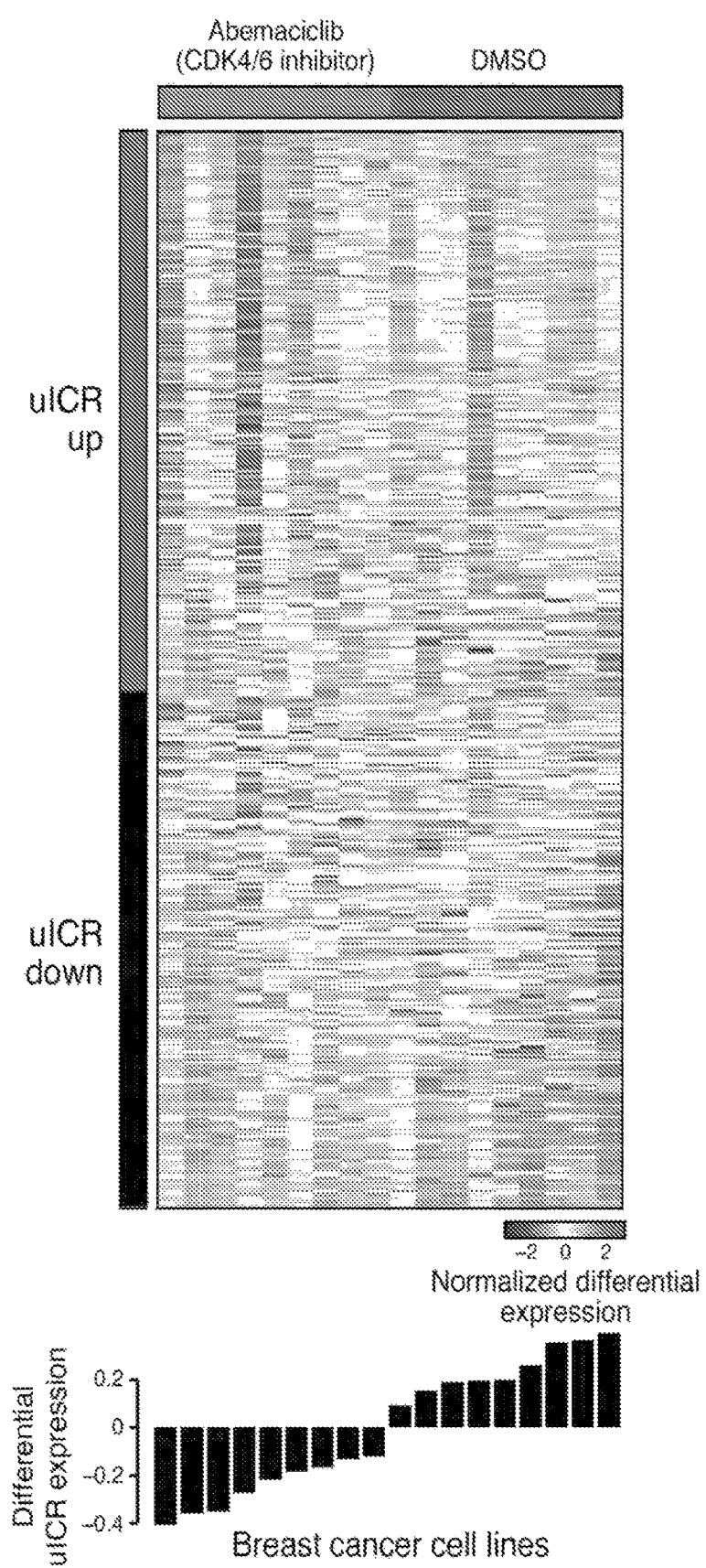

To test this assumption, Applicants first analyzed a recently published data set (30) in breast cancer cell lines and in vivo models and showed that CDK4/6 inhibition through abemaciclib treatment represses the ICR state defined by our signatures (FIG. 3A-B, FIG. 10C). Applicants found that the CDK4/6 inhibitor abemaciclib strongly represses uICR-up (which includes CDK4) and induced uICR-down (which includes the D-cyclin, CCND3). Indeed, abemaciclib, approved for the treatment of BRCA-mutated breast cancer, was recently shown to trigger anti-tumor activity by inducing type III interferon production and suppressing T regulatory cells (30). Furthermore it was shown to sensitize solid tumors to anti-PDL1 in mouse models (30) in an RB-dependent manner.

Figure 41:
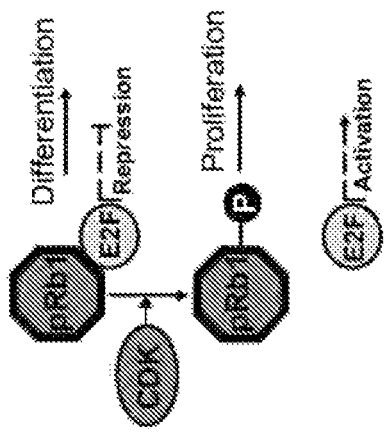
FIG. 41 illustrates that CDK4/6 inhibitors sensitize melanoma cells.
Figure 43:
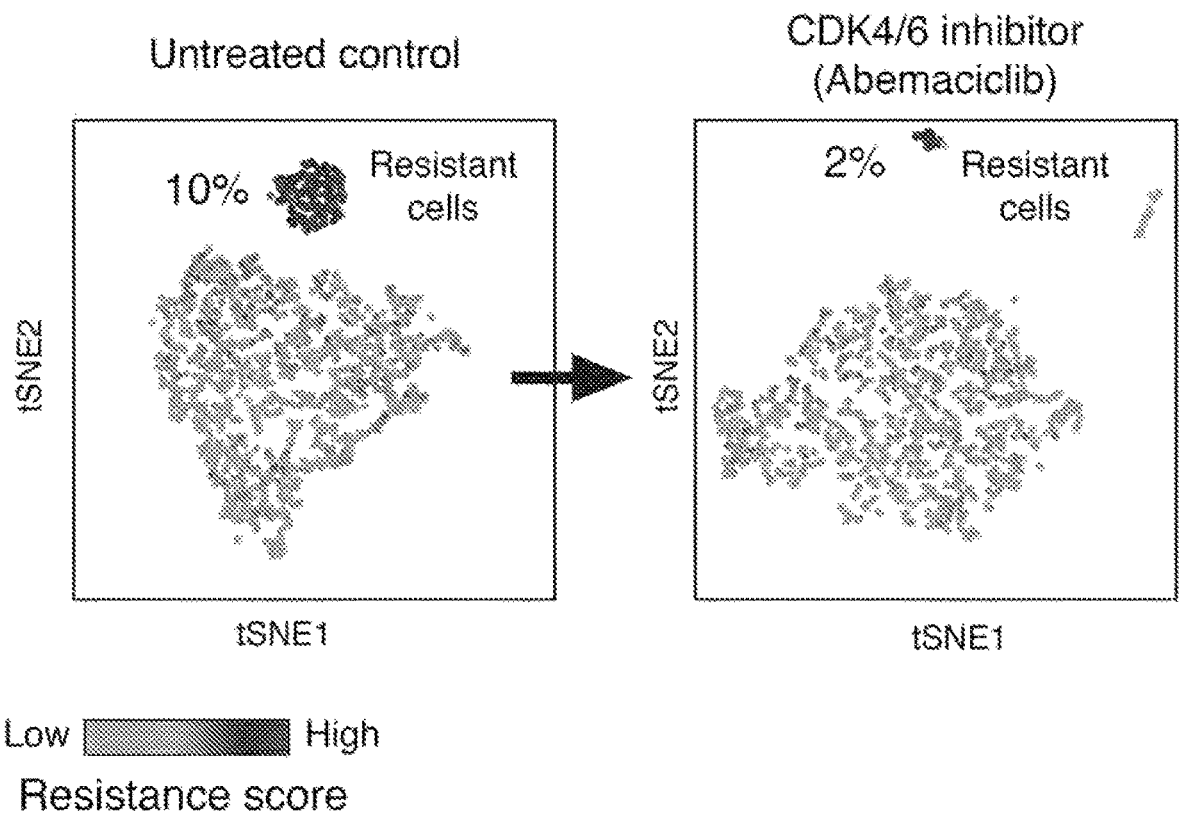
FIG. 43 illustrates that CDK4/6 inhibitors eliminate a resistant subpopulation of melanoma cells.

To determine this effect in melanoma, Applicants identified melanoma cell lines in the Cancer Cell Line Encyclopedia (CCLE) with the strongest expression of the uICR signature, including IGR37, UACC257 (both RB-sufficient) and A2058 (RB-deficient). Applicants performed scRNA-seq on these cell lines before and after treatment with abemaciclib for 1 week (FIG. 41). In both IGR37 and UACC257, Applicants saw a decrease in the expression of the uICR state ($P<3.59*10^{-34}$, one-sided t-test). The single-cell resolution of the data revealed that in IGR37 there was a subpopulation of cells with an exceptionally strong expression of the uICR signature prior to the treatment with abemaciclib (FIG. 43). This population decreased from 10% before treatment (2,454 cells) to 2% in the post-treatment condition (1,570 cells). In contrast, the RB-deficient cell line A2058 did not show changes in the uICR expression, consistent with the hypothesis that this effect depends on RB-sufficiency.

Figure 42:
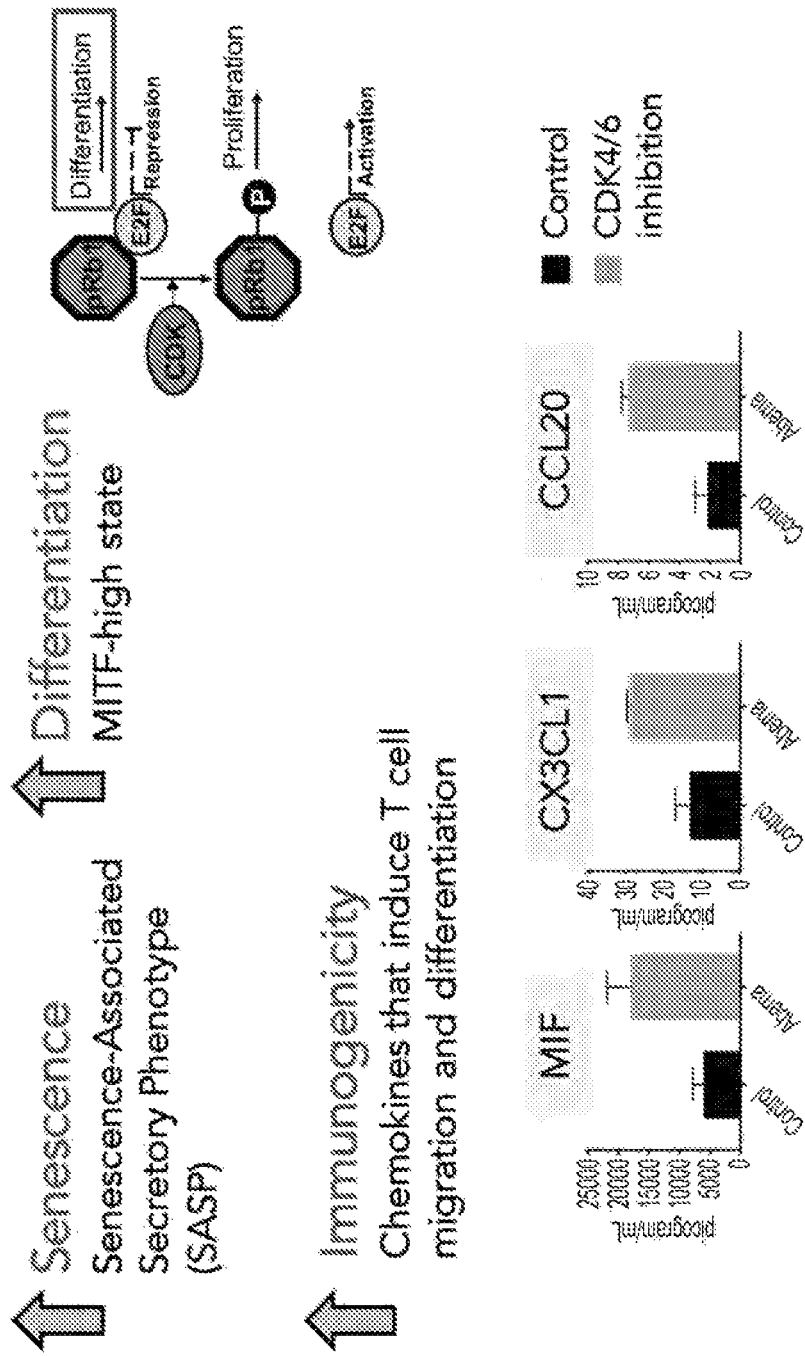
FIG. 42 illustrates that CDK4/6 inhibitors induce markers of differentiation, senescence and immunogenicity in melanoma.

Interestingly, Applicants found that DNMT1 is repressed while ERV-3 is induced in IGR37 and UACC257 cells post-treatment. These findings support previous observations that CDK4/6 inhibition leads to DNMT1 repression, allowing the methylation of endogenous retroviral genes (ERVs). The induction of ERVs triggers 'viral mimicry' and a double-stranded RNA (dsRNA) response, which stimulates type III IFN production to activate IFN-stimulated genes. Interestingly, Applicants also find that abemaciclib induces the expression of an MITF signature (Tirosh I, et al., Science. 2016 Apr. 8; 352(6282):189-96) and of the SASP module (FIG. 42). The resistant cells, which are eradicated or altered by abemaciclib, had the lowest expression of the MITF and SASP signatures. While this pattern is decoupled from the expression of the MITF gene itself, it nonetheless indicates that, unlike the mechanism described in breast cancer cells (30), abemaciclib might trigger SASP and cell differentiation in melanoma cells.

To explore the potential of abemaciclib to induce T cell mediated toxicity to tumor cells, Applicants leveraged a patient-derived co-culture model of melanoma cells and ex-vivo expanded tumor infiltrating lymphocytes (TILs) from a metastatic melanoma lesion. Following one week of treatment of tumor cells with abemaciclib, cells were treated with their autologous TILs vs. control, and surviving tumor cells were submitted to scRNA-seq. The exposure to TILs reduced the expression of the uICR signature, both in the control and abemaciclib-treated cells ($P<4.91*10^{-13}$). The treatment with abemaciclib further intensifies these effects, such that in the abemaciclib-treated cells there was an increase in a sensitive (ICR-low) subpopulation of cells post-TILs (FIG. 42). These sensitive cells are also characterized by a low expression of DNMT1, overexpression of ERV-3, and higher expression of the MITF and SASP modules. Furthermore, Applicants measured 40 human cytokines/chemokines in the conditioned media of abemaciclib treated cancer cells (before co-culture) and found the induction of several secreted factors (FIG. 42): macrophage inhibition factor (MIF), CX3CL1 a chemokine that induces migration and adhesion of T and NK cells and is linked to clinical outcomes in immunotherapy treatment (38, 39), and CCL20, an important factor for T cell differentiation that may enhance immunity in melanoma (40).

The relevance of the uICR as a resistance program is further supported by several lines of evidence. First, the induced uICR is overexpressed in uveal melanoma, which resides in an immune-privileged environment and has very low response rates to immunotherapy (31, 32), compared to cutaneous melanoma (FIG. 3D). Second, perturbations of genes from the repressed resistance program (uICR-down) in malignant melanoma cells conferred resistance to cytotoxic CD8 T cells in a genome-wide CRISPR KO screen ($P=6.37*10^{-3}$, hypergeometric test). Third, malignant cells in the resistant state substantially repress interaction routes with other cell types in the tumor (FIG. 3E), as defined by cognate pairs of interacting surface molecules (materials and methods), including MHC I:TCR (T cells), CD58:CD2 (T cells), and IL1RAP:IL1B (macrophages).

These results support a model, in which malignant cells from ICR tumors either had active resistance programs prior to treatment or induced the resistance program upon ICI exposure. Because some of the malignant cells from the TN patients expressed the resistance programs (FIG. 2B,H) Applicants next tested their prognostic value in independent datasets and cohorts. To this end, Applicants used both the full uICR and further filtered/refined uICR signatures. The refined signatures include only uICR genes that were also co-regulated with genes whose inhibition enhanced melanoma cell resistance to T cell mediated killing in functional screens (28) (table S6, materials and methods); the oncogenic-ICR and Exclusion signatures show the same behavior (FIG. 4E-H, FIGS. 11-13).

The uICR programs are prognostic and predictive for response in external data sets. First, the signatures strongly associated with survival in 431 TCGA melanoma patients (who did not receive ICI, FIG. 4A, FIG. 11), even after controlling for tumor purity and T cell infiltration, a known prognostic marker in melanoma (33, 34). Furthermore, combining resistance signatures and T cell infiltration levels yielded a significantly stronger association of patient survival than either alone (COX p-value=$1.4*10^{-8}$, FIG. 4A, right). Other proposed mechanisms, such as dedifferentiation of melanoma cells (35), as reflected by an MITF-low signature, and other malignant signatures from the single-cell profiles (e.g., cell cycle and the AXL program) (13), did not show an association to patient survival, indicating that mere variation across malignant cells is insufficient as a prognostic signature. Second, the signatures were associated with benefit of ICI in published pre-treatment and early on-treatment bulk expression profiles. In a lung cancer mouse model, which was mostly free of confounding genetic variability, the uICR clearly separated anti-CTLA-4 responders from non-responders based on early on-treatment profiles ($P=3.6*10^{-7}$, one-sided t-test, FIG. 4B) (36). In bulk pre treatment RNA-Seq data from 27 melanoma patients that were subsequently treated with Pembrolizumab (5), the uICR program was lower in the five complete responders, though just above statistical significance ($P=6.3*10^{-2}$, FIG. 4C). In bulk pre-treatment RNA-Seq data from 42 melanoma patients that were subsequently treated with the CTLA-4 inhibitor ipilimumab (4), the uICR program was significantly lower in the two complete responders ($P=5.2*10^{-3}$).

To test the predictive value of the resistance program in a larger independent setting, Applicants assembled a validation cohort of 112 patients with metastatic melanoma who underwent pretreatment biopsy and bulk RNA-Seq followed by Pembrolizumab (anti-PD-1) therapy (FIG. 1A, table S1). The cohort was collected in a different hospital and country (Germany), and samples were processed and sequenced on the same platform at the Broad Institute (materials and methods). Applicants evaluated the performances of the malignant resistance modules in predicting anti-PD-1 responses, with respect to three parameters (materials and methods): (1) progression-free survival (PFS, recorded for 104 of the 112 patients), (2) clinical benefit (CB, defined as either partial or complete response by RECIST criteria), and (3) complete response (CR). To compare the performance of the predictors to prior knowledge and clinically used markers, Applicants assembled a set of 32 other transcriptional signatures, including the top hits of two ICR functional CRISPR screens (28, 37) (table S10).

Figure 4A:
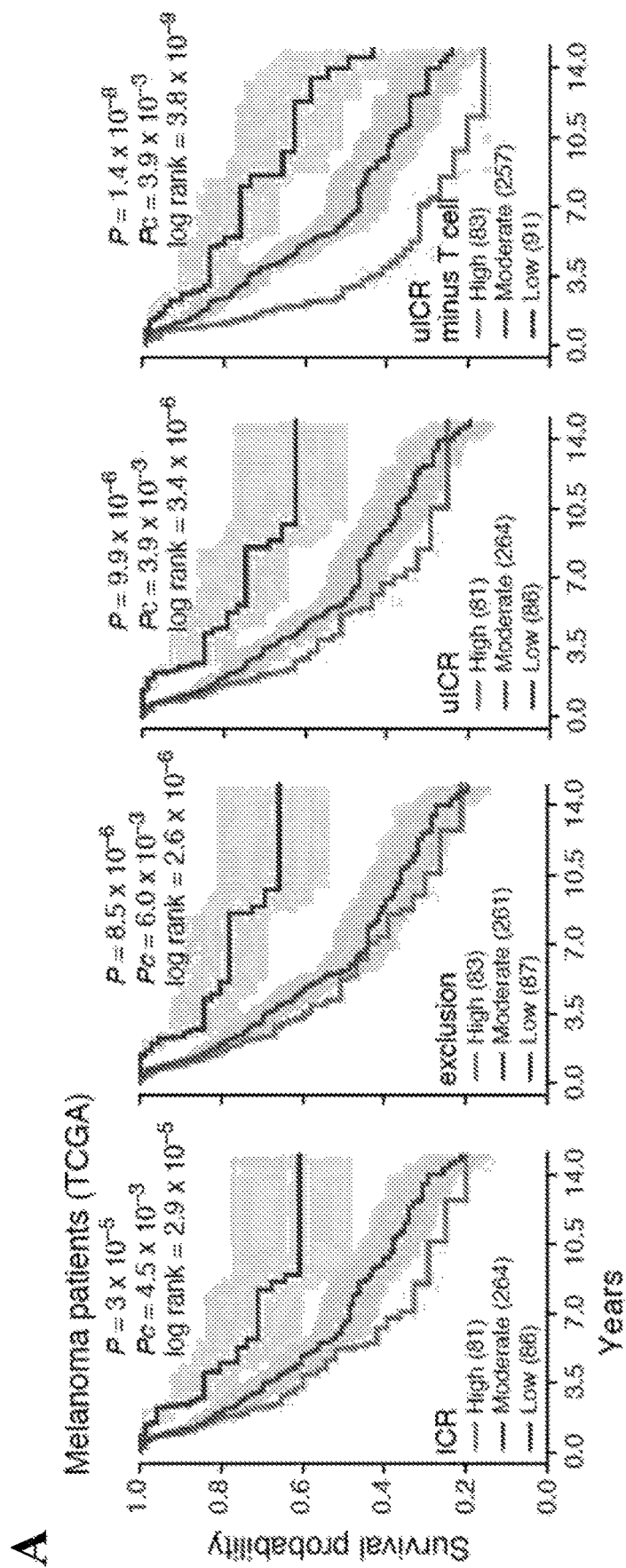
FIG. 4 illustrates that the resistance signatures in malignant cells are prognostic and predictive in validation cohorts. (A) Resistance signatures predict melanoma patient survival based in bulk RNA-seq from TCGA (37). Kaplan-Meier (KM) plots are stratified by high (top 25%), low (bottom 25%), or intermediate (neither high nor low) expression of the respective signature. Pc p-values test if the signature further enhances the predictive power of models with T-cell infiltration levels as a covariate. See FIG. 11 for additional signatures. (B, C) Resistance signatures distinguish clinical benefit (CB) and non-CB in mouse models and melanoma patients. Box plots show the distribution of the OE score of the uICR in bulk RNA-Seq from a lung cancer mouse model treated with anti-CTLA-4 therapy (35) (B) or from biopsies of melanoma patients prior to treatment with pembrolizumab (5). Middle line: median; box edges: 25th and 75th percentiles, whiskers: most extreme points that do not exceed $\pm IQR*1.5$; further outliers are marked individually. P-value: one-sided t-test. (D-F) Resistance signatures predict melanoma patient outcomes following pembrolizumab treatment from pre treatment RNA-Seq in an independent cohort of 112 patients. (D) KM plots of progression-free survival (PFS) for the 104 patients in the cohort with available PFS data, when the patients are stratified by high (top 25%), low (bottom 25%), or intermediate (neither high nor low) expression of the respective signature. Prediction is enhanced when controlling for cell cycle as a confounder (two right plots, materials and methods). See FIGS. 12 to 13. (E) Bar plot shows predictive value for PFS for the 104 patients as in (D) with a COX regression model that accounts for inferred T-cell infiltration levels ($-\log_{10}$(p-value), x axis). Light blue bars: enhances PFS; grey bars: reduces PFS. Bars with black border denote the new signatures identified in this study for malignant resistance. Dashed line: p<0.05. Resistance signatures are significantly more predictive compared to others (P=3.37*10$^{-6}$, Wilcoxon-ranksum test)). (F) Distribution of OE scores (y axis) of each signature in the pre-treatment bulk RNA-Seq profiles, showing patients with either intrinsic resistance (Non-CB, n=49) or with clinical benefit (CB, n=39), with the latter also further stratified based on duration of response (CB<6 mo, n=5; 6 mo<CB<1 year, n=9; CB>1 year, n=25). Twenty-four patients with unknown response or stable disease are not shown here (see FIG. 14). Distinctions are enhanced when accounting for inferred T-cell infiltration levels (right). P1 and P2 are the one-sided t-test p-value obtained when comparing the non-CB patients to the CB or CB>1 yr patients, respectively. The AUC at the top was obtained when predicting long-term CB (CB>1 yr) in all patients with a recorder response (n=101). Box plots formatted as in (B). (G) Box-plots show the distribution of OE scores (y axis) of each signature in the pre-treatment bulk RNA-Seq profiles, for patients with complete response (CR, n=14), partial response (PR, n=25), or progressive disease (PD, n=49). P is the one-sided t-test p-value obtained when comparing the CR patients to the PR and PD patients. The AUC at the top was obtained when predicting CR in all patients with a recorder response (n=101). (H) Bar plot shows predictive value for predicting complete response with the different signatures ($-\log_{10}$(t-test p-value), x-axis) in 101 patients with a recorded response. Light blue bars: positive impact; grey bars: negative impact. Bars with black border denote the new signatures identified in this study for malignant resistance. Dashed line: p=0.05. Resistance signatures are significantly more predictive compared to other signatures (P=1.64*10-8, Wilcoxon ranksum test). AUC values are marked next to the bar for each significant association. (I) Model for ICR based on this study.
Figure 4D:
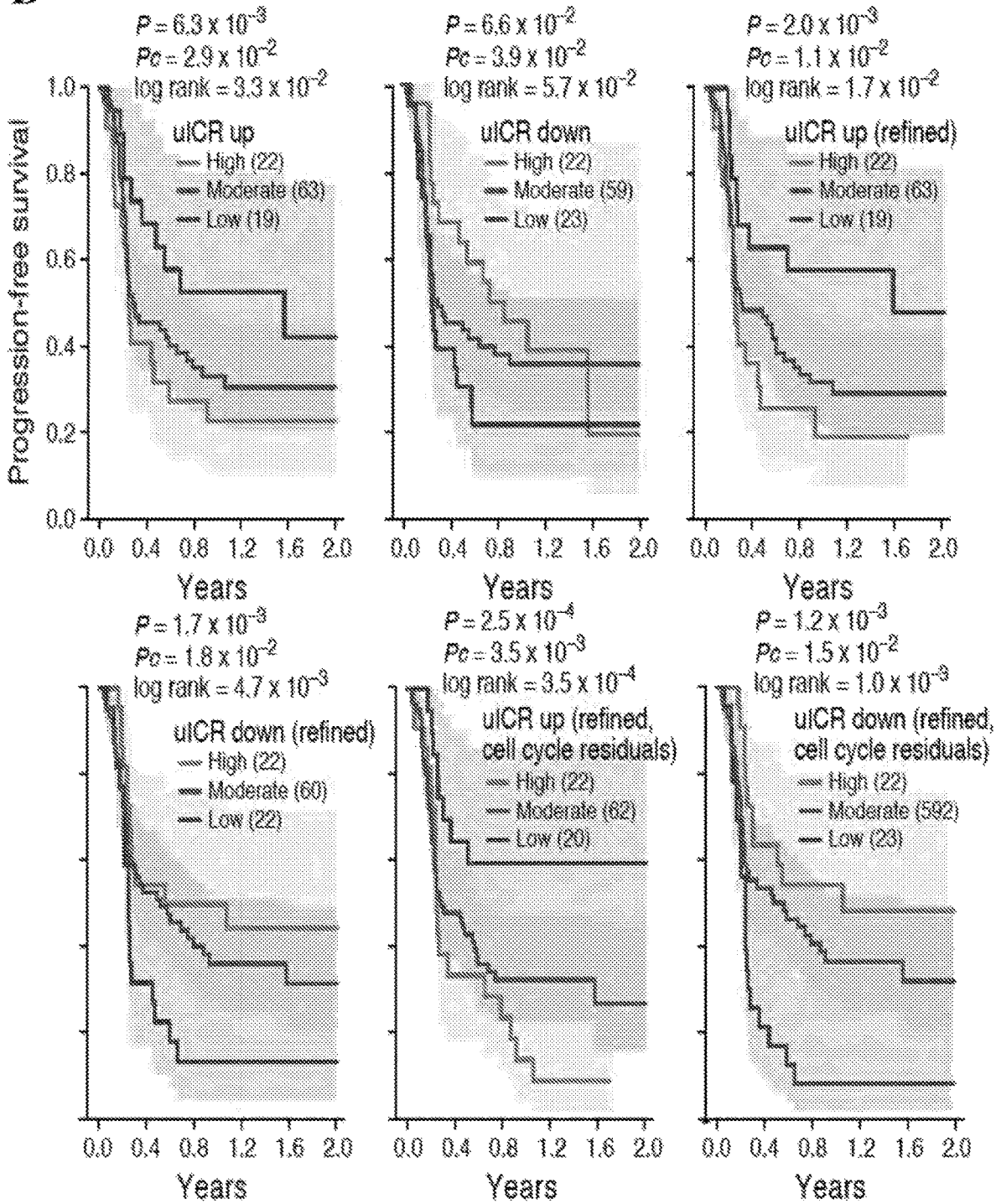
Figure 4E:
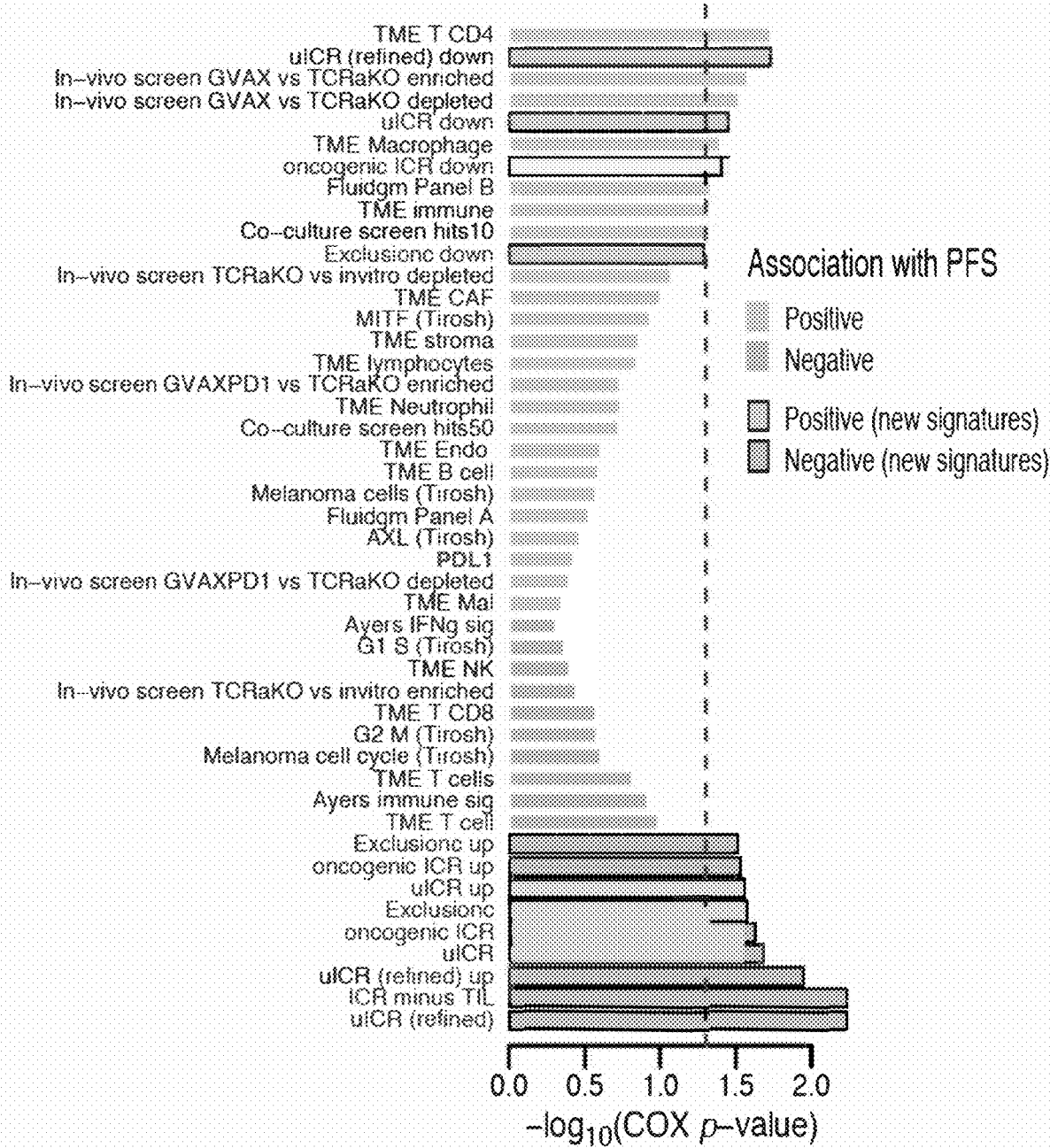

Our malignant cell resistance signatures were predictive of PFS in the validation cohort (FIG. 4D,E, FIGS. 12 and 13). Their predictive value was significant even when accounting for other known predictors of ICR response, including inferred T cell infiltration levels and PD-L1 expression (FIGS. 12E and 13E). Although cell cycle alone is not associated with CB (COX P>0.25), filtering the cell-cycle component from the uICR overexpression score (materials and methods) further improved the PFS predictions (FIG. 4D, right), suggesting that a tumor ICR level should be evaluated conditioning on its proliferation level. The additional predictive value of the malignant resistance signatures beyond T cell infiltration was significantly higher than that of other signatures ($P=3.37*10^{-6}$, Wilcoxon-ranksum test), and they were the only ones negatively associated with PFS. Other alternative predictors were either not predictive or highly associated with T cell infiltration levels, such that they did not provide an additive predictive value once accounting for T cell infiltration levels (FIG. 4E).

Figure 14:
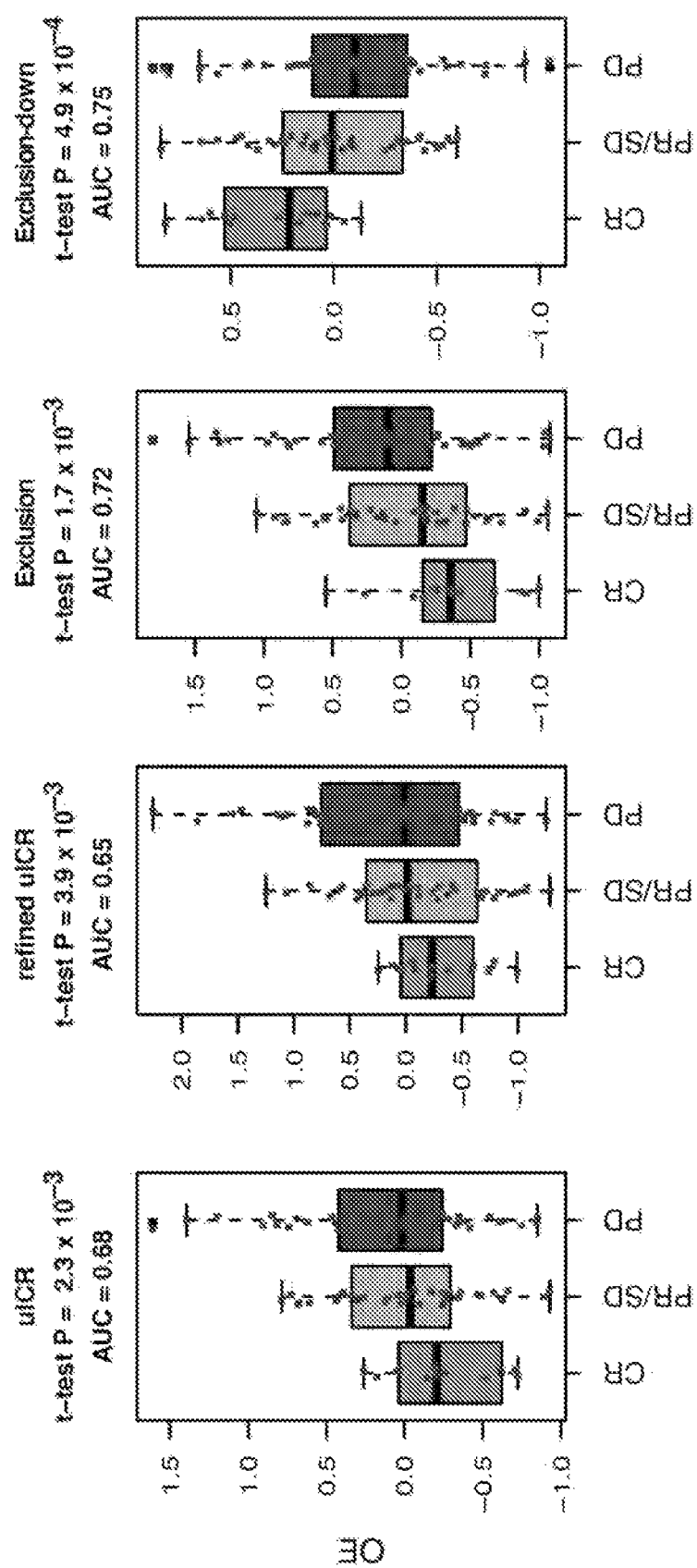
FIG. 14 illustrates the expression of the resistance signatures in 101 melanoma patients, stratified according to their clinical response to pembrolizumab. Distribution of OE scores (y axis) of each signature in the pre-treatment bulk RNA-Seq profiles, showing overall 101 patients with complete response (CR, n=14), partial response or stable disease (PR/SD, n=38), or progressive disease (PD, n=49). P is the one-sided t-test p-value obtained when comparing the CR patients to the PR, SD and PD patients. AUC is also marked on top. Middle line: median; box edges: 25th and 75th percentiles; whiskers: most extreme points that do not exceed ±IQR*1.5.

The uICR state was overexpressed in patients with CB vs. non-CB (FIG. 4F). Applicants noted however that some CB patients had high pre-treatment uICR expression and hypothesized that these patients, while experiencing an initial CB, might cease to respond quickly. Indeed, when stratifying patients with CB based on the duration of their response (>12 months, <12 months but >6 months, and <6 months), Applicants found that patients with an initial CB but high uICR score pretreatment were significantly more likely to experience subsequent progressive disease (FIG. 4F). Indeed, patients with rapid progression, that is CB<6 months had the highest uICR score, even compared to those with non-CB. Consistently, the resistance signatures were most accurate in predicting patients with complete responses ($P<6.31*10^{-3}$, one-sided t-test, FIG. 4G, FIG. 14). In this task, they were superior to all the other alternative predictors ($P=1.64*10^{-8}$, Wilcoxon ranksum test), all of which, including the clinically used markers, failed to predict complete response (FIG. 4I).

Finally, Applicants explored intrinsic vs. acquired uICR programs in an additional independent cohort, collected in yet another hospital (materials and methods), consisting of 90 samples from 26 patients with metastatic melanoma who underwent both pre-treatment and post-progression biopsies with bulk RNA-Seq, including 17 patients with on-treatment biopsy (FIG. 1A). The ICR state was induced following ICI compared to pre-ICI lesions from the same patient ($P=1.26*10^{-4}$ and 0.01, for the refined uICR and uICR-up, respectively; mixed-effect test, materials and methods). However, inter-patient variation in uICR expression was significantly higher than intra-patient changes ($P<10^{-8}$, ANOVA). This suggests that one pre treatment sample per patient may suffice to evaluate ICR for many patients, and that intrinsic resistance may be more prevalent than acquired resistance, consistent with clinical observations (3). Notably, Applicants did not observe an induction in uICR expression following RAF/MEK-inhibition (materials and methods), indicating that the ICR state is specific to ICI therapy and not merely a marker of a generally drug resistant tumor ecosystem.

Discussion

Applicants discovered new features linked to response and resistance to immunotherapy in metastatic melanoma with a strong prognostic and predictive value in independent patient cohorts. T cell profiles from ICR patients reflect variability in T cell responses, which are often decoupled from the clinical response. In some ICR patients, T cells manifest substantial clonal expansions, in others higher frequency of T cell proliferation, or a shift in the cytotoxicity/exhaustion balance. While more data is needed to distinguish between proper and insufficient T cell response to ICI, the results suggest that malignant cell-autonomous programs may be another key contributor to ICR, even in the presence of properly activated T cells (FIG. 4I).

Malignant cell programs that suppress interactions with the tumor microenvironment, modulate key inflammatory pathways and activate mechanisms of T cell exclusion were distinguishing features of ICR tumors. These may be jointly controlled as a single coherent resistance program to confer ICR, through master regulators like Myc and CDK4/6. While these programs were initially identified in post-progression samples using scRNA-Seq, Applicants validated their predictive value in a pre-ICI cohort and explored their expression in matched pre/post specimens of ICI-treated patients. The ICR signatures Applicants identified were superior to a comprehensive and diverse set of alternative predictors in several ways, especially in predicting complete responders and patients that responded for more than 6 months. Unlike other predictors, the ICR signatures have a significant additional predictive value beyond pre-treatment T cell infiltration levels, indicating that they highlight new and yet unappreciated aspects of ICR. In light of these results, the signatures may help stratify patients for ICI beyond currently used biomarkers.

The pathways represented in the resistance program also highlight potential mechanistic causes of ICR that could be reversed by combining ICI with other drugs. Combination of ICI with CDK4/6 inhibitors (such as abemaciclib) may be particularly attractive in light of the findings that abemaciclib reverses the resistant oncogenic state and that there are distinctions between the cell cycle programs of malignant cells and T cells.

The malignant resistance programs may be relevant in other subtypes of melanoma and even in other lineage-independent cancer types. Among different types of melanoma, uveal melanoma has more active resistance programs compared to cutaneous melanoma (FIG. 3D); across cancers, the resistance program is higher in some cancer types that are less responsive to immunotherapy and/or arise from immune-privileged tissues (eye, testis) and lower in some of the more responsive tissues (head and neck, kidney, skin, lung) (FIG. 15). This distinction, however, is imperfect, and additional, tumor-specific resistance programs may be discovered by similar strategies. Our study uncovers an improved, potentially clinically applicable biomarker for patient selection, provides a rationale to examine novel mechanisms of ICR, and reveals guiding principles to further dissect and repress mechanistic underpinnings that mediate ICI resistance.

Applicants demonstrated that cancer cell-autonomous ICR programs identified by scRNA-Seq predict clinical response (per RECIST criteria) and progression-free survival in two independent cohorts: one of patients who underwent RNA-seq of matched pre-treatment and progression (ICR) specimens; and another of 112 melanoma patients with pre-treatment RNA-seq who receive anti-PD-1 monotherapy. Applicants also validated the prognostic value of these cell programs in TCGA. Lastly, Applicants demonstrated that pharmacological reversal of these oncogenic cell states can be achieved by CDK4/6-inhibition, and explored the impact of this treatment in melanoma at the single-cell level. To determine the role of T cell exclusion from the THE as a potential mechanism of ICR, Applicants performed spatially resolved 30-plex single-cell protein analysis of matching FFPE specimens from 16 of the patients who also underwent scRNA-seq. Thus, the presented analytical platforms provide a promising approach to understanding drug resistance within preserved tumor ecosystems.

In conclusion, this study provides a high-resolution landscape of oncogenic ICR states, identifies clinically predictive signatures, and forms a basis to develop novel therapeutic strategies that could overcome immunotherapy resistance in melanoma.

TABLE S1

Clinical characteristics of the patients and samples in the scRNA-Seq cohort, and in the two validation cohorts.

scRNA-Seq cohort

| Sample | Cohort | Age | Sex | Treatment | Treatment group | Lesion type | Site |
| --- | --- | --- | --- | --- | --- | --- | --- |
| Mel53 | Tirosh et al. 2016 | 77 | F | None | TN | metastasis | Subcutaneous back lesion |
| Mel58 | Tirosh et al. 2016 | 83 | M | Ipilimumab | ICR | metastasis | Subcutaneous leg lesion |
| Mel60 | Tirosh et al. 2016 | 60 | M | Trametinib, ipilimumab | ICR | metastasis | Spleen |
| Mel71 | Tirosh et al. 2016 | 79 | M | None | TN | metastasis | Transverse colon |
| Mel72 | Tirosh et al. 2016 | 57 | F | IL-2, nivolumab, ipilimumab + anti-KIR-Ab | ICR | metastasis | External iliac lymph node |
| Mel74 | Tirosh et al. 2016 | 63 | M | Nivolumab | ICR | metastasis | Terminal Ileum |
| Mel75 | Tirosh et al. 2016 | 80 | M | Ipilimumab + nivolumab, WDVAX | ICR | metastasis | Subcutaneous leg lesion |

TABLE S1-continued

Clinical characteristics of the patients and samples in the
scRNA-Seq cohort, and in the two validation cohorts.
scRNA-Seq cohort

| | | | | | | | |
|---|---|---|---|---|---|---|---|
| Mel78 | Tirosh et al. 2016 | 73 | M | WDVAX, ipilimumab + nivolumab | ICR | metastasis | Small bowel |
| Mel79 | Tirosh et al. 2016 | 74 | M | None | TN | metastasis | Axillary lymph node |
| Mel80 | Tirosh et al. 2016 | 86 | F | None | TN | metastasis | Axillary lymph node |
| Mel81 | Tirosh et al. 2016 | 43 | F | None | TN | metastasis | Axillary lymph node |
| Mel82 | Tirosh et al. 2016 | 73 | F | None | TN | metastasis | Axillary lymph node |
| Mel84 | Tirosh et al. 2016 | 67 | M | None | TN | primary tumor | Acral primary |
| Mel88 | Tirosh et al. 2016 | 54 | F | Tremelimumab + MEDI3617 | ICR | metastasis | Cutanoues met |
| Mel89 | Tirosh et al. 2016 | 67 | M | None | TN | metastasis | Axillary lymph node |
| Mel94 | Tirosh et al. 2016 | 54 | F | IFN, ipilimumab + nivolumab | ICR | metastasis | Iliac lymph node |
| Mel126 | Additional | 63 | M | Ipilimumab, nivolumab | ICR | metastasis | Soft tissue |
| Mel04.3 | Additional | 81 | M | Ipilimumab | CB | metastasis | Skin |
| Mel110 | Additional | 74 | M | ipilimumab + angiopoietin 2 inhibitor, Temezlolamide, Pembrolizumab | ICR | metastasis | R adrenal metastasis |
| Mel121.1 | Additional | 74 | M | S/p Pembrolizumab | ICR | metastasis | Skin |
| Mel106 | Additional | 67 | M | Prior treatment: nivolumab + ipilimumab | ICR | metastasis | Necrotic L axillary lymph nodes |
| Mel75.1 | Additional | 81 | M | Ipilimumab + nivolumab, WDVAX, Pembrolizumab | ICR | metastasis | Soft tissue |
| Mel98 | Additional | 47 | F | S/p IFN, s/p ipilimumab + GMCSF | ICR | metastasis | L thigh soft tissue metastasis |
| Mel102 | Additional | 72 | F | S/p nivolumab + ipilimumab | ICR | metastasis | Fragmented pieces of (R) adrenal gland metastasis |
| Mel129PA | Additional | 63 | M | None | TN | primary tumor | Skin |
| Mel129PB | Additional | 63 | M | None | TN | primary tumor | Skin |
| Mel116 | Additional | 85 | M | None | TN | metastasis | Lymph node |
| Mel103 | Additional | 58 | M | None | TN | metastasis | Lymph node |
| Mel105 | Additional | 77 | M | None | TN | primary tumor | Skin |
| Mel112 | Additional | 76 | M | None | TN | metastasis | Bulky (L) axillary metastasis |
| Mel194 | Additional | 68 | M | Nivolumab + lirilumab (anti-kit), Nivolumab, Ipilimumab, Pan-RAF-inhibitor, Pembrolizumab | ICR | metastasis | L anterior shoulder subcutaneous |
| Mel478 | Additional | 54 | F | None | TN | metastasis | Transanal rectal mass |
| Mel128 | Additional | 37 | M | None | TN | metastasis | Lymph node |

| Cohort 1 | Sex, n | Number of therapies prior to anti-PD-1 therapy, n | RECIST category |
|---|---|---|---|
| Patients 1-112 | Female, 49<br>Male, 56<br>n/a, 7 | No prior treatment, 49<br>1, 34<br>2, 14<br>3, 6<br>7, 2<br>n/a, 7 | PD, 49<br>SD, 13<br>PR, 25<br>CR, 14<br>n/a, 11 |

TABLE S1-continued

Clinical characteristics of the patients and samples in the scRNA-Seq cohort, and in the two validation cohorts.

scRNA-Seq cohort

| Cohort 2 | Number of samples per patient, n |
|---|---|
| Patients 1-26 | 2, 10 |
| 90 samples | 3, 8 |
| | 4, 3 |
| | 6, 2 |
| | 7, 2 |
| | 8, 1 |

TABLE S2

Table S2. Quality measures of scRNA-Seq experiments.

| Cell type | Median no. of detected genes | Median no. of aligned reads | No. of TN cells | No. of ICR cells | Total no. of cells |
|---|---|---|---|---|---|
| B. cell | 3774 | 164400 | 463 | 355 | 818 |
| CAF | 5518 | 357423 | 61 | 45 | 106 |
| Endothelial cell | 5057 | 304326 | 87 | 17 | 104 |
| Macrophage | 5670 | 654482 | 161 | 259 | 420 |
| Mal | 5482 | 335563 | 1193 | 825 | 2018 |
| NK | 3909 | 147376 | 44 | 48 | 92 |
| CD4 T cell | 4036 | 220614 | 420 | 436 | 856 |
| CD8 T cell | 4064 | 264494 | 720 | 1039 | 1759 |
| T cell (unresolved) | 3827 | 234410 | 298 | 408 | 706 |
| Low quality cell | 732 | 24991 | 1386 | 1551 | 2937 |
| ? | 3433 | 221421 | 183 | 124 | 307 |
| All cells | 3559 | 377141 | 5016 | 5107 | 10123 |

TABLE S4

Table S4. Cell type signatures that were derived from the analysis of the scRNA-seq data (see section Data-driven signatures of specific cell-types).

| B cell | CAF | Endothelial cell | Macrophage | Malignant cell | NK cell | T cell | CD4 T cell |
|---|---|---|---|---|---|---|---|
| ADAM19 | ABI3BP | A2M | ACP5 | AATF | CCL4 | AAK1 | AQP3 |
| ADAM28 | ACTA2 | ADAM15 | ACSL1 | ACN9 | CD244 | ACAP1 | CCR4 |
| AFF3 | ADAM12 | ADAMTS9 | ACSL3 | ACSL3 | CST7 | AKNA | CD28 |
| BANK1 | ADAMTS2 | ADCY4 | ADAMDEC1 | AHCY | CTSW | APOBEC3G | CD4 |
| BCL11A | ANTXR1 | AFAP1L1 | ADAP2 | AIF1L | GNLY | ARAP2 | CD40LG |
| BIRC3 | ASPN | APLNR | ADORA3 | AK2 | GZMA | ARHGEF1 | CD5 |
| BLK | C1S | AQP1 | ADPGK | ALX1 | GZMB | ASB2 | DGKA |
| BLNK | CALD1 | ARHGEF15 | AIF1 | AMD1 | HOPX | ATHL1 | F5 |
| BTLA | CCDC80 | CALCRL | AKR1A1 | ANKRD20A12P | ID2 | BCL11B | FAAH2 |
| CCR6 | CD248 | CCL14 | ALDH2 | ANKRD54 | IL2RB | BTN3A2 | FOXP3 |
| CCR7 | CDH11 | CD200 | ALDH3B1 | AP1S2 | KLRB1 | CBLB | ICOS |
| CD19 | CERCAM | CD34 | AMICA1 | APOA1BP | KLRC1 | CCL4 | IL6R |
| CD1C | COL12A1 | CD93 | ANKRD22 | APOC2 | KLRD1 | CCL5 | IL7R |
| CD22 | COL14A1 | CDH5 | AP1B1 | APOD | KLRF1 | CD2 | PASK |
| CD24 | COL1A1 | CFI | AQP9 | APOE | KLRK1 | CD247 | PBXIP1 |
| CD37 | COL1A2 | CLDN5 | ATF5 | ATP1A1 | NCAM1 | CD27 | SLAMF1 |
| CD52 | COL3A1 | CLEC14A | ATG3 | ATP1B1 | NKG7 | CD28 | SPOCK2 |
| CD79A | COL5A1 | COL15A1 | ATG7 | ATP5C1 | PRF1 | CD3D | TCF7 |
| CD79B | COL5A2 | COL4A1 | ATP6V0B | ATP5G1 | PTGDR | CD3E | TNFSF8 |
| CD82 | COL6A1 | COL4A2 | ATP6V0D1 | ATP5G2 | SH2D1B | CD3G | |
| CHMP7 | COL6A2 | CRIP2 | ATP6V1B2 | ATP6V0E2 | XCL1 | CD5 | |
| CIITA | COL6A3 | CXorf36 | BCL2A1 | ATP6V1C1 | | CD6 | |
| CLEC17A | COL8A1 | CYYR1 | BID | ATP6V1E1 | | CD7 | |
| CNR2 | CREB3L1 | DARC | BLVRA | ATP6V1G1 | | CD8A | |
| COL19A1 | CXCL14 | DCHS1 | BLVRB | AZGP1 | | CD8B | |
| COL4A3 | CYBRD1 | DOCK6 | C11orf75 | BAIAP2 | | CD96 | |
| CR2 | DCN | DOCK9 | C15orf48 | BANCR | | CDC42SE2 | |
| CXCR5 | DPT | DYSF | C19orf38 | BCAN | | CELF2 | |
| | | | C1orf162 | | | | |

TABLE S4-continued

Table S4. Cell type signatures that were derived from the analysis of the scRNA-seq data (see section Data-driven signatures of specific cell-types).

| | | | | | | |
|---|---|---|---|---|---|---|
| ELK2AP | EFEMP2 | ECE1 | C1QA | BCAS3 | CLEC2D | |
| FAIM3 | FBLN1 | ECSCR | C1QB | BCHE | CNOT6L | |
| FAM129C | FBLN5 | EGFL7 | C1QC | BIRC7 | CST7 | |
| FCER2 | FGF7 | ELK3 | C2 | BZW2 | CTLA4 | |
| FCRL1 | GPR176 | ELTD1 | C3AR1 | C10orf90 | CTSW | |
| FCRL2 | HSPB6 | EMCN | C5AR1 | C11orf31 | CXCL13 | |
| FCRL5 | INHBA | ENG | C9orf72 | C12orf76 | CXCR3 | |
| FCRLA | ISLR | EPAS1 | CAPG | C17orf89 | CXCR6 | |
| HLA-DOB | ITGA11 | EPHB4 | CARD9 | C1orf43 | DEF6 | |
| HLA-DQA2 | LOX | ERG | CASP1 | C1orf85 | DENND2D | |
| HVCN1 | LPAR1 | ESAM | CCR1 | C4orf48 | DGKA | |
| IGLL1 | LTBP2 | FGD5 | CCR2 | CA14 | DTHD1 | |
| IGLL3P | LUM | FKBP1A | CD14 | CA8 | DUSP2 | |
| IGLL5 | MAP1A | FLT4 | CD163 | CACYBP | EMB | |
| IRF8 | MEG3 | GALNT18 | CD274 | CAPN3 | EVL | |
| KBTBD8 | MIR100HG | GPR116 | CD300C | CBX3 | FASLG | |
| KIAA0125 | MRC2 | HERC2P2 | CD300E | CCDC47 | FYN | |
| KIAA0226L | MXRA8 | HSPG2 | CD300LB | CCND1 | GATA3 | |
| LOC283663 | MYL9 | HYAL2 | CD300LF | CCT2 | GPR171 | |
| LRMP | NID2 | ICA1 | CD302 | CCT3 | GPR174 | |
| LTB | OLFML3 | ID1 | CD33 | CCT6A | GPRIN3 | |
| MS4A1 | PALLD | IL3RA | CD4 | CCT8 | GRAP2 | |
| NAPSB | PCDH18 | ITGB4 | CD68 | CDH19 | GZMA | |
| NCOA3 | PCOLCE | KDR | CD80 | CDH3 | GZMB | |
| P2RX5 | PDGFRA | LAMA5 | CD86 | CDK2 | GZMH | |
| PAX5 | PDGFRB | LDB2 | CECR1 | CHCHD6 | GZMK | |
| PLEKHF2 | PDGFRL | LOC100505495 | CFP | CITED1 | GZMM | |
| PNOC | PLAC9 | MALL | CLEC10A | CLCN7 | HNRNPA1P10 | |
| POLD4 | PODN | MMRN1 | CLEC12A | CLNS1A | ICOS | |
| POU2AF1 | PRRX1 | MMRN2 | CLEC4A | CMC2 | IFNG | |
| POU2F2 | RARRES2 | MYCT1 | CLEC4E | COA6 | IKZF1 | |
| QRSL1 | RCN3 | NOS3 | CLEC5A | COX5B | IKZF3 | |
| RALGPS2 | SDC2 | NOTCH4 | CLEC7A | COX7A2 | IL12RB1 | |
| RPL13 | SFRP2 | NPDC1 | CMKLR1 | COX7C | IL2RB | |
| RPS20 | SLIT3 | PALMD | CNPY3 | CRYL1 | IL2RG | |
| RPS23 | SMOC2 | PCDH17 | COTL1 | CSAG1 | IL32 | |
| SEL1L3 | SPOCK1 | PDE2A | CPVL | CSAG2 | IL7R | |
| SELL | SULF1 | PDLIM1 | CREG1 | CSAG3 | INPP4B | |
| SMIM14 | SVEP1 | PECAM1 | CSF1R | CSPG4 | IPCEF1 | |
| SNX29 | TAGLN | PLVAP | CSF2RA | CTNNB1 | ITGAL | |
| SNX29P1 | THBS2 | PLXND1 | CSF3R | CYC1 | ITK | |
| SPIB | THY1 | PODXL | CSTA | CYP27A1 | JAK3 | |
| ST6GAL1 | TMEM119 | PRCP | CTSB | DAAM2 | JAKMIP1 | |
| STAG3 | TPM1 | PREX2 | CTSC | DANCR | KLRC4 | |
| STAP1 | TPM2 | PTPRB | CTSD | DAP3 | KLRD1 | |
| TCL1A | | PVRL2 | CTSH | DCT | KLRK1 | |
| TLR10 | | RAMP2 | CTSS | DCXR | LAG3 | |
| TMEM154 | | RAMP3 | CXCL10 | DDIT3 | LAT | |
| TNFRSF13B | | RHOJ | CXCL16 | DDT | LCK | |
| VPREB3 | | ROBO4 | CXCL9 | DFNB31 | LEPROTL1 | |
| WDFY4 | | S1PR1 | CXCR2P1 | DLL3 | LIME1 | |
| ZCCHC7 | | SDPR | CYBB | DNAH14 | LOC100130231 | |
| | | SELP | CYP2S1 | DNAJA4 | MAP4K1 | |
| | | SHROOM4 | DAPK1 | DSCR8 | MIAT | |
| | | SLCO2A1 | DHRS9 | DUSP4 | NELL2 | |
| | | SMAD1 | DMXL2 | EDNRB | NKG7 | |
| | | STOM | DNAJC5B | EIF3C | NLRC3 | |
| | | SYNPO | EBI3 | EIF3D | NLRC5 | |
| | | TAOK2 | EMR2 | EIF3E | OXNAD1 | |
| | | TEK | EPSTI1 | EIF3H | PAG1 | |
| | | TENC1 | F13A1 | EIF3L | PARP8 | |
| | | TGFBR2 | FAM157B | ENO1 | PCED1B | |
| | | TGM2 | FAM26F | ENO2 | PCED1B-AS1 | |
| | | THBD | FBP1 | ENTHD1 | PDCD1 | |
| | | TIE1 | FCER1G | ENTPD6 | PIK3IP1 | |
| | | TM4SF1 | FCGR1A | ERBB3 | PIM2 | |
| | | TM4SF18 | FCGR1B | ESRP1 | PIP4K2A | |
| | | TMEM255B | FCGR1C | ETV4 | PPP2R5C | |
| | | TSPAN18 | FCGR2A | ETV5 | PRDM1 | |
| | | TSPAN7 | FCGR2C | EXOSC4 | PRF1 | |
| | | VWF | FCN1 | EXTL1 | PRKCQ | |
| | | ZNF385D | FGL2 | FAHD2B | PSTPIP1 | |
| | | | FOLR2 | FAM103A1 | PTPN22 | |
| | | | FPR1 | FAM178B | PTPN7 | |
| | | | FPR2 | FANCL | PVRIG | |
| | | | FPR3 | FARP2 | PYHIN1 | |
| | | | FTH1 | FASN | RAB27A | |

TABLE S4-continued

Table S4. Cell type signatures that were derived from the analysis of the scRNA-seq data (see section Data-driven signatures of specific cell-types).

| | | |
|---|---|---|
| FTL | FBXO32 | RAPGEF6 |
| FUCA1 | FBXO7 | RARRES3 |
| FUOM | FDFT1 | RASAL3 |
| GABARAP | FKBP4 | RASGRP1 |
| GATM | FMN1 | RGS1 |
| GBP1 | FXYD3 | RHOF |
| GCA | GALE | RNF213 |
| GK | GAPDH | RUNX3 |
| GLA | GAPDHS | SCML4 |
| GLRX | GAS2L3 | SEMA4D |
| GLUL | GAS5 | 1-Sep |
| GM2A | GAS7 | SH2D1A |
| GNA15 | GDF15 | SH2D2A |
| GPBAR1 | GJB1 | SIRPG |
| GPR34 | GPATCH4 | SIT1 |
| GPR84 | GPM6B | SKAP1 |
| GPX1 | GPNMB | SLA2 |
| GRN | GPR137B | SPATA13 |
| HCAR2 | GPR143 | SPN |
| HCAR3 | GPS1 | SPOCK2 |
| HCK | GSTP1 | STAT4 |
| HK2 | GYG2 | SYTL3 |
| HK3 | H2AFZ | TARP |
| HLA-DMA | HAX1 | TBC1D10C |
| HLA-DMB | HIST1H2BD | TC2N |
| HLA-DPA1 | HIST3H2A | TESPA1 |
| HLA-DPB1 | HMG20B | THEMIS |
| HLA-DPB2 | HMGA1 | TIGIT |
| HLA-DRA | HPGD | TNFAIP3 |
| HLA-DRB1 | HPS4 | TNFRSF9 |
| HLA-DRB5 | HPS5 | TOX |
| HLA-DRB6 | HSP90AA1 | TRAF1 |
| HMOX1 | HSP90AB1 | TRAT1 |
| HSPA6 | HSPA9 | TTC39C |
| HSPA7 | HSPD1 | UBASH3A |
| IFI30 | HSPE1 | WIPF1 |
| IFNGR1 | IGSF11 | ZAP70 |
| IFNGR2 | IGSF3 | ZC3HAV1 |
| IGFLR1 | IGSF8 | |
| IGSF6 | INPP5F | |
| IL18 | IRF4 | |
| IL1B | ISYNA1 | |
| IL1RN | KCNJ13 | |
| IL4I1 | LAGE3 | |
| IL8 | LDHB | |
| IRF5 | LDLRAD3 | |
| KCNMA1 | LEF1-AS1 | |
| KYNU | LHFPL3-AS1 | |
| LAIR1 | LINC00473 | |
| LGALS2 | LINC00518 | |
| LGMN | LINC00673 | |
| LILRA1 | LOC100126784 | |
| LILRA2 | LOC100127888 | |
| LILRA3 | LOC100130370 | |
| LILRA5 | LOC100133445 | |
| LILRA6 | LOC100505865 | |
| LILRB1 | LOC146481 | |
| LILRB2 | LOC340357 | |
| LILRB3 | LONP2 | |
| LILRB4 | LOXL4 | |
| LILRB5 | LZTS1 | |
| LIPA | MAGEA1 | |
| LOC729737 | MAGEA12 | |
| LRRC25 | MAGEA2 | |
| LST1 | MAGEA2B | |
| LTA4H | MAGEA3 | |
| LYZ | MAGEA4 | |
| MAFB | MAGEA6 | |
| MAN2B1 | MAGEC1 | |
| MARCO | MDH1 | |
| MFSD1 | MDH2 | |
| MILR1 | MFI2 | |
| MNDA | MFSD12 | |
| MOB1A | MIA | |
| MPEG1 | MIF | |
| MPP1 | MITF | |
| MS4A4A | MLANA | |

TABLE S4-continued

Table S4. Cell type signatures that were derived from the analysis of the scRNA-seq data (see section Data-driven signatures of specific cell-types).

| | |
|---|---|
| MS4A6A | MLPH |
| MS4A7 | MOK |
| MSR1 | MRPS21 |
| MTMR14 | MRPS25 |
| MYD88 | MRPS26 |
| NAAA | MRPS6 |
| NADK | MSI2 |
| NAGA | MXI1 |
| NAGK | MYO10 |
| NAIP | NAV2 |
| NCF2 | NDUFA4 |
| NCF4 | NDUFB9 |
| NCOA4 | NDUFS2 |
| NFAM1 | NEDD4L |
| NINJ1 | NELFCD |
| NLRC4 | NHP2 |
| NLRP3 | NME1 |
| NMI | NOP58 |
| NPC2 | NPM1 |
| NPL | NSG1 |
| OAS1 | NT5C3 |
| OAZ1 | NT5DC3 |
| OLR1 | OSTM1 |
| OSCAR | PACSIN2 |
| P2RY12 | PAGE5 |
| P2RY13 | PAICS |
| PAK1 | PAX3 |
| PCK2 | PEBP1 |
| PILRA | PEG10 |
| PLA2G7 | PFDN2 |
| PLAUR | PHB |
| PLBD1 | PHLDA1 |
| PLEKHO1 | PIGY |
| PLIN2 | PIR |
| PPT1 | PLEKHB1 |
| PRAM1 | PLP1 |
| PRKCD | PMEL |
| PSAP | POLR2F |
| PTAFR | PPIL1 |
| PYCARD | PRAME |
| RAB20 | PSMB4 |
| RASSF4 | PSMD4 |
| RBM47 | PUF60 |
| RELT | PYGB |
| RGS10 | PYURF |
| RGS18 | QDPR |
| RGS19 | RAB17 |
| RGS2 | RAB38 |
| RHBDF2 | RAN |
| RILPL2 | RAP1GAP |
| RIPK2 | RGS20 |
| RNASE6 | ROPN1 |
| RNASET2 | ROPN1B |
| RNF13 | RPL38 |
| RNF130 | RPS6KA5 |
| RNF144B | RSL1D1 |
| RTN1 | RTKN |
| S100A8 | S100A1 |
| S100A9 | S100B |
| SAMHD1 | SCD |
| SAT1 | SDC3 |
| SDS | SEC11C |
| SECTM1 | SEMA3B |
| SEMA4A | SERPINA3 |
| SERPINA1 | SERPINE2 |
| SIGLEC1 | SGCD |
| SIGLEC5 | SGK1 |
| SIGLEC9 | SHC4 |
| SIRPB1 | SLC19A2 |
| SIRPB2 | SLC24A5 |
| SLAMF8 | SLC25A13 |
| SLC11A1 | SLC25A4 |
| SLC15A3 | SLC26A2 |
| SLC1A3 | SLC3A2 |
| SLC29A3 | SLC45A2 |
| SLC31A2 | SLC5A3 |
| SLC7A7 | SLC6A15 |

TABLE S4-continued

Table S4. Cell type signatures that were derived from the analysis of the scRNA-seq data (see section Data-driven signatures of specific cell-types).

| | |
|---|---|
| SLCO2B1 | SLC7A5 |
| SMPDL3A | SNCA |
| SNX10 | SNHG16 |
| SOD2 | SNHG6 |
| SPI1 | SNRPC |
| SPINT2 | SNRPD1 |
| STAT1 | SNRPE |
| STX11 | SOD1 |
| TBXAS1 | SORD |
| TGFBI | SORT1 |
| THEMIS2 | SOX10 |
| TIFAB | SPCS1 |
| TLR1 | SPRY4 |
| TLR2 | ST13 |
| TLR5 | ST3GAL4 |
| TLR8 | ST3GAL6 |
| TMEM106A | ST3GAL6-AS1 |
| TMEM176A | ST6GALNAC2 |
| TMEM176B | STIP1 |
| TMEM37 | STK32A |
| TNFAIP2 | STMN1 |
| TNFAIP8L2 | STX7 |
| TNFSF13 | STXBP1 |
| TNFSF13B | SYNGR1 |
| TPP1 | TBC1D7 |
| TREM1 | TBCA |
| TREM2 | TEX2 |
| TWF2 | TFAP2A |
| TYMP | TFAP2C |
| TYROBP | TMEM147 |
| UBE2D1 | TMEM14B |
| VAMP8 | TMEM177 |
| VMO1 | TMEM251 |
| VSIG4 | TMX4 |
| ZNF385A | TNFRSF21 |
| | TOM1L1 |
| | TOMM20 |
| | TOMM22 |
| | TOMM6 |
| | TOMM7 |
| | TOP1MT |
| | TRIB2 |
| | TRIM2 |
| | TRIM63 |
| | TRIML2 |
| | TRMT112 |
| | TSNAX |
| | TTLL4 |
| | TTYH2 |
| | TUBB2B |
| | TUBB4A |
| | TYR |
| | TYRP1 |
| | UBL3 |
| | UQCRH |
| | UTP18 |
| | VAT1 |
| | VDAC1 |
| | VPS72 |
| | WBSCR22 |
| | XAGE1A |
| | XAGE1B |
| | XAGE1C |
| | XAGE1D |
| | XAGE1E |
| | XRCC6 |
| | XYLB |
| | ZCCHC17 |
| | ZFAS1 |
| | ZFP106 |
| | ZNF280B |
| | ZNF330 |
| | ZNF692 |

TABLE S4-continued

Table S4. Cell type signatures that were derived from the analysis of the scRNA-seq data (see section Data-driven signatures of specific cell-types).

| B cell | CD8 T cell | Immune cell | | Lympho-cyte | Stroma cell |
|---|---|---|---|---|---|
| ADAM19 | AKAP5 | AAK1 | HLA-DRB6 | AAK1 | A2M |
| ADAM28 | APOBEC3C | ACAP1 | HMHA1 | ACAP1 | ABI3BP |
| AFF3 | APOBEC3G | ACP5 | HMOX1 | ADAM19 | ACTA2 |
| BANK1 | ARHGAP9 | ACSL1 | HNRNPA1P10 | ADAM28 | ADAM12 |
| BCL11A | ATP8A1 | ADAM19 | HOPX | AFF3 | ADAM15 |
| BIRC3 | BTN3A1 | ADAM28 | HSH2D | AKAP5 | ADAMTS2 |
| BLK | CBLB | ADAMDEC1 | HSPA6 | AKNA | ADAMTS9 |
| BLNK | CCL4 | ADAP2 | HSPA7 | ANKRD44 | ADCY4 |
| BTLA | CCL4L1 | ADORA3 | HVCN1 | APOBEC3C | AFAP1L1 |
| CCR6 | CCL4L2 | ADPGK | ICOS | APOBEC3D | ANTXR1 |
| CCR7 | CCL5 | AFF3 | ID2 | APOBEC3G | APLNR |
| CD19 | CD27 | AIF1 | IFI30 | AQP3 | APP |
| CD1C | CD7 | AKAP5 | IFNG | ARAP2 | AQP1 |
| CD22 | CD8A | AKNA | IFNGR1 | ARHGAP15 | ARHGEF15 |
| CD24 | CD8B | AKR1A1 | IFNGR2 | ARHGAP9 | ASPN |
| CD37 | CD96 | ALDH2 | IGFLR1 | ARHGEF1 | BGN |
| CD52 | CLEC2D | ALDH3B1 | IGLL1 | ASB2 | C1R |
| CD79A | CRTAM | ALOX5 | IGLL3P | ATHL1 | C1S |
| CD79B | CST7 | ALOX5AP | IGLL5 | ATP2A3 | CALCRL |
| CD82 | CTSW | AMICA1 | IGSF6 | ATP8A1 | CALD1 |
| CHMP7 | CXCL13 | ANKRD22 | IKZF1 | BANK1 | CCDC80 |
| CIITA | CXCR6 | ANKRD44 | IKZF3 | BCL11A | CCL14 |
| CLEC17A | DTHD1 | AOAH | IL10RA | BCL11B | CD200 |
| CNR2 | DUSP2 | AP1B1 | IL12RB1 | BIRC3 | CD248 |
| COL19A1 | EOMES | APOBEC3C | IL16 | BLK | CD34 |
| COL4A3 | FASLG | APOBEC3D | IL18 | BLNK | CD93 |
| CR2 | FYN | APOBEC3G | IL1B | BTLA | CDH11 |
| CXCR5 | GPR171 | AQP3 | IL1RN | BTN3A1 | CDH5 |
| ELK2AP | GZMA | AQP9 | IL2RB | BTN3A2 | CERCAM |
| FAIM3 | GZMB | ARAP2 | IL2RG | C16orf54 | CFI |
| FAM129C | GZMH | ARHGAP15 | IL32 | CBLB | CLDN5 |
| FCER2 | GZMK | ARHGAP30 | IL4I1 | CCL4 | CLEC14A |
| FCRL1 | ID2 | ARHGAP4 | IL6R | CCL4L1 | COL12A1 |
| FCRL2 | IFNG | ARHGAP9 | IL7R | CCL4L2 | COL14A1 |
| FCRL5 | IKZF3 | ARHGDIB | IL8 | CCL5 | COL15A1 |
| FCRLA | IL2RB | ARHGEF1 | INPP4B | CCR4 | COL1A1 |
| HLA-DOB | ITGA4 | ARPC3 | INPP5D | CCR6 | COL1A2 |
| HLA-DQA2 | ITGB7 | ARRB2 | IPCEF1 | CCR7 | COL3A1 |
| HVCN1 | JAKMIP1 | ASB2 | IRF5 | CD19 | COL4A1 |
| IGLL1 | KIR2DL4 | ATF5 | IRF8 | CD1C | COL4A2 |
| IGLL3P | KLRC1 | ATG3 | ISG20 | CD2 | COL5A1 |
| IGLL5 | KLRC2 | ATG7 | ITGA4 | CD22 | COL5A2 |
| IRF8 | KLRC3 | ATHL1 | ITGAL | CD24 | COL6A1 |
| KBTBD8 | KLRC4 | ATP2A3 | ITGAM | CD244 | COL6A2 |
| KIAA0125 | KLRC4-KLRK1 | ATP6V0B | ITGAX | CD247 | COL6A3 |
| KIAA0226L | KLRD1 | ATP6V0D1 | ITGB2 | CD27 | COL8A1 |
| LOC283663 | KLRK1 | ATP6V1B2 | ITGB7 | CD28 | CREB3L1 |
| LRMP | LAG3 | ATP8A1 | ITK | CD37 | CRIP2 |
| LTB | LOC100506776 | BANK1 | JAK3 | CD3D | CXCL14 |
| MS4A1 | LYST | BCL11A | JAKMIP1 | CD3E | CXorf36 |
| NAPSB | MIR155HG | BCL11B | KBTBD8 | CD3G | CYBRD1 |
| NCOA3 | NELL2 | BCL2A1 | KCNMA1 | CD4 | CYYR1 |
| P2RX5 | NKG7 | BID | KIAA0125 | CD40LG | DARC |
| PAX5 | OASL | BIN2 | KIAA0226L | CD5 | DCHS1 |
| PLEKHF2 | PARP8 | BIRC3 | KIR2DL4 | CD52 | DCN |
| PNOC | PDCD1 | BLK | KLRB1 | CD6 | DOCK6 |
| POLD4 | PIP4K2A | BLNK | KLRC1 | CD69 | DOCK9 |
| POU2AF1 | PRF1 | BLVRA | KLRC2 | CD7 | DPT |
| POU2F2 | PRKCH | BLVRB | KLRC3 | CD79A | DYSF |
| QRSL1 | PSTPIP1 | BTK | KLRC4 | CD79B | ECE1 |
| RALGPS2 | PTPN22 | BTLA | KLRC4-KLRK1 | CD82 | ECSCR |
| RPL13 | PVRIG | BTN3A1 | KLRD1 | CD8A | EFEMP2 |
| RPS20 | PYHIN1 | BTN3A2 | KLRF1 | CD8B | EGFL7 |
| RPS23 | RAB27A | C11orf75 | KLRK1 | CD96 | EHD2 |
| SEL1L3 | RARRES3 | C15orf48 | KYNU | CDC42SE2 | ELK3 |
| SELL | RUNX3 | C16orf54 | LAG3 | CELF2 | ELTD1 |
| SMIM14 | SAMD3 | C19orf38 | LAIR1 | CHMP7 | EMCN |
| SNX29 | SH2D1A | C1orf162 | LAPTM5 | CIITA | ENG |
| SNX29P1 | SLA2 | C1QA | LAT | CLEC17A | EPAS1 |
| SPIB | SLAMF6 | C1QB | LAT2 | CLEC2D | EPHB4 |
| ST6GAL1 | SYTL3 | C1QC | LBH | CNOT6L | ERG |
| STAG3 | TARP | C2 | LCK | CNR2 | ESAM |
| STAP1 | THEMIS | C3AR1 | LCP1 | COL19A1 | FBLN1 |
| TCL1A | TIGIT | C5AR1 | LCP2 | COL4A3 | FBLN5 |

TABLE S4-continued

Table S4. Cell type signatures that were derived from the analysis of the scRNA-seq data (see section Data-driven signatures of specific cell-types).

| | | | | | |
|---|---|---|---|---|---|
| TLR10 | TNFRSF9 | C9orf72 | LEPROTL1 | CORO1A | FBN1 |
| TMEM154 | TNIP3 | CAPG | LGALS2 | CR2 | FGD5 |
| TNFRSF13B | TOX | CARD9 | LGMN | CRTAM | FGF7 |
| VPREB3 | TTC24 | CASP1 | LILRA1 | CST7 | FKBP1A |
| WDFY4 | WIPF1 | CBLB | LILRA2 | CTLA4 | FLT4 |
| ZCCHC7 | XCL1 | CCL3 | LILRA3 | CTSW | FSTL1 |
| | XCL2 | CCL4 | LILRA5 | CXCL13 | GALNT18 |
| | | CCL4L1 | LILRA6 | CXCR3 | GNG11 |
| | | CCL4L2 | LILRB1 | CXCR4 | GPR116 |
| | | CCL5 | LILRB2 | CXCR5 | GPR176 |
| | | CCR1 | LILRB3 | CXCR6 | HERC2P2 |
| | | CCR2 | LILRB4 | CYFIP2 | HSPB6 |
| | | CCR4 | LILRB5 | CYTIP | HSPG2 |
| | | CCR6 | LIMD2 | DEF6 | HYAL2 |
| | | CCR7 | LIME1 | DENND2D | ICA1 |
| | | CD14 | LIPA | DGKA | ID1 |
| | | CD163 | LITAF | DTHD1 | ID3 |
| | | CD19 | LOC100130231 | DUSP2 | IFITM3 |
| | | CD1C | LOC100506776 | ELK2AP | IGFBP4 |
| | | CD2 | LOC283663 | EMB | IGFBP7 |
| | | CD22 | LOC729737 | EOMES | IL3RA |
| | | CD24 | LPXN | EVL | INHBA |
| | | CD244 | LRMP | EZR | ISLR |
| | | CD247 | LRRC25 | F5 | ITGA11 |
| | | CD27 | LSP1 | FAAH2 | ITGA5 |
| | | CD274 | LST1 | FAIM3 | ITGB4 |
| | | CD28 | LTA4H | FAM129C | KDR |
| | | CD300A | LTB | FAM65B | LAMA5 |
| | | CD300C | LY86 | FASLG | LAMB1 |
| | | CD300E | LY9 | FCER2 | LDB2 |
| | | CD300LB | LYN | FCRL1 | LOC100505495 |
| | | CD300LF | LYST | FCRL2 | LOX |
| | | CD302 | LYZ | FCRL3 | LPAR1 |
| | | CD33 | M6PR | FCRL5 | LTBP2 |
| | | CD37 | MAFB | FCRLA | LUM |
| | | CD38 | MAN2B1 | FOXP3 | MALL |
| | | CD3D | MAP4K1 | FYB | MAP1A |
| | | CD3E | 1-Mar | FYN | MEG3 |
| | | CD3G | MARCO | GATA3 | MIR100HG |
| | | CD4 | MFSD1 | GNLY | MMP2 |
| | | CD40LG | MIAT | GPR171 | MMRN1 |
| | | CD48 | MILR1 | GPR174 | MMRN2 |
| | | CD5 | MIR155HG | GPRIN3 | MRC2 |
| | | CD52 | MNDA | GRAP2 | MXRA8 |
| | | CD53 | MOB1A | GZMA | MYCT1 |
| | | CD6 | MPEG1 | GZMB | MYL9 |
| | | CD68 | MPP1 | GZMH | NFIB |
| | | CD69 | MS4A1 | GZMK | NID2 |
| | | CD7 | MS4A4A | GZMM | NNMT |
| | | CD72 | MS4A6A | HLA-DOB | NOS3 |
| | | CD74 | MS4A7 | HLA-DQA2 | NOTCH4 |
| | | CD79A | MSR1 | HMHA1 | NPDC1 |
| | | CD79B | MTMR14 | HNRNPA1P10 | OLFML3 |
| | | CD80 | MYD88 | HOPX | PALLD |
| | | CD82 | MYO1F | HSH2D | PALMD |
| | | CD83 | NAAA | HVCN1 | PCDH17 |
| | | CD84 | NADK | ICOS | PCDH18 |
| | | CD86 | NAGA | ID2 | PCOLCE |
| | | CD8A | NAGK | IFNG | PDE2A |
| | | CD8B | NAIP | IGLL1 | PDGFRA |
| | | CD96 | NAPSB | IGLL3P | PDGFRB |
| | | CD97 | NCAM1 | IGLL5 | PDGFRL |
| | | CDC42SE2 | NCF1 | IKZF1 | PDLIM1 |
| | | CECR1 | NCF1B | IKZF3 | PECAM1 |
| | | CELF2 | NCF1C | IL12RB1 | PLAC9 |
| | | CFP | NCF2 | IL16 | PLVAP |
| | | CHMP7 | NCF4 | IL2RB | PLXND1 |
| | | CIITA | NCKAP1L | IL2RG | PODN |
| | | CLEC10A | NCOA3 | IL32 | PODXL |
| | | CLEC12A | NCOA4 | IL6R | PPIC |
| | | CLEC17A | NELL2 | IL7R | PRCP |
| | | CLEC2D | NFAM1 | INPP4B | PREX2 |
| | | CLEC4A | NINJ1 | IPCEF1 | PRRX1 |
| | | CLEC4E | NKG7 | IRF8 | PTPRB |
| | | CLEC5A | NLRC3 | ISG20 | PTRF |
| | | CLEC7A | NLRC4 | ITGA4 | PVRL2 |
| | | CMKLR1 | NLRC5 | ITGAL | PXDN |

TABLE S4-continued

Table S4. Cell type signatures that were derived from the analysis of the scRNA-seq data (see section Data-driven signatures of specific cell-types).

| | | | |
|---|---|---|---|
| CNOT6L | NLRP3 | ITGB7 | RAMP2 |
| CNPY3 | NMI | ITK | RAMP3 |
| CNR2 | NPC2 | JAK3 | RARRES2 |
| COL19A1 | NPL | JAKMIP1 | RCN3 |
| COL4A3 | OAS1 | KBTBD8 | RHOJ |
| CORO1A | OASL | KIAA0125 | ROBO4 |
| COTL1 | OAZ1 | KIAA0226L | S1PR1 |
| CPVL | OLR1 | KIR2DL4 | SDC2 |
| CR2 | OSCAR | KLRB1 | SDPR |
| CREG1 | OXNAD1 | KLRC1 | SELP |
| CRTAM | P2RX5 | KLRC2 | SFRP2 |
| CSF1R | P2RY12 | KLRC3 | SHROOM4 |
| CSF2RA | P2RY13 | KLRC4 | SLCO2A1 |
| CSF3R | PAG1 | KLRC4-KLRK1 | SLIT3 |
| CST7 | PAK1 | KLRD1 | SMAD1 |
| CSTA | PARP15 | KLRF1 | SMOC2 |
| CTLA4 | PARP8 | KLRK1 | SPARC |
| CTSB | PARVG | LAG3 | SPARCL1 |
| CTSC | PASK | LAT | SPOCK1 |
| CTSD | PAX5 | LBH | STOM |
| CTSH | PBXIP1 | LCK | SULF1 |
| CTSS | PCED1B | LEPROTL1 | SVEP1 |
| CTSW | PCED1B-AS1 | LIMD2 | SYNPO |
| CXCL10 | PCK2 | LIME1 | TAGLN |
| CXCL13 | PDCD1 | LOC100130231 | TAOK2 |
| CXCL16 | PIK3AP1 | LOC100506776 | TEK |
| CXCL9 | PIK3IP1 | LOC283663 | TENC1 |
| CXCR2P1 | PIK3R5 | LRMP | TGFBR2 |
| CXCR3 | PILRA | LTB | TGM2 |
| CXCR4 | PIM2 | LY9 | THBD |
| CXCR5 | PION | LYST | THBS2 |
| CXCR6 | PIP4K2A | MAP4K1 | THY1 |
| CYBA | PLA2G7 | MIAT | TIE1 |
| CYBB | PLAC8 | MIR155HG | TM4SF1 |
| CYFIP2 | PLAUR | MS4A1 | TM4SF18 |
| CYP2S1 | PLBD1 | NAPSB | TMEM119 |
| CYTH4 | PLCB2 | NCAM1 | TMEM255B |
| CYTIP | PLEK | NCOA3 | TPM1 |
| DAPK1 | PLEKHA2 | NELL2 | TPM2 |
| DAPP1 | PLEKHF2 | NKG7 | TSPAN18 |
| DEF6 | PLEKHO1 | NLRC3 | TSPAN7 |
| DENND2D | PLIN2 | NLRC5 | VWF |
| DGKA | PNOC | OASL | ZNF385D |
| DHRS9 | POLD4 | OXNAD1 | |
| DMXL2 | POU2AF1 | P2RX5 | |
| DNAJC5B | POU2F2 | PAG1 | |
| DOCK2 | PPM1K | PARP15 | |
| DOCK8 | PPP2R5C | PARP8 | |
| DOK2 | PPT1 | PASK | |
| DOK3 | PRAM1 | PAX5 | |
| DTHD1 | PRDM1 | PBXIP1 | |
| DUSP2 | PRF1 | PCED1B | |
| EBI3 | PRKCB | PCED1B-AS1 | |
| ELK2AP | PRKCD | PDCD1 | |
| EMB | PRKCH | PIK3IP1 | |
| EMR2 | PRKCQ | PIM2 | |
| EOMES | PSAP | PIP4K2A | |
| EPSTI1 | PSMB10 | PLAC8 | |
| EVI2A | PSTPIP1 | PLEKHA2 | |
| EVI2B | PTAFR | PLEKHF2 | |
| EVL | PTGDR | PNOC | |
| EZR | PTK2B | POLD4 | |
| F13A1 | PTPN22 | POU2AF1 | |
| F5 | PTPN6 | POU2F2 | |
| FAAH2 | PTPN7 | PPM1K | |
| FAIM3 | PTPRC | PPP2R5C | |
| FAM105A | PTPRCAP | PRDM1 | |
| FAM129C | PVRIG | PRF1 | |
| FAM157B | PYCARD | PRKCH | |
| FAM26F | PYHIN1 | PRKCQ | |
| FAM49B | QRSL1 | PSTPIP1 | |
| FAM65B | RAB20 | PTGDR | |
| FASLG | RAB27A | PTPN22 | |
| FBP1 | RAC2 | PTPN7 | |
| FCER1G | RALGPS2 | PTPRC | |
| FCER2 | RAPGEF6 | PTPRCAP | |
| FCGR1A | RARRES3 | PVRIG | |

TABLE S4-continued

Table S4. Cell type signatures that were derived from the analysis of the scRNA-seq data (see section Data-driven signatures of specific cell-types).

| | | |
|---|---|---|
| FCGR1B | RASAL3 | PYHIN1 |
| FCGR1C | RASGRP1 | QRSL1 |
| FCGR2A | RASSF4 | RAB27A |
| FCGR2C | RASSF5 | RAC2 |
| FCGR3A | RBM47 | RALGPS2 |
| FCGR3B | RCSD1 | RAPGEF6 |
| FCN1 | RELT | RARRES3 |
| FCRL1 | RGS1 | RASAL3 |
| FCRL2 | RGS10 | RASGRP1 |
| FCRL3 | RGS18 | RGS1 |
| FCRL5 | RGS19 | RHOF |
| FCRLA | RGS2 | RHOH |
| FERMT3 | RHBDF2 | RNF213 |
| FGD2 | RHOF | RPL13 |
| FGD3 | RHOG | RPS20 |
| FGL2 | RHOH | RPS23 |
| FGR | RILPL2 | RUNX3 |
| FOLR2 | RIPK2 | SAMD3 |
| FOXP3 | RNASE6 | SCML4 |
| FPR1 | RNASET2 | SEL1L3 |
| FPR2 | RNF13 | SELL |
| FPR3 | RNF130 | SEMA4D |
| FTH1 | RNF144B | 1-Sep |
| FTL | RNF213 | SH2D1A |
| FUCA1 | RPL13 | SH2D1B |
| FUOM | RPS20 | SH2D2A |
| FYB | RPS23 | SIRPG |
| FYN | RPS6KA1 | SIT1 |
| GABARAP | RTN1 | SKAP1 |
| GATA3 | RUNX3 | SLA2 |
| GATM | S100A8 | SLAMF1 |
| GBP1 | S100A9 | SLAMF6 |
| GBP5 | SAMD3 | SMIM14 |
| GCA | SAMHD1 | SNX29 |
| GK | SAMSN1 | SNX29P1 |
| GLA | SASH3 | SP140 |
| GLRX | SAT1 | SPATA13 |
| GLUL | SCIMP | SPIB |
| GM2A | SCML4 | SPN |
| GNA15 | SDS | SPOCK2 |
| GNLY | SECTM1 | ST6GAL1 |
| GPBAR1 | SEL1L3 | STAG3 |
| GPR171 | SELL | STAP1 |
| GPR174 | SELPLG | STAT4 |
| GPR183 | SEMA4A | STK17B |
| GPR34 | SEMA4D | STK4 |
| GPR84 | 1-Sep | SYTL3 |
| GPRIN3 | SERPINA1 | TARP |
| GPSM3 | SH2D1A | TBC1D10C |
| GPX1 | SH2D1B | TC2N |
| GRAP2 | SH2D2A | TCF7 |
| GRB2 | SIGLEC1 | TCL1A |
| GRN | SIGLEC14 | TESPA1 |
| GZMA | SIGLEC5 | THEMIS |
| GZMB | SIGLEC7 | TIGIT |
| GZMH | SIGLEC9 | TLR10 |
| GZMK | SIRPB1 | TMC8 |
| GZMM | SIRPB2 | TMEM154 |
| HAVCR2 | SIRPG | TNFAIP3 |
| HCAR2 | SIT1 | TNFRSF13B |
| HCAR3 | SKAP1 | TNFRSF9 |
| HCK | SLA | TNFSF8 |
| HCLS1 | SLA2 | TNIP3 |
| HCST | SLAMF1 | TOX |
| HK2 | SLAMF6 | TRAF1 |
| HK3 | SLAMF7 | TRAF3IP3 |
| HLA-DMA | SLAMF8 | TRAT1 |
| HLA-DMB | SLC11A1 | TSC22D3 |
| HLA-DOB | SLC15A3 | TTC24 |
| HLA-DPA1 | SLC1A3 | TTC39C |
| HLA-DPB1 | SLC29A3 | UBASH3A |
| HLA-DPB2 | SLC31A2 | VPREB3 |
| HLA-DQA1 | SLC7A7 | WDFY4 |
| HLA-DQA2 | SLCO2B1 | WIPF1 |
| HLA-DQB1 | SMAP2 | XCL1 |
| HLA-DQB2 | SMIM14 | XCL2 |
| HLA-DRA | SMPDL3A | ZAP70 |

TABLE S4-continued

Table S4. Cell type signatures that were derived from the analysis of the scRNA-seq data (see section Data-driven signatures of specific cell-types).

| | | |
|---|---|---|
| HLA-DRB1 | SNX10 | ZC3HAV1 |
| HLA-DRB5 | SNX20 | ZCCHC7 |
| SNX29 | TMEM176A | |
| SNX29P1 | TMEM176B | |
| SOD2 | TMEM37 | |
| SP140 | TNFAIP2 | |
| SPATA13 | TNFAIP3 | |
| SPI1 | TNFAIP8 | |
| SPIB | TNFAIP8L2 | |
| SPINT2 | TNFRSF13B | |
| SPN | TNFRSF9 | |
| SPOCK2 | TNFSF13 | |
| SRGN | TNFSF13B | |
| ST6GAL1 | TNFSF8 | |
| STAG3 | TNIP3 | |
| STAP1 | TOX | |
| STAT1 | TPP1 | |
| STAT4 | TRAF1 | |
| STK17B | TRAF3IP3 | |
| STK4 | TRAT1 | |
| STX11 | TREM1 | |
| STXBP2 | TREM2 | |
| SYK | TSC22D3 | |
| SYTL3 | TTC24 | |
| TAGAP | TTC39C | |
| TARP | TWF2 | |
| TBC1D10C | TYMP | |
| TBXAS1 | TYROBP | |
| TC2N | UBASH3A | |
| TCF7 | UBE2D1 | |
| TCL1A | UCP2 | |
| TESPA1 | VAMP8 | |
| TGFBI | VAV1 | |
| THEMIS | VMO1 | |
| THEMIS2 | VPREB3 | |
| TIFAB | VSIG4 | |
| TIGIT | WDFY4 | |
| TLR1 | WIPF1 | |
| TLR10 | XCL1 | |
| TLR2 | XCL2 | |
| TLR5 | ZAP70 | |
| TLR8 | ZC3HAV1 | |
| TMC8 | ZCCHC7 | |
| TMEM106A | ZNF385A | |
| TMEM154 | | |

TABLE S5

Table S5. The ICR signatures of the different immune cell types: B-cells, macrophages, CD4 and CD8 T cells.

| CD8-T-cell-up | CD8-T-cell-down | macrophage-up | macrophage-down | B-cell-up | B-cell-down | CD4-T-cell-up | CD4-T-cell-down |
|---|---|---|---|---|---|---|---|
| CEP19 | ACP5 | APOL1 | A2M | C6orf62 | MTRNR2L1 | PRDM1 | CHI3L2 |
| EXO5 | AKNA | CD274 | ADAP2 | CDC42 | MTRNR2L10 | | RPL13A |
| FAM153C | BTN3A2 | CSTB | ADORA3 | CNN2 | MTRNR2L3 | | |
| FCRL6 | CCDC141 | DCN | ARL4C | FOXP1 | MTRNR2L4 | | |
| GBP2 | CD27 | HLA-DPB2 | ASPH | FYB | RGS2 | | |
| GBP5 | CDC42SE1 | HLA-DQA1 | BCAT1 | GRB2 | | | |
| HSPA1B | DDIT4 | HLA-G | C11orf31 | | | | |
| IER2 | FAU | HSPA8 | C3 | | | | |
| IRF1 | FKBP5 | HSPB1 | C3AR1 | | | | |
| KLRK1 | GPR56 | IL18BP | C6orf62 | | | | |
| LDHA | HAVCR2 | TMEM176A | CAPN2 | | | | |
| LOC100506083 | HLA-B | UBD | CD200R1 | | | | |
| MBOAT1 | HLA-C | | CD28 | | | | |
| SEMA4D | HLA-F | | CD9 | | | | |
| SIRT3 | IL6ST | | CD99 | | | | |
| SPDYE2 | ITGA4 | | COMT | | | | |
| SPDYE2L | KIAA1551 | | CREM | | | | |
| STAT1 | KLF12 | | CRTAP | | | | |
| STOM | MIR155HG | | CYFIP1 | | | | |
| UBE2Q2P3 | MTA2 | | DDOST | | | | |
| | MTRNR2L1 | | DHRS3 | | | | |

TABLE S5-continued

Table S5. The ICR signatures of the different immune cell types: B-cells, macrophages, CD4 and CD8 T cells.

| CD8-T-cell-up | CD8-T-cell-down | macrophage-up | macrophage-down | B-cell-up | B-cell-down | CD4-T-cell-up | CD4-T-cell-down |
|---|---|---|---|---|---|---|---|
| | MTRNR2L3 | | EGFL7 | | | | |
| | PIK3IP1 | | EIF1AY | | | | |
| | RPL26 | | ETS2 | | | | |
| | RPL27 | | FCGR2A | | | | |
| | RPL27A | | FOLR2 | | | | |
| | RPL35A | | GATM | | | | |
| | RPS11 | | GBP3 | | | | |
| | RPS16 | | GNG2 | | | | |
| | RPS20 | | GSTT1 | | | | |
| | RPS26 | | GYPC | | | | |
| | SPOCK2 | | HIST1H1E | | | | |
| | SYTL3 | | HPGDS | | | | |
| | TOB1 | | IFI44L | | | | |
| | TPT1 | | IGFBP4 | | | | |
| | TTN | | ITGA4 | | | | |
| | TXNIP | | KCTD12 | | | | |
| | WNK1 | | LGMN | | | | |
| | ZFP36L2 | | LOC441081 | | | | |
| | | | LTC4S | | | | |
| | | | LYVE1 | | | | |
| | | | MERTK | | | | |
| | | | METTL7B | | | | |
| | | | MS4A4A | | | | |
| | | | MS4A7 | | | | |
| | | | MTSS1 | | | | |
| | | | NLRP3 | | | | |
| | | | OLFML3 | | | | |
| | | | PLA2G15 | | | | |
| | | | PLXDC2 | | | | |
| | | | PMP22 | | | | |
| | | | POR | | | | |
| | | | PRDX2 | | | | |
| | | | PTGS1 | | | | |
| | | | RNASE1 | | | | |
| | | | ROCK1 | | | | |
| | | | RPS4Y1 | | | | |
| | | | S100A9 | | | | |
| | | | SCAMP2 | | | | |
| | | | SEPP1 | | | | |
| | | | SESN1 | | | | |
| | | | SLC18B1 | | | | |
| | | | SLC39A1 | | | | |
| | | | SLC40A1 | | | | |
| | | | SLC7A8 | | | | |
| | | | SORL1 | | | | |
| | | | SPP1 | | | | |
| | | | STAB1 | | | | |
| | | | TMEM106C | | | | |
| | | | TMEM86A | | | | |
| | | | TMEM9 | | | | |
| | | | TNFRSF1B | | | | |
| | | | TNFRSF21 | | | | |
| | | | TPD52L2 | | | | |
| | | | ULK3 | | | | |
| | | | ZFP36L2 | | | | |

TABLE S6

Table S6. The oncogenic resistance signatures: oncogenic-ICR, exclusion, uICR, and the refined uICR.

| Genes up-regulated in ICR malignant cells (1 denotes the gene is included in the signature, and 0 otherwise) | | | | Genes down-regulated in ICR malignant cells (1 denotes the gene is included in the signature, and 0 otherwise) | | | |
|---|---|---|---|---|---|---|---|
| uICR-up genes (immune resistance) | oncogenic-ICR-up (post treatment) | Exclusion-up | uICR-up (refined) | uICR-down genes | oncogenic-ICR-down | Exclusion-down | uICR-down (refined) |
| ACAT1 | 0 | 1 | 0 | A2M | 1 | 1 | 0 |
| ACP5 | 0 | 1 | 0 | ACSL3 | 1 | 0 | 0 |
| ACTB | 1 | 0 | 0 | ACSL4 | 1 | 0 | 0 |
| ACTG1 | 0 | 1 | 0 | ADM | 1 | 0 | 0 |
| ADSL | 0 | 1 | 0 | AEBP1 | 1 | 0 | 1 |
| AEN | 1 | 0 | 0 | AGA | 1 | 1 | 0 |

TABLE S6-continued

Table S6. The oncogenic resistance signatures: oncogenic-ICR, exclusion, uICR, and the refined uICR.

| Genes up-regulated in ICR malignant cells (1 denotes the gene is included in the signature, and 0 otherwise) | | | | Genes down-regulated in ICR malignant cells (1 denotes the gene is included in the signature, and 0 otherwise) | | | |
|---|---|---|---|---|---|---|---|
| uICR-up genes (immune resistance) | oncogenic-ICR-up (post treatment) | Exclusion-up | uICR-up (refined) | uICR-down genes | oncogenic-ICR-down | Exclusion-down | uICR-down (refined) |
| AK2 | 0 | 1 | 0 | AHNAK | 1 | 1 | 1 |
| ANP32E | 1 | 0 | 0 | ANGPTL4 | 1 | 0 | 0 |
| APP | 0 | 1 | 0 | ANXA1 | 1 | 1 | 0 |
| ASAP1 | 0 | 1 | 0 | ANXA2 | 1 | 0 | 0 |
| ATP5A1 | 1 | 0 | 0 | APLP2 | 1 | 1 | 0 |
| ATP5D | 0 | 1 | 0 | APOC2 | 0 | 1 | 1 |
| ATP5G2 | 1 | 0 | 0 | APOD | 1 | 0 | 1 |
| BANCR | 0 | 1 | 0 | APOE | 1 | 0 | 1 |
| BCAN | 0 | 1 | 0 | ARF5 | 0 | 1 | 0 |
| BZW2 | 1 | 1 | 0 | ARL6IP5 | 1 | 0 | 0 |
| C17orf76-AS1 | 1 | 1 | 0 | ATF3 | 1 | 0 | 0 |
| C1QBP | 1 | 1 | 1 | ATP1A1 | 1 | 1 | 0 |
| C20orf112 | 1 | 0 | 0 | ATP1B1 | 1 | 1 | 0 |
| C6orf48 | 0 | 1 | 0 | ATP1B3 | 1 | 0 | 0 |
| CA14 | 1 | 1 | 0 | ATRAID | 0 | 1 | 0 |
| CBX5 | 1 | 0 | 0 | B2M | 1 | 1 | 1 |
| CCT2 | 1 | 0 | 1 | BACE2 | 1 | 0 | 0 |
| CCT3 | 1 | 1 | 0 | BBX | 1 | 0 | 0 |
| CCT6A | 0 | 1 | 1 | BCL6 | 1 | 0 | 0 |
| CDK4 | 1 | 0 | 0 | C10orf54 | 0 | 1 | 1 |
| CEP170 | 0 | 1 | 0 | C4A | 0 | 1 | 0 |
| CFL1 | 1 | 0 | 0 | CALU | 1 | 0 | 0 |
| CHP1 | 0 | 1 | 0 | CASP1 | 1 | 0 | 0 |
| CNRIP1 | 1 | 0 | 0 | CAST | 1 | 0 | 0 |
| CRABP2 | 1 | 0 | 0 | CAV1 | 1 | 0 | 0 |
| CS | 1 | 0 | 0 | CBLB | 0 | 1 | 0 |
| CTPS1 | 1 | 1 | 0 | CCND3 | 1 | 1 | 0 |
| CYC1 | 0 | 1 | 0 | CD151 | 1 | 1 | 0 |
| DAP3 | 0 | 1 | 0 | CD44 | 1 | 0 | 0 |
| DCAF13 | 1 | 0 | 1 | CD47 | 1 | 1 | 0 |
| DCT | 1 | 1 | 0 | CD58 | 1 | 0 | 0 |
| DDX21 | 0 | 1 | 0 | CD59 | 1 | 1 | 0 |
| DDX39B | 1 | 0 | 0 | CD63 | 1 | 0 | 1 |
| DLL3 | 1 | 0 | 0 | CD9 | 1 | 0 | 0 |
| EDNRB | 0 | 1 | 0 | CDH19 | 1 | 1 | 0 |
| EEF1D | 0 | 1 | 0 | CHI3L1 | 1 | 0 | 0 |
| EEF1G | 1 | 1 | 0 | CHN1 | 0 | 1 | 0 |
| EEF2 | 0 | 1 | 0 | CLIC4 | 1 | 0 | 0 |
| EIF1AX | 0 | 1 | 0 | CLU | 0 | 1 | 0 |
| EIF2S3 | 1 | 1 | 0 | CPVL | 0 | 1 | 0 |
| EIF3E | 0 | 1 | 0 | CRELD1 | 1 | 0 | 0 |
| EIF3K | 1 | 1 | 0 | CRYAB | 1 | 0 | 0 |
| EIF3L | 0 | 1 | 0 | CSGALNACT1 | 1 | 0 | 0 |
| EIF4A1 | 1 | 1 | 1 | CSPG4 | 1 | 0 | 0 |
| EIF4EBP2 | 1 | 0 | 0 | CST3 | 1 | 1 | 0 |
| ESRP1 | 0 | 1 | 0 | CTSA | 1 | 0 | 0 |
| FAM174B | 1 | 0 | 0 | CTSB | 1 | 1 | 0 |
| FAM178B | 0 | 1 | 0 | CTSD | 1 | 1 | 1 |
| FAM92A1 | 0 | 1 | 0 | CTSL1 | 1 | 1 | 0 |
| FBL | 1 | 0 | 0 | DAG1 | 1 | 0 | 0 |
| FBLN1 | 1 | 0 | 0 | DCBLD2 | 1 | 0 | 0 |
| FOXRED2 | 1 | 0 | 0 | DDR1 | 1 | 1 | 0 |
| FTL | 1 | 1 | 0 | DDX5 | 1 | 0 | 0 |
| FUS | 1 | 0 | 0 | DPYSL2 | 1 | 1 | 0 |
| GABARAP | 1 | 0 | 0 | DSCR8 | 0 | 1 | 0 |
| GAS5 | 1 | 1 | 0 | DUSP4 | 1 | 0 | 0 |
| GNB2L1 | 1 | 1 | 0 | DUSP6 | 1 | 1 | 0 |
| GPATCH4 | 1 | 0 | 0 | DYNLRB1 | 0 | 1 | 0 |
| GPI | 1 | 1 | 0 | ECM1 | 1 | 0 | 0 |
| GRWD1 | 1 | 0 | 0 | EEA1 | 1 | 0 | 1 |
| GSTO1 | 0 | 1 | 0 | EGR1 | 1 | 0 | 0 |
| H3F3A | 1 | 0 | 0 | EMP1 | 1 | 1 | 1 |
| H3F3AP4 | 1 | 0 | 0 | EPHX2 | 1 | 0 | 0 |
| HMGA1 | 1 | 0 | 0 | ERBB3 | 1 | 0 | 0 |
| HNRNPA1 | 1 | 0 | 0 | EVA1A | 1 | 0 | 0 |
| HNRNPA1P10 | 1 | 0 | 0 | EZH1 | 1 | 0 | 0 |
| HNRNPC | 1 | 0 | 0 | EZR | 0 | 1 | 0 |
| HSPA8 | 1 | 0 | 0 | FAM3C | 1 | 1 | 0 |
| IDH2 | 1 | 0 | 0 | FBXO32 | 1 | 0 | 1 |
| IFI16 | 0 | 1 | 0 | FCGR2C | 1 | 0 | 0 |
| ILF2 | 1 | 1 | 1 | FCRLA | 1 | 0 | 0 |
| IMPDH2 | 0 | 1 | 0 | FGFR1 | 1 | 1 | 0 |

TABLE S6-continued

Table S6. The oncogenic resistance signatures: oncogenic-ICR, exclusion, uICR, and the refined uICR.

| Genes up-regulated in ICR malignant cells (1 denotes the gene is included in the signature, and 0 otherwise) | | | | Genes down-regulated in ICR malignant cells (1 denotes the gene is included in the signature, and 0 otherwise) | | | |
| --- | --- | --- | --- | --- | --- | --- | --- |
| uICR-up genes (immune resistance) | oncogenic-ICR-up (post treatment) | Exclusion-up | uICR-up (refined) | uICR-down genes | oncogenic-ICR-down | Exclusion-down | uICR-down (refined) |
| ISYNA1 | 1 | 0 | 0 | FLJ43663 | 1 | 0 | 0 |
| ITM2C | 1 | 0 | 0 | FOS | 1 | 0 | 0 |
| KIAA0101 | 1 | 0 | 0 | FYB | 0 | 1 | 1 |
| LHFPL3-AS1 | 0 | 1 | 0 | GAA | 1 | 1 | 0 |
| LOC100190986 | 0 | 1 | 0 | GADD45B | 1 | 0 | 0 |
| LYPLA1 | 0 | 1 | 0 | GATSL3 | 0 | 1 | 1 |
| MAGEA4 | 1 | 0 | 1 | GEM | 1 | 0 | 0 |
| MARCKS | 0 | 1 | 0 | GOLGB1 | 1 | 0 | 0 |
| MDH2 | 1 | 1 | 0 | GPNMB | 1 | 0 | 0 |
| METAP2 | 1 | 0 | 0 | GRN | 1 | 1 | 0 |
| MID1 | 1 | 0 | 0 | GSN | 1 | 1 | 0 |
| MIR4461 | 1 | 0 | 0 | HCP5 | 0 | 1 | 1 |
| MLLT11 | 1 | 0 | 0 | HLA-A | 1 | 0 | 1 |
| MPZL1 | 1 | 0 | 0 | HLA-B | 1 | 1 | 1 |
| MRPL37 | 0 | 1 | 0 | HLA-C | 1 | 1 | 1 |
| MRPS12 | 0 | 1 | 0 | HLA-E | 1 | 0 | 1 |
| MRPS21 | 1 | 0 | 0 | HLA-F | 1 | 1 | 1 |
| MYC | 0 | 1 | 0 | HLA-H | 1 | 1 | 1 |
| NACA | 1 | 0 | 0 | HPCAL1 | 1 | 0 | 0 |
| NCL | 1 | 1 | 0 | HSPA1A | 1 | 1 | 0 |
| NDUFS2 | 1 | 0 | 0 | HSPA1B | 0 | 1 | 0 |
| NF2 | 0 | 1 | 0 | HTATIP2 | 1 | 0 | 0 |
| NID1 | 0 | 1 | 0 | ID2 | 0 | 1 | 0 |
| NOLC1 | 1 | 1 | 0 | IFI27L2 | 0 | 1 | 0 |
| NONO | 1 | 0 | 1 | IFI35 | 1 | 0 | 0 |
| NPM1 | 0 | 1 | 0 | IGF1R | 1 | 0 | 0 |
| NUCKS1 | 0 | 1 | 0 | IL1RAP | 1 | 0 | 0 |
| OAT | 0 | 1 | 0 | IL6ST | 1 | 0 | 0 |
| PA2G4 | 1 | 0 | 1 | ISCU | 0 | 1 | 0 |
| PABPC1 | 1 | 1 | 0 | ITGA3 | 1 | 1 | 1 |
| PAFAH1B3 | 1 | 0 | 0 | ITGA6 | 1 | 0 | 0 |
| PAICS | 0 | 1 | 0 | ITGA7 | 0 | 1 | 0 |
| PFDN2 | 1 | 0 | 0 | ITGB1 | 1 | 0 | 0 |
| PFN1 | 1 | 0 | 0 | ITGB3 | 1 | 1 | 0 |
| PGAM1 | 1 | 0 | 1 | ITM2B | 1 | 0 | 0 |
| PIH1D1 | 1 | 0 | 0 | JUN | 1 | 0 | 0 |
| PLTP | 0 | 1 | 0 | KCNN4 | 1 | 1 | 0 |
| PPA1 | 1 | 0 | 1 | KLF4 | 1 | 0 | 0 |
| PPIA | 1 | 0 | 1 | KLF6 | 1 | 0 | 0 |
| PPP2R1A | 1 | 0 | 0 | KRT10 | 0 | 1 | 0 |
| PSAT1 | 0 | 1 | 0 | LAMP2 | 1 | 0 | 1 |
| PSMD4 | 1 | 0 | 0 | LEPROT | 1 | 0 | 0 |
| PTMA | 1 | 0 | 0 | LGALS1 | 1 | 0 | 0 |
| PYCARD | 0 | 1 | 0 | LGALS3 | 1 | 0 | 0 |
| RAN | 1 | 0 | 0 | LGALS3BP | 1 | 0 | 0 |
| RASA3 | 0 | 1 | 0 | LOC100506190 | 0 | 1 | 0 |
| RBM34 | 1 | 0 | 0 | LPL | 1 | 0 | 0 |
| RNF2 | 1 | 0 | 0 | LRPAP1 | 1 | 0 | 0 |
| RPAIN | 1 | 0 | 0 | LTBP3 | 0 | 1 | 0 |
| RPL10 | 0 | 1 | 0 | LYRM9 | 0 | 1 | 1 |
| RPL10A | 1 | 1 | 0 | MAEL | 0 | 1 | 0 |
| RPL11 | 1 | 1 | 0 | MAGEC2 | 1 | 0 | 0 |
| RPL12 | 1 | 1 | 0 | MAP1B | 0 | 1 | 0 |
| RPL13 | 1 | 1 | 0 | MATN2 | 0 | 1 | 0 |
| RPL13A | 1 | 1 | 0 | MFGE8 | 1 | 1 | 1 |
| RPL13AP5 | 1 | 0 | 0 | MFI2 | 1 | 1 | 0 |
| RPL14 | 0 | 1 | 0 | MIA | 1 | 1 | 1 |
| RPL17 | 1 | 1 | 0 | MRPS6 | 0 | 1 | 0 |
| RPL18 | 1 | 1 | 0 | MT1E | 1 | 0 | 0 |
| RPL18A | 1 | 1 | 1 | MT1M | 1 | 0 | 0 |
| RPL21 | 1 | 0 | 0 | MT1X | 1 | 0 | 0 |
| RPL26 | 1 | 0 | 1 | MT2A | 1 | 1 | 0 |
| RPL28 | 1 | 1 | 0 | NDRG1 | 0 | 1 | 0 |
| RPL29 | 1 | 0 | 0 | NEAT1 | 1 | 0 | 0 |
| RPL3 | 1 | 1 | 0 | NFKBIA | 1 | 1 | 0 |
| RPL30 | 0 | 1 | 0 | NFKBIZ | 1 | 0 | 0 |
| RPL31 | 1 | 0 | 1 | NNMT | 1 | 0 | 0 |
| RPL35 | 0 | 1 | 0 | NPC1 | 1 | 1 | 0 |
| RPL36A | 1 | 0 | 0 | NPC2 | 1 | 0 | 1 |
| RPL37 | 1 | 0 | 0 | NR4A1 | 1 | 0 | 0 |
| RPL37A | 1 | 1 | 0 | NSG1 | 1 | 0 | 1 |
| RPL39 | 1 | 1 | 0 | OCIAD2 | 0 | 1 | 0 |

TABLE S6-continued

Table S6. The oncogenic resistance signatures: oncogenic-ICR, exclusion, uICR, and the refined uICR.

| Genes up-regulated in ICR malignant cells (1 denotes the gene is included in the signature, and 0 otherwise) | | | | Genes down-regulated in ICR malignant cells (1 denotes the gene is included in the signature, and 0 otherwise) | | | |
|---|---|---|---|---|---|---|---|
| uICR-up genes (immune resistance) | oncogenic-ICR-up (post treatment) | Exclusion-up | uICR-up (refined) | uICR-down genes | oncogenic-ICR-down | Exclusion-down | uICR-down (refined) |
| RPL4 | 1 | 1 | 0 | PAGE5 | 0 | 1 | 0 |
| RPL41 | 1 | 0 | 0 | PDK4 | 1 | 0 | 0 |
| RPL5 | 1 | 1 | 0 | PERP | 0 | 1 | 0 |
| RPL6 | 1 | 1 | 0 | PKM | 0 | 1 | 0 |
| RPL7 | 0 | 1 | 0 | PLP2 | 1 | 0 | 0 |
| RPL7A | 0 | 1 | 0 | PRKCDBP | 1 | 0 | 0 |
| RPL8 | 1 | 1 | 0 | PRNP | 1 | 0 | 0 |
| RPLP0 | 1 | 1 | 0 | PROS1 | 1 | 0 | 1 |
| RPLP1 | 1 | 1 | 0 | PRSS23 | 1 | 0 | 0 |
| RPS10 | 1 | 1 | 0 | PSAP | 1 | 0 | 0 |
| RPS11 | 1 | 1 | 1 | PSMB9 | 1 | 0 | 0 |
| RPS12 | 1 | 0 | 0 | PTRF | 1 | 0 | 0 |
| RPS15 | 0 | 1 | 1 | RDH5 | 0 | 1 | 1 |
| RPS15A | 1 | 1 | 0 | RNF145 | 1 | 0 | 0 |
| RPS16 | 1 | 1 | 0 | RPS4Y1 | 1 | 0 | 0 |
| RPS17 | 1 | 1 | 0 | S100A13 | 0 | 1 | 0 |
| RPS17L | 1 | 1 | 0 | S100A6 | 1 | 1 | 0 |
| RPS18 | 1 | 1 | 0 | S100B | 1 | 0 | 0 |
| RPS19 | 1 | 1 | 0 | SAT1 | 1 | 0 | 0 |
| RPS2 | 0 | 1 | 0 | SCARB2 | 1 | 0 | 0 |
| RPS21 | 1 | 0 | 1 | SCCPDH | 1 | 0 | 0 |
| RPS23 | 1 | 0 | 0 | SDC3 | 1 | 0 | 0 |
| RPS24 | 1 | 1 | 0 | SEL1L | 1 | 0 | 0 |
| RPS26 | 1 | 0 | 0 | SEMA3B | 1 | 0 | 0 |
| RPS27 | 1 | 1 | 0 | SERPINA1 | 0 | 1 | 1 |
| RPS27A | 1 | 0 | 0 | SERPINA3 | 1 | 1 | 0 |
| RPS3 | 1 | 1 | 0 | SERPINE2 | 1 | 1 | 0 |
| RPS3A | 0 | 1 | 0 | SGCE | 1 | 1 | 0 |
| RPS4X | 1 | 1 | 0 | SGK1 | 1 | 0 | 0 |
| RPS5 | 1 | 1 | 1 | SLC20A1 | 1 | 0 | 0 |
| RPS6 | 1 | 0 | 0 | SLC26A2 | 1 | 1 | 0 |
| RPS7 | 1 | 1 | 0 | SLC39A14 | 1 | 0 | 0 |
| RPS8 | 1 | 1 | 0 | SLC5A3 | 1 | 1 | 0 |
| RPS9 | 1 | 1 | 0 | SNX9 | 0 | 1 | 0 |
| RPSA | 1 | 1 | 0 | SOD1 | 1 | 0 | 0 |
| RSL1D1 | 0 | 1 | 0 | SPON2 | 0 | 1 | 0 |
| RUVBL2 | 1 | 0 | 1 | SPRY2 | 1 | 0 | 0 |
| SAE1 | 1 | 0 | 1 | SQSTM1 | 1 | 0 | 0 |
| SCD | 1 | 1 | 0 | SRPX | 1 | 0 | 0 |
| SCNM1 | 1 | 0 | 0 | STOM | 1 | 0 | 0 |
| SERBP1 | 0 | 1 | 0 | SYNGR2 | 1 | 0 | 0 |
| SERPINF1 | 1 | 1 | 0 | SYPL1 | 1 | 0 | 0 |
| SET | 1 | 0 | 0 | TAPBP | 1 | 0 | 1 |
| SF3B4 | 1 | 0 | 0 | TAPBPL | 1 | 0 | 0 |
| SHMT2 | 1 | 0 | 0 | TF | 1 | 0 | 0 |
| SKP2 | 1 | 0 | 0 | TGOLN2 | 1 | 0 | 0 |
| SLC19A1 | 0 | 1 | 0 | THBD | 0 | 1 | 0 |
| SLC25A3 | 1 | 0 | 0 | TIMP1 | 1 | 1 | 0 |
| SLC25A5 | 0 | 1 | 0 | TIMP2 | 1 | 0 | 1 |
| SLC25A6 | 0 | 1 | 0 | TIMP3 | 1 | 0 | 0 |
| SMS | 1 | 0 | 0 | TIPARP | 1 | 0 | 0 |
| SNAI2 | 1 | 1 | 0 | TM4SF1 | 1 | 1 | 0 |
| SNHG16 | 0 | 1 | 0 | TMBIM6 | 0 | 1 | 0 |
| SNHG6 | 1 | 1 | 0 | TMED10 | 1 | 0 | 0 |
| SNRPE | 1 | 0 | 1 | TMED9 | 1 | 0 | 0 |
| SORD | 0 | 1 | 0 | TMEM66 | 1 | 0 | 0 |
| SOX4 | 1 | 1 | 0 | TMX4 | 1 | 0 | 0 |
| SRP14 | 1 | 0 | 0 | TNC | 1 | 0 | 0 |
| SSR2 | 1 | 0 | 0 | TNFSF4 | 0 | 1 | 1 |
| TIMM13 | 0 | 1 | 0 | TPP1 | 1 | 1 | 0 |
| TIMM50 | 1 | 1 | 0 | TRIML2 | 0 | 1 | 1 |
| TMC6 | 1 | 0 | 0 | TSC22D3 | 1 | 1 | 0 |
| TOP1MT | 0 | 1 | 0 | TSPYL2 | 0 | 1 | 0 |
| TP53 | 1 | 0 | 0 | TXNIP | 0 | 1 | 0 |
| TRAP1 | 0 | 1 | 0 | TYR | 1 | 0 | 0 |
| TRPM1 | 1 | 0 | 0 | UBC | 1 | 1 | 0 |
| TSR1 | 1 | 0 | 0 | UPP1 | 1 | 0 | 0 |
| TUBA1B | 1 | 0 | 0 | XAGE1A | 0 | 1 | 0 |
| TUBB | 1 | 0 | 0 | XAGE1B | 0 | 1 | 0 |
| TUBB4A | 0 | 1 | 0 | XAGE1C | 0 | 1 | 0 |
| TULP4 | 1 | 0 | 0 | XAGE1D | 0 | 1 | 0 |
| TXLNA | 0 | 1 | 0 | XAGE1E | 0 | 1 | 0 |

TABLE S6-continued

Table S6. The oncogenic resistance signatures: oncogenic-ICR, exclusion, uICR, and the refined uICR.

| Genes up-regulated in ICR malignant cells (1 denotes the gene is included in the signature, and 0 otherwise) | | | | Genes down-regulated in ICR malignant cells (1 denotes the gene is included in the signature, and 0 otherwise) | | | |
|---|---|---|---|---|---|---|---|
| uICR-up genes (immune resistance) | oncogenic-ICR-up (post treatment) | Exclusion-up | uICR-up (refined) | uICR-down genes | oncogenic-ICR-down | Exclusion-down | uICR-down (refined) |
| TYRP1 | 0 | 1 | 0 | ZBTB20 | 1 | 0 | 0 |
| UBA52 | 1 | 0 | 1 | ZBTB38 | 1 | 0 | 0 |
| UCK2 | 0 | 1 | 0 | | | | |
| UQCRFS1 | 1 | 1 | 0 | | | | |
| UQCRH | 1 | 0 | 1 | | | | |
| USP22 | 1 | 0 | 0 | | | | |
| VCY1B | 1 | 0 | 0 | | | | |
| VDAC2 | 1 | 0 | 1 | | | | |
| VPS72 | 1 | 0 | 0 | | | | |
| YWHAE | 1 | 0 | 0 | | | | |
| ZFAS1 | 0 | 1 | 0 | | | | |
| ZNF286A | 1 | 0 | 0 | | | | |

TABLE S7

Genes differentially expressed in CD8 T cells of the CB patient compared to those of the ICR patients.

| Up-regulated in CB vs. ICR | Down-regulated in CB vs. ICR |
|---|---|
| ALOX5AP | AKIRIN2 |
| C1D | APIP |
| C3orf14 | ARL5A |
| CCL5 | ASF1B |
| CCR2 | ATP6V0C |
| CD52 | ATP9B |
| CDC26 | BRAT1 |
| CIDECP | BRD7 |
| CISH | C17orf89 |
| COX5B | C1GALT1C1 |
| CRIP1 | C4orf48 |
| CTSW | CALR |
| CXCR6 | CCDC137 |
| DDX3Y | CDC73 |
| EDF1 | CDCA7 |
| EIF1AY | CDK1 |
| FAM127B | CENPM |
| FASLG | CEP78 |
| FAU | CHMP6 |
| FCGR3A | CITED2 |
| FTL | CLINT1 |
| GZMA | CMTM7 |
| GZMB | COTL1 |
| GZMH | CRIPT |
| HCG26 | CSNK1G3 |
| HCST | CYB5R4 |
| HLA-A | DCPS |
| HLA-C | DNAJB14 |
| HLA-DQA2 | DND1 |
| HLA-H | DPH3 |
| HSPA1B | EFR3A |
| ID2 | EMC2 |
| KDM5D | EML3 |
| LAIR2 | FAM160B1 |
| MIR4461 | FAM168B |
| MTRNR2L1 | FAM46C |
| MTRNR2L10 | FAM53C |
| MTRNR2L6 | FAM69A |
| NACA | FARSB |
| NCF4 | FBXO22 |
| NDUFA13 | FEM1A |
| NDUFS5 | FTSJD1 |
| NDUFV2 | GATAD2A |
| RBPJ | GET4 |
| RNASEK | GGA3 |
| RPL10 | GLTSCR2 |
| RPL11 | GNL3 |
| RPL12 | GOLT1B |
| RPL13 | GPR137B |

TABLE S7-continued

Genes differentially expressed in CD8 T cells of the CB patient compared to those of the ICR patients.

| Up-regulated in CB vs. ICR | Down-regulated in CB vs. ICR |
|---|---|
| RPL13AP5 | GTDC1 |
| RPL15 | HIST1H1E |
| RPL17 | HMGA1 |
| RPL18 | HMHA1 |
| RPL18A | HSF1 |
| RPL19 | IARS2 |
| RPL21 | IL6ST |
| RPL23 | JUNB |
| RPL23A | KATNA1 |
| RPL24 | KIAA1429 |
| RPL26 | LATS1 |
| RPL29 | LOC100294145 |
| RPL30 | LRIG2 |
| RPL32 | MAN2A1 |
| RPL35 | MAP3K2 |
| RPL35A | MB21D1 |
| RPL36 | MCM2 |
| RPL36AL | MCM4 |
| RPL37A | MED23 |
| RPL4 | MGEA5 |
| RPL41 | MPLKIP |
| RPL6 | MRPS33 |
| RPL7 | MZT1 |
| RPL7A | NAGK |
| RPL9 | NEK1 |
| RPLP1 | NOA1 |
| RPLP2 | NPC2 |
| RPS10 | NUDT1 |
| RPS11 | NUP107 |
| RPS12 | OSGEP |
| RPS13 | PARP10 |
| RPS14 | PELI1 |
| RPS15 | PGS1 |
| RPS15A | PITHD1 |
| RPS16 | PLEKHF2 |
| RPS18 | POLR3E |
| RPS19 | PPIF |
| RPS20 | PPP1R21 |
| RPS24 | PRKAB1 |
| RPS25 | PSMD2 |
| RPS27 | PTGDR |
| RPS27A | PYGO2 |
| RPS3 | RAB11B |
| RPS3A | RABEP1 |
| RPS4X | RALB |
| RPS4Y1 | REC8 |
| RPS5 | REEP4 |
| RPS6 | RNF216P1 |
| RPS8 | RNF219 |

TABLE S7-continued

Genes differentially expressed in CD8 T cells of the CB patient compared to those of the ICR patients.

| Up-regulated in CB vs. ICR | Down-regulated in CB vs. ICR |
|---|---|
| SAMD3 | RPIA |
| SELM | RPS6KA5 |
| SH3BGRL3 | RPSAP58 |
| SYMPK | SFSWAP |
| TMSB10 | SGSM2 |
| TMSB4X | SLC1A5 |
| TNFSF4 | SLC25A26 |
| TPT1 | SLC33A1 |
| TXLNG2P | SLC39A3 |
| | SLC7A5 |
| | SMC1A |
| | SMC4 |
| | SNX4 |
| | SPPL2A |
| | STAT1 |
| | STX17 |
| | SYPL1 |
| | TAF1B |
| | TAF6 |
| | TCERG1 |
| | TCF7 |
| | TEKT4P2 |
| | TERF2IP |
| | TIMM44 |
| | TMEM161B |
| | TMEM170A |
| | TMEM189 |
| | TMEM69 |
| | TMX4 |
| | TNIP1 |
| | TNPO1 |
| | TOP2A |
| | TPX2 |
| | TRIB2 |
| | TSC22D1 |
| | TUBGCP3 |
| | TYMS |
| | UBA5 |
| | UBE2J1 |
| | UBE2Q2 |
| | UBE2T |
| | USP38 |
| | UVRAG |
| | WDR18 |
| | ZBED6 |
| | ZBTB20 |
| | ZFYVE28 |
| | ZNF259 |
| | ZNF511 |

TABLE S8

Table S8. Cell-cycle signatures specific to CD8 T cells.

| Up-regulated in cycling CD8 T cells | Down-regulated in cycling CD8 T cells |
|---|---|
| ACTG1 | AOAH |
| ANXA5 | ATHL1 |
| ARHGDIB | C11orf21 |
| ARL6IP1 | CCL3L1 |
| ARPC2 | CD37 |
| ATP5L | CISH |
| CD74 | CX3CR1 |
| CNTRL | DENND2D |
| CORO1A | GNPDA1 |
| COTL1 | GZMM |
| COX6A1 | IL11RA |
| COX6C | IL7R |
| COX8A | KLRB1 |
| DDOST | LDLRAP1 |
| GALM | LINC00612 |
| GMFG | LY9 |
| GNG5 | NR4A3 |
| HLA-DRA | PDGFD |
| HP1BP3 | PLCB2 |
| LCP1 | PTGDR |
| LRRFIP1 | RAB37 |
| MPC2 | RPS27 |
| MT2A | SORL1 |
| NDUFA4 | TRIM22 |
| NDUFC2 | TRMU |
| NUP50 | TTN |
| PCBP1 | UPRT |
| PKM | ZNF121 |
| POLR2A | |
| PSMB2 | |
| SNX1 | |
| SRRM1 | |
| TMA7 | |
| VIM | |
| YWHAE | |
| YWHAQ | |

TABLE S9

The topmost differentially expressed gene sets in the malignant cells from ICR vs. TN tumors

| Gene set | t-test p-value (−log10(|P|), positive = higher in ICR, negative = lower in ICR) t-test p-value | mixed effects p-value | N = No. of genes in the gene set | N · qc = No. of used genes | N/N · qc |
|---|---|---|---|---|---|
| GO_RESPONSE_TO_ENDOPLASMIC_RETICULUM_STRESS | −36.49 | −4.05 | 233 | 147 | 0.63 |
| GO_CELLULAR_COPPER_ION_HOMEOSTASIS | −44.3 | −4.04 | 13 | 9 | 0.69 |
| GO_CELLULAR_RESPONSE_TO_ZINC_ION | −215.84 | −4 | 16 | 7 | 0.44 |
| ENDOPLASMIC_RETICULUM_MEMBRANE | −42.56 | −3.93 | 85 | 55 | 0.65 |
| GO_REGULATION_OF_ENDOTHELIAL_CELL_APOPTOTIC_PROCESS | −52.39 | −3.79 | 42 | 14 | 0.33 |
| METALLOTHIONEINS | −208.11 | −3.72 | 13 | 6 | 0.46 |

TABLE S9-continued

The topmost differentially expressed gene sets in the malignant cells from ICR vs. TN tumors

| Gene set | t-test p-value (−log10(\|P\|), positive = higher in ICR, negative = lower in ICR) t-test p-value | mixed effects p-value | N = No. of genes in the gene set | N · qc = No. of used genes | N/N · qc |
|---|---|---|---|---|---|
| GO_INTRAMOLECULAR_OXIDOREDUCTASE_ACTIVITY_TRANSPOSING_S_S_BONDS | −40.53 | −3.64 | 22 | 14 | 0.64 |
| NUCLEAR_ENVELOPE_ENDOPLASMIC_RETICULUM_NETWORK | −38.41 | −3.59 | 94 | 62 | 0.66 |
| GO_CELLULAR_RESPONSE_TO_VITAMIN_D | −78.74 | −3.56 | 14 | 4 | 0.29 |
| KEGG_SNARE_INTERACTIONS_IN_VESICULAR_TRANSPORT | −17.6 | −3.43 | 38 | 23 | 0.61 |
| ENDOPLASMIC_RETICULUM_PART | −44.43 | −3.43 | 97 | 65 | 0.67 |
| GO_COPPER_ION_HOMEOSTASIS | −38.11 | −3.38 | 16 | 12 | 0.75 |
| KEGG_ECM_RECEPTOR_INTERACTION | −163.89 | −3.35 | 84 | 35 | 0.42 |
| GO_ENDOPLASMIC_RETICULUM_GOLGI_INTERMEDIATE_COMPARTMENT | −40.27 | −3.3 | 105 | 64 | 0.61 |
| GO_BLOOD_VESSEL_MORPHOGENESIS | −153.28 | −3.3 | 364 | 117 | 0.32 |
| GO_PLATELET_DERIVED_GROWTH_FACTOR_RECEPTOR_BINDING | −62.32 | −3.24 | 15 | 5 | 0.33 |
| GO_ANGIOGENESIS | −148.37 | −3.23 | 293 | 102 | 0.35 |
| GO_RESPONSE_TO_ZINC_ION | −76.24 | −3.22 | 55 | 21 | 0.38 |
| PID_INTEGRIN_CS_PATHWAY | −172.58 | −3.19 | 26 | 9 | 0.35 |
| GOLGI_MEMBRANE | −53.05 | −3.13 | 45 | 26 | 0.58 |
| GO_TRANSITION_METAL_ION_TRANSMEMBRANE_TRANSPORTER_ACTIVITY | −61.25 | −3.12 | 39 | 19 | 0.49 |
| POSITIVE_REGULATION_OF_CELL_PROLIFERATION | −31.46 | −3.11 | 149 | 48 | 0.32 |
| GO_MUSCLE_CELL_MIGRATION | −164.41 | −3.11 | 18 | 10 | 0.56 |
| NUCLEAR_ORPHAN_RECEPTOR | −83.44 | −3.09 | 3 | 2 | 0.67 |
| GO_POSITIVE_REGULATION_OF_EXTRINSIC_APOPTOTIC_SIGNALING_PATHWAY_VIA_DEATH_DOMAIN_RECEPTORS | −75.37 | −3.08 | 17 | 11 | 0.65 |
| GO_PHOSPHOTRANSFERASE_ACTIVITY_FOR_OTHER_SUBSTITUTED_PHOSPHATE_GROUPS | −32.33 | −3.07 | 19 | 11 | 0.58 |
| ST_INTERLEUKIN_13_PATHWAY | −2.38 | −3.03 | 7 | 2 | 0.29 |
| WOUND_HEALING | −148 | −3.02 | 54 | 13 | 0.24 |
| C/EBP | −38.85 | −3 | 10 | 3 | 0.3 |
| GO_INSULIN_LIKE_GROWTH_FACTOR_BINDING | −62.71 | −2.98 | 25 | 11 | 0.44 |
| MUSCLE_DEVELOPMENT | −122.53 | −2.98 | 93 | 29 | 0.31 |
| GO_PLATELET_ALPHA_GRANULE_MEMBRANE | −104.99 | −2.96 | 13 | 7 | 0.54 |
| GO_MANNOSIDASE_ACTIVITY | −28.46 | −2.95 | 15 | 5 | 0.33 |
| GO_POSITIVE_REGULATION_OF_ADHERENS_JUNCTION_ORGANIZATION | −61.36 | −2.95 | 21 | 9 | 0.43 |
| GO_NEGATIVE_REGULATION_OF_EPITHELIAL_CELL_APOPTOTIC_PROCESS | −70.48 | −2.95 | 35 | 8 | 0.23 |
| ENDOPLASMIC_RETICULUM | −50.01 | −2.94 | 294 | 180 | 0.61 |
| CELL_FATE_COMMITMENT | −72.59 | −2.94 | 13 | 3 | 0.23 |
| GO_ENDOPLASMIC_RETICULUM_GOLGI_INTERMEDIATE_COMPARTMENT_MEMBRANE | −65.43 | −2.93 | 63 | 38 | 0.6 |
| GO_NEGATIVE_REGULATION_OF_INTERLEUKIN_8_PRODUCTION | −126.57 | −2.93 | 15 | 5 | 0.33 |
| PID_TNF_PATHWAY | −73 | −2.92 | 46 | 22 | 0.48 |
| GO_RECEPTOR_REGULATOR_ACTIVITY | −92.97 | −2.92 | 45 | 10 | 0.22 |
| GO_EXTRACELLULAR_STRUCTURE_ORGANIZATION | −107.25 | −2.92 | 304 | 111 | 0.37 |
| ER_GOLGI_INTERMEDIATE_COMPARTMENT | −12.41 | −2.91 | 24 | 20 | 0.83 |
| GO_RESPONSE_TO_CADMIUM_ION | −124.5 | −2.9 | 40 | 25 | 0.62 |
| GO_HEPARAN_SULFATE_PROTEOGLYCAN_BIOSYNTHETIC_PROCESS | −31.95 | −2.89 | 23 | 8 | 0.35 |
| GO_AXON_REGENERATION | −144.4 | −2.88 | 24 | 9 | 0.38 |
| ENDOMEMBRANE_SYSTEM | −21.95 | −2.87 | 220 | 137 | 0.62 |
| HALLMARK_IL6_JAK_STAT3_SIGNALING | −170.22 | −2.87 | 87 | 40 | 0.46 |
| GO_HEPARAN_SULFATE_PROTEOGLYCAN_METABOLIC_PROCESS | −30.74 | −2.86 | 28 | 8 | 0.29 |
| GO_POSITIVE_REGULATION_OF_CELL_JUNCTION_ASSEMBLY | −88.33 | −2.85 | 24 | 11 | 0.46 |
| GO_VASCULATURE_DEVELOPMENT | −143.79 | −2.84 | 469 | 153 | 0.33 |
| CELLULAR_CATION_HOMEOSTASIS | −96.84 | −2.83 | 106 | 32 | 0.3 |
| GO_CELL_SUBSTRATE_JUNCTION_ASSEMBLY | −79.64 | −2.82 | 41 | 19 | 0.46 |
| PID_FRA_PATHWAY | −55.92 | −2.81 | 37 | 17 | 0.46 |
| GO_REGULATION_OF_ADHERENS_JUNCTION_ORGANIZATION | −63.38 | −2.81 | 50 | 22 | 0.44 |
| GO_CELL_ADHESION_MEDIATED_BY_INTEGRIN | −81.75 | −2.81 | 12 | 8 | 0.67 |
| GO_SARCOLEMMA | −216.58 | −2.81 | 125 | 37 | 0.3 |

TABLE S9-continued

The topmost differentially expressed gene sets in the malignant cells from ICR vs. TN tumors

| Gene set | t-test p-value (−log10(\|P\|), positive = higher in ICR, negative = lower in ICR) t-test p-value | mixed effects p-value | N = No. of genes in the gene set | N · qc = No. of used genes | N/N · qc |
|---|---|---|---|---|---|
| GO_NEGATIVE_REGULATION_OF_ENDOTHELIAL_CELL_APOPTOTIC_PROCESS | −38.24 | −2.8 | 27 | 7 | 0.26 |
| GO_CORECEPTOR_ACTIVITY | −68.21 | −2.79 | 38 | 11 | 0.29 |
| GO_REGULATION_OF_INTERLEUKIN_8_BIOSYNTHETIC_PROCESS | −12.85 | −2.78 | 12 | 3 | 0.25 |
| REACTOME_EXTRINSIC_PATHWAY_FOR_APOPTOSIS | −55.38 | −2.78 | 13 | 8 | 0.62 |
| HALLMARK_HYPOXIA | −112.24 | −2.78 | 200 | 116 | 0.58 |
| GO_ER_NUCLEUS_SIGNALING_PATHWAY | −28.31 | −2.75 | 34 | 25 | 0.74 |
| HOMOPHILIC_CELL_ADHESION | −55 | −2.74 | 16 | 4 | 0.25 |
| GO_SNAP_RECEPTOR_ACTIVITY | −20.16 | −2.73 | 38 | 22 | 0.58 |
| HALLMARK_EPITHELIAL_MESENCHYMAL_TRANSITION | −128.55 | −2.73 | 200 | 110 | 0.55 |
| GO_CELLULAR_RESPONSE_TO_CADMIUM_ION | −155.05 | −2.73 | 15 | 9 | 0.6 |
| GO_BASAL_LAMINA | −27.9 | −2.72 | 21 | 6 | 0.29 |
| CELL_CELL_ADHESION | −40.27 | −2.72 | 86 | 19 | 0.22 |
| POSITIVE_REGULATION_OF_MULTICELLULAR_ORGANISMAL_PROCESS | −45.51 | −2.71 | 66 | 18 | 0.27 |
| FIBROBLAST | −73.88 | −2.71 | 6 | 3 | 0.5 |
| GO_ATPASE_COMPLEX | −80.46 | −2.7 | 24 | 7 | 0.29 |
| GO_INTRINSIC_COMPONENT_OF_EXTERNAL_SIDE_OF_PLASMA_MEMBRANE | −68.1 | −2.69 | 27 | 7 | 0.26 |
| PID_INTEGRIN3_PATHWAY | −78.14 | −2.68 | 43 | 22 | 0.51 |
| CATION_HOMEOSTASIS | −93.05 | −2.68 | 109 | 32 | 0.29 |
| GO_CELL_SUBSTRATE_ADHESION | −162.02 | −2.68 | 164 | 58 | 0.35 |
| GO_INTRINSIC_APOPTOTIC_SIGNALING_PATHWAY_IN_RESPONSE_TO_ENDOPLASMIC_RETICULUM_STRESS | −37.62 | −2.67 | 32 | 18 | 0.56 |
| GO_POSITIVE_REGULATION_OF_CELL_MATRIX_ADHESION | −57.1 | −2.66 | 40 | 15 | 0.38 |
| GO_NEGATIVE_REGULATION_OF_GLYCOPROTEIN_METABOLIC_PROCESS | −60.19 | −2.66 | 15 | 10 | 0.67 |
| GO_NEGATIVE_REGULATION_OF_TYPE_2_IMMUNE_RESPONSE | −162.47 | −2.66 | 11 | 4 | 0.36 |
| REACTOME_ACTIVATION_OF_CHAPERONES_BY_ATF6_ALPHA | −22.85 | −2.64 | 13 | 8 | 0.62 |
| GO_NEGATIVE_REGULATION_OF_DNA_RECOMBINATION | −13.63 | −2.63 | 16 | 8 | 0.5 |
| GO_CELLULAR_RESPONSE_TO_TOPOLOGICALLY_INCORRECT_PROTEIN | −22.73 | −2.63 | 122 | 81 | 0.66 |
| GO_CELLULAR_RESPONSE_TO_CALCIUM_ION | −69.45 | −2.63 | 49 | 18 | 0.37 |
| GO_SECRETORY_GRANULE_MEMBRANE | −133.42 | −2.63 | 78 | 28 | 0.36 |
| GOLGI_VESICLE_TRANSPORT | −13.68 | −2.62 | 48 | 37 | 0.77 |
| REACTOME_DIABETES_PATHWAYS | −20.26 | −2.62 | 133 | 80 | 0.6 |
| GO_NEGATIVE_REGULATION_OF_GLYCOPROTEIN_BIOSYNTHETIC_PROCESS | −23.98 | −2.61 | 12 | 9 | 0.75 |
| CAHOY_ASTROGLIAL | −197.11 | −2.61 | 100 | 37 | 0.37 |
| GO_HEMIDESMOSOME_ASSEMBLY | −95.2 | −2.6 | 12 | 5 | 0.42 |
| GO_FIBRINOLYSIS | −98.47 | −2.6 | 21 | 6 | 0.29 |
| GO_PROTEIN_COMPLEX_INVOLVED_IN_CELL_ADHESION | −171.74 | −2.6 | 30 | 10 | 0.33 |
| ST_IL_13_PATHWAY | −1.56 | −2.59 | 7 | 2 | 0.29 |
| POSITIVE_REGULATION_OF_PROTEIN_MODIFICATION_PROCESS | −37.38 | −2.58 | 29 | 9 | 0.31 |
| HALLMARK_UV_RESPONSE_UP | −67.14 | −2.57 | 158 | 93 | 0.59 |
| CELL_MIGRATION | −87.02 | −2.57 | 96 | 34 | 0.35 |
| ATPASE_ACTIVITY_COUPLED_TO_TRANSMEMBRANE_MOVEMENT_OF_IONS_PHOSPHORYLATIVE_MECHANISM | −130.2 | −2.57 | 20 | 5 | 0.25 |
| GO_INTEGRIN_BINDING | −94.95 | −2.56 | 105 | 48 | 0.46 |
| HALLMARK_TNFA_SIGNALING_VIA_NFKB | −154.11 | −2.56 | 200 | 108 | 0.54 |
| GO_PLATELET_ALPHA_GRANULE | −164.05 | −2.56 | 75 | 35 | 0.47 |
| PID_INTEGRIN1_PATHWAY | −89.65 | −2.55 | 66 | 34 | 0.52 |
| GO_CATION_TRANSPORTING_ATPASE_COMPLEX | −119.68 | −2.55 | 16 | 4 | 0.25 |
| PROTEIN_AMINO_ACID_LIPIDATION | −35.59 | −2.54 | 24 | 19 | 0.79 |
| GO_NEGATIVE_REGULATION_OF_LIPID_STORAGE | −92.01 | −2.54 | 17 | 6 | 0.35 |
| GO_BASEMENT_MEMBRANE_ORGANIZATION | −26.24 | −2.53 | 11 | 7 | 0.64 |
| POSITIVE_REGULATION_OF_CYTOKINE_PRODUCTION | −41.65 | −2.53 | 15 | 5 | 0.33 |
| BIOCARTA_SODD_PATHWAY | −37.42 | −2.52 | 10 | 8 | 0.8 |

TABLE S9-continued

The topmost differentially expressed gene sets in the malignant cells from ICR vs. TN tumors

| Gene set | t-test p-value (−log10(\|P\|), positive = higher in ICR, negative = lower in ICR) | mixed effects p-value | N = No. of genes in the gene set | N · qc = No. of used genes | N/N · qc |
|---|---|---|---|---|---|
| GO_PERK_MEDIATED_UNFOLDED_PROTEIN_RESPONSE | −39.21 | −2.52 | 12 | 10 | 0.83 |
| PHOSPHOLIPID_METABOLIC_PROCESS | −44.83 | −2.52 | 74 | 42 | 0.57 |
| Targets of NFAT_Q6 | −53.2 | −2.52 | 246 | 80 | 0.33 |
| BIOCARTA_STRESS_PATHWAY | −71.76 | −2.52 | 25 | 10 | 0.4 |
| CYTOPLASM_ORGANIZATION_AND_BIOGENESIS | −67.96 | −2.51 | 15 | 7 | 0.47 |
| Targets of FREAC3_01 | −23.28 | −2.5 | 251 | 65 | 0.26 |
| GO_COLLAGEN_BINDING | −84.49 | −2.5 | 65 | 27 | 0.42 |
| PID_INTEGRIN4_PATHWAY | −35.75 | −2.49 | 11 | 4 | 0.36 |
| CELL_SURFACE | −42.55 | −2.49 | 79 | 27 | 0.34 |
| GO_PHOSPHATE_TRANSMEMBRANE_TRANSPORTER_ACTIVITY | −14.32 | −2.48 | 30 | 16 | 0.53 |
| NAIVE_VS_ACTIVATED_CD8_TCELL_DN | −38.5 | −2.48 | 200 | 81 | 0.4 |
| MEMBRANE_LIPID_BIOSYNTHETIC_PROCESS | −20.36 | −2.47 | 49 | 29 | 0.59 |
| GO_GLYCEROPHOSPHOLIPID_CATABOLIC_PROCESS | −27.95 | −2.47 | 13 | 7 | 0.54 |
| GO_INTERSTITIAL_MATRIX | −81.96 | −2.47 | 14 | 3 | 0.21 |
| GO_REGULATION_OF_EXTRINSIC_APOPTOTIC_SIGNALING_PATHWAY_VIA_DEATH_DOMAIN_RECEPTORS | −103.8 | −2.47 | 55 | 32 | 0.58 |
| INORGANIC_ANION_TRANSPORT | −151.85 | −2.47 | 18 | 4 | 0.22 |
| REACTOME_CLASS_B_2_SECRETIN_FAMILY_RECEPTORS | −62.64 | −2.46 | 88 | 19 | 0.22 |
| GO_DECIDUALIZATION | −99.39 | −2.46 | 21 | 7 | 0.33 |
| GO_MULTI_MULTICELLULAR_ORGANISM_PROCESS | −129.03 | −2.46 | 213 | 62 | 0.29 |
| NABA_BASEMENT_MEMBRANES | −19.18 | −2.45 | 40 | 12 | 0.3 |
| GO_PROTEINACEOUS_EXTRACELLULAR_MATRIX | −60.88 | −2.45 | 356 | 86 | 0.24 |
| GO_EXTRACELLULAR_MATRIX | −121.18 | −2.45 | 426 | 116 | 0.27 |
| GO_INTEGRIN_MEDIATED_SIGNALING_PATHWAY | −129.11 | −2.45 | 82 | 36 | 0.44 |
| SECRETION | −34.16 | −2.44 | 178 | 68 | 0.38 |
| GO_CARBOHYDRATE_DERIVATIVE_CATABOLIC_PROCESS | −62.72 | −2.44 | 174 | 76 | 0.44 |
| HALLMARK_APOPTOSIS | −184.35 | −2.44 | 161 | 111 | 0.69 |
| LIPOPROTEIN_METABOLIC_PROCESS | −34.84 | −2.43 | 33 | 21 | 0.64 |
| LIPOPROTEIN_BIOSYNTHETIC_PROCESS | −36.48 | −2.43 | 26 | 19 | 0.73 |
| GO_BASEMENT_MEMBRANE | −54.56 | −2.43 | 93 | 32 | 0.34 |
| REACTOME_UNFOLDED_PROTEIN_RESPONSE | −13.89 | −2.42 | 80 | 58 | 0.72 |
| GO_LIPOPROTEIN_BIOSYNTHETIC_PROCESS | −63.03 | −2.42 | 85 | 40 | 0.47 |
| GO_HYDROLASE_ACTIVITY_ACTING_ON_GLYCOSYL_BONDS | −65.4 | −2.42 | 122 | 44 | 0.36 |
| GO_REGULATION_OF_VIRAL_ENTRY_INTO_HOST_CELL | −72.07 | −2.42 | 28 | 12 | 0.43 |
| BIOCARTA_IL1R_PATHWAY | −72.17 | −2.41 | 33 | 12 | 0.36 |
| HALLMARK_IL2_STAT5_SIGNALING | −199.12 | −2.41 | 200 | 91 | 0.46 |
| GO_NEGATIVE_REGULATION_OF_SMALL_GTPASE_MEDIATED_SIGNAL_TRANSDUCTION | −72.25 | −2.4 | 40 | 14 | 0.35 |
| GO_GROWTH_FACTOR_BINDING | −107.54 | −2.39 | 123 | 46 | 0.37 |
| GO_METALLOENDOPEPTIDASE_INHIBITOR_ACTIVITY | −118.81 | −2.39 | 14 | 5 | 0.36 |
| TTAYRTAA_Targets of E4BP4_01 | −133.15 | −2.39 | 265 | 74 | 0.28 |
| GO_REGULATION_OF_T_HELPER_2_CELL_DIFFERENTIATION | −200.19 | −2.39 | 11 | 3 | 0.27 |
| CELL_ACTIVATION | −24.51 | −2.38 | 77 | 17 | 0.22 |
| GO_EXTRACELLULAR_MATRIX_COMPONENT | −46.21 | −2.38 | 125 | 47 | 0.38 |
| GO_RESPONSE_TO_AXON_INJURY | −138.03 | −2.38 | 48 | 19 | 0.4 |
| GO_FORMATION_OF_PRIMARY_GERM_LAYER | −93.37 | −2.37 | 110 | 33 | 0.3 |
| HYDROLASE_ACTIVITY_ACTING_ON_ACID_ANHYDRIDESCATALYZING_TRANSMEMBRANE_MOVEMENT_OF_SUBSTANCES | −126.69 | −2.37 | 39 | 14 | 0.36 |
| GO_CELLULAR_RESPONSE_TO_PROSTAGLANDIN_STIMULUS | −41.78 | −2.36 | 24 | 10 | 0.42 |
| GO_NEGATIVE_REGULATION_OF_MULTICELLULAR_ORGANISMAL_METABOLIC_PROCESS | −55.1 | −2.36 | 12 | 6 | 0.5 |
| GO_NEGATIVE_REGULATION_OF_GROWTH | −96.42 | −2.36 | 236 | 85 | 0.36 |
| GO_REGULATION_OF_ERK1_AND_ERK2_CASCADE | −121.13 | −2.36 | 238 | 74 | 0.31 |
| GO_CELL_MATRIX_ADHESION | −156.53 | −2.36 | 119 | 42 | 0.35 |
| PID_P38_MKK3_6PATHWAY | −11.76 | −2.35 | 26 | 9 | 0.35 |
| GO_ACROSOMAL_MEMBRANE | −98.54 | −2.35 | 22 | 8 | 0.36 |

TABLE S9-continued

The topmost differentially expressed gene sets in the malignant cells from ICR vs. TN tumors

| Gene set | t-test p-value (−log10(|P|), positive = higher in ICR, negative = lower in ICR) t-test p-value | mixed effects p-value | N = No. of genes in the gene set | N · qc = No. of used genes | N/N · qc |
|---|---|---|---|---|---|
| BLOOD_COAGULATION | −133.89 | −2.35 | 43 | 12 | 0.28 |
| GO_REGULATION_OF_INTERLEUKIN_2_PRODUCTION | −134.5 | −2.35 | 48 | 19 | 0.4 |
| GO_IRE1_MEDIATED_UNFOLDED_PROTEIN_RESPONSE | −17.39 | −2.34 | 56 | 44 | 0.79 |
| GO_PROTEIN_HETEROOLIGOMERIZATION | −31.48 | −2.34 | 113 | 44 | 0.39 |
| GO_NEGATIVE_REGULATION_OF_SODIUM_ION_TRANSPORT | −110.08 | −2.34 | 11 | 4 | 0.36 |
| MEMBRANE_FUSION | −27.59 | −2.33 | 28 | 15 | 0.54 |
| KEGG_GLYCOSPHINGOLIPID_BIOSYNTHESIS_GANGLIO_SERIES | −46.27 | −2.33 | 15 | 6 | 0.4 |
| GO_REGULATION_OF_CELL_SUBSTRATE_ADHESION | −62.07 | −2.33 | 173 | 67 | 0.39 |
| GO_REGULATION_OF_PROTEIN_GLYCOSYLATION | −18.5 | −2.32 | 14 | 5 | 0.36 |
| GO_PLASMA_MEMBRANE_FUSION | −40.77 | −2.32 | 26 | 8 | 0.31 |
| GO_COMPACT_MYELIN | −55.03 | −2.31 | 15 | 8 | 0.53 |
| Targets of CDPCR1_01 | −74.82 | −2.31 | 130 | 33 | 0.25 |
| AMINO_ACID_DERIVATIVE_BIOSYNTHETIC_PROCESS | −10.41 | −2.3 | 10 | 4 | 0.4 |
| KEGG_GLYCOSAMINOGLYCAN_BIOSYNTHESIS_CHONDROITIN_SULFATE | −61.3 | −2.3 | 22 | 6 | 0.27 |
| GO_REGULATION_OF_CELL_MATRIX_ADHESION | −63.63 | −2.3 | 90 | 34 | 0.38 |
| GO_ANTIMICROBIAL_HUMORAL_RESPONSE | −81.25 | −2.3 | 52 | 14 | 0.27 |
| GO_NEGATIVE_REGULATION_OF_PROTEIN_KINASE_B_SIGNALING | −47.66 | −2.29 | 36 | 16 | 0.44 |
| GO_RESPONSE_TO_OXYGEN_LEVELS | −69.16 | −2.29 | 311 | 127 | 0.41 |
| GO_RESPONSE_TO_TRANSITION_METAL_NANOPARTICLE | −89.78 | −2.29 | 148 | 63 | 0.43 |
| GO_FIBRONECTIN_BINDING | −106.39 | −2.29 | 28 | 16 | 0.57 |
| GO_POSITIVE_REGULATION_OF_INTERLEUKIN_2_PRODUCTION | −147.35 | −2.29 | 31 | 12 | 0.39 |
| GO_ENDOPLASMIC_RETICULUM_LUMEN | −32.2 | −2.28 | 201 | 84 | 0.42 |
| GO_POSITIVE_REGULATION_OF_EXTRINSIC_APOPTOTIC_SIGNALING_PATHWAY | −52.86 | −2.28 | 53 | 35 | 0.66 |
| GO_CELLULAR_RESPONSE_TO_OXYGEN_LEVELS | −58.67 | −2.28 | 143 | 55 | 0.38 |
| REACTOME_INTEGRIN_CELL_SURFACE_INTERACTIONS | −89.69 | −2.28 | 79 | 37 | 0.47 |
| EXTRACELLULAR_REGION_PART | −125.68 | −2.28 | 338 | 88 | 0.26 |
| GO_SECRETORY_GRANULE_LUMEN | −157.29 | −2.28 | 85 | 31 | 0.36 |
| GO_SNARE_COMPLEX | −17.36 | −2.27 | 53 | 28 | 0.53 |
| KEGG_GLYCOSAMINOGLYCAN_DEGRADATION | −47 | −2.27 | 21 | 9 | 0.43 |
| ATPASE_ACTIVITY_COUPLED_TO_TRANSMEMBRANE_MOVEMENT_OF_IONS | −133.35 | −2.27 | 24 | 9 | 0.38 |
| GO_NEGATIVE_REGULATION_OF_COAGULATION | −196.17 | −2.27 | 48 | 13 | 0.27 |
| REACTOME_TRANSPORT_OF_VITAMINS_NUCLEOSIDES_AND_RELATED_MOLECULES | −10.14 | −2.26 | 31 | 9 | 0.29 |
| GO_IRON_ION_BINDING | −18.16 | −2.26 | 163 | 42 | 0.26 |
| GO_ACETYLGLUCOSAMINYLTRANSFERASE_ACTIVITY | −38.97 | −2.26 | 49 | 19 | 0.39 |
| GO_POSITIVE_REGULATION_OF_RECEPTOR_MEDIATED_ENDOCYTOSIS | −75.46 | −2.26 | 47 | 13 | 0.28 |
| HALLMARK_UV_RESPONSE_DN | −95.37 | −2.26 | 144 | 64 | 0.44 |
| GO_CELL_ADHESION_MOLECULE_BINDING | −113.26 | −2.26 | 186 | 74 | 0.4 |
| REACTOME_CELL_SURFACE_INTERACTIONS_AT_THE_VASCULAR_WALL | −148.37 | −2.26 | 91 | 38 | 0.42 |
| GO_UBIQUITIN_UBIQUITIN_LIGASE_ACTIVITY | −10.5 | −2.25 | 13 | 7 | 0.54 |
| GO_N_GLYCAN_PROCESSING | −37.67 | −2.25 | 20 | 5 | 0.25 |
| GO_BRANCH_ELONGATION_OF_AN_EPITHELIUM | −38.53 | −2.25 | 17 | 4 | 0.24 |
| REACTOME_TRANSPORT_OF_GLUCOSE_AND_OTHER_SUGARS_BILE_SALTS_AND_ORGANIC_ACIDS_METAL_IONS_AND_AMINE_COMPOUNDS | −70.87 | −2.25 | 89 | 18 | 0.2 |
| GO_BASAL_PLASMA_MEMBRANE | −102.25 | −2.25 | 33 | 9 | 0.27 |
| GO_PLATELET_DEGRANULATION | −156.77 | −2.25 | 107 | 51 | 0.48 |
| PDZ_DOMAIN_BINDING | −29.47 | −2.24 | 14 | 4 | 0.29 |
| BIOCARTA_GATA3_PATHWAY | −52.32 | −2.24 | 16 | 4 | 0.25 |
| GO_NEGATIVE_REGULATION_OF_CELL_SUBSTRATE_ADHESION | −81.77 | −2.24 | 53 | 25 | 0.47 |
| AMINE_BIOSYNTHETIC_PROCESS | −12.25 | −2.23 | 15 | 7 | 0.47 |
| GO_REGULATION_OF_RECEPTOR_ACTIVITY | −13.59 | −2.23 | 117 | 30 | 0.26 |
| GO_PYRIMIDINE_NUCLEOSIDE_CATABOLIC_PROCESS | −79.61 | −2.23 | 21 | 8 | 0.38 |
| GO_CIRCULATORY_SYSTEM_DEVELOPMENT | −132.21 | −2.23 | 788 | 233 | 0.3 |

TABLE S9-continued

The topmost differentially expressed gene sets in the malignant cells from ICR vs. TN tumors

| Gene set | t-test p-value (−log10(\|P\|), positive = higher in ICR, negative = lower in ICR) t-test p-value | mixed effects p-value | N = No. of genes in the gene set | N · qc = No. of used genes | N/N · qc |
|---|---|---|---|---|---|
| GO_MATURE_B_CELL_DIFFERENTIATION | −21.54 | −2.22 | 17 | 7 | 0.41 |
| GO_OLIGOSACCHARIDE_CATABOLIC_PROCESS | −24.14 | −2.22 | 12 | 7 | 0.58 |
| GO_RESPONSE_TO_PROSTAGLANDIN | −38.47 | −2.22 | 34 | 11 | 0.32 |
| GO_OXIDOREDUCTASE_ACTIVITY_ACTING_ON_ THE_CH_NH2_GROUP_OF_DONORS_OXYGEN_ AS_ACCEPTOR | −60.87 | −2.22 | 15 | 5 | 0.33 |
| ST_TUMOR_NECROSIS_FACTOR_PATHWAY | −96.67 | −2.22 | 29 | 17 | 0.59 |
| GO_REGULATION_OF_INTERLEUKIN_8_SECRETION | −101.51 | −2.22 | 19 | 8 | 0.42 |
| GO_REGULATION_OF_MEMBRANE_PROTEIN_ ECTODOMAIN_PROTEOLYSIS | −157.88 | −2.22 | 21 | 9 | 0.43 |
| ER_TO_GOLGI_VESICLE_MEDIATED_TRANSPORT | −4.83 | −2.21 | 18 | 15 | 0.83 |
| PID_TCR_JNK_PATHWAY | −26.53 | −2.21 | 14 | 6 | 0.43 |
| REACTOME_IL1_SIGNALING | −34.94 | −2.21 | 39 | 16 | 0.41 |
| GO_POSITIVE_REGULATION_OF_IMMUNOGLOBULIN_ SECRETION | −97.18 | −2.21 | 11 | 4 | 0.36 |
| PID_AP1_PATHWAY | −129.76 | −2.2 | 70 | 31 | 0.44 |
| Targets of LMO2COM_01 | −20.1 | −2.19 | 264 | 72 | 0.27 |
| GO_RESPONSE_TO_STARVATION | −41.8 | −2.19 | 154 | 70 | 0.45 |
| GO_MEMBRANE_RAFT_ORGANIZATION | −114.17 | −2.19 | 17 | 12 | 0.71 |
| COAGULATION | −131.28 | −2.19 | 44 | 12 | 0.27 |
| GO_SULFATE_TRANSPORT | −73.24 | −2.18 | 14 | 3 | 0.21 |
| Targets of STAT5A_02 | −73.82 | −2.18 | 141 | 42 | 0.3 |
| GO_SECRETORY_GRANULE | −145.5 | −2.18 | 352 | 114 | 0.32 |
| GO_REGULATION_OF_COAGULATION | −149.09 | −2.18 | 88 | 26 | 0.3 |
| GO_CELL_SURFACE | −169.9 | −2.18 | 757 | 217 | 0.29 |
| GO_NUCLEOTIDE_TRANSMEMBRANE_TRANSPORT | −6.85 | −2.17 | 12 | 7 | 0.58 |
| PROTEIN_TRANSPORTER_ACTIVITY | −7.67 | −2.17 | 14 | 7 | 0.5 |
| ENDOPLASMIC_RETICULUM_LUMEN | −16.08 | −2.17 | 14 | 12 | 0.86 |
| GO_REGULATION_OF_PEPTIDYL_SERINE_ PHOSPHORYLATION | −34.4 | −2.17 | 118 | 37 | 0.31 |
| LIPID_RAFT | −83.19 | −2.17 | 29 | 16 | 0.55 |
| GO_CELLULAR_RESPONSE_TO_EXTERNAL_STIMULUS | −74.77 | −2.16 | 264 | 114 | 0.43 |
| GO_REGULATION_OF_EXTRINSIC_APOPTOTIC_ SIGNALING_PATHWAY | −97.55 | −2.16 | 153 | 77 | 0.5 |
| GO_RESPONSE_TO_DRUG | −144.63 | −2.16 | 431 | 159 | 0.37 |
| GO_REGULATION_OF_EXTRACELLULAR_MATRIX_ DISASSEMBLY | −147.71 | −2.16 | 14 | 4 | 0.29 |
| REACTOME_ACTIVATION_OF_CHAPERONE_ GENES_BY_XBP1S | −15.37 | −2.15 | 46 | 35 | 0.76 |
| GO_DENDRITE_MORPHOGENESIS | −17.1 | −2.15 | 42 | 12 | 0.29 |
| GO_MATURE_B_CELL_DIFFERENTIATION_ INVOLVED_IN_IMMUNE_RESPONSE | −27.87 | −2.15 | 13 | 6 | 0.46 |
| GO_CELLULAR_RESPONSE_TO_MECHANICAL_STIMULUS | −133.12 | −2.15 | 80 | 32 | 0.4 |
| GO_HETEROTYPIC_CELL_CELL_ADHESION | −138.66 | −2.15 | 27 | 9 | 0.33 |
| BIOCARTA_LYM_PATHWAY | −58.96 | −2.14 | 11 | 7 | 0.64 |
| HINATA_NFKB_MATRIX | −78.15 | −2.14 | 10 | 7 | 0.7 |
| GO_NEGATIVE_REGULATION_OF_RHO_PROTEIN_ SIGNAL_TRANSDUCTION | −83.78 | −2.14 | 14 | 8 | 0.57 |
| GO_TELOMERE_LOCALIZATION | −8.52 | −2.13 | 11 | 4 | 0.36 |
| INTRINSIC_TO_ENDOPLASMIC_RETICULUM_ MEMBRANE | −11.39 | −2.13 | 24 | 14 | 0.58 |
| CELLULAR_HOMEOSTASIS | −61.96 | −2.13 | 147 | 45 | 0.31 |
| GO_CELL_MIGRATION_INVOLVED_IN_SPROUTING_ ANGIOGENESIS | −87.08 | −2.13 | 15 | 4 | 0.27 |
| GO_GASTRULATION | −36.59 | −2.12 | 155 | 46 | 0.3 |
| PID_IL1_PATHWAY | −68.25 | −2.12 | 34 | 15 | 0.44 |
| GO_ENDOPEPTIDASE_ACTIVITY | −81.63 | −2.12 | 448 | 135 | 0.3 |
| INTEGRAL_TO_ENDOPLASMIC_RETICULUM_MEMBRANE | −9.58 | −2.11 | 24 | 14 | 0.58 |
| REACTOME_ACTIVATION_OF_CHAPERONE_GENES_BY_ ATF6_ALPHA | −16.39 | −2.11 | 11 | 7 | 0.64 |
| GO_ZINC_II_ION_TRANSPORT | −38.12 | −2.11 | 26 | 13 | 0.5 |
| RYAAAKNNNNNNTTGW_UNKNOWN | −51.33 | −2.11 | 84 | 22 | 0.26 |
| GGARNTKYCCA_UNKNOWN | −56.64 | −2.11 | 78 | 24 | 0.31 |
| GO_MEMBRANE_HYPERPOLARIZATION | −86.71 | −2.11 | 11 | 3 | 0.27 |
| PID_INTEGRIN_A9B1_PATHWAY | −88.11 | −2.11 | 25 | 11 | 0.44 |
| GO_MEMBRANE_ASSEMBLY | −113.44 | −2.11 | 25 | 10 | 0.4 |
| GO_ALCOHOL_TRANSMEMBRANE_TRANSPORTER_ACTIVITY | −135.7 | −2.11 | 24 | 5 | 0.21 |

TABLE S9-continued

The topmost differentially expressed gene sets in the malignant cells from ICR vs. TN tumors

| Gene set | t-test p-value (−log10(\|P\|), positive = higher in ICR, negative = lower in ICR) t-test p-value | mixed effects p-value | N = No. of genes in the gene set | N · qc = No. of used genes | N/N · qc |
|---|---|---|---|---|---|
| LEUKOCYTE_ACTIVATION | −21.62 | −2.1 | 69 | 16 | 0.23 |
| GO_POSITIVE_REGULATION_OF_PEPTIDYL_SERINE_PHOSPHORYLATION | −60.49 | −2.1 | 88 | 29 | 0.33 |
| GO_OXALATE_TRANSPORT | −81.43 | −2.09 | 12 | 3 | 0.25 |
| GO_MEMBRANE_BIOGENESIS | −92.93 | −2.09 | 30 | 12 | 0.4 |
| GO_SECRETORY_VESICLE | −133.02 | −2.09 | 461 | 143 | 0.31 |
| REACTOME_EXTRACELLULAR_MATRIX_ORGANIZATION | −29.23 | −2.08 | 87 | 25 | 0.29 |
| Targets of ATargets of 01 | −45.86 | −2.08 | 259 | 109 | 0.42 |
| ATPASE_ACTIVITY_COUPLED_TO_MOVEMENT_OF_SUBSTANCES | −130.08 | −2.08 | 40 | 14 | 0.35 |
| GO_ENDOPLASMIC_RETICULUM_CHAPERONE_COMPLEX | −3.32 | −2.07 | 11 | 8 | 0.73 |
| GO_CIS_GOLGI_NETWORK | −25.98 | −2.07 | 40 | 23 | 0.57 |
| GO_RESPONSE_TO_OXIDATIVE_STRESS | −58.41 | −2.07 | 352 | 165 | 0.47 |
| Targets of FOXD3_01 | −77.69 | −2.07 | 199 | 45 | 0.23 |
| HYDROLASE_ACTIVITY_HYDROLYZING_O_GLYCOSYL_COMPOUNDS | −37.78 | −2.06 | 37 | 13 | 0.35 |
| Targets of CEBP_Q2_01 | −52.02 | −2.06 | 267 | 76 | 0.28 |
| GO_REGULATION_OF_CELL_JUNCTION_ASSEMBLY | −53.46 | −2.06 | 68 | 27 | 0.4 |
| GO_PEPTIDASE_ACTIVITY | −53.89 | −2.06 | 663 | 202 | 0.3 |
| GO_REGULATION_OF_EPITHELIAL_CELL_APOPTOTIC_PROCESS | −88.51 | −2.06 | 59 | 20 | 0.34 |
| ACTIVE_TRANSMEMBRANE_TRANSPORTER_ACTIVITY | −98.29 | −2.06 | 122 | 31 | 0.25 |
| GO_REGULATION_OF_PEPTIDASE_ACTIVITY | −127.28 | −2.06 | 392 | 176 | 0.45 |
| GO_RESPONSE_TO_FOOD | −15.02 | −2.05 | 19 | 5 | 0.26 |
| GO_PROTEIN_DEGLYCOSYLATION | −21.99 | −2.05 | 21 | 13 | 0.62 |
| GO_AMINOGLYCAN_CATABOLIC_PROCESS | −66.41 | −2.05 | 68 | 27 | 0.4 |
| INTEGRAL_TO_ORGANELLE_MEMBRANE | −12.43 | −2.04 | 50 | 27 | 0.54 |
| LYMPHOCYTE_ACTIVATION | −16.18 | −2.04 | 61 | 15 | 0.25 |
| BIOCARTA_VITCB_PATHWAY | −23.55 | −2.04 | 11 | 6 | 0.55 |
| NEGATIVE_REGULATION_OF_SECRETION | −25.56 | −2.04 | 13 | 5 | 0.38 |
| MEMBRANE_LIPID_METABOLIC_PROCESS | −61.37 | −2.04 | 101 | 55 | 0.54 |
| GO_CELL_CELL_CONTACT_ZONE | −91.65 | −2.04 | 64 | 21 | 0.33 |
| KEGG_COMPLEMENT_AND_COAGULATION_CASCADES | −112.22 | −2.04 | 69 | 28 | 0.41 |
| GO_NEGATIVE_REGULATION_OF_WOUND_HEALING | −182.92 | −2.04 | 58 | 13 | 0.22 |
| NUCLEOTIDE_KINASE_ACTIVITY | −0.4 | −2.03 | 13 | 5 | 0.38 |
| GO_ENDODERM_FORMATION | −52.71 | −2.03 | 50 | 20 | 0.4 |
| GO_GLYCOLIPID_BIOSYNTHETIC_PROCESS | −58.12 | −2.03 | 62 | 33 | 0.53 |
| M1_MACROPHAGES | −77.24 | −2.03 | 54 | 25 | 0.46 |
| RESPONSE_TO_WOUNDING | −137.23 | −2.03 | 190 | 58 | 0.31 |
| GO_REGULATION_OF_ASTROCYTE_DIFFERENTIATION | −149.91 | −2.03 | 27 | 7 | 0.26 |
| GO_HOST | −4.29 | −2.02 | 12 | 8 | 0.67 |
| GO_REGULATION_OF_CHOLESTEROL_HOMEOSTASIS | −29.21 | −2.02 | 11 | 4 | 0.36 |
| GO_REGULATION_OF_SODIUM_ION_TRANSMEMBRANE_TRANSPORT | −67.2 | −2.02 | 48 | 14 | 0.29 |
| TIL_HCC_C9_CD4_GZMK | −75.21 | −2.02 | 10 | 5 | 0.5 |
| SUGAR_BINDING | −98.2 | −2.02 | 34 | 7 | 0.21 |
| GO_APICAL_PLASMA_MEMBRANE | −139.37 | −2.02 | 292 | 74 | 0.25 |
| GO_REGULATION_OF_SODIUM_ION_TRANSPORT | −143 | −2.02 | 77 | 22 | 0.29 |
| GO_UDP_GLYCOSYLTRANSFERASE_ACTIVITY | −33.38 | −2.01 | 139 | 38 | 0.27 |
| GO_OXIDOREDUCTASE_ACTIVITY_ACTING_ON_THE_CH_NH2_GROUP_OF_DONORS | −37.81 | −2.01 | 19 | 6 | 0.32 |
| GO_ENDODERM_DEVELOPMENT | −49.7 | −2.01 | 71 | 21 | 0.3 |
| GO_CARBOHYDRATE_BINDING | −65.62 | −2.01 | 277 | 72 | 0.26 |
| Targets of OCT1_Q5_01 | −69.32 | −2.01 | 273 | 64 | 0.23 |
| GO_MATERNAL_PROCESS_INVOLVED_IN_FEMALE_PREGNANCY | −72.71 | −2.01 | 60 | 21 | 0.35 |
| GO_SODIUM_POTASSIUM_EXCHANGING_ATPASE_COMPLEX | −141.23 | −2.01 | 11 | 3 | 0.27 |
| HALLMARK_COAGULATION | −166.89 | −2.01 | 138 | 64 | 0.46 |
| SULFURIC_ESTER_HYDROLASE_ACTIVITY | −49.62 | −2 | 16 | 4 | 0.25 |
| GO_RESPONSE_TO_UV | 39.84 | 2 | 126 | 60 | 0.48 |
| FATTY_ACID_OXIDATION | 17.45 | 2 | 18 | 12 | 0.67 |
| GO_PROTEIN_SUMOYLATION | 74.55 | 2.01 | 115 | 68 | 0.59 |
| GO_POSITIVE_REGULATION_OF_DNA_REPAIR | 59.89 | 2.01 | 38 | 17 | 0.45 |
| GO_CHROMOSOMAL_REGION | 54.33 | 2.01 | 330 | 159 | 0.48 |
| GO_NEGATIVE_REGULATION_OF_DEFENSE_RESPONSE_TO_VIRUS | 42.57 | 2.01 | 18 | 8 | 0.44 |

TABLE S9-continued

The topmost differentially expressed gene sets in the malignant cells from ICR vs. TN tumors

| Gene set | t-test p-value (−log10(\|P\|), positive = higher in ICR, negative = lower in ICR) t-test p-value | mixed effects p-value | N = No. of genes in the gene set | N · qc = No. of used genes | N/N · qc |
|---|---|---|---|---|---|
| KEGG_LIMONENE_AND_PINENE_DEGRADATION | 40.9 | 2.01 | 10 | 7 | 0.7 |
| NUCLEAR_HORMONE_RECEPTOR_BINDING | 39.05 | 2.01 | 28 | 15 | 0.54 |
| CELLULAR_PROTEIN_COMPLEX_DISASSEMBLY | 35.57 | 2.01 | 13 | 7 | 0.54 |
| BIOCARTA_VEGF_PATHWAY | 21.87 | 2.01 | 29 | 15 | 0.52 |
| GO_FILAMENTOUS_ACTIN | 8.26 | 2.01 | 20 | 6 | 0.3 |
| GO_DNA_METHYLATION_OR_DEMETHYLATION | 2.5 | 2.01 | 59 | 22 | 0.37 |
| GO_REGULATION_OF_TELOMERASE_ACTIVITY | 68.25 | 2.02 | 43 | 17 | 0.4 |
| GO_HORMONE_RECEPTOR_BINDING | 23.76 | 2.02 | 168 | 73 | 0.43 |
| GO_REGULATION_OF_MITOCHONDRIAL_OUTER_MEMBRANE_PERMEABILIZATION_INVOLVED_IN_APOPTOTIC_SIGNALING_PATHWAY | 17.67 | 2.02 | 43 | 23 | 0.53 |
| GO_DNA_HELICASE_COMPLEX | 50.82 | 2.03 | 14 | 9 | 0.64 |
| GO_VIRAL_GENOME_REPLICATION | 28.4 | 2.03 | 21 | 13 | 0.62 |
| GO_REGULATION_OF_SPINDLE_ASSEMBLY | 8.3 | 2.03 | 15 | 11 | 0.73 |
| TAAYNRNNTCC_UNKNOWN | 3.81 | 2.03 | 172 | 44 | 0.26 |
| GO_REGULATION_OF_TELOMERE_MAINTENANCE_VIA_TELOMERE_LENGTHENING | 108.58 | 2.04 | 50 | 26 | 0.52 |
| BIOCARTA_EIF2_PATHWAY | 19.87 | 2.04 | 11 | 7 | 0.64 |
| GO_REGULATION_OF_CHROMATIN_SILENCING | 70.9 | 2.05 | 21 | 9 | 0.43 |
| GO_MICROTUBULE | 70.74 | 2.05 | 405 | 173 | 0.43 |
| GO_POSITIVE_REGULATION_OF_PROTEIN_LOCALIZATION_TO_NUCLEUS | 60.95 | 2.05 | 129 | 53 | 0.41 |
| GO_NEGATIVE_REGULATION_OF_TELOMERE_MAINTENANCE_VIA_TELOMERE_LENGTHENING | 59.17 | 2.05 | 17 | 12 | 0.71 |
| Targets of E2F_Q6_01 | 44.57 | 2.05 | 240 | 111 | 0.46 |
| PROTEIN COMPLEX DISASSEMBLY | 32.97 | 2.05 | 14 | 7 | 0.5 |
| GO_PEROXISOME_PROLIFERATOR_ACTIVATED_RECEPTOR_BINDING | 23 | 2.05 | 15 | 4 | 0.27 |
| GO_FEMALE_MEIOTIC_DIVISION | 19.4 | 2.05 | 26 | 10 | 0.38 |
| GO_POSITIVE_REGULATION_OF_MRNA_PROCESSING | 7.84 | 2.05 | 32 | 20 | 0.62 |
| GO_MICROTUBULE_CYTOSKELETON_ORGANIZATION | 7.79 | 2.05 | 348 | 134 | 0.39 |
| Targets of AP4_Q6_01 | 21.61 | 2.06 | 255 | 71 | 0.28 |
| REACTOME_TRANSPORT_OF_MATURE_MRNA_DERIVED_FROM_AN_INTRONLESS_TRANSCRIPT | 36.77 | 2.07 | 33 | 26 | 0.79 |
| AUXILIARY_TRANSPORT_PROTEIN_ACTIVITY | 9.03 | 2.07 | 26 | 6 | 0.23 |
| GO_POSITIVE_REGULATION_OF_TELOMERE_MAINTENANCE_VIA_TELOMERE_LENGTHENING | 96.96 | 2.08 | 33 | 14 | 0.42 |
| GO_NEGATIVE_REGULATION_OF_CHROMOSOME_ORGANIZATION | 77.33 | 2.08 | 96 | 49 | 0.51 |
| RNA_DEPENDENT_ATPASE_ACTIVITY | 48.48 | 2.08 | 18 | 14 | 0.78 |
| GO_MIRNA_BINDING | 31.2 | 2.08 | 16 | 5 | 0.31 |
| GO_G1_DNA_DAMAGE_CHECKPOINT | 31.15 | 2.08 | 73 | 44 | 0.6 |
| GO_TELOMERE_ORGANIZATION | 47.03 | 2.09 | 104 | 49 | 0.47 |
| DNA_INTEGRITY_CHECKPOINT | 25.86 | 2.09 | 24 | 11 | 0.46 |
| GO_CYTOPLASMIC_MICROTUBULE | 33.85 | 2.1 | 57 | 27 | 0.47 |
| GO_UBIQUITIN_LIKE_PROTEIN_LIGASE_BINDING | 27.06 | 2.1 | 264 | 154 | 0.58 |
| GO_POSITIVE_REGULATION_OF_ERYTHROCYTE_DIFFERENTIATION | 12.02 | 2.1 | 23 | 7 | 0.3 |
| GO_REGULATION_OF_HISTONE_H3_K9_ACETYLATION | 27.95 | 2.11 | 14 | 4 | 0.29 |
| GO_DNA_BINDING_BENDING | 19.1 | 2.11 | 20 | 6 | 0.3 |
| GO_MACROPHAGE_ACTIVATION_INVOLVED_IN_IMMUNE_RESPONSE | 10.16 | 2.11 | 11 | 3 | 0.27 |
| NEGATIVE_REGULATION_OF_IMMUNE_SYSTEM_PROCESS | 8.83 | 2.11 | 14 | 3 | 0.21 |
| GO_DNA_INTEGRITY_CHECKPOINT | 37.37 | 2.12 | 146 | 72 | 0.49 |
| GO_REGULATION_OF_SPINDLE_ORGANIZATION | 15.42 | 2.12 | 20 | 14 | 0.7 |
| GO_CHROMATIN_BINDING | 78.09 | 2.13 | 435 | 148 | 0.34 |
| GO_VIRAL_LATENCY | 68.81 | 2.13 | 11 | 9 | 0.82 |
| DNA_HELICASE_ACTIVITY | 52.6 | 2.13 | 25 | 15 | 0.6 |
| GO_NUCLEAR_CHROMOSOME_TELOMERIC_REGION | 62.34 | 2.14 | 132 | 66 | 0.5 |
| GO_POSITIVE_REGULATION_OF_GLUCOSE_IMPORT_IN_RESPONSE_TO_INSULIN_STIMULUS | 13.76 | 2.14 | 12 | 4 | 0.33 |
| GO_CELL_CELL_RECOGNITION | 92.12 | 2.15 | 60 | 13 | 0.22 |
| GO_RIBONUCLEOPROTEIN_GRANULE | 90.49 | 2.15 | 148 | 87 | 0.59 |
| CONTRACTILE_FIBER_PART | 82.69 | 2.15 | 23 | 8 | 0.35 |
| GO_MITOTIC_NUCLEAR_DIVISION | 44.49 | 2.15 | 361 | 187 | 0.52 |
| GO_CELL_CYCLE_PHASE_TRANSITION | 35.91 | 2.16 | 255 | 127 | 0.5 |

TABLE S9-continued

The topmost differentially expressed gene sets in the malignant cells from ICR vs. TN tumors

| Gene set | t-test p-value | mixed effects p-value | N = No. of genes in the gene set | N · qc = No. of used genes | N/N · qc |
|---|---|---|---|---|---|
| Targets of OCT1_02 | 29.34 | 2.16 | 214 | 50 | 0.23 |
| GO_BINDING_OF_SPERM_TO_ZONA_PELLUCIDA | 99.01 | 2.17 | 33 | 9 | 0.27 |
| GO_POSITIVE_REGULATION_OF_DNA_BIOSYNTHETIC_PROCESS | 81.19 | 2.17 | 59 | 23 | 0.39 |
| TRANSLATION_FACTOR_ACTIVITY_NUCLEIC_ACID_BINDING | 69.02 | 2.17 | 39 | 29 | 0.74 |
| REACTOME_CELL_DEATH_SIGNALLING_VIA_NRAGE_NRIF_AND_NADE | 32.08 | 2.17 | 60 | 22 | 0.37 |
| GO_EMBRYONIC_HEMOPOIESIS | 17.18 | 2.17 | 20 | 6 | 0.3 |
| GO_POSITIVE_REGULATION_OF_TELOMERE_MAINTENANCE | 98.25 | 2.18 | 47 | 24 | 0.51 |
| GO_ADENYL_NUCLEOTIDE_BINDING | 83.66 | 2.19 | 1514 | 548 | 0.36 |
| GO_DAMAGED_DNA_BINDING | 66.18 | 2.19 | 63 | 38 | 0.6 |
| GO_SPINDLE_POLE | 31.43 | 2.19 | 126 | 54 | 0.43 |
| GO_CENTROSOME_CYCLE | 7.5 | 2.19 | 45 | 18 | 0.4 |
| CONTRACTILE_FIBER | 88.84 | 2.2 | 25 | 8 | 0.32 |
| AEROBIC_RESPIRATION | 53.17 | 2.2 | 15 | 13 | 0.87 |
| RESPONSE_TO_RADIATION | 39 | 2.2 | 60 | 16 | 0.27 |
| PID_IL3_PATHWAY | 9.65 | 2.2 | 27 | 10 | 0.37 |
| GO_TRANSCRIPTION_EXPORT_COMPLEX | 52.59 | 2.21 | 13 | 12 | 0.92 |
| GO_POSITIVE_REGULATION_OF_DNA_TEMPLATED_TRANSCRIPTION_ELONGATION | 47.81 | 2.21 | 23 | 16 | 0.7 |
| PID_INSULIN_GLUCOSE_PATHWAY | 18.14 | 2.22 | 26 | 11 | 0.42 |
| GO_POSITIVE_REGULATION_OF_MRNA_METABOLIC_PROCESS | 17.19 | 2.22 | 45 | 27 | 0.6 |
| ZF-MIZ | 11.83 | 2.22 | 7 | 4 | 0.57 |
| GO_MRNA_3_UTR_BINDING | 52.16 | 2.23 | 48 | 26 | 0.54 |
| REACTOME_PURINE_METABOLISM | 48.02 | 2.23 | 33 | 22 | 0.67 |
| DNA_REPLICATION_INITIATION | 9.15 | 2.23 | 16 | 7 | 0.44 |
| GO_REGULATION_OF_CHROMATIN_ORGANIZATION | 70.88 | 2.24 | 152 | 61 | 0.4 |
| GO_NEGATIVE_REGULATION_OF_GENE_SILENCING | 42.63 | 2.24 | 19 | 5 | 0.26 |
| BIOCARTA_G1_PATHWAY | 41.82 | 2.24 | 28 | 10 | 0.36 |
| GO_CELL_CYCLE_CHECKPOINT | 54.94 | 2.25 | 194 | 93 | 0.48 |
| GO_PROTEIN_N_TERMINUS_BINDING | 25.88 | 2.25 | 103 | 64 | 0.62 |
| GO_ENDODEOXYRIBONUCLEASE_ACTIVITY | 48.57 | 2.26 | 51 | 21 | 0.41 |
| GO_ASPARTATE_METABOLIC_PROCESS | 31.42 | 2.26 | 11 | 5 | 0.45 |
| GO_POSITIVE_REGULATION_OF_CELLULAR_RESPONSE_TO_INSULIN_STIMULUS | 16.99 | 2.26 | 23 | 6 | 0.26 |
| GO_RESPONSE_TO_ACIDIC_PH | 16.79 | 2.26 | 21 | 5 | 0.24 |
| GO_ENDOLYSOSOME_MEMBRANE | 16.29 | 2.27 | 11 | 5 | 0.45 |
| GO_MYOFILAMENT | 82.74 | 2.28 | 24 | 6 | 0.25 |
| GO_REGULATION_OF_SIGNAL_TRANSDUCTION_BY_P53_CLASS_MEDIATOR | 53.98 | 2.28 | 162 | 73 | 0.45 |
| MACROMOLECULAR_COMPLEX_DISASSEMBLY | 38.21 | 2.28 | 15 | 8 | 0.53 |
| PID_P73PATHWAY | 17.96 | 2.28 | 79 | 41 | 0.52 |
| GO_RIBONUCLEOTIDE_BINDING | 81.21 | 2.29 | 1860 | 694 | 0.37 |
| GO_REGULATION_OF_PROTEIN_ACETYLATION | 48.57 | 2.29 | 64 | 27 | 0.42 |
| GO_NEGATIVE_REGULATION_OF_CELL_CYCLE_PROCESS | 44.5 | 2.29 | 214 | 104 | 0.49 |
| GO_MEIOTIC_CELL_CYCLE | 22.02 | 2.3 | 186 | 58 | 0.31 |
| GO_ALDEHYDE_CATABOLIC_PROCESS | 17.84 | 2.3 | 13 | 9 | 0.69 |
| M_PHASE_OF_MITOTIC_CELL_CYCLE | 46.52 | 2.31 | 85 | 47 | 0.55 |
| PID_CMYB_PATHWAY | 41.73 | 2.31 | 84 | 36 | 0.43 |
| REACTOME_DOUBLE_STRAND_BREAK_REPAIR | 40.26 | 2.31 | 24 | 9 | 0.38 |
| REGULATION_OF_MITOSIS | 40.4 | 2.32 | 41 | 20 | 0.49 |
| GO_CELL_CYCLE_G2_M_PHASE_TRANSITION | 28.36 | 2.32 | 138 | 77 | 0.56 |
| TCCCRNNRTGC_UNKNOWN | 23.51 | 2.32 | 213 | 111 | 0.52 |
| GO_NUCLEAR_CHROMOSOME | 70.81 | 2.33 | 523 | 222 | 0.42 |
| GO_CHROMATIN_DNA_BINDING | 69.13 | 2.33 | 80 | 35 | 0.44 |
| Targets of COUP_DR1_Q6 | 66.25 | 2.33 | 247 | 94 | 0.38 |
| ATP_DEPENDENT_DNA_HELICASE_ACTIVITY | 62.62 | 2.33 | 11 | 8 | 0.73 |
| GO_MITOTIC_DNA_INTEGRITY_CHECKPOINT | 39.42 | 2.33 | 100 | 56 | 0.56 |
| GO_PROTEIN_C_TERMINUS_BINDING | 25.24 | 2.33 | 186 | 81 | 0.44 |
| GO_P53_BINDING | 85.62 | 2.34 | 67 | 23 | 0.34 |
| M_PHASE | 45.04 | 2.35 | 114 | 55 | 0.48 |
| GO_CORONARY_VASCULATURE_DEVELOPMENT | 30.33 | 2.35 | 37 | 9 | 0.24 | t-test p-value (−log10(|P|), positive = higher in ICR, negative = lower in ICR)

TABLE S9-continued

The topmost differentially expressed gene sets in the malignant cells from ICR vs. TN tumors

| Gene set | t-test p-value (−log10(\|P\|), positive = higher in ICR, negative = lower in ICR) | mixed effects p-value | N = No. of genes in the gene set | N · qc = No. of used genes | N/N · qc |
|---|---|---|---|---|---|
| GO_NEGATIVE_REGULATION_OF_DNA_DEPENDENT_DNA_REPLICATION | 9.47 | 2.35 | 16 | 5 | 0.31 |
| Targets of E2F1_Q4_01 | 60.41 | 2.36 | 228 | 90 | 0.39 |
| MICROTUBULE_CYTOSKELETON_ORGANIZATION_AND_BIOGENESIS | 50.93 | 2.36 | 35 | 18 | 0.51 |
| GO_NEGATIVE_REGULATION_OF_VIRAL_RELEASE_FROM_HOST_CELL | 21.79 | 2.37 | 16 | 9 | 0.56 |
| REACTOME_APOPTOSIS_INDUCED_DNA_FRAGMENTATION | 13.69 | 2.37 | 13 | 8 | 0.62 |
| GO_CHROMOSOME | 75.27 | 2.38 | 880 | 390 | 0.44 |
| DNA_DEPENDENT_ATPASE_ACTIVITY | 64.91 | 2.38 | 22 | 13 | 0.59 |
| GO_NUCLEOSOMAL_DNA_BINDING | 79.26 | 2.39 | 30 | 22 | 0.73 |
| GO_DNA_DOUBLE_STRAND_BREAK_PROCESSING | 21.71 | 2.39 | 20 | 9 | 0.45 |
| GO_MICROTUBULE_ORGANIZING_CENTER_ORGANIZATION | 15.43 | 2.39 | 84 | 40 | 0.48 |
| Targets of E2F_Q4_01 | 69.24 | 2.4 | 237 | 100 | 0.42 |
| GO_ORGANELLE_ASSEMBLY | 55.85 | 2.4 | 495 | 214 | 0.43 |
| GO_REGULATION_OF_PROTEIN_INSERTION_INTO_MITOCHONDRIAL_MEMBRANE_INVOLVED_IN_APOPTOTIC_SIGNALING_PATHWAY | 13.8 | 2.4 | 29 | 15 | 0.52 |
| PID_PI3KCI_AKT_PATHWAY | 5.36 | 2.41 | 35 | 16 | 0.46 |
| REACTOME_DESTABILIZATION_OF_MRNA_BY_BRF1 | 57.41 | 2.42 | 17 | 13 | 0.76 |
| GO_POSITIVE_REGULATION_OF_CHROMATIN_MODIFICATION | 52.36 | 2.42 | 85 | 35 | 0.41 |
| HISTONE_METHYLTRANSFERASE_ACTIVITY | 26.67 | 2.42 | 11 | 4 | 0.36 |
| REACTOME_PLATELET_SENSITIZATION_BY_LDL | 22.83 | 2.42 | 16 | 6 | 0.38 |
| PROTEIN_AMINO_ACID_ADP_RIBOSYLATION | 20.94 | 2.42 | 10 | 3 | 0.3 |
| PROTEIN_PHOSPHATASE_TYPE_2A_REGULATOR_ACTIVITY | 37.57 | 2.43 | 14 | 7 | 0.5 |
| CONDENSED_CHROMOSOME | 47.3 | 2.44 | 34 | 16 | 0.47 |
| GTTRYCATRR_UNKNOWN | 16.7 | 2.44 | 172 | 45 | 0.26 |
| MITOCHONDRIAL_TRANSPORT | 44.92 | 2.45 | 21 | 19 | 0.9 |
| REACTOME_INTEGRATION_OF_PROVIRUS | 80.22 | 2.46 | 16 | 6 | 0.38 |
| GO_POSITIVE_REGULATION_OF_MRNA_SPLICING_VIA_SPLICEOSOME | 46.81 | 2.46 | 14 | 6 | 0.43 |
| GO_NEGATIVE_REGULATION_OF_MITOTIC_CELL_CYCLE | 36.32 | 2.46 | 199 | 100 | 0.5 |
| ST_FAS_SIGNALING_PATHWAY | 29.53 | 2.46 | 65 | 31 | 0.48 |
| GO_POSITIVE_REGULATION_OF_DNA_REPLICATION | 68.55 | 2.47 | 86 | 31 | 0.36 |
| GO_NEGATIVE_REGULATION_OF_DNA_REPLICATION | 64.35 | 2.47 | 55 | 25 | 0.45 |
| RRCCGTTA_UNKNOWN | 36.84 | 2.47 | 87 | 52 | 0.6 |
| GO_CHROMATIN | 66.61 | 2.48 | 441 | 168 | 0.38 |
| GO_RESPONSE_TO_FUNGICIDE | 17.51 | 2.48 | 11 | 4 | 0.36 |
| GO_GLOBAL_GENOME_NUCLEOTIDE_EXCISION_REPAIR | 16.24 | 2.49 | 32 | 25 | 0.78 |
| GO_DNA_CATABOLIC_PROCESS | 16.38 | 2.5 | 27 | 13 | 0.48 |
| GO_ATP_DEPENDENT_DNA_HELICASE_ACTIVITY | 54.77 | 2.51 | 34 | 19 | 0.56 |
| MRNA_BINDING | 90.95 | 2.52 | 23 | 17 | 0.74 |
| PID_AURORA_B_PATHWAY | 31.45 | 2.52 | 39 | 19 | 0.49 |
| CELL_CYCLE_PHASE | 53 | 2.53 | 170 | 78 | 0.46 |
| GO_AU_RICH_ELEMENT_BINDING | 29.36 | 2.54 | 23 | 12 | 0.52 |
| GO_REGULATION_OF_MICROTUBULE_POLYMERIZATION_OR_DEPOLYMERIZATION | 19.11 | 2.54 | 178 | 88 | 0.49 |
| GO_SUMO_BINDING | 13.84 | 2.54 | 14 | 5 | 0.36 |
| Targets of CEBPGAMMA_Q6 | 46.47 | 2.55 | 257 | 78 | 0.3 |
| HMG | 13.08 | 2.55 | 51 | 17 | 0.33 |
| GO_REGULATION_OF_PROTEIN_PHOSPHATASE_TYPE_2A_ACTIVITY | 33.51 | 2.57 | 24 | 11 | 0.46 |
| KEGG_BETA_ALANINE_METABOLISM | 64.25 | 2.58 | 22 | 11 | 0.5 |
| GO_RNA_POLYMERASE_II_DISTAL_ENHANCER_SEQUENCE_SPECIFIC_DNA_BINDING | 55.57 | 2.59 | 65 | 28 | 0.43 |
| GO_PEPTIDYL_AMINO_ACID_MODIFICATION | 43.76 | 2.59 | 841 | 340 | 0.4 |
| GO_NEGATIVE_REGULATION_OF_TELOMERASE_ACTIVITY | 29.05 | 2.59 | 15 | 7 | 0.47 |
| Targets of AP2REP_01 | 27.21 | 2.61 | 178 | 57 | 0.32 |
| GO_MITOTIC_SPINDLE_ORGANIZATION | 21.78 | 2.61 | 69 | 32 | 0.46 |
| KEGG_GLYOXYLATE_AND_DICARBOXYLATE_METABOLISM | 60.42 | 2.62 | 16 | 10 | 0.62 |
| GO_MITOTIC_CELL_CYCLE_CHECKPOINT | 53.4 | 2.62 | 139 | 75 | 0.54 |
| GO_REGULATION_OF_CELL_CYCLE_ARREST | 50.41 | 2.62 | 108 | 52 | 0.48 |
| GO_REGULATION_OF_DNA_TEMPLATED_TRANSCRIPTION_ELONGATION | 46.41 | 2.62 | 44 | 25 | 0.57 |
| GO_RESPONSE_TO_AMMONIUM_ION | 32.19 | 2.62 | 51 | 11 | 0.22 |
| GO_REGULATION_OF_THYMOCYTE_APOPTOTIC_PROCESS | 49.18 | 2.63 | 12 | 4 | 0.33 |

TABLE S9-continued

The topmost differentially expressed gene sets in the malignant cells from ICR vs. TN tumors

| Gene set | t-test p-value (−log10(|P|), positive = higher in ICR, negative = lower in ICR) | | N = No. of genes in the gene set | N · qc = No. of used genes | N/N · qc |
|---|---|---|---|---|---|
| | t-test p-value | mixed effects p-value | | | |
| GO_POSITIVE_REGULATION_OF_MITOCHONDRIAL_OUTER_MEMBRANE_PERMEABILIZATION_INVOLVED_IN_APOPTOTIC_SIGNALING_PATHWAY | 19.54 | 2.63 | 36 | 19 | 0.53 |
| GO_NEGATIVE_REGULATION_OF_TELOMERE_MAINTENANCE | 62.11 | 2.64 | 26 | 17 | 0.65 |
| GO_CHROMOSOME_TELOMERIC_REGION | 64.33 | 2.65 | 162 | 79 | 0.49 |
| GO_REGULATION_OF_GENE_SILENCING | 48.57 | 2.65 | 52 | 16 | 0.31 |
| PID_ATM_PATHWAY | 33.28 | 2.66 | 34 | 12 | 0.35 |
| REACTOME_E2F_ENABLED_INHIBITION_OF_PRE_REPLICATION_COMPLEX_FORMATION | 17.78 | 2.66 | 10 | 6 | 0.6 |
| GO_REGULATION_OF_EXECUTION_PHASE_OF_APOPTOSIS | 88.61 | 2.67 | 24 | 11 | 0.46 |
| MICROTUBULE | 51.63 | 2.67 | 32 | 22 | 0.69 |
| BIOCARTA_ATRBRCA_PATHWAY | 37.5 | 2.67 | 21 | 8 | 0.38 |
| GO_NEGATIVE_REGULATION_OF_RESPONSE_TO_BIOTIC_STIMULUS | 20.91 | 2.68 | 30 | 14 | 0.47 |
| GO_POSITIVE_REGULATION_OF_PROTEIN_IMPORT_INTO_NUCLEUS_TRANSLOCATION | 7.78 | 2.69 | 13 | 5 | 0.38 |
| GO_NEGATIVE_REGULATION_OF_EPITHELIAL_CELL_MIGRATION | 6.17 | 2.7 | 53 | 21 | 0.4 |
| Targets of E2F1_Q6_01 | 71.47 | 2.71 | 238 | 98 | 0.41 |
| GO_ORGANIC_ACID_BINDING | 25.77 | 2.71 | 209 | 68 | 0.33 |
| GO_AMINO_ACID_BINDING | 78.19 | 2.73 | 108 | 36 | 0.33 |
| MITOTIC_SPINDLE_ORGANIZATION_AND_BIOGENESIS | 41.3 | 2.73 | 10 | 5 | 0.5 |
| CHROMOSOMEPERICENTRIC_REGION | 29.45 | 2.74 | 31 | 14 | 0.45 |
| GO_REGULATION_OF_DNA_REPLICATION | 86.77 | 2.75 | 161 | 66 | 0.41 |
| YAATNRNNNYNATT_UNKNOWN | 70.49 | 2.75 | 104 | 27 | 0.26 |
| GO_LYMPHOID_PROGENITOR_CELL_DIFFERENTIATION | 77.56 | 2.78 | 11 | 3 | 0.27 |
| Targets of E2F_Q3_01 | 60.66 | 2.79 | 235 | 89 | 0.38 |
| PID_P38_MK2_PATHWAY | 31.15 | 2.82 | 21 | 12 | 0.57 |
| REACTOME_RECRUITMENT_OF_NUMA_TO_MITOTIC_CENTROSOMES | 26.59 | 2.82 | 10 | 7 | 0.7 |
| DNA_RECOMBINATION | 70.64 | 2.85 | 47 | 18 | 0.38 |
| GO_GLYOXYLATE_METABOLIC_PROCESS | 55.35 | 2.86 | 28 | 14 | 0.5 |
| MITOTIC_CELL_CYCLE_CHECKPOINT | 22.04 | 2.86 | 21 | 10 | 0.48 |
| Targets of EFC_Q6 | 17.64 | 2.86 | 268 | 84 | 0.31 |
| Targets of E2F_Q3 | 45.09 | 2.87 | 227 | 91 | 0.4 |
| REACTOME_E2F_MEDIATED_REGULATION_OF_DNA_REPLICATION | 40.93 | 2.87 | 35 | 13 | 0.37 |
| Targets of ER_Q6_02 | 15.46 | 2.87 | 252 | 79 | 0.31 |
| GO_POSITIVE_REGULATION_OF_PROTEIN_ACETYLATION | 43.79 | 2.88 | 36 | 12 | 0.33 |
| CELL_CYCLE_PROCESS | 52.7 | 2.89 | 193 | 87 | 0.45 |
| Targets of E2F1_Q6 | 63.66 | 2.9 | 232 | 101 | 0.44 |
| GO_MODULATION_BY_SYMBIONT_OF_HOST_CELLULAR_PROCESS | 8.45 | 2.92 | 28 | 11 | 0.39 |
| REACTOME_EARLY_PHASE_OF_HIV_LIFE_CYCLE | 76.06 | 2.94 | 21 | 10 | 0.48 |
| SPINDLE_POLE | 22.59 | 2.94 | 18 | 9 | 0.5 |
| GO_POSITIVE_REGULATION_OF_PROTEIN_EXPORT_FROM_NUCLEUS | 44.14 | 2.95 | 19 | 7 | 0.37 |
| GO_GTPASE_ACTIVATING_PROTEIN_BINDING | 21.58 | 2.95 | 14 | 7 | 0.5 |
| TRANSCRIPTION_ELONGATION_REGULATOR_ACTIVITY | 23.11 | 2.99 | 12 | 7 | 0.58 |
| GO_POSITIVE_REGULATION_OF_DNA_METABOLIC_PROCESS | 102.41 | 3.01 | 185 | 76 | 0.41 |
| KEGG_BUTANOATE_METABOLISM | 29.15 | 3.01 | 34 | 17 | 0.5 |
| GO_NUCLEAR_CHROMATIN | 52.27 | 3.03 | 291 | 111 | 0.38 |
| GO_REGULATION_OF_MICROTUBULE_BASED_PROCESS | 24.01 | 3.04 | 243 | 106 | 0.44 |
| GO_FOLIC_ACID_BINDING | 53.44 | 3.06 | 14 | 3 | 0.21 |
| Targets of E2F1DP1RB_01 | 65.74 | 3.1 | 231 | 96 | 0.42 |
| Targets of E2F4DP1_01 | 60.9 | 3.1 | 239 | 100 | 0.42 |
| BIOCARTA_RB_PATHWAY | 33.67 | 3.1 | 13 | 7 | 0.54 |
| GO_POSITIVE_REGULATION_OF_PROTEIN_IMPORT | 26.61 | 3.11 | 104 | 35 | 0.34 |
| SGCGSSAAA_Targets of E2F1DP2_01 | 57.9 | 3.12 | 168 | 77 | 0.46 |
| SPINDLE_ORGANIZATION_AND_BIOGENESIS | 51.5 | 3.13 | 11 | 6 | 0.55 |

TABLE S9-continued

The topmost differentially expressed gene sets in the malignant cells from ICR vs. TN tumors

| Gene set | t-test p-value ($-\log_{10}(|P|)$, positive = higher in ICR, negative = lower in ICR) t-test p-value | mixed effects p-value | N = No. of genes in the gene set | N · qc = No. of used genes | N/N · qc |
|---|---|---|---|---|---|
| Targets of E2F1DP1_01 | 71.16 | 3.17 | 235 | 97 | 0.41 |
| GO_POSITIVE_REGULATION_OF_NUCLEOCYTOPLASMIC_TRANSPORT | 29.3 | 3.19 | 121 | 40 | 0.33 |
| REACTOME_TGF_BETA_RECEPTOR_SIGNALING_IN_EMT_EPITHELIAL_TO_MESENCHYMAL_TRANSITION | 66.6 | 3.2 | 16 | 6 | 0.38 |
| BIOCARTA_TEL_PATHWAY | 35.54 | 3.21 | 18 | 10 | 0.56 |
| Targets of E2F1DP2_01 | 71.9 | 3.22 | 235 | 97 | 0.41 |
| DNA_DAMAGE_RESPONSESIGNAL_TRANSDUCTION | 42.9 | 3.24 | 35 | 13 | 0.37 |
| Targets of E2F_02 | 70.15 | 3.28 | 235 | 98 | 0.42 |
| BIOCARTA_CHREBP2_PATHWAY | 19.81 | 3.28 | 42 | 17 | 0.4 |
| PID_BARD1_PATHWAY | 56.99 | 3.32 | 29 | 15 | 0.52 |
| GO_NEGATIVE_REGULATION_OF_ORGANELLE_ORGANIZATION | 54.33 | 3.34 | 387 | 184 | 0.48 |
| REACTOME_MITOTIC_G2_G2_M_PHASES | 45.21 | 3.36 | 81 | 47 | 0.58 |
| Targets of E2F4DP2_01 | 72.15 | 3.4 | 235 | 97 | 0.41 |
| DNA_DAMAGE_RESPONSESIGNAL_TRANSDUCTION_BY_P53_CLASS_MEDIATOR | 39.26 | 3.44 | 13 | 7 | 0.54 |
| REACTOME_TGF_BETA_RECEPTOR_SIGNALING_ACTIVATES_SMADS | 40.84 | 3.46 | 26 | 12 | 0.46 |
| Targets of E2F1_Q3 | 79.97 | 3.47 | 244 | 97 | 0.4 |
| NEGATIVE_REGULATION_OF_ANGIOGENESIS | 107.96 | 3.51 | 13 | 3 | 0.23 |
| Targets of CMYB_01 | 41.11 | 3.52 | 249 | 106 | 0.43 |
| GO_RNA_CAP_BINDING_COMPLEX | 25.05 | 3.54 | 14 | 6 | 0.43 |
| PROTEIN_N_TERMINUS_BINDING | 65.41 | 3.56 | 38 | 22 | 0.58 |
| GO_PRONUCLEUS | 49.72 | 3.57 | 15 | 9 | 0.6 |
| PID_DNA_PK_PATHWAY | 69.37 | 3.63 | 16 | 9 | 0.56 |
| GO_RESPONSE_TO_COBALT_ION | 77.24 | 3.64 | 13 | 7 | 0.54 |
| GGAMTNNNNNTCCY_UNKNOWN | 108.65 | 3.67 | 117 | 41 | 0.35 |
| Targets of SMAD3_Q6 | 25.73 | 3.74 | 239 | 56 | 0.23 |
| Targets of E2F_Q4 | 70.57 | 3.77 | 234 | 99 | 0.42 |
| REACTOME_LOSS_OF_NLP_FROM_MITOTIC_CENTROSOMES | 64.59 | 3.84 | 59 | 34 | 0.58 |
| REACTOME_RECRUITMENT_OF_MITOTIC_CENTROSOME_PROTEINS_AND_COMPLEXES | 67.72 | 3.9 | 66 | 39 | 0.59 |
| Targets of E2F_Q6 | 72.88 | 3.99 | 232 | 97 | 0.42 |
| Targets of MYCMAX_B (Myc and MAX targets) | 138.78 | 4.02 | 268 | 108 | 0.4 |
| GO_NEGATIVE_REGULATION_OF_ENDOTHELIAL_CELL_MIGRATION | 13.25 | 4.42 | 39 | 16 | 0.41 |
| GO_RESPONSE_TO_ARSENIC_CONTAINING_SUBSTANCE | 68.55 | 4.46 | 29 | 18 | 0.62 |
| GO_REGULATION_OF_CIRCADIAN_RHYTHM | 93.03 | 5.08 | 103 | 29 | 0.28 |
| GO_ENDODEOXYRIBONUCLEASE_ACTIVITY_PRODUCING_5_PHOSPHOMONOESTERS | 26.73 | 5.36 | 12 | 4 | 0.33 |

TABLE S10

Signatures that were used as alternative ICR predictors.

| Signature name | Description | Reference |
|---|---|---|
| AXL (Tirosh) | | Tirosh et al Science 2016 |
| Melanoma cell cycle (Tirosh) | | Tirosh et al Science 2016 |
| G1 S (Tirosh) | | Tirosh et al Science 2016 |
| G2 M (Tirosh) | | Tirosh et al Science 2016 |
| Melanoma cells (Tirosh) | | Tirosh et al Science 2016 |
| MITF (Tirosh) | | Tirosh et al Science 2016 |
| TME B cell | | Tumor microenvironment (TME): Current study |
| TME CAF | | TME: Current study |
| TME Endo | | TME: Current study |
| TME Mal | | TME: Current study |
| TME NK | | TME: Current study |
| TME Neutrophil | | TME: Current study |
| TME T cells | | TME: Current study |
| TME T CD4 | | TME: Current study |
| TME T CD8 | | TME: Current study |
| TME Macrophage | | TME: Current study |
| TME immune cells | | TME: Current study |
| TME lymphocytes | | TME: Current study |
| TME meyloid | | TME: Current study |
| TME stroma | | TME: Current study |
| Fluidgm Panel A | | www.fluidigm.com/applications/advanta-immuno-oncology-gene-expression-assay |
| Fluidgm Panel B | | www.fluidigm.com/applications/advanta-immuno-oncology-gene-expression-assay |
| in-vivo screen GVAXPD1 vs TCRaKO depleted | | Manguso et al. Cell 2017 |
| in-vivo screen GVAX vs TCRaKO depleted | | Manguso et al. Cell 2017 |
| in-vivo screen TCRaKO vs in-vitro depleted | | Manguso et al. Cell 2017 |
| in-vivo screen GVAXPD1 vs TCRaKO enriched | | Manguso et al. Cell 2017 |
| in-vivo screen GVAX vs TCRaKO enriched | | Manguso et al. Cell 2017 |
| in-vivo screen TCRaKO vs in-vitro enriched | | Manguso et al. Cell 2017 |
| co-culture screen top 10 hits | | Patel et al. Nature 2017 |
| co-culture screen top 50 hits | | Patel et al. Nature 2017 |
| Ayers IFNg sig | | Ayers et al. JCI 2017 |
| Ayers immune sig | | Ayers et al. JCI 2017 |

| TME B cell | TME CAP | TME Endo | TME Mal | TME NK | TME T cells | TME T CD4 | TME T CD8 | TME Macrophage | TME immune | TME lymphocytes | TME meyloid | TME stroma |
|---|---|---|---|---|---|---|---|---|---|---|---|---|
| ADAM19 | ABI3BP | A2M | ABTB2 | CCL4 | CXCL13 | AQP3 | APOBEC3C | ACP5 | ACAP1 | ADAM28 | ADAP2 | ABI3BP |
| ADAM28 | ACTA2 | ADAM15 | ACN9 | CD244 | CST7 | CCR4 | APOBEC3G | ACRBP | ADAM28 | APOBEC3G | AIF1 | ACTA2 |
| AFF3 | ADAM12 | ADCY4 | ACSL3 | CST7 | RARRES3 | CCR8 | CBLB | ADAMDEC1 | ADAP2 | BANK1 | AMICA1 | ADAM12 |
| BANK1 | ADAMTS2 | AFAP1L1 | AHCY | CTSW | KLRC4 | CD28 | CCL4 | ADAP2 | AFF3 | BCL11A | BCL2A1 | ADCY4 |
| BCL11A | ANTXR1 | AQP1 | AIF1L | GNLY | EMB | CD4 | CCL4L1 | ADORA3 | AIF1 | BCL11B | C1orf162 | AFAP1L1 |
| BIRC3 | ASPN | ARHGEF15 | AK2 | GZMA | TESPA1 | CD40LG | CCL4L2 | ALDH2 | AKNA | BIRC3 | C1QA | APP |
| BLK | AXL | CALCRL | ALX1 | GZMB | LAT | CD5 | CCL5 | ANKRD22 | ALOX5 | BLK | C1QB | AQP1 |

TABLE S10-continued

Signatures that were used as alternative ICR predictors.

| Col1 | Col2 | Col3 | Col4 | Col5 | Col6 | Col7 | Col8 | Col9 | Col10 | Col11 | Col12 |
|---|---|---|---|---|---|---|---|---|---|---|---|
| BLNK | BGN | CCL14 | ANKRD54 | HOPX | CD28 | CD8A | DGKA | C1QA | ALOX5AP | BLNK | ARHGAP29 |
| BTLA | C1R | CD200 | AP1S2 | ID2 | IL2RG | CD8B | FAAH2 | C1QB | AMICA1 | CBLB | BGN |
| CCR6 | C1S | CD34 | APOA1BP | IL2RB | DUSP2 | CRTAM | FOXP3 | C1QC | ANKRD44 | CCL4 | C1R |
| CCR7 | C3 | CD93 | APOC2 | KLRB1 | PAG1 | CST7 | ICOS | C1orf162 | AOAH | CCL4L1 | C1S |
| CD19 | CALD1 | CDH5 | APOD | KLRC1 | TRAT1 | CTSW | IL7R | C3AR1 | APOBEC3G | CCL4L2 | CALCRL |
| CD1C | CCDC80 | CFI | APOE | KLRD1 | PPP2R5C | CXCL13 | LOC100128420 | CAPG | ARHGAP15 | CCL5 | CALD1 |
| CD22 | CD248 | CLDN5 | ATP1A1 | KLRF1 | SKAP1 | DTHD1 | MAL | CARD9 | ARHGAP30 | CD19 | CCDC80 |
| CD24 | CDH11 | CLEC14A | ATP1B1 | KLRK1 | CD96 | DUSP2 | PASK | CASP1 | ARHGAP9 | CD2 | CD14 |
| CD37 | CERCAM | COL4A2 | ATP5C1 | NKG7 | GPRIN3 | EOMES | PBXIP1 | CCR2 | ARHGDIB | CD22 | CD163 |
| CD79A | CKAP4 | CRIP2 | ATP5G1 | PRF1 | CDC42SE2 | FCRL6 | SLAMF1 | CD163 | ARRB2 | CD247 | CD33 |
| CD79B | COL12A1 | CXorf36 | ATP5G2 | PTGDR | GRAP2 | GZMA | SPOCK2 | CD300C | B2M | CD27 | CD4 |
| CHMP7 | COL14A1 | CYYR1 | ATP6V0E2 | SH2D1B | GZMM | GZMB |  | CD33 | BANK1 | CD28 | CD68 |
| CIITA | COL1A1 | DARC | ATP6V1C1 |  | RGS1 | GZMH |  | CD4 | BCL11A | CD37 | CD200 |
| CLEC17A | COL1A2 | DOCK6 | ATP6V1E1 |  | SLA2 | GZMK |  | CD68 | BCL11B | CD3D | CD248 |
| CNR2 | COL3A1 | DOCK9 | ATP6V1G1 |  | LOC100130231 | ID2 |  | CD86 | BCL2A1 | CD3E | CD34 |
| COL19A1 | COL5A1 | ECE1 | AZGP1 |  | PDCD1 | IFNG |  | CEBPA | BIN2 | CD3G | CDH11 |
| CR2 | COL5A2 | ECSCR | BAIAP2 |  | ICOS | IKZF3 |  | CECR1 | BIRC3 | CD5 | CDH5 |
| CXCR5 | COL6A1 | EGFL7 | BANCR |  | EVL | ITGAE |  | CLEC10A | BLK | CD52 | CFH |
| ELK2AP | COL6A2 | ELK3 | BCAN |  | TC2N | JAKMIP1 |  | CLEC5A | BLNK | CD6 | CFI |
| FAIM3 | COL6A3 | ELTD1 | BCAS3 |  | LAG3 | KLRC4 |  | CMKLR1 | BTK | CD7 | CLDN5 |
| FAM129C | COL8A1 | EMCN | BCHE |  | CBLB | KLRC4-KLRK1 |  | CPVL | C16orf54 | CD79A | CLEC14A |
| FCER2 | CREB3L1 | ENG | BIRC7 |  | LCK | KLRD1 |  | CSF1R | C1QA | CD79B | COL12A1 |
| FCRL1 | CTSK | EPHB4 | BZW2 |  | TTC39C | KLRK1 |  | CTSB | C1QB | CD8A | COL14A1 |
| FCRL2 | CXCL12 | ERG | C10orf90 |  | NLRC5 | MIR155HG |  | CTSC | C1QC | CD8B | COL15A1 |
| FCRL5 | CXCL14 | ESAM | C11orf31 |  | CD5 | NKG7 |  | CTSH | C3AR1 | CD96 | COL1A1 |
| FCRLA | CYBRD1 | FGD5 | C17orf89 |  | ASB2 | PRF1 |  | CXCL10 | C5AR1 | CLEC2D | COL1A2 |
| HLA-DOB | DCN | FLT4 | C1orf43 |  | PTPN22 | RAB27A |  | CXCL9 | CASP1 | CST7 | COL3A1 |
| HLA-DQA2 | DPT | GALNT18 | C1orf85 |  | RAPGEF6 | RUNX3 |  | CXCR2P1 | CBLB | CTSW | COL4A1 |
| HVCN1 | ECM2 | GNG11 | C4orf48 |  | TNFRSF9 | TARP |  | CYBB | CCL3 | CXCR5 | COL4A2 |
| IGLL1 | EFEMP2 | GPR116 | CA14 |  | SH2D2A | TNFRSF9 |  | CYP2S1 | CCL4 | DENND2D | COL5A1 |
| IGLL3P | FAM114A1 | GPR146 | CA8 |  | GPR174 | TOX |  | DMXL2 | CCL4L1 | DGKA | COL5A2 |
| IGLL5 | FAT1 | HSPG2 | CACYBP |  | ITK |  |  | DNAJC5B | CCL4L2 | DUSP2 | COL6A1 |
| IRF8 | FBLN1 | HYAL2 | CAPN3 |  | PCED1B |  |  | EBI3 | CCL5 | EEF1A1 | COL6A2 |
| KIAA0125 | FBLN2 | ICA1 | CBX3 |  | CD247 |  |  | EPSTI1 | CCR1 | EZR | COL6A3 |
| KIAA0226L | FBLN5 | ID1 | CCDC47 |  | DGKA |  |  | F13A1 | CCR6 | FAIM3 | CRIP2 |
| LOC283663 | FGF7 | IL3RA | CCT2 |  | AAK1 |  |  | FAM26F | CD14 | FAM129C | CTGF |
| LTB | FSTL1 | ITGB4 | CCT3 |  | SH2D1A |  |  | FBP1 | CD163 | FCER2 | CXCL12 |
| MS4A1 | GPR176 | KDR | CCT6A |  | BTN3A2 |  |  | FCER1G | CD19 | FCRL1 | CXorf36 |
| NAPSB | GPX8 | LAMA5 | CCT8 |  | PTPN7 |  |  | FCGR1A | CD2 | FCRLA | CYBRD1 |
| P2RX5 | HSPB6 | LDB2 | CDH19 |  | UBASH3A |  |  | FCGR1C | CD22 | FYN | CYR61 |
| PAX5 | IGFBP6 | LOC100505495 | CDH3 |  | ACAP1 |  |  | FOLR2 | CD244 | GNLY | DCHS1 |
| PLEKHF2 | INHBA | MALL | CDK2 |  | FASLG |  |  | FPR3 | CD247 | GZMA | DCN |
| PNOC | ISLR | MMRN1 | CELSR2 |  | INPP4B |  |  | FUCA1 | CD27 | GZMB | DOCK6 |
| POU2AF1 | ITGA11 | MMRN2 | CHCHD6 |  | ARAP2 |  |  | FUOM | CD28 | GZMK | DPT |
| POU2F2 | ITGBL1 | MYCT1 | CITED1 |  | CD3G |  |  | GATM | CD300A | HLA-DMA | ECSCR |
| QRSL1 | LOX | NOS3 | CLCN7 |  | IL7R |  |  | GM2A | CD33 | HOPX | EFEMP1 |
| RALGPS2 | LPAR1 | NOTCH4 | CLNS1A |  | 1-Sep |  |  | GNA15 | CD37 | HVCN1 | EFEMP2 |
| SEL1L3 | LRP1 | NPDC1 | CMC2 |  | SCML4 |  |  | GPBAR1 | CD38 | ID2 | EGFL7 |
| SNX29P1 | LTBP2 | PALMD | COA6 |  | IKZF3 |  |  | GPR34 | CD3D | IGLL5 | EHD2 |
| SPIB |  | PCDH17 | COX7A2 |  | GATA3 |  |  | GPX1 | CD3E | IKZF3 | ELK3 |
| ST6GAL1 |  | PDE2A | CRYL1 |  | PIM2 |  |  | HLA-DMA |  | IL2RB | ELN |
|  |  |  |  |  |  |  |  |  |  |  | ELTD1 |
|  |  |  |  |  |  |  |  |  |  |  | EMCN |
|  |  |  |  |  |  |  |  |  |  |  | ENG |
|  |  |  |  |  |  |  |  |  |  |  | EPAS1 |
|  |  |  |  |  |  |  |  |  |  |  | EPHB4 |

TABLE S10-continued

Signatures that were used as alternative ICR predictors.

| | | | | | | |
|---|---|---|---|---|---|---|
| STAG3 | LUM | CSAG1 | NKG7 | HLA-DMB | CD3G | IL32 | IL4I1 | ERG |
| STAP1 | MAP1A | PECAM1 | CSAG2 | KLRK1 | HLA-DPB2 | CD4 | IL7R | IL8 | ESAM |
| TCL1A | MEG3 | PIVAP | CSAG3 | SIT1 | HLA-DRB1 | CD48 | IRF8 | IRF5 | FAM114A1 |
| TLR10 | MFAP4 | PLXND1 | CSAG4 | DEF6 | HLA-DRB5 | CD5 | ITK | KYNU | FAP |
| VPREB3 | MFAP5 | PODXL | CSPG4 | GZMH | HLA-DRB6 | CD52 | JAK3 | LAIR1 | FBLN1 |
| WDFY4 | MIR100HG | PRCP | CYC1 | LIME1 | HMOX1 | CD53 | KLRB1 | LILRA1 | FBLN2 |
| | MMP2 | PTPRB | CYP27A1 | GZMA | IFI30 | CD6 | KLRC4 | LILRA2 | FBLN5 |
| | MRC2 | PVRL2 | DAAM2 | JAK3 | IL4I1 | CD68 | KLRD1 | LILRA3 | FBN1 |
| | MXRA5 | RAMP2 | DANCR | DENND2D | IRF5 | CD69 | KLRK1 | LILRA6 | FGF7 |
| | MXRA8 | RAMP3 | DAP3 | SEMA4D | KCNMA1 | CD7 | LAG3 | LILRB1 | FHL1 |
| | MYL9 | RHOJ | DCT | SIRPG | KYNU | CD72 | LAT | LILRB2 | FN1 |
| | NID2 | ROBO4 | DCXR | CLEC2D | LAIR1 | CD74 | LCK | LILRB3 | FSTL1 |
| | NUPR1 | S1PR1 | DDT | CD8B | LGALS2 | CD79A | LOC283663 | LILRB4 | GNG11 |
| | OLFML2B | SDPR | DLGAP1 | THEMIS | LILRB1 | CD79B | LTB | LRRC25 | GPR116 |
| | OLFML3 | SELP | DLL3 | NLRC3 | LILRB4 | CD83 | LY9 | LST1 | HSPG2 |
| | PALLD | SHROOM4 | DNAH14 | ZAP70 | LILRB5 | CD86 | MAP4K1 | LYZ | HTRA1 |
| | PCDH18 | SLCO2A1 | DNAJA4 | IL12RB1 | LIPA | CD8A | MS4A1 | MAFB | HYAL2 |
| | PCOLCE | SMAD1 | DSCR8 | CTSW | MAFB | CD8B | NAPSB | MAN2B1 | ID1 |
| | PDGFRA | STOM | DUSP4 | MAP4K1 | MAN2B1 | CD96 | NKG7 | MFSD1 | ID3 |
| | PDGFRB | TEK | EDNRB | IFNG | MARCO | CDC42SE2 | PARP15 | MNDA | IFITM3 |
| | PDGFRL | TGM2 | EIF3C | SPOCK2 | MFSD1 | CECR1 | PAX5 | MPEG1 | IGFBP4 |
| | PLAC9 | THBD | EIF3D | DTHD1 | MPEG1 | CELF2 | PCED1B-AS1 | MPP1 | IGFBP7 |
| | PODN | TIE1 | EIF3E | APOBEC3G | MS4A4A | CIITA | PDCD1 | MS4A4A | IL33 |
| | PRRX1 | TM4SF1 | EIF3H | PSTPIP1 | MS4A6A | CLEC2D | PLAC8 | MS4A6A | ISLR |
| | RARRES2 | TM4SF18 | EIF3L | CD2 | MS4A7 | CLEC4A | POU2AF1 | MS4A7 | KDR |
| | RCN3 | TMEM255B | ENO1 | PRF1 | MSR1 | CLEC7A | POU2F2 | MSR1 | LAMA5 |
| | SDC1 | TSPAN7 | ENO2 | BCL11B | MTMR14 | CORO1A | PRDM1 | MXD1 | LAMB1 |
| | SDC2 | TSPAN18 | ENTHD1 | PARP8 | NAGA | CPVL | PRF1 | NAIP | LAMC1 |
| | SEC24D | VWF | ENTPD6 | CXCR3 | NPC2 | CSF1R | PTPN7 | NCF2 | LDB2 |
| | SERPINF1 | ZNF385D | ERBB3 | CELF2 | OAS1 | CSF2RA | PTPRCAP | NINJ1 | LHFP |
| | SFRP2 | | ESRP1 | CCL5 | OLR1 | CSF3R | PYHIN1 | NPC2 | LIMA1 |
| | SFRP4 | | ETV4 | IL32 | PLA2G7 | CST7 | RHOH | NPL | LIMS2 |
| | SLIT3 | | ETV5 | PRKCQ | PPT1 | CSTA | RNF213 | PILRA | LOX |
| | SMOC2 | | EXOSC4 | WIPF1 | PTPRO | CSTB | RPL13 | PPT1 | LOXL2 |
| | SPARC | | EXTL1 | GZMK | RASSF4 | CTSC | RPS27 | PSAP | LPAR1 |
| | SPOCK1 | | FAHD2B | ATHL1 | RGS10 | CTSD | RPS3A | PTAFR | LTBP2 |
| | SPON1 | | FAM103A1 | ZC3HAV1 | RHBDF2 | CTSS | RPS6 | PYCARD | LUM |
| | SULF1 | | FAM178B | CD7 | RNASE6 | CTSW | RUNX3 | RAB20 | MAP1B |
| | SVEP1 | | FANCL | CD3D | RNASET2 | CXCL16 | 1-Sep | RASSF4 | MEG3 |
| | TAGLN | | FARP2 | RASGRP1 | RTN1 | CXCR4 | SH2D1A | RBM47 | MEAP4 |
| | THBS2 | | FASN | TBC1D10C | SDS | CXCR5 | SH2D2A | RGS2 | MGP |
| | THY1 | | FBXO32 | TRAF1 | SIGLEC1 | CYBA | SIRPG | RNASE6 | MMP2 |
| | TMEM119 | | FBXO7 | ARHGEF1 | SLAMF8 | CYBB | SIT1 | RNF130 | MXRA8 |
| | TPM1 | | FDFT1 | TARP | SLC15A3 | CYFIP2 | SKAP1 | RNF144B | MYCT1 |
| | TPM2 | | FKBP4 | SPATA13 | SLC6A12 | CYTH4 | SP140 | S100A8 | MYL9 |
| | VCAN | | FMN1 | PCED1B-AS1 | SLC7A7 | CYTIP | SPOCK2 | S100A9 | NFIB |
| | | | FOXD3 | RUNX3 | SLCO2B1 | DENND2D | STAP1 | SAT1 | NID2 |
| | | | FXYD3 | CD6 | SPINT2 | DGKA | STAT4 | SERPINA1 | NNMT |
| | | | GAPDH | CD8A | TFEC | DOCK2 | TARP | SIGLEC1 | NPDC1 |
| | | | GAS2L3 | NELL2 | TIFAB | DOCK8 | TIGIT | SIGLEC9 | OLFML3 |
| | | | | TNFAIP3 | TNFSF13 | DOK2 | TMC8 | SIRPB1 | PALLD |

TABLE S10-continued

Signatures that were used as alternative ICR predictors.

| | | | | |
|---|---|---|---|---|
| GAS5 | IPCEF1 | TPP1 | DOK3 | TOX | SLAMF8 | PCOLCE |
| GAS7 | CXCR6 | TREM2 | DUSP2 | VPREB3 | SLC7A7 | PDGFRA |
| GDF15 | ITGAL | TYMP | EEF1A1 | ZAP70 | SLCO2B1 | PDGFRB |
| GJB1 | RHOF | VAMP8 | EPSTI1 | | SPI1 | PDLIM1 |
| GPATCH4 | STAT4 | VSIG4 | EVI2A | | SPINT2 | PLAC9 |
| GPM6B | PVRIG | ZNF385A | EVI2B | | TBXAS1 | PLVAP |
| GPNMB | TIGIT | | EZR | | TFEC | PLXND1 |
| GPR137B | CD27 | | FAIM3 | | THEMIS2 | PODN |
| GPR143 | ZNF831 | | FAM129C | | TLR2 | PODXL |
| GSTP1 | RNF213 | | FAM26F | | TNFRSF10C | PPAP2A |
| GYG2 | SYTL3 | | FAM49B | | TNFSF13 | PPIC |
| H2AFZ | CNOT6L | | FAM65B | | TPP1 | PRCP |
| HIST1H2BD | SPN | | FBP1 | | TREM1 | PRRX1 |
| HIST3H2A | GPR171 | | FCER1G | | VSIG4 | PRSS23 |
| HMG20B | AKNA | | FCER2 | | ZNF385A | PTPRB |
| HMGA1 | FYN | | FCGR1A | | | PTRF |
| HPGD | RASAL3 | | FCGR1B | | | PXDN |
| HPS4 | CCL4 | | FCGR2A | | | RAMP2 |
| HPS5 | TOX | | FCGR2C | | | RAMP3 |
| HSP90AA1 | PRDM1 | | FCGR3A | | | RARRES2 |
| HSP90AB1 | PIP4K2A | | FCGR3B | | | RCN3 |
| HSPA9 | CTLA4 | | FCN1 | | | RHOJ |
| HSPD1 | GZMB | | FCRL1 | | | ROBO4 |
| HSPE1 | HNRNPA1P10 | | FCRLA | | | S100A16 |
| IGSF11 | CD3E | | FERMT3 | | | S1PR1 |
| IGSF3 | IKZF1 | | FGD2 | | | SELM |
| IGSF8 | JAKMIP1 | | FGD3 | | | SERPINH1 |
| INPP5F | PYHIN1 | | FGL2 | | | SLCO2A1 |
| ISYNA1 | MIAT | | FGR | | | SMAD1 |
| KCNJ13 | LEPROTL1 | | FPR1 | | | SPARC |
| LAGE3 | OXNAD1 | | FPR2 | | | SPARCL1 |
| LDHB | RAB27A | | FPR3 | | | SULF1 |
| LDLRAD3 | IL2RB | | FTH1 | | | SYNPO |
| LEF1-AS1 | KLRD1 | | FTL | | | TAGLN |
| LHFPL3-AS1 | PIK3IP1 | | FYB | | | TEK |
| LINC00473 | | | FYN | | | TFPI |
| LINC00518 | | | G0S2 | | | TGFBI1I |
| LINC00673 | | | GBP5 | | | THBS1 |
| LOC100126784 | | | GLUL | | | THBS2 |
| LOC100127888 | | | GNA15 | | | THY1 |
| LOC100130370 | | | GNLY | | | TIE1 |
| LOC100133445 | | | GPR183 | | | TM4SF1 |
| LOC100505865 | | | GPSM3 | | | TMEM204 |
| LOC146481 | | | GPX1 | | | TMEM255B |
| LOC340357 | | | GRB2 | | | TNS1 |
| LONP2 | | | GZMA | | | TPM1 |
| LOXL4 | | | GZMB | | | TPM2 |
| LZTS1 | | | GZMK | | | VCL |
| MAGEA1 | | | HAVCR2 | | | VWF |
| MAGEA12 | | | HCK | | | |
| MAGEA2 | | | HCLS1 | | | |

TABLE S10-continued

Signatures that were used as alternative ICR predictors.

| | |
|---|---|
| MAGEA2B | HCST |
| MAGEA3 | HK3 |
| MAGEA4 | HLA-B |
| MAGEA6 | HLA-C |
| MAGEC1 | HLA-DMA |
| MDH1 | HLA-DMB |
| MFI2 | HLA-DOB |
| MFSD12 | HLA-DPA1 |
| MIA | HLA-DPB1 |
| MIF | HLA-DPB2 |
| MITF | HLA-DQA1 |
| MLANA | HLA-DQA2 |
| MLPH | HLA-DQB1 |
| MOK | HLA-DQB2 |
| MRPS21 | HLA-DRA |
| MRPS25 | HLA-DRB1 |
| MRPS26 | HLA-DRB5 |
| MRPS6 | HLA-G |
| MSI2 | HMHA1 |
| MXI1 | HOPX |
| MYO10 | HVCN1 |
| NAV2 | ID2 |
| NDUFA4 | IFI30 |
| NDUFB9 | IGFLR1 |
| NEDD4L | IGLL5 |
| NELFCD | IGSF6 |
| NHP2 | IKZF1 |
| NME1 | IKZF3 |
| NOP58 | IL10RA |
| NPM1 | IL16 |
| NSG1 | IL1RN |
| NT5DC3 | IL2RB |
| OSTM1 | IL2RG |
| PACSIN2 | IL32 |
| PAGE5 | IL4I1 |
| PAICS | IL7R |
| PAX3 | IL8 |
| PEG10 | INPP5D |
| PFDN2 | IRF5 |
| PHB | IRF8 |
| PHLDA1 | ITGAL |
| PIGY | ITGAM |
| PIR | ITGAX |
| PKNOX2 | ITGB2 |
| PLEKHB1 | ITK |
| PLP1 | JAK3 |
| PLXNB3 | KLRB1 |
| PMEL | KLRC4 |
| POLR2F | KLRD1 |
| PPIL1 | KLRK1 |
| PPM1H | KYNU |

TABLE S10-continued

Signatures that were used as alternative ICR predictors.

| | |
|---|---|
| PRAME | LAG3 |
| PSMB4 | LAIR1 |
| PUF60 | LAPTM5 |
| PYGB | LAT |
| PYURF | LAT2 |
| QDPR | LCK |
| RAB17 | LCP1 |
| RAB38 | LCP2 |
| RAP1GAP | LILRA1 |
| RGS20 | LILRA2 |
| RNF43 | LILRA3 |
| ROPN1 | LILRA6 |
| ROPN1B | LILRB1 |
| RPL38 | LILRB2 |
| RSL1D1 | LILRB3 |
| RTKN | LILRB4 |
| S100A1 | LIMD2 |
| S100B | LITAF |
| SCD | LOC283663 |
| SDC3 | LRRC25 |
| SEC11C | LSP1 |
| SEMA3B | LST1 |
| SERPINA3 | LTB |
| SERPINE2 | LY86 |
| SGCD | LY9 |
| SGK1 | LYN |
| SH3D21 | LYST |
| SHC4 | LYZ |
| SLC19A2 | M6PR |
| SLC24A5 | MAFB |
| SLC25A13 | MAN2B1 |
| SLC25A4 | MAP4K1 |
| SLC26A2 | 1-Mar |
| SLC3A2 | MFSD1 |
| SLC45A2 | MNDA |
| SLC5A3 | MPEG1 |
| SLC6A15 | MPP1 |
| SLC6A8 | MS4A1 |
| SLC7A5 | MS4A4A |
| SNCA | MS4A6A |
| SNHG16 | MS4A7 |
| SNHG6 | MSR1 |
| SNRPC | MXD1 |
| SNRPD1 | MYO1F |
| SNRPE | NAIP |
| SOD1 | NAPSB |
| SORD | NCF1 |
| SORT1 | NCF1B |
| SOX10 | NCF1C |
| SOX6 | NCF2 |
| SPCS1 | NCF4 |

TABLE S10-continued

Signatures that were used as alternative ICR predictors.

| | |
|---|---|
| SPRY4 | NCKAP1L |
| ST13 | NINJ1 |
| ST3GAL4 | NKG7 |
| ST3GAL6 | NPC2 |
| ST3GAL6-AS1 | NPL |
| ST6GALNAC2 | PAG1 |
| STIP1 | PARP15 |
| STK32A | PARVG |
| STMN1 | PAX5 |
| STX7 | PCED1B-AS1 |
| STXBP1 | PDCD1 |
| SYNGR1 | PIK3AP1 |
| TBC1D7 | PIK3R5 |
| TBCA | PILRA |
| TEX2 | PIM2 |
| TFAP2A | PION |
| TFAP2C | PLAC8 |
| TMEM147 | PLCB2 |
| TMEM14B | PLEK |
| TMEM177 | PLEKHA2 |
| TMEM251 | POU2AF1 |
| TMX4 | POU2F2 |
| TNFRSF21 | PPT1 |
| TOM1L1 | PRDM1 |
| TOMM20 | PRF1 |
| TOMM22 | PSAP |
| TOMM6 | PSMB10 |
| TOMM7 | PSTPIP1 |
| TOP1MT | PTAFR |
| TRIB2 | PTK2B |
| TRIM2 | PTPN6 |
| TRIM63 | PTPN7 |
| TRIM9 | PTPRC |
| TRIML2 | PTPRCAP |
| TRMT112 | PYCARD |
| TSPAN10 | PYHIN1 |
| TTLL4 | RAB20 |
| TTYH2 | RAC2 |
| TUBB2B | RASSF4 |
| TUBB4A | RBM47 |
| TYR | RGS1 |
| TYRP1 | RGS19 |
| UBL3 | RGS2 |
| UQCRH | RHOF |
| UTP18 | RHOG |
| VAT1 | RHOH |
| VDAC1 | RNASE6 |
| VPS72 | RNASET2 |
| WBSCR22 | RNF130 |
| XAGE1A | RNF144B |
| XAGE1B | RNF213 |

TABLE S10-continued

Signatures that were used as alternative ICR predictors.

| | |
|---|---|
| XAGE1C | RPL13 |
| XAGE1D | RPS27 |
| XAGE1E | RPS3A |
| XYLB | RPS6 |
| ZCCHC17 | RPS6KA1 |
| ZFP106 | RUNX3 |
| ZNF280B | S100A8 |
| ZNF330 | S100A9 |
| | SAMHD1 |
| | SAMSN1 |
| | SASH3 |
| | SAT1 |
| | SCIMP |
| | SELL |
| | SELPLG |
| | 1-Sep |
| | SERPINA1 |
| | SH2D1A |
| | SH2D2A |
| | SIGLEC1 |
| | SIGLEC14 |
| | SIGLEC7 |
| | SIGLEC9 |
| | SIRPB1 |
| | SIRPG |
| | SIT1 |
| | SKAP1 |
| | SLA |
| | SLAMF6 |
| | SLAMF7 |
| | SLAMF8 |
| | SLC7A7 |
| | SLCO2B1 |
| | SNX10 |
| | SP140 |
| | SPI1 |
| | SPINT2 |
| | SPN |
| | SPOCK2 |
| | SRGN |
| | STAP1 |
| | STAT4 |
| | STK17B |
| | STXBP2 |
| | SYK |

TABLE S10-continued

Signatures that were used as alternative ICR predictors.

TAGAP
TARP
TBC1D10C
TBXAS1
TFEC
THEMIS2
TIGIT
TLR1
TLR2
TMC8
TNFRSF10C
TNFRSF9
TNFSF13
TOX
TPP1
TRAF3IP3
TREM1
TYROBP
UCP2
VAMP8
VAV1
VNN2
VPREB3
VSIG4
WIPF1
ZAP70
ZNF385A

TABLE S11

Signatures of Expanded T cells
Up/down regulated in expanded T cells compared to non-expanded T cells.

| up (expanded) | down (expanded) | up (all) | | down (all) | |
|---|---|---|---|---|---|
| ABCD2 | ALOX5AP | ABCD2 | NAB1 | AAK1 | MCM5 |
| ADAM28 | ANXA1 | ADAM28 | NCALD | AHNAK | MRPS24 |
| AIM2 | ARL4C | AIM2 | NEK7 | ALOX5AP | MRPS34 |
| AKAP5 | C12orf75 | AKAP5 | NFAT5 | ANAPC15 | MUTYH |
| AP1AR | CAMK4 | AKAP8L | NMB | ANXA1 | MXD4 |
| ARID5A | CD200R1 | ANAPC4 | NOD2 | AP5S1 | MYH9 |
| ARNT | CD44 | AP1AR | NOTCH1 | APOBEC3G | NDUFB9 |
| ATHL1 | CD5 | AQR | NSUN2 | ARL4C | NEDD8 |
| ATP2C1 | COX7A2 | ARID5A | OPA1 | ASF1B | NFKBIZ |
| BCOR | DBF4 | ARNT | ORMDL3 | ATG16L2 | NR4A3 |
| CADM1 | EMP3 | ATHL1 | OSBPL3 | AURKA | NUP37 |
| CCL3L3 | FAM46C | ATM | PAPOLA | BOLA3 | PCK2 |
| DGKD | FOSB | ATP2C1 | PARP11 | BUB1 | PCNA |
| DTHD1 | GZMH | ATXN7L1 | PCED1B | C12orf75 | PDCD5 |
| ETV1 | HMGA1 | BCOR | PCM1 | C3orf38 | PDE4B |
| G3BP1 | KIAA0101 | C17orf59 | PDE7B | CAMK4 | PFDN2 |
| HSPA1B | KLRG1 | C18orf25 | PDGFD | CARD16 | PHLDA1 |
| ID3 | LIME1 | CADM1 | PDXDC2P | CCR5 | POLR2K |
| ITM2A | LMNB1 | CAV1 | PIK3AP1 | CCR7 | PRDX3 |
| KCNK5 | MAB21L3 | CCL3L3 | PIKFYVE | CD200R1 | PRPF4 |
| KLRC2 | NR4A3 | CD200 | PJA2 | CD44 | PRR5L |
| KLRC3 | PCK2 | CDC73 | PRKCH | CD5 | PXN |
| KLRC4 | PCNA | CEP85L | PROSER1 | CD97 | RDH11 |
| KLRK1 | PDCD5 | DDX3Y | PSTPIP1 | CKS1B | REXO2 |
| LOC220729 | PDE4B | DDX6 | PTPN6 | COX7A2 | RNASEH2C |
| LONP2 | PFDN2 | DGKD | PYHIN1 | DBF4 | RNASEK |
| LRBA | RDH11 | DGKH | RALGDS | DNAJC9 | RPUSD3 |
| LYST | S100A10 | DNAJA2 | RCBTB2 | DTYMK | RTCA |
| NAB1 | S100A4 | DTHD1 | RGS2 | ECE1 | S100A10 |
| NMB | SAMD3 | ELF1 | RGS4 | ECHS1 | S100A4 |
| PAPOLA | SPOCK2 | ELMO1 | RHOB | ELL | S100A6 |
| PDE7B | TKT | ETNK1 | RIN3 | EMP3 | S1PR1 |
| PIK3AP1 | TNF | ETV1 | RNF19A | F2R | SAMD3 |
| PRKCH | TOB1 | FAIM3 | RWDD2B | FAM46C | SELL |
| PROSER1 | TOMM7 | FBXW11 | S100PBP | FAM50B | SLIRP |
| PTPN6 | TUBA1C | FCRL3 | SATB1 | FOSB | SPOCK2 |
| PYHIN1 | UGDH-AS1 | FOXN2 | SDAD1 | FOXP1 | STX16 |
| RGS2 | | G3BP1 | SEC24C | GMCL1 | TANK |
| RGS4 | | GALT | SERINC3 | GNPTAB | TKT |
| S100PBP | | GFOD1 | SFI1 | GPR183 | TMEM173 |
| SH2D1B | | GNG4 | SH2D1B | GTF3C6 | TNF |
| SNAP47 | | HIF1A | SKIV2L | GYPC | TNFAIP3 |
| SPDYE8P | | HIST1H2BG | SLC30A7 | GZMA | TNFSF4 |
| SPRY2 | | HIST2H2BE | SLC7A5P1 | GZMH | TOB1 |
| SYVN1 | | HSPA1B | SLFN11 | HAUS4 | TOMM5 |
| TACO1 | | HSPB1 | SNAP47 | HMGA1 | TOMM7 |
| THADA | | ID3 | SOD1 | HMOX2 | TPT1 |
| TP53INP1 | | IL6ST | SPATA13 | INSIG1 | TUBA1B |
| TSC22D1 | | INPP5B | SPDYE8P | ITM2C | TUBA1C |
| UBA7 | | INPP5F | SPRY2 | KIAA0101 | TUBB4B |
| ZMYM2 | | IRF8 | STT3B | KLF6 | TXN |
| | | ITM2A | SYVN1 | KLRB1 | UBE2Q2P3 |
| | | KCNK5 | TACO1 | KLRG1 | UCHL3 |
| | | KDM4C | TBC1D23 | LEF1 | UGDH-AS1 |
| | | KLRC2 | TBC1D4 | LIME1 | UQCRB |
| | | KLRC3 | THADA | LMNB1 | VIM |
| | | KLRC4 | TNFRSF9 | LTB | WBP11 |
| | | KLRD1 | TNIP1 | LY6E | ZNF683 |
| | | KLRK1 | TP53INP1 | MAB21L3 | |
| | | LOC100190986 | TRAF5 | | |
| | | LOC220729 | TSC22D1 | | |
| | | LOC374443 | TTI2 | | |
| | | LONP2 | TTTY15 | | |
| | | LRBA | TXNDC11 | | |
| | | LRRC8D | UBA7 | | |
| | | LSM14A | VMA21 | | |
| | | LY9 | VPRBP | | |
| | | LYST | WWC3 | | |
| | | MBP | ZBED5 | | |
| | | MED13 | ZMYM2 | | |
| | | MGA | ZMYM5 | | |
| | | MGEA5 | ZNF384 | | |

TABLE S11-continued

Signatures of Expanded T cells
Up/down regulated in expanded T cells compared to non-expanded T cells.

| up (expanded) | down (expanded) | up (all) | down (all) |
|---|---|---|---|
| | | MS4A1 | ZNF468 |
| | | MST4 | ZNF83 |
| | | NAA16 | |

Example 2—Immunotherapy Resistance Signature from 26 Melanoma Tumors

Figure 17:
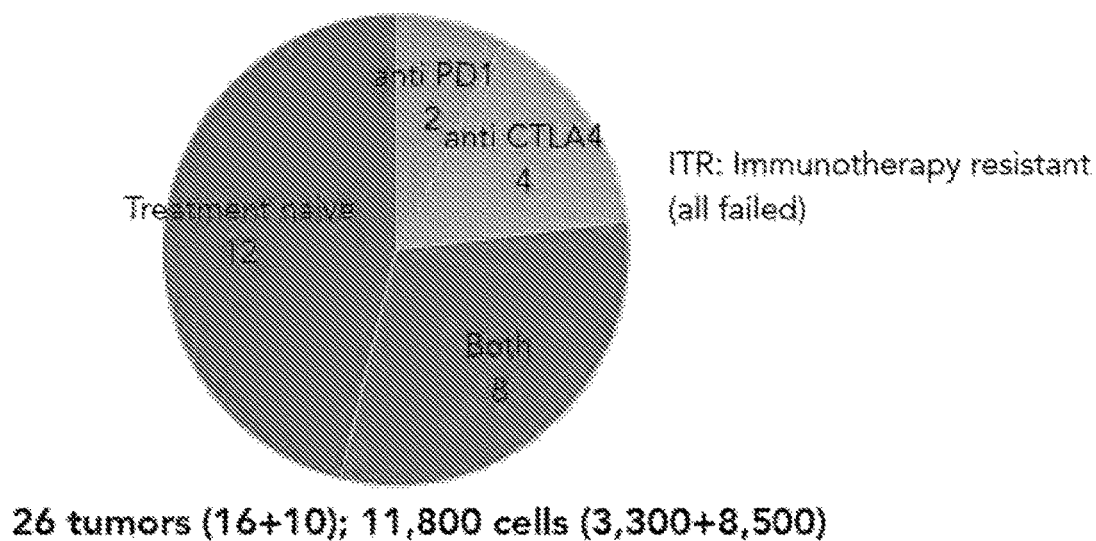
FIG. 17 illustrates an overview of the patients analyzed.

Applicants performed single-cell RNA-seq on 26 melanoma tumors (12 treatment naïve, 14 post immunotherapy) (FIG. 17). Applicants discovered that immunotherapy leads to profound transcriptional alterations in both the malignant and immune cells. Applicants also discovered that these transcriptional programs are associated the response to immunotherapy by analyzing prior data sets (Hugo et al. Cell. 2016 Mar. 24; 165(1):35-44. doi: 10.1016/j.cell.2016.02.065; and Riaz et al. Nature Genetics 48, 1327-1329 (2016) doi: 10.1038/ng.3677). Applicants also discovered that these transcriptional programs are associated Intra-tumor: heterogeneity, location, and antigen presentation. Applicants explored and characterized the effect immunotherapies have on different cell types within the tumor (i.e., Malignant cells, CD8/CD4 T-cells, B cells and Macrophages). The data includes twenty six samples (14 post immunotherapy, 8 anti-CTLA4 & anti-PD-1, 2 anti-PD1 (Nivolumab), 4 anti-CTLA4 (Ipilimumab), and 12 treatment naïve (FIG. 17).

Figure 18:
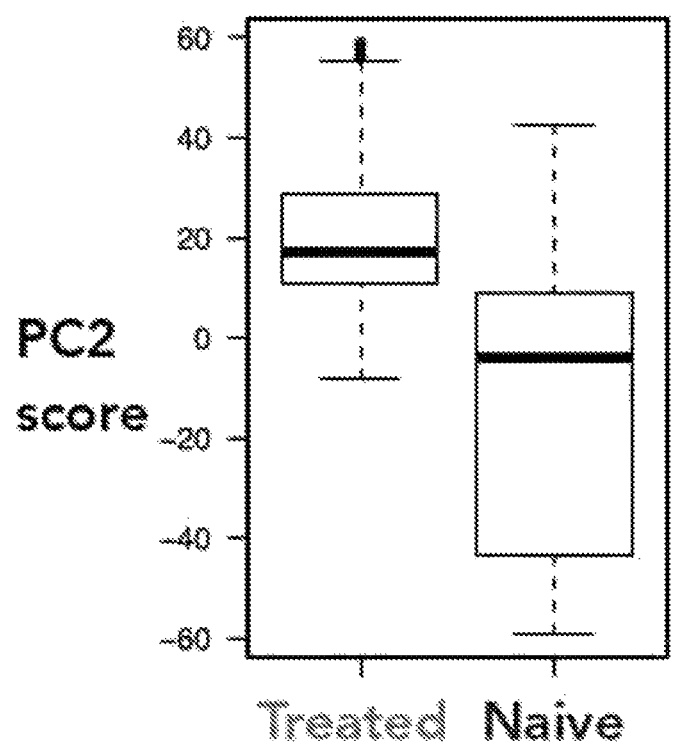
FIG. 18 illustrates the separation of immunotherapy treated and untreated tumors by Principle Component (PC) analysis.

Applicants performed principal component analysis on the expression data. The second Principle Component (PC) separates between immunotherapy resistant and untreated tumors (FIG. 18). Applicants discovered that treatment is the main source of variation in malignant cells between tumors, reflected by the difference in the score of malignant cells from treatment naive and resistant tumors on the second principle component.

Figure 19:
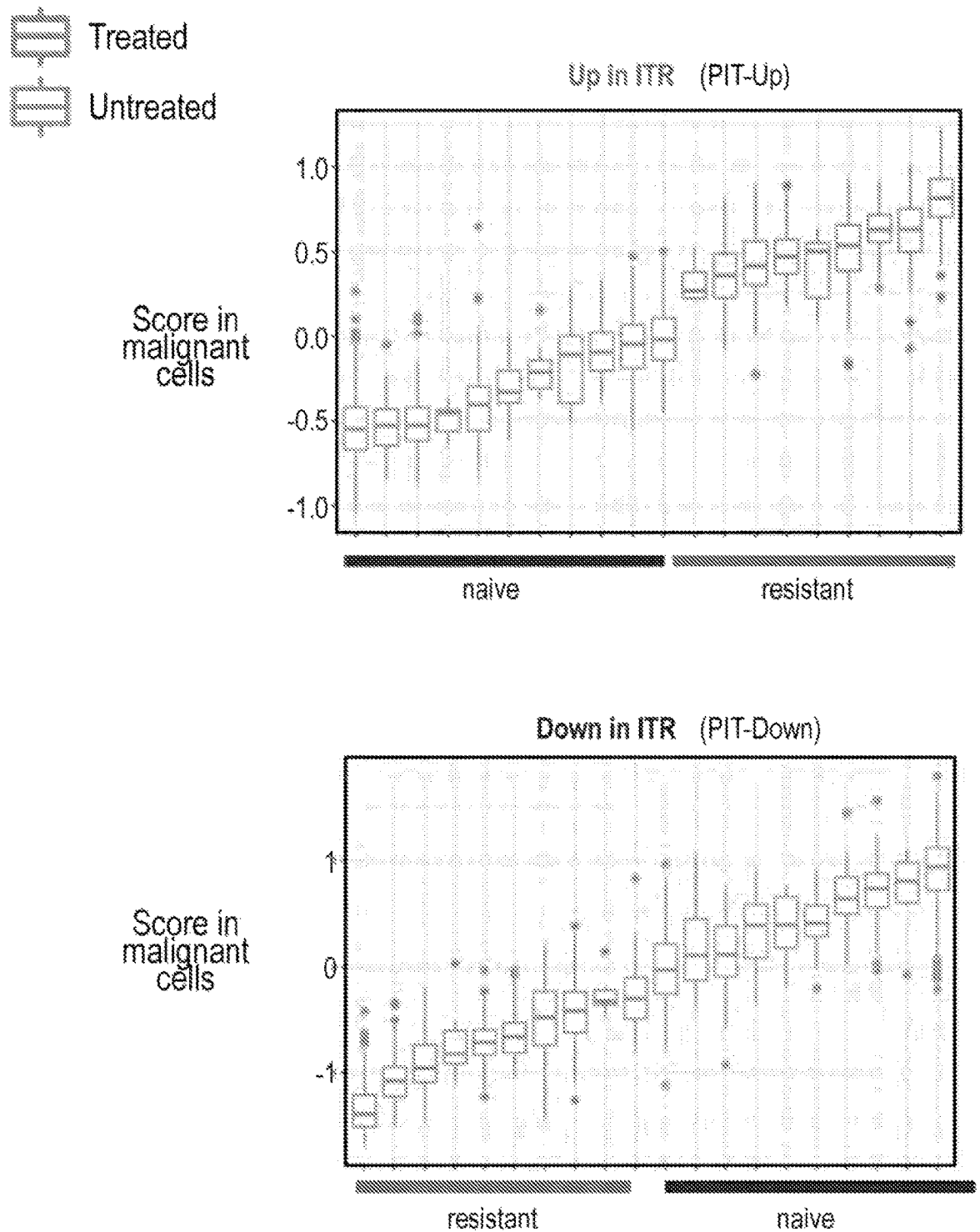
FIG. 19 illustrates the correlation between the resistance signature and patients that are naïve or resistant to immunotherapy.

Applicants analyzed the transcriptome of the malignant cells to identify cell states that are associated with immunotherapy. To this end, Applicants identified differentially expressed genes and derived two post-immunotherapy (PIT) modules, consisting of genes that are up (PIT-up) or down (PIT-down) regulated in PIT malignant cells compared to the untreated ones. In comparison to the treatment naive tumors, all the PIT tumors overexpress the PIT-up module and underexpress the PIT-down module, such that there is a spectrum of expression levels also within each patient group and within the malignant cell population of a single tumor (FIG. 19). The genes within each module are co-expressed, while the two modules are anti-correlated with each other, not only across tumors but also within the malignant cell population of a single tumor. Additionally, the two modules have heavy and opposite weights in the first principle components of the malignant single-cell expression profiles, indicating that immunotherapy is one of the main sources of inter-tumor heterogeneity in the data.

Figure 20:
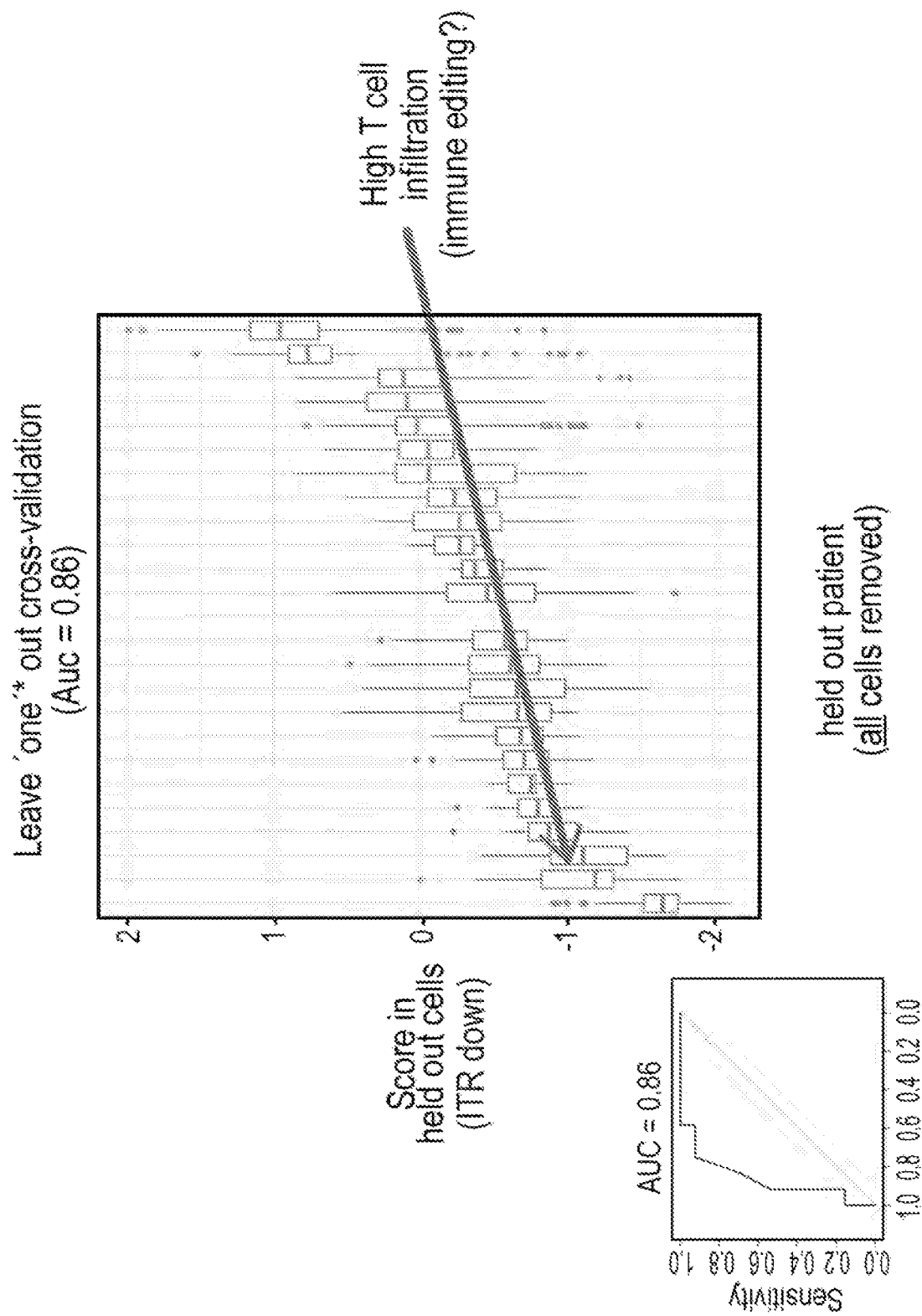
FIG. 20 illustrates a leave-one-out cross validation analysis.
Figure 21:
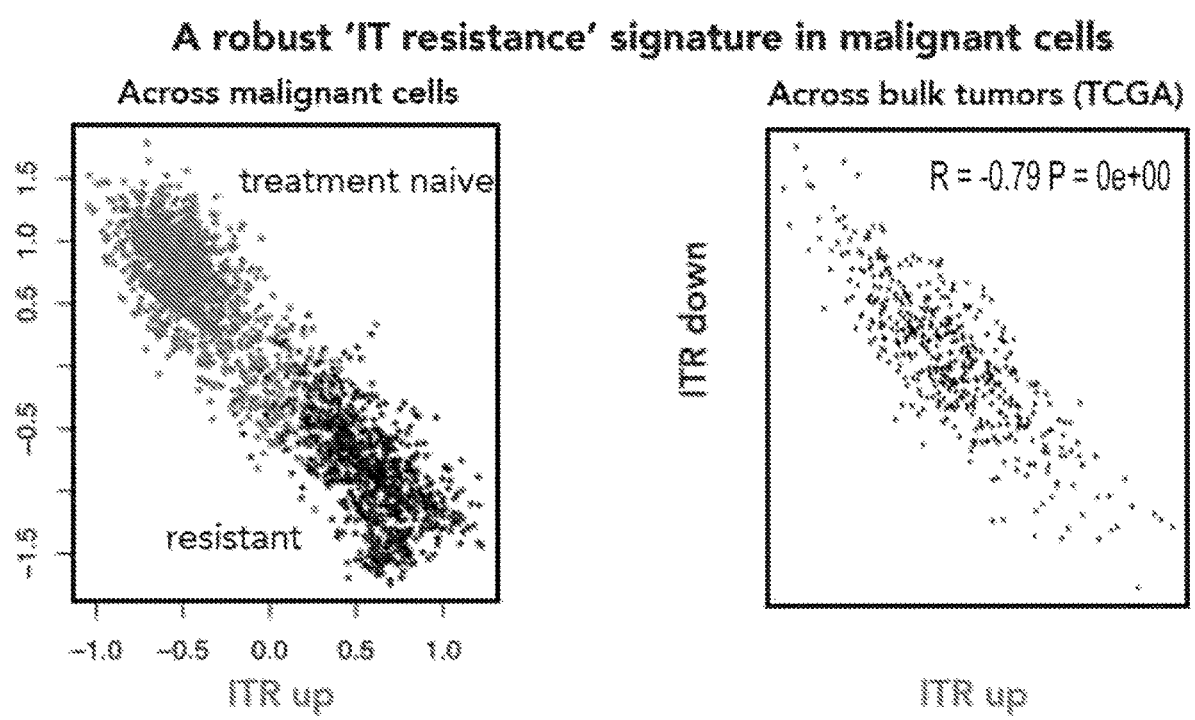
FIG. 21 illustrates mutual exclusive expression of the ITR up and down genes across malignant cells, and their anti-correlation in TCGA.

Applicants applied down sampling and cross-validation to confirm that the PIT modules are robust and generalizable (FIG. 20). More specifically, Applicants repeatedly identified the signatures without accounting for the data of one of the tumors, and showed that the modules were similar to those derived with the full dataset. Furthermore, the modules that were derived based on a training data could still correctly classify the test tumor as either PIT or treatment naive. The signature is very robust. If Applicants leave out all the malignant cells from a given tumor, recalculate it and then assign the cells, Applicants make only one "error" when guessing if the tumor is treatment naive or ITR. This one tumor has a particularly high T cell infiltration. These results testify that, while more data and samples will enable us to refine these modules, the resulting modules are not likely to change substantially. The signature is also supported by the mutual exclusive expression of the up and down genes across malignant cells, and their anti-correlation in TCGA (FIG. 21).

Figure 22:
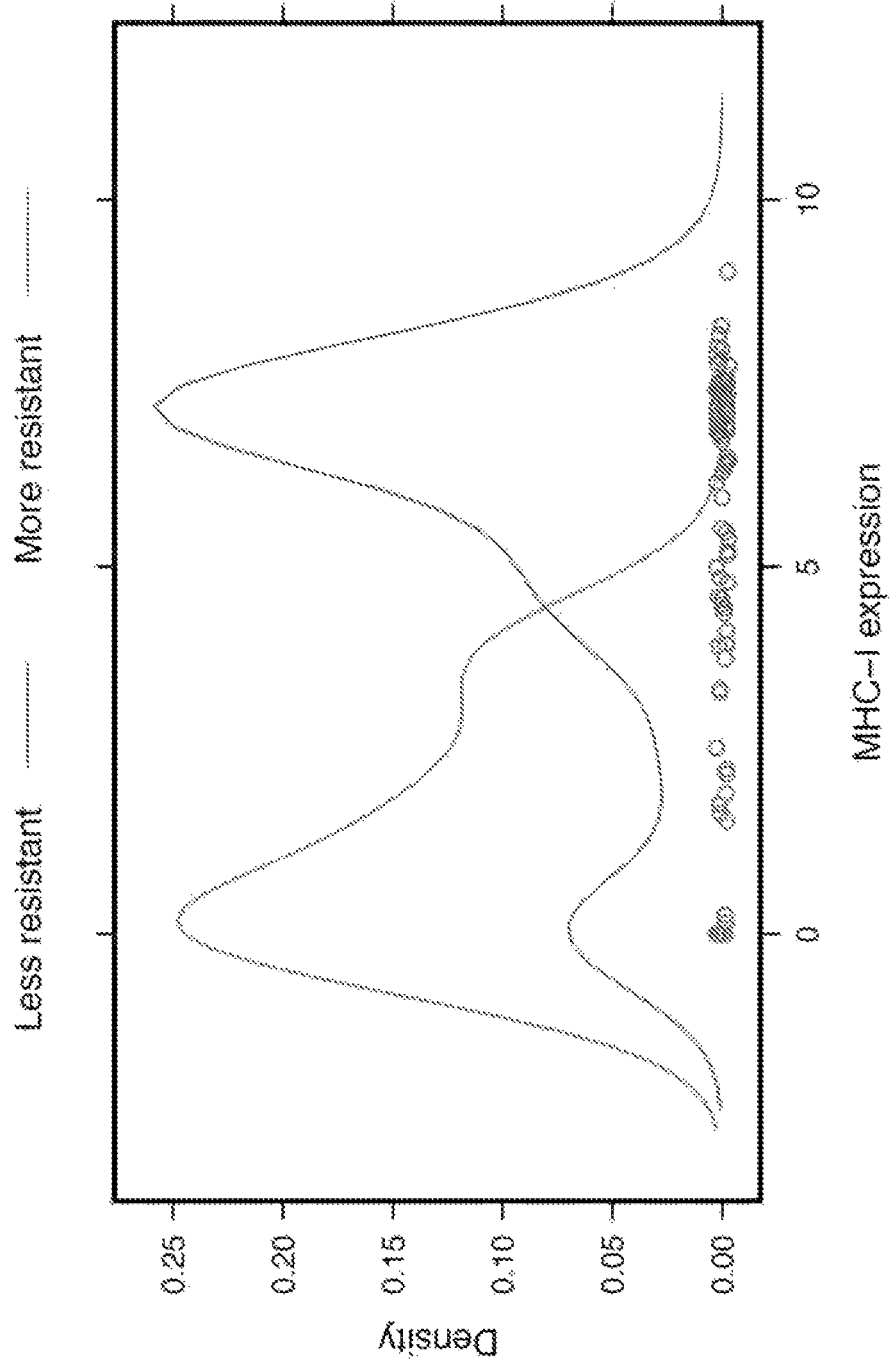
FIG. 22 illustrates the correlation between the resistance signature and MHC-I expression.
Figure 23:
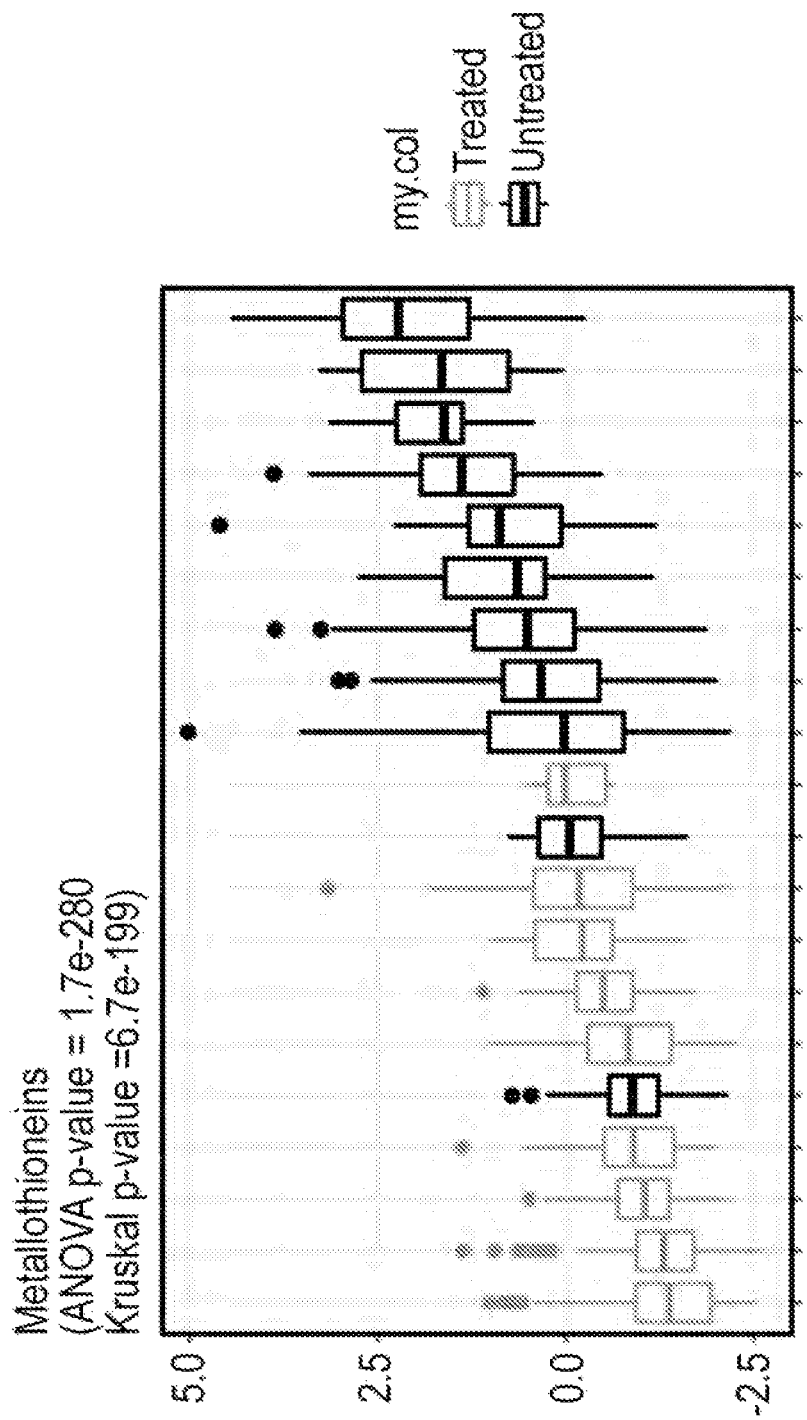
FIG. 23 illustrates the association of metallothionein expression and treated and untreated subjects.

Gene set enrichment analysis of the PIT programs highlights well-established immune-evasion mechanisms as the down-regulation of MHC class I antigen presentation machinery and interferon gamma signaling in PIT cells (Table 1). Cells with less MHC-I expression are more resistant to immunotherapy (FIG. 22). Additionally, it has been recently shown that melanoma tumors that are resistant to ipilimumab therapy contain genomic defects in IFN-gamma pathway genes, and that the knockdown of IFNGR1 promotes tumor growth and reduces mouse survival in response to anti-CTLA-4 therapy. The PIT-down program is also enriched with genes involved in coagulation, IL2-STAT5 signaling, TNFα signaling via NFkB, hypoxia, and apoptosis. The PIT-up program is tightly linked to MYC. It is enriched with MYC targets and according to the connectivity map data (c-map)—MYC knockout alone is able to repress the expression of the entire PIT-up signature. Supporting these findings, it has been shown that MYC modulates immune regulatory molecules, such that its inactivation in mouse tumors enhances the antitumor immune response. Interestingly, Applicants find that metallothioneins (MTs) are overrepresented in the PIT-down program, and show that their expression alone separates between the PIT and untreated samples (FIG. 23). MTs are a family of metal-binding proteins that function as immune modulators and zinc regulators. The secretion of MTs to the extracellular matrix can suppress T-cells and promote T-cell chemotaxis. Interestingly, it has been recently shown that MT2A is a key regulator of CD8 T-cells, such that its inhibition promotes T-cell functionality in the immunosuppressive tumor microenvironment (Singer et al. Cell. 2016 Sep. 8; 166(6): 1500-1511). The underexpression of MTs in the malignant cells of post-immunotherapy tumors could potentially be linked to the role of MT2A in T-cells and to the abundance of zinc in the tumor microenvironment.

TABLE 1

| Pathway | Genes |
|---|---|
| MHC class I antigen presentation machinery | CTSB, HLA-A, HLA-C, HLA-E, HLA-F, PSME1, TAP1, TAPBP |
| Coagulation | ANXA1, CD9, CFB, CTSB, FN1, ITGB3, LAMP2, PROS1, PRSS23, SERPINE1, SPARC, TF |
| TNFα signaling via NFkB | ATF3, BCL6, BIRC3, CD44, EGR1, GADD45B, GEM, JUNB, KLF4, KLF6, NR4A1, PDE4B, SERPINE1, TAP1, TNC |
| IL2/STAT5 signaling | AHNAK, AHR, CCND3, CD44, EMP1, GADD45B, |
| Metallothioneins | IFITM3, IGF1R, ITGA6, KLF6, NFKBIZ, PRNP, RNH1 MT1E, MT1F, MT1G, MT1M, MT1X, MT2A |
| MYC targets | EIF4A1, FBL, HDAC2, ILF2, NCBP1, NOLC1, PABPC1, PRDX3, RPS3, RUVBL2, SRSF7 |

Functional classification of PIT module genes.

Applicants identified an immunotherapy resistance signature by identifying genes that were up and down regulated in immunotherapy treated subjects as compared to untreated subjects (Table 2, 3). The signature was compared to clinical data of subjects that were complete responders to immunotherapy, partial responders and non-responders. The data was also compared to subjects with high survival and low survival.

TABLE 2

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| ANXA1 | 7.58E-02 | 8.19E-01 | -202.40 | -2.44 | -200.00 | -3.02 | FALSE | -2.64 | -1.37 |
| EMP1 | 4.92E-01 | 8.96E-02 | -189.84 | -20.93 | -75.82 | -2.58 | FALSE | 0.69 | 0.60 |
| TSC22D3 | 4.26E-01 | 4.63E-01 | -175.14 | -13.19 | -82.60 | -2.43 | FALSE | -1.52 | -0.32 |
| MT2A | 4.06E-02 | 7.81E-01 | -174.76 | -18.16 | -67.52 | -4.41 | FALSE | -2.83 | -1.80 |
| CTSB | 4.03E-01 | 5.87E-01 | -165.96 | -25.70 | -112.90 | -2.50 | FALSE | -0.44 | 0.56 |
| TM4SF1 | 1.76E-01 | 7.74E-01 | -164.10 | 5.621836397 | -165.5071875 | -1.14 | FALSE | 0.45 | 0.32 |
| CDH19 | 4.35E-02 | 4.15E-01 | -155.59 | -3.79 | -42.42 | -1.53 | FALSE | -2.24 | -1.86 |
| MIA | 3.62E-01 | 4.96E-01 | -152.98 | -4.22 | -60.91 | -1.53 | FALSE | -1.60 | -0.91 |
| SERPINE2 | 2.27E-02 | 1.70E-01 | -151.17 | -31.78 | -46.03 | -1.68 | FALSE | -3.66 | -3.12 |
| SERPINA3 | 1.43E-01 | 4.64E-01 | -148.25 | 13.63 | -229.59 | -1.37 | FALSE | -2.64 | -2.04 |
| S100A6 | 2.91E-01 | 2.01E-01 | -128.57 | -12.30 | -49.34 | -2.42 | FALSE | -0.40 | -0.47 |
| ITGA3 | 3.35E-02 | 9.20E-01 | -123.57 | 1.88215819 | -83.80670184 | -0.97 | FALSE | -0.51 | -0.49 |
| SLC5A3 | 4.64E-01 | 4.71E-01 | -119.83 | 1.06 | -96.80 | -1.71 | FALSE | -6.19 | -4.10 |
| A2M | 3.01E-02 | 4.38E-01 | -118.06 | -15.73720409 | -30.29161959 | -1.07 | FALSE | -2.81 | -1.47 |
| MFI2 | 3.67E-01 | 4.22E-01 | -117.29 | -3.06 | -44.01 | -1.41 | FALSE | 0.46 | 0.38 |
| CSPG4 | 7.50E-02 | 2.24E-01 | -112.90 | -5.56 | -30.13 | -1.87 | FALSE | -1.60 | -1.41 |
| AHNAK | 5.70E-02 | 7.09E-01 | -112.83 | -12.69 | -13.16 | -2.03 | FALSE | -0.45 | -0.38 |
| APOC2 | 6.76E-01 | 1.57E-01 | -111.01 | 4.108007818 | -92.34012794 | -0.52 | FALSE | -0.55 | 0.51 |
| ITGB3 | 1.66E-01 | 3.79E-01 | -110.25 | 0.79 | -109.99 | -1.75 | FALSE | -2.25 | -1.42 |
| NNMT | 4.47E-01 | 6.63E-01 | -110.12 | -1.62 | -122.65 | -2.51 | FALSE | -2.28 | -0.87 |
| ATP1A1 | 2.34E-01 | 4.92E-01 | -107.58 | -19.25 | -26.63 | -1.40 | FALSE | 0.52 | 0.30 |
| SEMA3B | 8.03E-02 | 9.69E-01 | -106.75 | -2.022007432 | -74.18998319 | -1.06 | FALSE | -1.65 | -1.08 |
| CD59 | 3.34E-02 | 7.57E-01 | -101.92 | -16.59 | -40.13 | -1.86 | FALSE | -1.71 | -0.90 |
| PERP | 1.03E-01 | 9.58E-01 | -99.65 | -2.61892627 | -123.0851115 | -1.13 | FALSE | 0.78 | -0.77 |
| EGR1 | 1.98E-01 | 8.54E-01 | -96.70 | -1.43 | -25.74 | -1.30 | FALSE | -0.80 | 0.30 |
| LGALS3 | 2.66E-01 | 6.41E-01 | -96.06 | -57.79606403 | 1.174991366 | -1.19 | FALSE | -0.42 | -0.50 |
| SLC26A2 | 1.86E-01 | 2.65E-01 | -95.69 | 0.615403346 | -34.74613485 | -0.92 | FALSE | -3.62 | -2.73 |
| CRYAB | 2.26E-02 | 5.72E-01 | -94.74 | 0.85 | -139.66 | -1.89 | FALSE | -0.84 | -0.63 |
| HLA-F | 4.70E-02 | 9.62E-01 | -94.42 | -12.84 | -23.07 | -1.82 | FALSE | -4.49 | -1.03 |
| MT1E | 1.78E-01 | 5.89E-01 | -92.61 | -14.66 | -27.25 | -3.00 | FALSE | -1.20 | -1.19 |
| KCNN4 | 1.88E-01 | 7.63E-01 | -92.09 | -1.36 | -108.90 | -2.56 | FALSE | -4.61 | -2.92 |
| CST3 | 1.87E-01 | 6.36E-01 | -90.32 | -3.11 | -43.51 | -2.19 | FALSE | -1.31 | 0.32 |
| CD9 | 6.23E-01 | 4.58E-01 | -89.32 | -9.57 | -19.34 | -2.77 | FALSE | 0.35 | -0.79 |
| TNC | 3.59E-01 | 6.45E-01 | -87.60 | -6.21 | -88.45 | -1.78 | FALSE | -2.72 | -1.10 |
| SGCE | 2.19E-02 | 3.21E-01 | -87.28 | -0.302176627 | -62.80958661 | -1.02 | FALSE | -3.12 | -1.69 |
| NFKBIZ | 2.32E-02 | 9.71E-01 | -86.67 | -4.35 | -30.64 | -2.89 | FALSE | -2.40 | -1.85 |
| PROS1 | 2.16E-02 | 4.37E-01 | -86.35 | -0.52 | -28.78 | -1.72 | FALSE | -0.40 | -0.71 |
| CAV1 | 6.55E-02 | 3.13E-01 | -85.42 | -24.08 | -6.13 | -1.34 | FALSE | -1.43 | -0.72 |
| MFGE8 | 2.64E-01 | 3.77E-01 | -84.81 | -12.26983949 | -19.33461436 | -1.07 | FALSE | -1.84 | -1.29 |
| IGFBP7 | 7.97E-01 | 9.60E-02 | -83.96 | -22.46 | -27.89 | -1.37 | FALSE | -0.37 | 0.88 |
| SLC39A14 | 1.73E-01 | 8.74E-01 | -83.65 | 0.52 | -37.30 | -1.97 | FALSE | -0.52 | -0.67 |
| CD151 | 2.53E-01 | 3.98E-01 | -83.63 | -2.11 | -33.44 | -1.90 | FALSE | -0.56 | -0.63 |
| SCCPDH | 5.51E-01 | 3.85E-01 | -83.37 | -3.18 | -20.08 | -1.68 | FALSE | -1.26 | -1.07 |
| MATN2 | 6.66E-01 | 2.81E-01 | -82.90 | -0.523529704 | -70.36560095 | -1.17 | FALSE | -0.34 | 0.68 |
| DUSP4 | 2.30E-01 | 3.73E-01 | -82.27 | -6.19379111 | -19.37401872 | -1.18 | FALSE | 0.58 | 0.60 |
| APOD | 3.39E-01 | 5.42E-01 | -81.89 | -9.70 | -15.76 | -1.58 | FALSE | -1.62 | -1.49 |
| GAA | 1.72E-01 | 6.87E-01 | -81.55 | -2.56 | -27.32 | -1.50 | FALSE | -1.23 | -0.56 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| CD58 | 1.48E−01 | 5.02E−01 | −81.12 | −1.03 | −40.89 | −2.52 | FALSE | −2.40 | −3.24 |
| HLA-E | 5.00E−02 | 9.47E−01 | −79.92 | −25.19 | −23.50 | −1.86 | FALSE | −3.54 | 0.48 |
| TIMP3 | 4.17E−01 | 8.28E−02 | −79.58 | −6.278620205 | −2.728290317 | −1.11 | FALSE | −1.13 | −1.19 |
| NR4A1 | 1.22E−01 | 6.52E−01 | −79.47 | −14.82 | −8.42 | −1.37 | FALSE | 0.32 | −0.51 |
| FXYD3 | 2.31E−02 | 8.64E−01 | −78.83 | −3.88 | −17.90 | −1.81 | FALSE | −0.47 | −0.96 |
| TAPBP | 9.56E−02 | 9.33E−01 | −78.23 | −9.90 | −25.67 | −1.40 | FALSE | −3.06 | 0.45 |
| CTSD | 2.10E−01 | 4.50E−01 | −76.29 | −35.68 | −12.15 | −1.73 | FALSE | 0.51 | 1.21 |
| NSG1 | 2.25E−01 | 5.26E−02 | −75.54 | −6.8850195 | −45.2569093 | −0.59 | FALSE | NA | NA |
| DCBLD2 | 1.51E−01 | 3.97E−01 | −75.17 | −2.70 | −30.36 | −2.50 | FALSE | −0.93 | −1.69 |
| GBP2 | 3.33E−02 | 4.65E−01 | −74.58 | −6.60 | −112.34 | −3.42 | FALSE | −9.49 | −2.53 |
| FAM3C | 2.17E−01 | 3.24E−01 | −73.79 | −1.099557442 | −34.2099212 | −0.80 | FALSE | −4.22 | −2.95 |
| CALU | 7.70E−01 | 2.45E−01 | −73.21 | −2.96 | −22.58 | −1.44 | FALSE | 0.34 | −0.56 |
| DDR1 | 1.30E−02 | 9.47E−01 | −72.94 | 1.320302264 | −41.93649931 | −0.93 | FALSE | −0.66 | −1.98 |
| TIMP1 | 2.44E−01 | 1.95E−01 | −72.66 | 0.832732502 | −44.31465375 | −1.27 | FALSE | −2.53 | −0.80 |
| LRPAP1 | 3.26E−01 | 5.82E−01 | −72.03 | −8.741825947 | −33.28409269 | −1.12 | FALSE | 0.55 | 0.62 |
| CD44 | 1.20E−01 | 7.83E−01 | −71.20 | −42.03 | −7.56 | −1.31 | FALSE | −1.20 | −0.70 |
| GSN | 1.83E−01 | 9.76E−02 | −71.17 | −7.066367901 | −8.379109684 | −1.25 | FALSE | −0.48 | −0.40 |
| PTRF | 1.20E−01 | 1.26E−01 | −70.87 | −11.99 | −21.89 | −2.19 | FALSE | −0.81 | −0.88 |
| CAPG | 3.42E−01 | 4.17E−01 | −70.60 | −17.12110776 | −3.792804113 | −1.21 | FALSE | −0.42 | 0.69 |
| CD47 | 1.14E−01 | 8.55E−01 | −68.77 | −5.84 | −21.44 | −2.75 | FALSE | −5.65 | −3.19 |
| CCND3 | 1.48E−01 | 7.90E−01 | −68.60 | −0.85 | −62.30 | −2.43 | FALSE | −0.65 | 0.43 |
| HLA-C | 1.63E−01 | 4.28E−01 | −68.47 | −22.92 | −13.18 | −1.33 | FALSE | −4.97 | −1.10 |
| CARD16 | 3.15E−01 | 9.14E−01 | −68.09 | −1.20 | −51.51 | −1.48 | FALSE | −0.65 | 0.50 |
| DUSP6 | 3.52E−01 | 3.46E−01 | −67.35 | −1.443530586 | −32.17071544 | −0.53 | FALSE | −4.33 | −2.45 |
| IL1RAP | 6.76E−03 | 4.53E−01 | −66.82 | −2.25 | −24.21 | −3.64 | FALSE | −1.77 | −1.51 |
| FGFR1 | 7.25E−02 | 1.31E−01 | −66.47 | 9.950506533 | −57.92951091 | −1.14 | FALSE | −0.49 | −0.62 |
| TRIML2 | 8.90E−01 | 1.20E−01 | −66.24 | 21.84557542 | −68.40922705 | −0.49 | FALSE | −1.47 | −1.52 |
| ZBTB38 | 7.00E−01 | 3.77E−01 | −65.84 | −6.25 | −8.44 | −1.64 | FALSE | −3.18 | −3.11 |
| PRSS23 | 6.42E−01 | 8.53E−02 | −63.62 | −0.34 | −35.59 | −1.53 | FALSE | −0.54 | 0.37 |
| S100B | 4.64E−01 | 6.74E−01 | −63.21 | −18.39689161 | −0.989534032 | −1.08 | FALSE | −1.72 | −0.73 |
| PLP2 | 1.29E−02 | 7.48E−01 | −63.01 | −3.16 | −7.46 | −1.46 | FALSE | 0.34 | −0.80 |
| LAMP2 | 2.64E−01 | 6.13E−01 | −62.96 | −5.73 | −13.68 | −1.48 | FALSE | −1.19 | −1.06 |
| FCGR2A | 8.31E−04 | 8.38E−01 | −62.40 | −0.623470411 | −28.64302633 | −0.93 | FALSE | −6.97 | −2.82 |
| LGALS1 | 7.24E−02 | 1.72E−01 | −61.40 | −12.41 | −1.43 | −1.38 | FALSE | 0.77 | 1.02 |
| NPC1 | 9.96E−02 | 4.70E−01 | −60.93 | −2.330822107 | −12.24708172 | −0.83 | FALSE | 0.37 | −0.31 |
| UBC | 6.96E−01 | 4.80E−01 | −60.76 | −6.83 | −41.63 | −1.69 | FALSE | −1.71 | −0.61 |
| TNFRSF12A | 8.03E−02 | 7.99E−01 | −60.31 | 1.73 | −37.68 | −1.53 | FALSE | −0.63 | −0.66 |
| SPON2 | 1.56E−01 | 2.67E−01 | −59.94 | −0.444813435 | −54.28549635 | −0.87 | FALSE | −0.62 | 0.47 |
| EEA1 | 4.38E−01 | 4.73E−01 | −59.50 | 0.680184335 | −13.23401918 | −1.02 | FALSE | −1.33 | −2.70 |
| CD63 | 7.00E−01 | 2.67E−01 | −59.49 | −14.73233445 | −14.29263209 | −1.30 | FALSE | 1.10 | 0.65 |
| SGK1 | 4.34E−01 | 3.83E−01 | −59.42 | −2.77588165 | −13.5729112 | −0.52 | FALSE | 0.63 | 0.68 |
| HPCAL1 | 1.03E−01 | 6.53E−02 | −59.22 | −8.70 | −10.48 | −1.83 | FALSE | −0.69 | −0.91 |
| HLA-B | 5.22E−02 | 8.84E−01 | −58.69 | −16.7731158 | −7.71200708 | −1.18 | FALSE | −5.85 | −0.79 |
| SERPINA1 | 5.48E−01 | 4.51E−01 | −58.50 | 4.67012442 | −61.13154453 | −0.74 | FALSE | −2.78 | 0.47 |
| JUN | 3.03E−01 | 7.09E−01 | −58.42 | 1.182777495 | −17.43164065 | −1.18 | FALSE | −0.89 | 0.32 |
| HLA-A | 4.98E−02 | 9.30E−01 | −58.18 | −26.50 | −18.12 | −1.46 | FALSE | −2.09 | −0.34 |
| RAMP1 | 5.43E−01 | 2.02E−01 | −58.03 | −11.93 | −63.50 | −1.60 | FALSE | 0.45 | 0.53 |
| TPP1 | 7.54E−02 | 8.18E−01 | −57.91 | −18.16810565 | −4.426800522 | −1.02 | FALSE | −0.70 | −0.41 |
| FYB | 1.49E−01 | 7.19E−01 | −57.13 | −2.867192419 | −45.73445912 | −0.52 | FALSE | −4.33 | −0.75 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| RDH5 | 1.02E−01 | 8.47E−01 | −56.99 | 1.683618144 | −39.48423368 | −0.59 | FALSE | −3.18 | −2.30 |
| SDC3 | 1.84E−01 | 4.92E−01 | −56.80 | −2.227320442 | −7.930319849 | −0.90 | FALSE | −1.46 | −0.67 |
| PRKCDBP | 2.03E−01 | 3.35E−01 | −56.58 | −3.45 | −25.88 | −2.48 | FALSE | −0.69 | −0.46 |
| CSGALNACT1 | 3.14E−01 | 1.30E−01 | −56.46 | −1.005860494 | −21.10234746 | −1.19 | FALSE | −5.34 | −3.85 |
| HLA-H | 2.38E−01 | 7.55E−01 | −56.36 | −26.8522345 | −2.691659575 | −0.99 | FALSE | −2.77 | −0.44 |
| CLEC2B | 9.68E−04 | 1.64E−01 | −55.69 | −3.93 | −40.47 | −1.87 | FALSE | −8.63 | −4.19 |
| ATP1B1 | 4.75E−01 | 9.93E−02 | −55.53 | 3.790248535 | −73.66520645 | −0.74 | FALSE | −3.09 | −1.56 |
| DAG1 | 2.86E−01 | 6.40E−01 | −55.41 | −3.15 | −5.62 | −1.66 | FALSE | −0.71 | −0.52 |
| NFKBIA | 5.25E−03 | 5.77E−01 | −55.35 | −7.315272323 | −17.05872829 | −1.05 | FALSE | −4.18 | −0.54 |
| SRPX | 3.36E−01 | 2.51E−01 | −55.12 | −7.37 | −3.79 | −2.09 | FALSE | −0.80 | −1.57 |
| CASP1 | 6.92E−02 | 8.19E−01 | −55.00 | −1.031280571 | −66.1978381 | −0.96 | FALSE | −1.32 | 0.38 |
| DPYSL2 | 1.23E−02 | 7.32E−01 | −54.92 | −1.056511462 | −99.22916498 | −1.14 | FALSE | −0.77 | 0.34 |
| S100A1 | 1.82E−01 | 1.09E−01 | −54.68 | −14.25397572 | −14.42420921 | −0.63 | FALSE | −0.61 | −0.78 |
| FLJ43663 | Inf | Inf | −54.67 | −6.490292736 | −10.57910257 | −1.20 | FALSE | −4.45 | −4.16 |
| UPP1 | 1.21E−01 | 7.67E−01 | −54.34 | −7.451372117 | −2.528276372 | −1.13 | FALSE | 1.67 | 1.17 |
| APOE | 3.46E−01 | 1.80E−01 | −54.14 | −4.357609216 | −10.06500479 | 0.32 | FALSE | 0.31 | 1.11 |
| LPL | 1.87E−01 | 1.61E−01 | −54.00 | −6.59 | −51.84 | −2.19 | FALSE | −0.45 | −0.45 |
| KLF4 | 3.63E−02 | 9.02E−01 | −53.99 | −0.31 | −23.01 | −2.34 | FALSE | −0.55 | −0.36 |
| SLC20A1 | 3.66E−01 | 3.38E−01 | −53.68 | 0.47 | −18.37 | −2.06 | FALSE | −2.41 | −1.61 |
| LGALS3BP | 1.92E−01 | 8.74E−01 | −53.62 | −12.98 | −5.64 | −1.68 | FALSE | −0.61 | 0.43 |
| LINC00116 | 4.39E−01 | 1.53E−01 | −53.33 | 0.38 | −29.09 | −1.90 | FALSE | NA | NA |
| RPS4Y1 | 8.64E−02 | 9.11E−01 | −53.11 | −64.09755214 | −3.82061851 | −0.66 | FALSE | 1.34 | 1.23 |
| SQRDL | 9.82E−02 | 8.26E−01 | −52.38 | −5.25 | −38.28 | −3.08 | FALSE | −3.94 | −1.26 |
| ITM2B | 2.72E−02 | 7.97E−01 | −52.21 | −10.23 | −13.51 | −1.63 | FALSE | −5.41 | −2.59 |
| TMX4 | 4.28E−01 | 2.58E−01 | −52.20 | −1.16 | −13.17 | −1.39 | FALSE | −2.83 | −1.33 |
| IL6ST | 1.01E−02 | 3.26E−01 | −52.05 | −2.89 | −6.37 | −1.61 | FALSE | −1.92 | −0.83 |
| BIRC3 | 1.72E−03 | 7.32E−01 | −51.42 | −7.23 | −41.19 | −4.32 | FALSE | −7.28 | −2.50 |
| ANXA2 | 4.45E−01 | 5.66E−01 | −51.27 | −12.18 | −8.25 | −2.15 | FALSE | 0.78 | 0.68 |
| ZBTB20 | 2.19E−01 | 7.01E−01 | −51.13 | −1.09 | −25.68 | −1.43 | FALSE | −0.42 | 0.31 |
| GRN | 9.79E−02 | 5.69E−01 | −51.04 | −3.33479904 | 10.58500961 | −0.92 | FALSE | 0.51 | 0.95 |
| SERPINE1 | 2.26E−01 | 8.94E−02 | −50.78 | 0.45 | 45.37 | −2.08 | FALSE | −1.78 | −0.47 |
| MT1X | 9.41E−02 | 7.92E−01 | −50.16 | −2.90 | −20.02 | −1.51 | FALSE | −1.45 | −2.13 |
| FCGR2C | 6.04E−04 | 3.75E−01 | −50.04 | −6.560207399 | −28.23432948 | −0.90 | FALSE | −5.71 | −2.00 |
| ACSL3 | 4.57E−01 | 3.37E−01 | −49.94 | −3.939970091 | −4.775352737 | −0.49 | FALSE | −0.93 | −1.32 |
| IFI27 | 2.77E−01 | 4.25E−01 | −49.91 | −24.12491388 | −7.193933103 | −1.12 | FALSE | −3.69 | −1.74 |
| AEBP1 | 7.23E−03 | 7.36E−01 | −49.86 | −0.652064041 | −9.791519511 | −1.24 | FALSE | −0.31 | 0.33 |
| TIPARP | 6.67E−02 | 5.81E−01 | −49.73 | −1.699010303 | −20.12848456 | −1.30 | FALSE | −2.25 | −1.20 |
| VAMP8 | 7.89E−02 | 4.82E−01 | −49.73 | −5.340727074 | −25.95153555 | −0.78 | FALSE | −0.77 | 1.19 |
| DST | 3.55E−01 | 6.19E−01 | −48.89 | −2.44 | −3.35 | −1.59 | FALSE | 0.47 | 0.55 |
| IFI35 | 1.88E−01 | 7.91E−01 | −48.67 | −7.02 | −6.98 | −2.31 | FALSE | −3.05 | −1.00 |
| ITGB1 | 3.60E−01 | 2.39E−01 | −48.52 | −3.58 | −9.62 | −2.66 | FALSE | −1.85 | −1.87 |
| BCL6 | 8.45E−02 | 8.06E−01 | −48.50 | −4.89 | −22.66 | −3.13 | FALSE | −4.25 | −1.89 |
| ERBB3 | 1.90E−01 | 6.37E−01 | −48.36 | −9.73134426 | −0.439078261 | −0.73 | FALSE | 0.53 | 0.33 |
| ZMYM6NB | 6.10E−01 | 1.14E−01 | −47.89 | −1.77 | −21.83 | −1.45 | FALSE | NA | NA |
| CLIC4 | 1.22E−01 | 3.15E−01 | −47.81 | −1.16 | −17.42 | −1.41 | FALSE | −4.55 | −3.87 |
| FOS | 4.13E−01 | 6.43E−01 | −47.57 | −6.386092681 | −1.042139346 | −0.73 | FALSE | −0.87 | −0.36 |
| IGF1R | 3.62E−01 | 4.41E−01 | −47.19 | −1.54 | −23.75 | −1.37 | FALSE | −0.36 | −0.58 |
| PLEKHB1 | 2.57E−02 | 3.38E−01 | −46.81 | 6.095867912 | 42.43208655 | −0.54 | FALSE | −1.60 | −1.68 |
| GOLGB1 | 5.56E−01 | 4.63E−01 | −46.38 | −4.661054566 | −8.368284482 | −1.24 | FALSE | −2.84 | −2.24 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| PSAP | 1.12E-01 | 7.72E-01 | -45.94 | -17.73630528 | 0.396372679 | -1.07 | FALSE | -0.67 | 0.69 |
| RNF145 | 4.06E-02 | 6.25E-01 | -45.93 | -4.00 | -9.25 | -2.29 | FALSE | -2.59 | -1.12 |
| CTSL1 | 5.49E-03 | 2.91E-01 | -45.88 | -13.12164871 | -18.65717439 | -0.84 | FALSE | 0.67 | 0.86 |
| SYNGR2 | 2.82E-03 | 7.59E-01 | -45.78 | -5.09168104 | -10.48190321 | -0.94 | FALSE | -1.25 | 0.81 |
| HTATIP2 | 8.60E-01 | 1.13E-01 | -45.69 | -2.00 | -19.85 | -2.43 | FALSE | -1.31 | -1.68 |
| KLF6 | 2.33E-02 | 6.52E-01 | -45.62 | -18.85 | 1.21 | -1.57 | FALSE | -0.45 | -0.44 |
| LOC541471 | Inf | Inf | -45.38 | -2.644136674 | -11.14964202 | -1.23 | FALSE | 1.16 | 1.08 |
| SAT1 | 2.24E-01 | 3.62E-01 | -44.81 | -30.71664031 | -1.26808839 | -0.55 | FALSE | -0.81 | 0.50 |
| FBXO32 | 1.79E-01 | 2.88E-01 | -44.73 | 0.322762583 | -6.16164852 | -0.32 | FALSE | 0.70 | 0.40 |
| S100A10 | 5.31E-03 | 6.74E-01 | -44.66 | -22.95 | 0.42 | -2.01 | FALSE | 0.38 | 0.48 |
| ATF3 | 4.52E-01 | 3.92E-01 | -44.63 | 1.63 | -38.08 | -2.50 | FALSE | -1.55 | 0.34 |
| SCARB2 | 8.77E-02 | 6.12E-01 | -44.43 | -2.576905156 | -2.015225226 | -1.16 | FALSE | -1.06 | -0.77 |
| GPNMB | 1.82E-01 | 7.59E-01 | -44.30 | -27.37333779 | -0.672876712 | -0.74 | FALSE | 0.44 | 0.73 |
| FCRLA | 7.03E-03 | 9.79E-01 | -44.01 | -10.35 | -13.12 | -1.87 | FALSE | -0.40 | 0.40 |
| CLU | 6.77E-01 | 4.88E-01 | -43.85 | 2.663183144 | -40.06196504 | -0.63 | FALSE | -1.13 | 0.40 |
| ADM | 6.89E-01 | 6.95E-02 | -43.84 | -4.543551718 | -28.96929856 | -0.76 | FALSE | 0.30 | 0.30 |
| TF | 5.05E-01 | 4.79E-01 | -43.65 | -8.72 | -51.07 | -1.33 | FALSE | -1.03 | -0.56 |
| CAST | 2.14E-02 | 8.85E-01 | -43.40 | -2.23 | -9.80 | -1.38 | FALSE | -1.51 | -1.09 |
| C10orf54 | 2.37E-01 | 5.08E-01 | -43.23 | -1.005464269 | -47.29182888 | -1.01 | FALSE | -3.61 | 0.82 |
| ITGA6 | 4.78E-01 | 4.15E-01 | -43.18 | -3.18 | -12.52 | -2.60 | FALSE | -3.43 | -1.94 |
| PSMB9 | 1.02E-01 | 7.61E-01 | -43.08 | -9.75 | -11.68 | -1.87 | FALSE | -6.40 | -1.66 |
| BACE2 | 3.23E-01 | 6.02E-01 | -43.02 | -1.544458411 | -3.818105651 | -0.83 | FALSE | 2.35 | 1.69 |
| GADD45B | 4.04E-01 | 1.97E-01 | -42.59 | -1.28 | -35.87 | -1.53 | FALSE | -1.56 | 0.60 |
| IFI27L2 | 4.94E-01 | 1.42E-01 | -42.51 | -11.43 | -4.73 | -1.31 | FALSE | -0.54 | -0.68 |
| FADS3 | 3.81E-01 | 5.31E-01 | -42.38 | -2.307281418 | -10.48779629 | -0.84 | FALSE | -0.73 | -0.64 |
| GPR155 | 4.45E-01 | 3.44E-01 | -42.36 | -1.727392739 | -9.730760161 | -0.67 | FALSE | -2.99 | -1.44 |
| IFNGR2 | 2.69E-02 | 5.64E-01 | -42.34 | -2.678730729 | -5.824501595 | -1.16 | FALSE | -2.71 | -1.79 |
| NEAT1 | 1.24E-03 | 9.34E-01 | -42.32 | -3.957711442 | -4.816575504 | -0.65 | FALSE | -2.07 | -2.38 |
| ARL6IP5 | 9.95E-02 | 8.05E-01 | -42.03 | -5.061500123 | -6.026877076 | -1.20 | FALSE | -4.08 | -2.21 |
| GJB1 | 6.66E-02 | 6.60E-01 | -42.02 | -3.94868444 | -3.639865415 | -0.32 | FALSE | -0.31 | 0.38 |
| ACSL4 | 6.24E-01 | 3.88E-01 | -41.97 | -1.75 | -14.86 | -2.59 | FALSE | -6.05 | -3.62 |
| ATP1B3 | 2.92E-02 | 6.43E-01 | -41.66 | -2.82 | -21.79 | -3.00 | FALSE | -0.52 | -0.79 |
| ECM1 | 1.35E-01 | 5.94E-01 | -41.65 | -2.62 | -6.36 | -1.47 | FALSE | 2.45 | 1.30 |
| APLP2 | 4.94E-01 | 1.91E-01 | -41.49 | 1.55753898 | -32.79252137 | -0.99 | FALSE | -1.94 | -2.11 |
| ANGPTL4 | 4.14E-01 | 2.31E-01 | -41.48 | -0.66 | -57.88 | -1.62 | FALSE | -0.39 | 0.38 |
| GPR56 | 7.32E-01 | 6.52E-01 | -41.45 | -18.86181027 | 6.113225588 | 0.32 | FALSE | 1.27 | 1.10 |
| SYPL1 | 2.59E-01 | 7.74E-01 | -41.38 | -2.204809487 | -11.39626417 | -1.08 | FALSE | -1.57 | -3.14 |
| FNDC3B | 2.11E-01 | 3.32E-01 | -41.27 | -1.78 | -19.28 | -1.86 | FALSE | -4.21 | -2.77 |
| CYBRD1 | 3.43E-01 | 9.88E-02 | -41.01 | -3.84 | -6.47 | -1.37 | FALSE | -1.60 | -1.51 |
| CTSA | 1.55E-01 | 5.79E-01 | -40.89 | -3.17 | -15.31 | -1.86 | FALSE | 0.49 | 0.68 |
| MCL1 | 4.84E-01 | 4.49E-01 | -40.82 | -0.665221316 | -21.44924463 | -1.22 | FALSE | -4.37 | -1.75 |
| LEF1 | 1.84E-01 | 7.45E-01 | -40.69 | -0.409062265 | -22.95759126 | -0.36 | FALSE | -0.88 | -0.46 |
| BBX | 2.43E-01 | 5.39E-01 | -40.61 | -0.61 | -21.43 | -1.67 | FALSE | -3.83 | -2.98 |
| FKBP5 | 5.46E-01 | 2.10E-01 | -40.55 | -9.0201160799 | -25.90285892 | -1.24 | FALSE | -1.88 | -0.53 |
| FAM114A1 | 7.76E-01 | 2.18E-01 | -40.47 | -3.16 | -18.85 | -1.90 | FALSE | -0.54 | -0.53 |
| LTBP3 | 1.66E-01 | 4.22E-01 | -40.27 | 3.20667713 | -16.87434626 | -0.99 | FALSE | -2.15 | -2.16 |
| HSPA1A | 9.37E-01 | 1.13E-01 | -40.16 | 9.037838299 | -41.23649886 | -0.31 | FALSE | 1.23 | 1.55 |
| EPHX2 | 1.42E-01 | 2.31E-01 | -40.08 | -1.222892988 | 48.82245871 | -1.07 | FALSE | 0.77 | 0.95 |
| ITGA7 | 6.60E-01 | 3.30E-01 | -40.03 | 15.86332961 | -39.83592494 | 0.37 | FALSE | 0.61 | -0.61 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| AGA | 2.23E-01 | 7.32E-01 | -39.91 | 0.536274519 | -9.136581859 | -0.68 | FALSE | -1.38 | -1.08 |
| LYRM9 | 7.78E-03 | 8.61E-03 | -39.80 | 1.964812062 | -24.63102517 | -0.69 | FALSE | NA | NA |
| CREG1 | 2.30E-01 | 6.57E-01 | -39.71 | -1.46 | -13.57 | -1.52 | FALSE | -3.57 | -3.22 |
| IFI6 | 4.46E-01 | 3.38E-01 | -39.64 | -15.10 | 0.69 | -1.73 | FALSE | -1.61 | -0.66 |
| JUNB | 3.17E-01 | 3.06E-01 | -39.64 | 1.25 | -18.40 | -1.74 | FALSE | -1.43 | -0.32 |
| SPTBN1 | 6.95E-03 | 6.68E-02 | -39.48 | -10.19774666 | 1.9742265 | -0.96 | FALSE | 0.37 | -0.44 |
| PRNP | 1.27E-01 | 7.68E-01 | -39.20 | -0.86 | -16.57 | -1.55 | FALSE | -2.85 | -2.80 |
| TNFSF4 | 9.86E-01 | 3.54E-03 | -38.88 | 16.30016407 | -42.88092111 | -0.42 | FALSE | -3.81 | -2.50 |
| C8orf40 | 2.61E-01 | 2.10E-01 | -38.60 | -0.90 | -18.77 | -2.97 | FALSE | -0.99 | -1.72 |
| SEL1L | 4.31E-01 | 4.74E-01 | -38.58 | -3.90 | -1.91 | -1.65 | FALSE | -3.19 | -2.36 |
| SNX9 | 8.39E-02 | 9.43E-01 | -38.40 | 4.21773408 | -17.87314667 | -0.31 | FALSE | -1.99 | -2.10 |
| KRT10 | 7.68E-01 | 1.86E-01 | -38.33 | 6.615582665 | -27.12457887 | -1.01 | FALSE | 2.72 | 0.66 |
| EPDR1 | 1.94E-01 | 1.86E-01 | -37.93 | 4.58 | -42.43 | -1.53 | FALSE | -0.35 | -0.76 |
| EGR2 | 2.42E-01 | 1.28E-01 | -37.72 | -0.332043956 | -14.27003379 | -1.16 | FALSE | -2.88 | -0.63 |
| GATSL3 | 1.63E-01 | 1.34E-02 | -37.61 | 7.800143337 | -24.63977081 | -0.35 | FALSE | -0.94 | -0.81 |
| COL16A1 | 3.73E-01 | 3.56E-01 | -37.54 | -2.47 | -38.81 | -1.42 | FALSE | -1.72 | -0.87 |
| CD55 | 5.71E-01 | 1.64E-01 | -37.49 | -1.97067768 | -9.604169548 | -0.97 | FALSE | -1.46 | -4.40 |
| CRELD1 | 5.86E-01 | 6.12E-01 | -37.35 | 5.47 | -34.69 | -1.57 | FALSE | -1.13 | -0.68 |
| SVIP | 5.84E-01 | 1.64E-01 | -37.25 | -0.974568455 | -25.31871464 | -0.74 | FALSE | -1.56 | -1.15 |
| NFE2L1 | 8.30E-02 | 8.74E-01 | -37.12 | -0.70 | -10.29 | -1.42 | FALSE | 1.23 | 0.70 |
| PRDX1 | 6.51E-01 | 4.55E-01 | -36.94 | -3.087427147 | -24.82199094 | -0.54 | FALSE | 0.70 | 0.62 |
| B2M | 4.43E-02 | 7.71E-01 | -36.89 | -21.10505197 | -26.41773682 | -1.10 | FALSE | -7.29 | -2.96 |
| PDE4DIP | 5.31E-01 | 5.09E-02 | -36.89 | -0.402602515 | -9.208907424 | -0.71 | FALSE | 0.49 | 0.41 |
| APOL1 | 1.22E-01 | 6.68E-01 | -36.88 | -1.287252758 | -17.14787261 | -0.74 | FALSE | -5.74 | -1.36 |
| CREB3L2 | 4.17E-01 | 4.63E-01 | -36.84 | 0.358284954 | -2.018391143 | -0.49 | FALSE | -0.60 | -0.70 |
| EVA1A | 1.57E-01 | 6.76E-01 | -36.71 | -0.761040106 | -18.07156414 | -0.66 | FALSE | NA | NA |
| TIMP2 | 1.13E-01 | 8.26E-01 | -36.71 | -0.626230588 | -4.251996112 | -0.64 | FALSE | 1.22 | 0.72 |
| STAT3 | 1.90E-01 | 6.70E-01 | -36.62 | -0.369941565 | -8.5293768 | -1.07 | FALSE | -3.12 | -0.90 |
| EZH1 | 5.10E-02 | 3.93E-01 | -36.54 | -0.417829156 | -9.6734554 | -1.13 | FALSE | -2.33 | -2.81 |
| SPRY2 | 1.85E-02 | 2.34E-01 | -36.26 | -1.08 | -25.28 | -1.61 | FALSE | -2.42 | -2.39 |
| ITGA10 | 6.22E-01 | 1.93E-01 | -36.13 | -2.05617709 | -7.093599209 | -0.71 | FALSE | -1.57 | -1.75 |
| TGOLN2 | 2.71E-01 | 6.43E-01 | -35.99 | -1.61 | -8.04 | -1.52 | FALSE | -2.20 | -1.14 |
| NFAT5 | 3.84E-02 | 6.11E-01 | -35.92 | -0.97 | -7.21 | -1.45 | FALSE | -2.99 | -2.31 |
| CD46 | 7.87E-02 | 3.15E-01 | -35.83 | -11.65 | -0.60 | -1.53 | FALSE | -4.30 | -4.97 |
| HLA-G | 1.55E-01 | 5.82E-01 | -35.67 | -28.13806449 | -4.324385401 | -1.15 | FALSE | -2.09 | -0.41 |
| NPC2 | 4.63E-03 | 2.90E-01 | -35.66 | -14.30417724 | 0.495091905 | -0.40 | FALSE | 0.54 | 1.18 |
| LOC100127888 | 6.29E-02 | 8.12E-01 | -35.63 | -11.84 | -3.62 | -1.37 | FALSE | 0.83 | -0.35 |
| LXN | 1.66E-01 | 5.62E-01 | -35.60 | -4.54 | -40.35 | -2.72 | FALSE | -0.74 | -0.38 |
| MT1M | 3.49E-01 | 2.33E-01 | -35.36 | -14.10 | -11.08 | -3.18 | FALSE | -0.69 | -0.68 |
| C16orf45 | 3.02E-03 | 6.46E-01 | -35.32 | -0.76 | -48.53 | -1.56 | FALSE | -2.09 | -1.93 |
| LOXL3 | 8.91E-01 | 4.37E-02 | -35.03 | 4.82 | -40.56 | -1.35 | FALSE | -3.28 | -1.82 |
| LINC00152 | 5.34E-01 | 3.79E-01 | -34.97 | -5.73 | -8.24 | -1.32 | FALSE | NA | NA |
| PDK4 | 6.52E-01 | 1.85E-01 | -34.90 | -5.780192629 | -25.27607059 | -0.98 | FALSE | -0.86 | -0.83 |
| GEM | 4.46E-01 | 1.12E-02 | -34.88 | 1.13 | -32.19 | -1.60 | FALSE | -1.36 | -0.81 |
| CCDC47 | 2.14E-01 | 1.23E-01 | -34.85 | 0.460464013 | -4.080093569 | -0.82 | FALSE | -0.76 | -0.68 |
| SAA1 | 2.70E-01 | 6.03E-01 | -34.50 | -14.25803074 | -33.7718886 | -1.07 | FALSE | -0.63 | -0.54 |
| FAP | 2.46E-01 | 1.13E-01 | -34.42 | 4.359167404 | -41.90455405 | -0.39 | FALSE | -0.67 | -0.60 |
| IER3 | 9.45E-02 | 7.96E-01 | -34.39 | 1.561694536 | -19.81249058 | -1.06 | FALSE | -1.68 | -2.71 |
| LEPROT | 6.81E-02 | 4.29E-01 | -34.35 | -3.84 | -3.79 | -1.37 | FALSE | -1.36 | -1.01 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| SQSTM1 | 3.08E-01 | 5.29E-01 | -34.34 | -8.65 | -2.82 | -1.56 | FALSE | -0.46 | -0.44 |
| TMEM66 | 1.03E-01 | 1.17E-01 | -34.23 | -6.335487056 | -14.24789241 | -1.11 | FALSE | -2.58 | -1.09 |
| BIN3 | 7.84E-02 | 8.47E-01 | -34.16 | -1.04 | -4.76 | -1.88 | FALSE | 0.32 | -0.68 |
| H2AFJ | 3.84E-02 | 5.04E-01 | -34.07 | -25.87241942 | 16.36684482 | -1.06 | FALSE | 2.18 | 1.36 |
| TAPBPL | 1.34E-01 | 7.56E-01 | -33.96 | -0.367921789 | -29.97601261 | -1.09 | FALSE | -2.88 | -0.43 |
| CHPF | 6.61E-01 | 4.31E-01 | -33.88 | 2.895612909 | -13.08869319 | -1.15 | FALSE | 0.71 | -0.37 |
| KIAA1551 | 3.03E-01 | 2.58E-01 | -33.84 | -2.17 | -10.79 | -2.28 | FALSE | NA | NA |
| CCPG1 | 6.35E-01 | 5.74E-01 | -33.73 | -2.59 | -3.53 | -1.41 | FALSE | -3.84 | -3.38 |
| CHI3L1 | 4.46E-01 | 4.28E-01 | -33.64 | 0.396603931 | -50.32339741 | -1.07 | FALSE | -3.88 | -1.18 |
| TNFRSF10B | 2.48E-01 | 3.26E-01 | -33.55 | -1.29 | -19.71 | -1.58 | FALSE | 0.41 | -0.32 |
| ENDOD1 | 3.12E-01 | 7.77E-01 | -33.51 | -2.51853644 | 1.041232189 | -1.04 | FALSE | -0.45 | -1.09 |
| CLIP1 | 1.44E-02 | 6.78E-01 | -33.48 | -2.054976195 | -6.358112418 | -1.14 | FALSE | -0.55 | -0.44 |
| TMBIM1 | 8.50E-02 | 9.38E-01 | -33.46 | -7.42 | -1.80 | -1.93 | FALSE | 0.33 | -0.34 |
| AHR | 5.02E-02 | 6.01E-01 | -33.45 | -2.02 | -16.52 | -2.41 | FALSE | -3.48 | -1.81 |
| TMED9 | 7.07E-02 | 4.41E-01 | -33.43 | 3.860348819 | -7.452321879 | -0.87 | FALSE | 0.49 | 0.55 |
| NPTN | 1.61E-01 | 6.54E-01 | -33.14 | -0.52 | -4.89 | -1.37 | FALSE | -2.34 | -2.31 |
| UBE2B | 1.90E-01 | 3.56E-01 | -33.08 | -4.50 | -9.49 | -2.60 | FALSE | -3.96 | -3.73 |
| SYNE2 | 8.23E-02 | 8.84E-01 | -33.05 | -8.739833095 | 3.942337418 | -0.55 | FALSE | -0.81 | 0.32 |
| MBNL1 | 8.92E-02 | 5.79E-01 | -32.82 | -5.43424163 | 0.46937185 | -1.05 | FALSE | -5.55 | -2.89 |
| FAM46A | 3.69E-02 | 2.02E-02 | -32.69 | 3.82 | -22.62 | -1.63 | FALSE | -1.06 | -1.10 |
| IL12RB2 | 4.14E-01 | 3.95E-01 | -32.68 | -16.46671472 | -5.376288421 | -0.96 | FALSE | -0.41 | 0.64 |
| DDIT3 | 7.65E-02 | 3.64E-02 | -32.63 | 1.447014332 | -19.27750288 | -1.20 | FALSE | -0.70 | -2.12 |
| FOSB | 1.43E-01 | 8.00E-01 | -32.49 | -0.796475507 | -4.31272261 | -1.06 | FALSE | -1.11 | 0.34 |
| CAV2 | 1.80E-01 | 2.59E-01 | -32.43 | -3.08 | -4.61 | -1.36 | FALSE | -1.69 | -1.13 |
| STOM | 3.22E-01 | 4.73E-01 | -32.40 | -4.411700006 | -0.601246398 | -0.40 | FALSE | -0.52 | 1.09 |
| SERINC1 | 6.29E-02 | 4.88E-01 | -32.30 | -3.03 | -11.26 | -1.69 | FALSE | -1.80 | -2.10 |
| MT1F | 5.29E-01 | 2.87E-01 | -32.19 | -10.67 | -7.72 | -1.67 | FALSE | -0.35 | 0.31 |
| FZD6 | 4.56E-02 | 4.75E-01 | -32.14 | -4.466223946 | -10.61084389 | -0.42 | FALSE | -2.55 | -3.38 |
| G6PD | 4.37E-02 | 7.80E-01 | -32.10 | 2.04 | -13.40 | -1.65 | FALSE | -0.35 | 0.40 |
| MVP | 4.11E-02 | 9.36E-01 | -32.00 | -2.51 | -3.07 | -1.43 | FALSE | -1.53 | -0.51 |
| TMED10 | 3.04E-01 | 4.70E-01 | -31.94 | -3.937577051 | -1.491101847 | -0.72 | FALSE | -0.78 | -1.04 |
| MCOLN3 | 5.15E-02 | 7.52E-01 | -31.92 | -1.592257374 | -34.95981505 | -1.28 | FALSE | 0.56 | 0.63 |
| C4A | 5.68E-02 | 7.73E-01 | -31.78 | 5.6383754 | -63.95587021 | -0.57 | FALSE | -3.86 | -0.65 |
| CHPT1 | 1.14E-02 | 9.36E-01 | -31.65 | -1.71 | -8.66 | -1.96 | FALSE | -0.92 | -0.97 |
| TOB1 | 1.63E-01 | 2.88E-01 | -31.63 | -3.499775851 | -9.257319016 | -0.60 | FALSE | 0.32 | -0.67 |
| ELK3 | 2.92E-01 | 4.28E-01 | -31.32 | 0.690617385 | -15.60885115 | -0.75 | FALSE | -1.57 | -1.23 |
| RND3 | 3.53E-01 | 5.03E-01 | -30.88 | -4.70 | -15.82 | -2.44 | FALSE | -1.33 | -1.28 |
| PHLDA1 | 1.23E-01 | 6.12E-01 | -30.88 | -3.554078519 | -12.08070285 | -1.05 | FALSE | -0.72 | -1.27 |
| TRIB1 | 2.16E-01 | 4.24E-01 | -30.87 | -4.102846583 | -7.012535992 | -1.14 | FALSE | -1.07 | -0.49 |
| PLOD3 | 6.85E-02 | 3.92E-01 | -30.70 | -4.529043691 | -0.521299179 | -1.19 | FALSE | 0.50 | -0.36 |
| DUSP1 | 2.31E-01 | 1.61E-01 | -30.66 | 0.662164296 | -14.274739 | -0.77 | FALSE | -1.45 | -0.31 |
| LAMA4 | 3.36E-01 | 1.86E-01 | -30.65 | 1.304437005 | -13.71409326 | -0.96 | FALSE | -2.08 | -1.15 |
| ALCAM | 1.39E-01 | 5.13E-01 | -30.52 | -0.324216688 | -7.2330932 | -1.26 | FALSE | -0.64 | 0.45 |
| PRKAR1A | 6.16E-01 | 5.09E-01 | -30.49 | -2.995748369 | -5.80777074 | -0.36 | FALSE | -2.49 | -1.59 |
| CYSTM1 | 1.56E-01 | 6.62E-01 | -30.37 | -5.01 | -1.52 | -1.52 | FALSE | NA | NA |
| MPZ | 7.95E-01 | 3.44E-02 | -30.22 | 3.827991239 | -17.8589262 | -0.79 | FALSE | -0.98 | -0.46 |
| REEP5 | 2.85E-01 | 2.83E-01 | -30.12 | -5.08 | -6.71 | -2.22 | FALSE | -0.94 | -0.57 |
| BCAP29 | 6.01E-02 | 2.85E-01 | -30.07 | -0.788569825 | -8.452538217 | -0.66 | FALSE | -3.69 | -3.59 |
| PLEC | 3.00E-01 | 1.49E-01 | -29.99 | 0.32314 | -11.40496196 | -1.07 | FALSE | -0.70 | -0.48 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| CBLB | 4.62E-02 | 6.91E-01 | -29.96 | 1.160755876 | -17.28521246 | -0.37 | FALSE | -0.90 | -0.37 |
| CHI3L2 | 4.24E-01 | 3.28E-01 | -29.83 | -4.908298993 | -29.80387401 | -1.50 | FALSE | -2.40 | -0.30 |
| GRAMD3 | 2.24E-02 | 1.27E-01 | -29.69 | -3.175491376 | -32.24829385 | -2.48 | FALSE | -1.28 | -0.61 |
| CAMP | 2.58E-01 | 2.56E-01 | -29.67 | -6.537864387 | -32.95941798 | -1.04 | FALSE | -1.50 | -0.43 |
| CSRP1 | 6.53E-01 | 4.51E-01 | -29.65 | -3.645548095 | -4.555036259 | -1.17 | FALSE | -1.00 | -1.12 |
| ARMCX3 | 5.62E-01 | 4.06E-02 | -29.33 | -6.284817238 | -0.591876729 | -1.90 | FALSE | -0.38 | -0.36 |
| CANX | 2.70E-01 | 5.34E-01 | -29.31 | -1.780081404 | -6.181232682 | -0.92 | FALSE | -0.75 | -0.53 |
| TXNIP | 1.58E-01 | 8.52E-01 | -29.27 | -0.527598171 | -4.214704474 | 0.37 | FALSE | -0.70 | 1.02 |
| S100A16 | 4.52E-01 | 6.89E-01 | -29.26 | 0.688460885 | -13.99697 | -0.84 | FALSE | -0.44 | -1.03 |
| HEXB | 3.66E-01 | 1.28E-01 | -29.23 | -6.435524884 | -0.371050963 | -1.21 | FALSE | -1.30 | -0.79 |
| WEE1 | 2.40E-01 | 3.83E-01 | -29.22 | -1.837664314 | -10.45776818 | -0.94 | FALSE | -2.16 | -1.20 |
| CTSO | 2.03E-01 | 3.03E-01 | -29.18 | -0.52913538 | -10.25117093 | -0.89 | FALSE | -3.34 | -0.64 |
| PLOD2 | 2.29E-02 | 2.76E-01 | -29.00 | -1.038914654 | -11.95269747 | -0.82 | FALSE | -1.68 | -0.99 |
| DAAM2 | 2.86E-01 | 8.20E-01 | -28.93 | 0.995149536 | -16.35413947 | -0.37 | FALSE | 0.33 | 0.31 |
| IQGAP1 | 2.26E-01 | 8.38E-01 | -28.81 | -5.892500327 | 3.999796242 | -1.01 | FALSE | -1.12 | -0.63 |
| ATP6V1B2 | 3.12E-02 | 9.33E-01 | -28.81 | -1.236034151 | -5.74856853 | -1.57 | FALSE | -0.42 | -0.37 |
| PSMB8 | 8.52E-02 | 7.24E-01 | -28.67 | -5.117567066 | -8.854518735 | -1.76 | FALSE | -4.67 | -1.59 |
| TES | 1.42E-01 | 5.00E-01 | -28.64 | -0.478011716 | -32.21555921 | -0.44 | FALSE | -0.88 | 0.34 |
| ABHD2 | 1.04E-01 | 6.28E-01 | -28.54 | -1.251595254 | -10.61895132 | -2.78 | FALSE | -1.09 | -0.84 |
| AKAP9 | 6.09E-01 | 1.96E-01 | -28.52 | 0.35918391 | -5.461432538 | -0.42 | FALSE | -2.69 | -2.68 |
| LIF | 6.70E-01 | 3.44E-01 | -28.52 | 3.073773887 | -28.07039375 | -1.10 | FALSE | -4.32 | -3.08 |
| PLK3 | 1.38E-01 | 8.45E-01 | -28.49 | 1.464108474 | -11.44618117 | -0.99 | FALSE | -0.50 | -0.36 |
| OSBPL5 | 6.95E-02 | 3.31E-02 | -28.46 | -2.269849969 | -0.980489184 | -1.32 | FALSE | -0.98 | -1.54 |
| ADIPOR2 | 1.68E-02 | 8.80E-01 | -28.35 | -0.839832233 | -5.706827917 | -1.02 | FALSE | 1.68 | 0.89 |
| S100A4 | 7.37E-01 | 6.12E-02 | -28.27 | -3.380134016 | -64.01199908 | -1.03 | FALSE | -1.02 | -0.40 |
| RTKN | 6.89E-01 | 3.62E-01 | -28.22 | -0.492129374 | -9.892228036 | -0.92 | FALSE | 0.53 | -0.68 |
| NR4A2 | 4.92E-02 | 6.31E-01 | -28.21 | -3.780760282 | -0.423389847 | -1.30 | FALSE | -2.24 | -1.22 |
| PPAPDC1B | 2.33E-01 | 9.19E-02 | -28.10 | -1.533802908 | -10.81399535 | -1.87 | FALSE | -1.98 | -1.79 |
| MAGEC2 | 6.50E-01 | 7.68E-02 | -28.07 | -2.1071117 | 41.34703335 | -1.46 | FALSE | -1.05 | -1.02 |
| PDE4B | 6.64E-01 | 2.67E-01 | -28.03 | -2.364902426 | -35.00944346 | -2.37 | FALSE | -3.27 | -0.50 |
| AQP3 | 3.72E-01 | 7.16E-01 | -28.03 | -9.058871123 | -22.68044058 | -1.01 | FALSE | 0.58 | 1.50 |
| RTP4 | 1.96E-02 | 8.07E-01 | -27.94 | -5.675337518 | -6.019705486 | -2.01 | FALSE | -2.18 | -0.74 |
| NIPAL3 | 7.84E-02 | 7.37E-01 | -27.58 | -2.025738972 | -2.559743987 | -0.76 | FALSE | -3.63 | -3.63 |
| PPP4R2 | 5.59E-01 | 3.37E-01 | -27.53 | -2.21758079 | -3.375501383 | -0.68 | FALSE | -2.28 | -1.72 |
| NDRG1 | 3.17E-01 | 1.99E-01 | -27.44 | -2.248121009 | -15.87689568 | -0.56 | FALSE | -3.88 | -3.05 |
| PFKP | 3.56E-02 | 1.73E-01 | -27.42 | 0.422114565 | -4.460264324 | -0.49 | FALSE | 1.20 | 0.49 |
| CD200 | 2.69E-01 | 5.64E-01 | -27.40 | -2.559052299 | -16.89013676 | -2.02 | FALSE | -2.30 | -0.77 |
| SLC2A3 | 5.69E-01 | 3.59E-01 | -27.38 | -1.861116025 | -1.247312253 | -0.79 | FALSE | 0.52 | 0.65 |
| TRIM51 | 1.23E-02 | 9.86E-01 | -27.38 | -22.00677143 | -5.876405839 | -0.74 | FALSE | NA | NA |
| TJP1 | 2.45E-01 | 2.61E-01 | -27.23 | 0.387152694 | -29.97857109 | -0.85 | FALSE | -0.81 | 0.36 |
| CPVL | 6.42E-01 | 1.96E-01 | -27.04 | 0.662656107 | -31.1873706 | -0.59 | FALSE | -1.29 | -0.44 |
| IFRD1 | 5.23E-02 | 1.74E-01 | -27.01 | 4.489953381 | -27.07247597 | -0.51 | FALSE | -1.74 | -3.39 |
| LMNA | 2.61E-01 | 7.35E-01 | -26.99 | -14.85556789 | 5.149222622 | -0.90 | FALSE | 0.57 | 0.39 |
| TMEM30A | 8.31E-02 | 1.20E-01 | -26.95 | 1.296738123 | -9.650459473 | -0.72 | FALSE | -4.05 | -4.59 |
| NAMPT | 2.38E-01 | 8.88E-01 | -26.92 | -0.599957745 | -8.35441204 | -1.27 | FALSE | -3.72 | -2.18 |
| INPP5F | 1.79E-01 | 4.31E-01 | -26.90 | -4.825022902 | 0.536466924 | -0.49 | FALSE | -2.07 | -1.43 |
| DLGAP1-AS1 | 9.43E-01 | 5.69E-02 | -26.86 | -0.873888664 | -5.983055739 | -0.56 | FALSE | NA | NA |
| ENTPD6 | 3.39E-01 | 2.81E-01 | -26.81 | 0.918823136 | -9.944809472 | -0.69 | FALSE | 0.64 | 0.62 |
| ANKRD36BP1 | 3.05E-01 | 8.29E-01 | -26.74 | -0.387440246 | -1.450487926 | -1.12 | FALSE | -0.84 | 0.33 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| DNASE2 | 3.82E-01 | 3.30E-01 | -26.66 | -5.79271027 | -3.087603241 | -1.13 | FALSE | -0.85 | -0.45 |
| PARP9 | 1.77E-02 | 9.10E-01 | -26.62 | -8.593426968 | -3.79735601 | -3.07 | FALSE | -6.05 | -2.17 |
| ETV4 | 4.66E-01 | 4.90E-01 | -26.48 | 2.154806287 | -40.7905761 | -0.37 | FALSE | -0.31 | -0.77 |
| AKR1C3 | 1.43E-01 | 4.41E-01 | -26.25 | -4.534550779 | -31.83008396 | -1.29 | FALSE | -0.42 | 0.41 |
| PIGT | 8.38E-01 | 1.37E-01 | -26.24 | 0.796637157 | -21.82796134 | -1.98 | FALSE | 1.11 | 0.71 |
| ANKRD28 | 6.58E-02 | 8.47E-01 | -26.18 | -0.835178911 | -1.880605312 | -1.05 | FALSE | -0.34 | -0.72 |
| TCN1 | 2.30E-01 | 3.90E-01 | -25.97 | 13.20783241 | -24.9560414 | -0.76 | FALSE | 0.85 | 0.51 |
| SERINC5 | 2.86E-01 | 3.40E-01 | -25.90 | -1.367509487 | -2.310450523 | -0.56 | FALSE | -0.35 | 0.98 |
| SLC38A2 | 2.45E-01 | 6.32E-01 | -25.84 | 5.887885708 | -14.851784 | -0.51 | FALSE | -3.06 | -2.13 |
| SLC16A3 | 4.77E-01 | 5.69E-03 | -25.80 | -1.860338009 | -2.425802885 | -0.48 | FALSE | -0.53 | 0.41 |
| ENO2 | 7.06E-02 | 3.19E-01 | -25.77 | -5.890890828 | -0.712932382 | -0.60 | FALSE | 0.64 | -0.60 |
| ADAM9 | 2.70E-02 | 5.60E-01 | -25.74 | 0.496294512 | -4.870672147 | -1.45 | FALSE | -0.75 | -0.46 |
| P4HA2 | 2.45E-01 | 1.78E-01 | -25.73 | 1.590533138 | -10.68944038 | -1.54 | FALSE | 0.67 | 0.58 |
| TRIM47 | 7.98E-02 | 9.46E-01 | -25.63 | -1.850462382 | -9.018178263 | -0.70 | FALSE | -0.52 | 0.36 |
| S100A13 | 1.28E-01 | 8.69E-01 | -25.59 | -0.978590241 | -3.665918361 | -0.34 | FALSE | 0.38 | -0.44 |
| SUMF2 | 3.63E-01 | 4.64E-01 | -25.55 | 1.576955308 | -9.135832478 | -1.47 | FALSE | 0.43 | -0.50 |
| LONP2 | 7.24E-02 | 6.03E-01 | -25.52 | -1.149798332 | -2.114676254 | -0.35 | FALSE | -0.92 | -0.99 |
| PJA2 | 1.03E-01 | 1.27E-02 | -25.34 | 0.664063647 | -8.490295655 | -1.46 | FALSE | -4.51 | -2.82 |
| NOTCH2 | 6.53E-02 | 9.23E-01 | -25.27 | 1.062830302 | -18.14375992 | -1.39 | FALSE | 1.89 | 1.93 |
| FLNA | 1.85E-01 | 6.62E-01 | -25.25 | 1.245245646 | -6.641620967 | -0.69 | FALSE | 1.17 | 1.24 |
| ETV5 | 1.03E-01 | 7.28E-01 | -25.16 | -2.425088433 | -2.095041157 | -0.33 | FALSE | 0.56 | 0.31 |
| IRF4 | 1.43E-01 | 1.55E-01 | -25.14 | -8.149769268 | -1.664389215 | -0.51 | FALSE | 1.06 | 1.71 |
| RNF213 | 1.31E-01 | 8.83E-01 | -25.03 | -2.256625015 | -0.442801921 | -0.70 | FALSE | -5.53 | -0.81 |
| ACTN1 | 8.63E-02 | 6.82E-01 | -24.87 | -2.392087133 | -0.461493171 | -0.63 | FALSE | 0.67 | 0.34 |
| MAP1B | 1.41E-01 | 3.16E-01 | -24.85 | 16.48663287 | -91.90376064 | -0.75 | FALSE | -1.34 | -0.72 |
| SIL1 | 7.50E-01 | 8.78E-02 | -24.81 | -0.575261468 | -7.539668952 | -2.88 | FALSE | -0.51 | 0.38 |
| PNPLA2 | 1.42E-02 | 9.22E-01 | -24.79 | -3.113307912 | -6.394818612 | -1.78 | FALSE | -1.19 | -0.63 |
| TSPYL2 | 6.78E-01 | 1.52E-01 | -24.72 | 3.778835825 | -9.370339528 | -0.51 | FALSE | -0.61 | 0.31 |
| SLC44A1 | 1.06E-01 | 6.28E-01 | -24.69 | -2.380864194 | -0.349647359 | -0.92 | FALSE | -0.51 | -0.39 |
| PARP4 | 6.46E-02 | 8.01E-01 | -24.68 | -4.159339969 | -4.597805687 | -1.69 | FALSE | -2.92 | -1.43 |
| THBD | 3.74E-01 | 3.56E-01 | -24.64 | 14.85253744 | -8.817215143 | -0.72 | FALSE | 0.36 | 0.50 |
| ATP6AP2 | 2.46E-01 | 2.24E-01 | -24.56 | -2.737231423 | -3.50521377 | -1.49 | FALSE | -4.10 | -3.54 |
| SLCO4A1 | 1.17E-01 | 4.29E-01 | -24.54 | -12.32577077 | -2.491285662 | -1.12 | FALSE | 0.53 | 0.32 |
| QDPR | 3.87E-01 | 3.01E-01 | -24.46 | 0.848626308 | -1.281479991 | -0.58 | FALSE | 0.93 | -0.37 |
| ACSL1 | 3.34E-01 | 7.20E-01 | -24.44 | -1.343355398 | -2.394218878 | -0.74 | FALSE | -0.52 | -0.42 |
| PHF17 | 1.88E-01 | 3.97E-01 | -24.41 | -2.536355562 | -9.66696095 | -0.67 | FALSE | -1.39 | -0.76 |
| PKM | 4.16E-01 | 3.42E-01 | -24.35 | 2.779782869 | -25.72454124 | 0.30 | FALSE | NA | NA |
| SUMF1 | 4.47E-02 | 9.62E-01 | -24.20 | 0.385589079 | -18.61768978 | -1.61 | FALSE | -0.41 | -0.67 |
| DIP2C | 1.35E-01 | 5.96E-01 | -24.12 | -0.899530856 | -0.456829866 | -0.77 | FALSE | 0.40 | -0.78 |
| CCDC109B | 1.35E-01 | 5.33E-01 | -24.12 | -5.921564373 | 20.89758313 | -2.54 | FALSE | -2.60 | -1.01 |
| CLCN3 | 3.24E-02 | 6.68E-01 | -24.11 | -1.199961056 | -0.424869674 | -1.19 | FALSE | 0.36 | -0.49 |
| UBE2L6 | 1.07E-01 | 9.31E-01 | -24.10 | -32.4126104 | -8.305731147 | -1.48 | FALSE | -7.72 | -2.59 |
| SNCA | 5.44E-02 | 5.43E-01 | -24.09 | -4.640547132 | 4.114790574 | -0.52 | FALSE | 1.38 | 0.88 |
| PCM1 | 8.07E-03 | 3.32E-01 | -24.08 | 0.54026566 | 0.722188884 | -0.72 | FALSE | -2.49 | -2.26 |
| GPR137B | 6.68E-01 | 6.10E-01 | -24.07 | -11.24242878 | 4.384258609 | -0.67 | FALSE | 0.75 | -0.31 |
| XPO7 | 2.20E-01 | 6.54E-01 | -24.04 | 1.12830525 | -11.77469529 | -2.28 | FALSE | 0.54 | -0.32 |
| ACTN4 | 2.89E-01 | 6.30E-01 | -23.85 | 1.040958249 | -7.668186482 | -1.69 | FALSE | -1.41 | -2.22 |
| SERINC3 | 5.28E-01 | 6.88E-02 | -23.84 | 0.812247624 | -7.880971405 | -1.79 | FALSE | -2.22 | -1.93 |
| RCAN1 | 4.73E-01 | 4.75E-01 | -23.82 | -7.64834132 | 1.424446662 | -1.57 | FALSE | -1.78 | -1.20 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| RHOB | 1.81E−01 | 2.40E−01 | −23.80 | −1.511826677 | −3.896080823 | −1.25 | FALSE | 1.01 | 0.81 |
| GNPTG | 5.17E−01 | 5.84E−01 | −23.63 | −2.367199494 | −5.629075389 | −1.60 | FALSE | 0.40 | −0.35 |
| SHC4 | 8.71E−02 | 8.28E−01 | −23.63 | 0.761842584 | −1.213412465 | −0.41 | FALSE | −0.92 | −0.56 |
| RGS2 | 5.33E−01 | 2.47E−01 | −23.60 | 0.640530514 | −35.26948489 | −0.86 | FALSE | −1.66 | −0.77 |
| LOC729013 | Inf | Inf | −23.34 | −1.347015309 | −7.739237399 | −0.38 | FALSE | NA | NA |
| SPTAN1 | 2.79E−01 | 6.02E−01 | −23.28 | −3.516248421 | −0.933499052 | −1.09 | FALSE | 1.33 | 1.92 |
| ROPN1B | 1.96E−01 | 5.51E−01 | −23.25 | −0.392244359 | −3.757229083 | −1.17 | FALSE | −0.37 | 0.31 |
| CD97 | 5.02E−02 | 6.09E−01 | −23.17 | −1.82842499 | −11.21440814 | −2.60 | FALSE | −4.58 | −1.91 |
| HIST1H2BD | 1.36E−01 | 7.30E−02 | −22.98 | −1.015586013 | −7.336021298 | −0.59 | FALSE | 0.44 | 0.52 |
| RNH1 | 3.44E−01 | 5.51E−01 | −22.98 | −15.57474178 | −1.489768126 | −2.73 | FALSE | −0.36 | −0.33 |
| LAMB2 | 1.53E−01 | 7.07E−01 | −22.88 | −5.223327364 | 6.005511857 | −0.66 | FALSE | 1.34 | 1.26 |
| CFB | 2.69E−01 | 6.21E−01 | −22.75 | −3.336017193 | −33.81936425 | −1.72 | FALSE | −5.01 | −1.30 |
| APOC1 | 3.51E−01 | 2.53E−01 | −22.72 | −5.24845496 | −10.93115237 | 0.56 | FALSE | −0.97 | 0.35 |
| CTTN | 2.95E−02 | 8.62E−01 | −22.68 | −21.47838673 | −14.37231691 | −0.93 | TRUE | 1.79 | 1.06 |
| SERPINI1 | 1.94E−01 | 3.95E−01 | −22.64 | 7.367752032 | −20.7152515 | −0.82 | FALSE | −2.81 | −2.79 |
| AQP1 | 3.61E−01 | 1.34E−02 | −22.54 | −3.04043337 | −24.54476544 | −1.11 | FALSE | −0.63 | −0.40 |
| C9orf89 | 1.20E−02 | 3.49E−01 | −22.49 | −0.827086987 | −7.744806672 | −2.09 | FALSE | −1.25 | −1.19 |
| IGSF8 | 6.93E−01 | 1.66E−02 | −22.42 | −3.56958779 | 3.520590252 | −0.34 | FALSE | 1.85 | 0.62 |
| LOXL4 | 3.71E−01 | 2.10E−01 | −22.33 | 1.334897324 | −7.476659986 | 0.30 | FALSE | −2.35 | −1.86 |
| PARP14 | 5.18E−02 | 9.01E−01 | −22.19 | −8.097178503 | −0.328886759 | −1.20 | FALSE | −7.56 | −1.95 |
| METTL7B | 8.30E−01 | 3.07E−01 | −22.13 | 5.765117863 | −28.52875728 | −0.53 | FALSE | −2.27 | −1.03 |
| DDIT4 | 1.02E−01 | 3.25E−01 | −22.11 | −5.255322514 | −6.5263049 | −0.30 | FALSE | −0.73 | 0.42 |
| ATP6AP1 | 6.86E−01 | 2.45E−01 | −22.08 | −2.478485511 | −4.57401432 | −1.25 | FALSE | 2.24 | 1.59 |
| EFCAB14 | 1.39E−01 | 7.38E−01 | −22.08 | −3.316119059 | −1.515729612 | −0.55 | FALSE | NA | NA |
| HIPK3 | 9.45E−02 | 3.66E−01 | −22.07 | −2.821393944 | −4.287750809 | −2.31 | FALSE | −2.16 | −1.20 |
| TRAM1 | 1.70E−01 | 3.45E−01 | −22.00 | −1.343023324 | −5.818549836 | −0.80 | FALSE | −2.96 | −0.93 |
| GNG12 | 1.51E−01 | 4.34E−01 | −21.98 | −3.285765565 | −0.610412559 | −1.15 | FALSE | −0.52 | −1.19 |
| HEXIM1 | 3.90E−01 | 6.89E−01 | −21.98 | 0.494765677 | −1.209847864 | −0.53 | FALSE | 0.77 | 0.59 |
| ARPC1B | 4.19E−01 | 5.02E−01 | −21.95 | −5.014848929 | −0.378721015 | −0.51 | FALSE | −0.44 | 0.43 |
| TBC1D10A | 7.46E−02 | 1.14E−01 | −21.92 | −0.552709866 | −1.475904674 | −0.40 | FALSE | −0.67 | −0.35 |
| CELF2 | 1.04E−03 | 9.09E−01 | −21.91 | −11.30510408 | 4.398026966 | −0.65 | FALSE | 0.72 | 1.32 |
| AASS | 2.27E−01 | 4.80E−01 | −21.87 | −2.5995481 | −6.596863423 | −0.58 | FALSE | −1.59 | −1.62 |
| BTG1 | 3.04E−02 | 8.04E−01 | −21.84 | −2.240405471 | −2.125110401 | 0.32 | FALSE | −2.35 | −2.87 |
| ITGB5 | 2.13E−01 | 3.37E−01 | −21.80 | 1.055482689 | −7.664663167 | −1.23 | FALSE | −0.39 | −0.59 |
| LRP10 | 2.33E−03 | 9.26E−01 | −21.76 | −2.643825963 | −0.575237992 | −0.86 | FALSE | 0.59 | 0.83 |
| APOBEC3G | 3.50E−01 | 1.02E−01 | −21.76 | −1.435926819 | −18.55196462 | −1.19 | FALSE | −7.99 | −3.16 |
| NBR1 | 1.91E−01 | 1.24E−01 | −21.73 | −0.401682359 | −7.030124647 | −1.45 | FALSE | −2.31 | −1.99 |
| ARHGAP18 | 6.67E−02 | 5.56E−01 | −21.70 | 1.549815958 | −6.08307845 | −0.91 | FALSE | −3.47 | −1.51 |
| RHBDF1 | 5.39E−01 | 3.26E−01 | −21.64 | −1.584125889 | −5.041016329 | −2.17 | FALSE | 0.56 | −0.47 |
| C2orf82 | 8.24E−01 | 1.09E−01 | −21.54 | −3.589476747 | −36.0767484 | −0.80 | FALSE | −0.76 | −1.03 |
| MRPS6 | 8.46E−01 | 6.04E−02 | −21.54 | 3.8198103 | −31.19537764 | −0.48 | FALSE | −3.76 | −2.64 |
| MFSD12 | 7.75E−02 | 7.20E−01 | −21.46 | −10.32875944 | 0.847324385 | −0.81 | FALSE | NA | NA |
| IL17RC | 3.20E−03 | 9.68E−01 | −21.46 | −0.950909415 | −6.903765831 | −1.33 | FALSE | 0.41 | 1.10 |
| ORMDL3 | 2.42E−01 | 4.01E−01 | −21.35 | 1.028831949 | −12.12181027 | −0.82 | FALSE | −1.56 | −0.43 |
| ERAP1 | 8.92E−03 | 8.00E−01 | −21.33 | −2.020343036 | −1.07433683 | −1.32 | FALSE | −4.25 | −0.52 |
| DHRS3 | 3.85E−01 | 1.49E−01 | −21.32 | −3.674737662 | −36.77125122 | −0.89 | FALSE | −3.81 | −1.01 |
| SMIM3 | 4.40E−01 | 1.74E−01 | −21.31 | −0.533091389 | −27.3010335 | −1.51 | FALSE | NA | NA |
| MTRNR2L7 | 9.55E−01 | 4.31E−01 | −21.30 | −0.641838996 | −0.838254683 | −0.36 | FALSE | NA | NA |
| MAN2B2 | 8.41E−02 | 6.73E−01 | −21.30 | −3.188196571 | −7.235940374 | −2.17 | FALSE | −0.67 | 0.35 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| UBA7 | 9.53E-03 | 9.62E-01 | -21.16 | -6.237460628 | -12.06515012 | -2.74 | FALSE | -7.29 | -1.47 |
| LOC100126784 | 2.74E-01 | 6.97E-01 | -21.12 | 0.617459169 | 1.538338712 | -0.33 | FALSE | 0.91 | 0.40 |
| ZMYND8 | 6.52E-01 | 4.23E-01 | -21.09 | 8.46997889 | -41.0598472 | -0.84 | FALSE | -0.71 | -0.77 |
| SERPINB1 | 7.69E-02 | 7.68E-01 | -21.08 | -7.082913363 | -3.513176367 | -1.08 | FALSE | -2.14 | -0.81 |
| TUG1 | 7.67E-01 | 2.24E-01 | -21.08 | 4.463316224 | -0.484401657 | -0.88 | FALSE | -0.47 | -0.64 |
| TMEM123 | 4.50E-01 | 4.45E-01 | -21.02 | 1.608148266 | -24.28280986 | -1.17 | FALSE | -3.65 | -3.37 |
| OPTN | 1.75E-02 | 9.00E-01 | -21.01 | -15.25531624 | 6.97858787 | -1.28 | FALSE | -1.82 | -0.67 |
| SPP1 | 1.58E-01 | 2.37E-01 | -20.95 | 29.30414836 | -15.67592791 | -0.31 | FALSE | -1.62 | -0.80 |
| VAMP5 | 2.01E-01 | 2.49E-01 | -20.80 | -18.9262028I | -2.119672202 | -2.52 | FALSE | -4.70 | -0.83 |
| PFN1P2 | 2.26E-01 | 5.20E-01 | -20.78 | -4.251955922 | 0.435712066 | -1.31 | TRUE | NA | NA |
| STRIP2 | 2.90E-01 | 6.75E-01 | -20.69 | 0.450218251 | -16.85333974 | 0.68 | FALSE | NA | NA |
| TERF2IP | 4.19E-01 | 4.95E-01 | -20.68 | -0.523959722 | -4.99899526 | -1.15 | FALSE | -2.47 | -2.74 |
| CALD1 | 4.76E-02 | 4.98E-01 | -20.63 | -0.95351804 | -3.241925514 | -0.49 | FALSE | -1.72 | -1.22 |
| SDC4 | 1.32E-01 | 5.67E-02 | -20.63 | -1.191859966 | -2.500483993 | -0.76 | FALSE | -1.75 | -1.20 |
| ST3GAL6 | 2.60E-02 | 4.09E-01 | -20.62 | -3.940416547 | 1.011466756 | -0.39 | FALSE | -1.54 | -1.76 |
| GABARAPL1 | 8.78E-02 | 5.78E-01 | -20.60 | 0.899609729 | -10.63072995 | -1.03 | FALSE | -1.21 | -1.70 |
| ATP2B4 | 3.11E-01 | 3.74E-01 | -20.51 | -4.945501045 | -0.713728198 | -0.82 | FALSE | 0.42 | -0.73 |
| TYR | 1.62E-01 | 8.43E-01 | -20.44 | -5.806227943 | 8.573828698 | 0.35 | FALSE | 0.95 | 0.74 |
| LPXN | 9.73E-02 | 5.50E-01 | -20.32 | -4.724249565 | -6.69091907 | -2.49 | FALSE | -2.90 | -0.99 |
| NT5DC3 | 3.85E-01 | 7.50E-01 | -20.30 | 3.824113566 | -9.439658069 | 0.87 | FALSE | 1.45 | 1.08 |
| TMEM43 | 2.13E-01 | 7.61E-01 | -20.29 | -0.777872969 | -10.65895763 | -1.87 | FALSE | -0.43 | -0.78 |
| PPFIBP1 | 4.24E-01 | 4.93E-01 | -20.24 | 1.128627461 | -0.721079442 | -0.79 | FALSE | -1.32 | -2.12 |
| HPS5 | 1.63E-01 | 5.31E-01 | -20.20 | -4.91611177 | -0.941788497 | -0.87 | FALSE | -1.99 | -1.23 |
| ST6GALNAC2 | 1.94E-01 | 4.17E-01 | -20.18 | -15.32664647 | 2.850160806 | -0.52 | FALSE | 0.64 | 0.45 |
| GANAB | 4.65E-01 | 2.60E-01 | -20.18 | 6.760249926 | -6.862001928 | -0.43 | FALSE | 0.73 | -0.34 |
| UBE2Z | 1.30E-01 | 7.08E-01 | -20.12 | 0.635275033 | 4.157138659 | -0.93 | FALSE | -0.40 | 0.34 |
| BHLHE40 | 2.74E-01 | 3.89E-01 | -20.08 | -15.75869206 | 0.460982512 | -1.07 | FALSE | 0.49 | 0.41 |
| ICAM1 | 1.40E-01 | 1.30E-01 | -20.07 | -5.42980278 | -4.227678526 | -0.90 | FALSE | -2.94 | -0.81 |
| MT1G | 2.64E-01 | 6.28E-01 | -20.07 | -6.619086183 | -19.45360494 | -1.78 | FALSE | -1.25 | -0.92 |
| TNFRSF1A | 1.73E-01 | 3.01E-01 | -20.05 | 1.213887782 | -9.901384801 | -2.19 | FALSE | -0.58 | -0.31 |
| CEACAM1 | 8.88E-02 | 2.21E-01 | -20.04 | -7.679312791 | -0.618868776 | -0.93 | FALSE | 0.31 | -0.35 |
| ATP6V0E2 | 1.88E-02 | 4.01E-01 | -20.03 | 1.928199495 | -14.26365141 | -0.52 | FALSE | 0.57 | 0.41 |
| IER2 | 6.61E-01 | 4.96E-01 | -20.02 | 4.109943558 | -25.7474651 | -0.51 | FALSE | -0.30 | 0.35 |
| PELI1 | 4.39E-01 | 3.28E-01 | -20.00 | 1.189921924 | -35.6465558 | -2.97 | FALSE | -2.64 | -1.15 |
| GLCE | 1.85E-01 | 3.72E-01 | -19.98 | 1.177969643 | -8.825783231 | -0.32 | FALSE | -1.80 | -2.12 |
| AFAP1L2 | 6.59E-01 | 4.14E-02 | -19.97 | -1.073567177 | -0.570275269 | -1.36 | FALSE | -2.23 | -1.19 |
| SRPR | 6.59E-01 | 3.13E-01 | -19.93 | -0.531970765 | -4.906202103 | -2.01 | FALSE | -0.93 | -1.11 |
| PEG10 | 6.25E-02 | 5.12E-01 | -19.79 | 9.864562142 | -70.65883456 | -0.36 | FALSE | -1.59 | -1.00 |
| CCND1 | 2.58E-01 | 5.24E-01 | -19.79 | -44.94838696 | 9.144440051 | -0.44 | FALSE | 0.93 | 0.81 |
| PDLIM5 | 1.61E-01 | 8.65E-01 | -19.73 | -1.229814252 | -4.441449396 | -0.81 | FALSE | -1.49 | -0.84 |
| PTTG1IP | 4.37E-01 | 4.41E-01 | -19.73 | -5.840061211 | 31.81674616 | -0.46 | FALSE | 1.42 | 0.70 |
| PIM3 | 1.43E-01 | 4.70E-01 | -19.67 | -2.05856412 | -2.93170429 | -0.43 | FALSE | -1.29 | -0.88 |
| LOXL2 | 1.30E-01 | 5.07E-02 | -19.66 | -2.227721553 | -17.75782926 | -1.59 | FALSE | 0.63 | 0.59 |
| CASP4 | 4.33E-02 | 5.13E-01 | -19.62 | -1.060183077 | -8.339833791 | -2.26 | FALSE | -2.39 | -0.56 |
| SLC39A6 | 2.57E-01 | 2.62E-01 | -19.62 | -7.554501206 | 2.808826234 | -0.42 | FALSE | 1.49 | 0.36 |
| MICA | 1.60E-02 | 3.12E-01 | -19.54 | -4.830115449 | -3.599631309 | -1.12 | FALSE | 1.47 | 1.02 |
| PTPRM | 4.72E-01 | 5.15E-01 | -19.50 | 0.81484529 | -4.358551311 | -0.92 | FALSE | 0.73 | 0.87 |
| IGFBP3 | 7.45E-01 | 6.80E-03 | -19.50 | -1.314794414 | -34.09760334 | -1.44 | FALSE | -1.60 | -1.31 |
| OCIAD2 | 6.65E-01 | 2.76E-01 | -19.49 | 1.305114076 | -79.98250015 | -0.31 | FALSE | -1.69 | -0.93 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| ASAH1 | 4.70E-01 | 3.55E-01 | -19.40 | -8.977291847 | 12.30969044 | -0.54 | FALSE | 1.02 | 0.93 |
| BAMBI | 7.62E-02 | 4.89E-01 | -19.40 | -7.127650082 | 0.371125258 | -0.66 | FALSE | 0.37 | -0.67 |
| CHN1 | 4.39E-01 | 1.42E-02 | -19.28 | 4.899749645 | -63.05446674 | -1.01 | FALSE | -2.08 | -1.63 |
| SORT1 | 2.69E-01 | 6.04E-01 | -19.05 | -0.346897384 | 4.214233311 | 0.30 | FALSE | 1.07 | 0.79 |
| SPARCL1 | 2.75E-01 | 7.92E-02 | -19.00 | -5.863651519 | -7.671589784 | -0.45 | FALSE | -0.51 | 0.84 |
| TYMP | 5.50E-02 | 7.40E-01 | -18.99 | -7.727093689 | -2.343707718 | -1.57 | FALSE | -2.68 | 0.30 |
| LYST | 3.98E-01 | 5.38E-01 | -18.94 | -2.644630966 | 2.41002413 | -0.84 | FALSE | -0.74 | 0.57 |
| PACSIN2 | 1.92E-01 | 4.29E-01 | -18.93 | -1.371299596 | -1.411697598 | -0.54 | FALSE | -0.34 | -0.40 |
| GNS | 6.32E-01 | 5.79E-01 | -18.78 | -4.823051083 | -3.286157821 | -1.51 | FALSE | -0.32 | 0.38 |
| CSTB | 1.50E-01 | 8.41E-02 | -18.77 | -10.13996322 | 12.45898834 | -0.64 | FALSE | 3.01 | 2.46 |
| PRR4 | 5.94E-01 | 3.79E-02 | -18.75 | 2.79869096 | -29.63571458 | -1.07 | FALSE | -0.94 | -1.61 |
| MFNG | 4.15E-01 | 6.44E-01 | 13.74 | 5.389614969 | -7.877828514 | 0.76 | FALSE | -3.24 | 1.32 |
| RNMTL1 | 6.42E-01 | 2.90E-02 | 13.76 | 5.382060026 | 3.630827576 | 0.81 | FALSE | 1.85 | 0.97 |
| 6-Sep | 3.42E-01 | 4.64E-01 | 13.79 | 4.196300143 | 5.140156942 | 1.00 | FALSE | -1.09 | 1.29 |
| TUBGCP4 | 1.83E-01 | 8.31E-01 | 13.81 | 3.017098753 | 1.78840835 | 1.56 | FALSE | 0.56 | 0.31 |
| ARHGEF1 | 1.00E-01 | 4.17E-01 | 13.83 | -0.583974655 | 21.57052633 | 1.53 | FALSE | -0.81 | 0.82 |
| 11-Sep | 1.16E-01 | 1.74E-01 | 13.88 | 1.430393629 | 24.22367679 | 0.89 | FALSE | 0.61 | 0.64 |
| PCOLCE | 2.45E-01 | 8.53E-02 | 13.90 | 60.72202561 | -6.40674755 | 1.57 | TRUE | -0.54 | -0.79 |
| SURF2 | 3.11E-01 | 8.17E-03 | 13.90 | 3.289195508 | 4.660965337 | 0.89 | FALSE | 1.86 | 0.96 |
| MRPL44 | 1.42E-01 | 2.49E-01 | 13.90 | -0.452623362 | 9.001640945 | 0.59 | FALSE | 0.66 | 0.47 |
| DCAF12 | 2.42E-01 | 2.44E-01 | 13.91 | 7.312065126 | 0.851451243 | 1.40 | FALSE | -0.37 | 0.47 |
| SAT2 | 5.10E-01 | 3.73E-01 | 13.92 | 12.75708283 | 5.628354728 | 1.21 | FALSE | -1.86 | -0.33 |
| TSNAX | 2.90E-01 | 5.50E-01 | 13.92 | 1.805752837 | 12.12793854 | 1.33 | FALSE | 1.18 | -2.50 |
| THOC3 | 8.77E-02 | 5.88E-01 | 13.92 | 18.24763977 | 1.957900047 | 0.65 | FALSE | 0.34 | 0.59 |
| PDCD5 | 7.35E-01 | 4.07E-01 | 13.98 | 6.751326589 | 6.836586916 | -0.35 | FALSE | 0.34 | -1.77 |
| MOCS3 | 3.15E-01 | 3.56E-02 | 14.00 | 1.434370227 | 2.043955951 | 0.95 | FALSE | 0.40 | -0.66 |
| RBM4B | 6.30E-01 | 1.64E-02 | 14.11 | 6.906518123 | 12.53811823 | 0.59 | FALSE | 2.66 | 0.38 |
| MTX1 | 6.94E-01 | 2.54E-01 | 14.12 | 5.91760368 | 2.667632146 | 1.24 | FALSE | 2.38 | 1.38 |
| PRPF4 | 5.54E-01 | 1.41E-01 | 14.16 | 8.189088103 | 2.044969562 | 0.86 | FALSE | -0.35 | 1.76 |
| HNRNPD | 5.99E-01 | 2.59E-01 | 14.17 | 4.315130309 | 7.503641237 | 1.01 | FALSE | 1.50 | 0.63 |
| MCM4 | 4.36E-01 | 2.25E-01 | 14.19 | 1.664350763 | 0.953479445 | 0.93 | FALSE | 0.51 | 1.57 |
| AP3M1 | 8.55E-02 | 5.45E-01 | 14.24 | 0.629153205 | 6.41742361 | 1.11 | FALSE | -1.93 | 0.84 |
| XIST | 7.44E-01 | 2.49E-01 | 14.30 | 29.59293181 | 7.697689322 | 0.45 | FALSE | 1.24 | -1.51 |
| FAM64A | 6.61E-01 | 8.41E-02 | 14.31 | 8.330570062 | -0.351042029 | 0.83 | FALSE | -0.40 | 0.88 |
| G3BP1 | 4.02E-01 | 3.85E-01 | 14.31 | 10.54566035 | 1.943806272 | -0.40 | FALSE | 0.76 | 0.45 |
| SNCG | 4.74E-01 | 1.77E-01 | 14.33 | 18.24763977 | -7.528207908 | 0.97 | FALSE | 4.66 | 2.26 |
| PI4KB | 6.25E-01 | 2.16E-01 | 14.34 | -0.797031323 | 29.52117947 | 0.41 | FALSE | -0.96 | 3.87 |
| DDX46 | 5.72E-01 | 7.29E-02 | 14.35 | 5.88404805 | 5.552908424 | 0.75 | FALSE | 0.34 | -0.52 |
| NNT | 3.32E-01 | 5.47E-01 | 14.37 | 14.45967163 | -6.905512186 | 1.70 | FALSE | 0.67 | 0.45 |
| TIMM17A | 8.05E-01 | 5.02E-02 | 14.40 | 4.529771377 | 5.274485432 | 0.98 | FALSE | 1.50 | -0.48 |
| FTSJ3 | 7.42E-01 | 2.64E-02 | 14.41 | 11.3059408 | 2.197523397 | 0.77 | FALSE | 0.90 | 1.16 |
| HNRNPM | 8.64E-01 | 8.82E-02 | 14.42 | 5.210267361 | 2.738024614 | 0.91 | FALSE | 1.75 | 1.26 |
| EXOSC6 | 3.95E-01 | 7.85E-01 | 14.43 | 0.458097878 | 5.662862445 | 2.19 | FALSE | 2.10 | 0.76 |
| IDH3B | 8.23E-01 | 8.08E-02 | 14.43 | 3.288279147 | 0.694931133 | 0.49 | TRUE | 3.41 | 1.15 |
| NHEJ1 | 6.12E-02 | 5.57E-01 | 14.45 | 0.7467667 | 10.01366284 | 2.85 | FALSE | -3.27 | 2.34 |
| COPS5 | 4.72E-01 | 2.19E-01 | 14.49 | 13.43972244 | -1.109684877 | 1.29 | FALSE | -0.35 | -3.87 |
| SBNO1 | 2.70E-01 | 6.76E-01 | 14.50 | 11.83280512 | 0.31530709 | 1.51 | FALSE | 0.51 | 0.40 |
| TXNDC17 | 8.75E-01 | 2.11E-01 | 14.51 | 19.93469228 | 1.537234956 | 0.37 | FALSE | -0.42 | -0.73 |
| HMG20A | 4.15E-01 | 2.71E-01 | 14.51 | 8.768995629 | 3.138684411 | 1.23 | FALSE | | -0.34 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| TRIB2 | 6.31E-01 | 4.40E-01 | 14.51 | -1.325156749 | 36.78331778 | 1.14 | FALSE | 0.56 | 0.37 |
| CSK | 1.54E-01 | 1.13E-01 | 14.53 | 1.783684971 | 3.908601844 | 0.83 | FALSE | 0.84 | 3.57 |
| B4GALT3 | 6.85E-02 | 3.24E-02 | 14.53 | 2.984723465 | 13.99293996 | 2.23 | FALSE | 0.64 | 0.69 |
| AIMP2 | 1.98E-01 | 2.26E-01 | 14.54 | 9.995109565 | 0.589234557 | 0.68 | FALSE | 3.46 | 1.01 |
| SUPT5H | 7.15E-01 | 1.21E-01 | 14.56 | 0.524094651 | 17.26213471 | 0.54 | FALSE | 2.66 | 1.82 |
| POSTN | 2.42E-01 | 9.71E-02 | 14.57 | 25.61569592 | -8.584718074 | 0.72 | FALSE | 0.46 | 0.73 |
| GTF2H2C | 6.04E-01 | 1.69E-01 | 14.58 | -0.403995243 | 5.926998115 | 2.48 | FALSE | -1.77 | -1.09 |
| GNL3 | 3.37E-01 | 4.02E-01 | 14.61 | 3.602849144 | 4.807218992 | 0.66 | FALSE | -1.34 | -1.91 |
| GBAS | 2.19E-01 | 2.58E-01 | 14.62 | 3.050038089 | 8.165505882 | 1.17 | FALSE | -1.66 | -2.61 |
| MEST | 4.42E-01 | 1.23E-01 | 14.64 | 26.73500059 | -1.521354639 | 0.45 | FALSE | 0.43 | 0.43 |
| CDH3 | 6.93E-02 | 4.14E-02 | 14.67 | -4.060021324 | 27.37588719 | 0.38 | FALSE | 3.88 | 3.59 |
| PLEKH1 | 5.88E-01 | 1.16E-01 | 14.68 | 3.793428817 | 7.780824818 | 0.33 | FALSE | 0.67 | 0.70 |
| ECHS1 | 1.07E-01 | 2.20E-01 | 14.72 | 1.041998674 | 13.08042231 | 1.96 | FALSE | 2.27 | 1.81 |
| SLC45A2 | 4.80E-01 | 3.24E-02 | 14.73 | 11.23157773 | 20.34505987 | 1.51 | FALSE | 2.62 | 2.58 |
| NEUROD1 | 5.30E-01 | 1.52E-01 | 14.75 | 11.86664298 | -10.86699078 | 0.69 | FALSE | -0.77 | -1.69 |
| ACTR1A | 2.03E-01 | 2.17E-02 | 14.76 | 0.616928184 | 16.24202821 | 0.49 | FALSE | 3.57 | 3.89 |
| CD24 | 2.14E-01 | 2.06E-01 | 14.78 | 1.079125614 | 1.079391239 | 0.79 | FALSE | 0.64 | 1.79 |
| LOC388796 | Inf | Inf | 14.79 | -0.443428997 | 8.562706973 | -0.46 | FALSE | 1.60 | 0.61 |
| CDC20 | 5.51E-01 | 4.34E-02 | 14.80 | 4.913073148 | 0.753666063 | 0.63 | FALSE | 2.89 | 2.24 |
| TPI1 | 4.34E-01 | 1.30E-01 | 14.82 | 5.327916572 | -0.744378475 | 0.77 | TRUE | 3.41 | 1.46 |
| NOC2L | 6.32E-01 | 2.28E-01 | 14.83 | 16.2653311 | -1.958200998 | 1.14 | TRUE | 1.46 | 0.80 |
| CHCHD1 | 1.48E-01 | 5.42E-03 | 14.88 | 2.622835248 | 9.47306062 | 0.94 | FALSE | 0.45 | 0.40 |
| ALDH1B1 | 6.57E-01 | 3.31E-01 | 14.98 | 0.922296057 | 19.44016174 | 2.22 | FALSE | 0.94 | 0.33 |
| NTHL1 | 3.95E-01 | 1.32E-01 | 15.01 | 10.15717558 | 2.446536902 | 1.34 | FALSE | 1.35 | 0.87 |
| RARRES2 | 2.25E-01 | 5.11E-01 | 15.05 | 4.873224671 | -0.301976127 | 0.91 | FALSE | -1.43 | -0.37 |
| SLC25A44 | 2.69E-01 | 1.85E-01 | 15.12 | 1.806177902 | 12.42707653 | 0.82 | FALSE | 2.81 | 2.10 |
| ECD | 3.16E-02 | 3.29E-01 | 15.16 | 0.508216518 | 14.92602402 | 1.10 | FALSE | -0.56 | -0.81 |
| ACBD6 | 4.72E-01 | 9.99E-02 | 15.18 | 4.54003142 | 6.492731101 | 0.49 | FALSE | 1.54 | -0.33 |
| AURKA | 4.90E-01 | 5.48E-03 | 15.18 | 4.926437071 | 1.29370898 | 1.38 | FALSE | 1.99 | 1.32 |
| PRMT1 | 5.78E-01 | 3.22E-01 | 15.22 | 7.873906975 | 2.414514677 | 0.56 | FALSE | 1.52 | 0.88 |
| GNB2L1 | 3.13E-02 | 4.07E-01 | 15.22 | 0.754171752 | 3.35276588 | 0.94 | TRUE | 0.40 | -0.33 |
| TOMM5 | 2.75E-02 | 5.50E-02 | 15.24 | 16.83196592 | 1.221893499 | 1.00 | FALSE | 1.00 | -0.31 |
| SNRPF | 2.17E-01 | 1.95E-01 | 15.27 | 15.00145479 | 3.094281947 | 0.67 | FALSE | 1.20 | 0.60 |
| KLHL9 | 1.47E-01 | 7.18E-01 | 15.27 | -0.397375031 | 24.81289951 | 0.85 | FALSE | -1.85 | -1.54 |
| RNPS1 | 1.42E-01 | 4.75E-01 | 15.29 | 2.320398903 | 3.782271567 | 1.76 | FALSE | 1.11 | 0.72 |
| RPL36 | 5.72E-02 | 3.71E-01 | 15.33 | 2.178512724 | 26.41709158 | -0.33 | FALSE | 0.50 | 0.33 |
| SLC25A11 | 6.01E-01 | 2.68E-01 | 15.38 | 12.13755268 | 0.76179644 | 0.69 | FALSE | 1.65 | 1.15 |
| FDPS | 3.64E-01 | 1.03E-01 | 15.41 | 3.097761019 | 7.762648036 | 0.62 | FALSE | 4.01 | 2.54 |
| PRPSAP2 | 4.16E-01 | 1.22E-01 | 15.41 | 9.218191038 | 2.298741055 | 1.45 | FALSE | -0.83 | -1.15 |
| HAUS1 | 2.26E-01 | 3.37E-01 | 15.43 | 5.352399583 | 1.247369224 | 0.96 | FALSE | -1.42 | -1.32 |
| POLR2A | 2.03E-01 | 8.81E-01 | 15.51 | 13.15051816 | 22.80329056 | 2.32 | FALSE | 4.89 | 3.89 |
| TDG | 9.85E-02 | 3.25E-02 | 15.51 | 6.013013072 | 1.030694741 | 1.73 | FALSE | -0.62 | -0.69 |
| EGLN2 | 1.62E-01 | 2.30E-01 | 15.51 | 4.254455956 | 6.344707044 | 1.09 | FALSE | 1.99 | 2.30 |
| CDCA5 | 5.88E-01 | 1.06E-01 | 15.53 | 5.285026282 | -0.307045502 | 0.82 | FALSE | 1.49 | 1.03 |
| EIF2S2 | 6.74E-01 | 1.23E-02 | 15.55 | 8.293233204 | -0.584561792 | 0.79 | FALSE | -1.33 | -2.61 |
| CACYBP | 5.67E-01 | 5.28E-02 | 15.56 | 2.448860208 | 6.784465091 | 1.43 | FALSE | -0.90 | -1.21 |
| TOMM22 | 5.29E-01 | 3.03E-03 | 15.57 | 11.70143787 | 1.10512845 | 1.41 | FALSE | 1.63 | 0.57 |
| GLUL | 4.19E-01 | 1.68E-01 | 15.60 | -0.524584718 | 13.62207707 | 0.68 | FALSE | -1.32 | 0.33 |
| KPNA2 | 2.93E-01 | 5.18E-03 | 15.60 | 4.991817798 | 6.639820973 | 0.58 | FALSE | 3.86 | 3.97 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| GTF2E1 | 2.03E-01 | 5.56E-01 | 15.64 | 0.78347328 | 2.048719802 | 1.04 | FALSE | -1.63 | -1.64 |
| LINC00665 | 1.28E-01 | 8.43E-01 | 15.74 | 1.516171688 | 5.780486589 | 1.43 | FALSE | NA | NA |
| TARS2 | 4.95E-01 | 1.64E-01 | 15.74 | 3.244718053 | 7.167953196 | 1.02 | FALSE | 2.01 | 1.13 |
| ZSWIM7 | 4.97E-01 | 4.57E-01 | 15.77 | 5.395171027 | 2.000749052 | 0.66 | FALSE | -0.62 | -1.46 |
| SPDYE5 | 2.06E-01 | 4.71E-01 | 15.80 | 0.748477234 | 8.22009067 | 1.06 | FALSE | -0.85 | -0.64 |
| LSM4 | 6.34E-01 | 1.59E-01 | 15.82 | 4.47062328 | 2.251693195 | 0.39 | FALSE | 3.16 | 1.48 |
| MYL9 | 4.21E-01 | 5.72E-02 | 15.88 | 0.696709556 | 7.750938059 | 0.63 | FALSE | 0.83 | 0.90 |
| ATP5B | 4.63E-01 | 7.46E-02 | 15.89 | 2.737412219 | 3.557050178 | 1.66 | FALSE | 3.60 | 1.19 |
| RGS3 | 2.55E-01 | 4.95E-01 | 15.91 | 6.172391972 | 3.484629082 | -0.38 | FALSE | -0.57 | 0.57 |
| CHTOP | 6.15E-01 | 8.77E-02 | 15.91 | 10.10615811 | 5.69056281 | 0.97 | FALSE | NA | NA |
| SMG7 | 5.02E-01 | 6.60E-03 | 15.93 | 5.209483431 | 11.99101659 | 2.02 | FALSE | 1.66 | 1.06 |
| EIF3J | 2.68E-01 | 1.88E-01 | 16.00 | 14.28593134 | -0.674223072 | 0.92 | FALSE | -2.31 | -3.82 |
| MGC2752 | Inf | Inf | 16.00 | 2.904335761 | 2.48840784 | 0.80 | FALSE | 1.05 | 0.69 |
| PAM | 3.98E-01 | 5.38E-03 | 16.04 | 0.83707537 | 10.51755539 | 0.48 | FALSE | -0.65 | -0.55 |
| GSTO1 | 6.07E-02 | 5.15E-01 | 16.05 | -1.337030558 | 62.19279211 | 0.95 | FALSE | 1.72 | 0.92 |
| RABEP1 | 8.74E-01 | 1.42E-01 | 16.06 | 21.2928448 | 4.656282388 | 0.49 | FALSE | -0.59 | -0.83 |
| KIF2C | 7.82E-02 | 4.29E-02 | 16.11 | 6.859855363 | 1.854270407 | 0.97 | FALSE | 2.25 | 1.77 |
| CCNB2 | 2.81E-01 | 2.26E-01 | 16.12 | 3.919230216 | 0.973041322 | 0.76 | FALSE | 1.37 | 0.69 |
| NEK5 | 1.56E-01 | 8.32E-01 | 16.17 | -0.324543846 | 3.958302922 | 0.56 | FALSE | 0.47 | -0.69 |
| PPIF | 3.27E-02 | 9.52E-02 | 16.22 | 4.347882752 | 2.129355273 | 0.32 | FALSE | 3.33 | 3.00 |
| C17orf49 | 8.03E-01 | 3.47E-01 | 16.22 | 9.736718533 | 0.87005317 | 0.67 | FALSE | -0.49 | 0.64 |
| EXOSC5 | 5.33E-01 | 4.78E-01 | 16.26 | 4.490272348 | 1.542142828 | 0.38 | FALSE | 0.48 | -0.45 |
| MAP1LC3C | 4.65E-01 | 1.06E-01 | 16.27 | -1.592062983 | 3.554313965 | 1.34 | FALSE | 0.54 | 1.25 |
| TUBB4A | 9.06E-02 | 5.47E-01 | 16.29 | -18.47518133 | 78.69139618 | 0.66 | TRUE | NA | NA |
| EIF3G | 2.66E-01 | 4.13E-01 | 16.30 | 0.485973534 | 14.91167008 | -0.34 | FALSE | 0.45 | 0.32 |
| KIRREL | 7.10E-01 | 1.91E-01 | 16.31 | 1.457831877 | 23.60960921 | 1.24 | FALSE | 1.50 | 2.01 |
| ID3 | 4.40E-01 | 4.62E-02 | 16.33 | 6.385801262 | 6.661876303 | 1.01 | FALSE | -0.70 | 0.37 |
| CCNB1IP1 | 9.37E-02 | 6.45E-01 | 16.37 | 1.083665256 | 8.087590455 | 0.98 | FALSE | 0.41 | -0.93 |
| IL6R | 1.64E-01 | 1.16E-01 | 16.40 | -1.548267241 | 43.85250904 | 1.24 | FALSE | 0.72 | 2.10 |
| RPS10 | 1.11E-01 | 1.50E-01 | 16.42 | 3.683944948 | 16.30339108 | 0.76 | FALSE | 0.71 | 0.42 |
| PKN1 | 5.51E-01 | 4.88E-01 | 16.42 | 13.74625835 | 3.306345432 | 0.70 | FALSE | -0.75 | -0.56 |
| C10orf32 | 7.21E-02 | 4.78E-01 | 16.43 | -1.253078131 | 10.41824098 | 1.99 | FALSE | -1.13 | -0.68 |
| SKA1 | 9.28E-02 | 2.26E-02 | 16.59 | 0.563847042 | 6.4942639 | 1.74 | FALSE | 1.34 | 1.20 |
| MRPS10 | 4.85E-01 | 8.68E-02 | 16.61 | 11.13816237 | 1.780643088 | 0.73 | FALSE | -0.56 | -1.54 |
| CKB | 7.19E-01 | 2.83E-01 | 16.62 | 0.94366682 | -0.673071985 | 0.87 | TRUE | 0.91 | 0.69 |
| CDCA8 | 6.65E-01 | 4.59E-02 | 16.62 | 5.935347842 | 3.409036488 | 0.85 | FALSE | 3.42 | 2.98 |
| ATP5A1 | 3.11E-01 | 3.82E-01 | 16.68 | 4.114811371 | 5.5164772 | 1.16 | FALSE | 2.11 | 1.65 |
| TTYH3 | 8.19E-02 | 6.55E-02 | 16.68 | -0.839172467 | 25.9981956 | 0.60 | FALSE | 6.36 | 5.75 |
| WDR6 | 2.40E-01 | 6.41E-01 | 16.69 | 2.8454458 | 1.146821125 | 2.13 | FALSE | 0.52 | 0.72 |
| SLC5A6 | 6.91E-01 | 2.34E-01 | 16.79 | 12.87746605 | 0.747794957 | 0.73 | FALSE | 1.64 | 1.27 |
| FAM213A | 2.19E-01 | 5.17E-02 | 16.83 | 0.649223104 | 18.38276775 | 1.31 | FALSE | NA | NA |
| SNRPA1 | 9.48E-01 | 1.16E-01 | 16.88 | 8.418866258 | 1.511738171 | 1.59 | FALSE | 0.34 | -0.32 |
| MARCKSL1 | 6.64E-01 | 2.42E-01 | 16.89 | 11.85693628 | -0.322901855 | 0.35 | FALSE | 0.54 | 1.18 |
| DDX39A | 6.91E-01 | 1.20E-01 | 16.91 | 0.618867402 | 13.25993888 | 0.54 | FALSE | NA | NA |
| BEX1 | 6.18E-01 | 4.03E-02 | 16.92 | 15.14930944 | -3.639527861 | 0.58 | FALSE | 0.98 | 0.40 |
| ZNF526 | 3.02E-01 | 5.04E-01 | 16.95 | 0.4369126 | 4.005769467 | 1.12 | FALSE | 1.81 | 0.94 |
| SMCR7L | 2.03E-01 | 2.97E-01 | 17.02 | 7.881351856 | 5.194504892 | 2.41 | FALSE | 2.29 | 1.25 |
| FAM126A | 5.19E-01 | 3.75E-02 | 17.08 | 4.35274429 | 8.584972 | 0.63 | FALSE | -1.33 | -1.06 |
| LSM14A | 5.40E-01 | 3.49E-01 | 17.11 | 0.425148121 | 20.86039965 | 0.55 | FALSE | -1.33 | -1.39 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| FDXR | 5.12E-01 | 4.05E-01 | 17.12 | 1.67368801 | 16.38331044 | 1.47 | FALSE | 2.00 | 1.47 |
| SLC19A1 | 5.55E-01 | 2.28E-01 | 17.15 | 5.585866639 | 14.84646384 | 0.81 | FALSE | 2.13 | 2.18 |
| GAGE12J | 1.82E-01 | 2.36E-01 | 17.16 | 17.96014408 | -14.68096465 | 0.33 | FALSE | -1.39 | -2.77 |
| OCA2 | 1.40E-01 | 2.52E-02 | 17.16 | -5.354814935 | 28.5171977 | 1.11 | FALSE | 5.56 | 3.33 |
| RBBP4 | 8.19E-01 | 1.59E-01 | 17.17 | 7.90217054 | 3.958262309 | 1.72 | FALSE | -0.54 | 0.47 |
| NIP7 | 1.48E-01 | 4.29E-01 | 17.34 | 7.740805625 | 3.790249229 | 0.73 | FALSE | 0.63 | -0.54 |
| PRPF31 | 6.36E-01 | 4.74E-01 | 17.37 | 3.746194298 | 5.153934765 | 0.79 | FALSE | 1.42 | 0.91 |
| MKI67IP | 4.95E-01 | 4.41E-01 | 17.46 | 5.342737904 | 3.950369618 | 0.74 | FALSE | -0.37 | -1.42 |
| TRUB2 | 7.07E-01 | 7.54E-02 | 17.48 | 4.61575142 | 4.893775965 | 2.04 | FALSE | 2.77 | 1.68 |
| METTL13 | 3.47E-01 | 4.85E-02 | 17.49 | 3.1052895 | 5.77183743 | 0.61 | FALSE | 2.17 | 1.65 |
| HMGB1 | 3.33E-01 | 2.08E-01 | 17.50 | 6.146315189 | 2.060104614 | 0.82 | FALSE | -1.52 | -1.07 |
| RCC1 | 6.07E-01 | 2.04E-01 | 17.52 | 6.917331724 | 3.981254561 | 0.87 | FALSE | 3.62 | 1.69 |
| RPA1 | 3.28E-01 | 4.21E-01 | 17.53 | 5.961074344 | 5.617977147 | 1.25 | FALSE | 1.36 | 1.23 |
| HNRNPUL1 | 1.01E-01 | 2.70E-01 | 17.55 | 0.680339536 | 16.42646971 | 0.56 | FALSE | 3.18 | 3.24 |
| NDUFV3 | 4.85E-01 | 2.61E-01 | 17.56 | 2.992981728 | 18.75771812 | 1.14 | FALSE | 2.18 | 2.14 |
| RQCD1 | 7.06E-01 | 1.40E-01 | 17.57 | 2.43503782 | 2.120791626 | -0.41 | FALSE | 1.93 | 1.80 |
| TCF4 | 3.80E-01 | 1.16E-01 | 17.62 | 9.236103162 | -2.679784236 | 0.53 | FALSE | -1.45 | -0.68 |
| C20orf27 | 4.98E-01 | 4.60E-01 | 17.62 | 7.631118695 | 10.61949581 | 0.86 | FALSE | 3.11 | 2.07 |
| CCT4 | 3.45E-01 | 9.10E-02 | 17.65 | 2.170402339 | 6.399317541 | 2.01 | FALSE | 0.42 | -0.48 |
| VPS53 | 1.15E-01 | 3.30E-01 | 17.69 | 0.335449031 | 37.01970924 | 1.02 | FALSE | 5.99 | 4.71 |
| WDR46 | 2.26E-01 | 4.31E-01 | 17.76 | 8.702406207 | 1.725874114 | 1.39 | FALSE | 1.37 | 0.53 |
| NEFL | 7.01E-01 | 2.22E-02 | 17.76 | 11.97364126 | -5.921165572 | 0.60 | FALSE | 1.26 | 0.51 |
| TCEA3 | 8.40E-01 | 7.29E-02 | 17.83 | 0.459042162 | 4.038014366 | 1.40 | FALSE | 0.52 | -0.40 |
| GAGE6 | 1.00E+00 | 1.00E+00 | 17.86 | 16.08931781 | -14.75860399 | 0.66 | FALSE | NA | NA |
| GALT | 1.33E-01 | 6.34E-01 | 17.87 | 1.976498011 | 20.98185221 | 2.04 | FALSE | -0.54 | 0.38 |
| SNRNP40 | 8.89E-01 | 5.60E-02 | 17.90 | 8.554249159 | 4.948734856 | 0.85 | FALSE | 0.87 | 1.24 |
| CRK | 8.58E-01 | 1.99E-01 | 17.94 | 3.670575611 | 7.55391113 | 0.91 | FALSE | 0.87 | 0.76 |
| GNL3L | 5.40E-01 | 2.97E-01 | 17.96 | 4.387265453 | 23.90814734 | 1.25 | FALSE | 2.02 | 2.37 |
| NUF2 | 7.59E-01 | 7.74E-02 | 17.97 | 4.131933124 | 3.647607035 | 1.05 | FALSE | -0.49 | -0.70 |
| SERPINB9 | 2.32E-01 | 9.95E-02 | 17.99 | -2.38056198 | 2.914786989 | 1.08 | FALSE | -1.77 | -0.41 |
| ZFP36L1 | 1.21E-01 | 4.84E-01 | 18.01 | 5.938605734 | 19.42990388 | 1.51 | FALSE | -0.55 | 0.31 |
| MRPS2 | 3.15E-02 | 1.72E-01 | 18.02 | 4.542140417 | 7.779275401 | 2.47 | FALSE | 6.06 | 4.32 |
| NENF | 7.99E-01 | 2.86E-01 | 18.04 | 6.800958187 | 30.65598274 | 1.02 | FALSE | 1.98 | 0.56 |
| DUSP12 | 8.17E-01 | 2.93E-01 | 18.14 | 3.468611254 | 6.132917887 | 1.25 | FALSE | -0.48 | -1.03 |
| FLJ30403 | 7.61E-02 | 8.71E-01 | 18.15 | -0.598011003 | 3.407988308 | 1.44 | FALSE | NA | NA |
| APEX1 | 7.41E-02 | 1.70E-01 | 18.19 | 5.445008003 | 9.919076697 | 0.96 | FALSE | -0.31 | -0.60 |
| NUP62 | 5.48E-01 | 4.64E-01 | 18.22 | 2.387450184 | 4.82254016 | 1.22 | FALSE | 1.90 | 3.41 |
| LYPLA2 | 4.25E-01 | 4.36E-01 | 18.23 | 13.82195911 | 2.615939526 | 1.18 | FALSE | 1.38 | 0.79 |
| EEF1D | 3.44E-01 | 6.12E-01 | 18.28 | 0.985759893 | 7.451311433 | 1.02 | FALSE | -0.45 | 1.00 |
| ABCF1 | 4.22E-01 | 1.35E-01 | 18.31 | 7.435248233 | 0.356070614 | 1.34 | FALSE | 3.23 | 2.37 |
| SKAP2 | 2.81E-01 | 3.45E-01 | 18.37 | 0.456404247 | 23.72086612 | 0.76 | TRUE | -5.45 | -3.16 |
| GPS2 | 6.67E-01 | 3.04E-01 | 18.40 | 4.308701037 | 7.881185647 | 0.55 | FALSE | 0.87 | -0.37 |
| SNRPA | 2.81E-01 | 1.16E-01 | 18.50 | 3.411530561 | 7.835454232 | 1.66 | FALSE | 1.41 | 1.64 |
| SNRPD1 | 5.32E-01 | 2.38E-02 | 18.60 | 21.15658975 | -0.554113785 | 0.82 | TRUE | 0.74 | -0.30 |
| NR2F6 | 5.66E-01 | 3.63E-01 | 18.64 | 8.495360144 | 6.727710363 | 1.64 | FALSE | 3.63 | 2.14 |
| IMPDH2 | 7.55E-02 | 4.30E-01 | 18.71 | 0.535373592 | 30.68574445 | 1.02 | FALSE | 1.81 | 1.03 |
| PSMC4 | 4.22E-01 | 1.04E-01 | 18.73 | 8.390998517 | 3.114001291 | 0.46 | FALSE | 1.33 | 2.37 |
| GPM6B | 3.21E-01 | 7.52E-01 | 18.77 | 4.862310428 | 33.47289854 | 0.32 | FALSE | -0.57 | -1.24 |
| SNRPE | 7.55E-01 | 3.43E-02 | 18.80 | 16.92686645 | 0.331937635 | 0.74 | TRUE | 1.03 | -0.49 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| ASS1 | 4.62E-01 | 1.92E-01 | 18.80 | 14.90230724 | -0.463357928 | 0.85 | FALSE | 0.92 | 1.15 |
| SF3B2 | 2.20E-01 | 6.96E-01 | 18.81 | 10.70469624 | 15.01569271 | 0.94 | FALSE | -0.31 | -0.94 |
| NDST1 | 3.03E-01 | 6.10E-02 | 18.82 | 7.522230908 | 12.72783941 | 0.34 | FALSE | 2.20 | 2.95 |
| RBM4 | 5.21E-01 | 4.82E-01 | 18.84 | 12.59107638 | 10.00071396 | 1.52 | FALSE | 0.55 | 0.52 |
| SERPINH1 | 9.28E-01 | 8.95E-03 | 18.85 | 37.928133 | 8.200485704 | 0.49 | FALSE | 0.99 | 0.91 |
| RBP1 | 8.03E-01 | 2.16E-01 | 18.86 | 12.31936246 | -4.522015287 | -0.31 | FALSE | 0.36 | -0.37 |
| SCO1 | 8.30E-01 | 2.85E-01 | 18.86 | 12.77091115 | 2.974478737 | 0.72 | FALSE | 0.54 | -0.48 |
| RAB20 | 7.25E-01 | 1.55E-01 | 18.87 | -0.538124767 | 16.58525585 | 1.08 | FALSE | -0.59 | 1.11 |
| CRABP2 | 4.46E-01 | 4.25E-02 | 18.88 | 5.991748766 | 0.818296256 | 0.73 | FALSE | 2.76 | 1.86 |
| AURKB | 5.17E-01 | 1.81E-02 | 18.88 | 9.869762355 | 0.859165871 | 0.75 | FALSE | 2.28 | 1.41 |
| DCTN5 | 1.03E-01 | 3.03E-01 | 18.90 | 3.150239057 | 6.140267676 | 1.32 | FALSE | 1.98 | 1.58 |
| POLD1 | 4.07E-01 | 2.17E-01 | 18.90 | 2.322155697 | 4.865956872 | 0.55 | FALSE | 1.04 | 1.35 |
| ENY2 | 6.49E-01 | 3.68E-01 | 18.91 | 24.95069297 | -0.410508403 | 1.77 | FALSE | -1.25 | -1.00 |
| QARS | 4.42E-02 | 3.13E-01 | 18.96 | 3.706877301 | 9.488292408 | 2.20 | FALSE | 2.33 | 1.73 |
| TOP1MT | 7.94E-01 | 1.59E-01 | 19.00 | 2.138074483 | 7.061622399 | 1.01 | FALSE | 0.46 | -0.34 |
| MPDU1 | 2.78E-01 | 1.02E-01 | 19.02 | 12.07276379 | 5.758652693 | 1.46 | FALSE | 2.19 | 2.00 |
| SMC3 | 1.43E-01 | 2.89E-01 | 19.04 | 2.200475748 | 26.65516067 | 1.37 | FALSE | -1.26 | -1.19 |
| DTD2 | 7.61E-02 | 7.38E-01 | 19.06 | 0.454680038 | 11.47425732 | 1.86 | FALSE | NA | NA |
| TATDN1 | 1.17E-01 | 6.67E-01 | 19.10 | 6.785825964 | 2.252004297 | 1.28 | FALSE | -2.97 | -3.70 |
| UQCRC2 | 2.53E-02 | 3.72E-01 | 19.12 | 7.938348231 | 5.090440135 | 0.94 | FALSE | 0.45 | -0.44 |
| RPP30 | 1.91E-01 | 2.11E-01 | 19.13 | 0.301420634 | 11.77733863 | 1.87 | FALSE | -0.60 | -1.17 |
| ATXN10 | 6.94E-01 | 2.97E-01 | 19.14 | 15.77144524 | 13.4473554 | 2.30 | FALSE | 0.57 | -0.50 |
| WDR81 | 9.64E-02 | 8.16E-01 | 19.17 | 1.702392177 | 25.93904876 | 1.27 | FALSE | 2.80 | 2.13 |
| PEPD | 5.58E-01 | 2.73E-01 | 19.18 | 4.936443511 | 11.49578245 | 1.14 | FALSE | 2.63 | 1.77 |
| GAGE2B | 2.57E-01 | 4.80E-01 | 19.18 | 17.70105474 | -15.35736178 | 0.61 | FALSE | -0.98 | -2.19 |
| FEN1 | 1.07E-01 | 2.62E-01 | 19.24 | 8.650445933 | 5.653847713 | 0.63 | FALSE | 1.14 | 0.66 |
| MRPS12 | 5.69E-01 | 1.66E-01 | 19.31 | 5.930175903 | 5.311619169 | 1.32 | FALSE | 2.84 | 1.58 |
| FKBP4 | 6.18E-01 | 5.52E-02 | 19.36 | 10.29840259 | 1.108434516 | 1.06 | FALSE | 3.95 | 2.47 |
| ALAS1 | 5.54E-01 | 3.19E-02 | 19.38 | 5.938125987 | 9.878635076 | 1.06 | FALSE | 1.02 | 1.71 |
| DPP9 | 1.83E-01 | 1.89E-01 | 19.42 | -0.678639926 | 18.41244692 | 0.58 | FALSE | 2.05 | 1.88 |
| ELAC2 | 5.97E-01 | 2.82E-01 | 19.45 | 12.02634776 | 3.287839364 | 0.85 | FALSE | 3.04 | 1.34 |
| RPS21 | 3.21E-01 | 5.10E-02 | 19.59 | 15.48074181 | 4.433652949 | 0.81 | FALSE | -0.61 | -0.82 |
| HYPK | 9.14E-02 | 8.26E-02 | 19.62 | 15.88253495 | -0.541561047 | 0.94 | TRUE | NA | NA |
| THEM4 | 3.55E-01 | 4.66E-01 | 19.63 | 2.641838036 | 14.1049993 | 1.04 | FALSE | 0.60 | -0.35 |
| NXN | 9.91E-01 | 1.25E-02 | 19.72 | -0.570380212 | 4.96539098 | 0.91 | FALSE | 0.84 | 1.70 |
| ABR | 3.48E-01 | 6.70E-01 | 19.73 | 1.706300196 | 19.36139174 | 0.77 | FALSE | 2.16 | 1.33 |
| DARS | 3.52E-01 | 2.45E-01 | 19.76 | 5.49558121 | 7.54473926 | 1.48 | FALSE | -1.49 | -3.22 |
| KCNAB2 | 6.30E-02 | 6.76E-01 | 19.79 | -3.601301043 | 82.174982 | 1.14 | FALSE | 1.31 | 1.95 |
| NUSAP1 | 1.31E-01 | 1.92E-01 | 19.90 | 4.885093685 | 2.576691979 | 0.97 | FALSE | 0.59 | 0.37 |
| STOML2 | 3.74E-01 | 6.99E-02 | 20.04 | 8.770091625 | 2.098212208 | 1.02 | FALSE | 0.98 | 0.41 |
| TOP2A | 7.94E-01 | 4.05E-02 | 20.04 | 4.271101052 | 1.775930792 | 1.05 | FALSE | 0.51 | 0.43 |
| INTS7 | 8.16E-01 | 4.00E-01 | 20.23 | 6.644416 | 3.720076088 | 0.79 | FALSE | 0.71 | 0.87 |
| MFAP4 | 2.69E-01 | 1.24E-01 | 20.27 | 17.64876071 | -2.070632726 | 1.07 | FALSE | 0.53 | 2.01 |
| MYADM | 1.93E-01 | 6.15E-01 | 20.29 | 10.61246616 | 11.67475742 | 1.39 | FALSE | 0.56 | 0.81 |
| POLR3C | 8.17E-01 | 1.79E-01 | 20.29 | 1.698797211 | 13.48631224 | 1.26 | FALSE | 2.24 | 0.39 |
| OXA1L | 1.12E-02 | 3.08E-01 | 20.35 | -0.321055708 | 42.38746933 | 2.14 | FALSE | 1.48 | 0.84 |
| RRP15 | 6.36E-01 | 1.43E-01 | 20.36 | 4.607755076 | 2.111990874 | 0.77 | FALSE | -0.71 | -2.44 |
| GAS5 | 1.29E-01 | 5.14E-01 | 20.37 | 0.472735128 | 48.15462574 | 0.76 | FALSE | 0.36 | -0.61 |
| HMGN1 | 6.43E-01 | 1.36E-01 | 20.39 | 6.749846284 | 4.090025383 | 2.61 | FALSE | -1.19 | -0.56 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| BIRC5 | 4.62E-01 | 2.77E-01 | 20.53 | 3.988960147 | 2.589116396 | 0.84 | FALSE | 2.08 | 1.65 |
| NEK2 | 8.14E-01 | 3.28E-02 | 20.55 | 5.416078429 | 2.176491052 | 1.71 | FALSE | 1.32 | 0.82 |
| RRS1 | 8.28E-01 | 1.39E-01 | 20.58 | 10.21643123 | 1.580673648 | 0.47 | FALSE | 0.67 | 0.47 |
| PPP5C | 4.71E-01 | 2.16E-01 | 20.62 | 1.771526742 | 8.368988743 | 0.76 | FALSE | 1.43 | 0.61 |
| ARPC5 | 1.89E-01 | 8.71E-02 | 20.70 | 1.972299705 | 13.38339241 | 1.47 | FALSE | -3.00 | -2.34 |
| TMEM206 | 3.87E-01 | 7.69E-02 | 20.75 | 8.747393842 | 9.677672637 | 2.21 | FALSE | 0.45 | -0.31 |
| GAGE4 | 9.87E-01 | 9.02E-01 | 20.76 | 20.72965183 | -14.00709129 | 0.42 | FALSE | -1.23 | -2.28 |
| EMI4 | 9.25E-01 | 8.77E-02 | 20.79 | 12.05217543 | 6.934825832 | 1.60 | FALSE | -0.36 | 0.76 |
| NT5DC2 | 1.03E-01 | 3.47E-02 | 20.89 | 8.113534256 | 5.662342879 | 0.87 | FALSE | 4.32 | 1.93 |
| GAGE12H | 6.82E-01 | 2.28E-01 | 20.99 | 18.51606224 | -13.97338677 | 0.70 | FALSE | NA | NA |
| PA2G4 | 1.68E-01 | 1.03E-01 | 21.05 | 5.49759507 | 1.679971385 | 1.66 | FALSE | 3.15 | 1.29 |
| LOC100133445 | 5.36E-01 | 3.78E-01 | 21.09 | -3.452678468 | 36.55092064 | 0.98 | FALSE | NA | NA |
| RRM2 | 4.18E-01 | 5.40E-02 | 21.19 | 3.042468097 | 2.545029055 | 0.55 | FALSE | 0.92 | 0.82 |
| GAGE2D | 8.73E-03 | 3.59E-01 | 21.20 | 20.08829393 | -14.28059448 | 0.62 | FALSE | -1.16 | -2.67 |
| MRPL9 | 8.73E-01 | 4.07E-03 | 21.35 | 5.97577942 | 6.146484827 | 1.12 | FALSE | 2.40 | 1.13 |
| TMEM11 | 4.08E-01 | 1.35E-01 | 21.40 | 20.12015326 | 1.018469789 | 0.89 | FALSE | 2.30 | 0.92 |
| TPM4 | 2.84E-01 | 6.94E-02 | 21.55 | 8.611761357 | 10.14109291 | -0.31 | FALSE | -0.32 | -0.56 |
| ESRG | 1.86E-01 | 7.18E-01 | 21.56 | -0.451092433 | 19.12852841 | 1.43 | FALSE | NA | NA |
| SLC25A5 | 1.55E-01 | 6.97E-02 | 21.57 | 2.102500624 | 13.09751618 | 0.79 | FALSE | 1.48 | 1.20 |
| CYP51A1 | 2.25E-01 | 6.21E-01 | 21.57 | -1.084958837 | 22.75159578 | 1.12 | FALSE | 0.48 | -0.53 |
| TBXA2R | 7.68E-01 | 7.92E-02 | 21.58 | -1.441369813 | 22.29805571 | 0.35 | FALSE | -0.58 | -0.43 |
| LOC100128252 | Inf | Inf | 21.59 | 25.17189358 | -14.09632693 | 1.63 | FALSE | NA | NA |
| SKA2 | 8.87E-01 | 9.62E-02 | 21.67 | 5.316547277 | 9.937930469 | 0.36 | FALSE | -0.60 | 0.37 |
| RUSC1 | 4.21E-02 | 3.03E-01 | 21.75 | 1.660172441 | 20.89322619 | 1.05 | FALSE | 2.59 | 1.08 |
| PSTPIP2 | 5.69E-01 | 3.55E-01 | 21.76 | -1.750472311 | 11.72131361 | 0.95 | FALSE | -2.63 | 0.44 |
| LMCD1 | 1.57E-01 | 9.29E-01 | 21.91 | 6.221082642 | 20.61172886 | 1.49 | FALSE | -0.68 | -0.33 |
| TIMM23 | 6.53E-03 | 8.93E-02 | 21.92 | 5.327664989 | 21.55010632 | 2.05 | FALSE | NA | NA |
| NARS2 | 5.28E-01 | 1.58E-01 | 21.93 | 7.661886481 | 16.67340475 | 2.07 | FALSE | 2.52 | 0.96 |
| STRAP | 6.79E-01 | 9.12E-02 | 21.97 | 4.999612565 | 3.189133343 | 1.86 | FALSE | 2.08 | 0.65 |
| XRCC5 | 7.17E-01 | 3.63E-01 | 22.00 | 10.2042523 | 3.783862242 | 1.85 | FALSE | 0.45 | -0.49 |
| EEF1G | 4.35E-03 | 2.58E-01 | 22.24 | 3.623195074 | 11.37785233 | 2.03 | FALSE | 0.57 | 0.44 |
| FLAD1 | 2.73E-01 | 6.07E-01 | 22.24 | 9.115959046 | 4.889900661 | 0.69 | FALSE | 5.30 | 3.34 |
| PRDX3 | 1.28E-01 | 9.01E-02 | 22.26 | 1.506889444 | 32.24191804 | 1.14 | FALSE | -2.28 | -1.43 |
| GAGE2E | 1.19E-01 | 7.54E-01 | 22.36 | 20.18764216 | -14.80560626 | 1.77 | FALSE | -1.21 | -2.41 |
| TUBGCP2 | 1.31E-01 | 2.55E-01 | 22.66 | -0.633889067 | 43.15291198 | 0.69 | FALSE | 0.85 | 1.13 |
| ORC6 | 7.21E-01 | 5.85E-02 | 22.71 | 0.700919811 | 7.219074042 | 0.99 | FALSE | NA | NA |
| GAGE12G | 4.76E-01 | 1.58E-01 | 22.73 | 21.55374302 | -14.04755971 | 1.94 | FALSE | NA | NA |
| TSTD1 | 3.33E-02 | 1.69E-01 | 22.77 | -4.022382197 | 28.17986342 | 0.65 | FALSE | 2.08 | 0.65 |
| GAGE12E | 8.00E-01 | 9.76E-01 | 22.80 | 22.0897866 | -14.2987637 | 0.77 | FALSE | -1.68 | -0.68 |
| GAGE12C | 6.13E-01 | 6.52E-01 | 22.81 | 22.08782445 | -14.30284956 | 0.63 | FALSE | NA | NA |
| NOP56 | 2.92E-01 | 4.14E-01 | 22.85 | 5.832178979 | 12.65094704 | 0.93 | FALSE | 1.58 | 0.68 |
| HNRNPA1P10 | 4.99E-01 | 1.32E-01 | 22.87 | 10.61174151 | 6.927854056 | 1.18 | FALSE | NA | NA |
| H3F3AP4 | 3.96E-01 | 2.94E-01 | 22.91 | 11.05089081 | 0.790953059 | 1.18 | FALSE | NA | NA |
| ALDH18A1 | 3.46E-01 | 6.95E-01 | 22.94 | 15.61796755 | 10.12846167 | 0.91 | FALSE | 1.76 | 1.87 |
| HN1 | 1.94E-01 | 2.20E-01 | 23.03 | 12.03860552 | 3.775525297 | 0.96 | FALSE | 1.78 | 1.68 |
| CPXM1 | 5.09E-01 | 5.05E-02 | 23.04 | 34.54741553 | -19.2357018 | 0.59 | FALSE | 2.24 | 1.64 |
| SEMA6A | 2.72E-01 | 3.38E-02 | 23.05 | 2.112698771 | 36.86586147 | 0.89 | FALSE | 5.02 | 3.59 |
| PLTP | 1.26E-01 | 2.53E-01 | 23.23 | 0.705496057 | 32.7770504 | -0.35 | FALSE | 0.93 | 1.16 |
| NAPRT1 | 1.05E-01 | 1.21E-01 | 23.49 | -2.243806067 | 26.63418143 | 1.37 | TRUE | 0.57 | 0.58 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| CPSF1 | 4.77E-01 | 5.25E-01 | 23.53 | 4.938813475 | 18.99445597 | 2.32 | FALSE | 0.49 | 1.64 |
| BUB3 | 5.98E-03 | 2.03E-01 | 23.57 | 3.787914349 | 14.66044954 | 0.94 | FALSE | -0.59 | -0.47 |
| RGS16 | 7.20E-01 | 1.09E-01 | 23.66 | 24.77150312 | 1.061623763 | 0.59 | FALSE | -1.88 | -0.96 |
| AFMID | 4.63E-01 | 6.89E-01 | 23.73 | 3.422504125 | 5.089000714 | 1.48 | FALSE | 0.59 | -0.43 |
| SSR2 | 8.95E-01 | 3.81E-02 | 23.74 | 3.23295404 | 13.35607135 | 0.81 | FALSE | 1.29 | 0.98 |
| NDUFAF6 | 1.88E-01 | 3.96E-01 | 23.75 | 10.7563607 | 2.527813066 | 1.97 | FALSE | NA | NA |
| HSD17B14 | 6.74E-01 | 1.51E-01 | 23.76 | 0.434598607 | 25.17510233 | 1.72 | FALSE | 1.16 | 1.55 |
| GPC3 | 5.12E-01 | 1.16E-02 | 23.81 | 28.39313231 | -5.63330805 | 1.17 | TRUE | 1.77 | 1.50 |
| PGAM1 | 1.41E-01 | 1.70E-01 | 23.81 | 1.192883052 | 16.0990166 | 0.93 | FALSE | 2.85 | 2.14 |
| C16orf88 | 7.89E-01 | 7.76E-02 | 23.89 | 16.56262336 | 4.404648103 | 2.01 | FALSE | 2.80 | 0.95 |
| MSTO1 | 6.69E-01 | 1.41E-01 | 23.89 | 4.649573196 | 15.34721826 | 2.10 | FALSE | 2.66 | 2.24 |
| TSTA3 | 3.55E-01 | 3.22E-01 | 23.94 | 3.15100581 | 16.37853925 | 2.68 | FALSE | 1.80 | 2.04 |
| UBAP2L | 1.55E-01 | 5.08E-01 | 23.97 | 1.815656305 | 18.64832265 | 1.97 | FALSE | 5.67 | 2.94 |
| C1orf198 | 9.00E-01 | 5.96E-04 | 24.06 | 3.577483523 | 22.4333289 | 0.58 | FALSE | 0.91 | 0.42 |
| MAP1LC3A | 9.31E-01 | 1.21E-01 | 24.10 | 3.104255127 | 16.39766697 | 0.32 | FALSE | -0.39 | -0.34 |
| ISG20L2 | 4.82E-02 | 7.63E-02 | 24.21 | 5.979207631 | 5.765211543 | 2.61 | FALSE | 3.40 | 2.02 |
| PHB2 | 2.37E-01 | 6.02E-01 | 24.23 | 5.049553302 | 6.970041892 | 0.90 | FALSE | 2.24 | 0.97 |
| SETDB1 | 4.06E-01 | 2.32E-01 | 24.24 | 7.633068319 | 13.36593165 | 0.89 | FALSE | 2.05 | 1.23 |
| MRPL15 | 7.82E-01 | 2.79E-01 | 24.35 | 14.96676665 | 0.581390132 | 0.63 | FALSE | 0.78 | 0.45 |
| MRPS16 | 1.40E-02 | 1.52E-01 | 24.39 | 2.641804679 | 22.5509111 | 1.30 | FALSE | 2.35 | 1.47 |
| EIF2S3 | 3.38E-01 | 1.48E-01 | 24.47 | 1.156094853 | 13.37497764 | 1.03 | FALSE | -0.58 | -0.91 |
| ACAA2 | 4.20E-01 | 3.56E-01 | 24.48 | 15.52042436 | 6.988920199 | 3.83 | FALSE | 1.04 | 0.47 |
| TYRP1 | 2.10E-01 | 6.41E-01 | 24.53 | -1.989085889 | 12.27448658 | 0.37 | TRUE | 4.01 | 3.07 |
| HDAC2 | 6.57E-01 | 4.07E-02 | 24.61 | 10.46242506 | 1.208332687 | 1.89 | FALSE | -0.33 | -0.87 |
| PIH1D1 | 4.87E-01 | 3.31E-01 | 24.70 | 6.126480848 | 5.911744655 | 0.82 | FALSE | 0.33 | -0.49 |
| KLHDC3 | 5.70E-01 | 5.28E-01 | 24.75 | 22.33788991 | 0.664001516 | 1.15 | FALSE | 0.64 | 0.44 |
| CBX5 | 3.09E-01 | 1.03E-01 | 24.89 | 9.713726735 | -0.310128775 | 1.22 | FALSE | 0.56 | 0.91 |
| GLOD4 | 4.51E-01 | 5.04E-01 | 25.00 | 7.219301782 | 20.68994046 | 1.38 | FALSE | 0.87 | 0.44 |
| ZNF146 | 8.68E-01 | 5.38E-02 | 25.03 | 9.080673457 | 6.819875157 | 1.59 | FALSE | -1.63 | -1.82 |
| NOP2 | 5.64E-01 | 7.22E-02 | 25.08 | 11.45230613 | 4.158086545 | 1.14 | FALSE | 4.00 | 1.65 |
| TTC39A | 7.10E-01 | 2.95E-01 | 25.13 | 0.597290641 | 46.83816572 | 1.24 | FALSE | 2.76 | 2.75 |
| SRSF7 | 7.30E-01 | 9.45E-02 | 25.21 | 8.342370883 | 11.02146198 | 2.23 | FALSE | NA | NA |
| LHFPL3-AS1 | 1.04E-01 | 8.00E-01 | 25.24 | -1.251309555 | 100.2514925 | 1.11 | FALSE | NA | NA |
| ARHGDIB | 6.71E-01 | 4.56E-01 | 25.26 | 5.905664136 | -2.352194126 | 0.72 | FALSE | -3.46 | 0.38 |
| CYC1 | 5.00E-01 | 3.51E-01 | 25.32 | 6.635231365 | 2.419386869 | 0.90 | FALSE | 1.34 | 1.07 |
| ECH1 | 4.73E-01 | 6.23E-01 | 25.36 | 1.907500873 | 11.830827 | 0.92 | FALSE | 0.78 | 0.46 |
| DECR1 | 2.26E-01 | 3.03E-01 | 25.39 | 7.937262507 | 8.725112226 | 1.50 | FALSE | 0.45 | 0.66 |
| SET | 6.42E-01 | 2.79E-01 | 25.45 | 4.492009689 | -0.831007838 | 0.72 | TRUE | 0.94 | 1.17 |
| MTG1 | 9.69E-02 | 1.90E-01 | 25.55 | 2.947736591 | 23.27249486 | 1.53 | FALSE | 1.11 | 1.61 |
| KIAA0020 | 1.64E-02 | 7.24E-02 | 25.57 | 9.60401931 | 20.8418105 | 3.17 | FALSE | -0.87 | -0.80 |
| TMEM204 | 6.97E-01 | 1.75E-02 | 25.57 | -1.118931472 | 23.08239672 | 1.12 | FALSE | 1.25 | 1.89 |
| TPX2 | 5.81E-01 | 1.52E-02 | 25.77 | 6.760853407 | 2.94437134 | 1.10 | FALSE | 2.34 | 1.50 |
| H19 | 5.96E-01 | 5.55E-02 | 25.91 | 23.61054168 | -2.068123588 | 1.12 | FALSE | 2.09 | 1.92 |
| CCT3 | 7.28E-01 | 3.59E-02 | 26.21 | 1.163472086 | 9.119575759 | 0.97 | TRUE | 2.53 | 1.55 |
| MAZ | 1.20E-01 | 6.09E-01 | 26.28 | 2.123839678 | 31.48304112 | 1.74 | FALSE | 3.12 | 2.51 |
| UBE2T | 4.62E-01 | 5.78E-03 | 26.39 | 5.398937996 | 6.61326871 | 1.01 | FALSE | 1.24 | 0.33 |
| FES | 6.27E-01 | 4.01E-01 | 26.47 | 3.382276111 | 18.36046107 | 0.93 | FALSE | -0.51 | 0.43 |
| VPS72 | 6.31E-01 | 5.39E-02 | 26.53 | 3.539245137 | 18.53462929 | 2.49 | FALSE | 2.18 | 0.88 |
| GAGE2A | 8.47E-01 | 5.06E-01 | 26.66 | 26.34578486 | -13.96862467 | 0.74 | FALSE | -1.31 | -2.19 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| TUFM | 2.00E-01 | 4.80E-01 | 26.80 | 8.01239921 | 6.859267668 | 1.22 | FALSE | 3.70 | 2.18 |
| ARHGAP4 | 5.56E-01 | 4.68E-01 | 26.84 | 0.711358224 | 23.06729832 | 0.64 | FALSE | -2.39 | 0.44 |
| CCT2 | 4.07E-01 | 1.05E-01 | 26.85 | 10.05194913 | 1.601942797 | 1.94 | TRUE | -0.36 | -1.08 |
| CDK1 | 2.44E-01 | 1.98E-01 | 26.89 | 8.429749705 | 4.579575038 | 1.09 | FALSE | 0.50 | 0.37 |
| TIMM22 | 7.29E-01 | 2.48E-01 | 27.00 | 11.76212824 | 8.691671484 | 2.40 | FALSE | 2.25 | 1.64 |
| UHRF1 | 1.91E-01 | 7.94E-02 | 27.05 | 11.51644137 | 3.212636756 | 0.59 | FALSE | 1.58 | 1.23 |
| PTGDS | 1.81E-01 | 3.97E-02 | 27.10 | 1.823688286 | 19.02431831 | 1.54 | FALSE | -0.48 | 2.64 |
| RPSA | 7.46E-02 | 4.38E-01 | 27.28 | 0.915567272 | 24.13544158 | 1.43 | FALSE | 0.54 | 0.86 |
| RPL29 | 4.20E-02 | 3.07E-01 | 27.64 | 2.972270992 | 52.83468434 | 0.64 | FALSE | 0.92 | 0.78 |
| CECR5 | 6.73E-02 | 2.16E-01 | 27.64 | 13.822315 | 12.73466581 | 1.44 | FALSE | 2.59 | 1.35 |
| HENMT1 | 7.20E-01 | 1.17E-01 | 27.70 | 10.6271938 | 2.355018229 | 0.47 | FALSE | NA | NA |
| SAMM50 | 7.10E-01 | 2.57E-02 | 27.73 | 5.612340388 | 28.91606056 | 1.76 | FALSE | 3.26 | 1.17 |
| PPAP2C | 6.46E-01 | 1.02E-01 | 27.88 | 13.08854512 | 13.32659581 | 0.63 | FALSE | 0.96 | 0.90 |
| TRAF7 | 4.61E-02 | 5.61E-01 | 28.04 | 6.064625478 | 9.78220488 | 1.01 | FALSE | 2.88 | 2.20 |
| NPL | 5.63E-01 | 3.07E-01 | 28.07 | 0.304899232 | 41.13940087 | 0.67 | FALSE | 0.45 | 0.83 |
| NOSIP | 7.94E-01 | 2.53E-01 | 28.19 | 7.332255255 | 5.086418955 | 0.83 | FALSE | 0.65 | 0.73 |
| UBE2C | 4.15E-01 | 8.94E-03 | 28.23 | 9.149834832 | 3.062410476 | 1.03 | FALSE | 2.08 | 1.46 |
| RPL13A | 1.11E-01 | 4.09E-01 | 28.31 | 1.051589093 | 14.62933637 | 0.79 | TRUE | -0.32 | 0.45 |
| TUBA1B | 4.48E-01 | 4.72E-01 | 28.35 | 7.11176895 | 4.011979889 | 1.64 | FALSE | 2.11 | 2.10 |
| MPZL1 | 9.84E-01 | 1.31E-02 | 28.40 | 2.648030647 | 32.98716246 | 1.58 | FALSE | 1.65 | 0.74 |
| LINC00439 | 8.10E-01 | 7.13E-02 | 28.43 | 11.2244352 | 1.289530792 | 0.65 | FALSE | NA | NA |
| NCBP1 | 5.60E-01 | 4.63E-01 | 28.57 | 5.488108351 | 20.39501388 | 3.16 | FALSE | 0.36 | 0.42 |
| SMIM15 | 5.85E-01 | 3.47E-01 | 28.60 | 6.239127759 | 8.28036221 | 0.36 | FALSE | NA | NA |
| UQCRH | 5.30E-01 | 2.97E-01 | 28.67 | 22.1641541 | -0.337282219 | 1.11 | TRUE | 1.42 | 0.46 |
| APP | 7.36E-01 | 7.63E-02 | 28.72 | 9.599129023 | 18.69879539 | 0.43 | FALSE | 0.36 | 0.59 |
| ADSL | 3.60E-01 | 4.89E-02 | 28.74 | 6.11432109 | 24.62523135 | 2.18 | FALSE | 0.56 | -0.90 |
| UCK2 | 4.01E-01 | 2.08E-01 | 28.95 | 9.052578861 | 3.566943066 | 1.07 | FALSE | 1.80 | 0.82 |
| TP53I11 | 7.37E-01 | 2.79E-01 | 29.06 | 17.31232886 | 3.337087794 | 1.14 | FALSE | 1.19 | 2.37 |
| GPATCH4 | 5.94E-01 | 1.85E-01 | 29.10 | 12.26517954 | 11.03023118 | 1.48 | FALSE | 0.81 | -0.34 |
| C20orf112 | 5.78E-01 | 1.41E-01 | 29.13 | 30.6975856 | 2.959060323 | 3.54 | FALSE | -0.60 | -0.46 |
| RPL17 | 4.53E-02 | 4.62E-01 | 29.30 | 5.134546488 | 21.69127968 | 1.41 | FALSE | -0.53 | -0.65 |
| BGN | 4.65E-01 | 1.30E-01 | 29.51 | 11.6481646 | 0.49018527 | 1.80 | FALSE | 1.45 | 2.25 |
| BCCIP | 4.09E-01 | 9.82E-02 | 29.59 | 5.686214848 | 17.77614765 | 1.64 | FALSE | -0.86 | -1.00 |
| CALM3 | 6.27E-01 | 2.48E-01 | 29.70 | 5.470474648 | 20.69905116 | 0.69 | FALSE | 2.37 | 2.29 |
| FAM178B | 7.63E-01 | 1.55E-02 | 29.73 | -0.777212747 | 24.88791609 | 0.43 | FALSE | 0.77 | 0.55 |
| PAICS | 3.90E-01 | 5.41E-01 | 29.76 | 3.312032659 | 24.26869834 | 1.74 | FALSE | 1.52 | 0.48 |
| TSR1 | 5.73E-01 | 1.43E-01 | 29.94 | 11.25783989 | 1.502635952 | 2.19 | FALSE | 0.94 | 0.32 |
| DDX21 | 5.48E-02 | 4.82E-01 | 29.97 | 3.930072862 | 12.6570417 | 0.62 | FALSE | -0.65 | -0.52 |
| METAP2 | 4.28E-01 | 4.93E-01 | 30.02 | 11.00208454 | 8.139440078 | 1.75 | FALSE | -0.92 | -2.24 |
| TPM1 | 1.25E-01 | 3.35E-01 | 30.15 | 16.47245443 | 3.780545609 | 1.38 | FALSE | -0.36 | 0.45 |
| CHP1 | 1.28E-03 | 7.38E-01 | 30.25 | -0.401031609 | 22.86929931 | 0.99 | FALSE | NA | NA |
| DDX50 | 4.87E-02 | 6.45E-01 | 30.29 | 4.624495525 | 16.84678101 | 1.01 | FALSE | -2.74 | -2.56 |
| RPL30 | 3.28E-01 | 5.91E-01 | 30.39 | 14.92031239 | 3.618436257 | 0.77 | FALSE | -0.63 | -0.43 |
| FBLN2 | 3.82E-01 | 2.03E-03 | 30.66 | 7.803353827 | 7.695710285 | 1.55 | FALSE | 0.87 | 1.75 |
| BANCR | 1.42E-01 | 5.48E-01 | 30.82 | 3.861608173 | 8.402734173 | 0.46 | FALSE | NA | NA |
| SCIN | 6.93E-01 | 5.54E-02 | 31.02 | -2.738650819 | 81.94658272 | 1.03 | FALSE | 0.70 | 1.60 |
| C19orf48 | 7.07E-01 | 2.88E-01 | 31.11 | 6.190544609 | 6.03867728 | 1.17 | FALSE | 2.31 | 1.10 |
| RPL5 | 2.21E-01 | 4.46E-01 | 31.16 | 6.752007916 | 6.997915457 | 1.15 | FALSE | -0.84 | -1.18 |
| SCD | 1.21E-01 | 6.04E-01 | 31.17 | -18.67992188 | 88.98473766 | 0.55 | TRUE | 0.71 | 0.59 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| MDH2 | 2.90E-01 | 2.00E-01 | 31.18 | 7.906322813 | 3.895302932 | 1.76 | TRUE | 2.21 | 0.97 |
| PRAME | 4.80E-01 | 4.11E-01 | 31.19 | 9.259758737 | 33.89245342 | 2.16 | FALSE | 0.32 | -0.41 |
| HNRNPA1 | 3.07E-01 | 1.30E-01 | 31.31 | 4.371453406 | 3.269972055 | 1.46 | TRUE | -0.33 | -0.43 |
| SCNM1 | 2.19E-01 | 1.06E-01 | 31.31 | 3.806661745 | 7.463417038 | 1.35 | TRUE | 1.13 | 0.51 |
| TUBB | 2.22E-01 | 2.35E-01 | 31.61 | 3.915227069 | 4.379109031 | 1.16 | TRUE | 2.41 | 1.48 |
| KLHDC8B | 1.33E-01 | 4.28E-01 | 31.64 | 2.496474168 | 41.31550213 | 1.51 | FALSE | 2.20 | 2.37 |
| ASAP1 | 2.03E-01 | 3.78E-01 | 31.68 | 3.393690401 | 25.61527297 | 1.04 | FALSE | 0.31 | 1.36 |
| CD68 | 1.98E-01 | 3.79E-01 | 31.75 | 1.979897879 | 50.21196829 | 0.57 | FALSE | -1.06 | 0.58 |
| ANP32E | 4.92E-01 | 2.24E-01 | 31.96 | 12.318966955 | 6.597294926 | 0.68 | FALSE | -1.10 | -0.82 |
| ITM2C | 9.63E-01 | 1.39E-02 | 32.08 | 8.323594178 | 9.180730963 | 0.37 | FALSE | 0.59 | 0.59 |
| VDAC2 | 8.01E-02 | 3.76E-01 | 32.24 | -1.012942241 | 29.46398783 | 0.83 | FALSE | 1.61 | 0.74 |
| EGFL8 | 4.52E-01 | 1.29E-01 | 32.55 | 12.73725487 | 42.56456272 | 1.01 | FALSE | 1.36 | 1.54 |
| RPS11 | 1.39E-01 | 2.94E-01 | 32.62 | 6.172582657 | 42.70200252 | 0.39 | FALSE | 0.32 | 0.36 |
| GRWD1 | 4.38E-01 | 5.24E-01 | 32.83 | 10.9143261 | 5.020040199 | 1.24 | FALSE | 5.62 | 3.78 |
| CS | 1.65E-01 | 7.41E-01 | 33.27 | 6.422065041 | 17.1233515 | 2.24 | FALSE | 5.08 | 2.61 |
| FAM92A1 | 1.80E-01 | 1.18E-02 | 33.62 | 23.12776574 | 3.344554005 | 0.74 | FALSE | -1.33 | -2.16 |
| NDUFS2 | 7.10E-01 | 9.12E-02 | 34.33 | 3.683553625 | 26.49606832 | 2.86 | FALSE | 1.87 | 0.56 |
| PPA1 | 1.68E-02 | 7.35E-01 | 34.57 | 4.191072237 | 36.24460964 | 1.33 | FALSE | -3.57 | -1.51 |
| THOC5 | 4.22E-01 | 3.11E-01 | 34.76 | 23.72211148 | 8.655594417 | 1.61 | FALSE | 0.56 | -0.39 |
| NF2 | 2.21E-01 | 4.46E-01 | 35.44 | 5.935951855 | 29.68303947 | 1.87 | FALSE | 3.24 | 2.59 |
| SMS | 3.48E-01 | 3.36E-01 | 35.45 | 10.57117775 | 7.554385933 | 3.53 | FALSE | 0.82 | 0.45 |
| MARCKS | 2.18E-01 | 8.98E-01 | 35.55 | 1.393466011 | 26.71905725 | 0.42 | TRUE | -0.60 | -0.35 |
| TRPM1 | 2.73E-02 | 4.37E-01 | 35.72 | -18.29374495 | 70.90187013 | 0.92 | TRUE | 3.10 | 2.37 |
| RPL10A | 4.87E-02 | 3.71E-01 | 35.75 | 6.395271832 | 19.89595719 | 1.43 | FALSE | 0.56 | 0.44 |
| LYPLA1 | 3.39E-01 | 5.06E-01 | 36.15 | 10.23638354 | 8.320184641 | 1.87 | FALSE | -2.44 | -1.87 |
| FBL | 5.03E-01 | 3.43E-01 | 36.53 | 4.637441097 | 24.85286255 | 1.35 | FALSE | 2.64 | 1.65 |
| ZNF286A | 9.41E-01 | 4.19E-02 | 36.53 | 14.1424198 | 2.768284631 | 1.36 | FALSE | -0.47 | -0.77 |
| LIMD2 | 5.49E-01 | 1.46E-01 | 36.60 | 2.122873767 | 9.295102203 | 1.17 | FALSE | -0.75 | 2.94 |
| TULP4 | 2.15E-01 | 8.43E-02 | 36.72 | 3.566475392 | 21.11741429 | 1.35 | FALSE | 0.87 | 1.16 |
| TIMM13 | 5.36E-01 | 2.65E-01 | 37.26 | 13.78610742 | 7.021803959 | 0.77 | FALSE | 2.20 | 1.24 |
| RPAIN | 5.60E-01 | 1.47E-01 | 37.35 | 20.39074062 | 4.484947614 | 1.21 | FALSE | -0.81 | -1.76 |
| RBM34 | 3.24E-01 | 2.16E-01 | 37.89 | 2.249744298 | 18.86752144 | 2.58 | FALSE | -1.41 | -2.72 |
| AHCY | 3.78E-01 | 5.00E-02 | 38.02 | 10.5770466 | 15.46879045 | 2.09 | FALSE | 2.49 | 1.19 |
| MLLT11 | 9.77E-01 | 1.52E-02 | 38.08 | 44.02874412 | -1.884444301 | 0.56 | TRUE | 0.76 | 0.55 |
| MYBBP1A | 6.00E-01 | 2.83E-01 | 38.23 | 29.53471619 | 4.324352219 | 1.57 | FALSE | 2.43 | 1.71 |
| AEN | 5.21E-02 | 2.42E-01 | 38.35 | 14.49457588 | 12.69107053 | 2.30 | FALSE | 3.38 | 2.32 |
| TRIM28 | 3.81E-01 | 3.31E-01 | 38.48 | 14.93519938 | 7.65022211 | 1.28 | FALSE | 2.93 | 2.05 |
| NOLC1 | 2.47E-02 | 2.92E-01 | 38.64 | 8.507240496 | 23.2024831 | 1.84 | FALSE | 3.61 | 2.77 |
| SHMT2 | 2.12E-01 | 1.72E-01 | 38.82 | 7.774111114 | 5.099441692 | 0.97 | FALSE | 2.62 | 1.34 |
| TYMS | 4.65E-01 | 1.60E-01 | 38.85 | 5.796612685 | 6.721259278 | 1.64 | FALSE | 2.02 | 1.91 |
| RPS12 | 3.71E-02 | 4.01E-01 | 38.95 | 6.3840810235 | 4.082782447 | 1.08 | FALSE | 0.45 | 0.39 |
| SORD | 2.73E-02 | 3.55E-01 | 38.98 | 9.939454508 | 11.49665193 | 2.10 | FALSE | 3.16 | 1.05 |
| RPL7 | 4.01E-01 | 3.36E-01 | 39.04 | 11.15340377 | 3.782743401 | 1.06 | FALSE | -0.38 | 0.30 |
| ESRP1 | 4.44E-01 | 4.55E-02 | 39.09 | 10.06244484 | 25.10697937 | 1.20 | FALSE | 2.42 | 1.76 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| BZW2 | 6.62E−01 | 1.05E−01 | 39.22 | 21.62172441 | 26.92442566 | 0.92 | FALSE | 1.37 | 0.90 |
| RPL18A | 8.24E−02 | 3.34E−01 | 39.43 | 2.878936474 | 36.69844039 | 0.51 | TRUE | 1.13 | 1.24 |
| CA14 | 3.81E−02 | 1.81E−01 | 39.82 | −3.998230163 | 67.43065241 | 0.77 | FALSE | 2.21 | 1.79 |
| SKP2 | 9.82E−01 | 1.14E−02 | 39.93 | 21.51868872 | 1.283417716 | 1.83 | FALSE | 1.68 | 1.42 |
| DCAF13 | 4.60E−01 | 2.72E−01 | 40.41 | 24.87612305 | 1.564297695 | 2.88 | TRUE | −1.21 | −1.72 |
| HMGA1 | 6.81E−02 | 6.40E−01 | 40.42 | 19.74301642 | 5.936479134 | 0.83 | FALSE | 0.84 | 0.52 |
| KIAA0101 | 4.38E−01 | 5.20E−02 | 41.14 | 5.177374736 | 9.34491776 | 1.31 | FALSE | −0.55 | −0.59 |
| CTPS1 | 8.43E−01 | 8.35E−02 | 41.34 | 24.76379084 | 7.765650207 | 1.78 | FALSE | NA | NA |
| PPP2R1A | 3.35E−01 | 5.52E−01 | 42.96 | 5.321317629 | 16.81313352 | 1.23 | FALSE | 5.38 | 2.24 |
| FBLN1 | 5.09E−01 | 4.76E−03 | 43.12 | 7.246750299 | 20.27949953 | 1.92 | FALSE | 1.65 | 2.28 |
| RNF2 | 8.06E−01 | 2.83E−02 | 43.71 | 8.672094386 | 7.736904785 | 2.07 | FALSE | −0.38 | −0.97 |
| CDCA7 | 6.15E−01 | 3.99E−02 | 43.91 | 5.924051047 | 11.47163669 | 1.55 | FALSE | 0.55 | 0.97 |
| RPS6 | 8.53E−02 | 5.20E−01 | 43.91 | 1.692897361 | 54.0756381 | 0.83 | TRUE | −1.35 | −1.38 |
| ILF2 | 8.63E−01 | 1.77E−03 | 45.26 | 6.943339213 | 14.84972817 | 1.39 | FALSE | 1.31 | 0.79 |
| RPL18 | 9.66E−02 | 2.25E−01 | 45.37 | 3.114484434 | 48.25066529 | 0.95 | FALSE | 1.39 | 1.27 |
| UQCRFS1 | 4.79E−01 | 1.04E−01 | 45.94 | 2.40443746 | 31.0840894 | 0.72 | FALSE | 3.57 | 1.57 |
| RUVBL2 | 7.03E−01 | 3.34E−01 | 46.06 | 9.456736484 | 13.39002528 | 1.57 | FALSE | 2.93 | 1.38 |
| RPL26 | 1.01E−01 | 1.65E−01 | 46.82 | 16.99198955 | 14.09396856 | 0.84 | FALSE | −2.08 | −2.60 |
| RPS27 | 1.47E−02 | 3.83E−01 | 47.85 | 6.873462208 | 48.31694024 | 0.66 | FALSE | −0.90 | 0.30 |
| CDKN2A | 5.27E−01 | 6.49E−01 | 48.20 | 1.937507613 | 16.9016692 | 0.77 | TRUE | −0.46 | −0.33 |
| MIR4461 | 9.23E−01 | 1.12E−02 | 48.20 | 5.488218285 | 21.56158776 | 1.49 | FALSE | NA | NA |
| TPM2 | 5.40E−01 | 2.36E−02 | 48.33 | 47.15134153 | 0.452068271 | 0.90 | TRUE | −0.30 | 0.49 |
| CNRIP1 | 4.03E−01 | 5.26E−01 | 48.87 | 10.22154305 | 16.25935254 | 1.06 | FALSE | −0.36 | −0.36 |
| PAFAH1B3 | 3.38E−01 | 4.49E−01 | 49.53 | 9.159237785 | 28.8635675 | 1.14 | FALSE | 1.48 | 0.86 |
| FAM174B | 6.29E−01 | 2.83E−01 | 50.07 | 15.22332615 | 36.22910751 | 1.63 | FALSE | 3.44 | 1.88 |
| USP22 | 4.57E−01 | 4.65E−01 | 51.05 | 32.02385954 | 8.721171083 | 1.03 | FALSE | 2.18 | 1.05 |
| GTSF1 | 8.47E−01 | 2.11E−01 | 51.20 | 89.51451745 | −29.39568184 | 1.35 | TRUE | −3.43 | −1.39 |
| ISYNA1 | 5.19E−01 | 3.37E−01 | 51.20 | 8.162255211 | 38.33773761 | 3.05 | FALSE | 1.99 | 1.79 |
| DLL3 | 8.77E−01 | 6.01E−02 | 51.70 | 14.88708119 | 20.30775936 | 3.27 | FALSE | 3.09 | 2.42 |
| TMC6 | 3.36E−01 | 5.51E−02 | 52.13 | 5.290669679 | 67.7112702 | 2.25 | FALSE | 2.61 | 3.47 |
| RPS18 | 7.25E−02 | 7.13E−01 | 52.28 | 27.56806633 | 18.63526549 | 0.69 | FALSE | 0.61 | 0.32 |
| NREP | 6.54E−01 | 6.71E−03 | 52.32 | 66.79439813 | −16.67629308 | 0.68 | TRUE | NA | NA |
| RPL21 | 3.07E−01 | 2.13E−01 | 52.38 | 3.737360847 | 14.06619494 | 2.11 | TRUE | −1.10 | −1.33 |
| RPS3 | 5.62E−02 | 3.60E−01 | 52.44 | 10.48799182 | 69.45371116 | 1.37 | FALSE | 0.97 | 0.76 |
| RPS5 | 2.04E−02 | 3.71E−01 | 56.38 | 4.847150055 | 32.71260656 | 0.81 | TRUE | 1.33 | 0.83 |
| EIF4A1 | 7.28E−01 | 1.85E−01 | 56.54 | 12.44176552 | 23.79777896 | 1.45 | FALSE | 1.80 | 0.60 |
| GPI | 1.17E−01 | 3.72E−01 | 57.12 | 1.130371128 | 45.76480744 | 1.30 | TRUE | 4.46 | 2.91 |
| BCAN | 7.45E−01 | 2.02E−01 | 57.20 | 2.308514409 | 72.97911384 | 0.48 | FALSE | 3.07 | 3.42 |
| FTL | 2.64E−01 | 3.99E−01 | 57.23 | 1.205064194 | 75.23699673 | 1.17 | FALSE | 0.51 | 2.31 |
| DCT | 3.01E−01 | 4.11E−01 | 58.58 | −1.023830081 | 123.9360976 | 0.58 | TRUE | 1.78 | 2.06 |
| RPS16 | 2.08E−01 | 4.47E−02 | 58.91 | 5.580237253 | 61.90003741 | 1.24 | TRUE | 0.90 | 0.61 |
| RPL6 | 1.02E−01 | 5.40E−01 | 60.07 | 16.14902123 | 9.904010704 | 2.18 | FALSE | −0.35 | −0.63 |
| IDH2 | 6.45E−01 | 1.16E−01 | 60.71 | 11.44171851 | 14.05976702 | 1.57 | FALSE | −0.31 | 1.14 |

TABLE 2-continued

Analysis of all gene expression data and clinical data

| | clinic.R.more | clinic.R.less | sc.All | sc.Old | sc.New | sc.Bulk | sc.Q.gene | tcga.Increased.risk | tcga.Increased.risk.beyond.T.cells |
|---|---|---|---|---|---|---|---|---|---|
| H3F3A | 3.97E-01 | 4.63E-01 | 61.79 | 14.22533613 | 3.667893274 | 1.73 | TRUE | -0.70 | -0.70 |
| EIF3K | 3.13E-01 | 9.04E-02 | 61.83 | 8.143610635 | 22.75126648 | 0.89 | FALSE | 2.25 | 1.49 |
| SAE1 | 7.36E-01 | 1.87E-01 | 64.08 | 5.547424178 | 19.20099815 | 1.27 | FALSE | 3.78 | 2.16 |
| TIMM50 | 6.48E-01 | 9.10E-02 | 65.03 | 5.084853086 | 35.29538079 | 1.29 | FALSE | 2.94 | 1.91 |
| RPS24 | 8.85E-02 | 3.75E-01 | 66.05 | 3.716330306 | 98.77989575 | 1.30 | FALSE | -0.64 | -0.62 |
| RPL28 | 1.50E-02 | 4.21E-01 | 67.31 | 5.83385988 | 54.9536147 | 0.71 | TRUE | 0.99 | 1.01 |
| MID1 | 1.41E-01 | 5.75E-01 | 68.45 | 30.60224621 | 19.98794862 | 1.40 | FALSE | 1.53 | 1.43 |
| MAGEA4 | 6.31E-01 | 2.50E-01 | 70.13 | 154.853259 | -37.77268982 | 0.76 | TRUE | -1.19 | -1.25 |
| SOX4 | 4.33E-01 | 3.28E-01 | 71.11 | 26.0610551 | 13.43061044 | 2.03 | FALSE | 1.15 | 0.82 |
| EIF4EBP2 | 4.09E-02 | 5.48E-01 | 71.92 | 4.991883552 | 41.12087104 | 1.61 | FALSE | 0.57 | 1.03 |
| SNAI2 | 3.83E-01 | 1.30E-01 | 75.43 | 7.149559432 | 49.17185344 | 1.36 | FALSE | 1.35 | 1.14 |
| FOXRED2 | 2.26E-01 | 4.31E-01 | 75.45 | 12.49982349 | 58.21339609 | 3.02 | FALSE | 3.28 | 1.62 |
| RPL13AP5 | 1.17E-01 | 2.55E-01 | 77.82 | 2.595272255 | 72.74029977 | 0.90 | TRUE | NA | NA |
| PABPC1 | 1.84E-01 | 6.67E-01 | 79.27 | 7.945824677 | 66.88581105 | 1.76 | FALSE | -0.44 | 0.64 |
| RPL8 | 1.61E-01 | 5.12E-01 | 79.52 | 0.613777713 | 40.16080849 | 1.75 | TRUE | 0.73 | 1.10 |
| RPS7 | 1.97E-01 | 2.87E-01 | 79.88 | 12.55655574 | 40.62711274 | 1.62 | FALSE | -0.52 | -0.79 |
| C1QBP | 4.72E-01 | 1.88E-01 | 84.82 | 24.30944797 | 14.37047936 | 1.82 | TRUE | 1.60 | 0.63 |
| TP53 | 5.16E-01 | 4.69E-01 | 85.56 | 32.44957009 | 13.44990773 | 1.60 | TRUE | 0.40 | 0.47 |
| C17orf76-AS1 | 7.92E-01 | 9.18E-02 | 87.51 | 6.678852726 | 62.53860033 | 1.51 | FALSE | NA | NA |
| PTP4A3 | 5.09E-01 | 1.18E-01 | 94.12 | 18.75491086 | 26.97417247 | 3.61 | FALSE | 1.56 | 1.83 |
| PFN1 | 3.26E-01 | 2.42E-01 | 96.68 | 20.383459 | 27.16487933 | 2.07 | FALSE | 1.34 | 2.82 |
| RPLP0 | 5.66E-02 | 6.51E-01 | 102.20 | 8.883720005 | 57.64453707 | 1.97 | TRUE | 1.37 | 0.73 |
| RPS19 | 1.31E-01 | 3.50E-01 | 116.49 | 8.842607397 | 97.09263286 | 1.07 | TRUE | 1.43 | 1.14 |
| SERPINF1 | 1.90E-01 | 4.68E-01 | 138.29 | 45.36545505 | 71.24671866 | 3.31 | FALSE | 0.79 | 0.87 |

TABLE 3

Down-regulated and Up-regulated genes post-immunotherapy treatment in malignant cells

| Down-regulated post-treatment | | Up-regulated post-treatment | |
|---|---|---|---|
| ABHD2 | ITM2B | ACAA2 | PRDX3 |
| ACSL4 | JUNB | ADSL | PSTPIP2 |
| AHNAK | KCNN4 | AEN | PTGDS |
| AHR | KIAA1551 | AHCY | PTP4A3 |
| AIM2 | KLF4 | ALDH1B1 | RBM34 |
| ANGPTL4 | KLF6 | ARHGEF1 | RBM4 |
| ANXA1 | LAMB1 | ARPC5 | RPL10A |
| ANXA2 | LAMP2 | ATXN10 | RPL17 |
| APOD | LGALS1 | ATXN2L | RPP30 |
| ATF3 | LGALS3BP | B4GALT3 | RPS3 |
| ATP1A1 | LINC00116 | BCCIP | RPS7 |
| ATP1B3 | LOC100127888 | BGN | RPSA |
| BBX | LOXL2 | C10orf32 | RUVBL2 |
| BCL6 | LOXL3 | C16orf88 | SAMM50 |
| BIRC3 | LPL | C17orf76-AS1 | SBNO1 |
| BSG | LXN | C20orf112 | SERPINF1 |
| C16orf45 | MAGEC2 | CDCA7 | SKP2 |
| C8orf40 | MFI2 | CECR5 | SLC45A2 |
| CALU | MIA | CPSF1 | SMC3 |
| CARD16 | MT1E | CS | SMG7 |
| CAV1 | MT1F | CTCFL | SMS |
| CBFB | MT1G | CTPS1 | SNAI2 |
| CCDC109B | MT1M | DLL3 | SORD |
| CCND3 | MT1X | DTD2 | SOX4 |
| CD151 | MT2A | ECHDC1 | SRCAP |
| CD200 | NFE2L1 | ECHS1 | SRSF7 |
| CD44 | NFKBIZ | EIF4A1 | STARD10 |
| CD46 | NNMT | EIF4EBP2 | TBXA2R |
| CD47 | NOTCH2 | EIF6 | THOC5 |
| CD58 | NR4A1 | EML4 | TIMM22 |
| CD59 | OS9 | ENY2 | TIMM23 |
| CD9 | P4HA2 | ESRG | TMC6 |
| CD97 | PDE4B | FAM174B | TOMM22 |
| CDH19 | PELI1 | FAM213A | TPM1 |
| CERS5 | PIGT | FBL | TSNAX |
| CFB | PMAIP1 | FBLN1 | TSR1 |
| CHI3L2 | PNPLA8 | FDXR | TSTA3 |
| CLEC2B | PPAPDC1B | FOXRED2 | TULP4 |
| CLIC4 | PRKCDBP | FXN | UBAP2L |
| COL16A1 | PRNP | GALT | UCHL5 |
| COL5A2 | PROS1 | GEMIN8 | UROS |
| CREG1 | PRSS23 | GLOD4 | VPS72 |
| CRELD1 | PSMB9 | GPATCH4 | WDR6 |
| CRYAB | PSME1 | HDAC2 | XPNPEP1 |
| CSPG4 | PTPMT1 | HMGN3 | XRCC5 |
| CST3 | PTRF | HSD17B14 | YDJC |
| CTNNAL1 | RAMP1 | IDH2 | ZFP36L1 |
| CTSA | RND3 | ILF2 | ZNF286A |
| CTSB | RNH1 | ISYNA1 | |
| CTSD | RPN2 | KIAA0020 | |
| DCBLD2 | S100A10 | KLHDC8B | |
| DCTN6 | S100A6 | LMCD1 | |
| EGR1 | SCCPDH | LOC100505876 | |
| EMP1 | SERINC1 | LYPLA1 | |
| EPDR1 | SERPINA3 | LZTS2 | |
| FAM114A1 | SERPINE1 | MAZ | |
| FAM46A | SERPINE2 | METAP2 | |
| FCRLA | SLC20A1 | MIDI | |
| FN1 | SLC35A5 | MIR4461 | |
| FNDC3B | SLC39A14 | MPDU1 | |
| FXYD3 | SLC5A3 | MPZL1 | |
| G6PD | SMIM3 | MRPS16 | |
| GAA | SPARC | MSTO1 | |
| GADD45B | SPRY2 | MTG1 | |
| GALNS | SQRDL | MYADM | |
| GBP2 | STAT1 | MYBBP1A | |
| GEM | SUMF1 | MYL6B | |
| GRAMD3 | TAP1 | NARS2 | |
| GSTM2 | TAPBP | NCBP1 | |
| HLA-A | TEKT4P2 | NDUFAF6 | |
| HLA-C | TF | NDUFS2 | |
| HLA-E | TFAP2C | NF2 | |
| HLA-F | TMEM43 | NHEJ1 | |
| HPCAL1 | TMX4 | NME6 | |
| HSP90B1 | TNC | NNT | |

TABLE 3-continued

Down-regulated and Up-regulated genes post-immunotherapy treatment in malignant cells

| Down-regulated post-treatment | | Up-regulated post-treatment |
|---|---|---|
| HTATIP2 | TNFRSF10B | NOLC1 |
| IFI27L2 | TNFRSF12A | NTHL1 |
| IFI44 | TSC22D3 | OAZ2 |
| IFI6 | TSPAN31 | OXA1L |
| IFITM3 | UBA7 | PABPC1 |
| IGF1R | UBC | PAICS |
| IGFBP3 | UBE2L6 | PAK1IP1 |
| IGFBP7 | XPO7 | PFN1 |
| IL1RAP | ZBTB20 | POLR2A |
| ITGA6 | ZDHHC5 | PPA1 |
| ITGB3 | ZMYM6NB | PRAME |

The signature was down-regulated in resistant tumors for genes associated with coagulation, apoptosis, TNF-alpha signaling via NFKB (NFKBIZ), Antigen processing and presentation (e.g., MHC-I, HSPA1A), metallothioneins (e.g., MT2A, MT1E) involved in metal storage, transport, and detoxification, and IFNGR2 (Gao et al. Cell 2016).

The signature was up-regulated in resistant tumors for genes associated with negative regulation of angiogenesis and MYC targets.

Serine protease inhibitors (SERPINs), which are involved in protease inhibition and control of coagulation and inflammation were differentially expressed in the signature. Prior studies relate to recurrent SERPINB3 and SERPINB4 mutations in patients who respond to anti-CTLA4 immunotherapy (Riaz et al. NG 2016). SERPINA3, SERPINA1, SERPINE2 were down-regulated in resistant tumors. SERPINF1, SERPINB9 were up-regulated in resistant tumors.

The resistance signature also strongly correlated with MHC-I expression (FIG. 22). One of the tumors in the cohort has a wide range of MHC-I expression in the malignant cells. Applicants filtered HLA genes from the resistance signature, and scored the malignant cells. The malignant cells with the highest resistance scores in this tumor under express MHC-I.

There are 13 different metallothioneins and 6 of them are moderately/highly expressed in the melanoma malignant cells. When Applicants scored the cells according to this mini-signature separation between the treated and untreated samples was observed (FIG. 23). Therefore, a signature only including metallothioneins may be used in the methods of the present invention.

The Prognostic Value of the Post-Immunotherapy Modules

Figure 24:
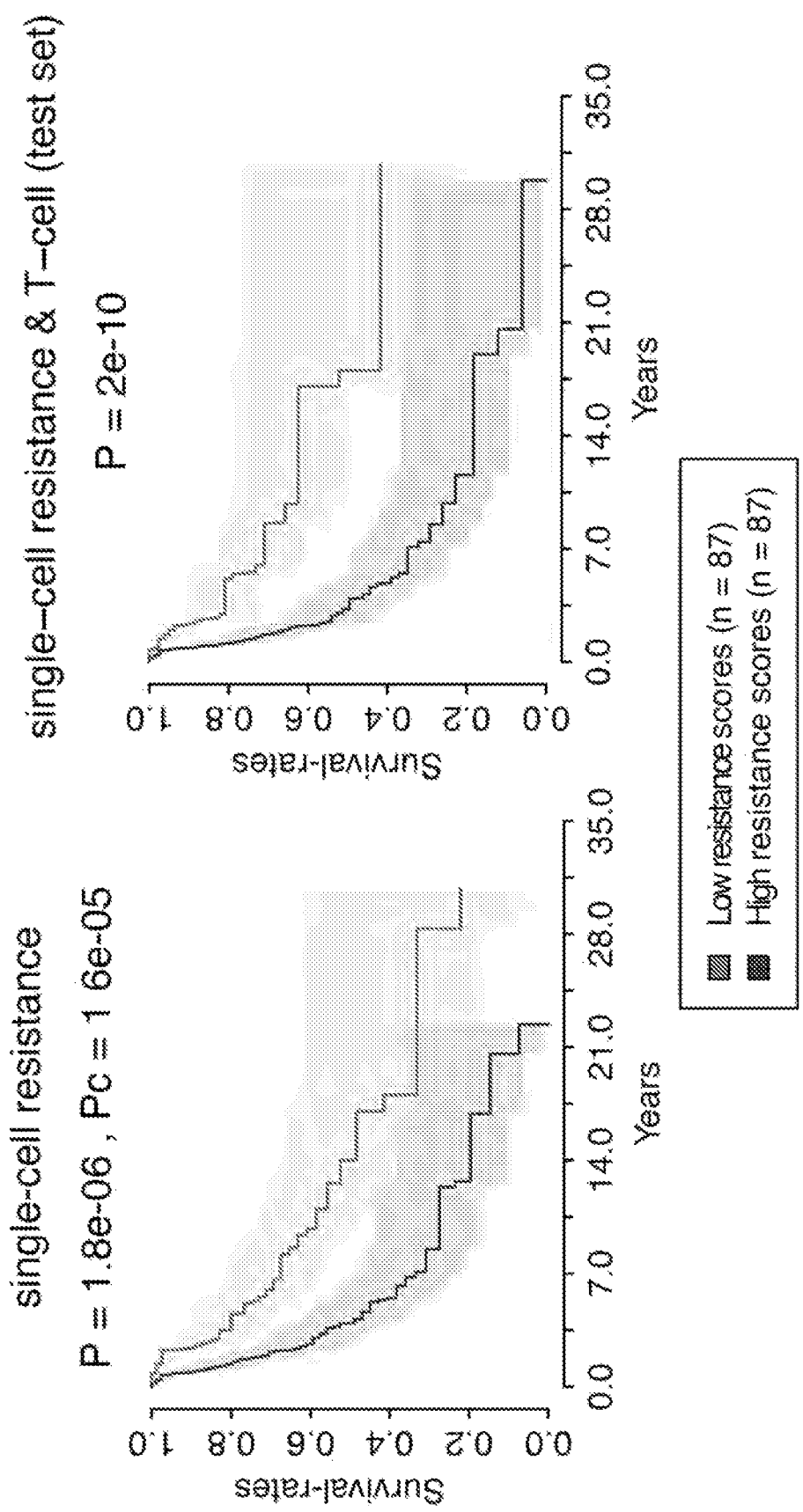
FIG. 24 illustrates the association of the resistance signature with prognosis.
Figure 25:
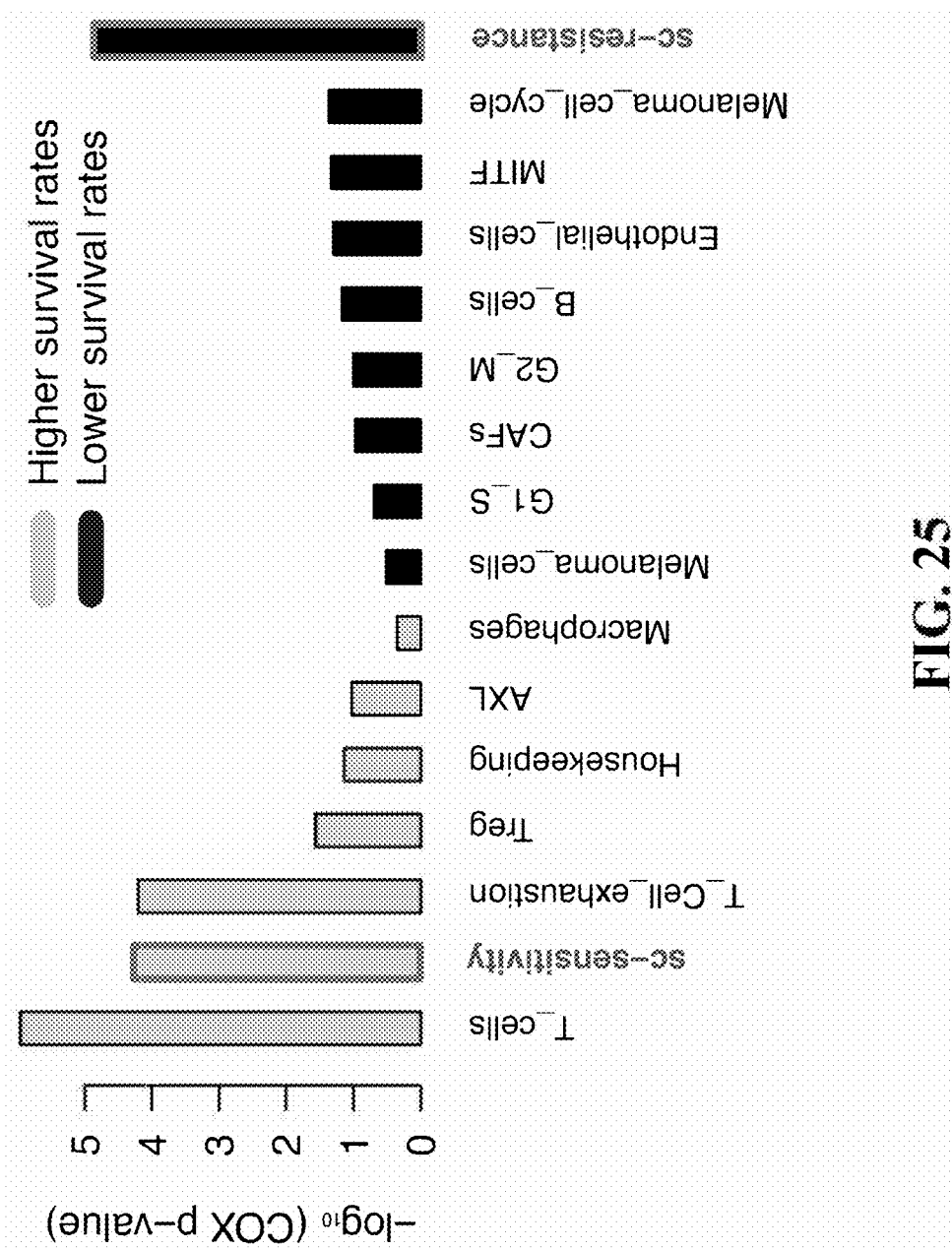
FIG. 25 illustrates the resistance signature compared to other single-cell based signatures.

Applicants discovered that the immunotherapy resistance signature was also predictive of survival rates in tumors. The prognostic value of the signature is significant ($P=1.6e-05$), even when accounting for T-cell infiltration scores as shown by analyzing samples in the cancer genome atlas (TCGA) (FIG. 24). The resistance signature performs better than other single-cell based signatures in predicting high and low survival rates (FIG. 25).

To further examine the generalizability of the PIT modules Applicants analyzed the bulk gene expression data of melanoma tumors from The Cancer Genome Atlas (TCGA). As Applicants saw at the single-cell level, Applicants find that the genes within each module are co-expressed across tumors, while the two modules are negatively correlated. Applicants postulated that higher expression of the PIT-up program and a lower expression of the PIT-down program might indicate that the tumor is more resilient against immune-mediated clearing, resulting in a more aggressive disease. To test this hypothesis, Applicants scored each tumor according to the immunotherapy modules and examined the prognostic value of these scores. Indeed, the immunotherapy scores are significantly associated with patient survival, such that the expression of the PIT-up (down) signature is associated with lower (higher) survival rates (FIGS. 24, 25).

To examine the significance of this finding Applicants performed the same analysis with signatures that were previously identified based on the analysis of the single-cell melanoma data (Tirosh et al., Dissecting the multicellular ecosystem of metastatic melanoma by single-cell RNA-seq. Science. 2016 Apr. 8; 352(6282):189-96). Applicants divided these signatures into two groups: (1) malignant signatures—signatures that describe the state of the malignant cells, as cell cycle, and the AXL and MITF signatures, which were previously shown to be associated with the response to targeted therapy; (2) tumor composition signatures that describe a specific cell type or the state of a non-malignant cell type within the tumor microenvironment. None of the malignant signatures is significantly associated with patient survival, indicating that mere variation across malignant cells is not sufficient to yield such results. The cell-type signatures are associated with patient survival, especially those that related to T-cell infiltration, though their prognostic signal is redundant when accounting for tumor purity. The latter is estimated based on CNVs.

Importantly, the prognostic value of the PIT scores is significant even when accounting for the tumor purity and T-cell infiltration scores. Interestingly, the PIT-up (down) scores are negatively (positively) correlated to the T-cell scores, as Applicants further describe herein. Nonetheless, the combination of the PIT and T-cell scores yields significantly more accurate predictions of patient survival compared to those obtained when using each score separately, indicating that the PIT modules capture tumor properties that cannot be explained just by T-cell infiltration levels.

Figure 26:
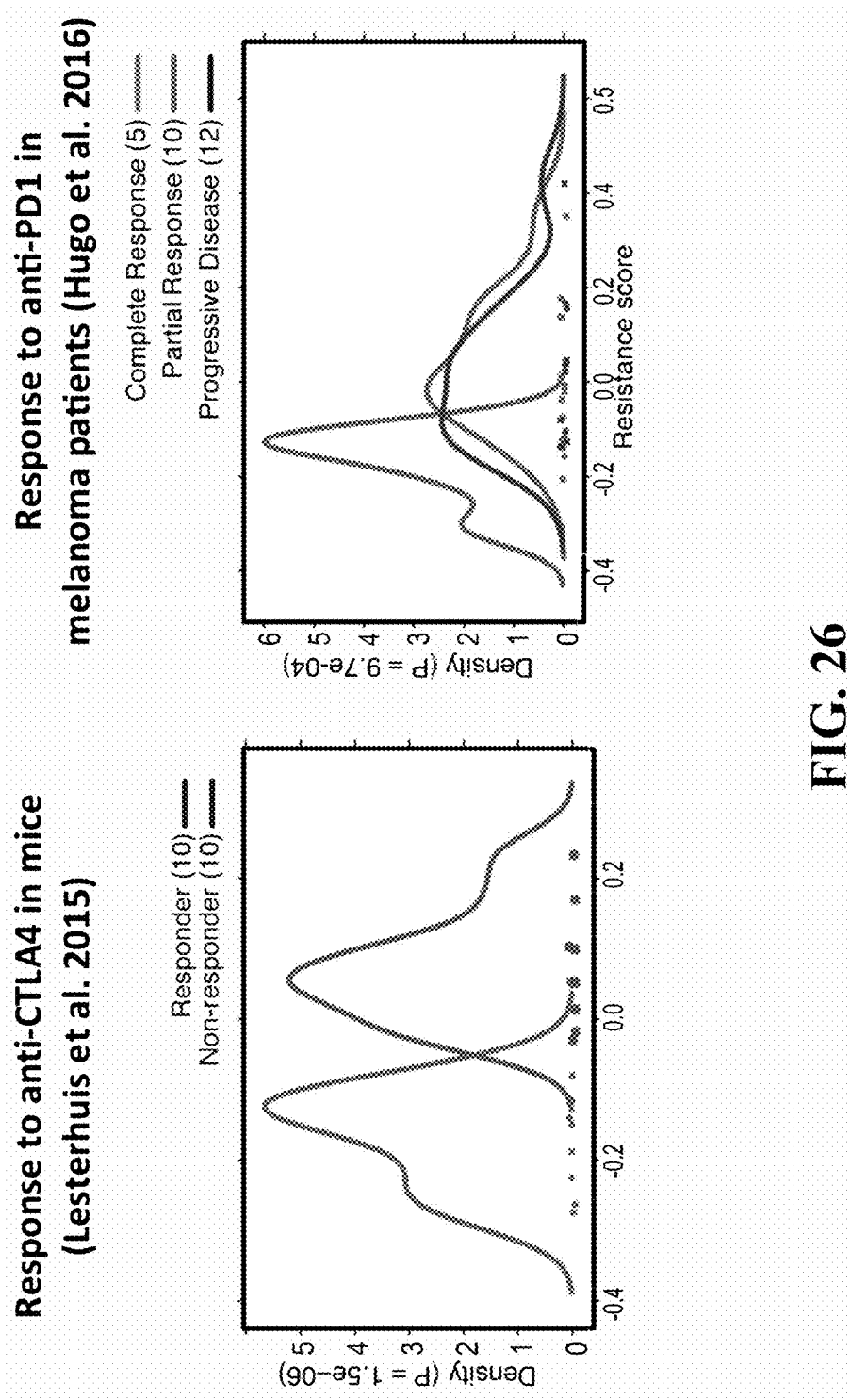
FIG. 26 illustrates that the ITR signature is predictive of eventual outcome in both mouse and human data.

The Post-Immunotherapy Modules are Associated with Response to Anti-PD1 and Anti-CTLA4 in the Clinic and in Mouse Models Immunotherapy introduces selective pressures that, in case of an unsuccessful treatment, are likely to increase the abundance of immunotherapy-resistant cells. The post-immunotherapy signatures Applicants derived might capture these resistant cell states, and, as such, may help to detect innate resistance to anti-PD-1 or anti-CTLA4 therapy-pretreatment. To examine this concept Applicants analyzed the gene expression profiles of responding (n=15) and non-responding (n=13) tumors sampled prior to anti-PD-1 therapy. Indeed, the tumors of responders overexpressed the PIT-down signature and underexpressed the PIT-up signature, resulting in accurate predictors of response to anti-PD-1 (P=3.38e-02 and 5.5e-04, Area Under the Receiver Operating Characteristic Curve (ROC-AUC)=0.91 and 0.77. In another gene expression cohort of pre-anti-CTLA-4 melanoma tumors the signatures did not yield a significant separation between the responders and non-responders. Therefore, Applicants set out to test the signatures in a more controlled setting of a murine model, in which genetically identical mice that experienced the same environment and treatment display a dichotomous response to anti-CTLA4. Indeed, responders scored higher for the PIT-down signature and lower for the PIT-up signature, resulting in accurate predictors of response to anti-CTLA4 in this model (P=1.2e-05, ROC-AUC=0.99). The ITR signature was predictive of eventual outcome in both mouse and human data. First, in a bulk RNA-Seq study of anti-CTLA4 therapy in mouse, the malignant ITR score predicted well non-responders compared to responders. Applicants analyzed 27 patients associated with anti-PD 1 response (Hugo et al., 2016). The malignant ITR was significantly lower in pre-treatment samples from patients with complete response compared to those with partial or no response (FIG. 26). The (5) complete-responders in the data of Hugo et al. scored lower for the sc-resistance signature compared to the other 22 patients (P=9.37e-04). These results indicate that the signatures identified capture cell states that are linked to anti-PD1 and anti-CTLA4 resistance.

Figure 27:
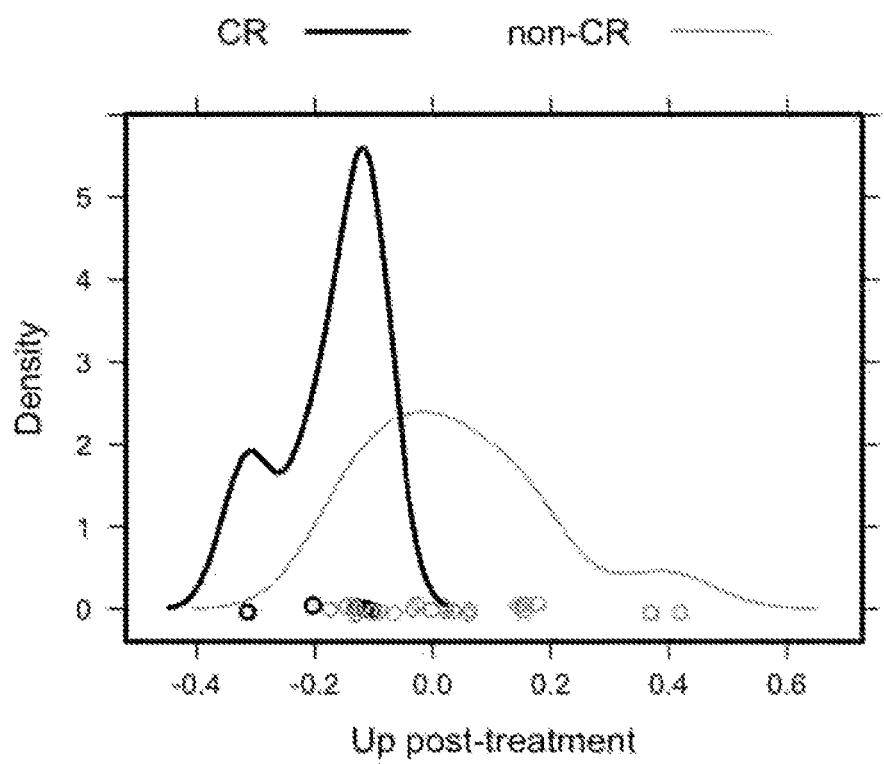
FIG. 27 illustrates the association of complete responders and non-complete responders to genes up-regulated post-treatment with immunotherapy.
Figure 28:
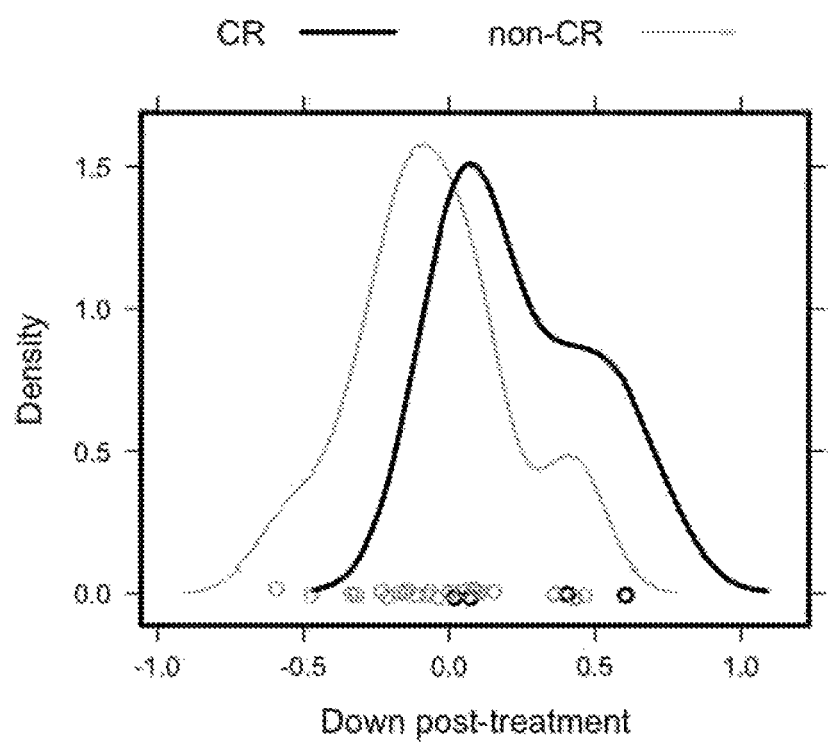
FIG. 28 illustrates the association of complete responders and non-complete responders to genes down-regulated post-treatment with immunotherapy.

Genes that were up-regulated in the resistant tumors (single cell) were down-regulated in CR vs. others (P=9.6e-14) and C/PR vs. NR (NS) (FIG. 27). Genes that were down-regulated in the resistant tumors (single cell) were up-regulated in CR vs. others (P=2.8e-11) and C/PR vs. NR (P=2.8e-03) (FIG. 28).

Associating Melanoma-Cell-Intrinsic States with T-Cell Infiltration and Exclusion.

Tumor infiltration with T cells is one of the strongest predictors of patient response to immune checkpoint inhibitors in various cancer types. Understanding the molecular mechanisms that underlie spontaneous T-cell infiltration could aid the development of therapeutic solutions for patients with non-inflamed tumors. Applicants leveraged the single-cell data and bulk gene expression cohorts of melanoma tumors to map malignant transcriptional states that are associated with T-cell infiltration or exclusion.

First, Applicants analyzed the single-cell data to derive a CD8 T-cell signature, consisting of genes that are primarily expressed by CD8 T-cells (Methods). Applicants used this signature to estimate the T-cell infiltration level of melanoma tumors based on their bulk gene expression profiles. Applicants show that patients with more T-cell infiltration, according to this measure, are more likely to respond to anti-CTLA4 and to MAGE-A3 antigen-specific immunotherapy, and have better overall survival. Next, Applicants identified based on the single-cell data genes that are expressed primarily by malignant melanoma cells. Applicants then searched for genes that are correlated with T cell abundance in the bulk TCGA gene expression cohort, while restricting the search only to the malignant-specific genes to derive an initial T-cell-infiltration signature (T cell exclusion signature (T-ex).

While the initial signature is informative, it is limited for two main reasons. First, there are only 384 genes that could be confidently defined as exclusively expressed by the malignant melanoma cells. Second, it cannot confidently identify genes whose expression in the malignant cells will exclude T-cells. To overcome these limitations, Applicants used the initial T-cell infiltration signature only as an anchor, and searched for genes whose expression level in the individual malignant cells is positively or negatively correlated to the overall expression of this initial signature. Applicants defined genes that are strongly positively (negatively) correlated to the initial signature as the infiltrated (non-infiltrated) module. Of note, non-malignant cells express most of the genes in these modules, and hence it would have been difficult to associate them with T-cell infiltration without leveraging the single-cell data.

The genes in the infiltrated module (exclusion-down) play a major role in antigen processing and presentation (HLA-AB/C, B2M, TAPBP) and interferon gamma response (e.g., IFI27, IFI35, IRF4, IRF9, STAT2). In certain embodiments, the infiltrated module includes the following genes: A2M, AEBP1, AHNAK, ANXA1, APOC2, APOD, APOE, ATP1A1, ATP1B1, C4A, CAPN3, CAV1, CD151, CD59, CD63, CDH19, CRYAB, CSPG4, CSRP1, CST3, CTSB, CTSD, DAG1, DDR1, DUSP6, ETV5, EVA1A, FBXO32, FCGR2A, FGFR1, GAA, GATSL3, GJB1, GRN, GSN, HLA-B, HLA-C, HLA-F, HLA-H, IFI35, IGFBP7, IGSF8, ITGA3, ITGA7, ITGB3, LAMP2, LGALS3, LOXL4, LRPAP1, LY6E, LYRM9, MATN2, MFGE8, MIA, MPZ, MT2A, MTRNR2L3, MTRNR2L6, NPC1, NPC2, NSG1, PERP, PKM, PLEKHB1, PROS1, PRSS23, PYGB, RDH5, ROPN1, S100A1, S 100A13, S 100A6, S100B, SCARB2, SCCPDH, SDC3, SEMA3B, SERPINA1, SERPINA3, SERPINE2, SGCE, SGK1, SLC26A2, SLC5A3, SPON2, SPP1, TIMP1, TIMP2, TIMP3, TM4SF1, TMEM255A, TMX4, TNFSF4, TPP1, TRIML2, TSC22D3, TXNIP, TYR, UBC and WBP2.

The non-infiltrated module (exclusion-up) is mainly enriched with MYC targets and MYC itself. It also includes STRAP, which is an inhibitor of TGF-beta signaling, and SMARCA4 (or BRG1)—a subunit of the BAF complex that has a key role in mediating beta-catenin signaling. The latter has been shown to promote T-cell exclusion in mice. In certain embodiments, the non-infiltrated module includes the following genes: AHCY, BZW2, CCNBIIP1, CCT6A, EEF2, EIF3B, GGCT, ILF3, IMPDH2, MDH2, MYBBP1A, NT5DC2, PAICS, PFKM, POLD2, PTK7, SLC19A1, SMARCA4, STRAP, TIMM13, TOP1MT, TRAP1 and USP22.

Figure 29:
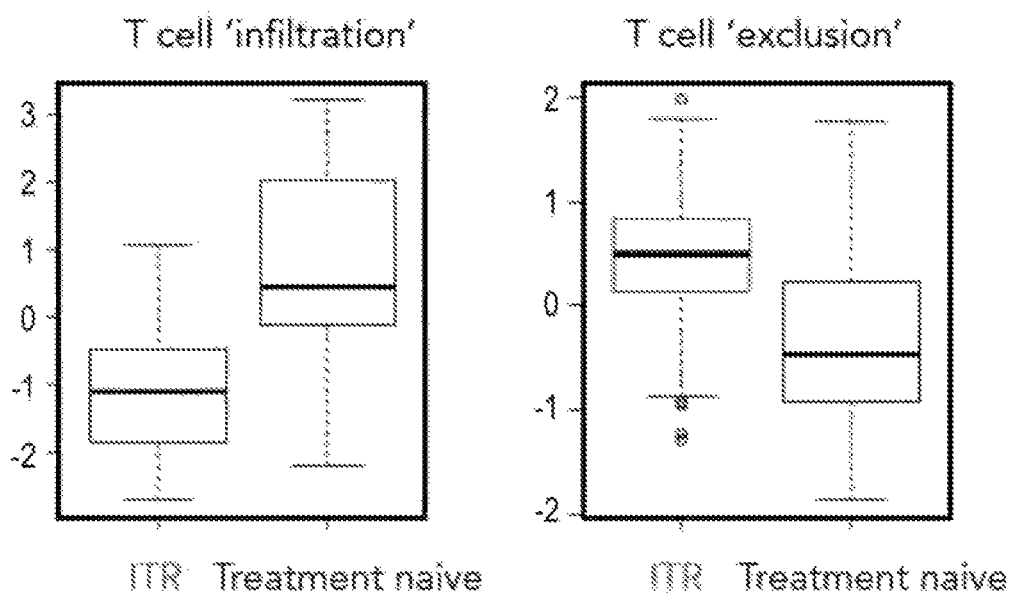
FIG. 29 illustrates that malignant cells ITR signatures have higher exclusion signatures and treatment naive malignant cells have higher infiltration signatures.

Interestingly, these results mirror and overlap the PIT signatures. When scoring the malignant cells according to these infiltration signatures Applicants find that the treatment naïve malignant cells score significantly higher for infiltration compared to the post-treatment malignant cells. In other words, malignant cells having the ITR signature have higher exclusion signatures and treatment naïve malignant cells have higher infiltration signatures (FIG. 29). These results indicate that cells which survive post-immunotherapy either reside in less infiltrated niches within the tumor or have increased capacity to exclude T-cells from their immediate microenvironment. Not being bound by a theory, malignant cells that survive immunotherapy are either to begin with are in a T cell excluded TME or became T cell excluding.

Immunotherapy Triggers Significant Transcriptional Changes in CD8 T-Cells

Figure 30:
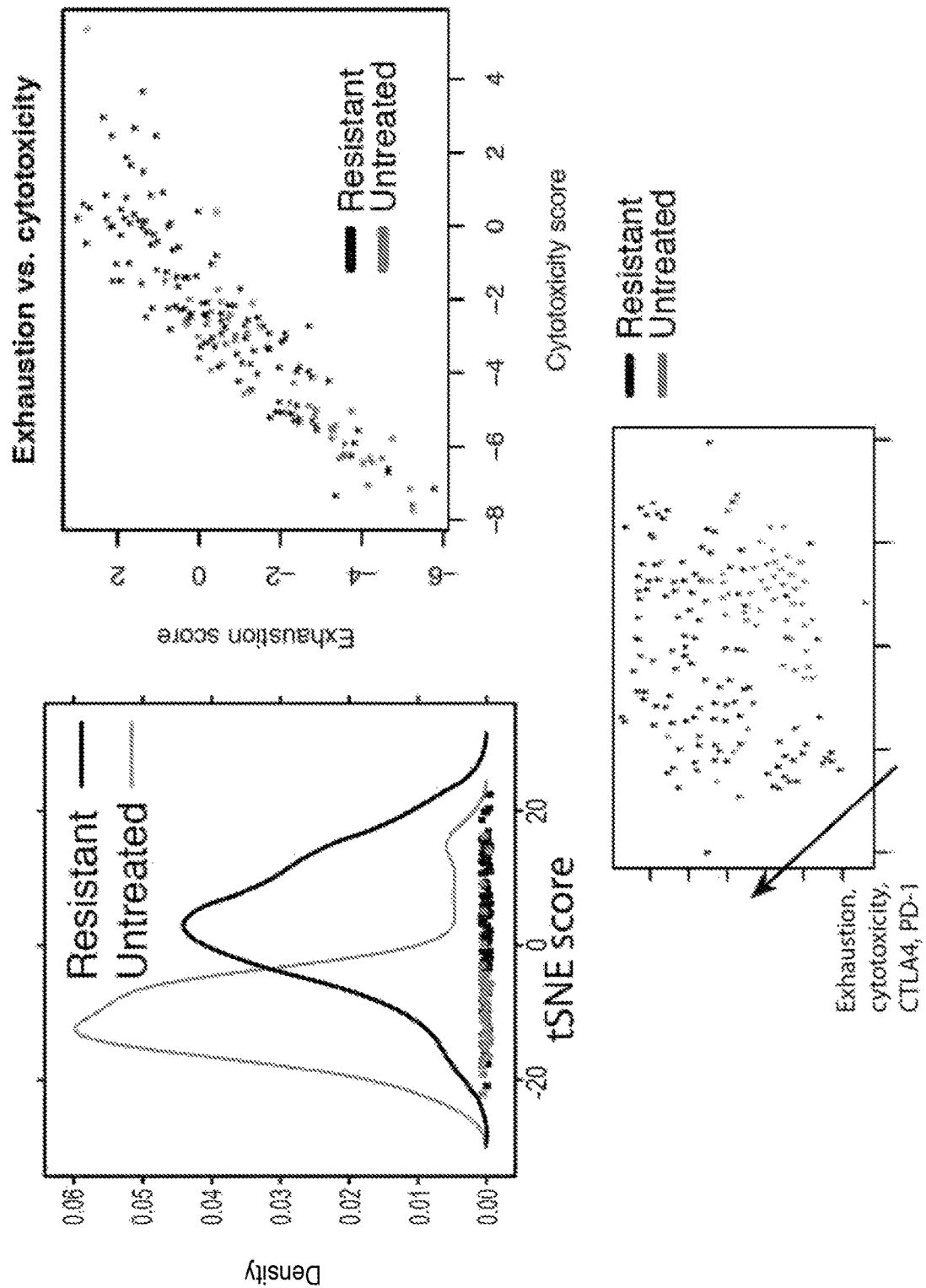
FIG. 30 illustrates analysis of CD8 T cells.
Figure 31:
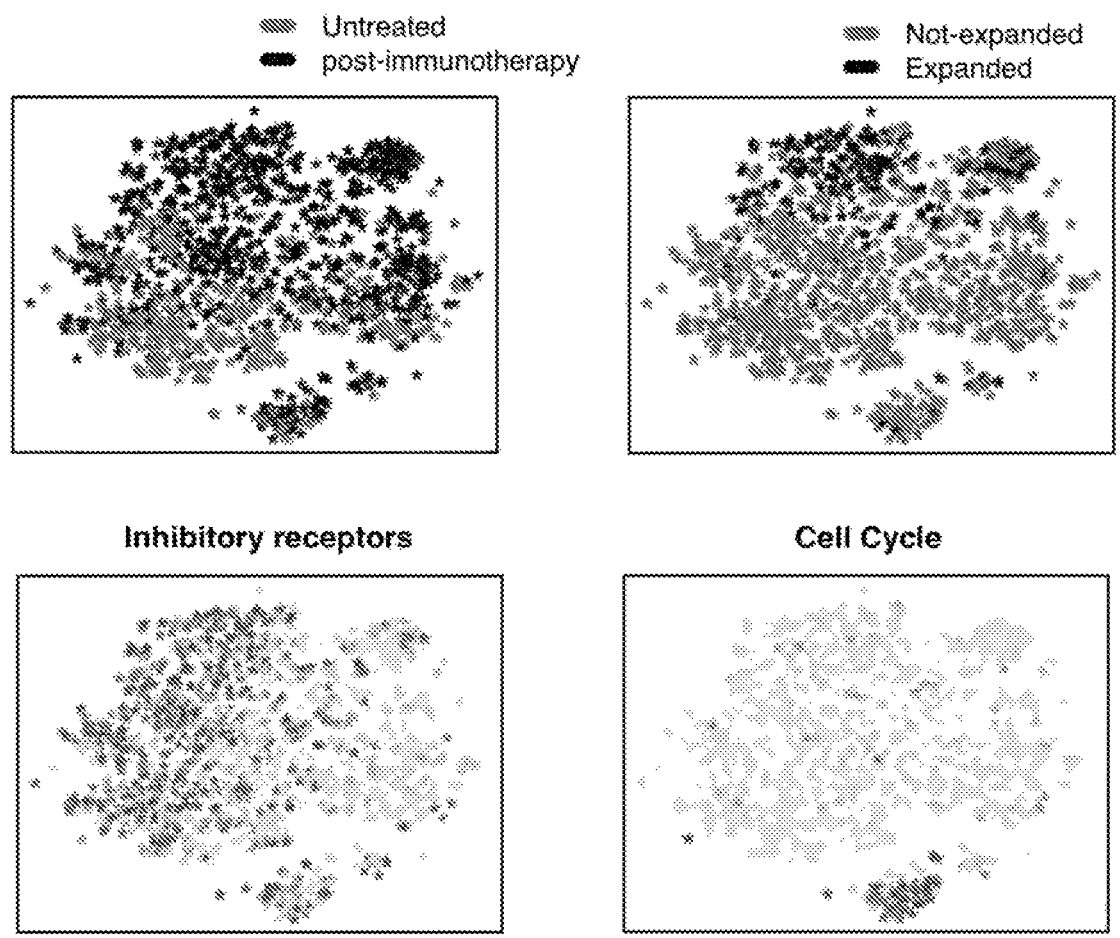
FIG. 31 illustrates analysis of CD8 T cells.

Next Applicants set out to map the transcriptional landscape of the immune cells and examine the association of these states with immunotherapy. Applicants performed the analysis separately for each cell type (CD8 T-cells, CD4 T-cells, B-cells, and macrophages). First, Applicants performed an unbiased analysis to explore the main sources of heterogeneity in melanoma CD8 T-cells. To this end, Applicants applied Principal Component Analysis (PCA) followed by nonlinear dimensionality reduction (t-distributed stochastic neighbor embedding (t-SNE)). Interestingly, in the first PCs and the t-SNE dimensions, the CD8 T-cells are segregated according to their treatment history, such that post-treatment cells cluster together and apart from the treatment naïve cells. These findings demonstrate that immunotherapy triggers significant transcriptional changes in CD8 T-cells, and highlight two additional and orthogonal sources of heterogeneity: one that is attributed to cell cycle, and another that is attributed to the expression of inhibitory checkpoints (FIGS. 30, 31).

Applicants performed supervised analyses to identify the genes and pathways that are differentially expressed in the post-immunotherapy CD8 T-cells compared to the treatment naïve cells. The resulting signatures indicate that the post-treatment CD8 T-cells are more cytotoxic and exhausted, such that naïve T-cell markers are downregulated, while IL-2 signaling, T-cell exhaustion and activation-dysfunction pathways are up regulated. Applicants then scored the CD8 T-cells according to these two signatures, revealing a spectrum of phenotypes also within the PIT and treatment naive populations, and within the CD8 T-cell population of the same tumor.

Applicants speculated that this spectrum might be related to clonal expansion. Clonal expansion occurs when T cells that recognize a specific (tumor) antigen proliferate to generate discernible clonal subpopulations defined by an identical T cell receptor (TCR) sequence. Applicants applied TraCeR to reconstruct the TCR chains of the T-cells and identify cells that are likely to be a part of the same clone (Stubbington et al., Nature Methods 13, 329-332 (2016)). Overall, Applicants identified 113 clones of varying sizes, three of which consist of more than 20 cells (FIG. 32). Specifically, Applicants used the TcR sequence to determine the clone of each T cell, and distinguished four categories: treatment naive or ITR, and expanded or not. Applicants analyzed their gene expression and saw that cells vary in two ways. First CD8 T cells from ITR patients have distinct expression, and this is especially pronounced in expanded cells. All the major expanded clones were in ITR samples, and only very few cells were expanded in treatment naive patients. These few expanded cells look more like cells from the treated patients. Similar to results reported in mice there is an expanded population of Bcl6+Tcf7+ cells in the ITR samples, some also CXCR5+. When Applicants turn to their functional state, Applicants observed that across all patients, regardless of treatment, some cells are more exhausted and others more naive.

Figure 33:
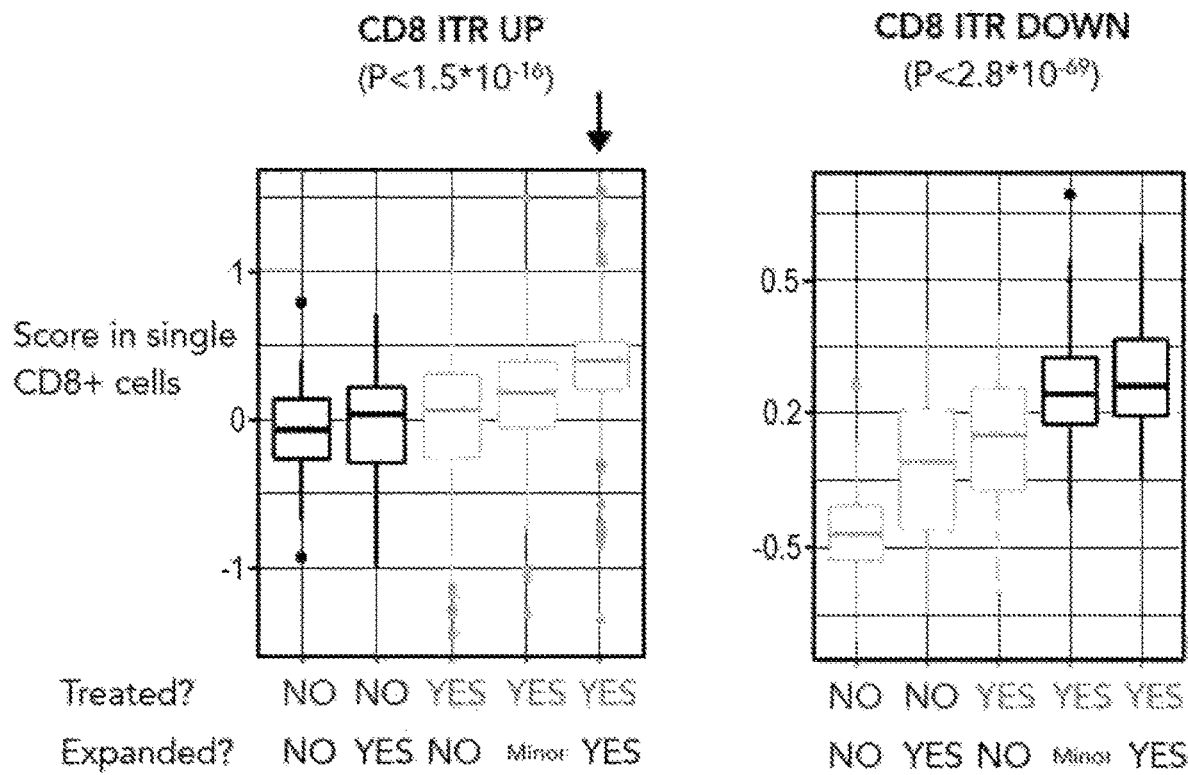
FIG. 33 illustrates that the CD8 ITR signature is strongly associated with clonal expansion.

These large clones are from post-treatment patients, indicating that immunotherapy is triggering T-cell activation and proliferation even when no objective clinical response is observed. Moreover, Applicants find that clonal expansion is strongly associated with the PIT scores, not only across all patients, but also when considering only the post-immunotherapy or treatment naïve cells. Next Applicants compared clonally expanded T-cells to the other T-cells within the same tumor to derive signatures of clonal expansion. By leveraging intra-tumor T-cell heterogeneity in this manner Applicants were able to mitigate the problem of batch effects. In concordance with the previous results Applicants find that genes, which are over (under) expressed post-immunotherapy, are overrepresented in the up (down) regulated clonal-expansion module (FIG. 33).

Not being bound by a theory, inhibition of genes, which are under expressed in the T-cells post immunotherapy, could potentially promote T-cell survival and expansion in the tumor microenvironment. Indeed, these genes are ranked significantly high in the results of an in-vivo shRNA screen that identified negative regulators of T-cell proliferation and survival in mice tumors (P=4.98e-03). All in all, these results suggest that post-immunotherapy T-cells are more activated, even in this cohort of non-responders.

TABLE 4

| Post-immunotherapy state in CD8 T-cells | Pathway | Genes |
|---|---|---|
| Up-regulated | Zinc TFs | ZBTB24, ZNF526, ZNF528, ZNF543, ZNF620, ZNF652, ZSCAN2, ZSCAN22 |
| | IFN gamma signaling | GBP2, GBP5, IRF1, PTPN2, STAT1 |
| | PD1 signaling | CD3D, CD3E, CD3G, HLA-DQA1, HLA-DQA2, HLA-DRB5, PDCD1 |
| Down-regulated | Cell cycle | BIRC5, BUB1, GMNN, MAD2L1, NDC80, TTN, UBE2C, ZWINT |
| | Negative regulators of T-cell survival/proliferation in the TME (Zhou et al. 2014) | CBLB, WNK1, PDCD1 |

Not being bound by a theory, immunotherapy is triggering transcriptional changes both in the malignant cells and in the CD8 T-cells. The results suggest that the T-cells become more effective, while the malignant cells become more "immune-edited" (e.g., evasion (MHC-1) vs. T-cell exclusion).

Example 3—C-Map Analysis

Drugs that could reduce the resistance signature were analyzed by c-map analysis. The analysis showed that the following drugs could reduce the immunotherapy resistance signature:
  PKC activators;
  NFKB pathway inhibitors;
  IGF1R inhibitors; and
  Reserpine (Used to control high blood pressure & psychotic symptoms and blocks the vesicular monoamine transporter (VMAT)).

The signature is associated with drug response/effects. There was an association between the toxicity of different drugs and their resistance scores (according to the resistance signatures). C-map results indicated drugs that can sensitize/de-sensitize the cells to immunotherapy. The results of this analysis are summarized in Tables 5-7.

TABLE 5

Drugs that modulate Gene Signature
The correlation between the resistance scores of the cell lines and their sensitivity (IC50) to the pertaining drug (based on the CCLE gene expression and the Garnett et al. Nature 2012)
Negative R -> more toxic/selective to the immuno-resistant cells.
Positive R -> less toxic/selective to the immuno-resistant cells.

| Drug | All.R | All.P | melanoma.R | melanoma.P |
|---|---|---|---|---|
| Pazopanib | −0.01 | 8.62E−01 | −0.48 | 3.27E−02 |
| Shikonin | −0.05 | 4.55E−01 | −0.48 | 3.97E−02 |
| Etoposide | −0.16 | 2.02E−02 | −0.48 | 4.05E−02 |
| JNK.9L | −0.13 | 4.97E−02 | −0.39 | 1.00E−01 |
| GSK.650394 | −0.17 | 1.02E−02 | −0.37 | 1.05E−01 |
| X681640 | −0.08 | 1.56E−01 | −0.37 | 1.55E−01 |
| Vinorelbine | −0.14 | 3.68E−02 | −0.34 | 1.54E−01 |
| AZD6482 | 0.16 | 1.46E−02 | −0.34 | 1.56E−01 |
| BIRB.0796 | −0.11 | 6.17E−02 | −0.33 | 2.13E−01 |
| NVP.BEZ235 | 0.00 | 9.79E−01 | −0.30 | 1.59E−01 |
| Roscovitine | 0.03 | 6.90E−01 | −0.30 | 4.37E−01 |
| Sunitinib | −0.04 | 6.12E−01 | −0.30 | 4.37E−01 |
| Gemcitabine | −0.05 | 4.18E−01 | −0.29 | 2.19E−01 |
| Epothilone.B | −0.05 | 4.40E−01 | −0.29 | 2.21E−01 |
| ATRA | −0.20 | 6.16E−04 | −0.28 | 3.14E−01 |
| VX.702 | −0.16 | 6.16E−03 | −0.27 | 2.62E−01 |
| QS11 | −0.17 | 7.40E−03 | −0.27 | 2.50E−01 |
| Lapatinib | 0.29 | 4.69E−04 | −0.27 | 4.93E−01 |
| BMS.536924 | 0.32 | 7.64E−05 | −0.25 | 5.21E−01 |

TABLE 5-continued

Drugs that modulate Gene Signature
The correlation between the resistance scores of the cell lines and their sensitivity (IC50) to the pertaining drug (based on the CCLE gene expression and the Garnett et al. Nature 2012)
Negative R -> more toxic/selective to the immuno-resistant cells.
Positive R -> less toxic/selective to the immuno-resistant cells.

| Drug | All.R | All.P | melanoma.R | melanoma.P |
|---|---|---|---|---|
| Vorinostat | −0.37 | 2.73E−11 | −0.25 | 3.02E−01 |
| PD.0332991 | −0.06 | 2.82E−01 | −0.22 | 3.75E−01 |
| Parthenolide | 0.08 | 3.55E−01 | −0.22 | 5.81E−01 |
| AZD.2281 | −0.18 | 1.72E−03 | −0.21 | 3.71E−01 |
| FTI.277 | 0.18 | 6.29E−03 | −0.21 | 3.85E−01 |
| IPA.3 | −0.08 | 2.14E−01 | −0.21 | 3.75E−01 |
| PF.562271 | 0.05 | 4.31E−01 | −0.20 | 4.10E−01 |
| PD.173074 | −0.18 | 1.89E−03 | −0.19 | 3.74E−01 |
| Tipifarnib | −0.09 | 1.93E−01 | −0.18 | 4.33E−01 |
| A.770041 | 0.24 | 4.60E−03 | −0.18 | 6.44E−01 |
| Z.LLNle.CHO | 0.23 | 5.71E−03 | −0.18 | 6.44E−01 |
| CEP.701 | −0.10 | 9.73E−02 | −0.17 | 4.75E−01 |
| PAC.1 | −0.09 | 1.52E−01 | −0.17 | 4.76E−01 |
| BI.2536 | 0.14 | 9.25E−02 | −0.17 | 6.78E−01 |
| GW843682X | 0.05 | 5.52E−01 | −0.17 | 6.78E−01 |
| Midostaurin | 0.06 | 3.70E−01 | −0.16 | 5.03E−01 |
| Metformin | −0.21 | 9.02E−05 | −0.16 | 4.24E−01 |
| ZM.447439 | −0.09 | 1.27E−01 | −0.14 | 5.21E−01 |
| Elesclomol | 0.07 | 2.48E−01 | −0.14 | 6.21E−01 |
| AZD7762 | −0.08 | 1.48E−01 | −0.14 | 5.68E−01 |
| Sorafenib | −0.03 | 7.33E−01 | −0.13 | 7.44E−01 |
| XMD8.85 | 0.00 | 9.81E−01 | −0.13 | 7.44E−01 |
| BAY.61.3606 | −0.05 | 4.84E−01 | −0.13 | 5.81E−01 |
| BI.D1870 | −0.02 | 7.72E−01 | −0.13 | 6.41E−01 |
| Doxorubicin | −0.03 | 6.08E−01 | −0.11 | 6.44E−01 |
| DMOG | 0.17 | 1.05E−02 | −0.10 | 6.78E−01 |
| BMS.509744 | 0.08 | 3.30E−01 | −0.10 | 8.10E−01 |
| Bosutinib | −0.05 | 3.91E−01 | −0.09 | 7.05E−01 |
| CMK | 0.17 | 3.68E−02 | −0.08 | 8.43E−01 |
| KIN001.135 | 0.19 | 2.39E−02 | −0.08 | 8.43E−01 |
| WZ.1.84 | 0.21 | 1.47E−02 | −0.08 | 8.43E−01 |
| AZD8055 | −0.11 | 5.79E−02 | −0.08 | 7.33E−01 |
| Paclitaxel | 0.18 | 3.31E−02 | −0.07 | 8.80E−01 |
| VX.680 | −0.01 | 9.30E−01 | −0.07 | 8.80E−01 |
| LFM.A13 | 0.12 | 5.87E−02 | −0.06 | 8.11E−01 |
| Methotrexate | −0.35 | 1.27E−09 | −0.06 | 8.42E−01 |
| NU.7441 | 0.10 | 1.02E−01 | −0.06 | 8.39E−01 |
| KU.55933 | 0.07 | 2.68E−01 | −0.05 | 8.48E−01 |
| JW.7.52.1 | 0.11 | 1.80E−01 | −0.05 | 9.12E−01 |
| OSI.906 | 0.06 | 3.67E−01 | −0.05 | 8.36E−01 |
| PD.0325901 | 0.23 | 4.75E−05 | −0.04 | 8.51E−01 |
| JNK.Inhibitor.VIII | 0.03 | 6.13E−01 | −0.04 | 9.00E−01 |
| Gefitinib | −0.02 | 6.99E−01 | −0.03 | 9.23E−01 |
| BMS.754807 | 0.01 | 8.32E−01 | −0.02 | 9.32E−01 |
| BIBW2992 | 0.04 | 5.07E−01 | −0.02 | 9.43E−01 |
| Salubrinal | −0.11 | 1.93E−01 | −0.02 | 9.82E−01 |
| Camptothecin.3 | 0.03 | 6.44E−01 | −0.01 | 9.57E−01 |
| Camptothecin.5 | 0.03 | 6.44E−01 | −0.01 | 9.57E−01 |
| A.443654 | 0.14 | 9.40E−02 | 0.00 | 1.00E+00 |
| Thapsigargin | −0.02 | 7.97E−01 | 0.00 | 9.92E−01 |
| NSC.87877 | −0.17 | 1.36E−02 | 0.01 | 9.86E−01 |

TABLE 5-continued

Drugs that modulate Gene Signature
The correlation between the resistance scores of the cell lines and their sensitivity (IC50) to the pertaining drug (based on the CCLE gene expression and the Garnett et al. Nature 2012)
Negative R -> more toxic/selective to the immuno-resistant cells.
Positive R -> less toxic/selective to the immuno-resistant cells.

| Drug | All.R | All.P | melanoma.R | melanoma.P |
|---|---|---|---|---|
| BX.795 | 0.03 | 6.53E−01 | 0.01 | 9.73E−01 |
| X17.AAG | 0.22 | 2.11E−04 | 0.03 | 9.26E−01 |
| Mitomycin.C | −0.12 | 7.40E−02 | 0.03 | 9.11E−01 |
| Temsirolimus | −0.12 | 4.14E−02 | 0.03 | 9.13E−01 |
| Docetaxel | 0.13 | 2.39E−02 | 0.03 | 8.84E−01 |
| Cyclopamine | 0.01 | 8.84E−01 | 0.03 | 9.48E−01 |
| Camptothecin | −0.12 | 3.84E−02 | 0.04 | 8.74E−01 |
| Camptothecin.4 | −0.12 | 3.84E−02 | 0.04 | 8.74E−01 |
| GDC0941 | 0.02 | 7.65E−01 | 0.04 | 8.41E−01 |
| Obatoclax.Mesylate | −0.05 | 4.59E−01 | 0.05 | 8.41E−01 |
| CGP.082996 | −0.01 | 9.29E−01 | 0.07 | 8.80E−01 |
| Bleomycin | −0.09 | 1.92E−01 | 0.08 | 7.53E−01 |
| AS601245 | −0.03 | 6.96E−01 | 0.08 | 7.29E−01 |
| Bryostatin.1 | −0.01 | 8.31E−01 | 0.08 | 7.29E−01 |
| Embelin | −0.01 | 9.13E−01 | 0.09 | 7.05E−01 |
| AKT.inhibitor.VIII | −0.10 | 1.35E−01 | 0.09 | 7.05E−01 |
| AP.24534 | 0.13 | 6.29E−02 | 0.09 | 7.05E−01 |
| RDEA119 | 0.27 | 1.44E−06 | 0.12 | 5.98E−01 |
| Nilotinib | −0.09 | 1.34E−01 | 0.13 | 6.00E−01 |
| CGP.60474 | 0.26 | 1.85E−03 | 0.13 | 7.44E−01 |
| S.Trityl.L.cysteine | 0.00 | 9.82E−01 | 0.13 | 7.44E−01 |
| Erlotinib | 0.18 | 4.08E−02 | 0.15 | 7.08E−01 |
| ABT.888 | −0.11 | 6.48E−02 | 0.15 | 5.17E−01 |
| MK.2206 | −0.09 | 1.47E−01 | 0.16 | 5.14E−01 |
| Dasatinib | 0.38 | 4.98E−06 | 0.17 | 6.78E−01 |
| MG.132 | 0.25 | 2.24E−03 | 0.17 | 6.78E−01 |
| PF.02341066 | 0.14 | 7.89E−02 | 0.17 | 6.78E−01 |
| Cisplatin | −0.01 | 8.94E−01 | 0.18 | 5.12E−01 |
| WH.4.023 | 0.23 | 5.25E−03 | 0.18 | 6.44E−01 |
| CI.1040 | 0.09 | 1.24E−01 | 0.20 | 4.74E−01 |
| SL.0101.1 | −0.06 | 2.74E−01 | 0.20 | 4.56E−01 |
| SB590885 | −0.11 | 5.08E−02 | 0.21 | 3.61E−01 |
| A.769662 | 0.06 | 3.85E−01 | 0.21 | 3.85E−01 |
| AZ628 | 0.17 | 4.24E−02 | 0.22 | 5.81E−01 |
| GSK269962A | 0.21 | 1.14E−02 | 0.22 | 5.81E−01 |
| MS.275 | 0.00 | 9.71E−01 | 0.22 | 5.81E−01 |
| Cytarabine | −0.02 | 7.54E−01 | 0.22 | 4.10E−01 |
| Axitinib | −0.19 | 1.11E−03 | 0.22 | 3.54E−01 |
| Vinblastine | −0.07 | 2.38E−01 | 0.23 | 3.91E−01 |
| Bicalutamide | 0.02 | 7.59E−01 | 0.24 | 2.99E−01 |
| PLX4720 | 0.07 | 2.41E−01 | 0.25 | 3.43E−01 |
| RO.3306 | 0.11 | 6.07E−02 | 0.25 | 2.41E−01 |
| AUY922 | 0.01 | 9.32E−01 | 0.26 | 2.75E−01 |
| GNF.2 | 0.27 | 1.27E−03 | 0.27 | 4.93E−01 |
| Lenalidomide | −0.11 | 5.30E−02 | 0.27 | 2.69E−01 |
| GDC.0449 | −0.12 | 3.17E−02 | 0.29 | 2.20E−01 |
| AICAR | −0.16 | 3.97E−03 | 0.30 | 1.33E−01 |
| AZD6244 | 0.17 | 4.19E−02 | 0.32 | 1.97E−01 |
| Nutlin.3a | −0.09 | 1.18E−01 | 0.32 | 1.36E−01 |
| Bexarotene | −0.01 | 9.08E−01 | 0.34 | 1.41E−01 |
| Imatinib | 0.15 | 6.78E−02 | 0.35 | 3.59E−01 |
| Rapamycin | 0.09 | 2.59E−01 | 0.35 | 3.59E−01 |
| GW.441756 | −0.09 | 1.17E−01 | 0.35 | 1.41E−01 |
| ABT.263 | −0.12 | 3.89E−02 | 0.37 | 8.43E−02 |
| CHIR.99021 | 0.19 | 3.91E−03 | 0.38 | 1.10E−01 |
| Bortezomib | 0.36 | 6.13E−06 | 0.38 | 3.13E−01 |
| Pyrimethamine | 0.09 | 2.84E−01 | 0.38 | 3.13E−01 |
| FH535 | −0.24 | 1.51E−04 | 0.40 | 8.41E−02 |
| AMG.706 | −0.04 | 4.43E−01 | 0.45 | 3.14E−02 |
| SB.216763 | 0.02 | 7.29E−01 | 0.46 | 4.84E−02 |
| AZD.0530 | 0.31 | 1.05E−04 | 0.53 | 1.48E−01 |
| PHA.665752 | 0.18 | 2.41E−02 | 0.68 | 5.03E−02 |
| NVP.TAE684 | 0.21 | 8.27E−03 | 0.72 | 3.69E−02 |

TABLE 6

Top 200 drugs that induce downregulated genes in the signature

| Rank | Score | Type (cp= compound, kd = knock-down, oe = over-expression, cc = cmap class) | ID | Name | Description |
|---|---|---|---|---|---|
| 1 | 99.95 | cc | | PKC Activator | — |
| 2 | 99.95 | kd | CGS001-10538 | BATF | basic leucine zipper proteins |
| 3 | 99.95 | kd | CGS001-25937 | WWTR1 | Hippo Signaling |
| 4 | 99.95 | kd | CGS001-7483 | WNT9A | Wingless-type MMTV integration sites |
| 5 | 99.95 | kd | CGS001-2837 | UTS2R | Urotensin receptor |
| 6 | 99.95 | kd | CGS001-7187 | TRAF3 | — |
| 7 | 99.95 | kd | CGS001-27242 | TNFRSF21 | Tumour necrosis factor (TNF) receptor family |
| 8 | 99.95 | kd | CGS001-7027 | TFDP1 | — |
| 9 | 99.95 | kd | CGS001-64783 | RBM15 | RNA binding motif (RRM) containing |
| 10 | 99.95 | kd | CGS001-8438 | RAD54L | — |
| 11 | 99.95 | kd | CGS001-8624 | PSMG1 | — |
| 12 | 99.95 | kd | CGS001-53632 | PRKAG3 | AMPK subfamily |
| 13 | 99.95 | kd | CGS001-5184 | PEPD | Methionyl aminopeptidase |
| 14 | 99.95 | kd | CGS001-4688 | NCF2 | Tetratricopeptide (TTC) repeat domain containing |
| 15 | 99.95 | kd | CGS001-11004 | KIF2C | Kinesins |
| 16 | 99.95 | kd | CGS001-22832 | KIAA1009 | — |
| 17 | 99.95 | kd | CGS001-10014 | HDAC5 | Histone deacetylases |
| 18 | 99.95 | kd | CGS001-2355 | FOSL2 | basic leucine zipper proteins |
| 19 | 99.95 | kd | CGS001-2864 | FFAR1 | Fatty acid receptors |
| 20 | 99.95 | kd | CGS001-51719 | CAB39 | — |
| 21 | 99.95 | kd | CGS001-604 | BCL6 | BTB/POZ domain containing |

TABLE 6-continued

Top 200 drugs that induce downregulated genes in the signature

| Rank | Score | Type (cp= compound, kd = knock-down, oe = over-expression, cc = cmap class) | ID | Name | Description |
|---|---|---|---|---|---|
| 22 | 99.95 | kd | CGS001-326 | AIRE | Zinc fingers, PHD-type |
| 23 | 99.93 | cp | BRD-K02526760 | QS-11 | ARFGAP inhibitor |
| 24 | 99.92 | kd | CGS001-23224 | SYNE2 | — |
| 25 | 99.92 | kd | CGS001-10267 | RAMP1 | Receptor (G protein-coupled) activity modifying proteins |
| 26 | 99.92 | kd | CGS001-4323 | MMP14 | Matrix metallopeptidase |
| 27 | 99.92 | kd | CGS001-9455 | HOMER2 | — |
| 28 | 99.92 | kd | CGS001-2852 | GPER | — |
| 29 | 99.92 | kd | CGS001-694 | BTG1 | — |
| 30 | 99.91 | cc | | NFKB Activation | — |
| 31 | 99.91 | oe | ccsbBroad304_00833 | IFNG | Interferons |
| 32 | 99.91 | oe | ccsbBroad304_02889 | WWTR1 | Hippo Signaling |
| 33 | 99.91 | oe | ccsbBroad304_00832 | IFNB1 | Interferons |
| 34 | 99.91 | oe | ccsbBroad304_00259 | CD40 | Tumour necrosis factor (TNF) receptor family |
| 35 | 99.91 | oe | ccsbBroad304_05881 | BCL2L2 | Serine/threonine phosphatases/Protein phosphatase 1, regulatory subunits |
| 36 | 99.91 | oe | ccsbBroad304_05390 | DUSP28 | Protein tyrosine phosphatases/Class I Cys-based PTPs: Atypical dual specificity phosphatases |
| 37 | 99.91 | oe | ccsbBroad304_06021 | KLF6 | Kruppel-like transcription factors |
| 38 | 99.91 | oe | ccsbBroad304_00954 | LYN | Src family |
| 39 | 99.91 | oe | ccsbBroad304_03926 | SLC39A8 | SLC39 family of metal ion transporters |
| 40 | 99.89 | cp | BRD-A52650764 | ingenol | PKC activator |
| 41 | 99.89 | kd | CGS001-54472 | TOLLIP | — |
| 42 | 99.89 | kd | CGS001-26472 | PPP1R14B | Serine/threonine phosphatases/Protein phosphatase 1, regulatory subunits |
| 43 | 99.89 | kd | CGS001-6927 | HNF1A | Homeoboxes/HNF class |
| 44 | 99.87 | kd | CGS001-79724 | ZNF768 | Zinc fingers, C2H2-type |
| 45 | 99.87 | kd | CGS001-6915 | TBXA2R | GPCR/Class A: Prostanoid receptors |
| 46 | 99.87 | kd | CGS001-51588 | PIAS4 | Zinc fingers, MIZ-type |
| 47 | 99.87 | kd | CGS001-8974 | P4HA2 | — |
| 48 | 99.87 | kd | CGS001-283455 | KSR2 | RAF family |
| 49 | 99.86 | oe | ccsbBroad304_00880 | IRF2 | — |
| 50 | 99.86 | oe | ccsbBroad304_00771 | HOXA5 | Homeoboxes/ANTP class: HOXL subclass |
| 51 | 99.86 | oe | ccsbBroad304_06260 | GATA3 | GATA zinc finger domain containing |
| 52 | 99.84 | kd | CGS001-7106 | TSPAN4 | Tetraspanins |
| 53 | 99.84 | kd | CGS001-93487 | MAPK1IP1L | — |
| 54 | 99.84 | kd | CGS001-10112 | KIF20A | Kinesins |
| 55 | 99.84 | kd | CGS001-3784 | KCNQ1 | Voltage-gated potassium channels |
| 56 | 99.84 | kd | CGS001-182 | JAG1 | CD molecules |
| 57 | 99.84 | kd | CGS001-1440 | CSF3 | Endogenous ligands |
| 58 | 99.82 | cp | BRD-K91145395 | prostratin | PKC activator |
| 59 | 99.82 | cp | BRD-K32744045 | disulfiram | Aldehyde dehydrogenase inhibitor |
| 60 | 99.82 | kd | CGS001-7525 | YES1 | Src family |
| 61 | 99.82 | kd | CGS001-7849 | PAX8 | Paired boxes |
| 62 | 99.82 | kd | CGS001-1845 | DUSP3 | Protein tyrosine phosphatases/Class I Cys-based PTPs: Atypical dual specificity phosphatases |
| 63 | 99.82 | kd | CGS001-1154 | CISH | SH2 domain containing |
| 64 | 99.81 | oe | ccsbBroad304_04728 | TWIST2 | Basic helix-loop-helix proteins |
| 65 | 99.81 | oe | ccsbBroad304_02048 | BCL10 | — |
| 66 | 99.8 | kd | CGS001-10196 | PRMT3 | Protein arginine N-methyltransferases |
| 67 | 99.79 | cp | BRD-A15079084 | phorbol-12-myristate-13-acetate | PKC activator |

TABLE 6-continued

Top 200 drugs that induce downregulated genes in the signature

| Rank | Score | Type (cp= compound, kd = knock-down, oe = over-expression, cc = cmap class) | ID | Name | Description |
|---|---|---|---|---|---|
| 68 | 99.79 | kd | CGS001-7090 | TLE3 | WD repeat domain containing |
| 69 | 99.79 | kd | CGS001-21 | ABCA3 | ATP binding cassette transporters/subfamily A |
| 70 | 99.78 | cc | | Ribonucleotide Reductase Inhibitor | — |
| 71 | 99.78 | kd | CGS001-23057 | NMNAT2 | — |
| 72 | 99.77 | oe | ccsbBroad304__03232 | VPS28 | — |
| 73 | 99.76 | kd | CGS001-115509 | ZNF689 | Zinc fingers, C2H2-type |
| 74 | 99.76 | kd | CGS001-9928 | KIF14 | Kinesins |
| 75 | 99.76 | kd | CGS001-3417 | IDH1 | — |
| 76 | 99.75 | cp | BRD-K88429204 | pyrimethamine | Dihydrofolate reductase inhibitor |
| 77 | 99.75 | cp | BRD-K25504083 | cytochalasin-d | Actin polymerization inhibitor |
| 78 | 99.75 | cp | BRD-K47983010 | BX-795 | IKK inhibitor |
| 79 | 99.74 | kd | CGS001-6909 | TBX2 | T-boxes |
| 80 | 99.74 | kd | CGS001-5577 | PRKAR2B | Protein kinase A |
| 81 | 99.73 | kd | CGS001-5469 | MED1 | — |
| 82 | 99.72 | oe | ccsbBroad304__07680 | NEK6 | NIMA (never in mitosis gene a)- related kinase (NEK) family |
| 83 | 99.72 | cp | BRD-A15010982 | HU-211 | Glutamate receptor antagonist |
| 84 | 99.72 | cp | BRD-K33106058 | cytarabine | Ribonucleotide reductase inhibitor |
| 85 | 99.71 | kd | CGS001-6857 | SYT1 | Synaptotagmins |
| 86 | 99.71 | kd | CGS001-4482 | MSRA | — |
| 87 | 99.71 | kd | CGS001-8321 | FZD1 | GPCR/Class F: Frizzled receptors |
| 88 | 99.71 | kd | CGS001-124583 | CANT1 | — |
| 89 | 99.71 | kd | CGS001-8312 | AXIN1 | Serine/threonine phosphatases/Protein phosphatase 1, regulatory subunits |
| 90 | 99.71 | kd | CGS001-8874 | ARHGEF7 | Rho guanine nucleotide exchange factors |
| 91 | 99.68 | oe | ccsbBroad304__03556 | SMU1 | WD repeat domain containing |
| 92 | 99.68 | oe | ccsbBroad304__06557 | MAOA | Catecholamine turnover |
| 93 | 99.68 | oe | ccsbBroad304__08282 | ATP6V1D | ATPases/V-type |
| 94 | 99.66 | kd | CGS001-8738 | CRADD | — |
| 95 | 99.65 | kd | CGS001-29890 | RBM15B | RNA binding motif (RRM) containing |
| 96 | 99.63 | kd | CGS001-3397 | ID1 | Basic helix-loop-helix proteins |
| 97 | 99.63 | kd | CGS001-26036 | ZNF451 | Zinc fingers, C2H2-type |
| 98 | 99.63 | kd | CGS001-9375 | TM9SF2 | — |
| 99 | 99.63 | kd | CGS001-10287 | RGS19 | Regulators of G-protein signaling |
| 100 | 99.63 | kd | CGS001-374291 | NDUFS7 | Mitochondrial respiratory chain complex/Complex I |
| 101 | 99.63 | kd | CGS001-51001 | MTERFD1 | — |
| 102 | 99.63 | oe | ccsbBroad304__06542 | LTBR | Tumor necrosis factor receptor superfamily |
| 103 | 99.61 | cp | BRD-A54632525 | BRD-A54632525 | — |
| 104 | 99.61 | kd | CGS001-5654 | HTRA1 | Serine peptidases/Serine peptidases |
| 105 | 99.61 | kd | CGS001-2673 | GFPT1 | — |
| 106 | 99.6 | kd | CGS001-11057 | ABHD2 | Abhydrolase domain containing |
| 107 | 99.58 | kd | CGS001-4835 | NQO2 | — |
| 108 | 99.58 | kd | CGS001-11329 | STK38 | NDR family |
| 109 | 99.58 | kd | CGS001-1666 | DECR1 | Short chain dehydrogenase/reductase superfamily/Classical SDR fold cluster 1 |
| 110 | 99.58 | kd | CGS001-4299 | AFF1 | — |
| 111 | 99.58 | oe | ccsbBroad304__07137 | WT1 | Zinc fingers, C2H2-type |
| 112 | 99.55 | kd | CGS001-22949 | PTGR1 | — |
| 113 | 99.55 | kd | CGS001-2071 | ERCC3 | General transcription factors |

TABLE 6-continued

Top 200 drugs that induce downregulated genes in the signature

| Rank | Score | Type (cp= compound, kd = knock-down, oe = over-expression, cc = cmap class) | ID | Name | Description |
|---|---|---|---|---|---|
| 114 | 99.55 | kd | CGS001-10668 | CGRRF1 | RING-type (C3HC4) zinc fingers |
| 115 | 99.55 | kd | CGS001-348 | APOE | Apolipoproteins |
| 116 | 99.54 | oe | ccsbBroad304_00282 | CDKN1A | — |
| 117 | 99.54 | oe | ccsbBroad304_01010 | MGST2 | Glutathione S-transferases/Microsomal |
| 118 | 99.51 | cp | BRD-K77908580 | entinostat | HDAC inhibitor |
| 119 | 99.5 | kd | CGS001-7371 | UCK2 | — |
| 120 | 99.5 | kd | CGS001-5198 | PFAS | — |
| 121 | 99.5 | kd | CGS001-51005 | AMDHD2 | — |
| 122 | 99.47 | kd | CGS001-5188 | PET112 | — |
| 123 | 99.47 | kd | CGS001-25836 | NIPBL | — |
| 124 | 99.47 | kd | CGS001-5891 | MOK | RCK family |
| 125 | 99.47 | kd | CGS001-1994 | ELAVL1 | RNA binding motif (RRM) containing |
| 126 | 99.45 | oe | ccsbBroad304_04891 | TMEM174 | — |
| 127 | 99.44 | cp | BRD-K73610817 | BRD-K73610817 | — |
| 128 | 99.44 | cp | BRD-K65814004 | diphenyleneiodonium | Nitric oxide synthase inhibitor |
| 129 | 99.44 | oe | ccsbBroad304_01388 | RELB | NFkappaB transcription factor family |
| 130 | 99.42 | kd | CGS001-8996 | NOL3 | — |
| 131 | 99.42 | kd | CGS001-64223 | MLST8 | WD repeat domain containing |
| 132 | 99.41 | kd | CGS001-929 | CD14 | CD molecules |
| 133 | 99.4 | oe | ccsbBroad304_07306 | TNFRSF10A | Tumour necrosis factor (TNF) receptor family |
| 134 | 99.4 | cp | BRD-K26818574 | BIX-01294 | Histone lysine methyltransferase inhibitor |
| 135 | 99.4 | cp | BRD-K92991072 | PAC-1 | Caspase activator |
| 136 | 99.39 | cc | | ATPase Inhibitor | — |
| 137 | 99.37 | kd | CGS001-1955 | MEGF9 | — |
| 138 | 99.37 | cp | BRD-K93034159 | cladribine | Adenosine deaminase inhibitor |
| 139 | 99.34 | kd | CGS001-2063 | NR2F6 | COUP-TF-like receptors |
| 140 | 99.33 | cp | BRD-K50841342 | PAC-1 | — |
| 141 | 99.32 | cc | | BCL2 And Related Protein Inhibitor | — |
| 142 | 99.32 | kd | CGS001-54386 | TERF2IP | — |
| 143 | 99.32 | kd | CGS001-1852 | DUSP9 | Protein tyrosine phosphatases/Class I Cys-based PTPs: MAP kinase phosphatases |
| 144 | 99.32 | kd | CGS001-1212 | CLTB | — |
| 145 | 99.32 | kd | CGS001-9459 | ARHGEF6 | Rho guanine nucleotide exchange factors |
| 146 | 99.31 | oe | ccsbBroad304_08010 | FBXO5 | F-boxes/other |
| 147 | 99.3 | kd | CGS001-9643 | MORF4L2 | — |
| 148 | 99.29 | kd | CGS001-22827 | PUF60 | RNA binding motif (RRM) containing |
| 149 | 99.29 | kd | CGS001-1349 | COX7B | Mitochondrial respiratory chain complex |
| 150 | 99.26 | kd | CGS001-79885 | HDAC11 | Histone deacetylases |
| 151 | 99.26 | kd | CGS001-4046 | LSP1 | — |
| 152 | 99.25 | kd | CGS001-3177 | SLC29A2 | SLC29 family |
| 153 | 99.24 | kd | CGS001-3326 | HSP90AB1 | Heat shock proteins/HSPC |
| 154 | 99.23 | kd | CGS001-1643 | DDB2 | WD repeat domain containing |
| 155 | 99.22 | kd | CGS001-8986 | RPS6KA4 | MSK subfamily |
| 156 | 99.22 | cp | BRD-K26664453 | cytochalasin-b | Microtubule inhibitor |
| 157 | 99.21 | cc | | Aldo Keto Reductase | — |
| 158 | 99.21 | oe | ccsbBroad304_01710 | TRAF2 | RING-type (C3HC4) zinc fingers |
| 159 | 99.21 | oe | ccsbBroad304_05941 | CBR3 | Short chain dehydrogenase/reductase superfamily/Classical SDR fold cluster 1 |

TABLE 6-continued

Top 200 drugs that induce downregulated genes in the signature

| Rank | Score | Type (cp= compound, kd = knock-down, oe = over-expression, cc = cmap class) | ID | Name | Description |
|---|---|---|---|---|---|
| 160 | 99.21 | kd | CGS001-5096 | PCCB | Carboxylases |
| 161 | 99.21 | oe | ccsbBroad304_06392 | HOXB7 | Homeoboxes/ANTP class: HOXL subclass |
| 162 | 99.18 | kd | CGS001-22955 | SCMH1 | Sterile alpha motif (SAM) domain containing |
| 163 | 99.17 | oe | ccsbBroad304_00773 | HOXA9 | Homeoboxes/ANTP class: HOXL subclass |
| 164 | 99.17 | kd | CGS001-3108 | HLA-DMA | Immunoglobulin superfamily/C1-set domain containing |
| 165 | 99.17 | oe | ccsbBroad304_05098 | MAGEB6 | — |
| 166 | 99.14 | oe | ccsbBroad304_01686 | TNFAIP3 | OTU domain containing |
| 167 | 99.13 | kd | CGS001-7690 | ZNF131 | BTB/POZ domain containing |
| 168 | 99.13 | kd | CGS001-23011 | RAB21 | RAB, member RAS oncogene |
| 169 | 99.13 | kd | CGS001-5106 | PCK2 | — |
| 170 | 99.13 | kd | CGS001-85315 | PAQR8 | — |
| 171 | 99.12 | oe | ccsbBroad304_01858 | FOSL1 | basic leucine zipper proteins |
| 172 | 99.12 | cp | BRD-K23984367 | sorafenib | — |
| 173 | 99.12 | cp | BRD-K72264770 | QW-BI-011 | Histone lysine methyltransferase inhibitor |
| 174 | 99.11 | kd | CGS001-11116 | FGFR1OP | — |
| 175 | 99.1 | kd | CGS001-4804 | NGFR | Tumour necrosis factor (TNF) receptor family |
| 176 | 99.08 | kd | CGS001-6676 | SPAG4 | — |
| 177 | 99.08 | kd | CGS001-63874 | ABHD4 | Abhydrolase domain containing |
| 178 | 99.07 | oe | ccsbBroad304_00389 | CTBP1 | — |
| 179 | 99.05 | kd | CGS001-7480 | WNT10B | Wingless-type MMTV integration sites |
| 180 | 99.05 | kd | CGS001-80351 | TNKS2 | Ankyrin repeat domain containing |
| 181 | 99.05 | kd | CGS001-2264 | FGFR4 | Type V RTKs: FGF (fibroblast growth factor) receptor family |
| 182 | 99.05 | kd | CGS001-1725 | DHPS | — |
| 183 | 99.05 | kd | CGS001-64170 | CARD9 | — |
| 184 | 99.03 | kd | CGS001-6259 | RYK | Type XV RTKs: RYK |
| 185 | 99.03 | kd | CGS001-54566 | EPB41L4B | — |
| 186 | 99.02 | kd | CGS001-308 | ANXA5 | Annexins |
| 187 | 99.01 | kd | CGS001-5257 | PHKB | — |
| 188 | 99 | kd | CGS001-7764 | ZNF217 | Zinc fingers, C2H2-type |
| 189 | 99 | kd | CGS001-5451 | POU2F1 | Homeoboxes/POU class |
| 190 | 98.98 | cp | BRD-K30677119 | PP-30 | RAF inhibitor |
| 191 | 98.98 | kd | CGS001-23368 | PPP1R13B | Ankyrin repeat domain containing |
| 192 | 98.98 | cp | BRD-A34208323 | VU-0404997-2 | Glutamate receptor modulator |
| 193 | 98.97 | kd | CGS001-4601 | MXI1 | Basic helix-loop-helix proteins |
| 194 | 98.97 | kd | CGS001-10247 | HRSP12 | — |
| 195 | 98.95 | kd | CGS001-8295 | TRRAP | TRRAP subfamily |
| 196 | 98.95 | kd | CGS001-26064 | RAI14 | Ankyrin repeat domain containing |
| 197 | 98.95 | kd | CGS001-5710 | PSMD4 | Proteasome (prosome, macropain) subunits |
| 198 | 98.95 | kd | CGS001-3312 | HSPA8 | Heat shock proteins/HSP70 |
| 199 | 98.93 | cp | BRD-K59456551 | methotrexate | Dihydrofolate reductase inhibitor |
| 200 | 98.93 | kd | CGS001-10327 | AKR1A1 | Aldo-keto reductases |

TABLE 7

| | | Top 200 drugs that repress upregulated genes in the signature | | | |
|---|---|---|---|---|---|
| Rank | Score | Type (cp = compound, kd = knock-down, oe = over-expression, cc = cmap class) | ID | Name | Description |
| 8875 | −99.95 | kd | CGS001-10254 | STAM2 | — |
| 8876 | −99.95 | kd | CGS001-5966 | REL | NFkappaB transcription factor family |
| 8877 | −99.95 | kd | CGS001-4609 | MYC | Basic helix-loop-helix proteins |
| 8878 | −99.95 | kd | CGS001-2079 | ERH | — |
| 8879 | −99.95 | kd | CGS001-2683 | B4GALT1 | Beta 4-glycosyltransferases |
| 8880 | −99.95 | kd | CGS001-406 | ARNTL | Basic helix-loop-helix proteins |
| 8872 | −99.92 | cc | | Aldo Keto Reductase | — |
| 8873 | −99.92 | kd | CGS001-8644 | AKR1C3 | Prostaglandin synthases |
| 8874 | −99.92 | kd | CGS001-2863 | GPR39 | GPCR/Class A: Orphans |
| 8870 | −99.91 | oe | ccsbBroad304_03864 | OVOL2 | Zinc fingers, C2H2-type |
| 8871 | −99.91 | oe | ccsbBroad304_08418 | FBXL12 | F-boxes/Leucine-rich repeats |
| 8866 | −99.89 | kd | CGS001-114026 | ZIM3 | Zinc fingers, C2H2-type |
| 8867 | −99.89 | kd | CGS001-51021 | MRPS16 | Mitochondrial ribosomal proteins/small subunits |
| 8868 | −99.89 | kd | CGS001-3265 | HRAS | RAS subfamily |
| 8869 | −99.89 | kd | CGS001-1643 | DDB2 | WD repeat domain containing |
| 8864 | −99.88 | kd | CGS001-6337 | SCNN1A | Epithelial sodium channels (ENaC) |
| 8865 | −99.88 | kd | CGS001-4191 | MDH2 | — |
| 8861 | −99.87 | kd | CGS001-26137 | ZBTB20 | BTB/POZ domain containing |
| 8862 | −99.87 | kd | CGS001-7227 | TRPS1 | GATA zinc finger domain containing |
| 8863 | −99.87 | kd | CGS001-95 | ACY1 | — |
| 8856 | −99.86 | oe | ccsbBroad304_00832 | IFNB1 | Interferons |
| 8857 | −99.86 | oe | ccsbBroad304_05982 | CDX2 | Homeoboxes/ANTP class: HOXL subclass |
| 8858 | −99.86 | oe | ccsbBroad304_06021 | KLF6 | Kruppel-like transcription factors |
| 8859 | −99.86 | oe | ccsbBroad304_01249 | PPARG | Peroxisome proliferator-activated receptors |
| 8860 | −99.86 | oe | ccsbBroad304_00472 | EBF1 | — |
| 8854 | −99.84 | kd | CGS001-7185 | TRAF1 | — |
| 8855 | −99.84 | kd | CGS001-5562 | PRKAA1 | AMPK subfamily |
| 8853 | −99.83 | kd | CGS001-7775 | ZNF232 | Zinc fingers, C2H2-type |
| 8852 | −99.82 | kd | CGS001-10525 | HYOU1 | Heat shock proteins/HSP70 |
| 8851 | −99.81 | oe | ccsbBroad304_07363 | AIFM1 | — |
| 8850 | −99.79 | cp | BRD-A81772229 | simvastatin | HMGCR inhibitor |
| 8847 | −99.77 | oe | ccsbBroad304_00747 | HLF | — |
| 8848 | −99.77 | oe | ccsbBroad304_00487 | EGR1 | Zinc fingers, C2H2-type |
| 8849 | −99.77 | oe | ccsbBroad304_04271 | MXD3 | Basic helix-loop-helix proteins |
| 8846 | −99.76 | kd | CGS001-5608 | MAP2K6 | MAPKK: STE7 family |
| 8844 | −99.75 | cc | | JAK Inhibitor | — |
| 8845 | −99.75 | cp | BRD-K91290917 | amodiaquine | Histamine receptor agonist |
| 8843 | −99.74 | kd | CGS001-9296 | ATP6V1F | ATPases/V-type |
| 8841 | −99.71 | kd | CGS001-6389 | SDHA | Mitochondrial respiratory chain complex |
| 8842 | −99.71 | kd | CGS001-6275 | S100A4 | EF-hand domain containing |
| 8839 | −99.68 | oe | ccsbBroad304_00833 | IFNG | Interferons |
| 8840 | −99.68 | oe | ccsbBroad304_07117 | UGCG | Glycosyltransferase family 2 domain containing |
| 8838 | −99.67 | kd | CGS001-8031 | NCOA4 | — |
| 8836 | −99.66 | kd | CGS001-7167 | TPI1 | — |
| 8837 | −99.66 | kd | CGS001-3419 | IDH3A | — |
| 8835 | −99.63 | kd | CGS001-5469 | MED1 | — |
| 8830 | −99.61 | cp | BRD-K52850071 | JAK3-Inhibitor-II | JAK inhibitor |
| 8831 | −99.61 | cp | BRD-K49049886 | CGS-15943 | Adenosine receptor antagonist |
| 8832 | −99.61 | kd | CGS001-115650 | TNFRSF13C | Tumour necrosis factor (TNF) receptor family |

TABLE 7-continued

Top 200 drugs that repress upregulated genes in the signature

| Rank | Score | Type (cp = compound, kd = knock-down, oe = over-expression, cc = cmap class) | ID | Name | Description |
|---|---|---|---|---|---|
| 8833 | −99.61 | kd | CGS001-6493 | SIM2 | Basic helix-loop-helix proteins |
| 8834 | −99.61 | kd | CGS001-7803 | PTP4A1 | Protein tyrosine phosphatases/Class I Cys-based PTPs: PRLs |
| 8829 | −99.59 | cc | | Aurora Kinase Inhibitor Grp2 | — |
| 8825 | −99.58 | cp | BRD-K37691127 | hinokitiol | Tyrosinase inhibitor |
| 8826 | −99.58 | kd | CGS001-5170 | PDPK1 | PDK1 family |
| 8827 | −99.58 | kd | CGS001-4199 | ME1 | — |
| 8828 | −99.58 | kd | CGS001-51295 | ECSIT | Mitochondrial respiratory chain complex assembly factors |
| 8822 | −99.55 | kd | CGS001-51520 | LARS | Aminoacyl tRNA synthetases/Class I |
| 8823 | −99.55 | kd | CGS001-2538 | G6PC | — |
| 8824 | −99.55 | kd | CGS001-2059 | EPS8 | — |
| 8819 | −99.54 | cp | BRD-K58299615 | RO-90-7501 | Beta amyloid inhibitor |
| 8820 | −99.54 | kd | CGS001-3485 | IGFBP2 | insulin-like growth factor (IGF) binding proteins |
| 8821 | −99.54 | cp | BRD-K85606544 | neratinib | EGFR inhibitor |
| 8813 | −99.53 | kd | CGS001-54472 | TOLLIP | — |
| 8814 | −99.53 | kd | CGS001-4998 | ORC1 | ATPases/AAA-type |
| 8815 | −99.53 | kd | CGS001-9020 | MAP3K14 | MAPKKK: STE-unique family |
| 8816 | −99.53 | kd | CGS001-355 | FAS | Tumour necrosis factor (TNF) receptor family |
| 8817 | −99.53 | kd | CGS001-10327 | AKR1A1 | Aldo-keto reductases |
| 8818 | −99.53 | kd | CGS001-178 | AGL | — |
| 8812 | −99.52 | cc | | HOX Gene | — |
| 8810 | −99.51 | cp | BRD-A19633847 | perhexiline | Carnitine palmitoyltransferase inhibitor |
| 8811 | −99.51 | cp | BRD-K47105409 | AG-490 | — |
| 8809 | −99.49 | oe | ccsbBroad304_00706 | GTF2B | General transcription factors |
| 8806 | −99.47 | oe | ccsbBroad304_05980 | CDKN1B | — |
| 8807 | −99.47 | kd | CGS001-8226 | HDHD1 | — |
| 8808 | −99.47 | kd | CGS001-5045 | FURIN | Subtilisin |
| 8805 | −99.45 | oe | ccsbBroad304_00772 | HOXA6 | Homeoboxes/ANTP class: HOXL subclass |
| 8804 | −99.44 | kd | CGS001-3309 | HSPA5 | Heat shock proteins/HSP70 |
| 8803 | −99.43 | oe | ccsbBroad304_00838 | IGFBP5 | insulin-like growth factor (IGF) binding proteins |
| 8802 | −99.4 | cp | BRD-K92991072 | PAC-1 | Caspase activator |
| 8801 | −99.39 | kd | CGS001-35 | ACADS | — |
| 8800 | −99.38 | kd | CGS001-3122 | HLA-DRA | Immunoglobulin superfamily/C1-set domain containing |
| 8799 | −99.37 | cp | BRD-K66296774 | fluvastatin | HMGCR inhibitor |
| 8798 | −99.36 | kd | CGS001-7525 | YES1 | Src family |
| 8797 | −99.35 | kd | CGS001-57178 | ZMIZ1 | Zinc fingers, MIZ-type |
| 8795 | −99.34 | kd | CGS001-3635 | INPP5D | Inositol polyphosphate phosphatases |
| 8796 | −99.34 | kd | CGS001-3416 | IDE | Pitrilysin |
| 8794 | −99.33 | cp | BRD-K07881437 | danusertib | Aurora kinase inhibitor |
| 8793 | −99.32 | cp | BRD-A50675702 | fipronil | GABA gated chloride channel blocker |
| 8792 | −99.29 | kd | CGS001-998 | CDC42 | — |
| 8791 | −99.28 | cc | | PI3K Inhibitor | — |
| 8787 | −99.26 | cc | | DNA-dependent Protein Kinase | — |
| 8788 | −99.26 | cp | BRD-K94441233 | mevastatin | HMGCR inhibitor |
| 8789 | −99.26 | oe | ccsbBroad304_02571 | TOMM34 | Tetratricopeptide (TTC) repeat domain containing |
| 8790 | −99.26 | oe | ccsbBroad304_01579 | SOX2 | SRY (sex determining region Y)-boxes |
| 8784 | −99.24 | kd | CGS001-5682 | PSMA1 | Proteasome subunits |
| 8785 | −99.24 | kd | CGS001-53347 | UBASH3A | — |

TABLE 7-continued

Top 200 drugs that repress upregulated genes in the signature

| Rank | Score | Type (cp = compound, kd = knock-down, oe = over-expression, cc = cmap class) | ID | Name | Description |
|---|---|---|---|---|---|
| 8786 | −99.24 | kd | CGS001-2782 | GNB1 | WD repeat domain containing |
| 8782 | −99.23 | oe | ccsbBroad304_11277 | HAT1 | Histone acetyltransferases (HATs) |
| 8783 | −99.23 | kd | CGS001-4323 | MMP14 | Matrix metallopeptidase |
| 8780 | −99.2 | kd | CGS001-79142 | PHF23 | Zinc fingers, PHD-type |
| 8781 | −99.2 | kd | CGS001-2664 | GDI1 | — |
| 8778 | −99.19 | cp | BRD-K48974000 | BRD-K48974000 | — |
| 8779 | −99.19 | kd | CGS001-4817 | NIT1 | — |
| 8777 | −99.18 | kd | CGS001-7126 | TNFAIP1 | BTB/POZ domain containing |
| 8775 | −99.17 | kd | CGS001-10497 | UNC13B | — |
| 8776 | −99.17 | kd | CGS001-57448 | BIRC6 | Inhibitors of apoptosis (IAP) protein family |
| 8772 | −99.15 | cp | BRD-K13514097 | everolimus | MTOR inhibitor |
| 8773 | −99.15 | cp | BRD-K59331372 | SB-366791 | TRPV antagonist |
| 8774 | −99.15 | cp | BRD-K78373679 | RO-3306 | CDK inhibitor |
| 8770 | −99.13 | oe | ccsbBroad304_02451 | HOXB13 | Homeoboxes/ANTP class: HOXL subclass |
| 8771 | −99.13 | kd | CGS001-7405 | UVRAG | — |
| 8769 | −99.12 | cp | BRD-K06217810 | BRD-K06217810 | — |
| 8768 | −99.11 | cc | | HMGCR Inhibitor | — |
| 8765 | −99.08 | kd | CGS001-55781 | RIOK2 | RIO2 subfamily |
| 8766 | −99.08 | kd | CGS001-7026 | NR2F2 | COUP-TF-like receptors |
| 8767 | −99.08 | kd | CGS001-7994 | KAT6A | Histone acetyltransferases (HATs) |
| 8762 | −99.07 | oe | ccsbBroad304_06131 | DUSP6 | Protein tyrosine phosphatases/Class I Cys-based PTPs: MAP kinase phosphatases |
| 8763 | −99.07 | kd | CGS001-4916 | NTRK3 | Type VII RTKs: Neurotrophin receptor/Trk family |
| 8764 | −99.07 | oe | ccsbBroad304_06394 | HOXC9 | Homeoboxes/ANTP class: HOXL subclass |
| 8761 | −99.06 | cp | BRD-K60623809 | SU-11652 | Tyrosine kinase inhibitor |
| 8758 | −99.03 | oe | ccsbBroad304_03574 | FBXW7 | F-boxes/WD-40 domains |
| 8759 | −99.03 | kd | CGS001-6772 | STAT1 | SH2 domain containing |
| 8760 | −99.03 | kd | CGS001-6768 | ST14 | Serine peptidases/Transmembrane |
| 8757 | −99.02 | kd | CGS001-64170 | CARD9 | — |
| 8753 | −98.98 | oe | ccsbBroad304_02048 | BCL10 | — |
| 8754 | −98.98 | cp | BRD-K50836978 | purvalanol-a | CDK inhibitor |
| 8755 | −98.98 | kd | CGS001-9601 | PDIA4 | Protein disulfide isomerases |
| 8756 | −98.98 | cp | BRD-K46056750 | AZD-7762 | CHK inhibitor |
| 8751 | −98.97 | kd | CGS001-1936 | EEF1D | — |
| 8752 | −98.97 | kd | CGS001-8192 | CLPP | ATPases/AAA-type |
| 8750 | −98.96 | kd | CGS001-5211 | PFKL | — |
| 8749 | −98.95 | kd | CGS001-23476 | BRD4 | Bromodomain kinase (BRDK) family |
| 8746 | −98.94 | cp | BRD-K97399794 | quercetin | Polar auxin transport inhibitor |
| 8747 | −98.94 | oe | ccsbBroad304_10487 | BPHL | — |
| 8748 | −98.94 | cp | BRD-K64890080 | BI-2536 | PLK inhibitor |
| 8745 | −98.93 | kd | CGS001-3927 | LASP1 | — |
| 8742 | −98.92 | kd | CGS001-7541 | ZFP161 | — |
| 8743 | −98.92 | kd | CGS001-56993 | TOMM22 | — |
| 8744 | −98.92 | kd | CGS001-1326 | MAP3K8 | MAPKKK: STE-unique family |
| 8739 | −98.91 | kd | CGS001-55038 | CDCA4 | — |
| 8740 | −98.91 | kd | CGS001-7840 | ALMS1 | — |
| 8741 | −98.91 | cp | BRD-A31159102 | fluoxetine | Selective serotonin reuptake inhibitor (SSRI) |
| 8736 | −98.89 | cc | | MTOR Inhibitor | — |
| 8737 | −98.89 | cc | | IGF1R Inhibitor | — |
| 8738 | −98.89 | oe | ccsbBroad304_01545 | SLC3A2 | SLC3 family |
| 8735 | −98.88 | cp | BRD-A75769826 | SDM25N | Opioid receptor antagonist |
| 8733 | −98.87 | cc | | EGFR Inhibitor | — |

TABLE 7-continued

Top 200 drugs that repress upregulated genes in the signature

| Rank | Score | Type (cp = compound, kd = knock-down, oe = over-expression, cc = cmap class) | ID | Name | Description |
|---|---|---|---|---|---|
| 8734 | −98.87 | cp | BRD-K64881305 | ispinesib | Kinesin-like spindle protein inhibitor |
| 8731 | −98.8 | oe | ccsbBroad304_00100 | RHOA | — |
| 8732 | −98.8 | cp | BRD-K05350981 | oligomycin-c | ATPase inhibitor |
| 8730 | −98.79 | kd | CGS001-949 | SCARB1 | — |
| 8729 | −98.78 | kd | CGS001-2114 | ETS2 | ETS Transcription Factors |
| 8728 | −98.77 | cp | BRD-K73610817 | BRD-K73610817 | — |
| 8725 | −98.74 | kd | CGS001-166793 | ZBTB49 | BTB/POZ domain containing |
| 8726 | −98.74 | kd | CGS001-55176 | SEC61A2 | — |
| 8727 | −98.74 | kd | CGS001-8313 | AXIN2 | — |
| 8723 | −98.73 | cp | BRD-A81177136 | KN-62 | Calcium-calmodulin dependent protein kinase inhibitor |
| 8724 | −98.73 | kd | CGS001-8792 | TNFRSF11A | Tumour necrosis factor (TNF) receptor family |
| 8722 | −98.72 | kd | CGS001-10600 | USP16 | Ubiquitin- specific peptidases |
| 8720 | −98.71 | kd | CGS001-117289 | TAGAP | Rho GTPase activating proteins |
| 8721 | −98.71 | kd | CGS001-11230 | PRAF2 | — |
| 8717 | −98.7 | oe | ccsbBroad304_06257 | GATA2 | GATA zinc finger domain containing |
| 8718 | −98.7 | cp | BRD-K55070890 | thiothixene | — |
| 8719 | −98.7 | cp | BRD-K09499853 | KU-0060648 | DNA dependent protein kinase inhibitor |
| 8715 | −98.69 | kd | CGS001-6777 | STAT5B | SH2 domain containing |
| 8716 | −98.69 | kd | CGS001-5184 | PEPD | Methionyl aminopeptidase |
| 8710 | −98.66 | oe | ccsbBroad304_06639 | NFYB | — |
| 8711 | −98.66 | cp | BRD-K68065987 | MK-2206 | AKT inhibitor |
| 8712 | −98.66 | kd | CGS001-55872 | PBK | TOPK family |
| 8713 | −98.66 | kd | CGS001-1482 | NKX2-5 | Homeoboxes/ANTP class: NKL subclass |
| 8714 | −98.66 | oe | ccsbBroad304_06393 | HOXC4 | Homeoboxes/ANTP class: HOXL subclass |
| 8709 | −98.62 | cc | | NFKB Pathway Inhibitor | — |
| 8705 | −98.61 | kd | CGS001-6256 | RXRA | Retinoid X receptors |
| 8706 | −98.61 | kd | CGS001-8833 | GMPS | — |
| 8707 | −98.61 | kd | CGS001-2021 | ENDOG | — |
| 8708 | −98.61 | oe | ccsbBroad304_01291 | MAP2K6 | MAPKK: STE7 family |
| 8703 | −98.6 | oe | ccsbBroad304_11796 | ULK3 | Unc-51-like kinase (ULK) family |
| 8704 | −98.6 | kd | CGS001-5524 | PPP2R4 | Serine/threonine phosphatases/Protein phosphatase 2, regulatory subunits |
| 8702 | −98.59 | kd | CGS001-27 | ABL2 | Abl family |
| 8701 | −98.58 | kd | CGS001-54623 | PAF1 | — |
| 8699 | −98.57 | kd | CGS001-11105 | PRDM7 | Zinc fingers, C2H2-type |
| 8700 | −98.57 | oe | ccsbBroad304_08681 | ADCK3 | ABC1-B subfamily |
| 8697 | −98.52 | kd | CGS001-5777 | PTPN6 | Protein tyrosine phosphatases |
| 8698 | −98.52 | cp | BRD-K02130563 | panobinostat | HDAC inhibitor |
| 8696 | −98.51 | kd | CGS001-4223 | MEOX2 | Homeoboxes/ANTP class: HOXL subclass |
| 8694 | −98.5 | oe | ccsbBroad304_00498 | ELK1 | ETS Transcription Factors |
| 8695 | −98.5 | kd | CGS001-47 | ACLY | — |
| 8693 | −98.48 | kd | CGS001-5434 | POLR2E | RNA polymerase subunits |
| 8692 | −98.47 | kd | CGS001-4351 | MPI | — |
| 8691 | −98.45 | kd | CGS001-5710 | PSMD4 | Proteasome (prosome, macropain) subunits |
| 8687 | −98.43 | cc | | HSP90 Inhibitor | — |
| 8688 | −98.43 | kd | CGS001-6259 | RYK | Type XV RTKs: RYK |
| 8689 | −98.43 | oe | ccsbBroad304_08879 | CASD1 | — |
| 8690 | −98.43 | oe | ccsbBroad304_00283 | CDKN2C | Ankyrin repeat domain containing |
| 8686 | −98.42 | kd | CGS001-29957 | SLC25A24 | Mitochondrial nucleotide transporter subfamily |

TABLE 7-continued

Top 200 drugs that repress upregulated genes in the signature

| Rank | Score | Type (cp = compound, kd = knock-down, oe = over-expression, cc = cmap class) | ID | Name | Description |
|---|---|---|---|---|---|
| 8683 | −98.41 | kd | CGS001-3312 | HSPA8 | Heat shock proteins/HSP70 |
| 8684 | −98.41 | cp | BRD-K36740062 | GSK-1070916 | Aurora kinase inhibitor |
| 8685 | −98.41 | cp | BRD-K98548675 | parthenolide | NFkB pathway inhibitor |
| 8681 | −98.39 | kd | CGS001-527 | ATP6V0C | ATPases/V-type |
| 8682 | −98.39 | kd | CGS001-513 | ATP5D | ATPases/F-type |
| 8678 | −98.38 | oe | ccsbBroad304_02864 | PRDX5 | — |
| 8679 | −98.38 | oe | ccsbBroad304_00817 | IDH2 | — |
| 8680 | −98.38 | oe | ccsbBroad304_03232 | VPS28 | — |
| 8677 | −98.37 | kd | CGS001-481 | ATP1B1 | ATPases/P-type |
| 8676 | −98.35 | kd | CGS001-3113 | HLA-DPA1 | Immunoglobulin superfamily/C1-set domain containing |
| 8672 | −98.34 | cp | BRD-K06147391 | telenzepine | Acetylcholine receptor antagonist |
| 8673 | −98.34 | cp | BRD-K78122587 | NNC-55-0396 | T-type calcium channel blocker |
| 8674 | −98.34 | cp | BRD-K14618467 | IKK-16 | IKK inhibitor |
| 8675 | −98.34 | kd | CGS001-26574 | AATF | — |

Applicants can also identify novel immunotherapy targets by looking for genes which are co-regulated with the immune-checkpoints (PDCD1, TIGIT, HAVCR2, LAG3, CTLA4) in CD4 and CD8 T-cells. For example, Applicants found CD27, an immune checkpoint and the target of an experimental cancer treatment (Varlilumab). The results of this analysis are for the top 200 genes summarized in Table 8.

TABLE 8

Top 200 genes that are co-regulated with immune-checkpoints

| | CD8.R | CD8.P | CD4.R | CD4.P |
|---|---|---|---|---|
| PDCD1 | 0.66 | 1.59E−215 | 0.60 | 1.03E−119 |
| CTLA4 | 0.63 | 4.88E−193 | 0.65 | 2.60E−145 |
| TIGIT | 0.63 | 1.11E−191 | 0.73 | 8.03E−204 |
| HAVCR2 | 0.62 | 1.39E−183 | 0.32 | 7.85E−30 |
| LAG3 | 0.55 | 7.66E−136 | | |
| LYST | 0.42 | 5.22E−76 | 0.26 | 1.67E−20 |
| CD8A | 0.40 | 3.93E−66 | −0.08 | 0.007523193 |
| TNFRSF9 | 0.39 | 1.13E−64 | 0.09 | 0.001435974 |
| CD27 | 0.39 | 6.38E−64 | 0.22 | 3.99E−15 |
| FAM3C | 0.34 | 1.47E−48 | | |
| CXCL13 | 0.34 | 1.47E−47 | 0.27 | 2.41E−21 |
| SP47 | 0.33 | 1.43E−46 | 0.11 | 0.000202982 |
| CBLB | 0.33 | 7.16E−46 | 0.20 | 1.64E−12 |
| SNX9 | 0.33 | 1.35E−45 | 0.11 | 6.89E−05 |
| SIRPG | 0.33 | 5.21E−45 | 0.33 | 2.62E−31 |
| TNFRSF1B | 0.33 | 1.09E−44 | 0.22 | 3.31E−15 |
| FCRL3 | 0.32 | 1.36E−41 | 0.26 | 9.32E−20 |
| VCAM1 | 0.31 | 3.44E−41 | | |
| DGKH | 0.31 | 1.67E−39 | | |
| PRDM1 | 0.30 | 3.07E−38 | 0.20 | 2.24E−12 |
| IGFLR1 | 0.30 | 6.12E−38 | 0.21 | 7.66E−14 |
| ETV1 | 0.30 | 1.03E−37 | | |
| RGS1 | 0.30 | 4.15E−37 | 0.30 | 3.35E−27 |
| WARS | 0.30 | 1.32E−36 | 0.14 | 4.98E−07 |
| MYO7A | 0.30 | 3.10E−36 | | |
| ITM2A | 0.29 | 2.65E−35 | 0.31 | 1.30E−27 |
| GBP2 | 0.29 | 1.24E−34 | 0.21 | 3.93E−13 |
| ENTPD1 | 0.28 | 1.21E−33 | 0.12 | 4.17E−05 |
| TOX | 0.28 | 2.39E−32 | 0.44 | 2.27E−58 |
| DUSP4 | 0.28 | 2.48E−32 | 0.36 | 1.94E−38 |
| TP53INP1 | 0.28 | 7.24E−32 | 0.23 | 2.04E−16 |
| GAPDH | 0.28 | 1.57E−31 | 0.36 | 1.21E−37 |
| DFNB31 | 0.27 | 6.10E−31 | | |
| ATHL1 | 0.27 | 1.19E−30 | 0.01 | 0.71761873 |
| TRAF5 | 0.27 | 2.83E−30 | 0.10 | 0.000897484 |
| CLEC2D | 0.27 | 5.88E−30 | −0.02 | 0.535704689 |
| SLA | 0.26 | 6.03E−29 | 0.20 | 1.37E−12 |
| CCL3 | 0.26 | 1.26E−28 | 0.04 | 0.161249379 |
| IL6ST | 0.26 | 2.25E−28 | 0.02 | 0.440674275 |
| PCED1B | 0.26 | 3.01E−28 | 0.21 | 3.65E−13 |
| RAB27A | 0.26 | 3.09E−28 | 0.13 | 6.49E−06 |
| CD7 | 0.26 | 3.23E−28 | 0.06 | 0.049851187 |
| ICOS | 0.25 | 3.99E−27 | 0.31 | 2.87E−28 |
| FUT8 | 0.25 | 1.41E−26 | 0.10 | 0.000314275 |
| RNF19A | 0.25 | 4.44E−26 | 0.29 | 1.51E−24 |
| TBC1D4 | 0.25 | 1.16E−25 | 0.31 | 6.28E−29 |
| FABP5 | 0.25 | 1.63E−25 | 0.18 | 2.19E−10 |
| B1 | 0.24 | 3.89E−24 | 0.24 | 9.16E−18 |
| TTN | 0.24 | 6.97E−24 | | |
| SRGN | 0.24 | 9.35E−24 | 0.36 | 1.61E−37 |
| SARDH | 0.24 | 2.50E−23 | 0.19 | 3.48E−11 |
| IFNG | 0.24 | 3.00E−23 | 0.14 | 4.84E−07 |
| INPP5F | 0.23 | 3.38E−23 | 0.14 | 4.75E−07 |
| RGS2 | 0.23 | 4.50E−23 | 0.18 | 7.21E−10 |
| CD38 | 0.23 | 5.61E−23 | 0.15 | 1.54E−07 |
| ID3 | 0.23 | 1.34E−22 | 0.05 | 0.066457964 |
| PHLDA1 | 0.23 | 1.35E−22 | 0.11 | 0.000184209 |
| TIMD4 | 0.23 | 3.53E−22 | | |
| PAM | 0.23 | 3.69E−22 | 0.28 | 2.82E−23 |
| PTMS | 0.23 | 1.99E−21 | | |
| CXCR6 | 0.22 | 6.84E−21 | 0.26 | 6.42E−20 |
| LBH | 0.22 | 1.48E−20 | 0.18 | 3.85E−10 |
| PRF1 | 0.22 | 1.90E−20 | 0.09 | 0.001065922 |
| ASB2 | 0.22 | 1.90E−20 | 0.29 | 8.22E−25 |
| KIR2DL4 | 0.22 | 2.29E−20 | | |
| STAT3 | 0.22 | 4.75E−20 | 0.05 | 0.063080818 |
| GLDC | 0.22 | 5.92E−20 | | |
| MIR155HG | 0.22 | 8.11E−20 | 0.15 | 9.54E−08 |
| CD8B | 0.22 | 1.10E−19 | −0.14 | 2.30E−06 |
| CD200 | 0.22 | 1.25E−19 | 0.25 | 1.49E−18 |
| CD2BP2 | 0.21 | 1.79E−19 | 0.17 | 5.47E−09 |
| CD84 | 0.21 | 2.59E−19 | 0.11 | 0.000105368 |
| CD2 | 0.21 | 3.46E−19 | 0.32 | 5.24E−31 |
| UBE2F | 0.21 | 3.72E−19 | 0.06 | 0.035820564 |
| TNS3 | 0.21 | 6.38E−19 | | |
| ATXN1 | 0.21 | 1.35E−18 | | |
| HNRPLL | 0.21 | 1.51E−18 | 0.26 | 1.96E−20 |
| FKBP1A | 0.21 | 2.34E−18 | 0.19 | 2.16E−11 |
| GALM | 0.21 | 2.95E−18 | 0.19 | 3.98E−11 |
| TOX2 | 0.20 | 6.98E−18 | 0.35 | 2.14E−35 |
| AFAP1L2 | 0.20 | 1.90E−17 | | |
| GEM | 0.20 | 2.64E−17 | 0.16 | 5.19E−08 |

TABLE 8-continued

Top 200 genes that are co-regulated with immune-checkpoints

| | CD8.R | CD8.P | CD4.R | CD4.P |
|---|---|---|---|---|
| HSPB1 | 0.20 | 2.75E−17 | 0.09 | 0.002636939 |
| CCL3L3 | 0.20 | 3.71E−17 | | |
| CADM1 | 0.20 | 3.76E−17 | | |
| GFOD1 | 0.20 | 3.88E−17 | | |
| SH2D2A | 0.20 | 3.90E−17 | 0.13 | 6.62E−06 |
| PKM | 0.20 | 4.16E−17 | 0.26 | 1.71E−19 |
| HAPLN3 | 0.20 | 9.31E−17 | −0.02 | 0.483961847 |
| MTSS1 | 0.20 | 1.03E−16 | | |
| ZNF79 | 0.20 | 1.79E−16 | 0.03 | 0.275651913 |
| EID1 | 0.19 | 2.53E−16 | 0.09 | 0.003034835 |
| ZBED2 | 0.19 | 2.96E−16 | 0.14 | 1.69E−06 |
| PTPN6 | 0.19 | 1.31E−15 | 0.04 | 0.210702886 |
| HMOX1 | 0.19 | 1.51E−15 | | |
| SAMSN1 | 0.19 | 1.97E−15 | 0.10 | 0.00025252 |
| SIT1 | 0.19 | 2.34E−15 | 0.08 | 0.007781849 |
| CCDC64 | 0.19 | 2.65E−15 | 0.09 | 0.000993524 |
| PTPN7 | 0.19 | 4.49E−15 | 0.25 | 3.66E−18 |
| NDFIP2 | 0.19 | 6.66E−15 | 0.17 | 6.39E−09 |
| CD74 | 0.19 | 7.63E−15 | 0.28 | 1.23E−22 |
| CREM | 0.18 | 1.94E−14 | 0.05 | 0.106041668 |
| IRF4 | 0.18 | 1.98E−14 | 0.16 | 4.09E−08 |
| ARNT | 0.18 | 2.23E−14 | 0.10 | 0.000571869 |
| TRPS1 | 0.18 | 2.93E−14 | | |
| ZC3H7A | 0.18 | 3.28E−14 | 0.14 | 1.33E−06 |
| RHOB | 0.18 | 3.58E−14 | | |
| ASXL2 | 0.18 | 3.99E−14 | | |
| ITGA4 | 0.18 | 4.04E−14 | 0.08 | 0.008613713 |
| CCL4L2 | 0.18 | 5.53E−14 | 0.11 | 0.000238679 |
| CCL4L1 | 0.18 | 5.69E−14 | 0.11 | 0.000238679 |
| IGF2R | 0.18 | 1.06E−13 | | |
| SOD1 | 0.18 | 1.26E−13 | 0.18 | 4.99E−10 |
| SYNGR2 | 0.18 | 1.31E−13 | 0.11 | 0.00010303 |
| PDE3B | 0.18 | 1.38E−13 | −0.11 | 0.000178183 |
| IFI16 | 0.18 | 1.43E−13 | 0.20 | 5.81E−12 |
| PDE7B | 0.18 | 1.46E−13 | | |
| SLC2A8 | 0.18 | 1.59E−13 | | |
| FYN | 0.17 | 2.58E−13 | 0.23 | 2.55E−16 |
| ARID5B | 0.17 | 4.06E−13 | 0.22 | 2.72E−15 |
| NFATC1 | 0.17 | 4.72E−13 | 0.10 | 0.000521207 |
| TPI1 | 0.17 | 4.96E−13 | 0.17 | 2.07E−09 |
| DTHD1 | 0.17 | 6.29E−13 | | |
| CD3E | 0.17 | 7.13E−13 | 0.03 | 0.271016862 |
| CRIM1 | 0.17 | 7.24E−13 | | |
| TMEM155 | 0.17 | 1.02E−12 | | |
| INPP4B | 0.17 | 1.66E−12 | −0.06 | 0.035577188 |
| OSBPL3 | 0.17 | 1.74E−12 | 0.16 | 4.35E−08 |
| LIMS1 | 0.17 | 1.76E−12 | 0.17 | 1.29E−09 |
| KCNK5 | 0.17 | 1.76E−12 | | |
| KLRC2 | 0.17 | 2.17E−12 | | |
| RGS4 | 0.17 | 3.04E−12 | | |
| ACP5 | 0.17 | 3.13E−12 | 0.19 | 5.03E−11 |
| DENND2D | 0.17 | 3.30E−12 | 0.01 | 0.631199717 |
| FAIM3 | 0.17 | 3.53E−12 | 0.04 | 0.189542882 |
| DDX3Y | 0.17 | 4.25E−12 | 0.00 | 0.907797482 |
| HLA-H | 0.16 | 4.66E−12 | 0.21 | 1.54E−13 |
| GPR56 | 0.16 | 5.64E−12 | 0.11 | 6.30E−05 |
| MAF | 0.16 | 5.82E−12 | 0.36 | 2.14E−38 |
| TRIM69 | 0.16 | 7.34E−12 | | |
| SEMA4A | 0.16 | 9.52E−12 | | |
| IL2RG | 0.16 | 1.04E−11 | 0.18 | 6.51E−10 |
| TMEM140 | 0.16 | 1.11E−11 | 0.09 | 0.00163736 |
| GMDS | 0.16 | 1.18E−11 | 0.08 | 0.008326449 |
| LITAF | 0.16 | 1.19E−11 | −0.05 | 0.063294972 |
| HSPA1A | 0.16 | 1.56E−11 | 0.11 | 0.000172577 |
| PAPOLA | 0.16 | 1.56E−11 | −0.01 | 0.70579933 |
| AHI1 | 0.16 | 2.36E−11 | 0.16 | 9.85E−09 |
| EZR | 0.16 | 2.40E−11 | 0.14 | 1.92E−06 |
| MIS18BP1 | 0.16 | 2.58E−11 | 0.17 | 6.15E−09 |
| HLA-A | 0.16 | 2.74E−11 | 0.32 | 9.78E−31 |
| PSTPIP1 | 0.16 | 3.27E−11 | 0.11 | 9.40E−05 |
| GBP5 | 0.16 | 3.71E−11 | 0.13 | 5.66E−06 |
| RIN3 | 0.16 | 3.77E−11 | | |
| HIF1A | 0.16 | 3.97E−11 | 0.06 | 0.048813828 |
| HLA-DRB6 | 0.16 | 4.67E−11 | | |
| PAG1 | 0.16 | 5.87E−11 | −0.08 | 0.003384546 |
| AKAP5 | 0.16 | 6.76E−11 | | |
| KLRC3 | 0.16 | 6.90E−11 | | |
| RFX5 | 0.16 | 8.25E−11 | 0.07 | 0.014179979 |
| UBB | 0.15 | 8.74E−11 | 0.13 | 5.13E−06 |
| TXNDC11 | 0.15 | 9.85E−11 | 0.14 | 1.74E−06 |
| FOXN2 | 0.15 | 1.00E−10 | 0.05 | 0.082411107 |
| DUSP16 | 0.15 | 1.15E−10 | 0.13 | 1.07E−05 |
| CD82 | 0.15 | 1.38E−10 | 0.18 | 1.30E−10 |
| PELI1 | 0.15 | 1.40E−10 | 0.20 | 6.92E−13 |
| AMIGO2 | 0.15 | 2.03E−10 | | |
| CCDC141 | 0.15 | 2.42E−10 | 0.06 | 0.036155173 |
| TNIP3 | 0.15 | 2.63E−10 | 0.10 | 0.000563452 |
| SAT1 | 0.15 | 2.71E−10 | 0.26 | 2.07E−20 |
| LRBA | 0.15 | 3.00E−10 | 0.12 | 2.66E−05 |
| HLA-DMA | 0.15 | 3.36E−10 | 0.20 | 2.02E−12 |
| MAPRE2 | 0.15 | 3.48E−10 | 0.10 | 0.000867905 |
| BIRC3 | 0.15 | 3.71E−10 | −0.01 | 0.720398325 |
| EPSTI1 | 0.15 | 4.13E−10 | 0.18 | 5.86E−10 |
| NCALD | 0.15 | 4.21E−10 | 0.22 | 5.12E−15 |
| ID2 | 0.15 | 4.32E−10 | −0.04 | 0.201480439 |
| NFAT5 | 0.15 | 4.95E−10 | 0.14 | 5.55E−07 |
| GOLIM4 | 0.15 | 6.33E−10 | | |
| ZBTB32 | 0.15 | 6.70E−10 | | |
| NDUFB3 | 0.15 | 6.70E−10 | 0.13 | 3.74E−06 |
| CALM3 | 0.15 | 7.24E−10 | 0.22 | 2.32E−14 |
| SHFM1 | 0.15 | 8.32E−10 | 0.09 | 0.000949937 |
| HLA-DRB5 | 0.15 | 9.22E−10 | 0.17 | 1.46E−09 |
| C21orf91 | 0.15 | 9.87E−10 | 0.07 | 0.011223721 |
| CCND2 | 0.15 | 1.09E−09 | 0.02 | 0.530718461 |
| BTLA | 0.14 | 1.29E−09 | 0.16 | 1.30E−08 |
| PRKCH | 0.14 | 1.31E−09 | 0.12 | 3.11E−05 |
| GALNT2 | 0.14 | 1.53E−09 | | |
| IKZF3 | 0.14 | 1.77E−09 | 0.12 | 3.13E−05 |
| AMICA1 | 0.14 | 2.14E−09 | −0.06 | 0.026070815 |
| STAT1 | 0.14 | 2.64E−09 | 0.05 | 0.064028082 |
| IRF8 | 0.14 | 2.81E−09 | | |
| ELF1 | 0.14 | 2.91E−09 | 0.02 | 0.548742854 |
| CD3D | 0.14 | 2.93E−09 | 0.16 | 5.77E−08 |
| RBPJ | 0.14 | 3.26E−09 | 0.12 | 2.32E−05 |
| BATF | 0.14 | 3.46E−09 | 0.34 | 3.15E−33 |
| LRRC8D | 0.14 | 3.57E−09 | 0.07 | 0.014705554 |
| PMF1 | 0.14 | 3.60E−09 | 0.10 | 0.000379898 |
| TNFSF4 | 0.14 | 4.01E−09 | | |

Example 4—Tumor Microenvironment Analysis in 26 Melanoma Tumors

T cells were also analyzed and the T cells contributed to the predicative value of the signature of the present invention (FIG. 30).

The novel microenvironment cell-type signatures were very much associated with survival in both immunotherapy treated patients, and in general. The genes which are up/down regulated in the immune cells after immunotherapy (CD4 T-cells, CD8 T-cells, B cells, and macrophages) are shown in Table 9.

TABLE 9

All Cell Type Signatures

| B cell | Macrophage | Malignant | | T cell cd4 | T cell cd8 |
|---|---|---|---|---|---|
| ADAM19 | AIF1 | ACOT7 | MFGE8 | AIM1 | APOBEC3G |
| AKAP2 | ALDH2 | ACSL3 | MFI2 | ANK3 | CBLB |
| BACH2 | ANPEP | ACTN1 | MGST3 | AQP3 | CCL4 |
| BANK1 | C15orf48 | ADAM15 | MIA | CAMK4 | CCL4L1 |
| BCL11A | C1orf162 | ADI1 | MIF | CCR4 | CCL4L2 |
| BLK | C1QA | AEBP1 | MITF | CCR8 | CCL5 |
| CD19 | C1QB | AGPAT1 | MLANA | CD28 | CD27 |
| CD1C | C1QC | AGRN | MLPH | CD40LG | CD8A |
| CD22 | C3AR1 | AHCY | MMP14 | DGKA | CD8B |
| CD79A | CCR1 | AIF1L | MORF4L2 | EML4 | CST7 |
| CD79B | CD14 | AKAP12 | MORN2 | FAAH2 | CTSW |
| CLEC17A | CD163 | AKT3 | MPZL1 | FBLN7 | CXCL13 |
| CNR2 | CD300A | ANXA5 | MRPL24 | FKBP5 | CXCR6 |
| COL19A1 | CD300C | APOA1BP | MT2A | FLT3LG | DTHD1 |
| COL4A3 | CD300LF | APOD | MTUS1 | FOXP3 | DUSP2 |
| CPNE5 | CD33 | APOE | MXI1 | FXYD5 | EOMES |
| CR2 | CD86 | ARL2 | MYH10 | IL6R | FASLG |
| CXCR5 | CFP | ARNT2 | MYO10 | IL7R | FCRL3 |
| EBF1 | CLEC10A | ARPC1A | MYO1D | ITGB2-AS1 | GBP5 |
| ELK2AP | CLEC12A | ASPH | NAV2 | JUNB | GZMA |
| FAM129C | CLEC4A | ATP1A1 | NCKAP1 | KLRB1 | GZMB |
| FAM177B | CLEC5A | ATP1B1 | NDST1 | LEPROTL1 | GZMH |
| FCER2 | CMKLR1 | ATP6V0A1 | NENF | LOC100128420 | GZMK |
| FCRL1 | CSF1R | B3GNT1 | NES | MAL | HCST |
| FCRL2 | CSF2RB | BACE2 | NGFRAP1 | OXNAD1 | HLA-A |
| FCRL5 | CSF3R | BAIAP2 | NGRN | PBXIP1 | HLA-B |
| FCRLA | CSTA | BCAN | NHSL1 | PIK3IP1 | HLA-H |
| HLA-DOB | CXCL9 | BIRC7 | NID1 | PIM2 | ID2 |
| IGJ | CXCR2P1 | BTBD3 | NME1 | PRKCQ-AS1 | IFNG |
| IGLL1 | DSC2 | C11orf24 | NME2 | RORA | IL2RB |
| IGLL3P | FAM26F | C17orf89 | NME4 | RPL35A | KLRC3 |
| IGLL5 | FBP1 | C1orf198 | NRP2 | RPL4 | KLRC4 |
| KIAA0125 | FCER1G | C1orf21 | NRSN2 | RPL6 | KLRC4-KLRK1 |
| KIAA0226L | FCGR1A | C1orf85 | NSG1 | RPS15A | KLRD1 |
| LOC283663 | FCGR1B | CALD1 | OSBPL1A | RPS27 | KRK1 |
| MS4A1 | FCGR1C | CALU | P4HA2 | RPS28 | LAG3 |
| P2RX5 | FCGR3A | CAPN3 | PACSIN2 | SEPT6 | LSP1 |
| PAX5 | FCGR3B | CAV1 | PAX3 | SLAMF1 | LYST |
| PNOC | FCN1 | CBR1 | PCDHGC3 | SORL1 | NKG7 |
| POU2AF1 | FOLR2 | CCND1 | PEG10 | SPOCK2 | PDCD1 |
| POU2F2 | FPR1 | CCT3 | PFDN2 | SUSD3 | PRF1 |
| RASGRP3 | FPR2 | CD151 | PFKM | TCF7 | PSTPIP1 |
| SEL1L3 | FPR3 | CD276 | PFN2 | TMEM66 | PYHIN1 |
| SNX29P1 | GGTA1P | CD59 | PGRMC1 | TNFRSF18 | RARRES3 |
| ST6GAL1 | GNA15 | CD63 | PHB | TNFRSF25 | SH2D1A |
| STAP1 | GPR84 | CD9 | PHLDB1 | TNFRSF4 | SH2D2A |
| SWAP70 | HCK | CDC42BPA | PIR | TNFSF8 | TARP |
| TCL1A | HK3 | CDC42EP4 | PKNOX2 | TRABD2A | TIG1T |
| TMEM154 | IGSF6 | CDH19 | PLEKHB1 | TSC22D3 | TNFRSF9 |
| VPREB3 | IL1B | CDK2 | PLK2 | TXK | TOX |
| | IL1RN | CDK2AP1 | PLOD1 | | |
| | IL4I1 | CECR7 | PLOD3 | | |
| | ITGAM | CELSR2 | PLP1 | | |
| | KYNU | CERCAM | PLS3 | | |
| | LGALS2 | CERS2 | PLXNA1 | | |
| | LILRA1 | CHCHD6 | PLXNB3 | | |
| | LILRA2 | CHL1 | PMEL | | |
| | LILRA3 | CHPF | PMP22 | | |
| | LILRA4 | CLDN12 | POLR2F | | |
| | LILRB2 | CLIC4 | POLR2L | | |
| | LILRB4 | CNIH4 | PON2 | | |
| | LILRB5 | CNN3 | PPT2 | | |
| | LST1 | CNP | PRAME | | |
| | MAFB | CNPY2 | PRDX4 | | |
| | MARCO | COA3 | PRDX6 | | |
| | MNDA | COL16A1 | PRKCDBP | | |
| | MRC1 | COMT | PROS1 | | |
| | MS4A4A | CRIP2 | PRSS23 | | |
| | MS4A6A | CRNDE | PSMB5 | | |
| | MSR1 | CRTAP | PTGFRN | | |
| | NCF2 | CRYAB | PTGR1 | | |
| | OLR1 | CSAG1 | PTK2 | | |
| | P2RY13 | CSAG3 | PTPLAD1 | | |
| | PILRA | CSPG4 | PTPRM | | |
| | PLAU | CSRP1 | PTPRS | | |
| | PLBD1 | CTDSPL | PTRH2 | | |

TABLE 9-continued

All Cell Type Signatures

| B cell | Macrophage | Malignant | T cell cd4 | T cell cd8 |
|---|---|---|---|---|
| | PLXDC2 | CTHRC1 | PTTG1IP | |
| | PRAM1 | CTNNAL1 | PYCR1 | |
| | RAB20 | CTNNB1 | PYGB | |
| | RAB31 | CTSF | PYGL | |
| | RASSF4 | CTSK | QDPR | |
| | RBM47 | CTTN | QPCT | |
| | RGS18 | CYB5R1 | RAB13 | |
| | S100A8 | CYP27A1 | RAB17 | |
| | S100A9 | CYSTM1 | RAB34 | |
| | SECTM1 | CYTH3 | RAB38 | |
| | SIGLEC1 | DAAM2 | RAI14 | |
| | SIGLEC7 | DCBLD2 | RBFOX2 | |
| | SIGLEC9 | DCT | RCAN1 | |
| | SLAMF8 | DDR1 | RCN1 | |
| | SLC31A2 | DDR2 | RCN2 | |
| | SLC43A2 | DIP2C | RDX | |
| | SLC7A7 | DLC1 | RGS20 | |
| | SLC8A1 | DNAH14 | RND3 | |
| | SLCO2B1 | DOCK7 | ROBO1 | |
| | SPI1 | DST | ROPN1 | |
| | STAB1 | DSTN | ROPN1B | |
| | TBXAS1 | DUSP6 | RTKN | |
| | TFEC | ECM1 | S100A1 | |
| | TGFBI | EDNRB | S100A13 | |
| | TLR2 | EFNA5 | S100A16 | |
| | TLR4 | EIF4EBP1 | S100B | |
| | TLR8 | EMP1 | SCARB1 | |
| | TMEM176A | ENTPD6 | SCCPDH | |
| | TMEM176B | EPS8 | SCD | |
| | TNFSF13 | ERBB3 | SDC3 | |
| | TNFSF13B | ETV4 | SOC4 | |
| | TREM2 | ETV5 | SDCBP | |
| | TYROBP | EVA1A | SELENBP1 | |
| | VSIG4 | EXOSC4 | SEMA3B | |
| | ZNF385A | FAM127A | SEMA3C | |
| | | FAM127B | SEMA6A | |
| | | FAM167B | SEPT10 | |
| | | FARP1 | SERPINA3 | |
| | | FARP2 | SERPINE2 | |
| | | FASN | SERPINH1 | |
| | | FKBP10 | SGCD | |
| | | FKBP4 | SGCE | |
| | | FKBP9 | SHC1 | |
| | | FN1 | SHC4 | |
| | | FNBP1L | SLC19A2 | |
| | | FRMD6 | SLC24A5 | |
| | | FSTL1 | SLC25A13 | |
| | | FXYD3 | SLC25A4 | |
| | | G6PC3 | SLC35B2 | |
| | | GALE | SLC39A1 | |
| | | GCSH | SLC39A6 | |
| | | GDF15 | SLC45A2 | |
| | | GJB1 | SLC6A15 | |
| | | GLI3 | SLC7A8 | |
| | | GNG12 | SMARCA1 | |
| | | GOLM1 | SNAI2 | |
| | | GPM6B | SNCA | |
| | | GPR143 | SNHG16 | |
| | | GPRC5B | SNRPE | |
| | | GSTA4 | SORT1 | |
| | | GSTP1 | SOX10 | |
| | | GULP1 | SOX13 | |
| | | GYG2 | SOX4 | |
| | | H1F0 | SPARC | |
| | | HIBADH | SPR | |
| | | HMCN1 | SPRY4 | |
| | | HMG20B | SPTBN1 | |
| | | HOXB7 | SRPX | |
| | | HOXC10 | SSFA2 | |
| | | HSBP1 | ST3GAL4 | |
| | | HSP90AB1 | ST5 | |
| | | HSPB1 | ST6GALNAC2 | |
| | | HSPD1 | STK32A | |
| | | HSPG2 | STMN1 | |
| | | IFI27 | STXBP1 | |
| | | IGF1R | SYNGR1 | |

TABLE 9-continued

All Cell Type Signatures

| B cell | Macrophage | Malignant | T cell cd4 | T cell cd8 |
|---|---|---|---|---|
| | IGFBP7 | TANC1 | | |
| | IGSF11 | TBC1D16 | | |
| | 1GSF3 | TBC1D7 | | |
| | IGSF8 | TCEAL4 | | |
| | IMPDH2 | TEAD1 | | |
| | ISYNA1 | TENC1 | | |
| | ITFG3 | TEX2 | | |
| | ITGA3 | TFAP2A | | |
| | ITGB3 | TIMP2 | | |
| | KIRREL | TIMP3 | | |
| | LAMB1 | TJP1 | | |
| | LAMB2 | TMEM147 | | |
| | LAMC1 | TMEM14C | | |
| | LAPTM4A | TMEM9 | | |
| | LAPTM4B | TMEM98 | | |
| | LDLRAD3 | TNFRSF19 | | |
| | LGALS1 | TOM1L1 | | |
| | LGALS3BP | TRIM2 | | |
| | LINC00473 | TRIM63 | | |
| | LINC00673 | TSC22D1 | | |
| | LMNA | TSPAN3 | | |
| | LOC100126784 | TSPAN4 | | |
| | LOC100130370 | TSPAN6 | | |
| | LOC645166 | TTLL4 | | |
| | LOXL4 | TUBB2A | | |
| | LRP6 | TUBB2B | | |
| | MAGEA12 | TUBB3 | | |
| | MAGEA2B | TYR | | |
| | MAGEA3 | UBL3 | | |
| | MAGEA6 | VAT1 | | |
| | MAGED1 | VIM | | |
| | MAGED2 | VKORC1 | | |
| | MAP1B | WASL | | |
| | MARCKSL1 | WBP5 | | |
| | MDK | WIPI1 | | |
| | MFAP2 | WLS | | |
| | | XAGE1A | | |
| | | XAGE1B | | |
| | | XAGE1C | | |
| | | XAGE1D | | |
| | | XAGE1E | | |
| | | XYLB | | |
| | | YWHAE | | |
| | | ZNF462 | | |

TABLE 10

Down-regulated and Up-regulated genes post-immunotherapy treatment in microenvironment

| T.cd8.up | T.cd8.down | T.cd4.up | T.cd4.down | Macro.up | Macro.down |
|---|---|---|---|---|---|
| AARS2 | LYRM7 | ACTN4 | MAL | AARS2 | ACTR2 | APOC1 | AREG |
| ABHD15 | MAP3K13 | ADAM10 | MAP1LC3A | ABI2 | ADRBK1 | APOE | ARF1 |
| ABI2 | MAP7D3 | AEN | MED21 | APOBEC3A | ANAPC11 | C17orf76-AS1 | BRE-AS1 |
| AK3 | MAPK13 | AIM1 | MGMT | APOL2 | ANKRD36BP1 | C1orf56 | CD55 |
| AKAP5 | MBOAT1 | AIP | MKNK2 | ARF6 | ARAP2 | CA2 | CREM |
| AKIP1 | ME2 | AKAP13 | MPG | C17orf76-AS1 | ASCC3 | CD81 | DUSP2 |
| ALG1 | MED18 | AKNA | MRPL47 | C1orf56 | ASMTL | CSTB | EREG |
| ANKRD40 | METTL16 | AMD1 | MRPL53 | C1QB | ATXN2L | CXCL9 | ETS2 |
| AP1G2 | METTL2B | ANKRD11 | MRPL54 | CASP10 | BCL6 | DBNDD2 | FKBP5 |
| AP3M1 | MFSD11 | ANKRD36BP1 | MSI2 | CCL5 | C22orf34 | DHRS4L2 | FOSB |
| AP3S2 | MIAT | APBB1IP | MT2A | CCND2 | CALM3 | DNAJC5B | GAPT |
| APOL2 | MLANA | APH1A | MXD4 | CD68 | CCNG1 | DYNC1I2 | HIF1A |
| ARF6 | MMS22L | APOBEC3G | MYCBP2 | CEP41 | CD200 | DYNLL1 | ICAM3 |
| ARIH2OS | MOCS3 | ARID1A | MYEOV2 | CLUAP1 | CD226 | FABP3 | IFI44L |
| ARMC10 | MREG | ARID2 | MYH9 | CNNM3 | CD3E | FOLR2 | IL1B |
| ARSA | MRPL44 | ARL1 | NACA | CTBP1 | CD40LG | FTL | LOC100130476 |
| ASB8 | MS4A1 | ARL4C | NAP1L1 | CXCR3 | CD58 | FUCA1 | MEF2C |
| ATP6V0A2 | MSH3 | ASF1B | NDC80 | CXCR6 | CD6 | GPNMB | NFIL3 |
| B2M | MTFMT | ATAD1 | NDE1 | DCAF10 | CDC42EP3 | HLA-J | NFKBIA |
| BCL6 | NAA16 | ATP5E | NDUFA12 | DNAJC14 | CHI3L2 | HSD11B1 | NFKBIZ |

TABLE 10-continued

Down-regulated and Up-regulated genes post-immunotherapy treatment in microenvironment

| T.cd8.up | | T.cd8.down | T.cd4.up | T.cd4.down | Macro.up | Macro.down |
|---|---|---|---|---|---|---|
| BLOC1S6 | NDNL2 | ATP5L | NDUFA13 | FAM126B | COX7C | HSD3B7 | NLRP3 |
| BMS1P1 | NEK2 | ATP5O | NDUFA2 | FAM134A | CPSF1 | HSPA7 | NR4A2 |
| BMS1P4 | NFKBIB | ATP6V0C | NDUFA4 | FAM153C | CTSA | HSPB1 | PPP1R15B |
| BMS1P5 | NME6 | ATP6V0E2 | NDUFA6 | FGD5-AS1 | CXCR5 | KLHDC8B | REL |
| BRIP1 | NOL9 | ATXN2L | NFATC2 | GBP4 | DDX39B | MGLL | RPSAP58 |
| C10orf32 | NPIPL3 | ATXN7L1 | NFKBIA | GBP5 | DDX3Y | MIR4461 | THBS1 |
| C12orf65 | NQO1 | AURKB | NFKB1Z | GNRHR2 | DHRS7 | MRPS15 | TNFAIP3 |
| C19orf40 | NT5DC3 | BCL11B | N1NJ2 | GPR56 | EHD1 | NOP10 | ZBTB16 |
| C1orf174 | NUAK2 | BCL2 | NIPBL | GSTM3 | EIF3L | NUPR1 | ZFP36 |
| C1orf210 | OCLN | BHLHE40-AS1 | NIT2 | GZMA | ERGIC3 | PCBD1 | |
| C1orf56 | OPHN1 | BIRC5 | NOP56 | HAUS2 | EXOC1 | PLA2G2D | |
| C1orf63 | ORC6 | BLMH | NPM1 | HERC2P4 | FAM172A | PLA2G7 | |
| C1QTNF6 | PACS2 | BLVRA | ORMDL3 | HLA-DRA | GNG5 | RAB20 | |
| C5orf24 | PAFAH1B2 | BRK1 | OST4 | HLA-DRB1 | GPRIN3 | SCARB1 | |
| C5orf33 | PAICS | BTF3 | PABPC1 | HNRNPH1 | HDDC2 | SLIRP | |
| C9orf3 | PAN3 | BTN3A2 | PAIP2 | INADL | HINT1 | ST3GAL5 | |
| C9orf85 | PAR-SN | BUB1 | PAM | KLRD1 | HIST1H1D | TIMP2 | |
| CACUL1 | PARP11 | BUB3 | PARK7 | LINC00439 | HIST1H1E | TMSB10 | |
| CAMLG | PARP3 | C1D | PARP8 | LOC100506469 | HIVEP2 | TRNAU1AP | |
| CCDC122 | PARP9 | CARD16 | PCBP1 | LOC284379 | HNRNPC | UBD | |
| CCR6 | PCGF5 | CARS | PCBP2 | LOC389641 | HS3ST3B1 | WSB2 | |
| CD160 | PDE12 | CASP4 | PDCD1 | LOC644961 | ICA1 | XIST | |
| CD24 | PER2 | CASP8 | PDCD5 | LOC727896 | ITM2A | YTHDF2 | |
| CD68 | PEX13 | CBLB | PER1 | MAP3K13 | ITPR1 | | |
| CENPN | PIGX | CCDC141 | PET117 | MCTS1 | KLF12 | | |
| CEP104 | PKNOX1 | CCDC167 | PFDN5 | NANOG | LCMT1 | | |
| CHP1 | PMEL | CCDC23 | PIK3IP1 | NXNL2 | LOC100216545 | | |
| CLCC1 | POU2AF1 | CCL4 | PIK3R5 | PIP4K2A | LOC100271836 | | |
| CLUAP1 | PPP1R3B | CCNB2 | PIN4 | PLEKHA2 | LOC285740 | | |
| CNNM3 | PQLC2 | CCND1 | PLCB2 | PPID | MAEA | | |
| COA1 | PRMT2 | CCND3 | PLEK | PRDM1 | MAP2K3 | | |
| COX10-AS1 | PSTPIP2 | CCNH | PLEKHM1 | PSTPIP2 | MAP4K1 | | |
| COX18 | PTPN2 | CCNK | PLIN2 | QRSL1 | MED21 | | |
| CPPED1 | QPRT | CCR1 | POGZ | RASSF3 | MKNK2 | | |
| CPT1A | RAB21 | CCR4 | PPIA | RBM43 | MRPL33 | | |
| CRK | RAB33B | CCR5 | PPM1G | RGS1 | MRPS2 | | |
| CSAD | RAD1 | CD2 | PRDM1 | RPP14 | MTERFD2 | | |
| CSNK1G1 | RASSF1 | CD200R1 | PRDX6 | RUNX1-IT1 | MTMR6 | | |
| CWC25 | RBBP5 | CD27 | PRMT10 | SBF2-AS1 | MYEOV2 | | |
| CYB5D2 | RBL1 | CD320 | PRPF8 | SCAI | NAB1 | | |
| CYP4V2 | RBMS2 | CD37 | PRR14L | SGOL1 | NDUFA4 | | |
| DCP1A | RDH10 | CD3D | PRRC2B | SLC25A51 | NEK7 | | |
| DESI1 | REL | CD3E | PTBP3 | SLC35E1 | NFATC1 | | |
| DGKD | RFC2 | CD3G | PTPN4 | SPDYE1 | NFATC2 | | |
| DHODH | RFT1 | CD4 | PTRHD1 | SPDYE2 | NINJ2 | | |
| DIP2A | RHD | CD7 | RAB1B | SPDYE2L | OST4 | | |
| DIS3 | RIOK3 | CD79A | RAPGEF1 | SPDYE7P | P2RX5 | | |
| DIS3L | RNF14 | CD81 | RASA1 | SWSAP1 | PAPD4 | | |
| DNASE1 | RNF141 | CDC42SE1 | RASA2 | THAP5 | PARL | | |
| DND1 | RPS6KA3 | CDK1 | RBM38 | TMEM120B | PASK | | |
| DTD2 | RUNDC1 | CENPK | RGS1 | TMEM192 | PCBP1 | | |
| EEF2K | S1PR2 | CHCHD2 | RGS10 | TP53RK | PDCD1 | | |
| EIF5A2 | SATB1 | CHI3L2 | RHBDD3 | TRMT10B | PFKL | | |
| ELMSAN1 | SCAI | CIRBP | RHOA | TSNAX | PHF3 | | |
| ESYT2 | SCAMP1 | CITED2 | RNASEK | TXNDC15 | PHF8 | | |
| EYA3 | SCML4 | CLASP1 | RPA3 | UGT8 | PIK3CG | | |
| F11R | SEC23IP | CLDND1 | RPL13A | UPK3BL | PLP2 | | |
| FAM126B | SEMA4D | CLECL1 | RPL14 | XIST | PON2 | | |
| FAM210B | SENP5 | COX17 | RPL18 | ZNF253 | PPP1CA | | |
| FAM215A | SERPINB1 | COX4I1 | RPL22 | ZNF276 | PRKCH | | |
| FAM217B | SERPINB6 | COX6A1 | RPL23 | ZSWIM7 | PRNP | | |
| FAM73A | SGCB | COX7A2L | RPL27 | | PRRC2B | | |
| FANCD2 | SGK3 | COX7C | RPL27A | | PTBP3 | | |
| FASTKD2 | SGOL1 | COX8A | RPL29 | | RBM25 | | |
| FBLIM1 | SH2D1B | CREB3L2 | RPL31 | | RERE | | |
| FBXL18 | SIRT5 | CSNK1D | RPL32 | | RGS3 | | |
| FBXW2 | SKP2 | CST7 | RPL34 | | RPL13A | | |
| FCRL3 | SLAMF7 | CTSC | RPL35 | | RPL14 | | |
| FCRL6 | SLC25A15 | CTSD | RPL35A | | RPL27 | | |
| FDPSL2A | SLC25A32 | CXCL13 | RPL36 | | RPL37 | | |
| FLCN | SLC25A51 | CXCR4 | RPL36A | | RPS26 | | |
| FLOT1 | SLC2A3 | CXCR6 | RPL36AL | | RPS4Y1 | | |
| FOXK1 | SLC30A6 | CYTIP | RPL37 | | RPS5 | | |
| FTO | SLC30A7 | DDIT4 | RPL37A | | SARDH | | |
| FXN | SLC31A1 | DDX6 | RPL38 | | SEC11C | | |

TABLE 10-continued

Down-regulated and Up-regulated genes post-immunotherapy treatment in microenvironment

| T.cd8.up | T.cd8.down | T.cd4.up | T.cd4.down | Macro.up | Macro.down |
|---|---|---|---|---|---|
| GALNT6 | SLC35A3 | DNAJB12 | RPL39 | | SEC16A |
| GATAD1 | SLC48A1 | DNAJC9 | RPLP0 | | SELT |
| GBP1 | SLC50A1 | DPM3 | RPRD2 | | SF3B1 |
| GBP2 | SLC7A5P2 | DTHD1 | RPS10 | | SFI1 |
| GBP4 | SMIM14 | DUSP4 | RPS13 | | SMARCE1 |
| GBP5 | SMYD4 | EBP | RPS16 | | SMG1P1 |
| GCLM | SNAPC3 | EEF1B2 | RPS17 | | SNHG5 |
| GDAP2 | SNHG7 | EEF1D | RPS17L | | SNRPN |
| GEMIN8 | SNIP1 | EEF2 | RPS20 | | SRRM2 |
| GGPS1 | SOAT1 | EHMT1 | RPS21 | | SSH2 |
| GLIPR1L2 | SPAST | EIF3F | RPS23 | | STAU1 |
| GLUD1P7 | SPRYD4 | EIF3G | RPS24 | | TATDN1 |
| GMEB1 | SRSF8 | EIF4B | RPS26 | | TCF7 |
| GNE | SS18 | ELK2AP | RPS28 | | THADA |
| GNG4 | STAT1 | EMB | RPS29 | | TIAM1 |
| GNRHR2 | STAT5B | ENSA | RPS4X | | TIGIT |
| GOLGA3 | STOM | ERAP2 | RPS5 | | TMEM59 |
| GPCPD1 | STYX | ERGIC3 | RPS7 | | TOX |
| GPR82 | SWSAP1 | ERH | RPS9 | | TOX2 |
| GTF2H2C | TADA2B | ERN1 | RPSA | | TYK2 |
| GTPBP5 | TADA3 | ETS1 | RSBN1 | | UBQLN1 |
| HAUS3 | TANGO2 | EVL | RUNX2 | | UQCR10 |
| HERC2P7 | TARS2 | FAM102A | RUNX3 | | UQCRH |
| HIST1H2BG | TATDN3 | FAM129A | S100A6 | | UTRN |
| HIVEP3 | TBC1D24 | FAM53B | SELL | | UXT |
| HMHA1 | TBCCD1 | FAM78A | SF3A1 | | WNK1 |
| HOGA1 | TERF1 | FAU | SHISA9 | | WWP2 |
| HOPX | TERF2 | FBXO5 | SIRPG | | ZFP36 |
| HSPA1B | THAP5 | FKBP5 | SLA | | ZNF217 |
| ICA1L | TLE3 | FNDC3A | SLC39A7 | | |
| ID3 | TM7SF3 | FOSB | SLC4A7 | | |
| IDO1 | TMEM123 | FOXP1 | SMG7 | | |
| IER2 | TMEM209 | FRYL | SNORD10 | | |
| IFITM3 | TMEM41A | G6PD | SNRNP200 | | |
| IFNAR1 | TMEM41B | GAS5 | SON | | |
| IFNLR1 | TNFA1P8L2-SCNM1 | GINS2 | SPOCK2 | | |
| IKBIP | TNFSF14 | GLRX | SRRM2 | | |
| IL10 | TPMT | GMCL1 | SSR4 | | |
| INIP | TRIM5 | GMFG | STK16 | | |
| INPP4B | TRIOBP | GMNN | SUMO2 | | |
| INPP5F | TSNAX | GNG5 | SUPV3L1 | | |
| IRAK4 | TTC39C | GNLY | SYNGR2 | | |
| IRF1 | TUBGCP4 | GOLGA8B | SYTL3 | | |
| IRF2BP2 | TYMP | GPR183 | TAF15 | | |
| ITGAX | UBE2Q2 | GPR56 | TAOK3 | | |
| ITK | UBOX5 | CRN | TAP2 | | |
| KCNK5 | UBXN2B | GSTM1 | TK1 | | |
| KDELC2 | UTP23 | GSTP1 | TLN1 | | |
| KDSR | VMP1 | GTF2B | TMED9 | | |
| KIAA0355 | WAC-AS1 | GTF3C6 | TMEM155 | | |
| KIAA1324 | WDR92 | GZMK | TMEM2 | | |
| KIAA1919 | XIAP | H2AFZ | TNFAIP3 | | |
| KIF18B | XKR9 | HDAC8 | TNFSF4 | | |
| KIF3A | ZBTB24 | HERC2P2 | TNFSF8 | | |
| KIN | ZBTB43 | HERPUD1 | TOB1 | | |
| KLHL28 | ZCCHC4 | HINT1 | TOMM7 | | |
| KLRC2 | ZFP14 | HIST1H1E | TOX | | |
| KLRC3 | ZFP36L1 | HIST1H3G | TP53INP1 | | |
| KLRD1 | ZMYM5 | HIST1H4C | TPX2 | | |
| KRAS | ZNF100 | HLA-DQA1 | TSC22D3 | | |
| LAIR1 | ZNF124 | HLA-DQA2 | TSPAN14 | | |
| LDHA | ZNF160 | HLA-DRB5 | TSPYL2 | | |
| LDLR | ZNF321P | HLA-F | TSTD1 | | |
| LIAS | ZNF333 | HLA-H | TTN | | |
| LINC00476 | ZNF37BP | HMBOX1 | TUBA4A | | |
| LLGL1 | ZNF483 | HUWE1 | TXK | | |
| LOC100131067 | ZNF526 | IFIT5 | TXNIP | | |
| LOC100131089 | ZNF528 | IL6ST | TYMS | | |
| LOC180132247 | ZNF529 | IQGAP1 | UBA52 | | |
| LOC100190986 | ZNF543 | IQGAP2 | UBE2C | | |
| LOC100268168 | ZNF548 | ISCU | UBE2T | | |
| LOC100271836 | ZNF549 | ISG20 | UCP2 | | |
| LOC10050812 | ZNF620 | ITGAD | UGDH-AS1 | | |
| LOC100505876 | ZNF652 | ITGB1 | UQCR11 | | |

TABLE 10-continued

Down-regulated and Up-regulated genes post-immunotherapy treatment in microenvironment

| T.cd8.up | | T.cd8.down | | T.cd4.up | T.cd4.down | Macro.up | Macro.down |
|---|---|---|---|---|---|---|---|
| LOC100506083 | ZNF665 | ITGB2 | UQCRB | | | | |
| LOC100652772 | ZNF669 | ITM2B | UQCRH | | | | |
| LOC202781 | ZNF683 | KDM5C | USB1 | | | | |
| LOC284023 | ZNF721 | KIAA1551 | UXT | | | | |
| LOC389641 | ZNF793 | KIR2DL4 | VCAM1 | | | | |
| LOC727896 | ZNF805 | KLF12 | VRK1 | | | | |
| LOC729603 | ZNF814 | KPNB1 | WDR83OS | | | | |
| LOC90834 | ZSCAN2 | LDHB | WNK1 | | | | |
| LRRC57 | ZSCAN22 | LENG8 | YEATS4 | | | | |
| LRRC58 | ZSCAN29 | LINC00493 | YWHAB | | | | |
| LY9 | ZSWIM7 | LINC00612 | ZBTB38 | | | | |
| | | LNPEP | ZC3H12A | | | | |
| | | LOC643406 | ZC3HC1 | | | | |
| | | LOC643733 | ZDHHC24 | | | | |
| | | LOC646214 | ZFP36L2 | | | | |
| | | LRRC37A4P | ZMYND8 | | | | |
| | | LSM6 | ZNF638 | | | | |
| | | MAD2L1 | ZWINT | | | | |
| | | MAEA | | | | | |

TABLE 11

Top Genes from Table 10

| T.cd8.up | T.cd8.down | T.cd4.up | T.cd4.down | Macro.up | Macro.down |
|---|---|---|---|---|---|
| AP1G2 | AKNA | CASP10 | CHI3L2 | NUPR1 | FKBP5 |
| AP3M1 | BCL2 | CXCR3 | COX7C | | LOC100130476 |
| APOL2 | CARD16 | CXCR6 | CXCR5 | | NLRP3 |
| ARF6 | CCDC141 | FAM153C | HIST1H1E | | THBS1 |
| C12orf65 | COX4I1 | FGD5-AS1 | HIVEP2 | | TNFAIP3 |
| CCDC122 | COX8A | GBP5 | ICA1 | | |
| CSAD | EIF3G | LOC727896 | NEK7 | | |
| CWC25 | FAU | NXNL2 | NFATC2 | | |
| DHODH | G6PD | RBM43 | NINJ2 | | |
| DIS3L | GLRX | RGS1 | PASK | | |
| FAM217B | GNLY | SLC35E1 | RPL13A | | |
| GBP2 | GPR56 | SPDYE1 | TCF7 | | |
| GDAP2 | HIST1H4C | | | | |
| HOPX | HLA-DRB5 | | | | |
| IKBIP | HUWE1 | | | | |
| KIAA1919 | ITGB2 | | | | |
| LOC727896 | MGMT | | | | |
| LOC90834 | MKNK2 | | | | |
| LRRC58 | NDC80 | | | | |
| MAP7D3 | NDUFA6 | | | | |
| MFSD11 | PIK3R5 | | | | |
| MOCS3 | RPL35A | | | | |
| PER2 | SYTL3 | | | | |
| POU2AF1 | TNFSF4 | | | | |
| PQLC2 | TOB1 | | | | |
| RAD1 | UCP2 | | | | |
| SGCB | WNK1 | | | | |
| SGOL1 | | | | | |
| SLC2A3 | | | | | |
| SNAPC3 | | | | | |
| SRSF8 | | | | | |
| SS18 | | | | | |
| STOM | | | | | |
| SWSAP1 | | | | | |
| TANGO2 | | | | | |
| TERF2 | | | | | |
| TMEM123 | | | | | |
| TMEM209 | | | | | |
| ZBTB43 | | | | | |
| ZNF160 | | | | | |
| ZNF528 | | | | | |
| ZNF543 | | | | | |

Example 5

Protein-Protein Interactions Between Genes in the Resistance Signatures

In line with the co/anti-regulatory patterns of the PIT-Up (ICR-Up) and PIT-Down (ICR-down) modules, a significantly large number of protein-protein interactions occur within and between the two modules (253 interactions, P=<1e-3,) (Table 12). The number of interactions is ~7 times more than expected (empirical p-value).

TABLE 12

| GeneA | GeneB |
|---|---|
| ACAA2 | PFN1 |
| ACAA2 | ATP1B3 |
| ACAA2 | ISYNA1 |
| ACSL4 | PTPMT1 |
| ACSL4 | HTATIP2 |
| ADSL | UBC |
| ADSL | XPNPEP1 |
| ADSL | PAICS |
| AEN | LZTS2 |
| AHNAK | FN1 |
| AHNAK | S100A10 |
| ALDH1B1 | UBC |
| ALDH1B1 | FN1 |
| ALDH1B1 | XPNPEP1 |
| ANXA1 | UCHL5 |
| ANXA1 | FN1 |
| ANXA2 | CTSB |
| ANXA2 | S100A10 |
| ANXA2 | MID1 |
| ANXA2 | FN1 |
| ANXA2 | LGALS1 |
| ARHGEF1 | CD44 |
| ARHGEF1 | FN1 |
| ATF3 | STAT1 |
| ATF3 | JUNB |
| ATP1A1 | UBC |
| ATP1A1 | ATP1B3 |
| ATP1B3 | PTP4A3 |
| ATP1B3 | HLA-C |
| ATP1B3 | RPL17 |
| ATXN10 | BSG |
| ATXN10 | FN1 |
| ATXN10 | MRPS16 |
| ATXN2L | GALNS |
| ATXN2L | PABPC1 |
| BCCIP | EIF6 |
| BCCIP | FAM46A |
| BCCIP | SORD |
| BCCIP | SMS |
| BCL6 | JUNB |
| BCL6 | HDAC2 |
| BCL6 | PELI1 |
| BIRC3 | UBC |
| BSG | OS9 |
| BSG | MYBBP1A |
| BSG | XPO7 |
| BSG | METAP2 |
| BSG | PTPMT1 |
| CALU | GAA |
| CALU | PRKCDBP |
| CALU | CTNNAL1 |
| CALU | HSP90B1 |
| CAV1 | CD44 |
| CAV1 | PTRF |
| CD151 | CD46 |
| CD44 | IGFBP3 |
| CD44 | FN1 |
| CD44 | NF2 |
| CD46 | CD9 |
| CD9 | LGALS3BP |
| CFB | FN1 |
| CPSF1 | POLR2A |
| CRELD1 | EIF6 |
| CRYAB | CS |

TABLE 12-continued

| GeneA | GeneB |
|---|---|
| CRYAB | SORD |
| CS | CTPS1 |
| CST3 | CTSB |
| CTSA | CTSD |
| CTSB | S100A10 |
| CTSB | SPRY2 |
| CTSD | UCHL5 |
| CTSD | HSP90B1 |
| DCBLD2 | ITM2B |
| DCTN6 | RPSA |
| ECHS1 | UCHL5 |
| ECHS1 | ISYNA1 |
| EGR1 | JUNB |
| EIF4A1 | PABPC1 |
| EIF4A1 | UCHL5 |
| EIF4A1 | RPSA |
| EIF4A1 | TMEM43 |
| EIF4A1 | ILF2 |
| EIF4A1 | FN1 |
| EIF6 | PAICS |
| EIF6 | PSME1 |
| EIF6 | FBL |
| EIF6 | RPL17 |
| EIF6 | RUVBL2 |
| EIF6 | TSNAX |
| EIF6 | KIAA0020 |
| EMP1 | SMIM3 |
| EPDR1 | NF2 |
| FAM213A | HLA-C |
| FAM46A | PRSS23 |
| FAM46A | SQRDL |
| FAM46A | FNDC3B |
| FBL | RUVBL2 |
| FBL | KLF6 |
| FBL | UBC |
| FBL | NOLC1 |
| FBL | RPL17 |
| FBL | RPS7 |
| FBL | RPS3 |
| FBL | FN1 |
| FBL | GPATCH4 |
| FBL | KIAA0020 |
| FBLN1 | FN1 |
| FN1 | IGFBP3 |
| FN1 | MIA |
| FN1 | TNC |
| FN1 | LGALS1 |
| FN1 | LYPLA1 |
| FN1 | RPL17 |
| FN1 | RNH1 |
| FN1 | G6PD |
| FN1 | PAICS |
| FN1 | SLC5A3 |
| FN1 | NCBP1 |
| FN1 | PPA1 |
| FN1 | XRCC5 |
| FN1 | RPSA |
| FN1 | RUVBL2 |
| FN1 | PRDX3 |
| FN1 | RPL10A |
| FN1 | RPS7 |
| FN1 | ILF2 |
| FN1 | PFN1 |
| FN1 | UBAP2L |
| FN1 | PABPC1 |
| FN1 | RPS3 |
| FN1 | UBC |
| FN1 | RBM4 |
| FN1 | TF |
| FOXRED2 | OS9 |
| FXYD3 | NR4A1 |
| G6PD | GBP2 |
| G6PD | TSTA3 |
| G6PD | IDH2 |
| GEM | LZTS2 |
| GLOD4 | NR4A1 |
| GLOD4 | NNMT |
| GLOD4 | PAICS |

TABLE 12-continued

| GeneA | GeneB |
| --- | --- |
| HDAC2 | SMC3 |
| HDAC2 | KLF4 |
| HDAC2 | RUVBL2 |
| HDAC2 | SNAI2 |
| HDAC2 | TSC22D3 |
| HLA-A | TAPBP |
| HLA-A | TAP1 |
| HLA-A | UBC |
| HLA-A | ITM2B |
| HLA-A | HLA-C |
| HLA-A | HLA-E |
| HLA-C | UBC |
| HLA-C | HLA-F |
| HLA-C | HLA-E |
| HLA-C | ITGA6 |
| HLA-E | HLA-F |
| HLA-E | ITGA6 |
| HSP90B1 | OS9 |
| HSP90B1 | TPM1 |
| HSP90B1 | RPN2 |
| HSP90B1 | TSR1 |
| HSP90B1 | STAT1 |
| IDH2 | UBC |
| IGF1R | IGFBP3 |
| IGFBP3 | TF |
| ILF2 | XRCC5 |
| ILF2 | RPL17 |
| ILF2 | RPL10A |
| ILF2 | RPS3 |
| ILF2 | SRSF7 |
| ILF2 | PRKCDBP |
| ILF2 | TOMM22 |
| ILF2 | PTRF |
| ILF2 | RUVBL2 |
| ILF2 | MYBBP1A |
| ILF2 | KIAA0020 |
| ITGA6 | LGALS3BP |
| KLF4 | KLF6 |
| LAMB1 | UBC |
| LGALS1 | LGALS3BP |
| LZTS2 | TSNAX |
| LZTS2 | SMIM3 |
| MID1 | RPS3 |
| MID1 | UBC |
| MTG1 | PRNP |
| MYBBP1A | NR4A1 |
| MYBBP1A | RPS3 |
| MYBBP1A | PTRF |
| NCBP1 | THOC5 |
| NCBP1 | SERPINE2 |
| NF2 | XRCC5 |
| NF2 | RPS3 |
| NF2 | RPS7 |
| NF2 | SMC3 |
| NOLC1 | PTRF |
| OXA1L | PTPMT1 |
| PABPC1 | RPSA |
| PABPC1 | RBM4 |
| PABPC1 | RPL10A |
| PABPC1 | RPL17 |
| PELI1 | UBC |
| PFN1 | UCHL5 |
| POLR2A | XRCC5 |
| POLR2A | SMC3 |
| POLR2A | PSMB9 |
| POLR2A | RUVBL2 |
| PRAME | UBC |
| PRDX3 | UCHL5 |
| PRDX3 | PSME1 |
| PROS1 | RPSA |
| PSMB9 | PSME1 |
| PSMB9 | UCHL5 |
| PTP4A3 | XPO7 |
| RND3 | SKP2 |
| RPL10A | RPS3 |
| RPL10A | RPL17 |
| RPL10A | RPSA |
| RPL10A | S100A10 |
| RPL10A | RPS7 |
| RPL17 | RPS3 |
| RPL17 | RPSA |
| RPN2 | UBC |
| RPS3 | RPS7 |
| RPS3 | RPSA |
| RPS3 | TPM1 |
| RPS3 | TSR1 |
| RPS3 | UBC |
| RPS3 | TSNAX |
| RPS7 | RPSA |
| RPS7 | TSR1 |
| RPSA | TSR1 |
| RUVBL2 | SRCAP |
| RUVBL2 | UCHL5 |
| RUVBL2 | UBC |
| RUVBL2 | VPS72 |
| SAMM50 | TOMM22 |
| SAMM50 | SQRDL |
| SAMM50 | SERINC1 |
| SMG7 | TSNAX |
| SMS | SORD |
| SORD | TPM1 |
| SRCAP | VPS72 |
| STAT1 | TSNAX |
| TAP1 | TAPBP |
| TPM1 | UBC |
| TSC22D3 | UBC |
| TSTA3 | UBC |
| UBA7 | UBE2L6 |
| UBC | UCHL5 |
| UBC | XPNPEP1 |
| UCHL5 | XPNPEP1 |

Example 6—Tumor Microenvironment Interaction Analysis

Figure 34:
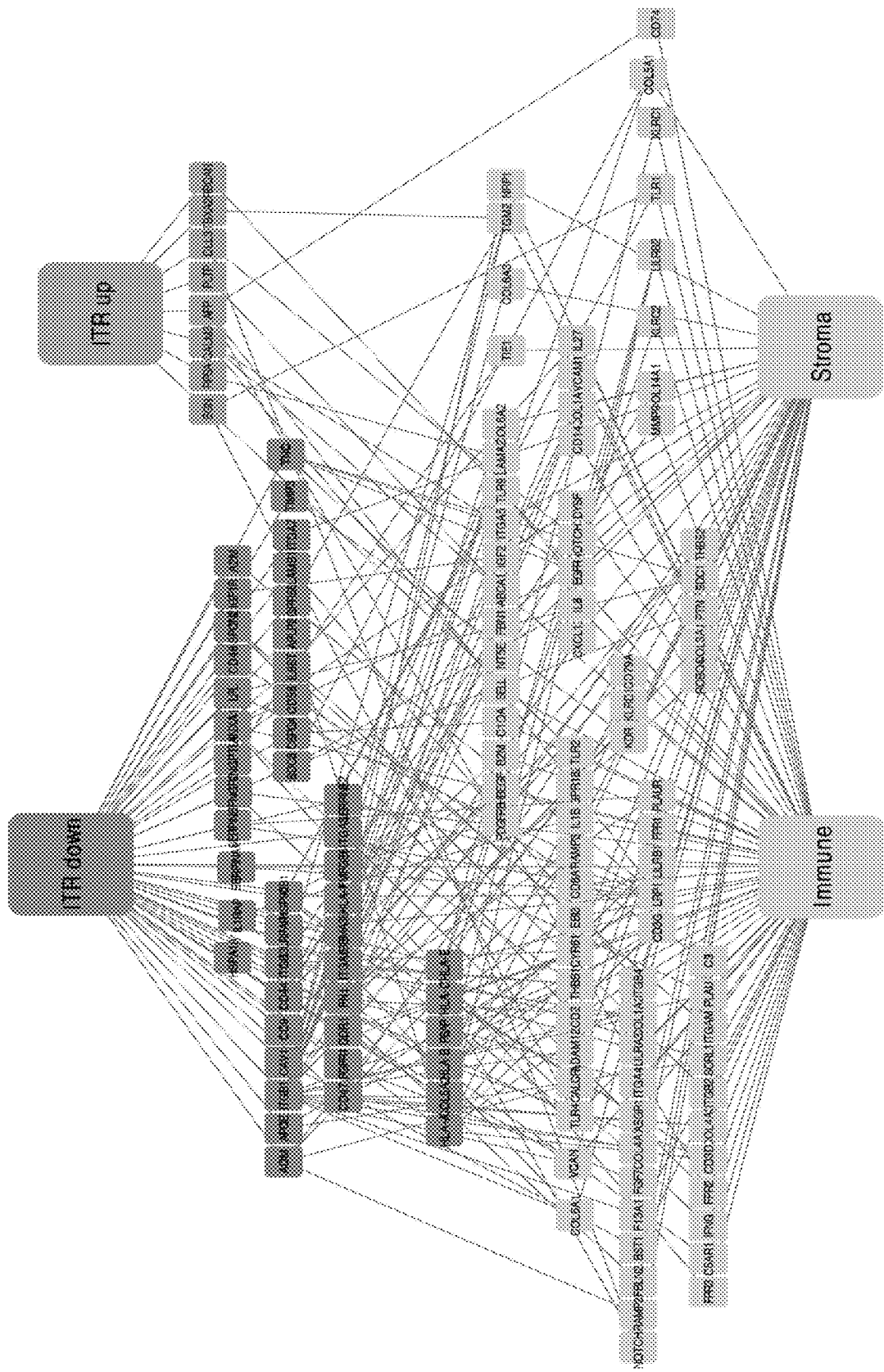
FIG. 34 illustrates an interaction map of genes in the ITR signature and immune and stromal genes.
Figure 35:
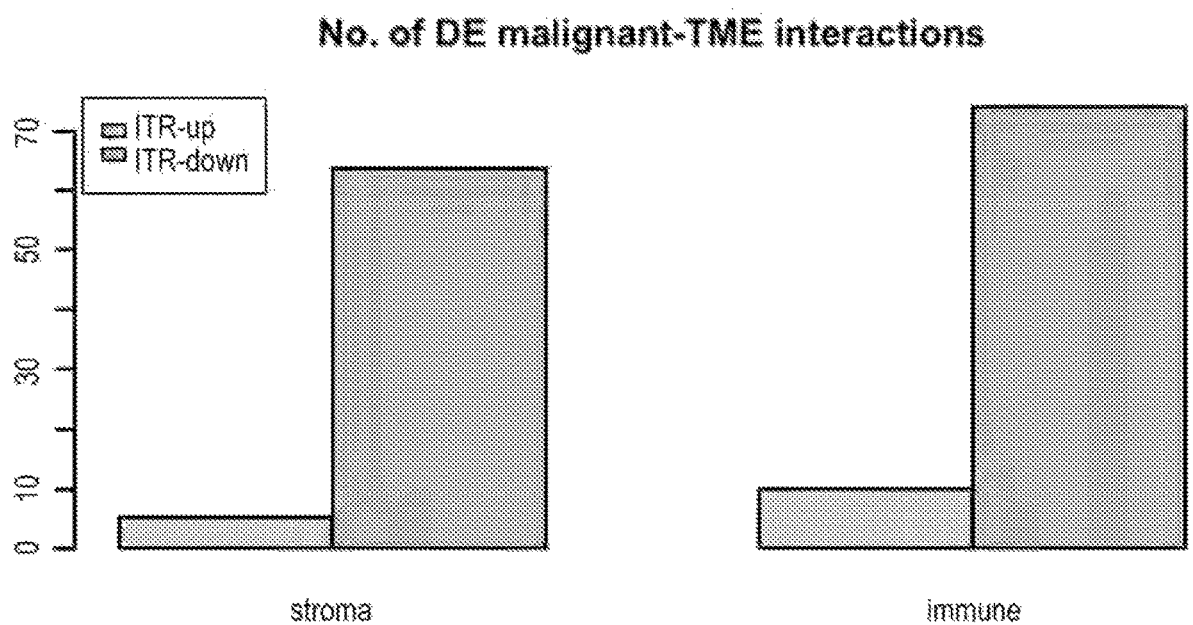
FIG. 35 illustrates the number of interactions between differentially expressed malignant genes and immune and stromal genes.

The ITR-down genes and ITR-up genes interact with stromal and immune genes. The ITR-down genes interact with more genes (FIGS. 34, 35). FIG. 33 shows that genes that are down in malignant cells in immunotherapy resistant samples are rich in interactors of immune and stromal cells. Conversely, few such interaction genes are induced in malignant cells in immunotherapy resistant samples.

Example 7—ITR Signature Scores from 26 Melanoma Tumors in Different Cancers

Figure 36:
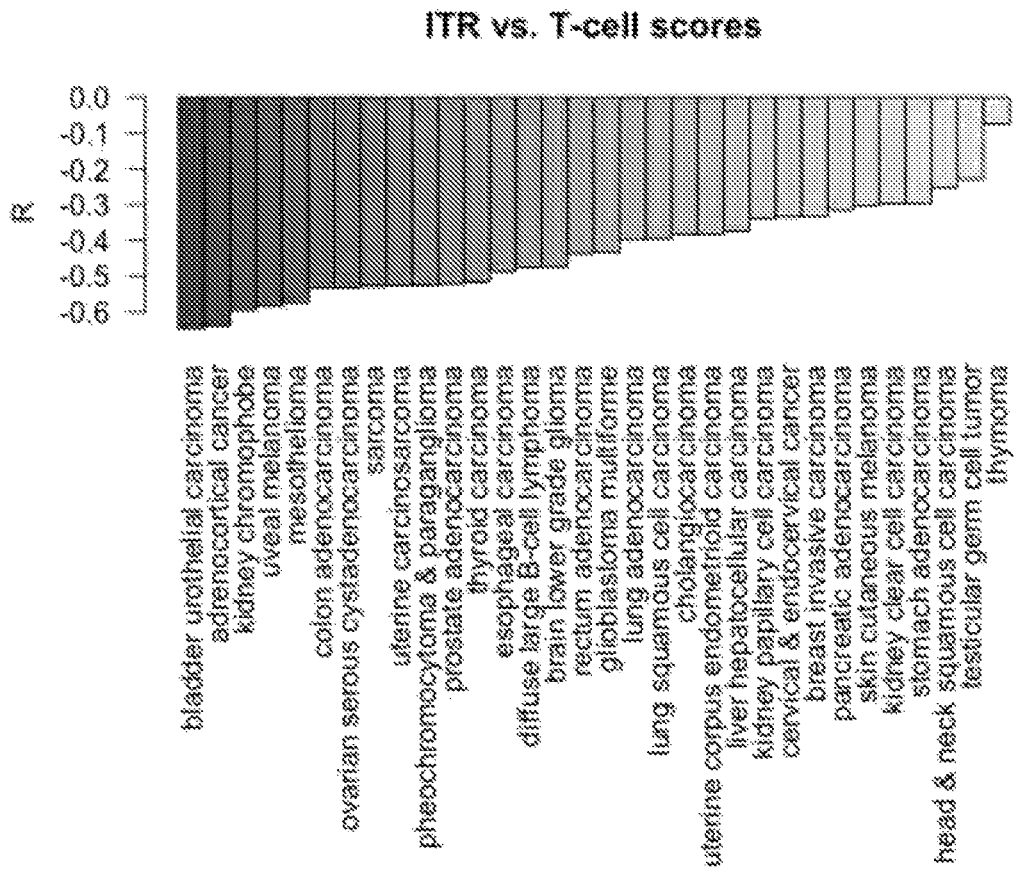
FIG. 36 illustrates ITR versus T cell scores in different cancers.
Figure 37:
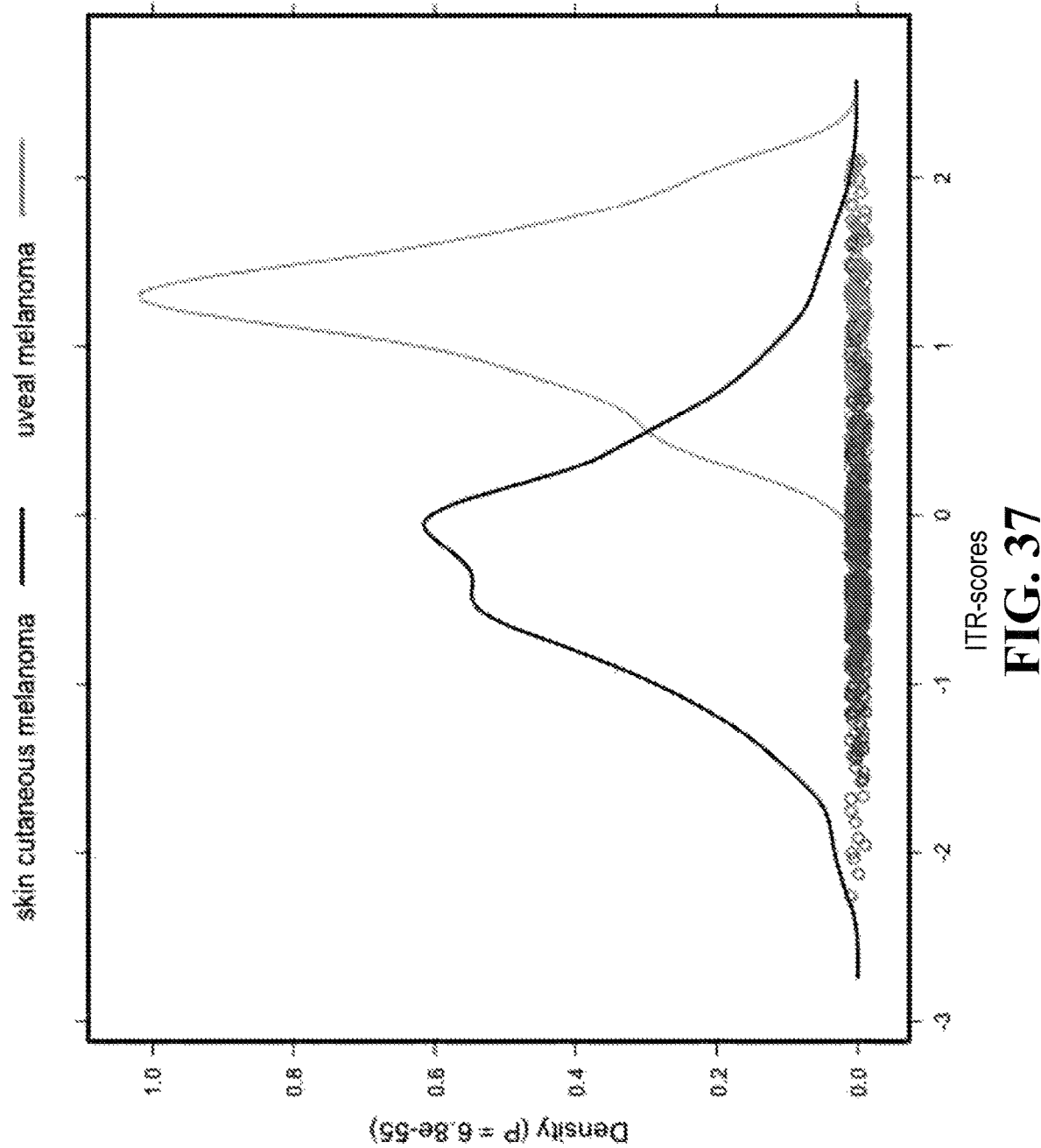
FIG. 37 illustrates ITR scores in two melanomas.

The ITR scores are different in different cancers (FIGS. 36, 37). Bladder cancer has the highest. Thymoma has the lowest. Uveal melanoma has the fourth highest. Applicants observed a difference in score between two melanomas (uveal and skin cutaneous). Not being bound by a theory, cancers with the highest ITR scores are more resistant to immunotherapy than cancers with a lower score. Not being bound by a theory, cancers with the highest ITR scores have a worse prognosis. The cancers on the right are more sensitive to immunotherapy (FIG. 36). Furthermore, they have less of an anti-correlation between ITR and T cell infiltration.

Figure 15A:
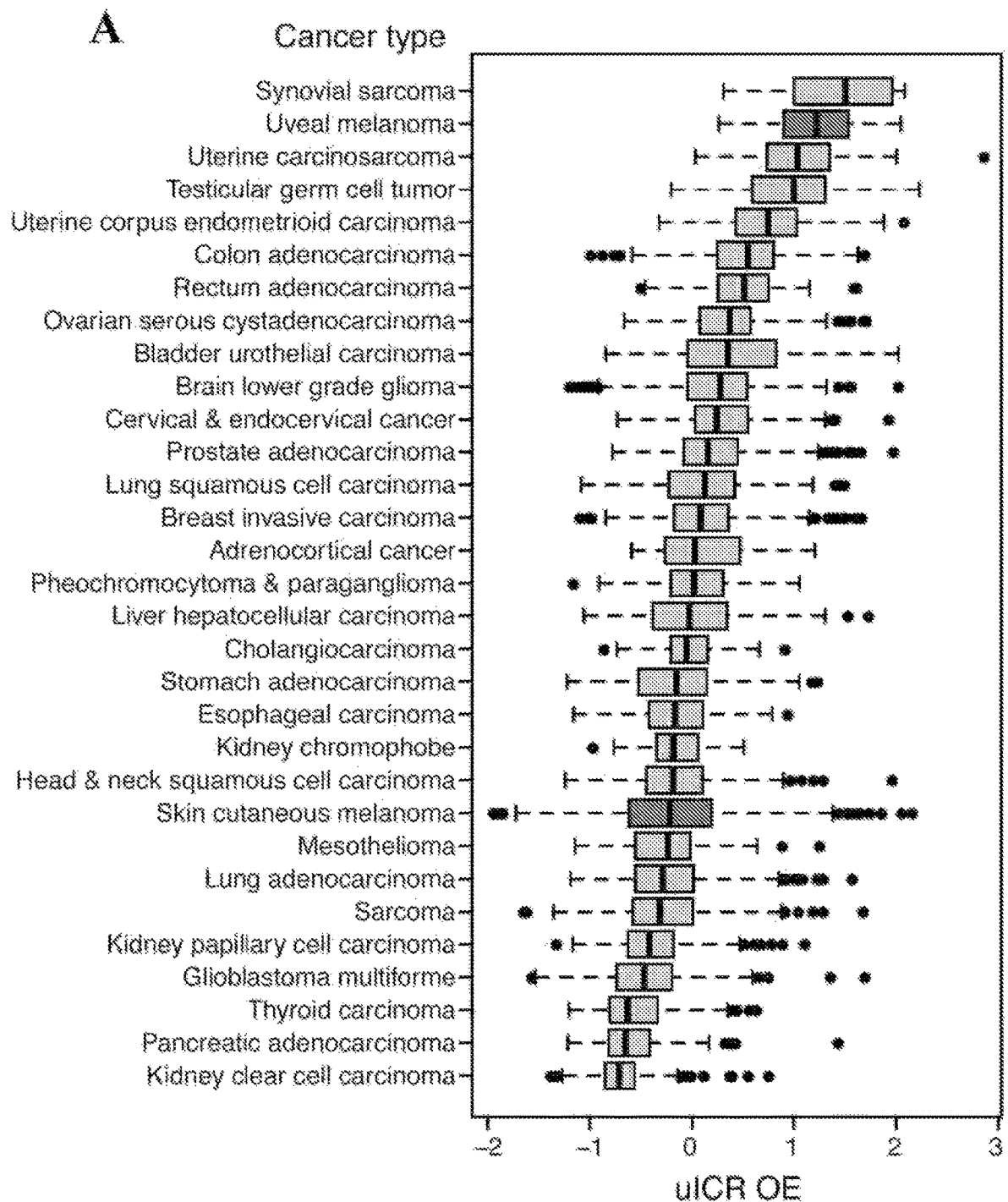
FIG. 15 illustrates pan-cancer analysis of the resistance signatures. Box-plots of the distribution of OE scores (x-axis) of the uICR signature in bulk RNA-seq profiles of 9,559 tumors across 33 cancer types (y-axis) from TCGA either scored (A) "as-is" or (B) with a regression-based process to control for TME-related signals (materials and methods). Middle line: median; box edges: 25th and 75th percentiles; whiskers: most extreme points that do not exceed ±IQR*1.5; points beyond the distance: single points.
Figure 15B:
Figure 16:
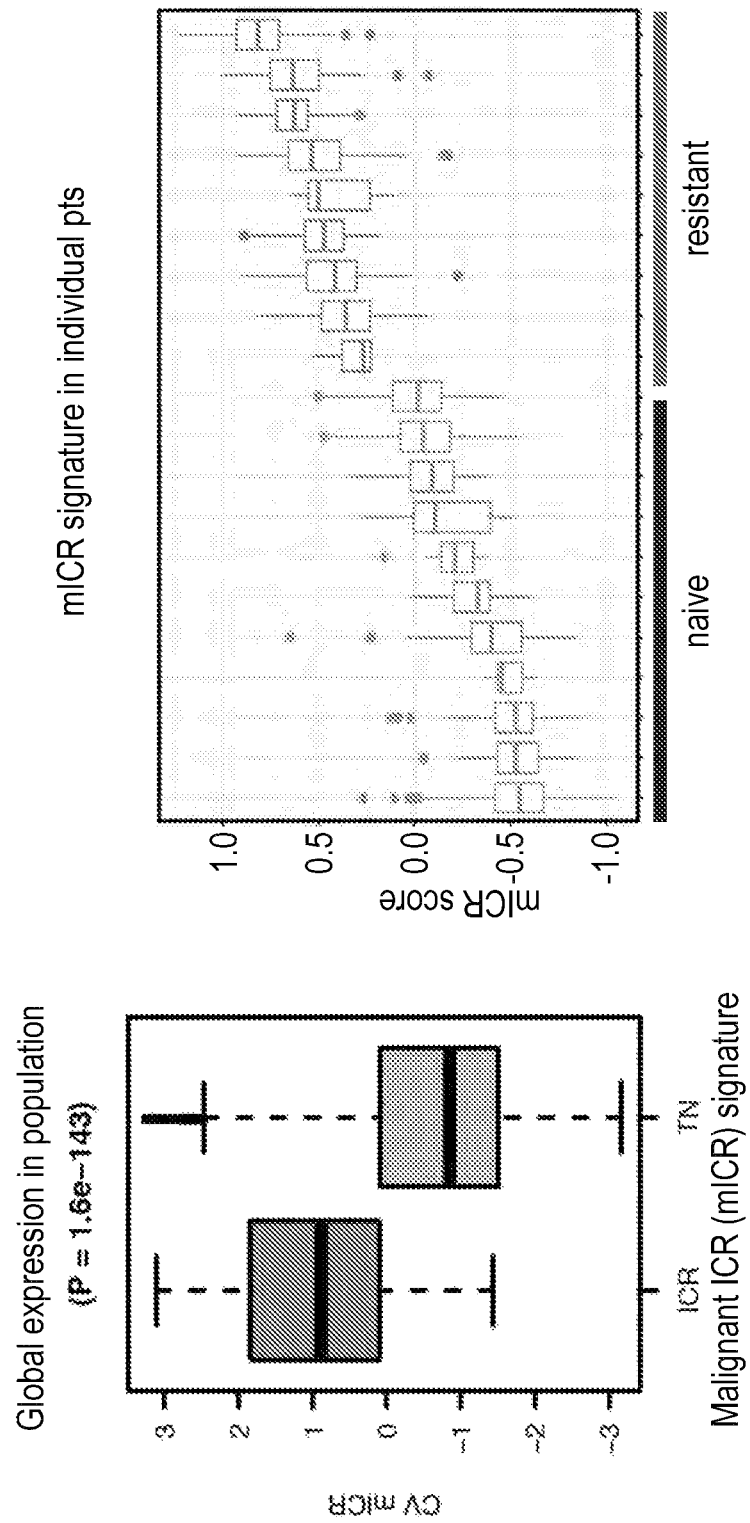
FIG. 16 illustrates that an unbiased analysis reveals a malignant cell state linked to ICR.

Example 8—Analysis of Single Cells from ER+ Metastatic Breast Cancer and Colon Cancer Applicants also analyzed single cells in other cancers having an ICR signature, (see, e.g., FIG. 15A, B). Applicants further extended the melanoma ecosystem studies to study response to immunotherapy, using massively parallel droplet scRNA-Seq to analyze cells from colon tumors, using snRNA-Seq methods to profile metastatic breast cancer samples and profiling pancreatic tumors. Cancer cells may be more or less resistant to immunotherapy based on uICR scores. Single cells in other cancers may be shifted to an immunotherapy sensitive signature by treating with CDK4/6 inhibitors. Analysis of this signature and measuring shifts in the signature after CDK4/6 inhibition can allow the proper administration of an immunotherapy in a combination treatment.

Figure 38:
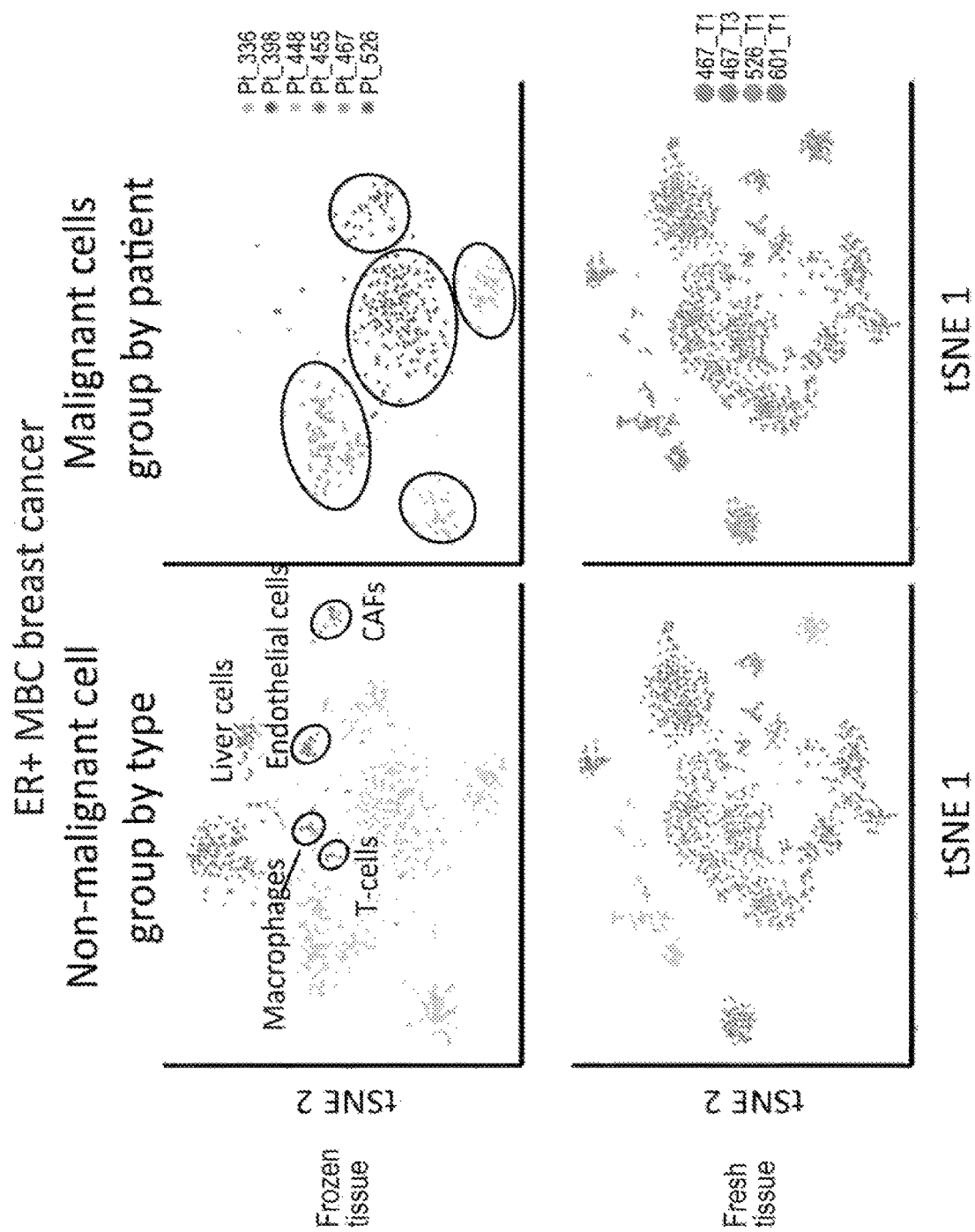
FIG. 38 illustrates tSNE analysis of ER+metastatic breast cancer using single nuclei RNA-seq (snRNA-seq) on fresh and frozen tissue samples.

Applicants analyzed ER+ metastatic breast cancer using single nuclei RNA-seq (snRNA-seq) on fresh and frozen tissue samples (FIG. 38). snRNA-seq as described herein is compatible with frozen tissue samples. Non-malignant cells clustered by cell type in both frozen and fresh tissue samples. Malignant cells clustered by patient.

Figure 39:
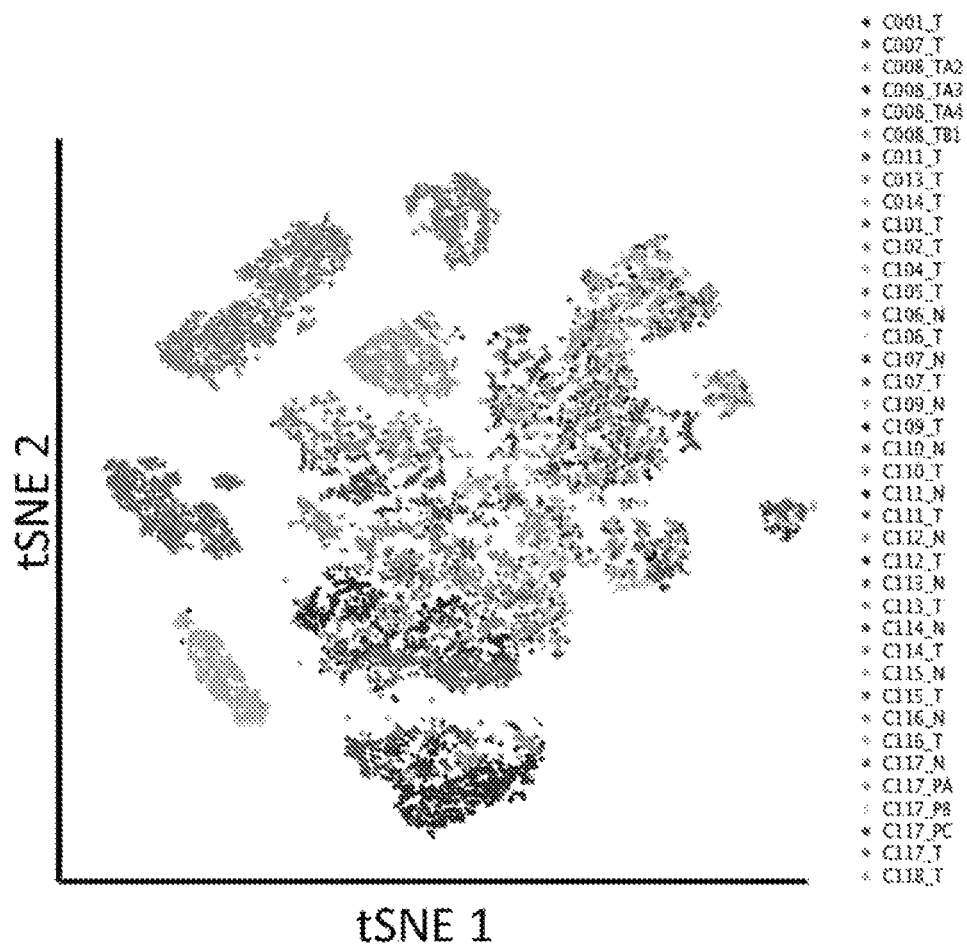
FIG. 39 illustrates tSNE analysis of 22 colon cancer samples using scRNA-seq.
Figure 40:
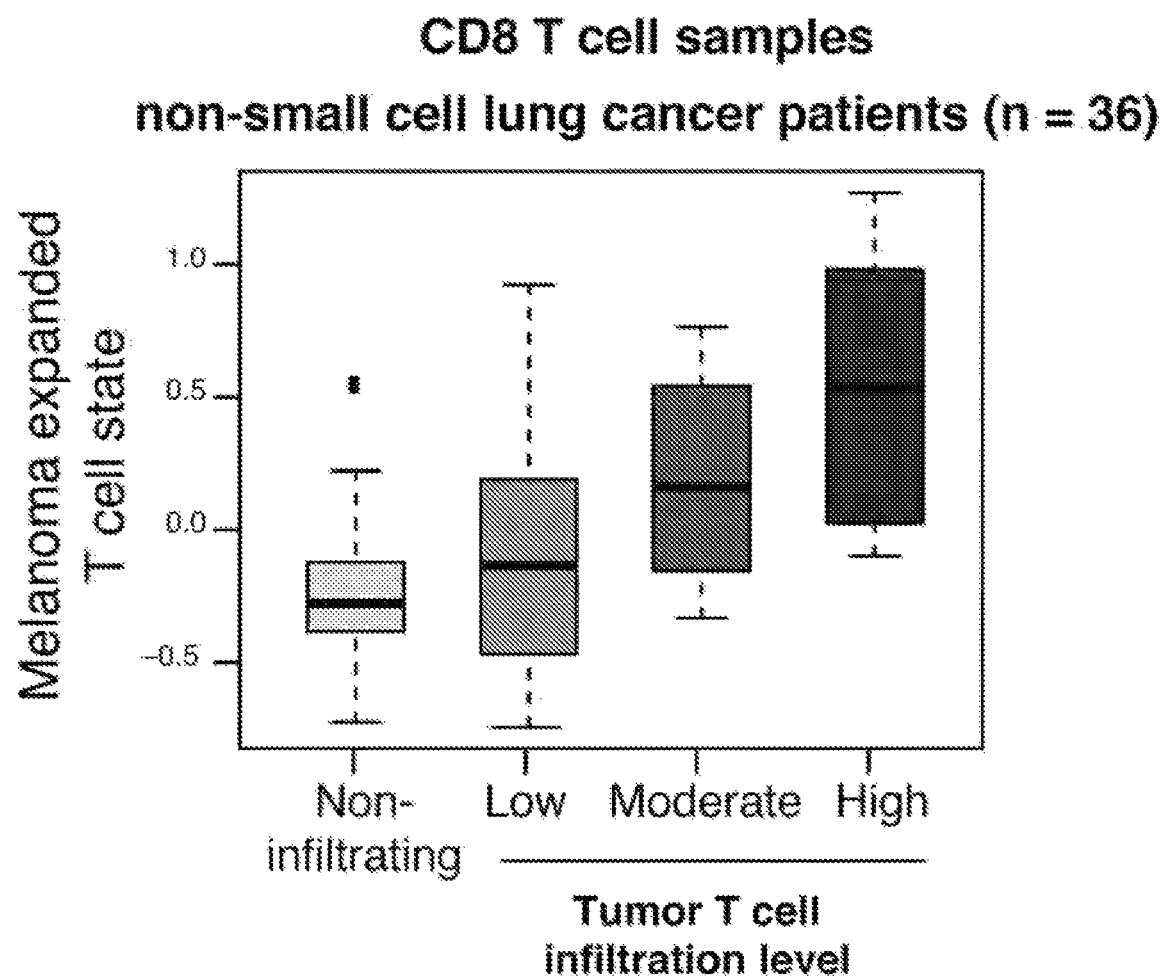
FIG. 40 illustrates that the expanded T cell state is highly correlated with the overall T cell infiltration level of tumors in an independent lung cancer cohort (Table S11).

Applicants analyzed 22 colon cancer samples using scRNA-seq (FIG. 39). With strict quality control (QC) on the 22 samples analyzed Applicants obtained 12,215 epithelial cells and 17,143 non-epithelial cells.

Example 9—Immunotherapy Resistance Signature

Immunotherapies have transformed the therapeutic landscape of several cancer types (Sharma and Allison, 2015). However, despite the durable responses in some patients, most patients' tumors manifest unpredictable resistance to immunotherapies (Gibney et al., 2016; Sharma et al., 2017). This hampers appropriate selection of patients for therapies, rational enrollment to clinical trials and the development of new therapeutic strategies that could overcome resistance (Sharma and Allison, 2015). Most non-responding patients manifest intrinsic resistance, reflected as continued tumor growth or occurrence of new metastatic lesions despite therapy, whereas some patients develop acquired resistance following an initial clinical disease regression. It is unknown whether these clinically discrete manifestations are associated with shared or distinct molecular mechanisms of resistance (Sharma et al., 2017).

Recent studies characterized resistance to immune checkpoint inhibitors (ICI) by analyzing Whole Exome Sequencing (WES) and transcriptional profiles of bulk tumors (Hugo et al., 2016; Mariathasan et al., 2018; Van Allen et al., 2015). These studies demonstrated that tumors with a high mutational load (Van Allen et al., 2015) and a high level of immune cell infiltration (Riaz et al., 2017; Tumeh et al., 2014) are more likely to respond, and linked ICI resistance in patients to functional immune evasion phenotypes, including defects in the JAK/STAT pathway (Zaretsky et al., 2016) and interferon gamma (IFN-γ) response (Gao et al., 2016; Zaretsky et al., 2016), impaired antigen presentation (Hugo et al., 2016; Zaretsky et al., 2016), and PTEN loss (Peng et al., 2016). While these studies significantly contributed to the understanding of the cancer-immune interplay, the resulting biomarkers where only partially predictive (Sharma et al., 2017). This may be due to the fact that they only reflect some facets of the causes of resistance (WES) or combine signals from malignant and non malignant (immune and stroma) cells (RNA and copy-number variations).

Because immune checkpoint inhibitors target the interactions between different cells in the tumor, their impact depends on multicellular circuits between malignant and non malignant cells (Tirosh et al., 2016a). In principle, resistance can stem from different compartment of the tumor's ecosystem, for example, the proportion of different cell types (e.g., T cells, macrophages, fibroblasts), the intrinsic state of each cell (e.g., memory or dysfunctional T cell), and the impact of one cell on the proportions and states of other cells in the tumor (e.g., malignant cells inducing T cell dysfunction by expressing PD-L1 or promoting T cell memory formation by presenting neoantigens). These different facets are inter-connected through the cellular ecosystem: intrinsic cellular states control the expression of secreted factors and cell surface receptors that in turn affect the presence and state of other cells, and vice versa. In particular, brisk tumor infiltration with T cell has been associated with patient survival and improved immunotherapy responses (Fridman et al., 2012), but the determinants that dictate if a tumor will have high ("hot") or low ("cold") levels of T cell infiltration are only partially understood. Among multiple factors, malignant cells may play an important role in determining this phenotype (Spranger et al., 2015). Resolving this relationship with bulk genomics approaches has been challenging; single-cell RNA-seq (scRNA-seq) of tumors (Li et al., 2017; Patel et al., 2014; Tirosh et al., 2016a, 2016b; Venteicher et al., 2017) has the potential to shed light on a wide range of immune evasion mechanisms and immune suppression programs.

Figure 44A:
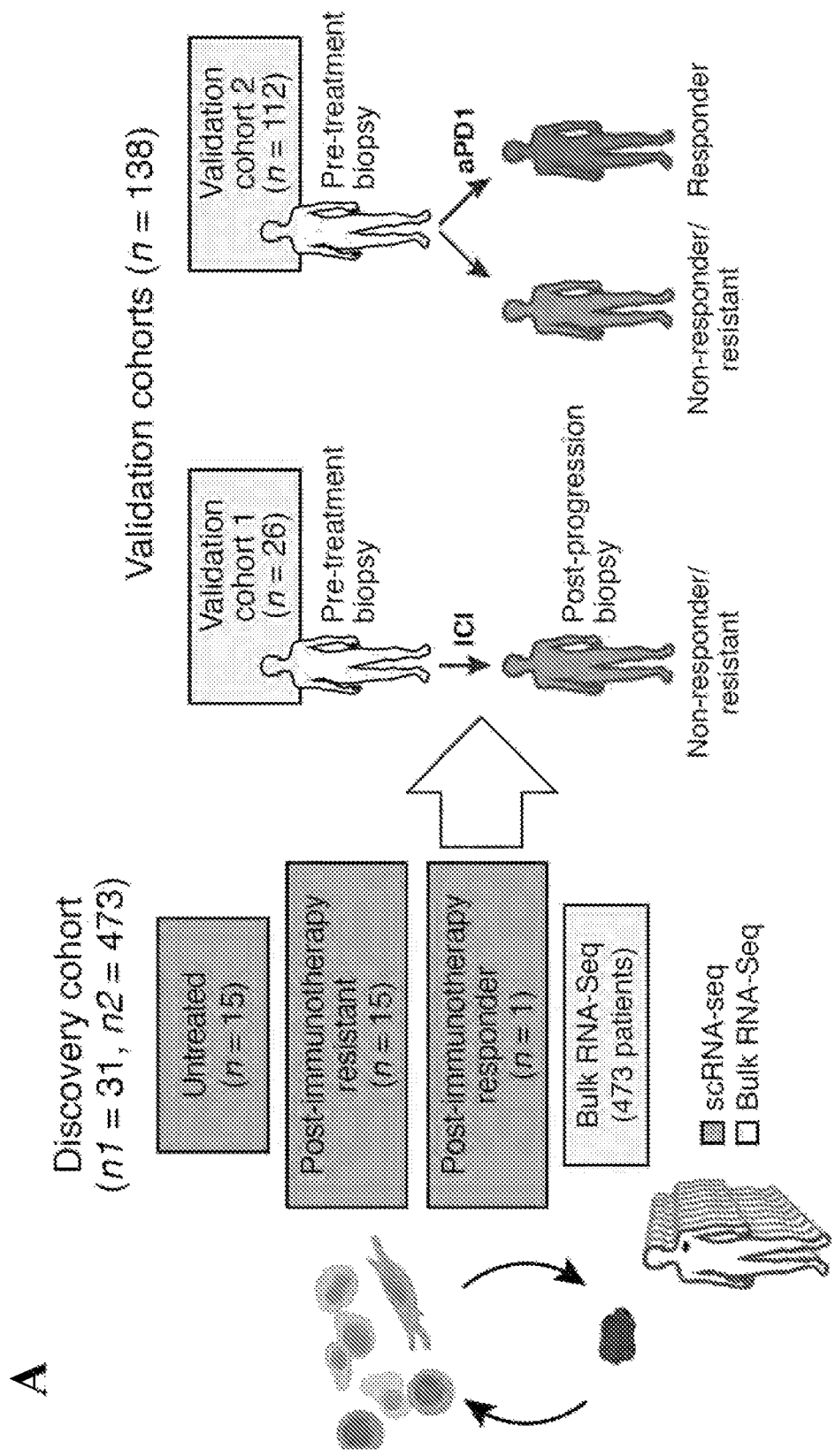
FIG. 44. Identification of a T cell exclusion program in malignant cells. (A) Study overview. 31 tumors from melanoma patients (discovery cohort) were profiled by scRNA-seq (left, tan) and integrated analytically with bulk RNA-Seq data from TCGA (473 melanoma tumors). The discovered program was tested in two validation cohorts of bulk RNA-Seq collected independently (right). (B) Analysis approach to discover malignant cell programs associated with immune cell infiltration or exclusion. (C-D) Distinct profiles of malignant and nonmalignant cells. tSNE plots of single-cell profiles (dots) from malignant (C) or nonmalignant (D) cells, shaded by post-hoc annotation (Methods, D left) or by tumor (C, D right). (E) Exclusion program. Expression (centered and scaled; bar) of the top genes (columns) in the exclusion program across the malignant cells (rows), sorted by untreated or post-treatment tumors (blue/grey bar, left) and clustered within each class. Leftmost bar: cycling and non-cycling cells within each group. Right: The overall expression (Methods) of the exclusion program in each cell. See also FIG. 51 and Tables S1-S3.
Figure 44B:
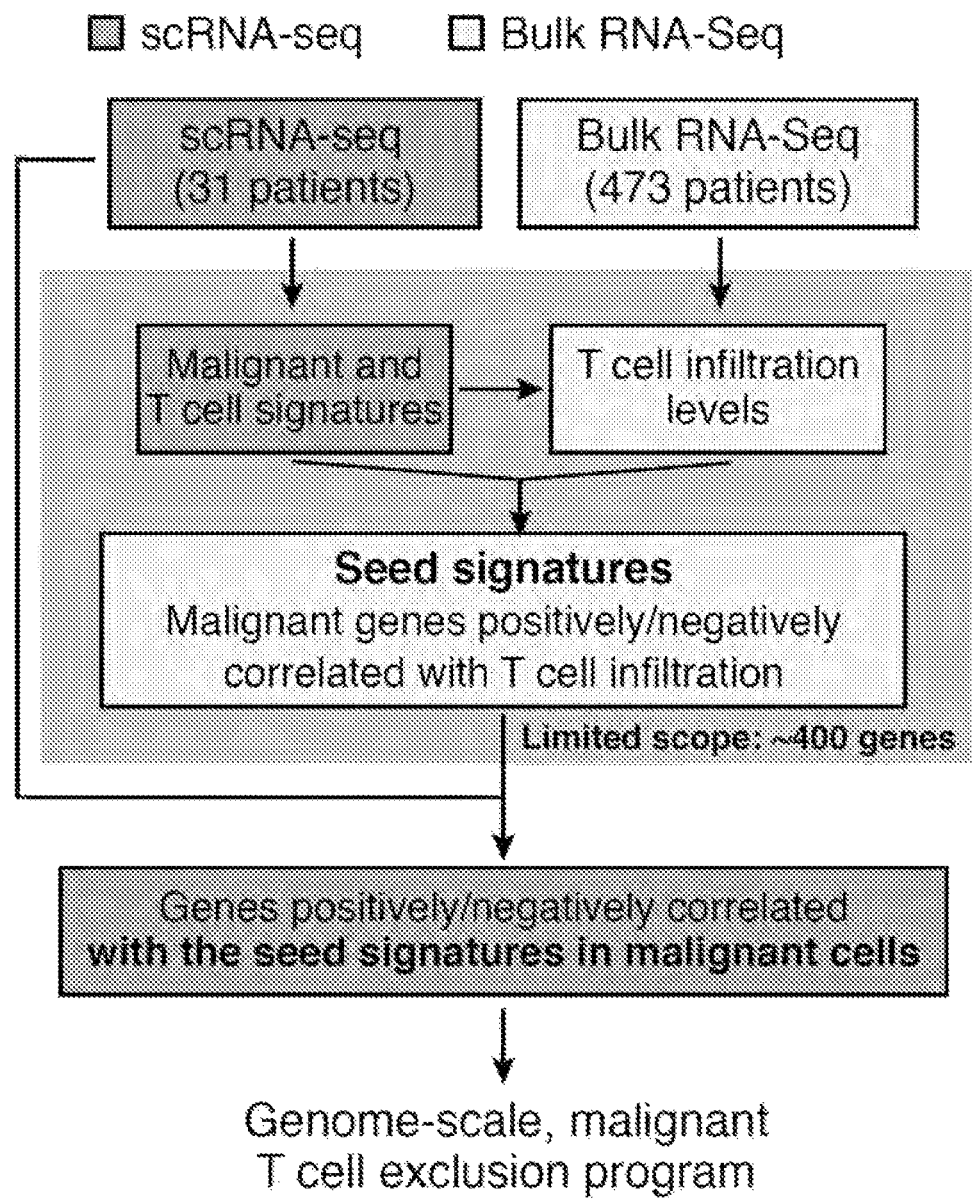

Here, Applicants used scRNA-seq and a new computational approach to identify immune evasion or suppression mechanisms in the melanoma ecosystem (FIG. 44A,B). Applicants developed a data-driven approach that integrates scRNA-seq with other data sources to characterize malignant cell states that drive immune resistance in melanoma (FIG. 44B). Applicants identified a program in malignant cells that is associated with T cell exclusion prior to immunotherapy, and with the melanoma cell states in patients who were resistant to immunotherapies. Applicants confirmed its presence in situ in tumors with multiplex protein imaging. This program predominantly reflects intrinsic resistance to immune checkpoint inhibitors (but not to RAF/MEK-targeted therapy) and its expression predicts responses to ICI and clinical outcomes in independent patient cohorts. Applicants further associated the CDK4/6 pathway with control of this program and showed that treatment with CDK4/6 inhibitors reverses it and promotes a senescent-like state. This work provides a new predictive biomarker for ICI response, suggests a new therapeutic modality that may re-sensitize malignant melanoma cells to ICI, and provides a general framework to study the effect of immunotherapies and other drugs on complex tumor ecosystems.

Results

Systematic Approach to Discover Malignant Cell Programs Associated with Immune Cell Infiltration or Exclusion To identify malignant cell programs that characterize "cold" melanoma tumors, Applicants devised a new strategy that combines scRNA-seq and bulk RNA-Seq data to relate the cellular state of one cell type (e.g., malignant cell states) to the cellular composition of the tumors (e.g., T cell infiltration vs. exclusion) (FIG. 44B). For clarity, Applicants describe the strategy in this specific context, though it can be applied to any two cell-types of interest. Applicants first use scRNA-seq profiles to define cell type specific signatures of T cells and of malignant cells in melanoma tumors. Next, Applicants use the T cell signature to estimate T cell infiltration levels in each of hundreds of tumors, based on their bulk RNA-Seq profile. Applicants then define a "seed exclusion program" by identifying genes from the malignant cell signature whose expression is strongly correlated (positively or negatively) with the T cell infiltration level across those bulk tumors. Because the seed program is identified only among a few hundred genes that are exclusively expressed by scRNA-Seq in malignant cells, it avoids contamination from the tumor microenvironment; however, important genes that promote exclusion or infiltration may also be expressed by non-malignant cells (e.g., MEW class I molecules). To recover these genes, Applicants finally return to the scRNA-seq data of the malignant cells and expand the seed program by searching for genes that are correlated with it across the single malignant cells, irrespective of their expression in other cell types. In this way, Applicants derive a genome-scale, malignant-cell exclusion program, consisting of genes induced ("up") or repressed ("down") by malignant cells in "cold" vs. "hot" tumors. Applicants can then score each cell or tumor for expression of the program, such that overexpression of the program is defined as the overexpression of its induced part and underexpression of its repressed part, and vice versa (Methods). Analysis of Clinical scRNA-Seq Identifies a Malignant Cell Program Associated with T Cell Exclusion from Melanoma Tumors Applicants applied the approach to 7,186 high-quality scRNA-seq profiles from the tumors of 31 melanoma patients, comprised of 2,987 cells from 16 newly collected patient tumors (FIG. 44A, Table S1—note that only in this example (9) cohort 1 is referred to as cohort 2 and cohort 2 is referred to as cohort 1), and 4,199 cells from 16 patients that Applicants previously reported (Tirosh et al., 2016a), along with 473 bulk RNA-seq melanoma profiles from The Cancer Genome Atlas (TCGA) (Akbani et al., 2015). Applicants dissociated individual cells from fresh tumor resections, isolated immune and non-immune cells by FACS based on CD45 staining, and profiled them with a modified full-length SMART-Seg2 protocol (Methods, Table S2). Applicants distinguished different cell subsets and genetic clones both by their expression profiles and by their inferred CNV profiles (Tirosh et al., 2016a) (Methods), identifying: malignant cells, CD8 and CD4 T cells, B cells, NK cells, macrophages, Cancer Associated Fibroblasts (CAFs) and endothelial cells (FIGS. 44C,D and 51, Tables S3 and S4). Overall, malignant cells primarily grouped by their tumor of origin (FIG. 44C), while the non-malignant cells grouped primarily by their cell type, and only then by their tumor of origin (FIG. 44D), as Applicants have previously reported for melanoma and other tumor types (Puram et al., 2017; Tirosh et al., 2016a; Venteicher et al., 2017).

The resulting exclusion program (FIG. 44E, Table S6) highlights the repression of diverse immune response pathways and the induction of a co-regulated gene module of Myc and CDK targets. The repressed genes were enriched for antigen processing and presentation genes (B2M, CTSB, CTSL1, HLA B/C/F, HSPA1A, HSPA1B, $P=4.19*10^{-7}$, hypergeometric test), immune modulation genes ($P=3.84*10^{-9}$, e.g., CD58 and the NFκB inhibitor, NFKBIA), and genes involved in the response to the complement system ($P=2.26*10^{-7}$, e.g., CD59 and C4A). CD58 KO in malignant cells was recently shown to enhance the survival of melanoma cells in a genome-scale CRISPR screen of melanoma/T cell co-cultures (Patel et al., 2017), and its genetic loss or epigenetic inactivation are frequent immune evasion drivers in diffuse large B cell lymphoma (Challa-Malladi et al., 2011). The induced genes included MYC and Myc targets ($P=2.8*10^{-14}$), many CDK7/8 targets ($P<3*10^{-9}$) (Oki et al., 2018), and transcription factors, such as SNAI2 and SOX4. Myc-activation has been previously linked to increased expression of immunosuppressive signals, including the upregulation of PD-L1 and β-catenin, which in turn inhibits dendritic cell recruitment to the tumor microenvironment via CCL4 (Spranger et al., 2015).

The Exclusion Program Characterizes Individual Malignant Cells from Patients Who Failed Immunotherapy To determine whether the malignant T cell exclusion program manifests in the context of immune checkpoint inhibitor therapy, Applicants leveraged the fact that the scRNA-seq cohort included both untreated patients and post-ICI patients who manifested intrinsic resistance. As clinical response rates to ICI vary, with up to 61% responders with combination therapies (Hodi et al., 2010; Larkin et al., 2015; Postow et al., 2015; Ribas et al., 2015), the untreated tumors Applicants profiled likely include both ICI sensitive and ICI resistant tumors, whereas the tumors from ICI resistant patients are expected to include primarily resistant malignant cells. Applicants thus turned to examine if the exclusion program is more pronounced in the malignant cells from ICI resistant vs. untreated patients. ScRNA-seq data provide particular power for such inter-patient comparisons, even when considering only a small number of tumors, because of the larger number of cells per tumor and because non malignant cells in the tumor microenvironment do not confound the analyses.

Applicants thus independently identified a post-treatment transcriptional program, consisting of features that distinguish individual malignant cells from post-ICI resistant tumors compared to malignant cells from untreated tumors (Table S6). Applicants found a robust post-treatment program, consisting of genes induced (up) and repressed (down) by malignant cells from the post-treatment resistant vs. untreated patients, which is stable and generalizable in cross-validation (Methods, FIG. 45A, AUC=0.83). In principle, the program might reflect both the overall impact of ICI therapy and intrinsic ICI resistance per se, but those cannot be directly distinguished based on the single-cell cohort, where Applicants did not have matched samples from the same patient or pre-treatment tumors from responders and non-responders. Applicants address this below by analyzing two independent validation cohorts.

Figure 44E:
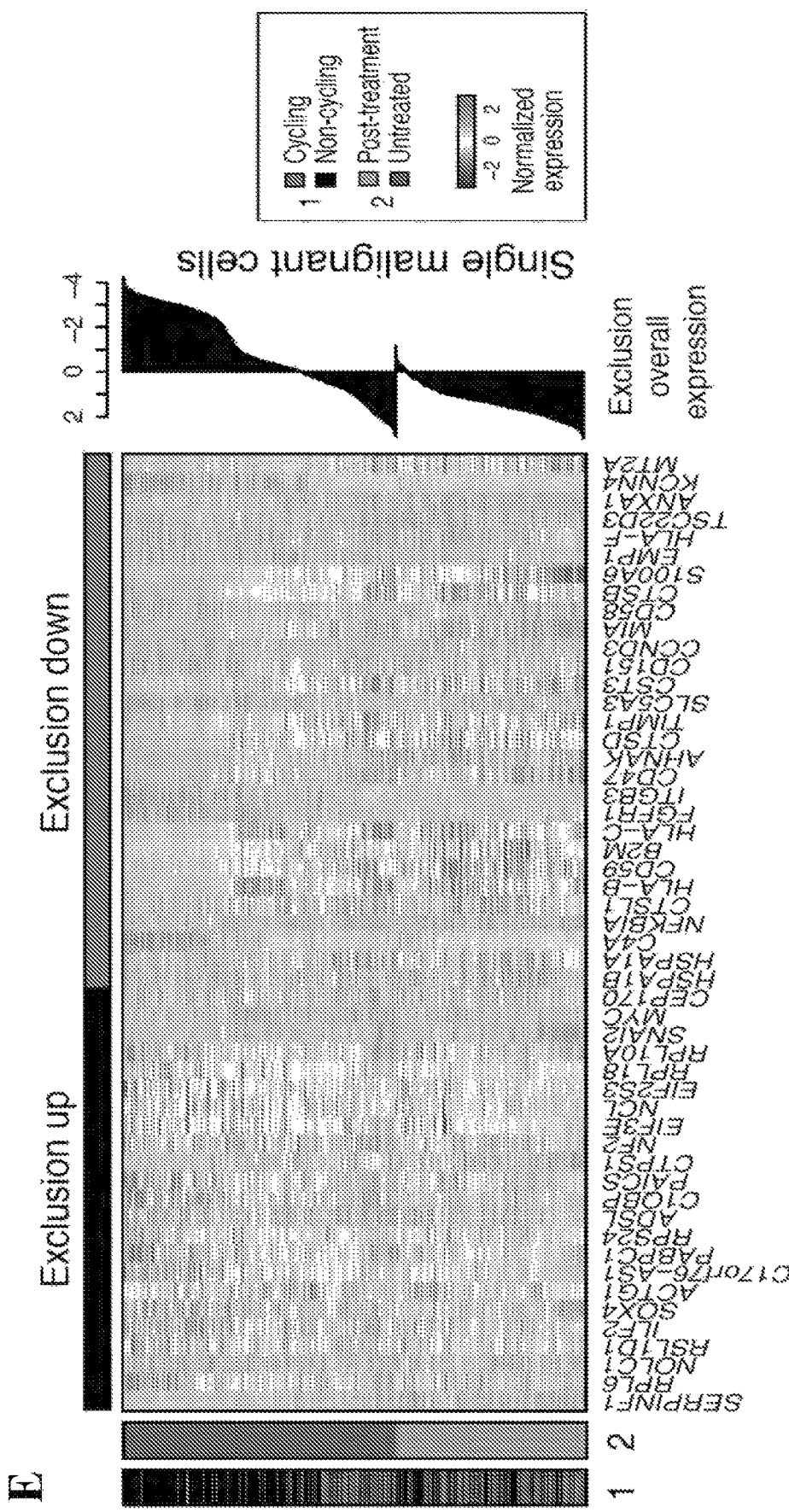

The post-treatment program substantially overlapped the exclusion program (FIGS. 44E and 45B,C, Table S6; $P<10^{-16}$, hypergeometric test, Jaccard index=0.27 and 0.23, for induced and repressed genes, respectively) and highlighted similar modules and pathways (FIG. 45D), even though the exclusion program was identified without considering the treatment status of the tumors in the scRNA-seq data and with bulk RNA-Seq data of untreated patients. Both programs robustly classified individual cells as untreated or post treatment (AUC=0.83 and 0.86 for cross-validation post-treatment and exclusion, respectively, FIG. 45A,E). In light of this congruence, Applicants defined a unified immune resistance program as the union of the corresponding post-treatment and exclusion programs, and used it in all subsequent analyses, unless indicated otherwise.

The Immune Resistance Program Reflects a Coherent Multifaceted State of Immune Evasion The program is consistent with several hallmarks of active immune evasion, suppression and exclusion. First, it is more pronounced in uveal melanoma, which resides in an immune-privileged environment and has very low response rates to immunotherapy, compared to cutaneous melanoma (FIG. 46A) (Algazi et al., 2016; Zimmer et al., 2015). Second, the inhibition of genes from the repressed component of the program in malignant melanoma cells conferred resistance to CD8 T cells in a genome-wide CRISPR KO screen ($P=6.37*10^{-3}$, hypergeometric test) (Patel et al., 2017). Third, malignant cells which express the program substantially repress a significant number of interaction routes with other cell types in the tumor microenvironment, including MEW I:TCR (T cells), CD58:CD2 (T cells), and IL1RAP:IL1B (macrophages) (FIG. 46B, Methods), as well as the overall Senescence Associated Secretory Phenotype (SASP) (P=4.3*10$^{-166}$ and 3.6*10$^{-3}$, one-sided t-test and mixed effects, respectively, FIG. 45D, right).

Figure 46C:
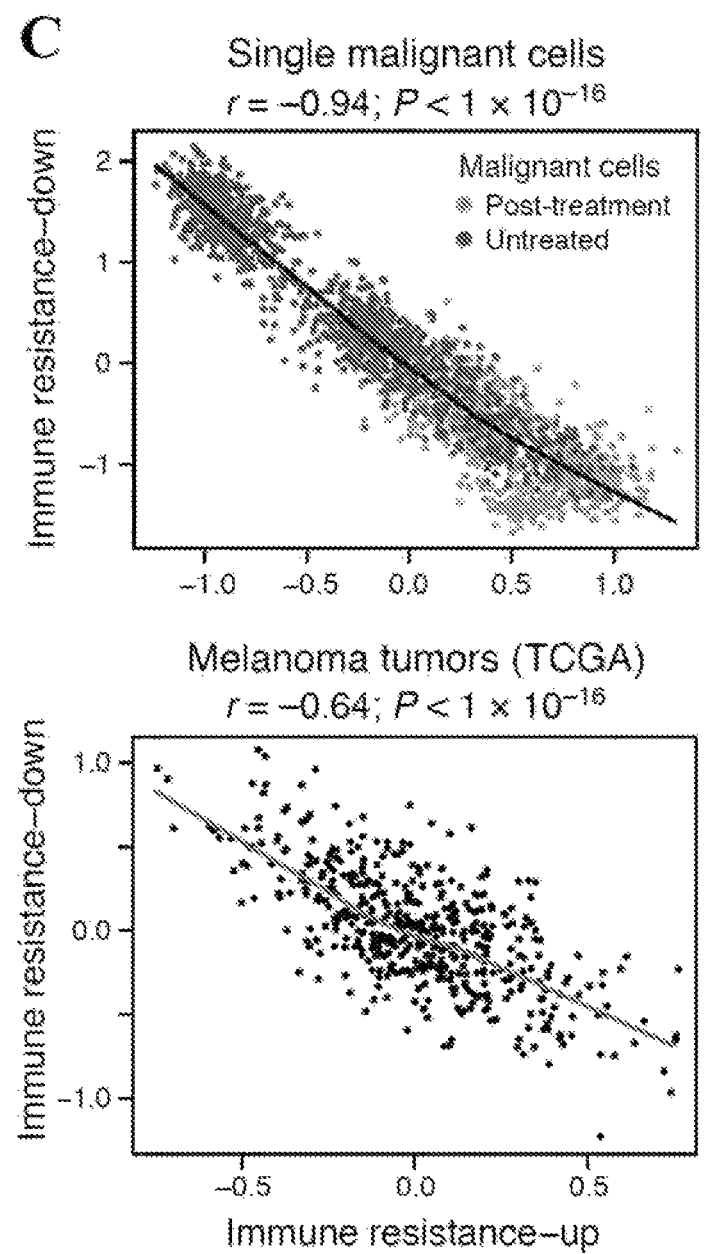
FIG. 46. The resistance program is a coherently regulated module that represses cell-cell interactions. (A) The immune resistance program is higher in uveal vs. cutaneous melanoma. The distribution of overall expression scores of the immune resistance program in cutaneous vs. uveal melanoma tumors from TCGA, scored after filtering tumor microenvironment contributions (Methods). (B) Cell-cell interaction genes are repressed in the immune resistance program. The number of genes (y axis, top) in each part of the program encoding proteins that engage in a physical interaction with other cell types and the significance of the corresponding enrichment (y axis, $-\log_{10}$(P-value), hypergeometric test, bottom). Values above the dashed line are statistically significant. (C-D) Co-regulation of the immune resistance program. (C) The overall expression of the induced (x axis) and repressed (y axis) parts of the immune resistance programs in each malignant cell (top, scRNA-seq data) and in cutaneous melanoma tumors (bottom, TCGA RNA-Seq data, after filtering tumor microenvironment signals). The Pearson correlation coefficient (r) and p-value are marked. (D) Gene-gene Pearson correlation coefficients (bar) between the genes in the resistance program, across individual malignant cells from the same tumor (top, average coefficient) or across cutaneous melanoma tumors from TCGA skin (bottom, after filtering tumor microenvironment effects). See also FIG. 52.
Figure 46D:
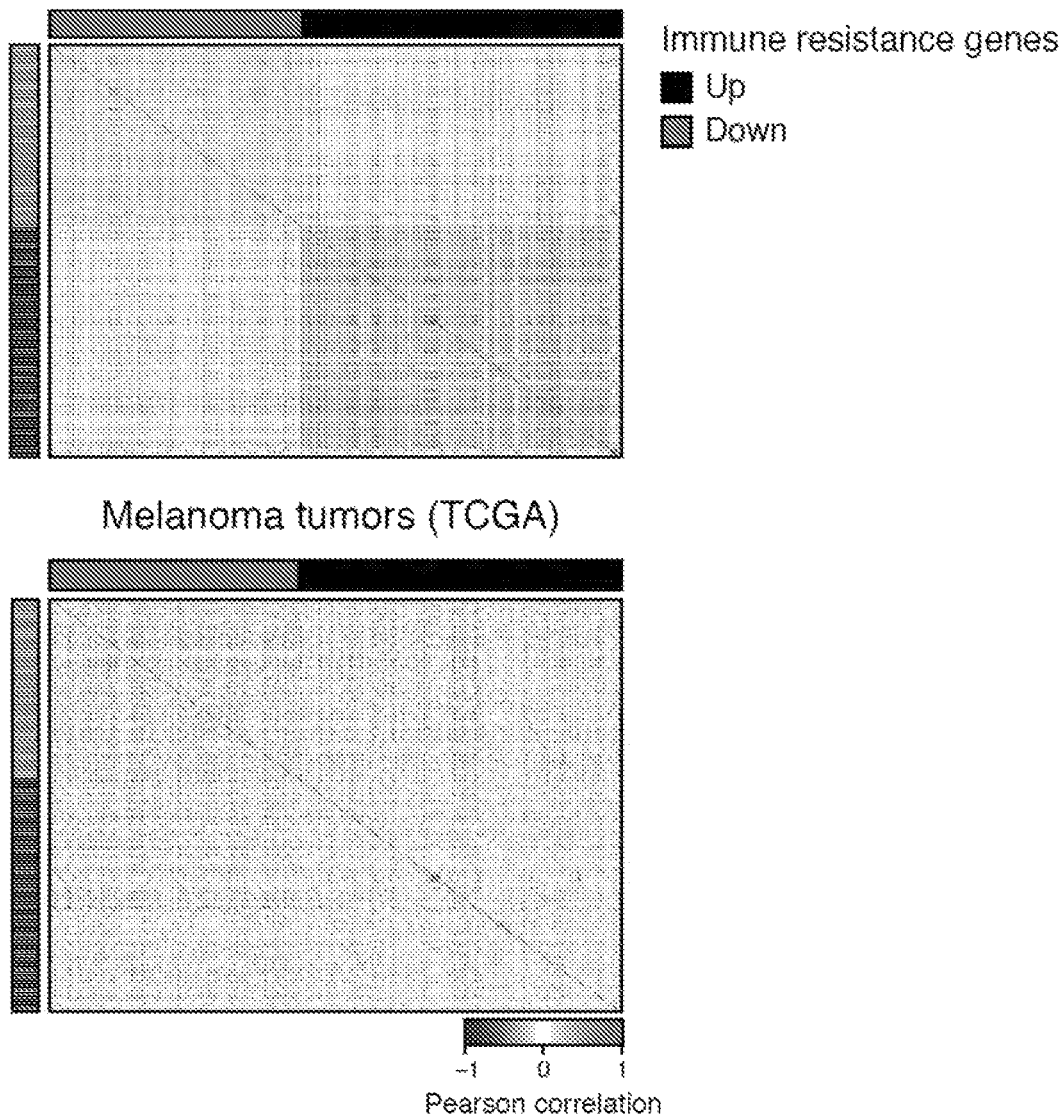

The program genes appear to be under shared control by one or a few master regulators, with opposing effects on the repressed and induced components of the program. There was a strong positive correlation within the induced or repressed genes, and a strong anti-correlation between the induced and repressed genes, both across single cells in the same tumor and across TCGA tumors (FIGS. 46C,D). The co-variation patterns were remarkably reproducible within each one of the tumors in the cohort (FIG. 52), such that any given aspect of the program (e.g., under-expression of MHC-1 genes in a cell) is coupled to the state of the entire program. Moreover, there is a significant overlap between the perturbations that reverse the expression of the program's repressed and induced components (p-value=2.33*10$^{-14}$, hypergeometric test), including the overexpression of IFN-γ and IFN-β and the knockdown of MYC (Subramanian et al., 2017). Indeed, MYC knockdown is among the top perturbation to repress the program, which is enriched for Myc targets.

Expression of Resistance Program Features in Malignant Cells in T Cell-Depleted Niches In Situ If the immune resistance program in malignant cells is associated with T cell exclusion, malignant and T cells should vary in their relative spatial distribution in tumors depending on the activity of the program. To explore this, Applicants used multiplexed immunofluorescence (t-CyCIF) (Lin et al., 2017) to stain histological sections of 19 tumors from the single-cell cohort for 14 proteins: six cell type markers (CD3, CD8, MHC-II, FOXP3, S100, and MITF) and eight members of the immune resistance program (induced: p53, CEP170, Myc, DLL3; repressed: HLA-A, c-Jun, SQSTM1, LAMP2). Following cell segmentation and estimation of antibody staining intensities (Methods), Applicants assigned cells (424,000 cells/image on average) into malignant cells (S100$^+$, MITF$^+$), T cells (CD3$^+$) and cytotoxic T cells (CD8$^+$); the rest were defined as uncharacterized.

To explore the association between the program markers and the "cold" phenotype, Applicants first generated a Delaunay neighborhood graph for each image (linking cells that are immediate neighbors) and computed the observed frequency of cell-to-cell interaction compared to that expected by chance, as recently described (Goltsev et al., 2017). Malignant cells were significantly more likely to reside next to other malignant cells, and significantly less likely to reside next to T cells (P<1*10$^{-16}$, binomial test, Methods). Next, for each frame in the imaged section (1,377 cells/frame on average; Methods), Applicants computed the fraction of T cells and the average expression of the different markers in the malignant cells. Applicants then quantified the association between expression of the immune resistance program markers and T cell infiltration levels across frames from the different images (Methods). Confirming this analysis approach, malignant cells in highly infiltrated niches had significantly higher levels of HLA-A (FIG. 47A, P=2.61*10$^{-46}$, mixed-effects). Moreover, in line with the predictions, malignant cells in cold/hot niches had significantly lower/higher levels of c-Jun (repressed in the resistance program) (FIG. 47B, P=2.85*10$^{-12}$, mixed-effects), whereas p53, induced in the resistance program) characterized cold niches (P=6.16*10$^{-7}$, mixed-effects). Applicants do note, however, that LAMP2 expression (repressed in the resistance program) was also associated with cold niches, potentially due to its post-transcriptional regulation (Feng et al., 2015).

Figure 47C:
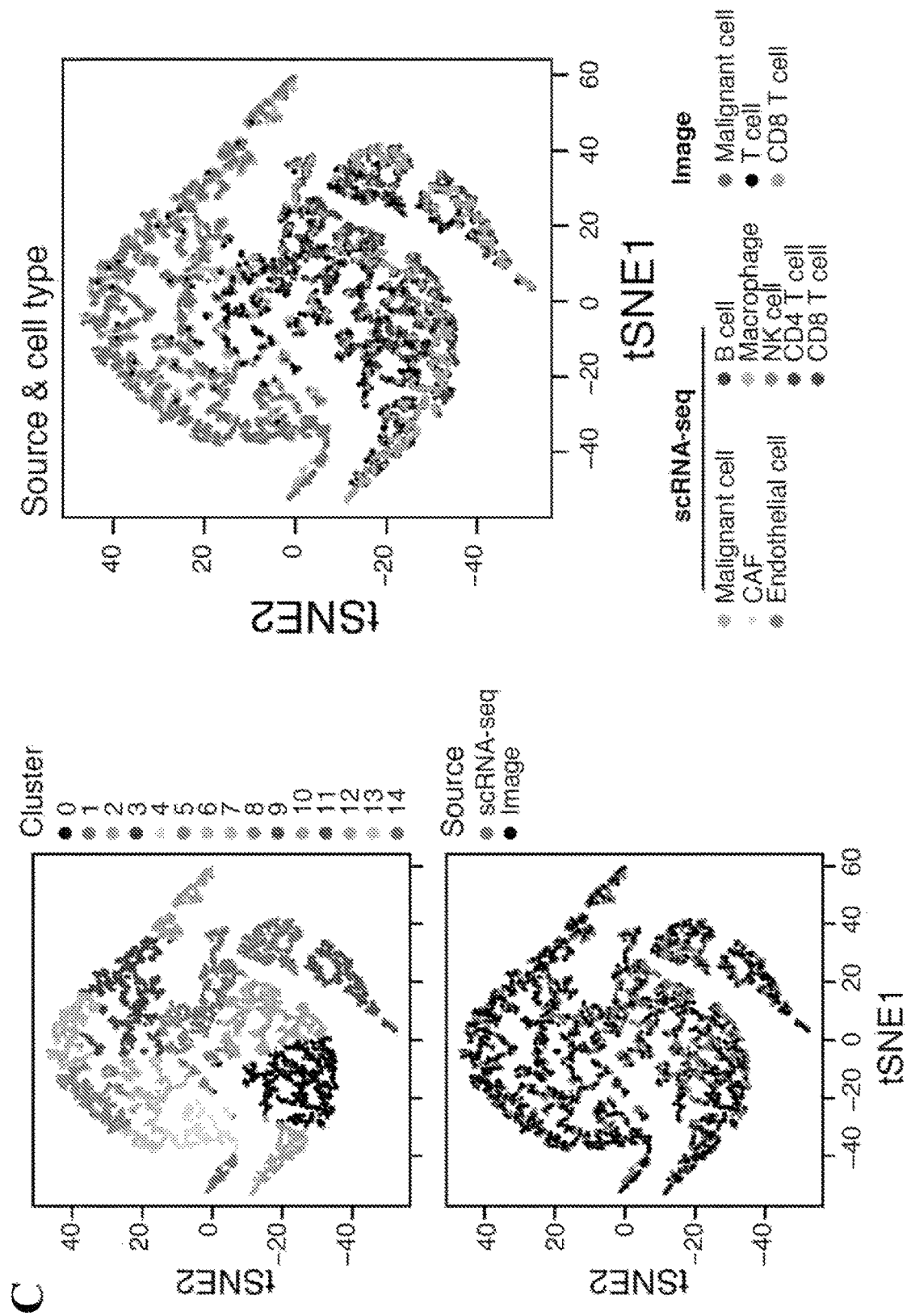
FIG. 47. The resistance program is associated with the cold niche in situ. (A B) Multiplex imaging relates resistance program genes to hot or cold niches. Malignant cells expressing high or low/moderate protein levels of HLA-A (A) and c-Jun (B) and their proximity to $CD3^+$ T cells (blue) or $CD3^+CD8^+$ T cells (cyan) in three representative tumors. (C) Congruence of multiplex protein and scRNA-seq profiles. Left and middle: tSNE plots of co-embedding of cells from the scRNA-seq data and the images of a specific tumor (Mel112; others shown in FIG. 53), with cells shaded by clusters (top left), data source (bottom left), and source and cell type (right). (D) Right: Log-odds ratio (bar, Methods) assessing for each pair of cell types (rows, columns) if they are assigned to the same cluster significantly more (>0) or less (<0) than expected by chance. See also FIG. 53.
Figure 47D:
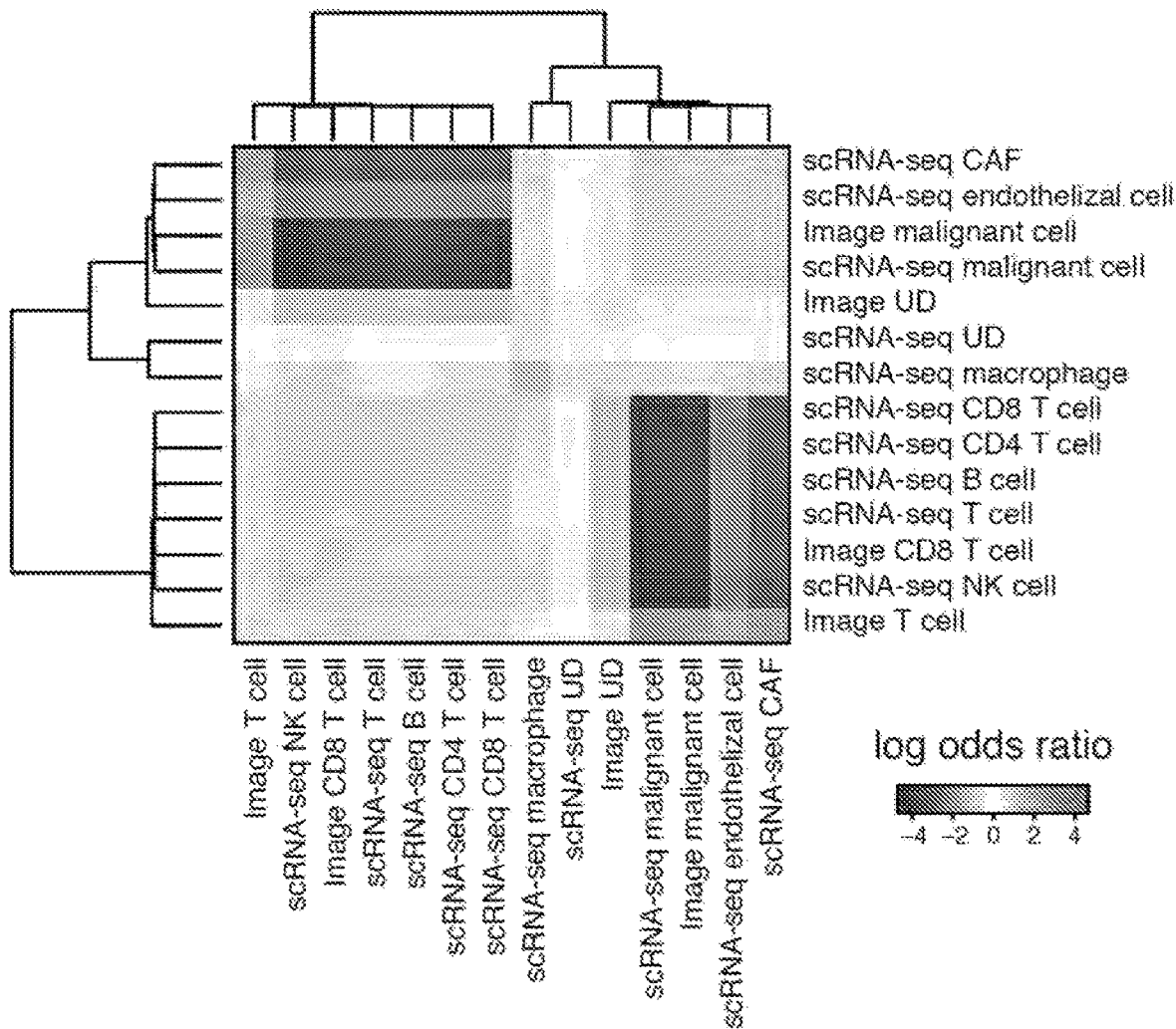

Finally, since only a few markers were analyzed in situ, Applicants tested whether scRNA-seq and multiplex in situ protein profiles can be combined to jointly learn cell states, using a variant of canonical correlation analysis (CCA) (Butler and Satija, 2017) (Methods). The cells were primarily embedded and clustered based on their cell types, and not according to source, confirming the congruence of the two datasets, and that the markers tested can link global transcriptional cell states to spatial organization in tissue (FIGS. 47C,D and 53). Taken together, these results support the association between the expression of the immune resistance program and the cold phenotype.

Figure 45C:
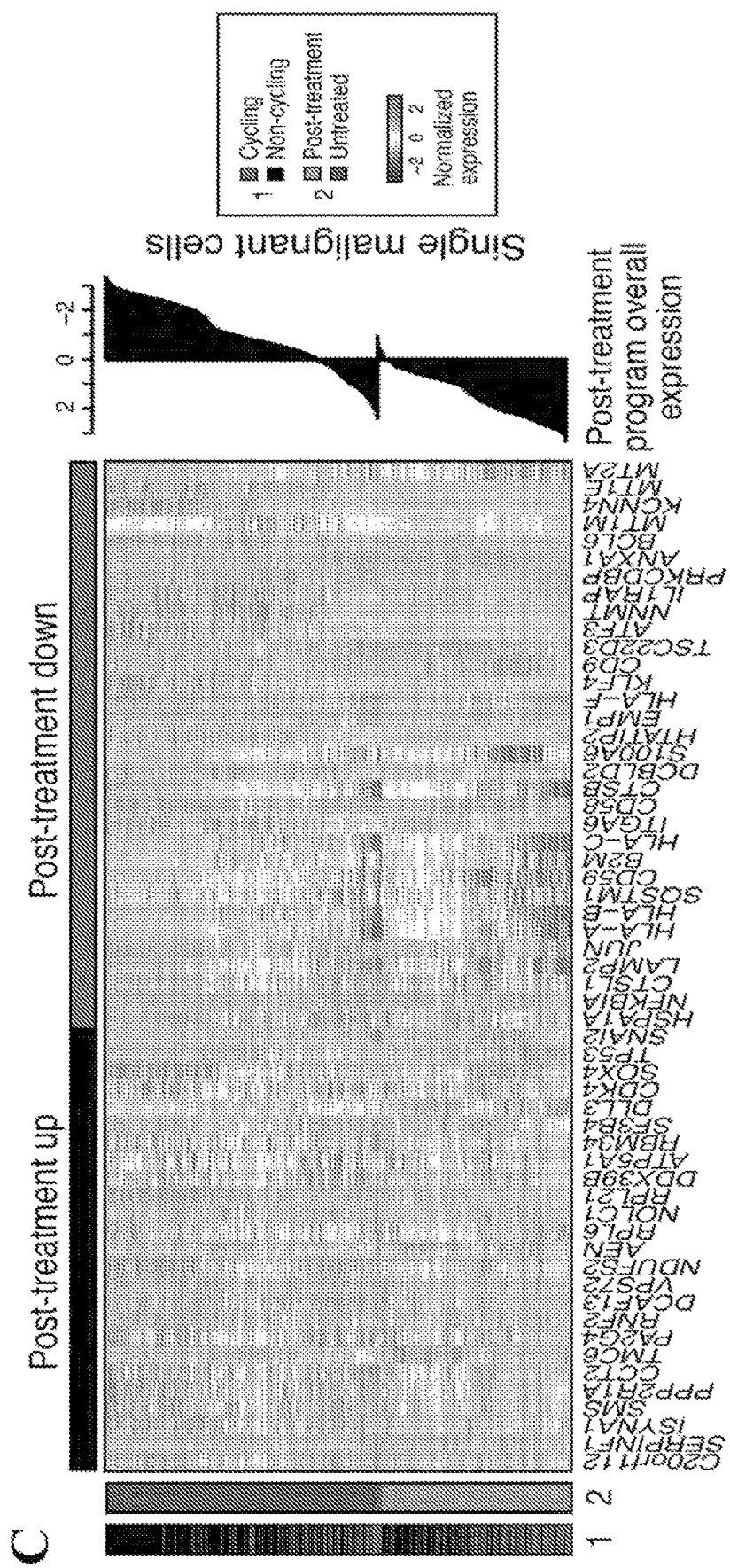
FIG. 45. Exclusion and resistance programs characterizing individual malignant cells from patients who failed immunotherapy. (A) Post-treatment program in malignant cells. Left: The Overall expression (Methods) of the post-treatment program in malignant cells from post-treatment (blue) and untreated (grey) patients, when obtained in a cross-validation (CV) procedure and tested on withheld data. Middle line: median; box edges: $25^{th}$ and $75^{th}$ percentiles, whiskers: most extreme points that do not exceed $\pm IQR*1.5$; further outliers are marked individually. Right: Receiver Operating Characteristic (ROC) curve of the performances of different programs in classifying cells as post-treatment or untreated; the CV post-treatment signature was obtained by leave-one (patient) out CV; the first and second Area Under the Curve (AUC) values are for classification of cells and samples, respectively. (B) Significant overlap between the exclusion and post-treatment programs. Venn diagram of the number of genes in each program and in their overlap. P-value: hypergeometric test. (C) Program genes. Expression (centered and scaled, bar) of the top genes (columns) in the post treatment program across the malignant cells (rows), sorted by untreated or post-treatment tumors (bar, left) and clustered within each class. Leftmost bar: cycling and non-cycling cells within each group. Right: overall expression of the post-treatment program in each cell. (D) Repressed and induced processes. The distribution of overall expression scores of differentially expressed gene sets in malignant cells from post-treatment (blue) and untreated (gray) tumors (formatted as in (A)). (E) The exclusion program is higher in post-treatment malignant cells. The distribution of overall expression scores of the exclusion program in malignant cells from post-treatment (blue) and untreated (gray) tumors. See also Tables S6 and S9.

The Immune Resistance Program is Intrinsic in Melanoma Cells Prior to Treatment and is Enhanced Specifically Post-Immunotherapy Applicants hypothesized that the immune resistance program, while more pronounced in the malignant cell of patients after ICI, in fact reflects an intrinsic resistance mechanism, present even before immunotherapy. First, the program is detected in TCGA tumors, which were all untreated. Second, while the program is more predominant in the malignant cells of the post-treatment resistant patients, it is also overexpressed in a subset of the malignant cells from untreated patients (FIGS. 44E and 45C, right plots). This is aligned with clinical observations that intrinsic ICI resistance is more prevalent than acquired ICI resistance (Sharma et al., 2017). However, because the scRNA-seq cohort did not include matched samples from the same patient or pre-treatment tumors from subsequent responders vs. non-responders, Applicants could not directly distinguish intrinsic resistance from post treatment effects.

To test this hypothesis, Applicants therefore analyzed an independent cohort of 90 specimens collected from 26 patients with metastatic melanoma who underwent ICI therapy, with bulk RNA-Seq from biopsies collected pre-treatment (n=29), on-treatment (n=35), and at the time of progression (n=26) (FIG. 44A, validation cohort 1). Applicants tested for changes in the program score during the course of treatment, while accounting for tumor composition (Methods). The program was induced in on- and post-treatment samples compared to pre-treatment samples from the same patient (P=1.36*10$^{-4}$ and 4.98*10$^{-2}$, immune resistance program, refined and non-refined, respectively, mixed-effect test, Methods), consistent with its overexpression in individual post-ICI malignant cells in the unmatched single-cell cohort (FIGS. 44E and 45C). However, inter patient variation in the program's expression was significantly higher than these intra-patient changes (P<10$^{-8}$, ANOVA). This suggested that the major differences between the post-treatment and untreated tumors in the single-cell cohort reflect, at least in part, intrinsic differences between the two groups, which preceded the treatment, which Applicants turned to assess in a second validation cohort (below). Notably, Applicants did not observe an induction in the program following RAF/MEK-inhibition, indicating that the immune resistance state it defines is specific to ICI therapy and not merely a generic marker of any drug resistant tumor.

The Immune Resistance Program Predicts Patient Survival and Clinical Responses to ICI The association of the program with T cell infiltration, its functional enrichment with immune evasion and exclusion mechanisms, its intrinsic expression in some malignant cells prior to treatment, and its further induction in post-ICI resistant lesions could make it a compelling biomarker for response to immunotherapy. To test this hypothesis, Applicants examined the program in multiple independent cohorts. Applicants used both the full program and one refined to the subset of genes that are co-regulated (positively) or anti-regulated (negatively) with genes whose inhibition desensitized melanoma cells to T cell mediated killing in functional screens (Patel et al., 2017) (Table S6, Methods) (The exclusion and post treatment programs show similar signals and trends; FIGS. 48E-H and 54-55).

The underexpression of the program was strongly associated with improved survival in 473 TCGA melanoma patients (who did not receive ICI immunotherapy, FIGS. 48A and 54), even after controlling for tumor purity and inferred T cell infiltration (Azimi et al., 2012; Bogunovic et al., 2009). Furthermore, combining the program with inferred T cell infiltration levels yielded significantly more accurate predictions of patient survival than either alone (COX p-value=$1.4*10^{-8}$, FIG. 48A, right). Other proposed mechanisms, such as de differentiation of melanoma cells (Landsberg et al., 2012), as reflected by an MITF-low signature, and other malignant cell signatures (e.g., cell cycle or the AXL program) (Tirosh et al., 2016a), did not show an association with patient survival, indicating that mere biological variation across malignant cells is insufficient as a prognostic signature.

The program expression in published pre-treatment and early on-treatment bulk expression profiles also distinguished eventual ICI responders from non-responders in those studies (FIGS. 48B,C). In a lung cancer mouse model, the program expression in early on-treatment profiles clearly separated anti-CTLA-4 responders from non-responders (P=$3.6*10^{-7}$, one-sided t-test, FIG. 48B) (Lesterhuis et al., 2015). In bulk pre-treatment RNA-Seq data from 27 melanoma patients that were subsequently treated with Pembrolizumab (anti-PD-1) (Hugo et al., 2016), the program was underexpressed in the five complete responders, though just above statistical significance (P=$6.3*10^{-2}$, one-sided t-test, FIG. 48C). In bulk pre treatment RNA-Seq data from 42 melanoma patients that were subsequently treated with the CTLA-4 inhibitor ipilimumab (Van Allen et al., 2015), the program was significantly lower in the two complete responders (P=$5.2*10^{-3}$, one-sided t-test).

To test the predictive value of the program in a larger independent setting, Applicants assembled a validation cohort of 112 patients with metastatic melanoma who underwent a pre-treatment biopsy and bulk RNA-Seq followed by Pembrolizumab (anti-PD-1) therapy (FIG. 44A, validation cohort 2, Table Si). The cohort was collected in a different hospital and country (Germany; Methods), and samples were processed and sequenced on the same platform (Methods). Applicants evaluated the program's performance in predicting anti-PD-1 responses as reflected by: (1) progression-free survival (PFS, recorded for 104 of the 112 patients), (2) clinical benefit (CB, defined as either partial or complete response by RECIST criteria), and (3) complete response (CR) (Methods). Applicants also compared the performance of the predictors to those of 32 other signatures, including the top hits of two functional CRISPR screens of resistance to T cells and ICI (Manguso et al., 2017; Patel et al., 2017) (Table S10, Methods).

Figure 48D:
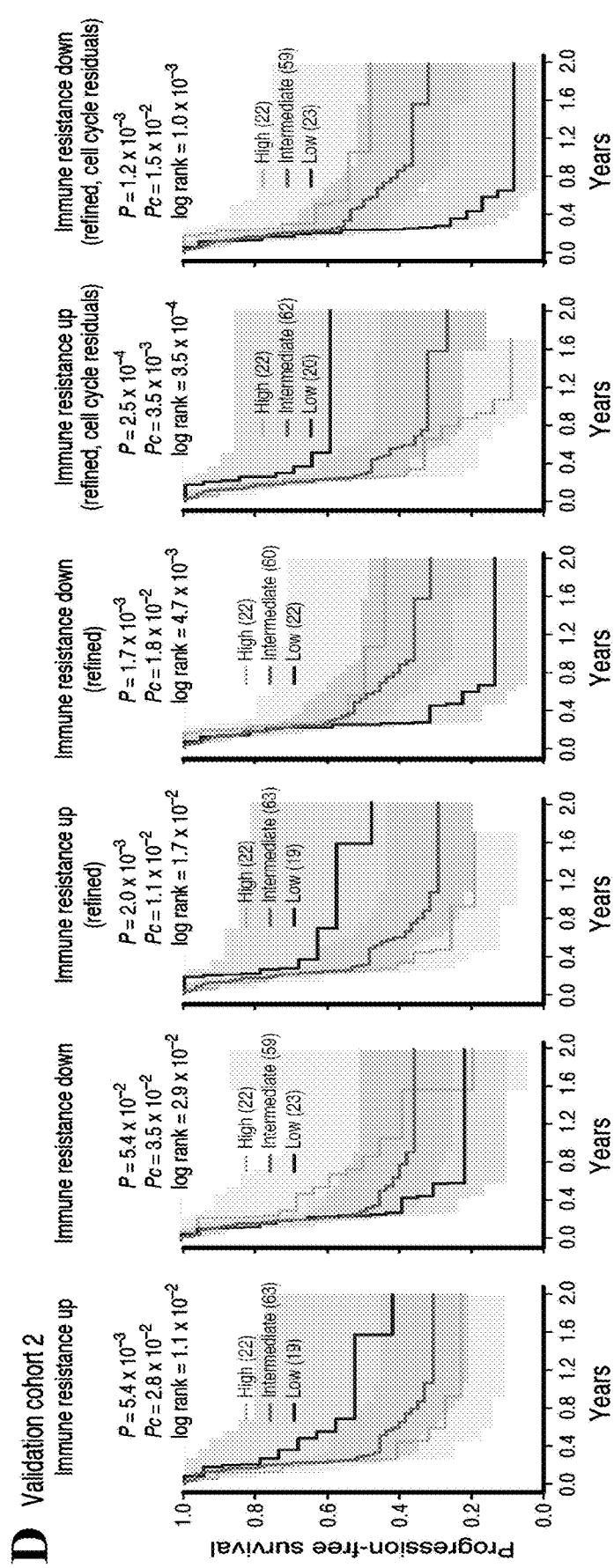
FIG. 48. The resistance program is prognostic and predictive in validation cohorts. (A) The program predicts melanoma patient survival based on bulk RNA-Seq from TCGA (Akbani et al., 2015). Kaplan-Meier (KM) plots stratified by high (top 25%), low (bottom 25%), or intermediate (remainder) expression of the respective program subset. P: COX regression p-value; Pc: COX regression p-value that tests if the program further enhances the predictive power of a model with inferred T cell infiltration levels as a covariate. (B, C) Resistance signatures distinguish responders and non-responders in mouse models and melanoma patients. The distribution of overall expression of the resistance program in bulk RNA-Seq from (B) a lung cancer mouse model treated with anti-CTLA-4 therapy (Lesterhuis et al., 2015) or (C) biopsies of melanoma patients collected prior to treatment with pembrolizumab (Hugo et al., 2016). Middle line: median; box edges: $25^{th}$ and $75^{th}$ percentiles, whiskers: most extreme points that do not exceed ±IQR*1.5; further outliers are marked individually. (D-F) The program predicts melanoma patient outcomes following pembrolizumab treatment from pre-treatment RNA-Seq in an independent cohort of 112 patients. (D) KM plots of progression-free survival (PFS) for the 104 patients in the cohort with available PFS data, stratified by high (top 25%), low (bottom 25%), or intermediate (remainder) expression of the respective program subset. (E) Predictive value for PFS ($-\log_{10}$(p-value), x axis, COX regression model that accounts for inferred T cell infiltration levels) for the 104 patients in (D). Blue/grey bars: positive/negative correlation between expression and PFS. Black border: subsets of the resistance program. Dashed line: p=0.05. (F) Overall expression of the resistance program (y axis) in the pre-treatment bulk RNA-Seq profiles of patients with intrinsic resistance (Non-CB, n=49) or clinical benefit (CB, n=39), latter further stratified by response duration (CB<6 mo, n=5; 6 mo<CB<1 year, n=9; CB>1 year, n=25). Twenty four patients with unknown response or stable disease are not shown here. P1 and P2: one-tailed t-test p-value when comparing the non-CB patients to the CB or to CB>1 yr patients, respectively. AUC for predicting CB>1 yr in all patients with a recorded response (n=101) is denoted. Box plots formatted as in (B). (G) Overall expression values of the resistance program (y axis) in the pre-treatment bulk RNA-Seq profiles of patients with complete response (CR, n=14), partial response (PR, n=25), or progressive disease (PD, n=49). P: one-tailed t-test p-value comparing CR patients to PR and PD patients. AUC for predicting CR in all patients with a recorded response (n=101). (H) Predictive value of different signatures for complete response ($-\log_{10}$(t-test p-value), x axis) in 101 patients with a recorded response. Blue/grey bars: expression associated with CR/non-CR, respectively. Black border: subsets of the resistance program. Dashed line: p=0.05. AUC values are marked next to the bar for each significant association. See also FIGS. 54, 55, 57 and Table S10.
Figure 48E:
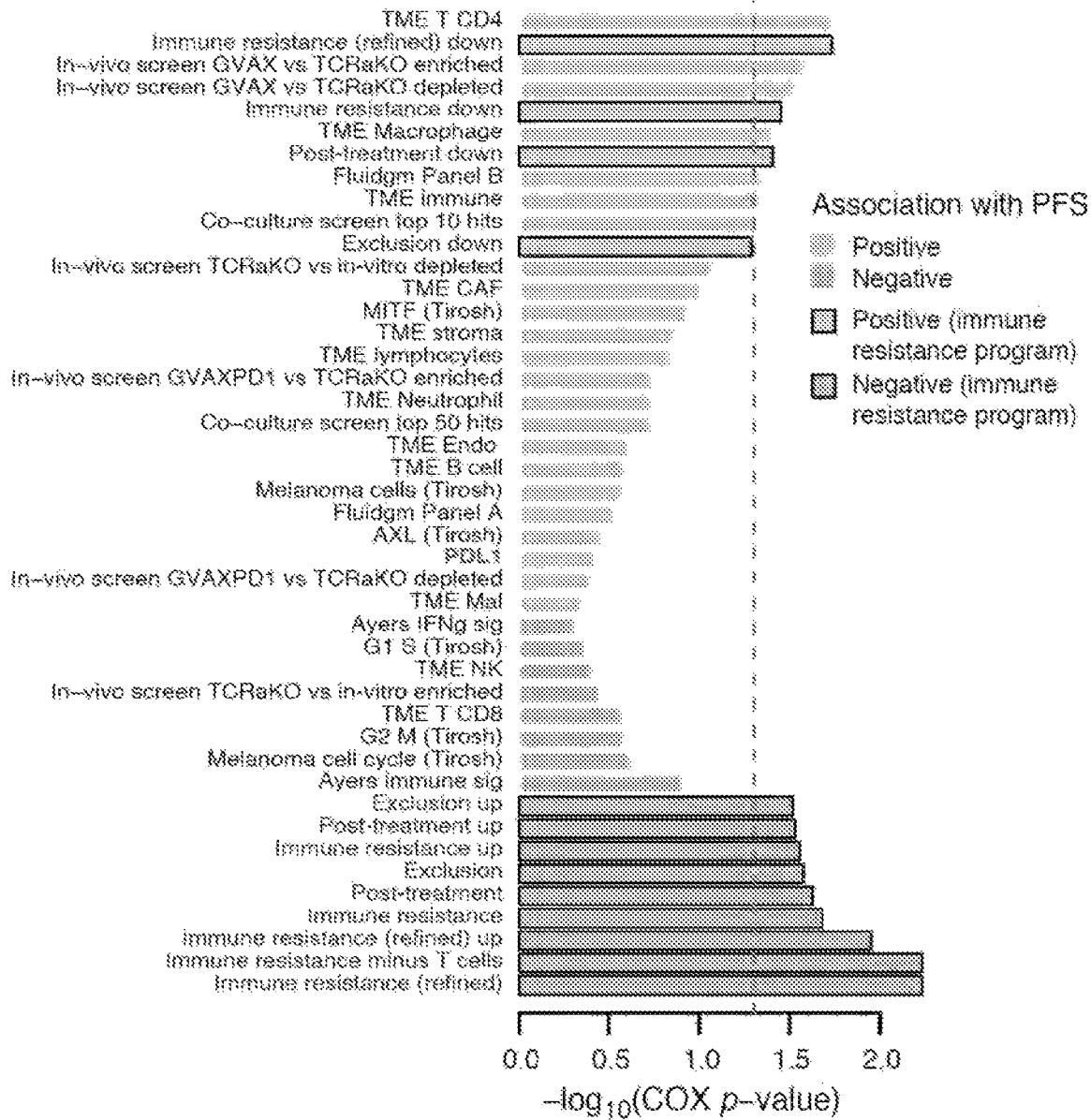
Figure 48H:
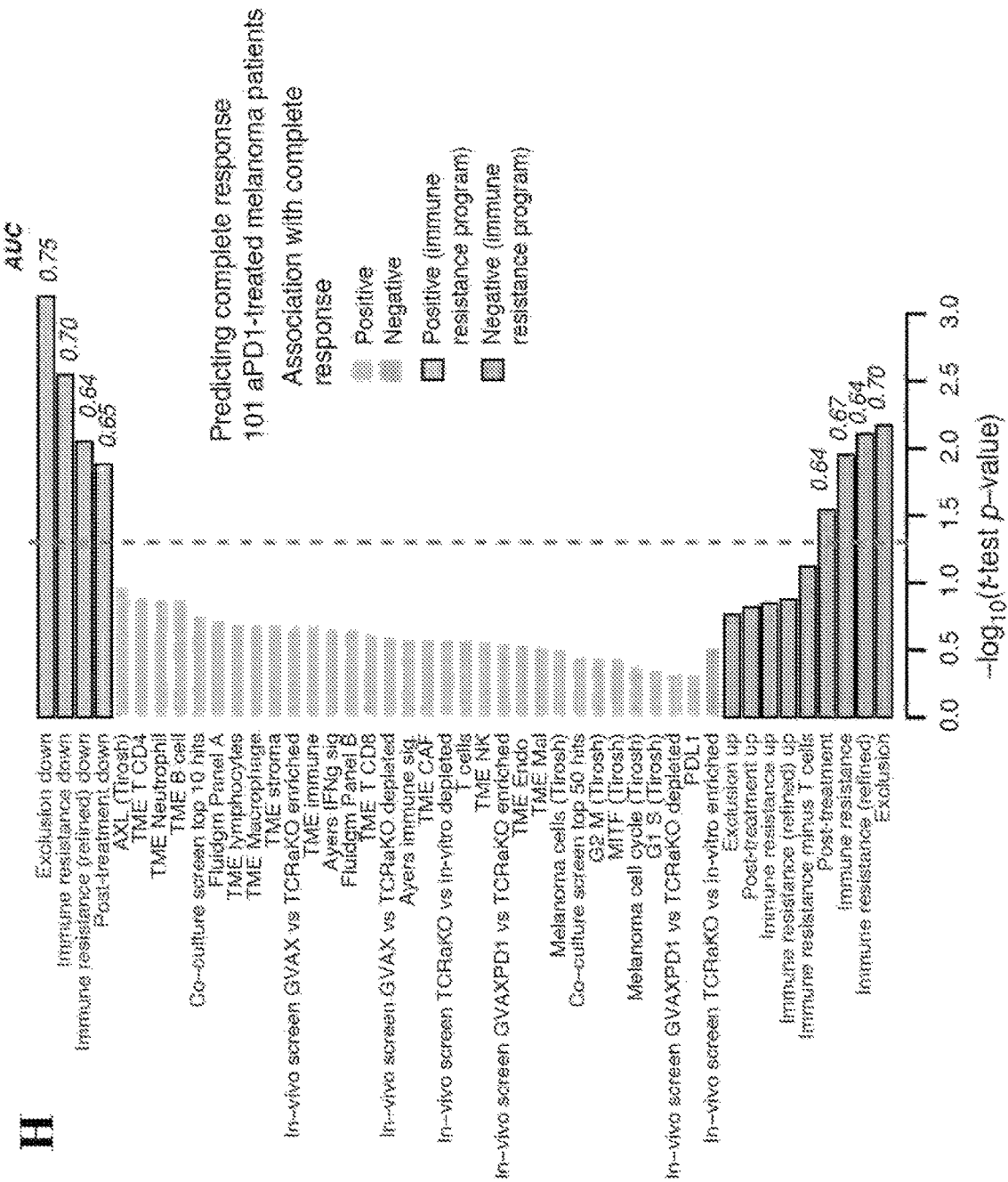

The programs were predictive of PFS in the validation cohort (FIGS. 48D and 55A-E), even when accounting for other known predictors of ICI response, including inferred T cell infiltration levels and PD-L1 expression (FIG. 55E). Although cell cycle alone is not associated with PFS (COX P>0.25), filtering the cell-cycle component from the program score (Methods, and below) further improved PFS predictions (FIG. 48D, right), suggesting that a tumor's immune resistance should be evaluated conditioning on its proliferation level. The program had a strong predictive value beyond T cell infiltration (P=$3.37*10^{-6}$, Wilcoxon-ranksum test), and was the only one negatively associated with PFS. Other alternative signatures were either not predictive or did not provide any additive predictive value once accounting for T cell infiltration levels (FIG. 48E).

The program was underexpressed in patients with clinical benefit (CB) compared to those without benefit (non-CB) (FIG. 48F). Nevertheless, some patients with clinical benefit had high pre-treatment expression of the program. Applicants hypothesized that these patients might cease to respond quickly, due to pre-existing intrinsically resistant cells, like those Applicants observed in the single-cell cohort and in validation cohort 1. Indeed, among patients with clinical benefit, those with high expression of the program pre-treatment were significantly more likely to experience subsequent progressive disease (FIG. 48F), and those with rapid progression (CB<6 months) had the highest scores of the program, even compared to those with no clinical benefit. Consistently, the program was most accurate in predicting patients with complete responses (P<$6.31*10^{-3}$, one-sided t-test, FIGS. 48G and 55F), outperforming all the other predictors (P=$1.64*10^{-8}$, Wilcoxon ranksum test), all of which, including clinically-used markers and inferred T cell infiltration levels, failed to predict complete response (FIG. 4811).

The Immune Resistance Program is Coherently Controlled by CDK4/6

Applicants reasoned that the program could be a compelling drug target: it was identified by its association with a critical process—T cell exclusion—that affects resistance to immunotherapy; it is a significantly predictive biomarker of ICI resistance; and it appears to be coherently regulated, such that a shared control mechanism could be targeted to reverse it.

To this end, Applicants identified drugs that were significantly more toxic to cell lines overexpressing the immune resistance program (controlling for cancer types, Methods), according to the efficacy measures of 131 drugs across 639 human cancer cell lines (Garnett et al., 2012). The top scoring drug was the CDK4/6-inhibitor palbociclib (P=$6.28*10^{-6}$, mixed-effects). Furthermore, the efficacy of CDK4/6 inhibition and the expression of the resistance program were also correlated in a study where the efficacies of CDK4/6 inhibitors palbociclib and abemaciclib were measured across a collection of cancer cell lines (P=$7.15*10^{-6}$, mixed-effects) (Gong et al., 2017).

Figure 56A:
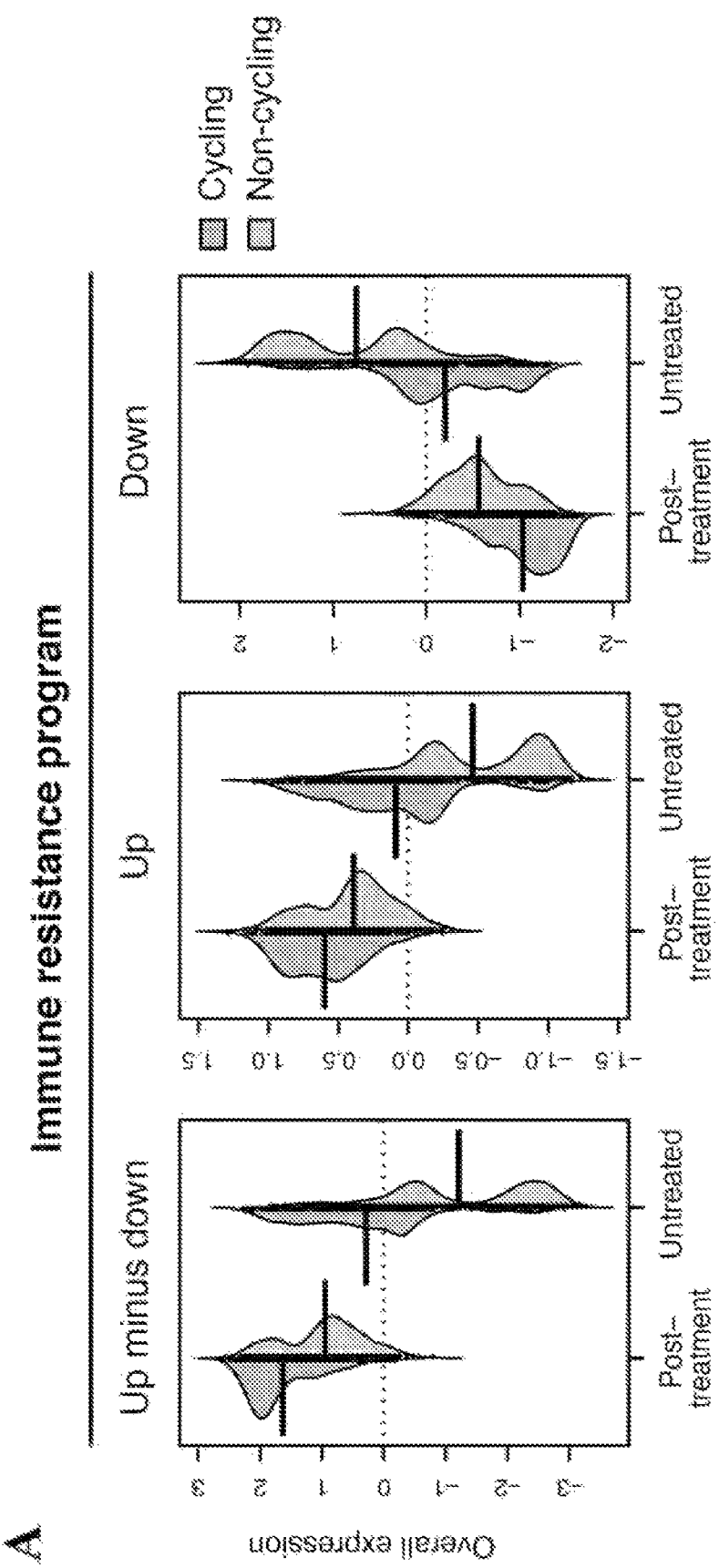
FIG. 56. Relationship between the resistance program and cell cycle; related to FIG. 49. (A, B) Higher expression of the resistance program in cycling cells. (A) Distribution of overall expression values of the resistance program (y axis) in cycling (grey) and non-cycling (blue) cells from either post-treatment or untreated tumors (x axis). Solid line: mean of the respective distribution; dashed line: mean across all malignant cells. (B) Expression of genes from the resistance program (rows) that are also differentially expressed in cycling vs. non-cycling malignant cells. Cells (columns) are sorted by untreated and post-treatment tumors and clustered within each set (bar on top); the cells' cycling status in each category is marked by the bar on top. (C) Abemaciclib represses the resistance program in breast cancer cell lines. The relative expression of all genes in the resistance program (rows) in abemaciclib-treated and control breast cancer cells lines (columns), based on the data in (Goel et al., 2017). Expression levels are relative to the basal expression level in each cell line. Bottom: overall expression (y axis) of the resistance program in each cell line (x axis).
Figure 56B:
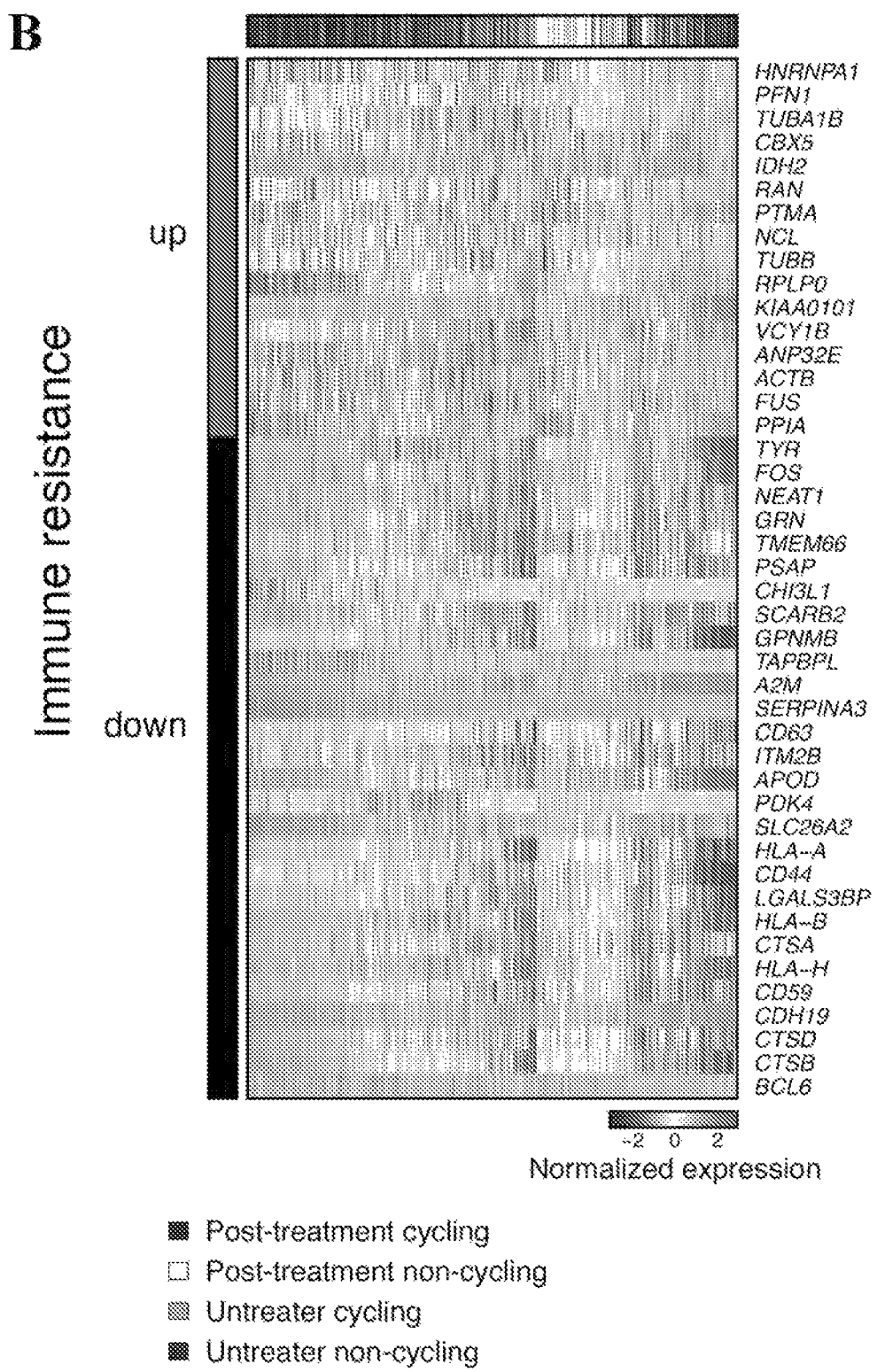
Figure 56C:
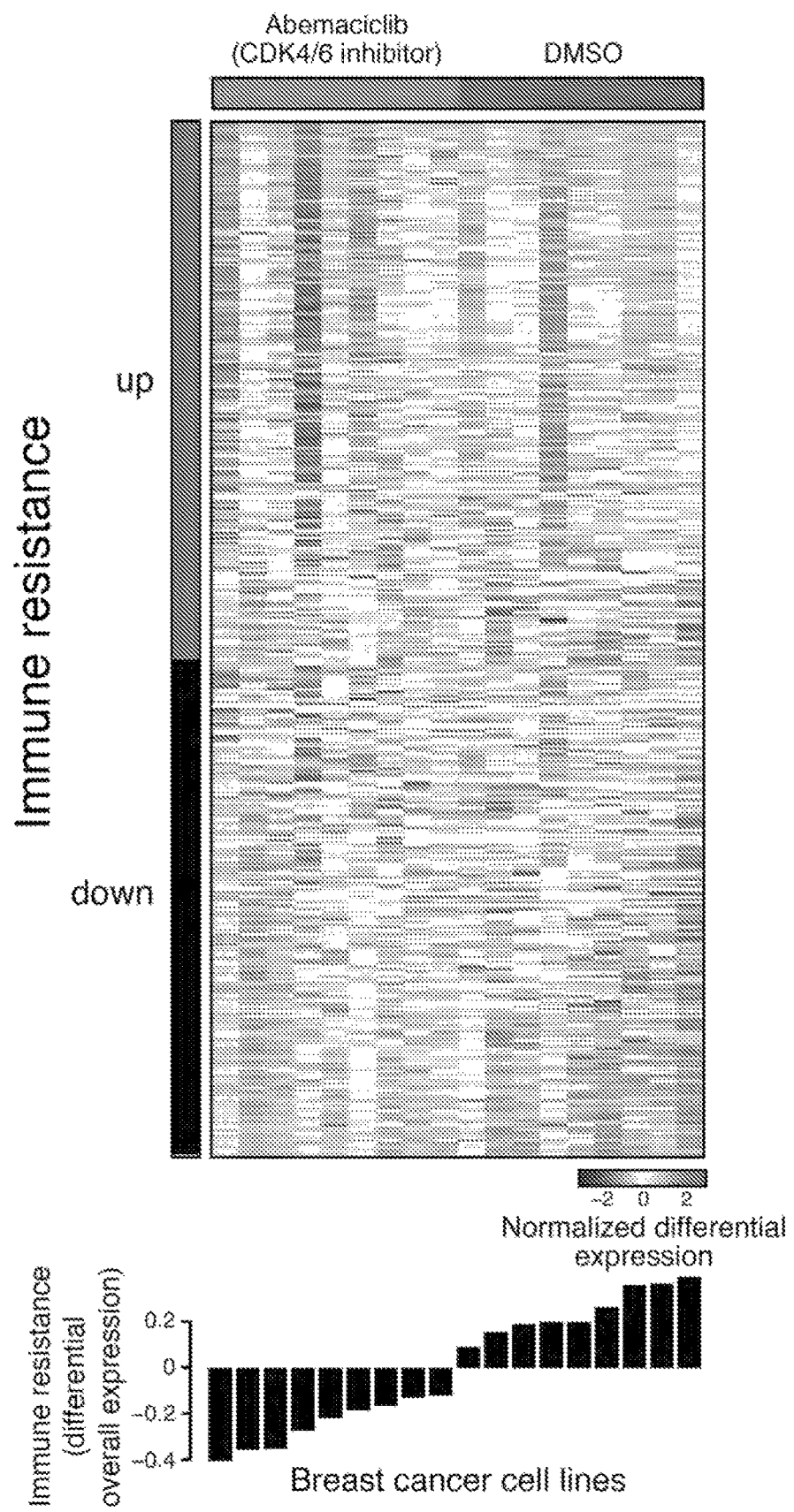

Applicants further hypothesized that CDK4 and 6 may act as the master regulators of the immune resistance program. First, both CDK4 itself and multiple CDK target genes, are members of the induced program (FIG. 45C, Table S6). Second, the program is more pronounced in cycling cells (where CDK4/6 are active), both within the same patient group and among cells of the same tumor (FIGS. 44E, 45C, and 56A,B, P<$10^{-16}$, mixed effects model). Importantly, the program is not merely a proxy of the cell's proliferation state: there was no significant difference between the fraction of cycling cells in untreated vs. post-treatment tumors (P=0.696, t-test), the program was nearly identical when identified only based on non-cycling cells, and —unlike the expression of the resistance program —the expression of cell cycle signatures was not associated with the efficacy of CDK4/6 inhibitors across the cell lines. Finally, Applicants analyzed recently published expression profiles (Goel et al., 2017) of breast cancer cell lines and in vivo mouse models and found that CDK4/6 inhibition by abemaciclib represses the program (FIGS. 49A-C and 56C). Thus, multiple lines of evidence suggest that CDK4/6 inhibition could repress the expression of the immune resistance program and shift the cancer cell population to a less immune resistant state.

CDK4/6 Inhibitors Repress the Immune Resistance Program in Malignant Melanoma Cells To test this hypothesis, Applicants studied the effect of abemaciclib on the immune resistance program in melanoma cell lines. Applicants selected three melanoma cell lines from the Cancer Cell Line Encyclopedia (Barretina et al., 2012) with a strong expression of the resistance program (Table S12), two of which are RB 1-sufficient (IGR37, UACC257) and one is RB1-deficient (A2058). Applicants profiled each cell line with scRNA-seq before and after treatment with abemaciclib for 1 week (FIGS. 49D-E), analyzing over 23,000 cells in these and follow-up conditions (below).

TABLE S12

The overall expression (OE) of the immune resistance signature across the CCLE melanoma cell lines.

| Melanoma cell line | Immune resistance OE |
|---|---|
| HMCB | 0.818 |
| LOXIMVI | 0.72 |
| UACC257 | 0.706 |
| CHL1 | 0.698 |
| IGR37 | 0.57 |
| MELHO | 0.522 |
| COLO741 | 0.5 |
| G361 | 0.476 |
| COLO679 | 0.468 |
| A2058 | 0.465 |
| SKMEL3 | 0.443 |
| GRM | 0.431 |
| SKMEL30 | 0.405 |
| MEWO | 0.371 |
| A375 | 0.368 |
| HS936T | 0.339 |
| K029AX | 0.308 |
| IPC298 | 0.261 |
| IGR1 | 0.243 |
| SKMEL1 | 0.238 |
| SKMEL5 | 0.182 |
| COLO783 | 0.174 |
| COLO849 | 0.082 |
| CJM | 0.06 |
| MELJUSO | 0.049 |
| COLO792 | 0.041 |
| UACC62 | 0.015 |
| MDAMB435S | 0.005 |
| IGR39 | 0 |
| WM2664 | −0.015 |
| WM88 | −0.045 |
| HS944T | −0.053 |
| RPMI7951 | −0.067 |
| WM983B | −0.09 |
| WM1799 | −0.091 |
| A101D | −0.097 |
| HS895T | −0.126 |
| SKMEL28 | −0.152 |
| SH4 | −0.226 |
| RVH421 | −0.227 |
| HT144 | −0.23 |
| SKMEL2 | −0.242 |
| COLO800 | −0.251 |
| HS294T | −0.264 |
| WM793 | −0.265 |
| HS852T | −0.341 |
| HS934T | −0.368 |
| COLO829 | −0.377 |
| HS839T | −0.386 |
| C32 | −0.427 |
| HS940T | −0.434 |
| HS688AT | −0.435 |
| HS939T | −0.464 |
| HS600T | −0.464 |
| COLO818 | −0.466 |
| HS695T | −0.5 |
| WM115 | −0.513 |
| MALME3M | −0.607 |
| SKMEL31 | −0.759 |
| SKMEL24 | −0.975 |

Figure 49C:
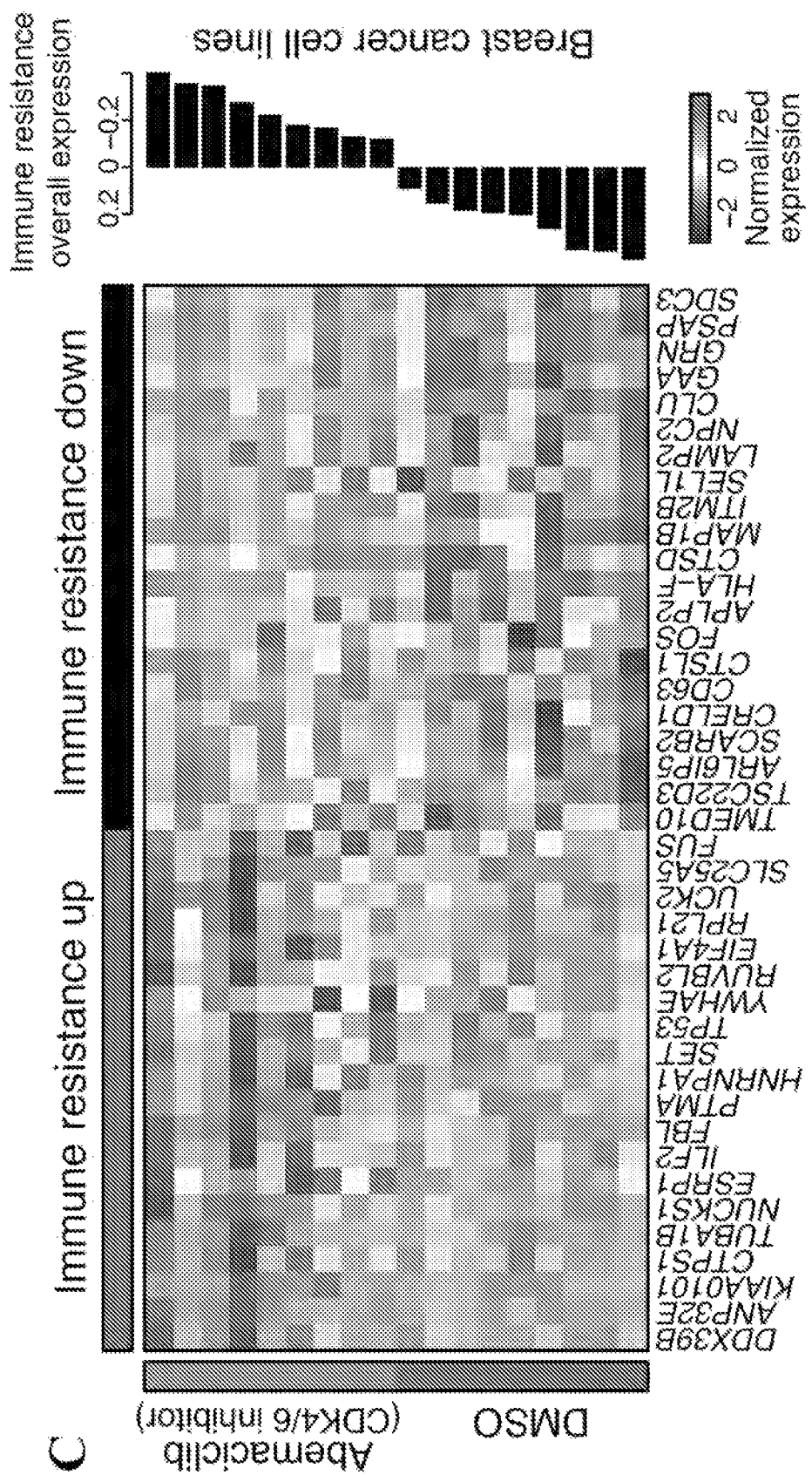
FIG. 49. The resistance program can be reversed by CDK4/6 inhibition. (A-C) Impact on breast cancer tumors and cell lines. (A) Significance (y axis, $-\log_{10}$(p-value), Wilcoxon rank sum test) of induction (dark green) or repression (light green) of the program subsets in breast cancer tumors from abemaciclib treated mice compared to vehicle (Goel et al., 2017). (B) Overall expression of the program in breast cancer cell lines (M361, MCF and M453) treated with abemaciclib ("abe") or with DMSO vehicle ("con"). Middle line: median; box edges: $25^{th}$ and $75^{th}$ percentiles, whiskers: most extreme points that do not exceed ±IQR*1.5; further outliers are marked individually. P-value: paired t-test. (C) Expression of 40 program genes (columns; shaded bar) that were most differentially expressed in abemaciclib-treated vs. control breast cancer cells lines (rows). Expression is normalized to each cell line's control. Right: overall expression values of the program for each cell line. (D G) CDK4/6 inhibition reverses the program in melanoma cell lines and induces the SASP. (D,E) tSNE plots of 4,024 IGR137 (D) and 7,340 UACC257 (E) melanoma cells, shaded by (left to right): treatment, clusters, or the expression of a cell cycle signature, resistance program, MITF signature, SASP signature and DNMT1. (F) Concentration (pg/ml, y axis) of secreted chemokines in the supernatant of melanoma cells treated for 7 days with abemaciclib (500 nM) or with DMSO control. P<0.01, *P<0.001 t-test. (G) Senescence associated alpha-galactosidase activity (green) and morphological alterations in melanoma cells treated for 10 days with abemaciclib (500 nM, right) vs. DMSO control (left). See also FIG. 56 and Table S12.
Figure 49D:
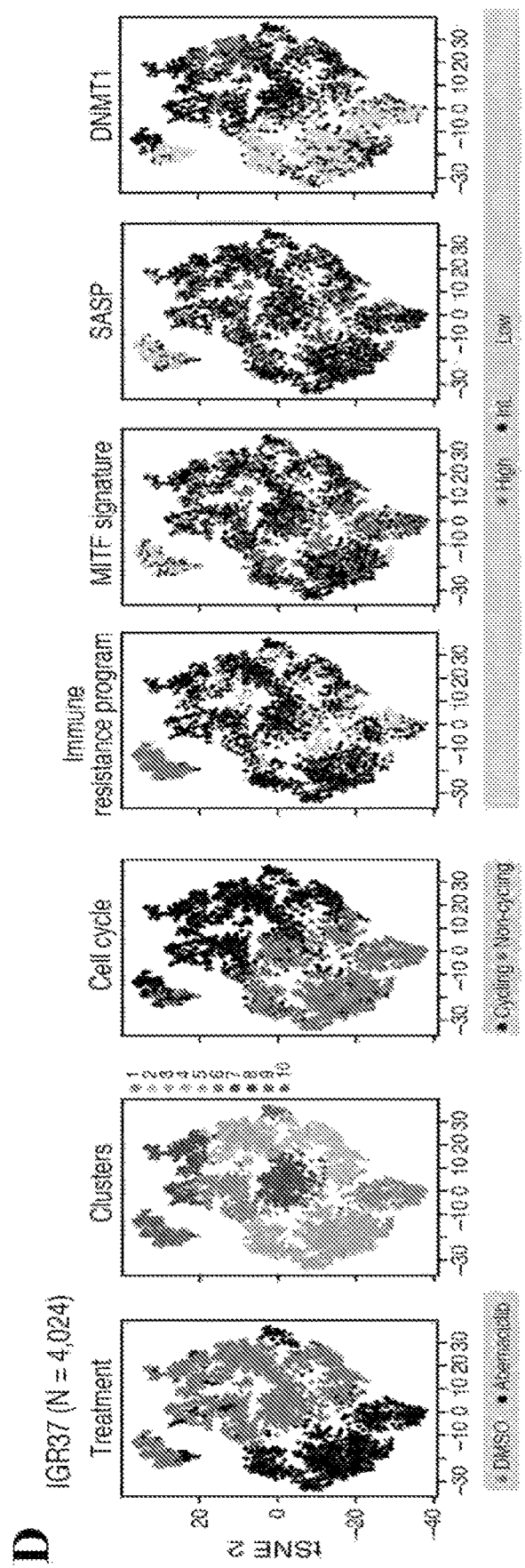

Consistent with the hypothesis, only in the RB-sufficient cell lines, abemaciclib dramatically decreased the proportion of cells overexpressing the immune resistance program and induced an immune response in the surviving cells. In the RB 1-sufficient lines, IGR37 and UACC257, 10% of the cells had exceptionally strong expression of the immune resistance program ("immune resistant" cells) prior to treatment, decreasing to 2% and 1% of cells post treatment, respectively ($P<1*10^{-30}$, hypergeometric test) (FIGS. 49D, E). In contrast, in the RB 1-deficient line A2058 the treatment did not repress the immune resistant state ($P>0.5$, one-sided t-test), consistent with the hypothesis that CDK4/6 inhibitors depend on RB1-sufficiency.

Moreover, in the two RB-sufficient lines, the remaining cells that underexpressed the immune resistance program, underwent substantial transcriptional changes, including the induction of key repressed component of the immune resistance program, such as the SASP. In particular, abemaciclib repressed the expression of DNMT1 ($P<2.23*10^{-106}$ likelihood-ratio test), consistent with previous observations (Goel et al., 2017) that CDK4/6 inhibition leads to DNMT1 repression, allowing the methylation of endogenous retroviral genes (ERVs), which in turn triggers a double-stranded RNA (dsRNA) response and stimulates type III IFN production (Goel et al., 2017). Following abemaciclib treatment there was also a higher portion of cells with increased expression of a MITF program (Tirosh et al., 2016a), which is repressed in "immune resistant" cells ($P<3.33*10^{-15}$, hypergeometric test, FIG. 49D,E).

In particular, abemaciclib induced SASP, which is a major repressed component in the resistance program. First, the SASP module was significantly induced at the transcriptional level ($P<3.91*10^{-12}$, hypergeometric test, FIGS. 49D, E). Moreover, when Applicants measured 40 human cytokines and chemokines in the conditioned media of abemaciclib treated cancer cells, Applicants found it induced several secreted factors (FIG. 49F), including macrophage inhibition factor (MIF), CX3 CL 1 (which induces migration and adhesion of T and NK cells and is linked to clinical outcomes in immunotherapy treatment (Herbst et al., 2014; Nelson and Muenchmeier, 2013)), and CCL20 (an important factor for T cell differentiation, which may enhance immunity in melanoma (Gordy et al., 2016)). Consistently, abemaciclib also induced alpha-galactosidase activity and morphological alterations that reflect cellular senescence (FIG. 49G). Thus, unlike the mechanism described in breast cancer cells (Goel et al., 2017), abemaciclib might trigger SASP and cell differentiation in malignant melanoma cells.

Finally, Applicants tested if the effect of abemaciclib treatment on malignant cells is impacted by the presence of tumor infiltrating lymphocytes (TILs) in a patient-derived co-culture model of melanoma cells and ex vivo expanded TILs from the same metastatic melanoma lesion. After treating the malignant cells with abemaciclib for one week, Applicants added autologous TILs to the cultures. Applicants compared scRNA-seq profiles between these melanoma cells and cells from similar co-cultures but without abemaciclib treatment, or from cultures with neither abemaciclib treatment nor TILs. Exposure to TILs reduced the expression of the immune resistance program, both in the control and in the abemaciclib-treated cells ($P<9.85*10^{-14}$, one-sided t-test). Abemaciclib further intensified these effects, as it further repressed the immune resistance program in both conditions (with and without the exposure to TILs, $P<3.60*10^{-7}$, one-sided t-test).

Discussion

Most melanoma patients have either intrinsic or acquired resistance to ICI, yet the systematic characterization of molecular resistance mechanisms has been limited. Here, Applicants leverage clinical scRNA-seq data and multiple cohorts to map malignant cell states associated with resistance to ICI, revealing a coherently co-regulated program that may be therapeutically targeted to overcome immune evasion and suppression.

The malignant cell resistance program showed prognostic and predictive power in several independent ICI cohorts, including a large new clinically annotated cohort of patients with pre-treatment (anti-PD-1) biopsies profiled by RNA-seq. The program outperformed other published biomarkers in the space, and may help to prospectively stratify patients to clinical trials and therapies. Even though the program was initially derived, in part, based on associations with inferred T cell infiltration levels, unlike many other biomarkers, it has a significant predictive value beyond T cell infiltration.

The program Applicants uncovered is primarily associated with intrinsic ICI resistance. It is manifested also in malignant cells of untreated patients in the single-cell cohort, and in bulk RNA-seq data from three independent cohorts of untreated patients: TCGA, a longitudinal cohort of ICI-treated patients (validation cohort 1), and a cohort of 112 pre-ICI patients (validation cohort 2). Among single cells of pre-treated patients, a subset (20.9% cells from 10 different patients) already overexpresses the program. In bulk samples collected before and after ICI, inter-patient variation exceeded intra-patient variation, further supporting an intrinsic role. In 112 melanoma patients, this pre-ICI inter-patient variation is tightly associated with ICI responses. Finally, the program is more pronounced after ICI failure, but not post targeted therapy, and thus it is unlikely to merely reflect the impact of any therapeutic intervention.

Some of the concepts established for drug resistance to targeted cancer therapies with RAF/MEK-inhibitors in melanoma may also be applicable to immunotherapies. Similar to the presence of a small sub-population of cells expressing a MITF-low program, which confers resistance to RAF/MEK-inhibitors, and rises in frequency under the pressure of a drug (Shaffer et al., 2017; Tirosh et al., 2016a, Hangauer et al., 2017; Viswanathan et al., 2017), patient tumors who have not been treated with ICI contain some cells expressing the immune resistance program. It is plausible that these cells are responsible for either intrinsic resistance to ICI or lie in protected niches, and thus emerge in the context of ICI resistance. Selective targeting of these cells in combination with ICI may delay or prevent ICI resistance.

Applicants have focused on malignant cells, but T cell states or clones, beyond their extent of infiltration, might also predict the success of ICI. Within the limitation of the unmatched single-cell cohort, comparing the individual T cells of untreated vs. post-treatment (resistant) patients, suggested that treatment has activated the T cells and caused their expansion (data not shown). While Applicants cannot rule out the presence of other intrinsic T cell dysfunction mechanisms, this is consistent with a model where, at least partly, malignant cells cause ICI resistance despite at least some T cell functionality.

Figure 50:
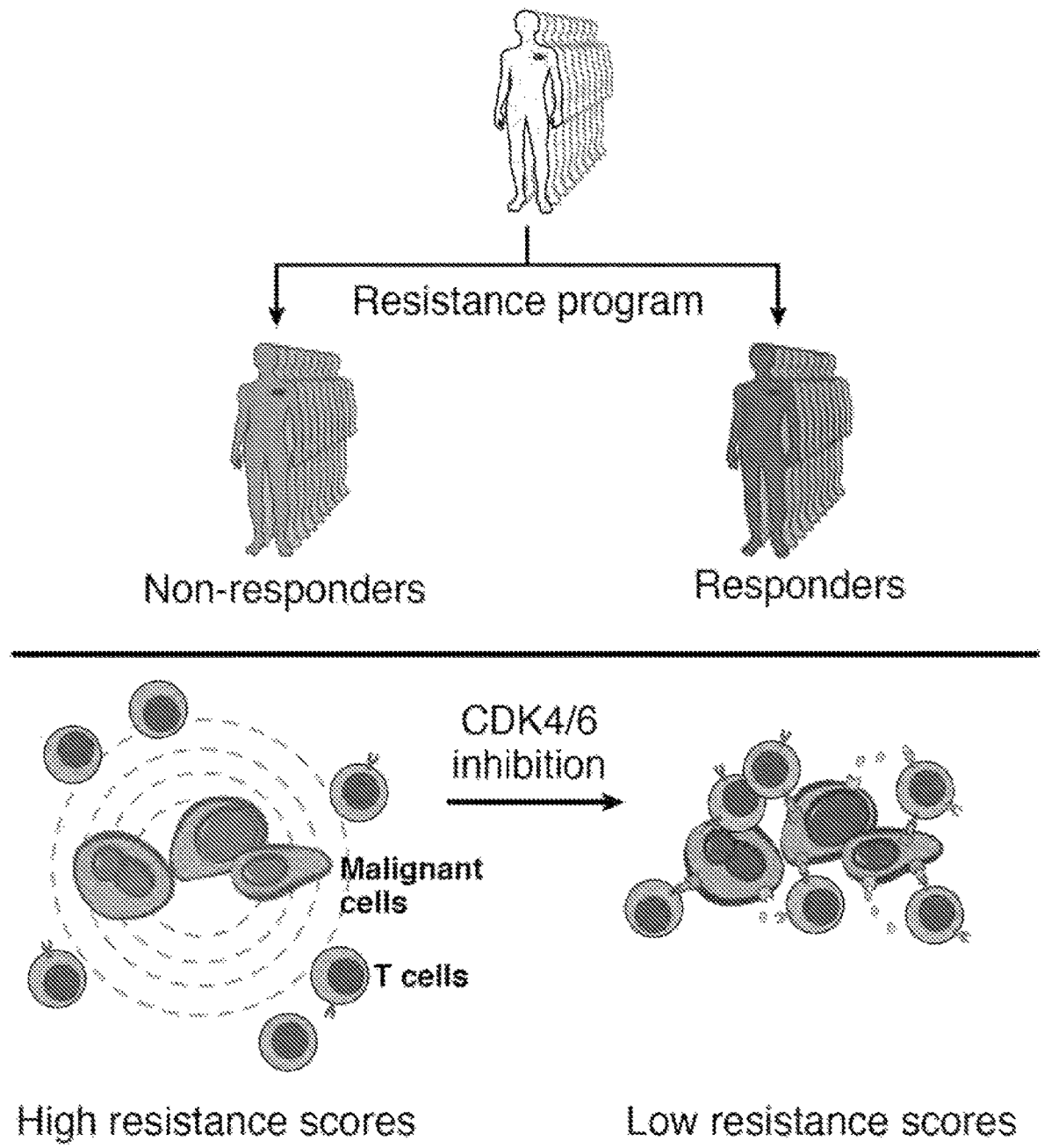
FIG. 50. Immune resistance model. Malignant cells that evade the immune system have a unique transcriptional state, which distinguishes between responders and non-responders to immunotherapy. This state is tightly linked to the exclusion of T cells from the tumor, the repression of SASP and cell-cell communication routes, and the inhibition of cytokine secretion. CDK4/6 inhibition can reverse this state in malignant cells.

Because of the potential functional role of the program and its coherent underlying regulation, compounds that repress it may sensitize malignant cells to immunotherapy and/or T-cell mediated killing (FIG. 50), especially in patients with a high intrinsic (pre-ICI) expression of the immune resistance program. Based on a systematic analysis of drug efficacies and the program features Applicants hypothesized that CDK4/6 inhibition could have such a sensitizing effect, and tested this in malignant melanoma cell lines and in co-cultures of patient cells with autologous TILs. CDK4/6 inhibition reversed the resistant transcriptional state: subpopulations of highly immune resistant cancer cells were dramatically reduced, either because the drug selectively eradicated them or because it triggered them to adopt a less immune resistant state. In parallel, CDK4/6 inhibition triggered the melanoma cells to adopt a senescent-like phenotype accompanied by secretion of key chemokines, which have been previously shown to enhance T cell responses (Gordy et al., 2016; Herbst et al., 2014; Nelson and Muenchmeier, 2013).

Figure 57A:
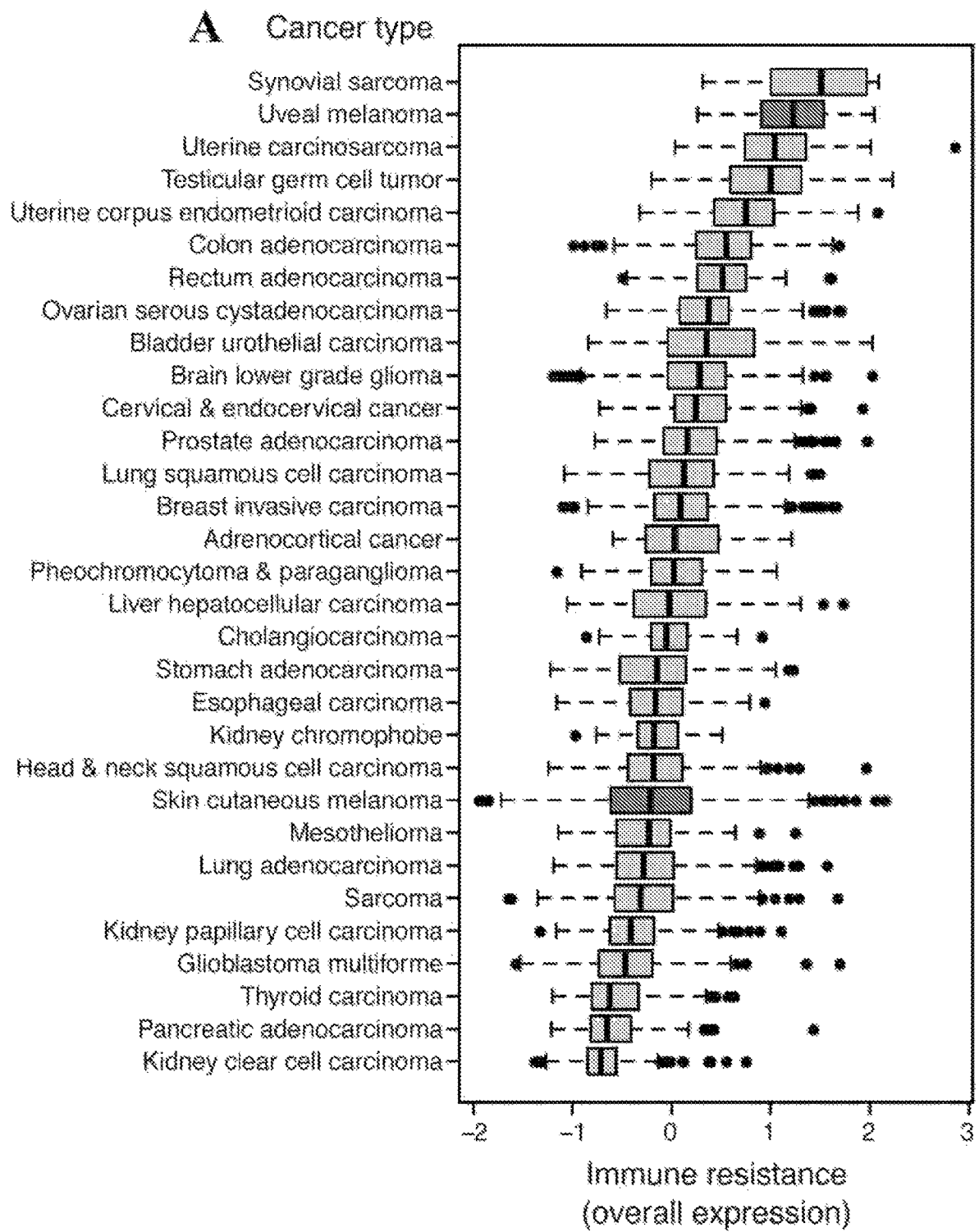
FIG. 57. Pan-cancer analysis of the resistance program; related to FIG. 48. (A-B) Overall expression of the resistance program (x axis) in 9,559 tumors from 33 cancer types (y axis) from TCGA. In (B) a regression-based approach controls for tumor microenvironment-related signals (Methods). Middle line: median; box edges: $25^{th}$ and $75^{th}$ percentiles, whiskers: most extreme points that do not exceed ±IQR*1.5; further outliers are marked individually.
Figure 57B:
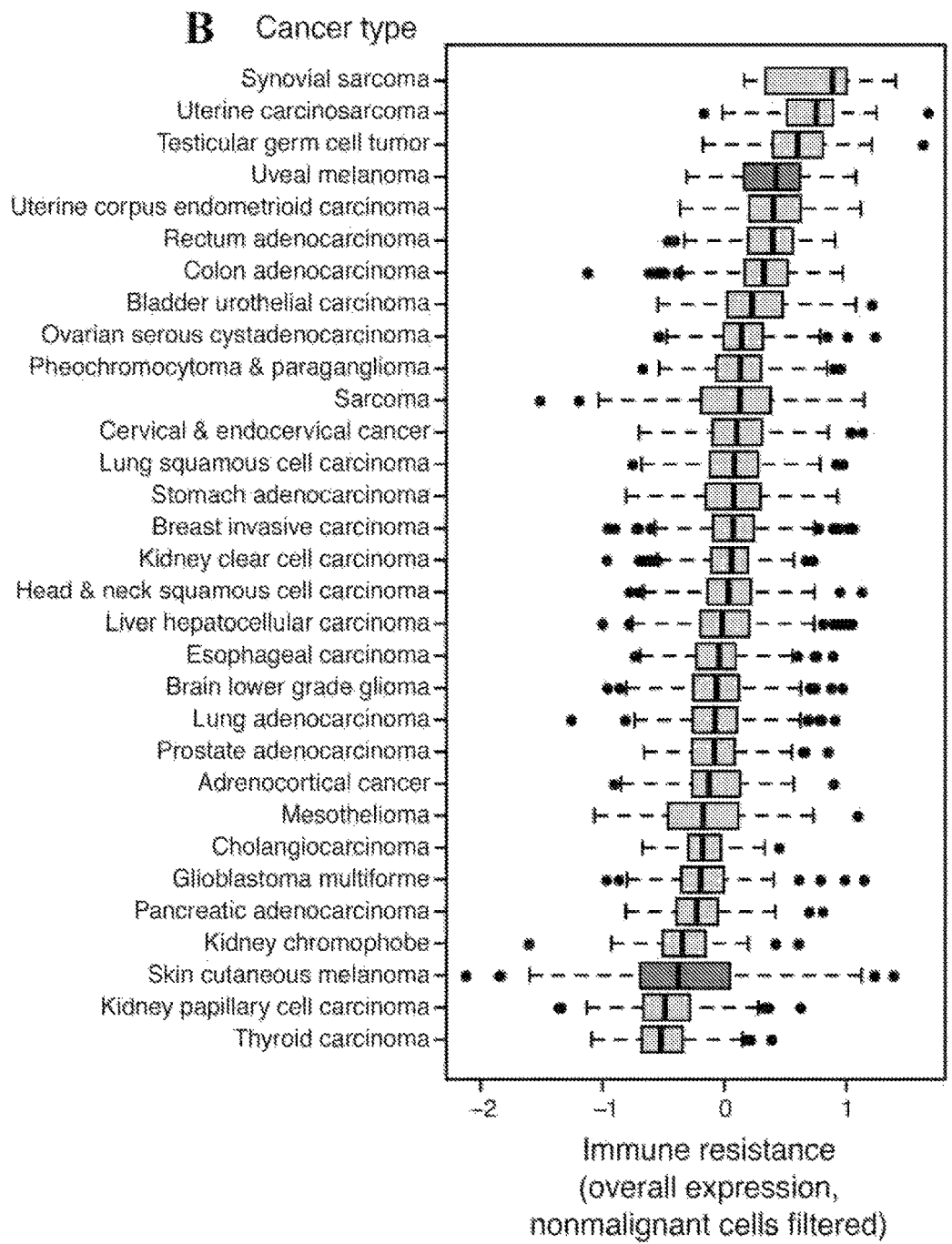

The malignant resistance programs may be relevant in other subtypes of melanoma as well as in other tumor types. Among different types of melanoma, uveal melanoma has more active resistance programs compared to cutaneous melanoma (FIG. 46A); across cancers, the immune resistance program is lower in some of the more responsive tumors (head and neck, kidney, skin, lung) and higher in tumor types that are less responsive to immunotherapy and/or arise from immune-privileged tissues (eye, testis) (FIG. 57). Interestingly, synovial sarcoma, which is driven by a single genomic aberration in the BAF complex, has the highest resistance scores. The BAF complex has been recently shown to play a key role in resistance to ICI immunotherapy (Miao et al., 2018; Pan et al., 2018). While this pan-cancer analysis is intriguing, it may still be impacted by the composition of the tumor microenvironment, which is challenging to control without single-cell data.

Future similar studies of other tumors could apply the approach to identify other tumor-specific resistance programs. For example, Applicants performed such analysis with the recent head and neck cancer single-cell cohort (Puram et al., 2017) and found that CAFs in cold tumors overexpressed genes up-regulated by TGFB1 ($P=1.70*10^{-7}$, hypergeometric test). Indeed, TGFB1 and TGFB signaling has been recently shown to be highly associated with lack of response to anti-PD-L1 treatment in urothelial cancer patients (Mariathasan et al., 2018). In line with the findings, co-administration of TGFB-blocking and anti-PD-L1 has been shown to modulated the tumor CAFs, which in turn facilitated T cell infiltration and tumor regression in mouse models (Mariathasan et al., 2018).

Overall, the analysis sheds light on the way cells shape and are being shaped by their microenvironment in tumors, and the approaches can be applied in other tumors to systematically map immune resistant malignant cell states, uncover improved biomarkers for patient selection, and reveal principles for the development of new therapeutics.

REFERENCES

1. P. Sharma, J. P. Allison, The future of immune checkpoint therapy. Science. 348, 56-61 (2015).
2. F. S. Hodi, Kluger H M, Sznol M, Durable, long-term survival in previously treated patients with advanced melanoma who received nivolumab monotherapy in a phase I trial. 2016 AACR Annu. Meet. Abstr. CT001 Present. Apr. 17, 2016.
3. P. Sharma, S. Hu-Lieskovan, J. A. Wargo, A. Ribas, Primary, Adaptive, and Acquired Resistance to Cancer Immunotherapy. Cell. 168, 707-723 (2017).
4. E. M. Van Allen et al., Genomic correlates of response to CTLA-4 blockade in metastatic melanoma. Science. 350, 207-211 (2015).
5. W. Hugo et al., Genomic and Transcriptomic Features of Response to Anti-PD-1 Therapy in Metastatic Melanoma. Cell. 165, 35-44 (2016).
6. P. C. Tumeh et al., PD-1 blockade induces responses by inhibiting adaptive immune resistance. Nature. 515, 568-571 (2014).
7. N. Riaz et al., Tumor and Microenvironment Evolution during Immunotherapy with Nivolumab. Cell. 0 (2017), doi:10.1016/j.cell.2017.09.028.
8. J. M. Zaretsky et al., Mutations Associated with Acquired Resistance to PD-1 Blockade in Melanoma. N. Engl. J. Med. 375, 819-829 (2016).
9. J. Gao et al., Loss of IFN-γ Pathway Genes in Tumor Cells as a Mechanism of Resistance to Anti-CTLA-4 Therapy. Cell. 167, 397-404.e9 (2016).
10. W. Peng et al., Loss of PTEN Promotes Resistance to T Cell-Mediated Immunotherapy. Cancer Discov. 6, 202-216 (2016).
11. S. Spranger, R. Bao, T. F. Gajewski, Melanoma-intrinsic β-catenin signalling prevents antitumour immunity. Nature. 523, 231-235 (2015).
12. G. T. Gibney, L. M. Weiner, M. B. Atkins, Predictive biomarkers for checkpoint inhibitor based immunotherapy. Lancet Oncol. 17, e542-e551 (2016).
13. I. Tirosh et al., Dissecting the multicellular ecosystem of metastatic melanoma by single-cell RNA-seq. Science. 352, 189-196 (2016).
14. A. P. Patel et al., Single-cell RNA-seq highlights intratumoral heterogeneity in primary glioblastoma. Science. 344, 1396-1401 (2014).
15. I. Tirosh et al., Single-cell RNA-seq supports a developmental hierarchy in human oligodendroglioma. Nature. 539, 309-313 (2016).
16. A. S. Venteicher et al., Decoupling genetics, lineages, and microenvironment in IDH mutant gliomas by single-cell RNA-seq. Science. 355 (2017), doi:10.1126/science.aai8478.
17. H. Li et al., Reference component analysis of single-cell transcriptomes elucidates cellular heterogeneity in human colorectal tumors. Nat. Genet. 49, 708-718 (2017).
18. E. A. Eisenhauer et al., New response evaluation criteria in solid tumours: revised RECIST guideline (version 1.1). Eur. J. Cancer Oxf Engl. 1990. 45, 228-247 (2009).
19. P. V. Kharchenko, L. Silberstein, D. T. Scadden, Bayesian approach to single-cell differential expression analysis. Nat. Methods. 11, 740-742 (2014).
20. P. Zhou et al., In vivo discovery of immunotherapy targets in the tumour microenvironment. Nature. 506, 52-57 (2014).
21. M. Singer et al., A Distinct Gene Module for Dysfunction Uncoupled from Activation in Tumor-Infiltrating T Cells. Cell. 166, 1500-1511.e9 (2016).
22. C. Zheng et al., Landscape of Infiltrating T Cells in Liver Cancer Revealed by Single-Cell Sequencing. Cell. 169, 1342-1356.e16 (2017).
23. M. J. T. Stubbington et al., T cell fate and clonality inference from single-cell transcriptomes. Nat. Methods. 13, 329-332 (2016).
24. R. Muthuswamy et al., NF-κB hyperactivation in tumor tissues allows tumor-selective reprogramming of the chemokine microenvironment to enhance the recruitment of cytolytic T effector cells. Cancer Res. 72, 3735-3743 (2012).
25. E. Pikarsky et al., NF-kappaB functions as a tumour promoter in inflammation-associated cancer. Nature. 431, 461-466 (2004). 26. J. Lamb et al., The Connectivity Map: using gene-expression signatures to connect small molecules, genes, and disease. Science. 313, 1929-1935 (2006).
27. J. M. Taube et al., Sci. Transl. Med., in press, doi: 10.1126/scitranslmed.3003689.
28. S. J. Patel et al., Identification of essential genes for cancer immunotherapy. Nature. 548, 537-542 (2017).
29. M. Challa-Malladi et al., Combined genetic inactivation of 02-Microglobulin and CD58 reveals frequent escape from immune recognition in diffuse large B cell lymphoma. Cancer Cell. 20, 728-740 (2011).
30. S. Goel et al., CDK4/6 inhibition triggers anti-tumour immunity. Nature. 548, 471-475 (2017).
31. L. Zimmer et al., Phase II DeCOG-study of ipilimumab in pretreated and treatment-naïve patients with metastatic uveal melanoma. PloS One. 10, e0118564 (2015).
32. A. P. Algazi et al., Clinical outcomes in metastatic uveal melanoma treated with PD-1 and PD-L1 antibodies. Cancer. 122, 3344-3353 (2016).
33. F. Azimi et al., Tumor-Infiltrating Lymphocyte Grade Is an Independent Predictor of Sentinel Lymph Node Status and Survival in Patients With Cutaneous Melanoma. J. Clin. Oncol. 30, 2678-2683 (2012).
34. D. Bogunovic et al., Immune profile and mitotic index of metastatic melanoma lesions enhance clinical staging in predicting patient survival. Proc. Natl. Acad. Sci. U.S.A 106, 20429-20434 (2009).
35. J. Landsberg et al., Melanomas resist T-cell therapy through inflammation-induced reversible dedifferentiation. Nature. 490, 412-416 (2012).
36. W. J. Lesterhuis et al., Network analysis of immunotherapy-induced regressing tumours identifies novel synergistic drug combinations. Sci. Rep. 5, srep12298 (2015).
37. R. T. Manguso et al., In vivo CRISPR screening identifies Ptpn2 as a cancer immunotherapy target. Nature. 547, 413-418 (2017).
38. Akbani, R., Akdemir, K. C., Aksoy, B. A., Albert, M., Ally, A., Amin, S. B., Arachchi, H., Arora, A., Auman, J. T., Ayala, B., et al. (2015). Genomic Classification of Cutaneous Melanoma. Cell 161, 1681-1696.
39. Ayers, M., Lunceford, J., Nebozhyn, M., Murphy, E., Loboda, A., Kaufman, D. R., Albright, A., Cheng, J. D., Kang, S. P., Shankaran, V., et al. (2017). IFN-γ-related mRNA profile predicts clinical response to PD-1 blockade. J. Clin. Invest. 127, 2930-2940.
40. Barretina, J., Caponigro, G., Stransky, N., Venkatesan, K., Margolin, A. A., Kim, S., Wilson, C. J., Lehar, J., Kryukov, G. V., Sonkin, D., et al. (2012). The Cancer Cell Line Encyclopedia enables predictive modelling of anti-cancer drug sensitivity. Nature 483, 603-607.

41. Benjamini, Y., and Hochberg, Y. (1995). Controlling the False Discovery Rate: A Practical and Powerful Approach to Multiple Testing. J. R. Stat. Soc. Ser. B Methodol. 57, 289-300.
42. Butler, A., and Satija, R. (2017). Integrated analysis of single cell transcriptomic data across conditions, technologies, and species. BioRxiv 164889.
43. Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinforma. Oxf Engl. 29, 15-21.
44. Ester, M., Kriegel, H.-P., Sander, J., and Xu, X. (1996). A density-based algorithm for discovering clusters a density-based algorithm for discovering clusters in large spatial databases with noise. In Proceedings of the Second International Conference on Knowledge Discovery and Data Mining, (Portland, Oregon: AAAI Press), pp. 226-231.
45. Fan, J., Salathia, N., Liu, R., Kaeser, G. E., Yung, Y. C., Herman, J. L., Kaper, F., Fan, J.-B., Zhang, K., Chun, J., et al. (2016). Characterizing transcriptional heterogeneity through pathway and gene set overdispersion analysis. Nat. Methods 13, 241-244.
46. Feng, Y., Yao, Z., and Klionsky, D. J. (2015). How to control self-digestion: transcriptional, post-transcriptional, and post-translational regulation of autophagy. Trends Cell Biol. 25, 354-363.
47. Fridman, W. H., Pages, F., Sautes-Fridman, C., and Galon, J. (2012). The immune contexture in human tumours: impact on clinical outcome. Nat. Rev. Cancer 12, 298-306.
48. Garnett, M. J., Edelman, E. J., Heidorn, S. J., Greenman, C. D., Dastur, A., Lau, K. W., Greninger, P., Thompson, I. R., Luo, X., Soares, J., et al. (2012). Systematic identification of genomic markers of drug sensitivity in cancer cells. Nature 483, 570-575.
49. Goel, S., DeCristo, M. J., Watt, A. C., BrinJones, H., Sceneay, J., Li, B. B., Khan, N., Ubellacker, J. M., Xie, S., Metzger-Filho, O., et al. (2017). CDK4/6 inhibition triggers anti-tumour immunity. Nature 548, 471-475.
50. Goltsev, Y., Samusik, N., Kennedy-Darling, J., Bhate, S., Hale, M., Vasquez, G., and Nolan, G. (2017). Deep profiling of mouse splenic architecture with CODEX multiplexed imaging. BioRxiv 203166.
51. Gong, X., Litchfield, L. M., Webster, Y., Chio, L.-C., Wong, S. S., Stewart, T. R., Dowless, M., Dempsey, J., Zeng, Y., Torres, R., et al. (2017). Genomic Aberrations that Activate D-type Cyclins Are Associated with Enhanced Sensitivity to the CDK4 and CDK6 Inhibitor Abemaciclib. Cancer Cell 32, 761-776.e6.
52. Gordy, J. T., Luo, K., Zhang, H., Biragyn, A., and Markham, R. B. (2016). Fusion of the dendritic cell-targeting chemokine MIP3a to melanoma antigen Gp100 in a therapeutic DNA vaccine significantly enhances immunogenicity and survival in a mouse melanoma model. J. Immunother. Cancer 4, 96.
53. Hangauer, M. J., Viswanathan, V. S., Ryan, M. J., Bole, D., Eaton, J. K., Matov, A., Galeas, J., Dhruv, H. D., Berens, M. E., Schreiber, S. L., et al. (2017). Drug-tolerant persister cancer cells are vulnerable to GPX4 inhibition. Nature 551, 247.
54. Herbst, R. S., Soria, J.-C., Kowanetz, M., Fine, G. D., Hamid, O., Gordon, M. S., Sosman, J. A., McDermott, D. F., Powderly, J. D., Gettinger, S. N., et al. (2014). Predictive correlates of response to the anti-PD-L1 antibody MPDL3280A in cancer patients. Nature 515, 563-567.
55. Hodi, F. S., O'Day, S. J., McDermott, D. F., Weber, R. W., Sosman, J. A., Haanen, J. B., Gonzalez, R., Robert, C., Schadendorf, D., Hassel, J. C., et al. (2010). Improved survival with ipilimumab in patients with metastatic melanoma. N. Engl. J. Med. 363, 711-723.
56. Holm, S. (1979). A Simple Sequentially Rejective Multiple Test Procedure. Scand. J. Stat. 6, 65-70.
57. Langmead, B., Trapnell, C., Pop, M., and Salzberg, S. L. (2009). Ultrafast and memory-efficient alignment of short DNA sequences to the human genome. Genome Biol. 10, R25.
58. Larkin, J., Chiarion-Sileni, V., Gonzalez, R., Grob, J. J., Cowey, C. L., Lao, C. D., Schadendorf, D., Dummer, R., Smylie, M., Rutkowski, P., et al. (2015). Combined Nivolumab and Ipilimumab or Monotherapy in Untreated Melanoma. N. Engl. J. Med. 373, 23-34.
59. Laurens Maaten (2009). Learning a Parametric Embedding by Preserving Local Structure. In Proceedings of the Twelfth International Conference on Artificial Intelligence and Statistics, David van Dyk, and Max Welling, eds. (PMLR), pp. 384-391.
60. Li, B., and Dewey, C. N. (2011). RSEM: accurate transcript quantification from RNA-Seq data with or without a reference genome. BMC Bioinformatics 12, 323.
61. Lin, J.-R., Izar, B., Mei, S., Wang, S., Shah, P., and Sorger, P. (2017). A simple open-source method for highly multiplexed imaging of single cells in tissues and tumours. BioRxiv 151738.
62. van der Maaten, L., and Hinton, G. (2008). Visualizing Data using t-SNE. 9, 2579-2605.
63. Mariathasan, S., Turley, S. J., Nickles, D., Castiglioni, A., Yuen, K., Wang, Y., Kadel Iii, E. E., Koeppen, H., Astarita, J. L., Cubas, R., et al. (2018). TGFβ attenuates tumour response to PD-L1 blockade by contributing to exclusion of T cells. Nature 554, 544-548.
64. McDavid, A., Finak, G., Chattopadyay, P. K., Dominguez, M., Lamoreaux, L., Ma, S. S., Roederer, M., and Gottardo, R. (2013). Data exploration, quality control and testing in single-cell qPCR-based gene expression experiments. Bioinforma. Oxf. Engl. 29, 461-467.
65. Miao, D., Margolis, C. A., Gao, W., Voss, M. H., Li, W., Martini, D. J., Norton, C., Bosse, D., Wankowicz, S. M., Cullen, D., et al. (2018). Genomic correlates of response to immune checkpoint therapies in clear cell renal cell carcinoma. Science 359, 801-806.
66. Nelson, P. J., and Muenchmeier, N. (2013). Membrane-anchored chemokine fusion proteins: A novel class of adjuvants for immunotherapy. Oncoimmunology 2, e26619.
67. Oki, S., Ohta, T., Shioi, G., Hatanaka, H., Ogasawara, O., Okuda, Y., Kawaji, H., Nakaki, R., Sese, J., and Meno, C. (2018). Integrative analysis of transcription factor occupancy at enhancers and disease risk loci in noncoding genomic regions.
68. Pan, D., Kobayashi, A., Jiang, P., Ferrari de Andrade, L., Tay, R. E., Luoma, A. M., Tsoucas, D., Qiu, X., Lim, K., Rao, P., et al. (2018). A major chromatin regulator determines resistance of tumor cells to T cell-mediated killing. Science 359, 770-775.
69. Postow, M. A., Chesney, J., Pavlick, A. C., Robert, C., Grossmann, K., McDermott, D., Linette, G. P., Meyer, N., Giguere, J. K., Agarwala, S. S., et al. (2015). Nivolumab and ipilimumab versus ipilimumab in untreated melanoma. N. Engl. J. Med. 372, 2006-2017.
70. Puram, S. V., Tirosh, I., Parikh, A. S., Patel, A. P., Yizhak, K., Gillespie, S., Rodman, C., Luo, C. L., Mroz, E. A., Emerick, K. S., et al. (2017). Single-Cell Transcriptomic Analysis of Primary and Metastatic Tumor Ecosystems in Head and Neck Cancer. Cell 171, 1611 1624. e24.
71. Ramilowski, J. A., Goldberg, T., Harshbarger, J., Kloppmann, E., Lizio, M., Satagopam, V. P., Itoh, M., Kawaji, H., Carninci, P., Rost, B., et al. (2015). A draft network of ligand-receptor-mediated multicellular signalling in human. Nat. Commun. 6, 7866.
72. Ribas, A., Puzanov, I., Dummer, R., Schadendorf, D., Hamid, O., Robert, C., Hodi, F. S., Schachter, J., Pavlick, A. C., Lewis, K. D., et al. (2015). Pembrolizumab versus investigator-choice chemotherapy for ipilimumab-refractory melanoma (KEYNOTE-002): a randomised, controlled, phase 2 trial. Lancet Oncol. 16, 908-918.
73. Rosvall, M., and Bergstrom, C. T. (2008). Maps of random walks on complex networks reveal community structure. Proc. Natl. Acad. Sci. U.S.A 105, 1118-1123.
74. Shaffer, S. M., Dunagin, M. C., Torborg, S. R., Torre, E. A., Emert, B., Krepler, C., Beqiri, M., Sproesser, K., Brafford, P. A., Xiao, M., et al. (2017). Rare cell variability and drug-induced reprogramming as a mode of cancer drug resistance. Nature 546, 431-435.
75. Shalek, A. K., Satija, R., Adiconis, X., Gertner, R. S., Gaublomme, J. T., Raychowdhury, R., Schwartz, S., Yosef, N., Malboeuf, C., Lu, D., et al. (2013). Single-cell transcriptomics reveals bimodality in expression and splicing in immune cells. Nature 498, 236-240.
76. Shalek, A. K., Satija, R., Shuga, J., Trombetta, J. J., Gennert, D., Lu, D., Chen, P., Gertner, R. S., Gaublomme, J. T., Yosef, N., et al. (2014). Single-cell RNA-seq reveals dynamic paracrine control of cellular variation. Nature 510, 363-369.
77. Shannon, P., Markiel, A., Ozier, O., Baliga, N. S., Wang, J. T., Ramage, D., Amin, N., Schwikowski, B., and Ideker, T. (2003). Cytoscape: a software environment for integrated models of biomolecular interaction networks. Genome Res. 13, 2498-2504.
78. Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc. Natl. Acad. Sci. U.S.A 102, 15545-15550.
79. Subramanian, A., Narayan, R., Corsello, S. M., Peck, D. D., Natoli, T. E., Lu, X., Gould, J., Davis, J. F., Tubelli, A. A., Asiedu, J. K., et al. (2017). A Next Generation Connectivity Map: L1000 Platform and the First 1,000, 000 Profiles. Cell 171, 1437-1452.e17.
80. Trombetta, J. J., Gennert, D., Lu, D., Satija, R., Shalek, A. K., and Regev, A. (2014). Preparation of Single-Cell RNA-Seq Libraries for Next Generation Sequencing. Curr. Protoc. Mol. Biol. Ed. Frederick M Ausubel Al 107, 4.22.1-4.22.17.
81. Viswanathan, V. S., Ryan, M. J., Dhruv, H. D., Gill, S., Eichhoff, O. M., Seashore-Ludlow, B., Kaffenberger, S. D., Eaton, J. K., Shimada, K., Aguirre, A. J., et al. (2017). Dependency of a therapy-resistant state of cancer cells on a lipid peroxidase pathway. Nature 547, 453.
82. Wagner, A., Regev, A., and Yosef, N. (2016). Revealing the vectors of cellular identity with single-cell genomics. Nat. Biotechnol. 34, 1145-1160.
83. Waltman, L., and van Eck, N.J. (2013). A smart local moving algorithm for large-scale modularity-based community detection. Eur. Phys. J. B 86.

Example 10—Materials and Methods

Patients

For the discovery cohort (single-cell RNA-Seq), tissue was procured under Institutional Review Board (IRB) approved protocols at Brigham and Women's Hospital and Dana-Farber Cancer Institute, Boston, MA. Patients were consented to these protocols (11-104) in clinic visits prior to surgery/biopsy. Patients included in the initial study and newly collected specimens are highlighted in table Si.

For validation cohorts (bulk-RNA-seq), patient tissue was collected under IRB protocols of the University Hospital Essen, Germany and Massachusetts General Hospital, Boston, MA (protocol 11-181) and The Wistar Institute, Philadelphia, PA (Human subjects protocol 2802240). Demographics of validation Cohort 1 are summarized in table S1. Validation Cohort 2 included 90 samples from 26 patients, with multiple biopsies per patient, taken before, during, or after various treatment regimens, including both targeted therapies and immunotherapies. Twelve patients had both pre- and post/on-ICI samples (table S1).

Tissue Handling and Tumor Disaggregation

Resected tumors were transported in DMEM (ThermoFisher Scientific, Waltham, MA) on ice immediately after surgical procurement. Tumors were rinsed with PBS (Life Technologies, Carlsbad, CA). A small fragment was stored in RNA-protect (Qiagen, Hilden, Germany) for bulk RNA and DNA isolation. Using scalpels, the remainder of the tumor was minced into tiny cubes<1 $mm^3$ and transferred into a 50 ml conical tube (BD Falcon, Franklin Lakes, NJ) containing 10 ml pre-warmed M199-media (ThermoFisher Scientific), 2 mg/ml collagenase P (Roche, Basel, Switzerland) and 10 U/μl DNase I (Roche). Tumor pieces were digested in this media for 10 minutes at 37° C., then vortexed for 10 seconds and pipetted up and down for 1 minute using pipettes of descending sizes (25 ml, 10 ml and 5 ml). If needed, this was repeated twice more until a single-cell suspension was obtained. This suspension was then filtered using a 70 μm nylon mesh (ThermoFisher Scientific) and residual cell clumps were discarded. The suspension was supplemented with 30 ml PBS (Life Technologies) with 2% fetal calf serum (FCS) (Gemini Bioproducts, West Sacramento, CA) and immediately placed on ice. After centrifuging at 580 g at 4° C. for 6 minutes, the supernatant was discarded and the cell pellet was re-suspended in PBS with 1% FCS and placed on ice prior to staining for FACS.

FACS

Single-cell suspensions were stained with CD45-FITC (VWR, Radnor, PA) and live/dead stain using Zombie Aqua (BioLegend, San Diego, CA) per manufacturer recommendations. First, doublets were excluded based on forward and sideward scatter, then Applicants gated on viable cells ($Aqua^{low}$) and sorted single cells ($CD45^+$ or $CD45^-$) into 96-well plates chilled to 4° C., pre-prepared with 10 μl TCL buffer (Qiagen) supplemented with 1% beta-mercaptoethanol (lysis buffer). Single-cell lysates were sealed, vortexed, spun down at 3,700 rpm at 4° C. for 2 minutes, placed on dry ice and transferred for storage at −80° C.

Single-Cell RNA-Seq

Whole Transcriptome amplification (WTA) was performed with a modified SMART-Seq2 protocol, as described previously (1, 2) with Maxima Reverse Transcriptase (Life Technologies) instead of Superscript II. Next, WTA products were cleaned with Agencourt XP DNA beads and 70% ethanol (Beckman Coulter, Brea, CA) and Illumina sequencing libraries were prepared using Nextera XT (Illumina, San Diego, CA), as previously described (2). The 96 samples of a multiwell plate were pooled, and cleaned with two 0.8× DNA SPRIs (Beckman Coulter). Library quality was assessed with a high sensitivity DNA chip (Agilent) and quantified with a high sensitivity dsDNA Quant Kit (Life Technologies).

For droplet-based scRNA-seq, experiments were performed on the 10× Genomics Chromium platform, with the Chromium Single Cell 3' Library & Gel Bead Kit v2 and Chromium Single Cell 3' Chip kit v2 according to the manufacturer's instructions in the Chromium Single Cell 3' Reagents Kits V2 User Guide. Briefly, 6,000 cells were re suspended in PBS supplemented with 0.04% BSA and loaded to each channel. The cells were then partitioned into Gel Beads in Emulsion in the GemCode instrument, where cell lysis and barcoded reverse transcription of RNA occurred, followed by amplification, shearing and 5' adaptor and sample index attachment.

Barcoded single-cell transcriptome libraries were sequenced with 38 bp paired end reads on an Illumina NextSeq 500 Instrument.

RNA-Capture and Bulk RNA-Seq of Validation Cohorts

RNA extraction from formalin-fixed, paraffin-embedded (FFPE) tissue slides was performed by the Genomics Platform of the Broad Institute (Cambridge, MA). For cDNA Library Construction total RNA was assessed for quality using the Caliper LabChip GX2 (Perkin Elmer). The percentage of fragments with a size greater than 200 nt (DV200) was calculated and an aliquot of 200 ng of RNA was used as the input for first strand cDNA synthesis using Illumina's TruSeq RNA Access Library Prep Kit. Synthesis of the second strand of cDNA was followed by indexed adapter ligation. Subsequent PCR amplification enriched for adapted fragments. The amplified libraries were quantified using an automated PicoGreen assay (Thermo Fisher Scientific, Cambridge, MA). 200 ng of each cDNA library, not including controls, were combined into 4-plex pools. Capture probes that target the exome were added, and hybridized for the recommended time. Following hybridization, streptavidin magnetic beads were used to capture the library-bound probes from the previous step. Two wash steps effectively remove any nonspecifically bound products. These same hybridization, capture and wash steps are repeated to assure high specificity. A second round of amplification enriches the captured libraries. After enrichment, the libraries were quantified with qPCR using the KAPA Library Quantification Kit for Illumina Sequencing Platforms (Illumina) and then pooled equimolarly. The entire process is performed in 96-well format and all pipetting is done by either Agilent Bravo or Hamilton Starlet. Pooled libraries were normalized to 2 nM and denatured using 0.1 N NaOH prior to sequencing. Flowcell cluster amplification and sequencing were performed according to the manufacturer's protocols using Illumina HiSeq 2000 or 2500 (Illumina). Each run was a 76 bp paired-end with an eight-base index barcode read. Data was analyzed using the Broad Picard Pipeline (broadinstitute.github.io/picard/) which includes de-multiplexing and data aggregation.

RNA-Seq Data Pre-Processing

BAM files were converted to merged, demultiplexed FASTQ files. The paired-end reads obtained with the SMART-Seq2 protocol were mapped to the UCSC hg19 human transcriptome using Bowtie (Langmead et al., 2009), and transcript-per-million (TPM) values were calculated with RSEM v1.2.8 in paired-end mode (Li and Dewey, 2011). The paired-end reads obtained with the 10× Genomics platform were mapped to the UCSC hg19 human transcriptome using STAR (Dobin et al., 2013), and gene counts/TPM values were obtained using the 10× Genomics computational pipeline (cellranger-2.1.0).

For bulk RNA-Seq data, expression levels of genes were quantified as $E_{i,j}=\log_2(TPM_{i,j}+1)$, where $TPM_{i,j}$ denotes the TPM value of gene i in sample j. For scRNA-seq data, expression levels were quantified as $E_{i,j}=\log_2(TPM_{i,j}/10+1)$, where $TPM_{i,j}$ denotes the TPM value of gene i in cell j. TPM values were divided by 10 because the complexity of the single-cell libraries is estimated to be within the order of 100,000 transcripts. The $10^{-1}$ factoring prevents counting each transcript ~10 times, which would have resulted in overestimating the differences between positive and zero TPM values. The average expression of a gene i across a population of N cells, denoted here as P, was defined as $$E_{i,p} = \log^2\left(1 + \frac{\sum_{j \in P} TPM_{i,j}}{N}\right)$$

For each cell, Applicants quantified the number of genes with at least one mapped read, and the average expression level of a curated list of housekeeping genes (Tirosh et al., 2016a). Applicants excluded all cells with either fewer than 1,700 detected genes or an average housekeeping expression (E, as defined above) below 3 (Table S2). For the remaining cells, Applicants calculated the average expression of each gene ($E_p$), and excluded genes with an average expression below 4, which defined a different set of genes in different analyses depending on the subset of cells included. In cases where Applicants analyzed different cell types together, Applicants removed genes only if they had an average $E_p$ below 4 in each of the different cell types that were included in the analysis. When analyzing CD45+ cells, Applicants excluded genes as described above only after the assignment of cells to cell types in order to prevent the filtering of genes that were expressed by less abundant cell types.

Data Imputation and Normalization

In all differential expression analyses, Applicants first modeled the read counts as a mixture of a negative binomial (NB) and Poisson components to estimate the expression levels, using SCDE (6) with the code provided in github.com/hms-dbmi/scde. The resulting normalized and imputed expression matrix, denoted as E', was used in the differential expression analyses because, for single genes, it provides a more accurate and sensitive estimation of their expression. Analysis of droplet-based scRNA-seq data (10× Genomics Chromium, above) was performed with the Seurat package (http://www.satijalab.org/seurat), using the likelihood-ratio test for differential gene expression analyses (McDavid et al., 2013).

Identifying Cell States Associated with Specific Tumor Compositions

Applicants combined scRNA-seq and bulk RNA-Seq data to characterize the state of a specific cell type in tumors with a specific cell type composition (FIG. 1B). The method takes as input scRNA-seq data and a cohort of RNA-Seq data, both collected from tumors of the same cancer type. For clarity Applicants describe the approach for malignant cells and T cells as applied here, though it can be applied to any pair of cell types.

1. Analyze the scRNA-seq data: (a) assign cells to cell types (see sections: Classification of malignant and stromal cells and Classification of immune cells); and (b) define a signature of malignant cells and a signature of T cells, consisting of genes which are primarily (specifically) expressed by malignant cells or T cells, respectively (see section: Cell-type specific signatures).

2. Analyze the bulk RNA-Seq data: (a) estimate the T cell infiltration level in each tumor by computing the overall expression (OE, see section: Computing the OE of gene signatures) of the T cell signature in each bulk sample; (b) compute the Spearman correlation coefficient between the expression of each of the genes in the malignant signature and the OE of the T cell signature across the bulk tumors; and (c) define the seed exclusion-up (down) signature as the top 20 malignant genes that are significantly negatively (positively) correlated in (b).

3. Analyze the scRNA-seq data of the malignant cells: (a) compute the OE of the seed exclusion signatures in each of the malignant cells; (b) compute the partial Spearman correlation coefficient between the expression of each gene and the OE of the seed exclusion signatures across the single malignant cells, while controlling for technical quality (the number of reads and genes that were detected in the cells).

4. Derive the final genome-scale exclusion signatures, defined as: (i) exclusion-up: genes which were significantly positively correlated with the seed exclusion-up signature and significantly negatively correlated with the seed exclusion-down signature in the analysis described in (3); and (ii) exclusion-down: genes which were significantly positively correlated with the seed exclusion-down signature and significantly negatively correlated with the seed exclusion-up signature in the analysis described in (3). In this analysis, a gene is defined as significantly correlated with a signature if it was among the 200 topmost correlated genes, with p-value<$10^{-10}$, and Pearson $|r|>0.1$. Applicants implemented the approach with our clinical scRNA-seq melanoma data and bulk RNA-Seq data of 473 Skin Cutaneous Melanoma (SKCM) tumors from TCGA (as provided in xenabrowser.net/datapages/).

Computing the OE of Gene Signatures

Gene modules are more robust to noise and provide more coherent signals than the expression of single genes (Shalek et al., 2013, 2014; Wagner et al., 2016). To compute the OE of a gene module or signature Applicants used a scheme that filters technical variation and highlights biologically meaningful patterns. The procedure is based on the notion that the measured expression of a specific gene is correlated with its true expression (signal), but also contains a technical (noise) component. The latter may be due to various stochastic processes in the capture and amplification of the gene's transcripts, sample quality, as well as variation in sequencing depth (Wagner et al., 2016). The signal-to-noise ratio varies, depending, among other variables, on gene transcript abundance.

Applicants therefore computed the OE of gene signatures in a way that accounts for the variation in the signal-to-noise ratio across genes and cells. Given a gene signature and a gene expression matrix E (as defined above), Applicants first binned the genes into 50 expression bins according to their average expression across the cells or samples. The average expression of a gene across a set of cells within a sample is $E_{i,p}$ (see: RNA-Seq data pre-processing) and the average expression of a gene across a set of N tumor samples was defined as:

$$\mathbb{E}_j[E_{ij}] = \sum_j \frac{E_{ij}}{N}.$$

Given a gene signature S that consists of K genes, with $k_b$ genes in bin b, Applicants sample random S-compatible signatures for normalization. A random signature is S-compatible with signature S if it consists of overall K genes, such that in each bin (b) it has exactly $k_b$ genes. The OE of signature S in cell or sample j is then defined as:

$$OE_j = \frac{\sum_{i \in S} C_{ij}}{\mathbb{E}_{\tilde{S}}[\sum_{i \in \tilde{S}} C_{ij}]}$$

Where $\tilde{S}$ is a random S-compatible signature, and $C_{ij}$ is the centered expression of gene i in cell or sample j, defined as $C_{ij}=E_{ij}-\mathbb{E}[E_{ij}]$. Because the computation is based on the centered gene expression matrix C, genes that generally have a higher expression compared to other genes will not skew or dominate the signal.

Applicants found that 100 random S-compatible signatures are sufficient to yield a robust estimate of the expected value $\mathbb{E}_{\tilde{S}}[\Sigma_{i\in\tilde{S}}C_{ij}]$. The distribution of the OE values was normal or a mixture of normal distributions, and, unlike the expression of a single gene, fulfilled the assumptions of the mixed effects models or hierarchal linear models that Applicants applied to study the differential expression of gene signatures (as described in the Inter patient single-cell differential expression analysis of gene sets section).

In cases where the OE of a given signature has a bimodal distribution across the cell population, it can be used to naturally separate the cells into two subsets. To this end, Applicants applied the Expectation Maximization (EM) algorithm for mixtures of normal distributions to define the two underlying normal distributions. Applicants then assigned cells to the two subsets, depending on the distribution (high or low) that they were assigned to.

Applicants use the term a transcriptional program (e.g., the immune resistant program) to characterize cell states which are defined by a pair of signatures, such that one (S up) is overexpressed and the other (S-down) is underexpressed. Applicants define the OE of such cell states as the OE of S-up minus the OE of S-down.

Classification of Malignant and Stromal Cells

In the non-immune compartment (CD45⁻ cells), Applicants distinguished malignant and non-malignant cells according to three criteria: (1) their inferred CNV profiles (5, 10); (2) under-expression of different non-malignant cell-type signatures; and (3) higher similarity to melanoma tumors than to adjacent normal tissue, based on the comparison to bulk RNA-seq profiles. Specifically: (1) to infer CNVs from the scRNA-Seq data Applicants used the approach described in (10) as implemented in the R code provided in github.com/broadinstitute/inferCNV with the default parameters. Cells with an average absolute CNV level that was below the 0.1 quantile of the entire CD45⁻ cell population were considered as potentially non-malignant according to this criterion. (2) Applicants used signatures of endothelial cells, stromal cells, and Cancer Associated Fibroblasts (CAFs), as provided in table S3. The signatures combine well-established markers from two sources (www.biolegend.com/cell markers and (5)). Applicants computed the OE of these three signatures in each of the CD45⁻ cells, while controlling for the impact of technical cell quality (as described in section Overall Expression (OE) of gene signatures). CD45⁻ cells that expressed any one of these three signatures above the 0.95 quantile were considered as non malignant according to this criterion. (3) Applicants downloaded the pan-cancer TCGA RNA-seqV2 expression data from xena.ucsc.edu, and log 2-transformed the RSEM-based gene quantifications. For each cell, Applicants computed the Spearman correlation between its profile (in TMP) and each bulk profile (in TPM) of 473 skin cutaneous melanoma samples and 727 normal solid tissues. Applicants then tested, for each cell, if it was more similar to the melanoma tumors compared to the normal tissues, by applying a one-sided Wilcoxon ranksum test on the correlation coefficients that were obtained for that cell. Cells that were more similar to the normal tissues (P<0.05, Wilcoxon ranksum test) were considered as potentially non malignant according to this criterion.

Figure 51A:
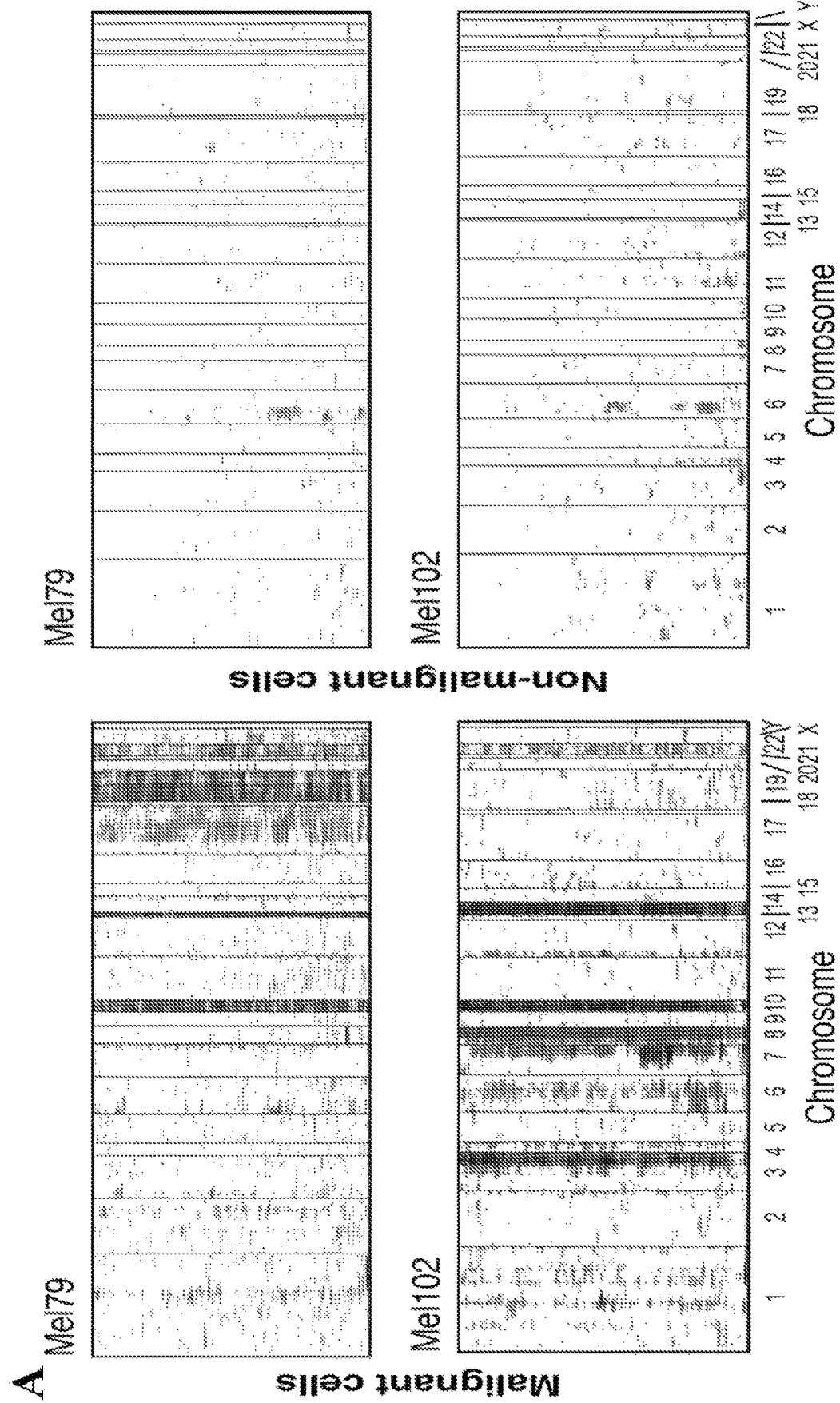
FIG. 51. Assignment of cells into cell types by scRNA-seq; related to FIG. 44. (A) Inferred large-scale CNVs distinguish malignant from nonmalignant cells. Shown are the inferred CNVs (amplification, deletion) along the chromosomes (x axis) for cells (y axis) in two representative tumors partitioned as malignant (left) or nonmalignant (right) by CD45 sorting and transcriptional features. (B-E) Congruence between different assignment methods. (B) Each plot shows the relation between two different scorings, by showing for CD45$^-$ cells the distribution of scores (y axis) by one scheme, stratified to two categories by another scheme. CNV: inference of malignant and nonmalignant CD45$^-$ cells (as in A, Methods); signature based: assignment of CD45$^-$ cells as malignant or stroma by scoring the corresponding expression signatures (Methods); differential similarity to melanoma: assignment of CD45$^-$ cells as malignant or nonmalignant by similarity to bulk melanoma tumors compared to normal tissue. Middle line: median; box edges: $25^{th}$ and $75^{th}$ percentiles, whiskers: most extreme points that do not exceed ±IQR*1.5; further outliers are marked individually. (C) Distribution of CNV-R-scores for cells called as malignant or nonmalignant. The CNV-R-score of a cell is the Spearman correlation coefficient (r) between the cell's CNV profile and its tumor's inferred CNV profile (Methods). (D) The distribution of CNV-R-scores across each identified cell subset. Box plots as in (B). (E) The CNV-R-score (y axis) vs. the overall CNV signal (x axis, Methods) for malignant and nonmalignant cells; Non-malignant cells with values that exceed the dashed lines were considered unresolved and were omitted from further analyses. (F-G) tSNE plots of all nonmalignant cells (dots), shaded by (F) overall expression (bar) of well-established cell type markers (Table S3), or (G) detection of CD4 or CD8 (CD8A or CD8B).
Figure 53A:
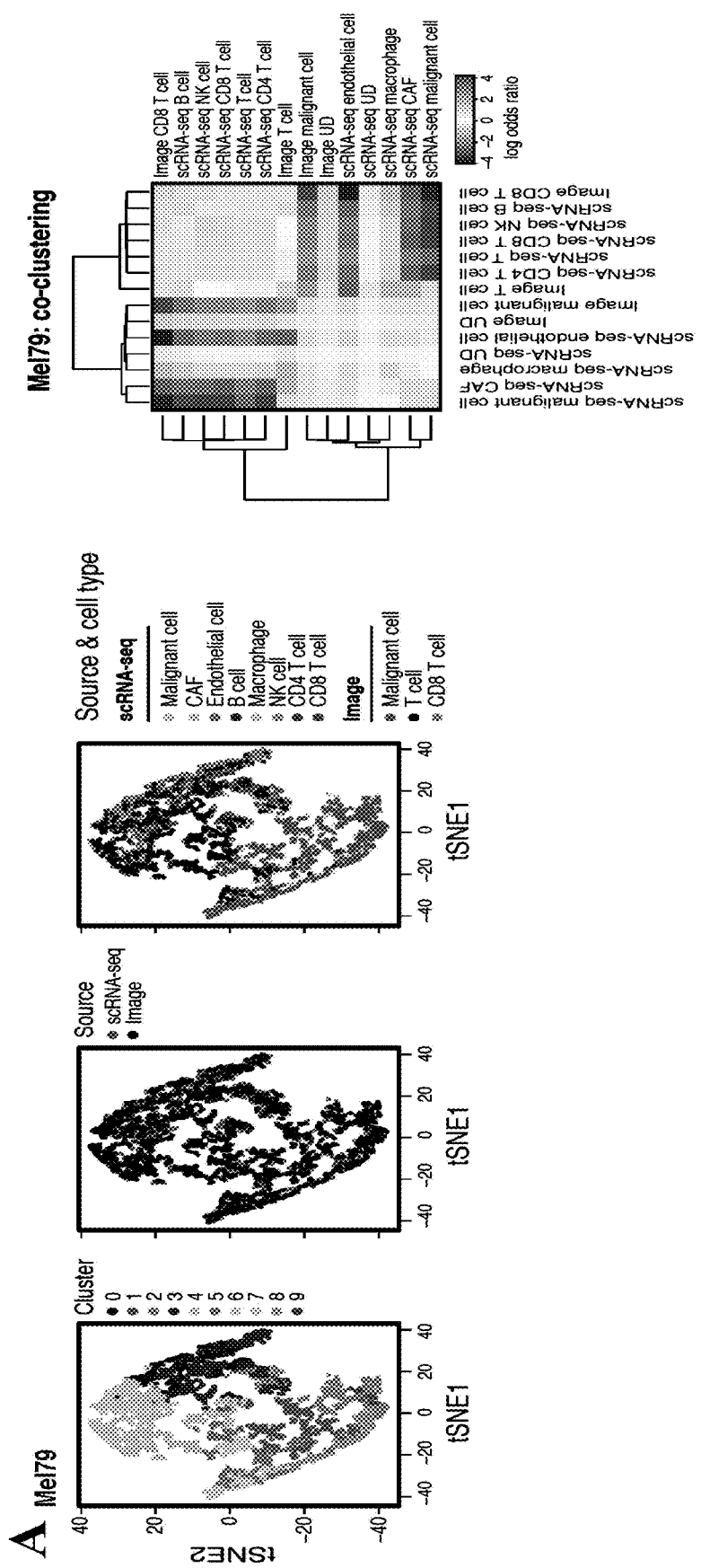
FIG. 53. Integrative analysis of scRNA-seq and spatial multiplex protein IHC data; related to FIG. 47. (A-D) Integrative analysis of scRNA-seq and CyCIF multiplex protein data from each of four tumors: (A) Mel79, (B) Mel80, (C) Mel74, and (D) Mel89. Left: tSNE plots of co-embedding of cells from scRNA-seq and images of each tumors, with cells shaded by (from left): clusters, data source, or source and cell type. Right: Log-odds ratio (bar, Methods) assessing for each pair of cell types (rows, columns) if they are assigned to the same cluster significantly more (>0) or less (<0) than expected by chance.
Figure 53B:
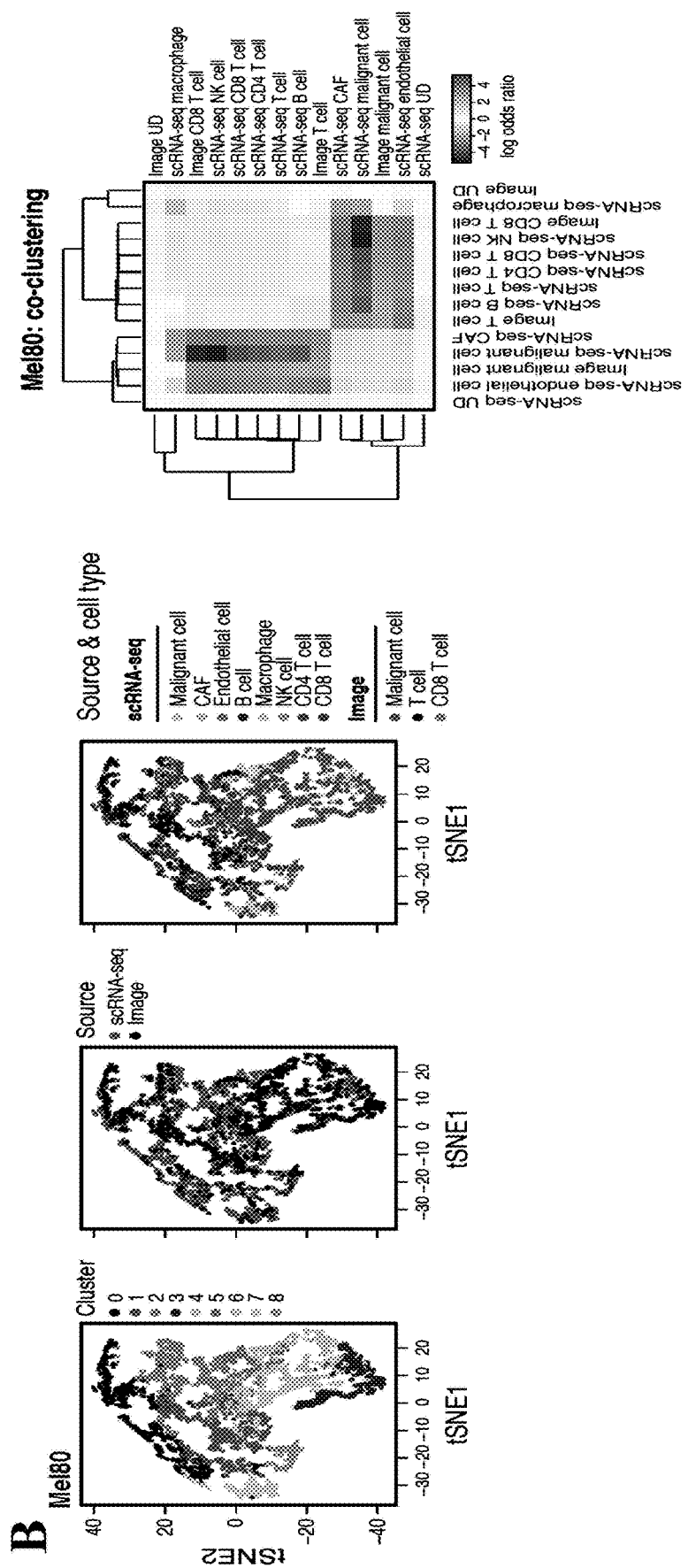
Figure 53C:
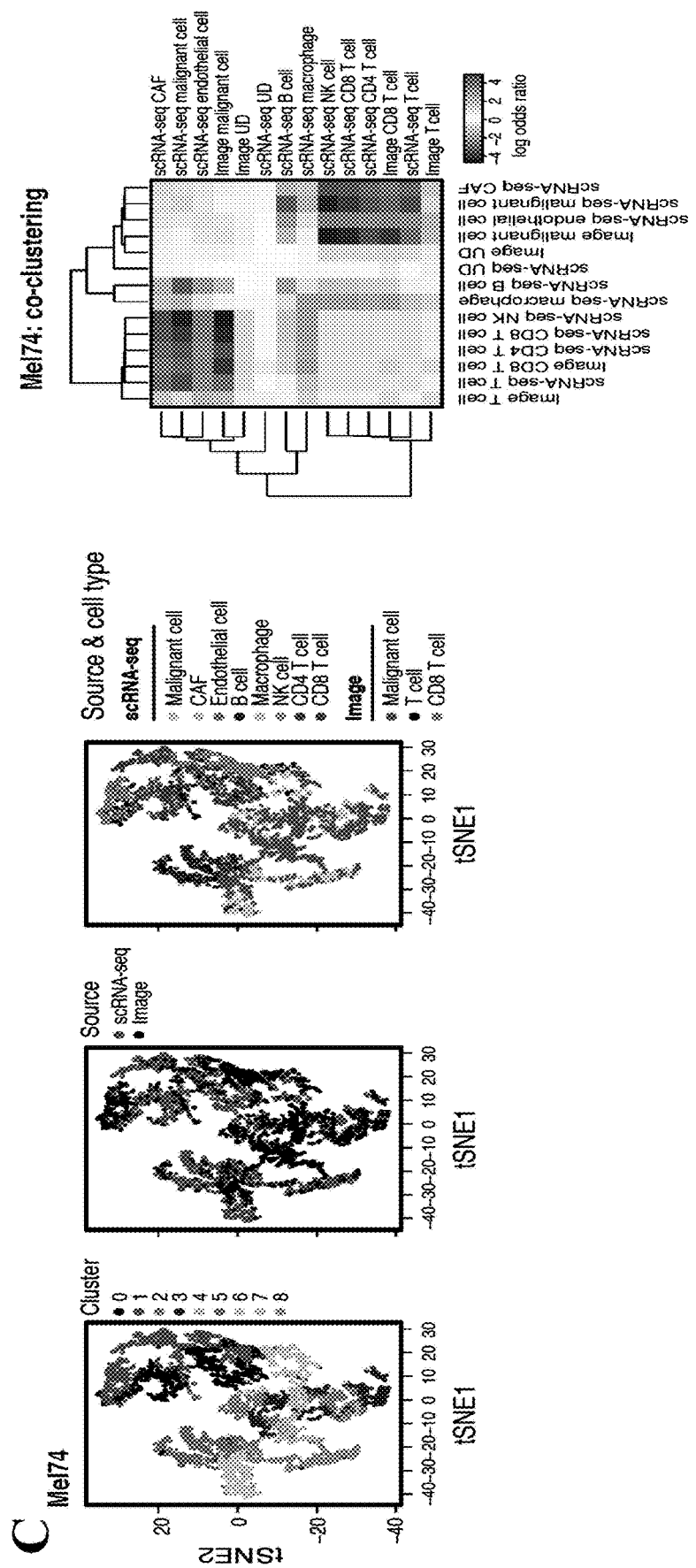
Figure 53D:
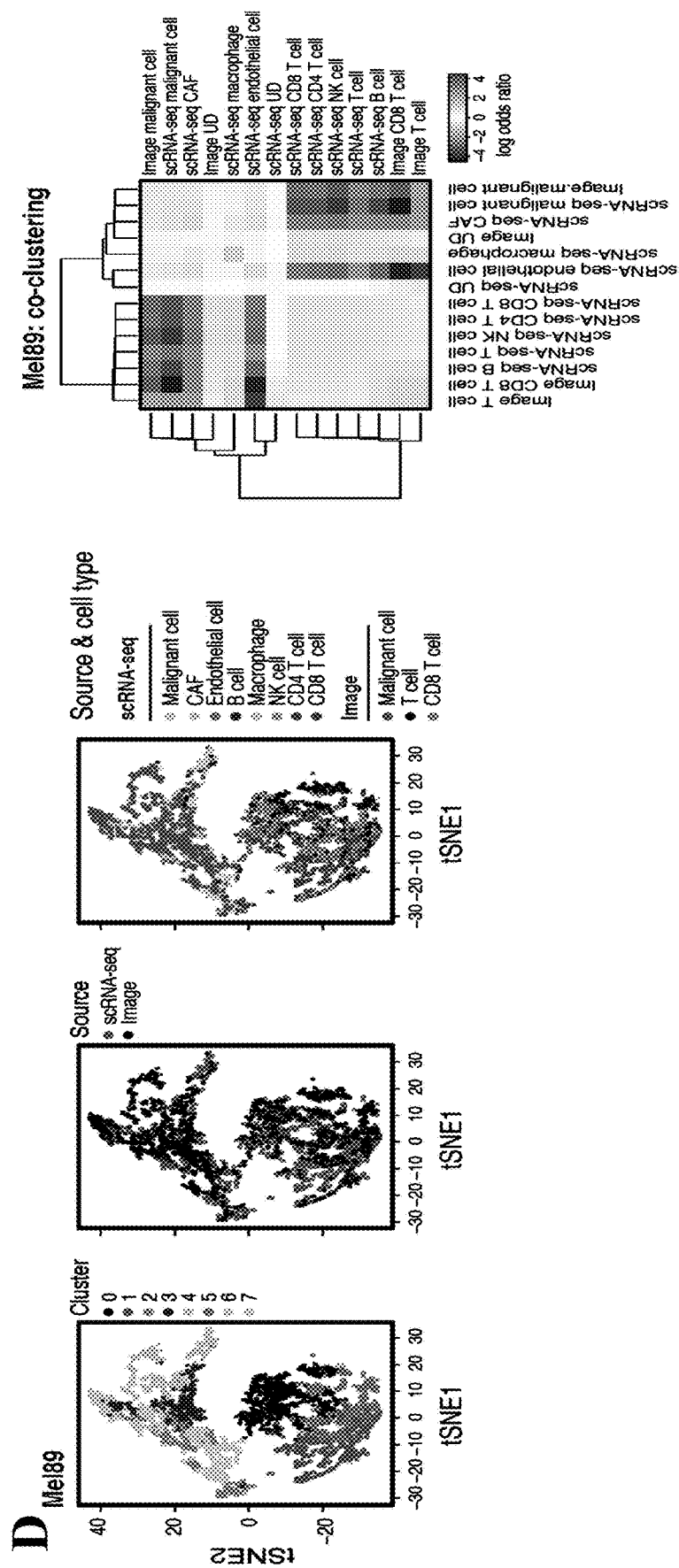

The cell assignments that were obtained by these three different criteria were highly consistent (FIGS. 51A, 51B, hypergeometric p-value<$10^{47}$). Cells that were identified as potentially nonmalignant according to one or more of these three criteria were defined as nonmalignant, and were omitted from further analyses of the malignant cells. The non-malignant CD45⁻ cells were further classified into CAFs and endothelial cells, if they overexpressed only one of the corresponding gene signatures, and as unresolved cells otherwise.

TABLE S3

Table S3. Cell type signatures that were used for cell classification.

| Endothelial Cell | Stromal Cell | CAF | Basophile | B cell | Eosinophil | Erythrocyte | Mast Cell | MDSC |
|---|---|---|---|---|---|---|---|---|
| VWF | MMP2 | FAP | ANPEP | BLK | C3AR1 | CD24 | ENPP3 | CCR7 |
| TEK | ICAM3 | THY1 | CCR3 | CD19 | C5AR1 | GYPA | KIT | CD1A |
| MCAM | TLR3 | DCN | CD44 | CD2 | CCR1 | PTPRC |  | CD1B |
| CD34 | MADCAM1 | COL1A1 | CD63 | CD22 | CCR3 |  |  | CD1C |
| CD68 | CD80 | CD86 | CSF1R | ENG | FCGR1A | FUT4 | ITGAL | ITGAM |
| CD3E | CD3G | CD8A | CD8B | CST7 | GZMA | GZMB | 1FNG | NKG7 |
| ENTPD1 | FOXP3 | IKZF2 | IL2RA | ISG20 | ITGAE | LAG3 | LRRC32 | NT5E |
| CD3D | CD3E | CD3G | CD4 |  |  |  |  |  |
| CD3E | CD3G | CD4 | IL17A | IL17F | IL1R1 | IL21 | IL22 | KLRB1 |
| GATA3 | 1RF4 | STAT6 |  |  |  |  |  |  |
| CD4 | CSF2 | CXCR4 | GATA3 | HAVCR1 | ICOS | IL10 | IL13 | IL1R1 |
| CXCR3 | DPP4 | HAVCR2 | IFNA1 | IFNGR1 | IL2 | KLRD1 | TNF | TNFSF11 |
| CD4 | CD40LG | CD84 | CXCR5 | ICOS | IL6R | PDCD1 | SLAMF1 | STAT3 |
| CD151 | CD226 | CD36 | CD46 | CD47 | CD48 | CD63 | CD69 | CD84 |
| CD4 | CD40 | CD80 | CD83 | CD86 | CD8A | CLEC4C | CMKLR1 | IL3RA |
| ITGA2 | ITGAM | ITGAX | KLRA1 | KLRB1 | KLRD1 | KLRK1 | NCAM1 | NCR1 |
| CEACAM8 | CSF3R | CXCR1 | CXCR2 | FCGR1A | FUT4 | ITGAM | 1TGAX | MME |
| CD4 | SELL |  |  |  |  |  |  |  |
| CD207 | CD209 | CD4 | CD40 | CD80 | CD83 | CD86 | CMKLR1 | DCX |
| ITGB3 | PECAM1 | SELP |  |  |  |  |  |  |
| CD207 | CD209 | CD4 | CD40 | CD80 | CD83 | CD86 | CMKLR1 | HLA-DOA |
| CD244 | CD52 | CD53 | CXCR3 | FCER2 | FUT4 | IL9R | ITGA4 | LAIR1 |
| CD40 | CD5 | CD69 | CD70 | CD79A | CD79B | CD80 | CD86 | CD93 |
| CD69 | ENPP3 | ICAM1 | IL3RA | LAMP1 | TLR4 |  |  |  |
| COL1A2 | COL6A1 | COL6A2 | COL6A3 |  |  |  |  |  |
| MMP1 | PDGFRA | TLR4 | THY1 | KIT | TIMP1 | ITGA4 | MMP9 | PDGFRB |
| 1TGB3 | PROCR | CDH5 | KDR | SELE | PECAM1 | ENG | ICAM 1 | FLT4 |
|  |  |  |  |  |  |  |  | NRP1 |
|  |  |  |  |  |  |  |  | PDCD1LG2 |

| Megakaryocyte | Myeloid Dendritic Cell | Naive T Cell | Neutrophil | NK Cell | Plasmacytoid Dendritic Cell | Platelet | T Follicular Helper |
|---|---|---|---|---|---|---|---|
| CD9 | CCR7 | CCR7 | ANPEP | B3GAT1 | CCR7 | BSG | BCL6 |
| GP1BA | CD1A | CD3D | C5AR1 | CD244 | CD1A | CCL5 | CD3D |
| ITGA2B | CD1B | CD3E | CD14 | CD69 | CD1B | CCR3 | CD3E |
| ITGAV | CD1C | CD3G | CD33 | IL2RB | CD1C | CD109 | CD3G |
| ITGAX | LAMP2 | LILRB4 | TLR2 | TLR4 |  |  |  |
| PRF1 |  |  |  |  |  |  |  |
| SELL | TNFRSF18 | TNFRSF4 |  |  |  |  |  |
| LINC-ROR | STAT3 |  |  |  |  |  |  |
| IL4 | IL5 | IL6 | PTGDR2 |  |  |  |  |
| TNFSF4 |  |  |  |  |  |  |  |
| CD9 | CNGB1 | CSF3R | FCGR2A | FCGR2B | GP1BA | ICAM2 | ITGA2 |
| ITGA4 | ITGAM | ITGAX | NRP1 | PDCD1LG2 | TLR9 |  |  |
| NKG2 | SIGLEC7 | SLAMF6 | SLAMF7 |  |  |  |  |
| PECAM 1 | SELL | TLR2 |  |  |  |  |  |
| ITGA4 | ITGAM | ITGAX | LY75 | NRP1 | PDCD1LG2 |  |  |
| HLA-DOB | HLA-DRA | HLA-DRB1 | HLA-DRB5 | HLA-DRB6 | ITGA4 | ITGAM | ITGAX |
| PTGDR2 | S100A9 | SIGLEC10 | SIGLEC8 |  |  |  |  |
| FCER2 | MS4A1 | PAX5 | PDCD1 | SDC1 | TNFRSF13B | TNFRSF13C | TNFRSF9 |
| MME | PECAM1 | TIMP2 | TLR1 | 1TGB1 | ICAM1 | ICAM2 | TLR2 |
| VCAM1 |  |  |  |  |  |  |  |
|  |  |  |  |  | ITGA6 |  |  |
|  |  |  |  |  | ITGAV |  |  |
|  |  |  |  |  | ITGB1 |  |  |
|  |  |  |  |  | ITGB3 |  |  |
|  |  |  |  |  | IAM3 |  |  |
|  |  |  |  |  | LAMP2 |  |  |

TABLE S3-continued

Table S3. Cell type signatures that were used for cell classification.

LRRC32
LYN
PECAM1
SELP
SPN
TNFSF14
VEGFA

| Th1 | Th2 | Th9 | Th17 | Th22 | Treg | Cytotoxic_T_cell | Macrophage |
|---|---|---|---|---|---|---|---|
| CCR1 | CCR3 | CD3D | CCR4 | AHR | CCR4 | CCL3 | CCR5 |
| CCR5 | CCR4 | CD3E | CCR6 | CCR10 | CD4 | CCL4 | CD14 |
| CD4 | CCR7 | CD3G | CD38 | CCR4 | CNGB1 | CD2 | CD163 |
| CSF2 | CCR8 | CD4 | CD3D | CCR6 | CTLA4 | CD3D | CD33 |
| ITGA2B | | | | | | | |
| LY75 | | | | | | | |
| TNFSF4 | | | | | | | |
| VCAM1 | | | | | | | |

The cell assignments that were obtained by these three different criteria were highly consistent (FIG. 5B, hypergeometric p-value<$10^{-16}$). Cells that were identified as potentially non-malignant according to one out of these three criteria were defined as non-malignant, and were omitted from further analyses of the malignant cells. The non-malignant cells were further classified into CAFs and endothelial cells, if they overexpressed the pertaining gene signatures, and as unresolved cells otherwise.

Classification of Immune Cells

To classify immune cells, Applicants first filtered CD45$^+$ cells that were potentially malignant or doublets of immune and malignant cells based on their inferred CNV profiles. To this end, Applicants defined the overall CNV level of a given cell as the sum of the absolute CNV estimates across all genomic windows. For each tumor, Applicants generated its CNV profile by averaging the CNV profiles of its malignant cells, when considering only those with the highest overall CNV signal (top 10%). Applicants then evaluate each cell by two values: (1) its overall CNV level, and (2) the Spearman correlation coefficient obtained when comparing the cell CNV profile to the CNV profile of its tumor. These two values were used to classify cells as malignant, non-malignant, and unresolved cells that were excluded from further analysis (FIG. 5C-E).

Next, Applicants applied two different clustering approaches to assign immune (CD45+) cells into cell types. In the first approach, Applicants clustered the CD45$^+$ cells according to 194 well-established markers of 22 immune cell subtypes (table S3; assembled from www.biolegend.com/cell markers and (5)). The clustering was performed in three steps: (1) Applicants computed the Principal Components (PCs) of the scRNA-seq profiles, while restricting the analysis to the 194 biomarker genes. Applicants used the top PCs that captured more than 50% of the cell-cell variation. In this case 10 PCs were used, but the results were robust and stable when using the first 5-15 PCs. (2) Applicants applied t-SNE (t-Distributed Stochastic Neighbor Embedding) to transform these first 10 PCs to a two-dimensional embedding, using the R implementation of the t-SNE method with the default parameters, as provided in lvdmaaten.github.io/tsne/. (3) Applicants applied a density clustering method, DBscan (11), on the two-dimensional t-SNE embedding that was obtained in (2). This process resulted in six clusters for which the top preferentially expressed genes included multiple known markers of particular cell types (FIG. 6).

To map between clusters and cell types Applicants compared (one sided t-test) each cluster to the other clusters according to the OE of the different cell-type signatures (table S3). The cell-type signature that was most significantly (t-test p-value<$10^{-10}$) overexpressed in the cluster compared to all other clusters was used to define the cluster identity. In this manner, Applicants annotated the clusters as CD8 and CD4 T cells, B cells, macrophages, and neutrophils (FIG. 1C). Cells that clustered with the CD8 T-cells and did not express CD8A or CD8B were labeled as NK cells if they overexpressed NK markers, otherwise they were considered as unresolved T-cells. T-cells that were clustered together with the CD4 T-cells and expressed CD8A or CD8B were also considered as unresolved T-cells. Unresolved T-cells were not used in further analyses of CD4 or CD8 T cells.

To assess the robustness of the assignments, Applicants applied another approach, and determined the concordance between the two assignments. In the second approach, Applicants first made initial cell assignments based on the OE of well-established cell-type makers: T-cells (CD2, CD3D, CD3E, CD3G), B-cells (CD19, CD79A, CD79B, BLK), and macrophages (CD163, CD14, CSF1R). Across all the CD45$^+$ cells, the OE levels of these signatures had binomial distributions. Applicants used the bimodal OE of each signature to assign cells to cell types (as described in section Overall Expression (OE) of gene signatures). Cells that were assigned to more than one cell type at this point were considered as unresolved. Cells that were defined as T-cells according to this measure were further classified as CD8 or CD4 T-cells if they expressed CD8 (CD8A or CD8B) or CD4, respectively. T-cells that expressed both CD4 and CD8 were considered as unresolved. As a result, 67.3% of the cells had an initial cell-type assignment.

Next, Applicants clustered the cells with the Infomap algorithm (12). Infomap decomposes an input graph into modules by deriving a compressive description of random walks on the graph. The input to the algorithm was an unweighted k-NN graph (k=50) that Applicants generated based on the expression of the 194 biomarker genes across the CD45$^+$ cells. Infomap produced 22 clusters, separating the different CD45$^+$ cells not only according to cell types but also according to various cell states. For each cluster, Applicants examined if it was enriched with cells of a specific cell type, according to the initial assignments. Nineteen clusters were enriched with only one cell type. The cells within these clusters were assigned to the cell type of their cluster, unless their initial assignment was different, and in this case, they were considered as unresolved.

The cell-type assignments that were obtained by the two approaches were highly concordant: 97% of the cells had the same assignment with both approaches.

Data-Driven Signatures of Specific Cell-Types

To identify cell-type signatures Applicants performed pairwise comparisons between the nine different cell types that Applicants identified: malignant cells, CD8 and CD4 T-cells, NK cells, B-cells, macrophages, neutrophils, CAFs, and endothelial cells. Applicants then performed pairwise comparisons between the different cell types via one-sided Wilcoxon ranksum-tests on the imputed and normalized data E' (see Data imputation and normalization). Genes that were overexpressed in a particular cell subtype compared to all other cell subtypes (Wilcoxon ranksum-test p-value<$10^{-5}$) were considered as cell-type specific. For cell types with less than 1,000 cells Applicants also ranked the genes based on the maximal p-value that was obtained when comparing the cell type to each of the other cell types; the bottom 100 genes that also passed the first filter were considered as cell type specific. As CD8 T-cells and NK cells had similar expression patterns, Applicants excluded NK cells from the analysis when identifying T-cell specific genes. In the analyses described above Applicants considered the CD4 and CD8 as one entity of T-cells, but also derived CD4 and CD8 specific signatures, by considering as separated entities. The lists of cell-type specific genes are provided in table S4.

Differential Expression Between TN and ICR

To identify potential signatures of resistance, Applicants searched for transcriptional features that distinguish between the cells of TN and ICR patients, for each cell category separately. Applicants analyzed each cell type that had a sufficient number (>100) of cells: malignant cells, macrophages, B cells, CD8 and CD4 T cells.

Applicants used sampling to mitigate the effects of outliers and prevent tumors with a particularly large number of cells of a given cell type from dominating the results. In each sampling, Applicants selected a subset of the tumors, sub-sampled at most 30 cells of the given type from each tumor, and identified differentially expressed genes between the ICR and TN cells. Differentially expressed genes were identified by applying SCDE (13), a Bayesian method that was specifically developed to detect single-cell differential expression. As input to SCDE Applicants used the normalized and imputed expression matrix E' (see Data imputation and normalization).

Applicants repeated the sampling procedure 500 times, and computed for each gene g the fraction of subsamples in which it was found to be significantly under ($F_{down,g}$) or over ($F_{up,g}$) expressed in the ICR population compared to the TN population (1z-score)>1.96). Genes with $F_{down,g}$ values larger than the 0.9 quantile of the $F_{down}$ distribution were considered as potentially down-regulated in the respective ICR population. Likewise, genes with $F_{up,g}$ values larger than the 0.9 quantile were considered as potentially up-regulated in the respective ICR population.

Applicants further filtered the signatures with two additional statistical tests that Applicants applied on the full scRNA-seq data (E') of the respective cell type (6). The first test was SCDE followed by multiple hypotheses correction (Holm-Bonferroni (14)). The second was a non-parametric empirical test, where Applicants performed a one-sided Wilcoxon ranksum test to examine if a given gene is differentially expressed in the ICR vs. TN cells. Applicants used E' and not the raw counts or log transformed TPM, as non-ordinal values violate the Wilcoxon ranksum assumptions. Applicants corrected for multiple hypotheses testing using the Benjamini & Hochberg approach (15), and obtained empirical p-values to ensure the differences in expression were not merely reflecting differences in cell quality (i.e., the number of aligned reads per cell). To this end Applicants generated 1,000 random permutations of the gene expression matrix E', such that each permutation preserves the overall distribution of each gene, as well as the association between the expression of each gene and cell quality. Applicants performed the Wilcoxon ranksum test on the permuted E' matrixes to compute the empirical p-values.

To assemble the final signatures, Applicants selected genes that fulfilled the subsampling criteria described above and were most significantly differentially expressed according to both the SCDE and empirical tests (top 200 genes with corrected P<0.05).

Mixed Effect Model for Testing the Differential Expression of Gene Signatures

To test the ability of a given gene signature to distinguish between the ICR and TN patients Applicants modeled the data with a mixed-effects model that accounts for the dependencies and structure in the data. Applicants used a hierarchical linear model (HLM) with two levels: (1) cell-level, and (2) sample-level. The sample-level controlled for the dependency between the scRNA-seq profiles of cells that were obtained from the same patient, having a sample-specific intercept. The model had overall five covariates. Level-1 covariates were the number of reads (log-transformed) and the number of genes that were detected in the respective cell. Level-2 covariates were the patient's gender, age, and treatment group, and a binary covariate that denotes if the sample was a metastatic or primary lesion. In the analyses of malignant cells, Applicants added another level-1 covariate that denoted which cells where cycling, based on the bimodal OE of the cell cycle signatures defined in (1) (see section Overall Expression (OE) of gene signatures).

To examine if a given signature was differentially expressed in the ICR compared to the TN group Applicants used the HLM model to quantify the significance of the association between each of the model covariates and the OE of the signature across the cells. Applicants applied this approach to examine the association between the treatment and the OE of the ICR and exclusion signatures. Applicants also tested annotated gene sets that Applicants downloaded from MSigDB v6.0 (16) to examine if certain pre-defined pathways and biological functions were differentially expressed in the ICR vs. TN cells (table S9, FIG. 2C).

Applicants implemented the HLM model in R, using the lme4 and lmerTest packages (CRAN.R-project.org/package=lme4, CRAN.R-project.org/package=lmerTest).

Cross Validation Analysis

To examine the generalizability of the oncogenic-ICR (mICR) signatures Applicants performed a cross-validation procedure. In each cross-validation round the test set consisted of all the cells of one patient, and the training set consisted of the data from all the other patients in the cohort. In each round Applicants used only the training data to generate mICR signatures (as described in Differential expression between TN and ICR), and computed the OE of the resulting mICR signatures in the cells of the test patient to obtain their resistance scores (mICR-up minus mICR-down). To center the expression matrix for the computation of the OE values, Applicants used all the malignant cells in the data, such that the resistance scores of one patient were relative to those of the other patients.

Integrating the Exclusion and Post-Treatment Programs

Applicants combined the post-treatment and exclusion programs with a simple union of the matching signatures, into the immune resistance gene program (Table S5). Applicants further refined the immune resistance program by integrating the scRNA-seq data with the results of a genome-scale CRISPR screen that identified gene KOs which sensitize malignant melanoma cells to T cell killing (Patel et al., 2017). Applicants defined our single malignant cells as putatively "resistant" if they underexpressed (lowest 1%) of one of the top hits of the screen: B2M, CD58, HLA-A, MLANA, SOX10, SRP54, TAP2, TAPBP. This underexpression did not reflect low cell quality, because these "resistant" cells had a higher number of genes and reads. These cells had significantly higher immune resistance scores ($P=2.24*10^{-18}$ and $1.59*10^{-3}$, t-test and mixed effects, respectively), and were enriched with cycling cells ($P=1.74*10^{-13}$, hypergeometric test). Applicants identified the topmost differentially expressed genes by comparing the "resistant" cells to other malignant cells, and included in the refined immune resistance-up (down) signature only 25 (35) immune resistance-up (down) genes that pass this additional differential expression test.

Figure 54E:
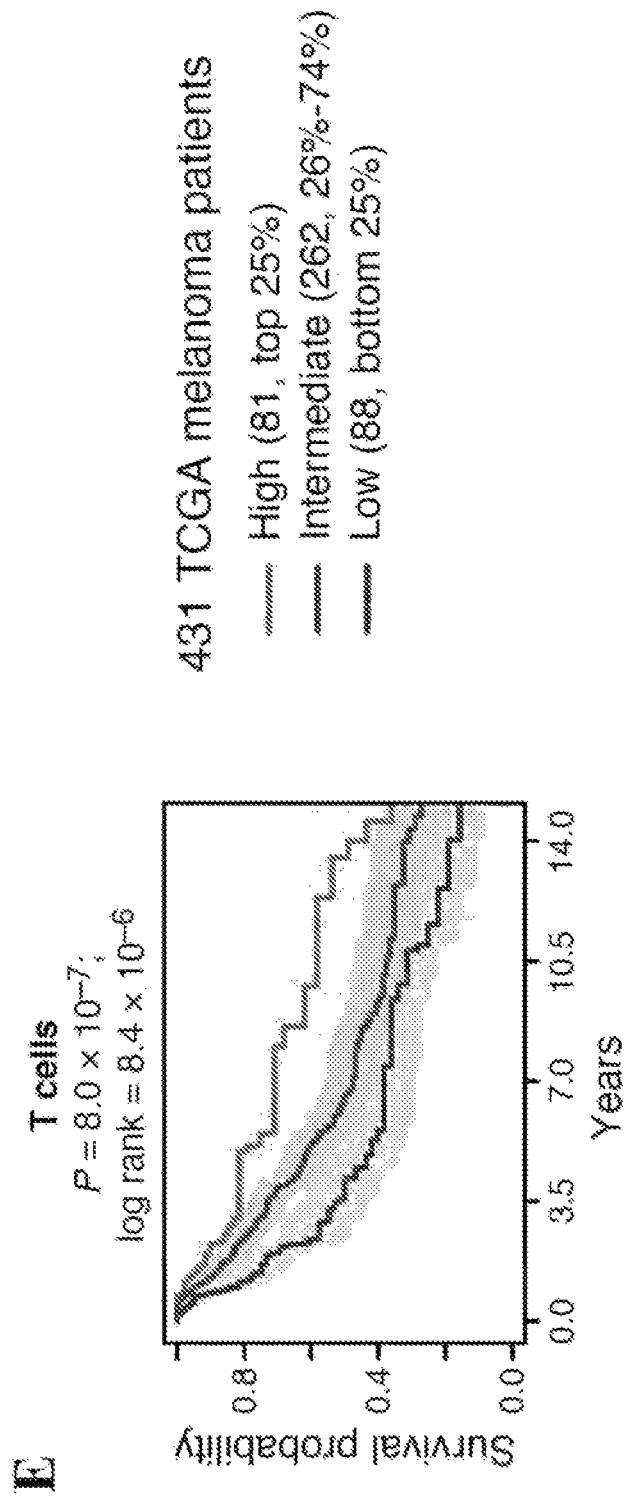
FIG. 54. The immune resistance program predicts survival of TCGA melanoma patients; related to FIG. 48. Kaplan-Meier (KM) plots stratified by high, intermediate or low Over expression of the respective signature in bulk RNA-Seq of TCGA tumors. P: COX regression p-value; Pc: COX regression p-value that tests if the program further enhances the predictive power of a model with inferred T cell infiltration levels as a covariate.

Applicants report the performances of all the resistance program subsets: exclusion, post-treatment, and their union (FIGS. 54-55). As comparators, Applicants used the hits of the co-culture screen along with other potentially prognostic signatures, to generate competing predictors of patient survival and response (FIGS. 5E,H, Table S7, see section Competing ICI response predictors).

T Cell Cytotoxicity and Exhaustion Signature Analysis

The analysis of T-cell exhaustion vs. T-cell cytotoxicity was performed as previously described (5), with six different exhaustion signatures, as provided in (1) and (17). First, Applicants computed the cytotoxicity and exhaustion scores of each CD8 T cell. Next, to control for the association between the expression of exhaustion and cytotoxicity markers, Applicants estimated the relationship between the cytotoxicity and exhaustion scores using locally-weighted polynomial regression (LOWESS, black line in FIG. 1E and FIG. S4B). Based on these values, Applicants defined T cells as functional if they fulfilled two criteria: (1) their cytotoxicity score was at the top 20% of the CD8 T cell population (across all patients), and (2) their exhaustion scores were lower than expected given their cytotoxicity scores (below the dashed line in FIG. 1E and FIG. 4SB). Applicants then applied a hypergeometric test to examine if the CD8 T cells of a given patient were enriched with functional cells.

Identifying T Cell Clones and Estimating the Fraction of Clonally Expanded T-Cells Applicants reconstructed the T-cell Receptors (TCRs) using TraCeR (18), with the Python package provided in github.com/Teichlab/tracer. TCR reconstruction significantly improved in the new cohort compared to previously analyzed patients (table Si): 92% CD8 T-cells had reconstructed TCRs, compared to only 50% such cells in the previously published cohort (FIG. 9A). This is likely due to shorter read length and lower sequencing depth in the previous study (1). Applicants assigned T cells to the clones defined in the TraCeR output. Reassuringly, cells from different patients were never falsely assigned to the same clone, and CD8 and CD4 T-cells were always assigned to different clones, even when they were obtained from the same tumor. In the CD8 T-cells Applicants detected 137 clones (FIG. 1F). In the CD4 T-cells Applicants detected only 29 clones, with at most 3 cells per clone.

The size and number of clones that Applicants identified in each tumor is affected by the number of T-cells that were sequenced from that tumor, and the success rate of TCR reconstruction. To estimate the fraction of clonally expanded T-cells in a given tumor Applicants therefore sampled its T-cells as follows. First, Applicants restricted the analysis to tumors with at least 20 CD8 T-cells with a full-length reconstructed TCR. Next, Applicants repeatedly sampled 20 cells from each tumor, such that, in each iteration, Applicants computed for every tumor the fraction of clonally expanded cells, namely, the fraction of sampled cells that shared their TCR with another cell within the sampled population. The average fraction of clonally expanded cells was used as an estimate of the T-cell clonal expansion level (FIG. 9B).

Cell Cycle Analysis

Applicants performed the following analysis to identify gene modules that characterize cycling cells specifically in CD8 T-cells (table S8). First, Applicants identified cycling cells in the CD8 T-cells and in the malignant cells based on the bimodal OE of a cell-cycle signature (the GO gene set cell cycle process, as defined in the Overall Expression (OE) of gene signatures section). Applicants then identified differentially expressed genes (with SCDE (13)) between the cycling and non-cycling cells, separately in the CD8 T-cells and in the malignant cells. Lastly, Applicants filtered from the resulting CD8 T-cell cycling signatures the genes that were also included in the corresponding malignant signatures.

Characterizing Malignant Cells in Non-Infiltrated Tumors

Applicants developed an approach that combines scRNA-seq and bulk RNA-seq data to characterizes the state of a specific cell type in tumors with a specific cell-type composition. Applicants applied it to identify oncogenic programs that are induced or repressed in malignant cells that reside in tumors or niches with low T-cell infiltration levels. For clarity, Applicants describe the approach for this specific application, but note that it can also be applied in various other settings, as long as the tumor composition can be well-defined, and the cell type of interest is adequately represented in the single-cell data.

Applicants implemented the following step-wise approach (FIG. 2F):

1. Applicants provided as input the signature of malignant cells and the signature of T-cells, defined above (section: Cell-type specific signatures).

2. Applicants obtained the bulk RNA-Seq data of 473 Skin Cutaneous Melanoma (SKCM) tumors from TCGA (as provided in xenabrowser.net/datapages/). On this bulk data Applicants (a) estimated of the T-cell infiltration level in each tumor by computing the OE of the T-cell signature in each of the bulk samples; (b) computed the Spearman correlation coefficient between the expression of each of the genes in the malignant signature and the OE of the T-cell signature across the 473 bulk tumors; and (c) defined the seed exclusion-up (down) signature as the top 20 malignant genes that were significantly negatively (positively) correlated in (b).

3. Applicants analyzed the scRNA-Seq data of the malignant cells in the following way. (a) Applicants computed the OE of the seed $T_{exc}$ signatures in each of the malignant cell profiles; (b) Applicants computed the partial Spearman correlation coefficient between the expression of each gene and the OE of the seed $T_{exc}$ signatures across the single malignant cells, while controlling for technical quality (the number of reads and genes that were detected in the cells).

4. Applicants derived the final genome-scale exclusion signatures, defined as: (i) exclusion-up: Genes which are significantly positively correlated with the seed $T_{exc}$-up signature and significantly negatively correlated with the seed $T_{exc}$-down signature; and (ii) exclusion$_c$-down: Genes which are significantly positively correlated with the seed $T_{exc}$-down signature and significantly negatively correlated with the seed exclusion-up signature. In this analysis, a gene was defined as significantly correlated with a signature if it was among the 200 topmost correlated genes, with P-value<$10^{-10}$, and |R|>0.1.

Integration of the Exclusion and Oncogenic-ICR Signatures

Applicants combined the mICR and Tex, signatures with a simple union of the matching signatures, into the uICR gene signatures. Applicants further refined the uICR signatures by identifying putative "resistant" malignant cells as those that underexpressed (lowest 1%) one of the top hits of a CRISPR screen (19) in malignant melanoma for resistance to T-cell killing: B2M, CD58, HLA-A, MLANA, SOX10, SRP54, TAP2, TAPBP. (This under-expression did not reflect low cell quality, because these "resistant" cells had a higher number of genes and reads. These cells had significantly higher uICR scores (P=$2.24*10^{-18}$ and $1.59*10^{-3}$, t-test and mixed effects, respectively), and were enriched with cycling cells (P=$1.74*10^{-13}$, hypergeometric test).) Applicants the topmost differentially expressed genes by comparing the "resistant" cells to other malignant cells (13), and included in the refined uICR-up (down) signature only 25 (35) uICR-up (down) genes that pass this additional differential expression test.

Applicants report the performances of all the resistance signatures: oncogenic-ICR, exclusion, and their union (uICR), with and without this additional refinement (FIGS. 11-13). For comparison, Applicants used the hits of the co-culture screen along with other potentially prognostic signatures, to generate competing predictors of patient survival and response (FIG. 4, E,H, table S10, see section Competing ICR predictors).

Cell-Cell Interaction Network

Applicants generated genome-scale cell-cell interactions networks by integrating (1) protein-protein interactions that were previously assembled by (20) as cognate ligand-receptor pairs, with (2) cell-subtype specific signatures from the single-cell profiles, identified as described above. The resulting network maps the physical interactions between the different cell subtypes that Applicants characterized. Each cell subtype and protein are represented by a node in the network. An edge between a cell subtype node and a ligand or receptor node denotes that this protein is included in the cell subtype signatures. An edge between two proteins denotes that they can physically bind to each other and mediate cell-cell interactions. A path from one cell subtype to another represents a potential route by which the cells can interact. For each cell subtype, Applicants defined a 'communication signature', which includes all the surface proteins that bind to the cell subtype signature proteins. To examine if the ICR malignant cells suppress their interactions with other cell subtypes Applicants examined if the different oncogenic resistance signatures were enriched (hypergeometric test) with genes from the different immune and stroma communication signatures' (FIG. 3E). An interactive map of the cell-cell interaction network is provided as supplementary files, and can be explored with Cytoscape (21) provided in www.cytoscape.org.

Survival and ICI-Response Predictions

To test if a given signature can predict survival or progression free-survival (PFS) Applicants first computed the OE of the signature in bulk RNA-Seq in each patient tumor. Next, Applicants used a Cox regression model with censored data to compute the association and its significance. To examine if the signature's predictive value was significant beyond T-cell infiltration levels Applicants computed for each sample the OE of the T-cell signature (above), used this as another covariate in the Cox regression model, and computed another p-value for the given signature, based on its association with survival or PFS in this two-covariate model.

To visualize the predictions of a specific signature in a Kaplan Meier (KM) plot, Applicants stratified the patients into three groups according to the OE of the signature: high or low expression correspond to the top or bottom 25% of the population, respectively; intermediate expression is between the upper and lower quartiles (26%-74%, interquartile range). Applicants used a one-sided logrank test to examine if there was a significant difference between these three patient groups in terms of their survival or PFS rates.

CB was defined according to the RECIST criteria, such that patients with a complete or partial response were defined as CB patients. Patients with progressive disease were defined as non-CB, and patients with more ill-defined response, as stable disease or marginal responses were excluded from this analysis. Applicants further stratified the CB patients according to the duration of the response: (1) less than 6 months, (2) more than 6 months and less than a year, and (3) more than a year (long-term CB). Applicants then applied one-sided t-tests to examine if the OE of the different signatures were differentially expressed in the CB vs. non-CB patients, or in the long-term CB patients compared to the non-CB patients. Finally, Applicants tested the ability of the different signatures to predict complete response by comparing (t-test) between the complete responders and the all other patients with a RECIST annotation (n=101, FIG. 4I1 and FIG. 14), and computing the Area Under the Curve (AUC) of the resulting Receiver Operating Characteristic (ROC) curve.

Multiplexed, Tissue Cyclic Immunofluorescence (t-CyCIF) of FFPE Tissue Slides

Formalin-fixed, paraffin-embedded (FFPE) tissue slides, 5 μm in thickness, were generated at the Brigham and Women's Hospital Pathology Core Facility from tissue blocks collected from patients under IRB-approved protocols (DFCI 11-104). Multiplexed, tissue cyclic immunofluorescence (t-CyCIF) was performed as described recently (Lin et al., 2017). For direct immunofluorescence, Applicants used the following antibodies: CEP170 (Abcam, ab84545), LAMP2 (R&D technologies, AF6228), MITF (Abcam, ab3201), DLL3 (Abcam, ab103102, Rab), MITF (Abcam, ab3201, Ms), S100a-488 (Abcam, ab207367), CD3-555 (Abcam, ab208514), CD8a-660 (eBioscience, 50-0008-80), cJUN-488 (Abcam, ab 193780), cMyc-555 (Abcam, ab201780), HLAA-647 (Abcam, ab199837), TP53-488 (Cell Signaling, 5429), SQSTM1-555 (Abcam, ab203430). Stained slides from each round of CycIF were imaged with a CyteFinder slide scanning fluorescence microscope (RareCyte Inc. Seattle WA) using either a 10× (NA=0.3) or 40× long-working distance objective (NA=0.6). Imagers software (RareCyte Inc.) was used to sequentially scan the region of interest in 4 fluorescence channels. Image processing, background subtraction, image registration, single-cell segmentation and quantification were performed as previously described (Lin et al., 2017).

Mapping Cell-Cell Interactions Based on Imaging Data

Given the processed imaging data, Applicants assigned cells into cell types by discretizing the log-transformed expression levels of the cell type markers (S100, MITF, CD3, and CD8). Applicants applied the EM algorithm for mixtures of normal distributions to characterize the two normal distributions for each of these cell type marker intensities. $S100^+/MITF^+/CD3^-/CD8^-$ cells were defined as malignant cells; $S100^-/MITF^-/CD3^+/CD8^-$ cells were defined as T cells, and $S100^-/MITF^-/CD3^+/CD8^+$ cells were defined as CD8 T cells; other cells were defined as uncharacterized.

For each image Applicants constructed a Delaunay (Gabriel) graph, where two cells are connected to each other if there is no other cell between them. Following the approach presented in (Goltsev et al., 2017), Applicants examined if cells of certain types were less/more likely to be connected to each other in the graph. To this end, Applicants computed the odds ratio of cell-cell interactions of cell type A and cell type B by computing the observed frequency of interactions divided by the expected theoretical frequency (calculated as the total frequency of edges incident to type A multiplied by the total frequency of edges incident to type B). Two cell types are less or more likely to interact than expected by chance if the log-transformed odds ratio is less or more than 0, respectively. The significance of the deviation from zero was tested using the binomial distribution test.

Next, Applicants examined the association between the expression of the different markers in the malignant cells and the level of T cell infiltration. Each image in our data was composed of a few hundred frames (119-648 frames/image), where each frame consists of 1,377 cells on average. In each frame, Applicants computed the fraction of T cells and the average expression of the different markers in the malignant cells. Applicants then used a hierarchical logistic regression model to quantify the associations. The independent variables included the average expression of the marker in the malignant cells of the frame (level-1), the average expression of normalization markers in the malignant cells of the frame (level-1), and the image the frame was sampled from (level-2). The dependent variable was the discretized T cell infiltration level of the frame, defining frames with high/low lymphocyte-fraction as "hot"/"cold", respectively. Applicants used different cutoffs to define hot/cold frames, such that a frame with a T cell fraction<Q was defined as cold. Applicants report the results that were consistent across multiple definitions of Q, and provide the p-value obtained with Q=the median T cell fraction across all frames from all images.

Integrating scRNA-Seq and Spatial Data

Applicants integrated the scRNA-seq and multiplexed immunofluorescence (t-CyCIF) data via a variant of Canonical Correlation Analysis (CCA), using the code provided in the R toolkit Seurat (Butler and Satija, 2017). CCA aims to identify shared correlation structures across datasets, such that each dataset provides multiple measurements of a gene-gene covariance structure, and patterns which are common to both datasets are identified. Cells from both sources are then represented in an aligned-CCA space (Butler and Satija, 2017).

In our application, each cell in the t-CyCIF data was represented by the log-transformed intensities of 14 markers. Each cell in the scRNA-seq data was represented by the imputed expression of the genes encoding the same 14 proteins. To impute the scRNA-seq data Applicants identified a signature for each marker, consisting of the top 50 genes which were mostly correlated with the marker expression across the cell population in the scRNA-seq data. Applicants then used the OE of the marker signature as a measure of its activity in the scRNA-seq data.

The cells from both sources were represented in the resulting aligned-CCA space. Next, Applicants used the first five aligned-CCA dimensions to cluster the cells and represented them in a 2D t-SNE embedding (Laurens Maaten, 2009). Clustering was preformed using a shared nearest neighbor (SNN) modularity optimization based clustering algorithm, which calculates k-nearest neighbors, constructs an SNN graph, and optimizes the modularity function to determine clusters (Waltman and van Eck, 2013).

To examine if cells clustered according to cell type or according to source Applicants computed the expected number of cells from each two categories to be assigned to the same cluster by chance, assuming a random distribution of cells into clusters. Applicants then used the observed vs. expected co-clustering ratio to quantify the deviation from the random distribution, and used the binomial test to compute the statistical significance of this deviation from random.

Survival and ICI-Response Predictions

To test if a given signature predicts survival or progression free-survival (PFS) Applicants first computed the OE of the signature in each tumor based on the bulk RNA-Seq data. Next, Applicants used a Cox regression model with censored data to compute the significance of the association between the OE values and prognosis. To examine if the signature's predictive value was significant beyond T cell infiltration levels Applicants computed for each sample the OE of our T cell signature (above), used this as another covariate in the Cox regression model, and computed another p-value for each signature, based on its association with survival or PFS in this two-covariate model.

To visualize the predictions of a specific signature in a Kaplan Meier (KM) plot, Applicants stratified the patients into three groups according to the OE of the signature: high or low expression correspond to the top or bottom 25% of the population, respectively, and intermediate otherwise. Applicants used a one-sided log-rank test to examine if there was a significant difference between these three patient groups in terms of their survival or PFS rates.

CB was defined according to RESICT criteria, such that patients with a complete or partial response were defined as CB patients. Patients with progressive disease were defined as non-CB, and patients with more ill-defined response, such as stable disease or marginal responses, were excluded from this analysis. Applicants further stratified the CB patients according to the duration of the response: (1) less than 6 months, (2) more than 6 months and less than a year, and (3) more than a year (long-term CB). Applicants applied one-sided t-tests to examine if the OE of the different signatures were differentially expressed in the CB vs. non-CB patients, or in the long-term CB patients compared to the non-CB patients. Finally, Applicants tested the ability of the different signatures to predict complete response by comparing (t-test) between the complete responders and all other patients with a RECIST annotation (n=101, FIGS. 5H and 55F), and computing the Area Under the Curve (AUC) of the resulting ROC curve.

Controlling for Cell Cycle Effects in the Resistance OE Scores

The single-cell data demonstrated that cycling cells have higher expression of resistance states, according to the oncogenic-ICR, exclusion, and uICR signatures. Since the tumor proliferation rate may be a dynamic and context-dependent property, it might be advisable to compare between tumors based on their basal resistance level, namely, after controlling for the cell cycle effect. To this end, Applicants compute for each tumor the OE of two cell cycle signatures (G1/S and G2/M signatures in table S10). Applicants then fitted a linear model to estimate the expected OE of the resistance signature, when using the OE of the two cell cycle signatures as covariates. The residuals of this linear model, which quantify the deviation from the expected resistance OE values, were considered as the basal resistance level. Applicants preformed this analysis with different resistance signatures (e.g., uICR, exclusion, etc.).

Alternative ICR Predictors

To compare the predictive value of the resistance signature to that of other signatures, Applicants repeated the prediction process, as describe in Survival and ICI-response predictions, for each of the following gene signatures (table S10): (1) Cell-type specific signatures identified from the scRNA-Seq (as described in the Cell-type specific signatures section); (2) Signatures that characterize oncogenic cell states in melanoma (the AXL-high, MITF-high, and cell cycle states from (1)); (3) Six different sets of genes whose guides were found to be differentially (FDR<0.05) depleted or enriched in the in vivo CRISPR screen of (22), designed to identify key regulators of immune evasion and ICR in melanoma, based on the pairwise comparisons of three experimental settings. The data was obtained from Table S1 of (22); (4) The genes whose guides were most preferentially and significantly enriched (top 10 and top 50) in the co-culture conditions in the genome-scale CRISPR screen of (19), also designed to identify key regulators of immune evasion and ICR in melanoma; (5) Immune-related signatures that were identified based on the analysis of multiple Pembrolizumab clinical datasets, and were shown to predict the response to Pembrolizumab in an independent cohort (23); (6) The Fluidigm Advanta™ Immuno-Oncology Gene Expression signatures (www.fluidigm.com/applications/advanta-immuno-oncology-gene-expression-assay); and (7) PDL1 expression.

Applicants summarize in table S10 the predictive value of each of these signatures when applied to predict melanoma (TCGA) patient survival, and the PFS, clinical benefit (CB), and complete response in the melanoma patients of the aPD1 cohort.

Comparison of Pre- and Post-Treatment Samples in Validation Cohort 2

Applicants used a mixed-effects model to represent the data and examine the association between the expression of various gene signatures and different treatment categories. The model included two levels. The first, sample-level, had 12 covariates, the first three denote whether the sample was exposed to: (1) targeted therapy (on/post RAF/MEK-inhibitors), (2) ICI (on/post), with or without an additional immunotherapy, (3) non-ICI immunotherapy (NK antibodies, IL2, IFN, or GM CSF) without ICI. The other 9 sample-level covariates control for potential changes in the tumor microenvironment by providing the OE of the different non-malignant cell subtype signatures that Applicants identified (table S4). The second, patient-level, controlled for the dependency between the scRNA-seq profiles of samples that were obtained from the same patient, having a patient-specific intercept that provided the baseline level for each patient.

Applicants used the mixed effects model to quantify the association between the different ICR signatures and the exposure to ICI or targeted therapy (the second and first sample-level covariates, respectively). When testing the association between the tumor composition and the treatments Applicants used the model described above without the 9 TME covariates.

Applicants implemented the HLM model in R, using the lme4 and lmerTest packages (CRAN.R-project.org/package=lme4, CRAN.R-project.org/package=lmerTest).

For each resistance signature, Applicants applied ANOVA to test if the inter-patient variation in the OE values was significantly greater than the intra-patient variation, and reported the least significant ANOVA p-value that was obtained.

Searching for Immune Sensitizing Drugs

Applicants performed the following analysis to identify drugs that could selectively eradicate malignant cells with a high expression of the resistance program, using efficacy measures of 131 drugs across 639 human cancer cell lines (Garnett et al., 2012). For each drug, Applicants defined sensitive cell lines as those with the lowest (bottom 10%) IC50 values. Applicants then used the gene expression provided in (Garnett et al., 2012), computed the OE of the resistance program in each of the 639 cells, and defined "resistant" cell lines as those with the highest OE values (top 10%). Next, for each drug Applicants built a hierarchical logistic regression model, where the dependent variable is the cell line's (drug-specific) binary sensitivity assignment, and the independent variables are the cell lines' "resistance" assignments (level-1) and cancer types (level-2). Drugs then were ranked based on the one-tailed p-values that quantify the significance of the positive association between the drug sensitivity (dependent) variable and the immune resistance (independent) variable.

Abemaciclib Treatment of Melanoma Cell Lines

Established melanoma cell lines IGR39, UACC62 and A2058 were acquired from the Cancer Cell Line Encyclopedia (CCLE) from the Broad Institute. Cells were treated every 3 days with 500 nM abemaciclib (LY2835219, MedChemExpress) or DMSO control. The doubling time of each cell line was established and lines were seeded such that cells collected for scRNA-seq were derived from culture dishes with ~50-60% confluency on day 7 of treatment. Cells were lifted off culture dishes using Versene solution (Life Technologies), washed twice in 1x PBS, counted and resuspended in PBS supplemented with 0.04% BSA for loading for scRNA-seq with the 10x Genomics platform.

Melanoma-TIL Co-Culture

An autologous pair of melanoma and TIL culture was provided by MD Anderson Cancer Center and were established using previously described protocols (Peng et al., 2016). Melanoma cells were pre-treated with 500 nM abemaciclib or DMSO control for 7 days followed by co-culture with autologous TILs (with an effector to target ratio of 5:1) for 48 hours. TILs were removed by pipetting of the supernatant, and the remaining melanoma cells were washed twice with PBS, lifted off the culture dish, and resuspended in PBS supplemented with 0.04% BSA for loading for scRNA-seq with the 10x Genomics platform.

Data Availability

Processed scRNA-seq data generated for this study is currently provided through the single-cell portal in a 'private' mode. To access the data login to the portal (portals.broadinstitute.org/single_cell) via the email account icr.review1@gmail.com, with the password icrreview1, and use the following link to view or download the data portal s.broadinstitute.org/single_cell/study/melanoma-immunotherapy-resistance. The processed data will also be available through the Gene Expression Omnibus (GEO), and raw scRNA-seq data will be deposited in dbGAP.

References for Materials and Methods

1. I. Tirosh et al., Dissecting the multicellular ecosystem of metastatic melanoma by single-cell RNA-seq. Science 352, 189-196 (2016).

2. S. Picelli et al., Smart-seq2 for sensitive full-length transcriptome profiling in single cells.
3. J. J. Trombetta et al., Preparation of Single-Cell RNA-Seq Libraries for Next Generation Sequencing.
4. B. Langmead, M. Trapnell C Fau-Pop, S. L. Pop M Fau-Salzberg, S. L. Salzberg, Ultrafast and memory-efficient alignment of short DNA sequences to the human genome.
5. B. Li, C. N. Dewey, RSEM: accurate transcript quantification from RNASeq data with or without a reference genome.
6. J. Fan et al., Characterizing transcriptional heterogeneity through pathway and gene set overdispersion analysis. Nat Meth 13, 241-244 (2016).
7. A. K. Shalek et al., Single-cell transcriptomics reveals bimodality in expression and splicing in immune cells. Nature 498, 236-240 (2013).
8. A. Wagner, A. Regev, N. Yosef, Revealing the vectors of cellular identity with single-cell genomics. Nat Biotech 34, 1145-1160 (2016).
9. A. K. Shalek et al., Single-cell RNA-seq reveals dynamic paracrine control of cellular variation. Nature 510, 363-369 (2014).
10. A. P. Patel et al., Single-cell RNA-seq highlights intratumoral heterogeneity in primary glioblastoma. Science (New York, N.Y.) 344, 1396-1401 (2014).
11. M. Ester, H.-P. Kriegel, #246, r. Sander, X. Xu, paper presented at the Proceedings of the Second International Conference on Knowledge Discovery and Data Mining, Portland, Oregon, 1996.
12. M. Rosvall, C. T. Bergstrom, Maps of random walks on complex networks reveal community structure. Proceedings of the National Academy of Sciences 105, 1118-1123 (2008).
13. P. V. Kharchenko, L. Silberstein, D. T. Scadden, Bayesian approach to single-cell differential expression analysis. Nat Meth 11, 740-742 (2014).
14. S. Holm, A Simple Sequentially Rejective Multiple Test Procedure. Scandinavian Journal of Statistics 6, 65-70 (1979).
15. Y. Benjamini, Y. Hochberg, Controlling the False Discovery Rate: A Practical and Powerful Approach to Multiple Testing. Journal of the Royal Statistical Society. Series B (Methodological) 57, 289-300 (1995).
16. A. Subramanian et al., Gene set enrichment analysis: A knowledge-based approach for interpreting genome-wide expression profiles. Proceedings of the National Academy of Sciences 102, 15545-15550 (2005).
17. C. Zheng et al., Landscape of Infiltrating T Cells in Liver Cancer Revealed by Single-Cell Sequencing.
18. M. J. T. Stubbington et al., T cell fate and clonality inference from single cell transcriptomes. Nat Meth 13, 329-332 (2016).
19. S. J. Patel et al., Identification of essential genes for cancer immunotherapy. Nature 548, 537-542 (2017).
20. J. A. Ramilowski et al., A draft network of ligand-receptor-mediated multicellular signalling in human. 6, 7866 (2015).
21. P. Shannon et al., Cytoscape: A Software Environment for Integrated Models of Biomolecular Interaction Networks. Genome Research 13, 2498-2504 (2003).
22. R. T. Manguso et al., In vivo CRISPR screening identifies Ptpn2 as a cancer immunotherapy target. Nature 547, 413-418 (2017).
23. M. Ayers et al., IFN-related mRNA profile predicts clinical response to PD-1 blockade. The Journal of Clinical Investigation 127, 2930-2940 (2017).
24. S. Goel et al., CDK4/6 inhibition triggers anti-tumour immunity. Nature 548, 471-475 (2017).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of treating a cancer in a subject comprising detecting whether an immune checkpoint inhibitor resistance (ICR) gene signature is expressed in malignant cells from a solid tumor sample obtained from the subject and administering a treatment,
wherein the ICR gene signature comprises upregulation of C1QBP, CCT2, CCT6A, DCAF13, EIF4A1, ILF2, MAGEA4, NONO, PA2G4, PGAM1, PPA1, PPIA, RPL18A, RPL26, RPL31, RPS11, RPS15, RPS21, RPS5, RUVBL2, SAE1, SNRPE, UBA52, UQCRH and VDAC2; and, optionally, downregulation of AEBP1, AHNAK, APOC2, APOD, APOE, B2M, C10orf54, CD63, CTSD, EEA1, EMP1, FBXO32, FYB, GATSL3, HCP5, HLA-A, HLA-B, HLA-C, HLA-E, HLA-F, HLA-H, ITGA3, LAMP2, LYRM9, MFGE8, MIA, NPC2, NSG1, PROS1, RDH5, SERPINA1, TAPBP, TIMP2, TNFSF4 and TRIML2, as compared to a reference level,
wherein if an ICR gene signature is detected in malignant cells the treatment comprises administering an agent capable of reducing expression or activity of said signature, wherein the agent comprises a small molecule CDK4/6 inhibitor selected from the group consisting of abemaciclib, palbociclib, and ribociclib, and
wherein if an ICR gene signature is not detected the treatment comprises administering an immunotherapy.

2. The method according to claim 1, wherein the method further comprises:
detecting whether the ICR signature is expressed in a tumor obtained from the subject after the treatment with the agent comprising a small molecule CDK4/6 inhibitor and administering an immunotherapy if said signature is reduced or below a reference level.

3. The method according to claim 1, wherein the immunotherapy comprises a check point inhibitor or adoptive cell transfer (ACT).

4. The method according to claim 3, wherein adoptive cell transfer comprises a CAR T cell or activated autologous T cells and wherein the checkpoint inhibitor comprises anti-CTLA4 or anti-PD1 therapy.

5. A method of treating a cancer in a subject comprising administering to the subject a therapeutically effective amount of an agent comprising a small molecule CDK4/6 inhibitor selected from the group consisting of abemaciclib, palbociclib, and ribociclib,
wherein the subject was treated with immune checkpoint inhibitors (ICI) and is resistant, and
wherein the subject has a solid tumor that expresses an ICR gene signature in malignant cells, said gene signature comprising upregulation of C1QBP, CCT2, CCT6A, DCAF13, EIF4A1, ILF2, MAGEA4, NONO, PA2G4, PGAM1, PPA1, PPIA, RPL18A, RPL26, RPL31, RPS11, RPS15, RPS21, RPS5, RUVBL2, SAE1, SNRPE, UBA52, UQCRH and VDAC2; and, optionally, downregulation of AEBP1, AHNAK, APOC2, APOD, APOE, B2M, C10orf54, CD63, CTSD, EEA1, EMP1, FBXO32, FYB, GATSL3, HCP5, HLA-A, HLA-B, HLA-C, HLA-E, HLA-F, HLA-H, ITGA3, LAMP2, LYRM9, MFGE8, MIA, NPC2, NSG1, PROS1, RDH5, SERPINA1, TAPBP, TIMP2, TNFSF4 and TRIML2, as compared to a reference level.

6. The method according to claim 5, wherein the small molecule CDK4/6 inhibitor is abemaciclib.

7. The method according to claim 5, wherein the method further comprises administering an immunotherapy to the subject.

8. The method of claim 7, wherein the immunotherapy comprises a check point inhibitor.

9. The method of claim 8, wherein the checkpoint inhibitor comprises anti-CTLA4 or anti-PD1 therapy.

10. The method according to claim 1, wherein the small molecule CDK4/6 inhibitor is abemaciclib.

* * * * *

UNITED STATES PATENT AND TRADEMARK OFFICE
CERTIFICATE OF CORRECTION

| | |
|---|---|
| PATENT NO. | : 11,913,075 B2 |
| APPLICATION NO. | : 16/499908 |
| DATED | : February 27, 2024 |
| INVENTOR(S) | : Aviv Regev et al. |

It is certified that error appears in the above-identified patent and that said Letters Patent is hereby corrected as shown below:

On the Title Page

On the page 3, in Column 1, under "Other Publications", Line 42, delete "of" and insert -- for --.

On the page 3, in Column 2, under "Other Publications", Line 56, delete "Immuno Therapy" and insert -- ImmunoTherapy --.

In the Specification

In Column 1, Line 23, delete "CA14051" and insert -- CA014051 --.

In Column 1, Line 59, delete "WNT-B" and insert -- WNT-β --.

In Column 1, Line 67, delete "non malignant" and insert -- non-malignant --.

In Column 3, Line 8, delete "EEF1 G," and insert -- EEF1G, --.

In Column 3, Line 23, delete "RPL13 AP5," and insert -- RPL13AP5, --.

In Column 6, Line 34, delete "1E135," and insert -- IFI35, --.

In Column 7, Line 59, delete "RPL13 AP5," and insert -- RPL13AP5, --.

In Column 9, Line 1, delete "EIF2 S3," and insert -- EIF2S3, --.

In Column 9, Line 48, delete "RPL13 AP5," and insert -- RPL13AP5, --.

In Column 9, Line 63, delete "RP 524," and insert -- RPS24, --.

In Column 10, Line 12, delete "non malignant" and insert -- non-malignant --.

Signed and Sealed this
Twenty-ninth Day of October, 2024

Katherine Kelly Vidal
*Director of the United States Patent and Trademark Office*

In Column 13, Line 1, delete "NFKb," and insert -- NFκb, --.

In Column 13, Line 57, delete "HSP90AB 1," and insert -- HSP90AB1, --.

In Column 13, Line 66, delete "MARCKSL 1," and insert -- MARCKSL1, --.

In Column 14, Line 3, delete "ND ST1," and insert -- NDST1, --.

In Column 14, Line 59, delete "0S9," and insert -- OS9, --.

In Column 15, Line 17, delete "PAKIIPI," and insert -- PAK1IP1, --.

In Column 15, Line 23, delete "TH005," and insert -- THOC5, --.

In Column 16, Line 42, delete "JUNG," and insert -- JUNB, --.

In Column 16, Line 47, delete "0S9," and insert -- OS9, --.

In Column 17, Line 33, delete "TH005," and insert -- THOC5, --.

In Column 21, Line 24, delete "CCNB11P1" and insert -- CCNB1IP1, --.

In Column 21, Line 37, delete "Nhcb," and insert -- NFκb, --.

In Column 21, Line 38, delete "IFNGR2," and insert -- IFNGR2; --.

In Column 22, Line 12, delete "pre treatment" and insert -- pre-treatment --.

In Column 24, Line 7, delete "pre treatment" and insert -- pre-treatment --.

In Column 25, Line 19, delete "non malignant" and insert -- non-malignant --.

In Column 28, Line 24, delete "post treatment" and insert -- post-treatment --.

In Column 30, Line 17, delete "(D G)" and insert -- (D-G) --.

In Column 32, Line 48, delete "2nd" and insert -- $2^{nd}$ --.

In Column 41, Line 7, delete "VHH" and insert -- $V_{HH}$ --.

In Column 41, Line 57, delete "0" and insert -- β --.

In Column 47, Line 10, delete "127 144;" and insert -- 127-144; --.

In Column 48, Line 32, delete "TES 1);" and insert -- TES1); --.

CERTIFICATE OF CORRECTION (continued)
U.S. Pat. No. 11,913,075 B2

In Column 51, Line 9, delete "CD8a" and insert -- CD8α --.

In Column 51, Line 17, delete "CD3;" and insert -- CD3ζ; --.

In Column 51, Line 20, delete "CD3-chain," and insert -- CD3ζ-chain, --.

In Column 51, Line 23, delete "iBB-CD3t" and insert -- 1BB-CD3ζ --.

In Column 51, Line 24, delete "CD3;" and insert -- CD3ζ; --.

In Column 51, Line 30, delete "Rib)," and insert -- R1b), --.

In Column 51, Line 33, delete "CD3t" and insert -- CD3ζ --.

In Column 51, Line 45, delete "CD11 a," and insert -- CD11a, --.

In Column 51, Line 60, delete "CD3" and insert -- CD3ζ --.

In Column 53, Line 12, delete "CD3t" and insert -- CD3ζ --.

In Column 53, Line 36, delete "CD3;" and insert -- CD3ζ; --.

In Column 53, Line 38, delete "CD3;" and insert -- CD3ζ; --.

In Column 53, Line 39, delete "FcεRT" and insert -- FcεRI --.

In Column 54, Line 27, delete "WIC" and insert -- MHC --.

In Column 55, Line 14, delete "CD3t" and insert -- CD3ζ --.

In Column 55, Line 52, delete "787 98)." and insert -- 787-98). --.

In Column 55, Line 63, delete "1 13," and insert -- 1-13, --.

In Column 57, Line 10, delete "CART" and insert -- CAR T --.

In Column 59, Line 25, delete "a" and insert -- α --.

In Column 59, Line 28, delete "a and 0" and insert -- α and β --.

In Column 59, Line 32, delete "a and 0" and insert -- α and β --.

In Column 61, Line 41, delete "CART" and insert -- CAR T --.

In Column 66, Line 1, delete "02" and insert -- β2 --.

CERTIFICATE OF CORRECTION (continued)
U.S. Pat. No. 11,913,075 B2

In Column 66, Line 2, delete "(02m)" and insert -- ($\beta$2m) --.

In Column 66, Line 2, delete "I/02m" and insert -- I/$\beta$2m --.

In Column 66, Line 14, delete "FACSVantage™" and insert -- FACSVantage™, --.

In Column 74, Line 12, delete "1 1000" and insert -- 1-1000 --.

In Column 76, Line 64, delete "US 2014 0242700" and insert -- US 2014-0242700 --.

In Column 77, Line 63, delete "PCT/US 14/41806," and insert -- PCT/US14/41806, --.

In Column 78, Lines 3-4, delete "PCT/US 14/41806," and insert -- PCT/US14/41806, --.

In Column 79, Line 55, delete "10.103 8" and insert -- 10.1038 --.

In Column 83, Line 24, delete "bibbed" and insert -- bilobed --.

In Column 90, Lines 1-2, delete "Smart-seg2"" and insert -- Smart-seq2" --.

In Column 90, Line 62, delete "post treatment" and insert -- post-treatment --.

In Column 92, Line 34, delete "Kornor" and insert -- Komor --.

In Column 92, Line 42, delete "hyperm Cation" and insert -- hypermutation --.

In Column 92, Line 44, delete "muta.genesis" and insert -- mutagenesis --.

In Column 93, Line 5, delete "non human" and insert -- non-human --.

In Column 94, Line 58, delete "51)," and insert -- S1), --.

In Column 94, Line 62, delete "51)." and insert -- S1). --.

In Column 95, Line 24, delete "Seg2" and insert -- Seq2 --.

In Column 95, Line 31, delete "non malignant" and insert -- non-malignant --.

In Column 95, Line 36, delete "$10^{17}$," and insert -- $10^{-17}$, --.

In Column 96, Line 59, delete "pre treatment" and insert -- pre-treatment --.

In Column 98, Line 65, delete "non malignant" and insert -- non-malignant --.

In Column 101, Line 52, delete "pre treatment" and insert -- pre-treatment --.

CERTIFICATE OF CORRECTION (continued)
U.S. Pat. No. 11,913,075 B2

In Column 102, Line 50, delete "411))." and insert -- 4H). --.

In Column 102, Line 63, delete "pre treatment" and insert -- pre-treatment --.

In Column 104, Line 33, delete "THE" and insert -- TME --.

In Columns 105-106, Line 29 (Table S1-continued), delete "Temezlolamide," and insert -- Temozolomide, --.

In Columns 107-108, Line 4 (Table S2), delete "B. cell" and insert -- B cell --.

In Column 230, Line 3, delete "anti-PD 1" and insert -- anti-PD1 --.

In Column 230, Lines 62-63, delete "(HLA-AB/C," and insert -- (HLA-A/B/C, --.

In Column 231, Line 9, delete "S 100A13, S 100A6," and insert -- S100A13, S100A6, --.

In Column 231, Line 23, delete "CCNBIIP1," and insert -- CCNB1IP1, --.

In Column 273, Lines 57-58, delete "non malignant" and insert -- non-malignant --.

In Column 273, Lines 62-63, delete "non malignant" and insert -- non-malignant --.

In Column 275, Line 2, delete "MEW" and insert -- MHC --.

In Column 275, Line 31, delete "Seg2" and insert -- Seq2 --.

In Column 275, Line 50, delete "HLA B/C/F," and insert -- HLA-B/C/F, --.

In Column 276, Line 20, delete "non malignant" and insert -- non-malignant --.

In Column 276, Lines 46-47, delete "post treatment" and insert -- post-treatment --.

In Column 277, Line 1, delete "MEW" and insert -- MHC --.

In Column 278, Line 34, delete "post treatment" and insert -- post-treatment --.

In Column 279, Line 8, delete "post treatment" and insert -- post-treatment --.

In Column 279, Line 38, delete "pre treatment" and insert -- pre-treatment --.

In Column 279, Line 48, delete "Si)." and insert -- S1). --.

In Column 280, Line 28, delete "4811)." and insert -- 48H). --.

In Column 281, Line 13, delete "RB 1" and insert -- RB1 --.

In Column 282, Line 25, delete "post treatment," and insert -- post-treatment, --.

In Column 282, Line 36, delete "10$^{-106}$" and insert -- 10$^{-106}$, --.

In Column 282, Line 55, delete "CX3 CL 1" and insert -- CX3CL1 --.

In Column 284, Line 58, delete "TGFB" and insert -- TGFβ --.

In Column 290, Line 5, delete "Si." and insert -- S1. --.

In Column 290, Line 59, delete "Seg2" and insert -- Seq2 --.

In Column 291, Line 59, delete "Seg2" and insert -- Seq2 --.

In Column 292, Lines 15-19, delete "$E_{i,p} = \log^2\left(1 + \frac{\sum_{j \in P} TPM_{i,j}}{N}\right)$" and insert -- $E_{i,p} = \log_2\left(1 + \frac{\sum_{j \in P} TPM_{i,j}}{N}\right)$ --.

In Column 294, Lines 5-9, delete "$OE_j = \frac{\sum_{i \in S} C_{ij}}{\mathbb{E}_{\tilde{S}}[\sum_{i \in \tilde{S}} C_{ij}]}$" and insert -- $OE_j = \frac{\sum_{i \in S} C_{ij}}{\mathbb{E}_{\tilde{S}}[\sum_{i \in \tilde{S}} C_{ij}]}$ --.

In Column 294, Line 64, delete "non malignant" and insert -- non-malignant --.

In Column 294, Line 66, delete "log 2" and insert -- log2- --.

In Column 295, Line 9, delete "non malignant" and insert -- non-malignant --.

In Column 296, Line 3, delete "10$^{47}$)." and insert -- 10$^{-17}$). --.

In Column 299, Line 52, delete "(1z-score)" and insert -- (|z-score| --.

In Column 301, Line 56, delete "Si):" and insert -- S1): --.

In Column 303, Line 13, delete "Tex," and insert -- T$_{exc}$ --.

In Column 303, Line 17, delete "underexpressed" and insert -- under-expressed --.

In Column 303, Line 61, delete "communication" and insert -- 'communication --.

Figure 4H:
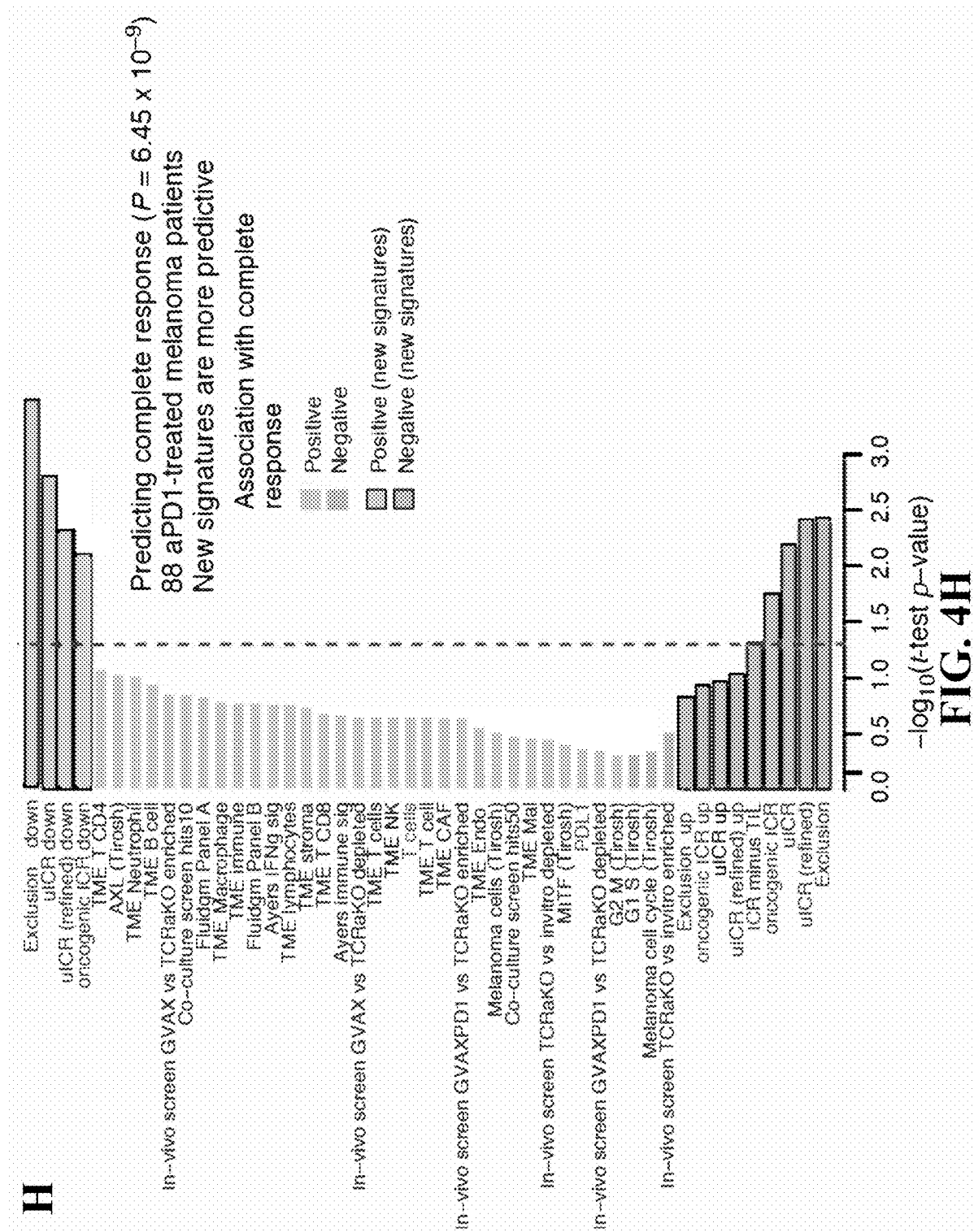
Figure 4I:
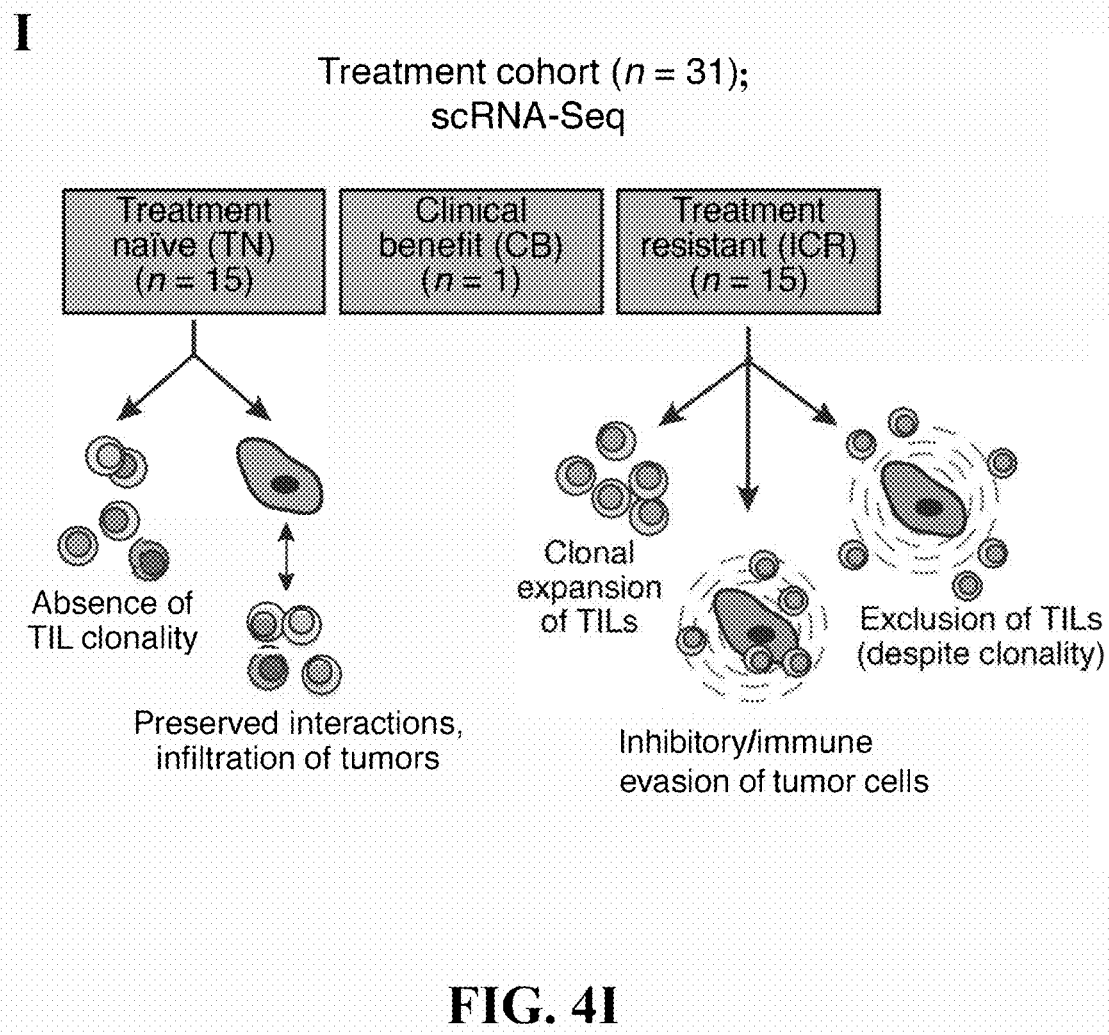

In Column 304, Line 36, delete "FIG. 411" and insert -- FIG. 4H --.

In Column 308, Lines 57-58, delete "portal s" and insert -- portals --.

SEQUENCE LISTING

<160> NUMBER OF SEQ ID NOS: 3

<210> SEQ ID NO 1
<211> LENGTH: 107
<212> TYPE: PRT
<213> ORGANISM: Homo sapiens

<400> SEQUENCE: 1

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

```
Trp Val Arg Ser Lys Arg Ser Arg Leu Leu His Ser Asp Tyr Met Asn
 65                  70                  75                  80

Met Thr Pro Arg Arg Pro Gly Pro Thr Arg Lys His Tyr Gln Pro Tyr
                 85                  90                  95

Ala Pro Pro Arg Asp Phe Ala Ala Tyr Arg Ser
                100             105

<210> SEQ ID NO 2
<211> LENGTH: 9
<212> TYPE: PRT
<213> ORGANISM: Homo sapiens

<400> SEQUENCE: 2

Ile Glu Val Met Tyr Pro Pro Pro Tyr
 1               5

<210> SEQ ID NO 3
<211> LENGTH: 107
<212> TYPE: PRT
<213> ORGANISM: Homo sapiens

<400> SEQUENCE: 3

Ile Glu Val Met Tyr Pro Pro Pro Tyr Leu Asp Asn Glu Lys Ser Asn
 1               5                  10                  15

Gly Thr Ile Ile His Val Lys Gly Lys His Leu Cys Pro Ser Pro Leu
                 20                  25                  30

Phe Pro Gly Pro Ser Lys Pro Phe Trp Val Leu Val Val Val Gly Gly
             35                  40                  45

Val Leu Ala Cys Tyr Ser Leu Leu Val Thr Val Ala Phe Ile Ile Phe
         50                  55                  60

Trp Val Arg Ser Lys Arg Ser Arg Leu Leu His Ser Asp Tyr Met Asn
 65                  70                  75                  80

Met Thr Pro Arg Arg Pro Gly Pro Thr Arg Lys His Tyr Gln Pro Tyr
                 85                  90                  95

Ala Pro Pro Arg Asp Phe Ala Ala Tyr Arg Ser
                100             105
```